(12) United States Patent
Yoshimoto et al.

(10) Patent No.: US 12,234,519 B2
(45) Date of Patent: *Feb. 25, 2025

(54) KIT, DEVICE, AND METHOD FOR DETECTING BLADDER CANCER

(71) Applicants: TORAY INDUSTRIES, INC., Tokyo (JP); NATIONAL CANCER CENTER, Tokyo (JP)

(72) Inventors: Makiko Yoshimoto, Kamakura (JP); Hiroko Sudo, Kamakura (JP); Satoko Kozono, Kamakura (JP); Junpei Kawauchi, Kamakura (JP); Takahiro Ochiya, Tokyo (JP); Hiroyuki Fujimoto, Tokyo (JP); Wataru Usuba, Tokyo (JP); Juntaro Matsuzaki, Tokyo (JP)

(73) Assignees: TORAY INDUSTRIES, INC., Tokyo (JP); NATIONAL CANCER CENTER, Tokyo (JP)

( * ) Notice: Subject to any disclaimer, the term of this patent is extended or adjusted under 35 U.S.C. 154(b) by 0 days.

This patent is subject to a terminal disclaimer.

(21) Appl. No.: 18/339,400

(22) Filed: Jun. 22, 2023

(65) Prior Publication Data

US 2024/0060142 A1 Feb. 22, 2024

Related U.S. Application Data

(62) Division of application No. 17/050,134, filed as application No. PCT/JP2019/017536 on Apr. 25, 2019, now Pat. No. 11,732,307.

(30) Foreign Application Priority Data

Apr. 25, 2018 (JP) ................................. 2018-084416

(51) Int. Cl.
C12Q 1/6886 (2018.01)

(52) U.S. Cl.
CPC ..... C12Q 1/6886 (2013.01); *C12Q 2600/158* (2013.01); *C12Q 2600/178* (2013.01)

(58) Field of Classification Search
None
See application file for complete search history.

(56) References Cited

U.S. PATENT DOCUMENTS

| | | |
|---|---|---|
| 2013/0084241 A1 | 4/2013 | Adam et al. |
| 2014/0200261 A1 | 7/2014 | Hoge et al. |
| 2014/0206852 A1 | 7/2014 | Hoge et al. |
| 2017/0130273 A1 | 5/2017 | Sudo et al. |
| 2017/0130275 A1 | 5/2017 | Kondou et al. |
| 2017/0130278 A1 | 5/2017 | Sudo et al. |
| 2017/0166975 A1 | 6/2017 | Kondou et al. |
| 2017/0356903 A1* | 12/2017 | Domenyuk ........ G01N 33/6896 |

FOREIGN PATENT DOCUMENTS

| | | |
|---|---|---|
| CA | 3 018 048 A1 | 10/2017 |
| CN | 106459867 A | 2/2017 |
| CN | 106471132 A | 3/2017 |
| EP | 3438284 A1 | 2/2019 |
| JP | 2013-67 A | 1/2013 |
| JP | 2017-38566 A | 2/2017 |
| WO | WO 2005/118806 A2 | 12/2005 |
| WO | WO 2014/152622 A1 | 9/2014 |
| WO | WO 2015/020122 A1 | 2/2015 |
| WO | WO 2015/190591 A1 | 12/2015 |
| WO | WO 2015/194615 A1 | 12/2015 |
| WO | WO 2017/171048 A1 | 10/2017 |

OTHER PUBLICATIONS

Armstrong (Molecular Cancer 2015 14:194).
De Long et al., "A non-invasive miRNA based assay to detect bladder cancer in cell-free urine", Am J Transl Res, 2015, vol. 7, No. 11, p. 2500-2509.
Du et al., "Cell-free microRNA expression signatures in urine serve as novel noninvasive biomarkers for diagnosis and recurrence prediction of bladder cancer", Oncotarget, 2017, vol. 8, No. 25, p. 40832-40842.
Dyrkjot (Cancer Research 2009, 69 (11) Jun. 1, 2009).
Ghorai (Frontiers in Genetics Apr. 2014 vol. 5 article 100).
International Search Report, issued in PCT/JP2019/017536, PCT/ISA/210, dated Jul. 23, 2019.
Japanese Office Action for corresponding Japanese Application No. 2020-515545, dated Apr. 25, 2023.
Lian et al., "Serum microRNAs as predictors of risk for non-muscle invasive bladder cancer," Oncotarget, vol. 9, No. 19, 2018, pp. 14895-14908, 14 pages total.
Partial Supplementary European Search Report for European Application No. 19792965.6, dated Apr. 20, 2022.
Song et al., "Expression Profile Analysis of microRNAs in Prostate Cancer by Next-Generation Sequencing," The Prostate, vol. 75, 2015, pp. 500-516, 17 pages total.
Usuba (Cancer Science 2019, 110:408-419 pub online Nov. 1, 2018).
Van Rhijn et al. "Urine Markers for Bladder Cancer Surveillance: A Systematic Review", European Urology, 2005, vol. 47, p. 736-748.
Written Opinion of the International Searching Authority, issued in PCT/JP2019/017536, PCT/ISA/237, dated Jul. 23, 2019.
Chinese Office Action and Search Report dated Jul. 29, 2023 for Application No. 201980027833.8.

* cited by examiner

*Primary Examiner* — Amanda Haney
(74) *Attorney, Agent, or Firm* — Birch, Stewart, Kolasch & Birch, LLP

(57) ABSTRACT

An embodiment according to the present invention provides a kit or device for detection of bladder cancer, and a method for detecting bladder cancer. An embodiment according to the present invention relates to: a kit or device for detection of bladder cancer, including a nucleic acid(s) capable of specifically binding to an miRNA(s) or a complementary strand(s) thereof in a sample from a subject; and a method for detecting bladder cancer, including measuring the miRNA(s) in vitro.

9 Claims, 28 Drawing Sheets
Specification includes a Sequence Listing.

KIT, DEVICE, AND METHOD FOR DETECTING BLADDER CANCER

CROSS-REFERENCE TO RELATED APPLICATIONS

This application is a Divisional of copending application Ser. No. 17/050,134, filed on Oct. 23, 2020, which is the National Phase under 35 U.S.C. § 371 of International Application No. PCT/JP2019/017536, filed on Apr. 25, 2019, which claims the benefit under 35 U.S.C. § 119(a) to Patent Application No. 2018-084416, filed in Japan on Apr. 25, 2018, all of which are hereby expressly incorporated by reference into the present application.

REFERENCE TO ELECTRONIC SEQUENCE LISTING

The application contains a Sequence Listing which has been submitted electronically in .XML format and is hereby incorporated by reference in its entirety. Said .XML copy, created on Jun. 19, 2023, is named "PH-7776-PCT-US-DIV1.xml" and is 692,061 bytes in size. The sequence listing contained in this .XML file is part of the specification and is hereby incorporated by reference herein in its entirety.

TECHNICAL FIELD

The present invention relates to a kit or device for detection of bladder cancer, comprising a nucleic acid capable of specifically binding to a specific miRNA or a complementary strand thereof, which is used for examining presence or absence of bladder cancer in a subject, and a method for detecting bladder cancer, comprising measuring the expression level of the miRNA.

BACKGROUND ART

A bladder is an organ in a pelvis and has a role of a kind of a bag for temporarily storing urine produced by a kidney after passing through a renal pelvis and a ureter. When a bladder is stretched due to urine that has accumulated, there is a function of feeling it as a desire to urinate and contracting the muscles to urinate. Inner surface of a bladder is covered with transitional epithelial cells and is highly elastic. It is known that bladder cancer is caused by canceration of the transitional epithelial cells, and the transitional epithelial cancer histologically accounts for 90% of all bladder cancers.

The death rate due to cancer among Japanese in 2008 was 547.7 out of 100,000, and the proportion of bladder cancer among causes of death is increasing year by year due to aging and influx of Western culture. Urothelial cancer including bladder cancer is a urological tumor with the second highest frequency after prostate cancer, and the number of patients in Japan was about 16,000 in 2002 mainly in the elderly. The morbidity is about four times higher in men than in women. It is known that smoking is greatly involved in the development of bladder cancer, and occupational exposure to aromatic amines is another established risk factor. According to the T factor in the TNM classification used to evaluate the degree of invasion, that is, the stage, bladder cancer is classified into three types, in order of increasing invasion: carcinoma in situ (Tis), superficial bladder cancer (Ta and T1), and invasive bladder cancer (T2 or higher). It is known that carcinoma in situ occurs in combination with superficial cancer and invasive cancer, or carcinoma in situ occurs alone. It is also known that carcinoma in situ may be overlooked even in the case of conducting definitive endoscopy since it is scattered in the mucous membrane of the bladder and spreads like crawling. Superficial bladder cancer is a cancer invasion of which remains on the surface of the bladder, that is, the superficial mucosa and the submucosa below and which rarely metastasizes to other organs. However, it is known that superficial bladder cancer tends to recur many times in the bladder, and follow-up examinations are highly important. It is known that invasive bladder cancer develops so as to extend to the muscles of the bladder and even outside the bladder like a root and tends to metastasize. Further, in the histological grade of bladder cancer shown by the High/Low grade, a High-grade bladder cancer is highly malignant and is likely to infiltrate and metastasize at an early stage, and therefore early detection is particularly highly important.

Treatment of bladder cancer is determined in consideration of degree of progression (Terms handling renal pelvis, ureter and bladder cancer, edited by The Japanese Urological Association, The Japanese Society of Pathology, and The Japan Radiological Society, published by KANEHARA & Co., LTD., 2011), metastasis, and general conditions. The standard method for treating bladder cancer is shown in Bladder Cancer Treatment Guidelines, edited by The Japanese Urological Association, 2015 edition, published by Igakutosho-shuppan Ltd. Currently, the most common treatments are surgical resection (transurethral resection of bladder tumor (TUR-BT), total cystectomy), radiation therapy, chemotherapy with anti-cancer agents, and intravesical BCG therapy. For invasive bladder cancer with a TNM classification of T2 or higher, total cystectomy is a standard treatment, and early detection is very important.

Further, the most reliable and common methods for detecting bladder cancer are currently cystoscopy and urine cytology. Cystoscopy is highly invasive, and urine cytology, which detects detached cancer cells microscopically, is a preferable method in view of invasion. However, it is reported that the specificity is about 94%, and the sensitivity is 35% (Non-Patent Literature 1).

Bladder cancer has a high recurrence rate and often recurs within two years. The recurrence rate after treatment is as high as 50 to 80%, and 10 to 25% thereof is detected as progressive invasive cancer into the muscular layer. Therefore, it is important to detect recurrence and treat it at an early stage to prolong patient survival.

Several urinary protein markers are now available as non-invasive clinical testing markers for bladder cancer. These marker tests have higher sensitivity than urine cytology. For example, in the NMP22 test for detecting a specific nuclear matrix protein NuMA, the sensitivity is 47 to 100%, and the specificity is 55 to 98% (Non-Patent Literature 1). Further, in BTAtrak test for detecting a specific complex of basal membrane fragments, the sensitivity is 60 to 83%, and the specificity is 60 to 79% (Non-Patent Literature 1).

Further, there have been reports of markers using gene expression as an index, such as miR-92a-2-5p, miR-150-3p, miR-1207-5p, miR-1202, miR-135a-3p, miR-1914-3p, miR-1469, miR-149-3p, and miR-663a shown in Patent Literature 1, miR-1254, miR-1246, and miR-92a-3p shown in Patent Literature 2, miR-191-5p and miR-940 shown in Non-Patent Literature 2, and miR-423-5p shown in Non-Patent Literature 3.

CITATION LIST

Patent Literature

Patent Literature 1: JP Patent Publication (Kokai) No. 2013-000067
Patent Literature 2: U.S. Patent Application Publication No. 2013/0084241

Non-Patent Literature

Non-Patent Literature 1: Bas W. G. van Rhijin et al., 2005, European Urology 47, pp. 736 to 748

Non-Patent Literature 2: Long J D et al., 2015, Am J Transl Res 7 (11), pp. 2500-2509

Non-Patent Literature 3: Du L et al., 2017, Oncotarget 8 (25), pp. 40832-40842

SUMMARY OF INVENTION

Problem to be Solved by Invention

Among widely used bladder cancer diagnosis methods, urine cytology has a low sensitivity of 35%. This is because there may be cases of low sensitivity depending on the type of sample, such as the case where it is particularly difficult to distinguish Low-grade samples in the High/Low classification of the histological grade, and there is still a problem that urine cytology is not a universal examination due to its high variability among the observers. Although it is said that the sensitivity of cystoendoscopy is as high as 90%, cystoendoscopy is actually a test that depends on the subjectivity of the operator. Differentiation from mucosal inflammation is often subtle, and if unknown, the cancer may be found as a result of having a short follow-up period and having a conclusion on the next cystoscopy, where there is a risk of overlooking. Further, since cystoendoscopy involves transurethral observation without anesthesia, it is painful for the patient. Particularly for men having a penis, the pain is significant, and there is also a problem of the burden of unnecessary tests. The above-mentioned indicators of existing proteins and gene expression have drawbacks such as poor specificity and/or sensitivity, and large variations in the measurement results depending on the timing of the test.

Accordingly, unnecessary additional examinations may be performed due to misclassification of non-bladder cancer patients as bladder cancer patients, or treatment opportunities may be lost by overlooking bladder cancer patients. Thus, a marker capable of determining bladder cancer correctly regardless of stage, degree of invasion, histological grade, or primary/recurrence with high accuracy has been desired. Further, Patent Literature 1 discloses a method for detecting bladder cancer from a urine sample, in which the accuracy was 86% for 36 patients in the validation group (among them, 27 patients had bladder cancer). However, the number of validation samples is insufficient, and a large amount of urine is necessary since the amount of nucleic acid in urine is very small. Therefore, the detection work is complicated and has not been put to practical use.

It is an object of the present invention to provide a disease diagnosis kit or device that is useful for non-invasive diagnosis and treatment of bladder cancer with a small amount of sample, and a method for determining (or detecting) bladder cancer.

Means for Solution to Problem

As a result of diligent studies in order to solve the above problems, the inventors have found genes available as bladder cancer detection markers from blood which can be collected minimally invasively, and that bladder cancer can be significantly detected using the genes, thereby accomplished the present invention.

SUMMARY OF INVENTION

That is, the present invention includes the following aspects.

(1) A kit for detection of bladder cancer, comprising a nucleic acid(s) capable of specifically binding to at least one polynucleotide selected from the following bladder cancer markers; miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-1282-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, and miR-937-5p, or to a complementary strand of the polynucleotide.

(2) The kit according to (1), wherein the nucleic acid(s) is a polynucleotide(s) selected from the group consisting of the following polynucleotides (a) to (e):

(a) a polynucleotide consisting of a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;

(b) a polynucleotide comprising a nucleotide sequence represented by any of SEQ ID NOs: 1 to 228;

(c) a polynucleotide consisting of a nucleotide sequence complementary to a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 228 or a nucleotide sequence derived from the nucleotide sequence by the replacement of u with t; and (e) a polynucleotide hybridizing under stringent conditions to any of the polynucleotides (a) to (d).

(3) The kit according to (1) or (2), wherein the kit further comprises a nucleic acid(s) capable of specifically binding to at least one polynucleotide selected from the following other bladder cancer markers: miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p and miR-940, or to a complementary strand of the polynucleotide.

(4) The kit according to (3), wherein the nucleic acid(s) is a polynucleotide(s) selected from the group consisting of the following polynucleotides (f) to (j):

(f) a polynucleotide consisting of a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 229 to 243;

(h) a polynucleotide consisting of a nucleotide sequence complementary to a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 229 to 243 or a nucleotide sequence derived from the nucleotide sequence by the replacement of u with t; and (j) a polynucleotide hybridizing under stringent conditions to any of the polynucleotides (to (i).

(5) A device for detection of bladder cancer, comprising a nucleic acid(s) capable of specifically binding to at least one polynucleotide selected from the following bladder cancer markers: miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, and miR-937-5p, or to a complementary strand of the polynucleotide.

(6) The device according to (5), wherein the nucleic acid(s) is a polynucleotide(s) selected from the group consisting of the following polynucleotides (a) to (e):

(a) a polynucleotide consisting of a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;

(b) a polynucleotide comprising a nucleotide sequence represented by any of SEQ ID NOs: 1 to 228;

(c) a polynucleotide consisting of a nucleotide sequence complementary to a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 228 or a nucleotide sequence derived from the nucleotide sequence by the replacement of u with t; and (e) a polynucleotide hybridizing under stringent conditions to any of the polynucleotides (a) to (d).

(7) The device according to (5) or (6), wherein the device further comprises a nucleic acid(s) capable of specifically binding to at least one polynucleotide selected from the following other bladder cancer markers: miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940, or to a complementary strand of the polynucleotide.

(8) The device according to (7), wherein the nucleic acid(s) is a polynucleotide(s) selected from the group consisting of the following polynucleotides (f) to (j):

(f) a polynucleotide consisting of a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 229 to 243;

(h) a polynucleotide consisting of a nucleotide sequence complementary to a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 229 to 243 or a nucleotide sequence derived from the nucleotide sequence by the replacement of u with t; and (j) a polynucleotide hybridizing under stringent conditions to any of the polynucleotides (to (i).

(9) The device according to any one of (5) to (8), wherein the device is a device for measurement by a hybridization technique.

(10) The device according to (9), wherein the hybridization technique is a nucleic acid array technique.

(11) A method for detecting bladder cancer, comprising: measuring an expression level(s) of at least one polynucleotide selected from the following bladder cancer markers: miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, and miR-937-5p in a sample from a subject; and evaluating in vitro whether or not the subject has bladder cancer using the measured expression level(s).

(12) The method according to (11), comprising: plugging the gene expression level(s) of the one or more polynucleotide(s) in the sample from the subject into a discriminant formula capable of discriminating the presence or absence of a bladder cancer distinctively, wherein the discriminant formula is created by using gene expression levels in samples from subjects known to have bladder cancer and gene expression levels in samples from subjects having no bladder cancer as training samples; and thereby evaluating whether or not the subject has a bladder cancer.

(13) The method according to (11) or (12), comprising: measuring an expression level(s) of the polynucleotide(s) by using a nucleic acid(s) capable of specifically binding to the polynucleotide(s) or to a complementary strand(s) of the polynucleotide(s), wherein the nucleic acid(s) is a polynucleotide(s) selected from the group consisting of the following polynucleotides (a) to (e):

(a) a polynucleotide consisting of a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;

(b) a polynucleotide comprising a nucleotide sequence represented by any of SEQ ID NOs: 1 to 228;

(c) a polynucleotide consisting of a nucleotide sequence complementary to a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;

(d) a polynucleotide comprising a nucleotide sequence complementary to a nucleotide sequence represented by any of SEQ ID NOs: 1 to 228 or a nucleotide sequence derived from the nucleotide sequence by the replacement of u with t; and (e) a polynucleotide hybridizing under stringent conditions to any of the polynucleotides (a) to (d).

(14) The method according to any one of (11) to (13), further comprising: measuring an expression level(s) of at least one polynucleotide selected from the following other bladder cancer markers: miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940.

(15) The method according to (14), comprising: measuring an expression level(s) of the polynucleotide(s) by using a nucleic acid(s) capable of specifically binding to the polynucleotide(s) or to a complementary strand(s) of the polynucleotide(s), wherein the nucleic acid(s) is a polynucleotide(s) selected from the group consisting of the following polynucleotides (f) to (j):

(f) a polynucleotide consisting of a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 229 to 243;

(h) a polynucleotide consisting of a nucleotide sequence complementary to a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;

(i) a polynucleotide comprising a nucleotide sequence complementary to a nucleotide sequence represented by any of SEQ ID NOs: 229 to 243 or a nucleotide sequence derived from the nucleotide sequence by the replacement of u with t; and (j) a polynucleotide hybridizing under stringent conditions to any of the polynucleotides (to (i).

(16) The method according to any one of (11) to (15), comprising: measuring an expression level(s) of target gene (s) in the sample from the subject by using the kit according to any one of (1) to (4) or the device according to any one of (5) to (10), wherein the kit or the device comprises a nucleic acid(s) capable of specifically binding to the polynucleotide(s) or to a complementary strand(s) of the polynucleotide(s).

(17) The method according to any one of (11) to (16), wherein the subject is a human.

(18) The method according to any one of (11) to (17), wherein the sample is blood, serum, or plasma.

DEFINITION OF TERMS

The terms used herein are defined as described below.

Abbreviations or terms such as nucleotide, polynucleotide, DNA, and RNA abide by "Guidelines for the preparation of specification which contain nucleotide and/or amino acid sequences" (edited by Japan Patent Office) and common use in the art.

The term "polynucleotide" used herein refers to a nucleic acid including any of RNA, DNA, and RNA/DNA (chimera). The DNA includes any of cDNA, genomic DNA, and synthetic DNA. The RNA includes any of total RNA, mRNA, rRNA, miRNA, siRNA, snoRNA, snRNA, non-coding RNA, and synthetic RNA. Here, the "synthetic DNA" and the "synthetic RNA" refer to a DNA and an RNA artificially prepared using, for example, an automatic nucleic acid synthesizer, on the basis of predetermined nucleotide sequences (which may be any of natural and non-natural sequences). The "non-natural sequence" is intended to be used in a broad sense and includes, for example, a sequence comprising substitution, deletion, insertion, and/or addition of one or more nucleotides (i.e., a variant sequence) and a sequence comprising one or more modified nucleotides (i.e., a modified sequence), which are different from the natural sequence. Herein, the term "polynucleotide" is used interchangeably with the term "nucleic acid."

The term "fragment" used herein is a polynucleotide having a nucleotide sequence that consists of a consecutive portion of a polynucleotide and desirably has a length of 15 or more nucleotides, preferably 17 or more nucleotides, and more preferably 19 or more nucleotides.

The term "gene" used herein is intended to include not only RNA and double-stranded DNA but also each single-stranded DNA such as a plus(+) strand (or a sense strand) or a complementary strand (or an antisense strand) constituting the duplex. The gene is not particularly limited by its length.

Thus, the "gene" used herein includes any of double-stranded DNA including human genomic DNA, single-stranded DNA (plus strand), single-stranded DNA having a sequence complementary to the plus strand (complementary strand), cDNA, microRNA (miRNA), their fragments, and human genome, and their transcripts, unless otherwise specified. The "gene" includes not only a "gene" represented by a particular nucleotide sequence (or SEQ ID NO) but also "nucleic acids" encoding RNAs having biological functions equivalent to RNA encoded by the gene, for example, a congener (i.e., a homolog or an ortholog), a variant (e.g., a genetic polymorph), and a derivative. Specific examples of such a "nucleic acid" encoding a congener, a variant, or a derivative can include a "nucleic acid" having a nucleotide sequence hybridizing under stringent conditions described later to a complementary sequence of a nucleotide sequence represented by any of SEQ ID NOs: 1 to 766 or a nucleotide sequence derived from the nucleotide sequence by the replacement of u with t. Regardless of whether or not there is a difference in functional region, the "gene" can comprise, for example, expression control regions, coding regions, exons, or introns. The "gene" may be contained in a cell or may exist alone after being released from a cell. Alternatively, the "gene" may be in a state enclosed in a vesicle referred to as an exosome.

The term "exosome" used herein is a vesicle that is encapsulated by the lipid bilayer and secreted from a cell. The exosome is derived from a multivesicular endosome and may incorporate biomaterials such as "genes" (e.g., RNA or DNA) or proteins when released to an extracellular environment. The exosome is known to be contained in a body fluid such as blood, serum, plasma, serum, or lymph.

The term "transcript" used herein refers to an RNA synthesized from the DNA sequence of a gene as a template. RNA polymerase binds to a site referred to as a promoter located upstream of the gene and adds ribonucleotides complementary to the nucleotide sequence of the DNA to the 3' end to synthesize an RNA. This RNA contains not only the gene itself but also the whole sequence from a transcription initiation site to the end of a poly A sequence, including expression control regions, coding regions, exons, or introns.

Unless otherwise specified, the term "microRNA (miRNA)" used herein is intended to mean a 15- to 25-nucleotide non-coding RNA that is transcribed as an RNA precursor having a hairpin-like structure, cleaved by a dsRNA-cleaving enzyme having RNase III cleavage activity, integrated into a protein complex referred to as RISC, and involved in suppression of mRNA translation. The term "miRNA" used herein includes not only a "miRNA" represented by a particular nucleotide sequence (or SEQ ID NO) but also a "miRNA" comprising a precursor of the "miRNA" (pre-miRNA or pri-miRNA) and having biological functions equivalent to miRNAs encoded thereby, such as a "miRNA" encoding a congener (i.e., a homolog or an ortholog), a variant such as a genetic polymorph, and a derivative. Such a "miRNA" encoding a precursor, a congener, a variant, or a derivative can be specifically identified using "miRBase release 21" (http://www.mirbase.org/), and examples thereof can include a "miRNA" having a nucleotide sequence hybridizing under stringent conditions described later to a complementary sequence of any particular nucleotide sequence represented by any of SEQ ID NOs: 1 to 766. The term "miRNA" used herein may be a gene product of a miR gene. Such a gene product includes a mature miRNA (e.g., a 15- to 25-nucleotide or 19- to 25-nucleotide non-coding RNA involved in suppression of mRNA translation as described above) or a miRNA precursor (e.g., pre-miRNA or pri-miRNA as described above).

The term "probe" used herein includes a polynucleotide that is used for specifically detecting an RNA resulting from the expression of a gene or a polynucleotide derived from the RNA, and/or a polynucleotide complementary thereto.

The term "primer" used herein includes consecutive polynucleotides that specifically recognize and amplify an RNA resulting from the expression of a gene or a polynucleotide derived from the RNA, and/or a polynucleotide complementary thereto.

In this context, the "complementary polynucleotide" (complementary strand or reverse strand) means a polynucleotide in a complementary relationship based on A:T (U) and G:C base pairs with the full-length sequence of a polynucleotide consisting of a nucleotide sequence defined by any of SEQ ID NOs: 1 to 766 or a nucleotide sequence derived from the nucleotide sequence by the replacement of u with t, or a partial sequence thereof (here, this full-length or partial sequence is referred to as a plus strand for the sake of convenience). However, such a complementary strand is not limited to a sequence completely complementary to the nucleotide sequence of the target plus strand and may have a complementary relationship to an extent that permits hybridization under stringent conditions to the target plus strand.

The term "stringent conditions" used herein refers to conditions under which a nucleic acid probe hybridizes to its target sequence to a detectably larger extent (e.g., a measurement value equal to or larger than "(a mean of background measurement values)+(a standard deviation of the background measurement values)×2") than that for other sequences. The stringent conditions are dependent on a sequence and differ depending on an environment where hybridization is performed. A target sequence complementary 100% to the nucleic acid probe can be identified by controlling the stringency of hybridization and/or washing conditions. Specific examples of the "stringent conditions" will be mentioned later.

The term "Tm value" used herein means a temperature at which the double-stranded moiety of a polynucleotide is denatured into single strands so that the double strands and the single strands exist at a ratio of 1:1.

The term "variant" used herein means, in the case of a nucleic acid, a natural variant attributed to polymorphism, mutation, or the like; a variant containing the deletion, substitution, addition, or insertion of 1, 2 or 3 or more (e.g., 1 to several) nucleotides in a nucleotide sequence represented by a SEQ ID NO, a nucleotide sequence derived from the nucleotide sequence by the replacement of u with t, or a partial sequence thereof, a variant containing the deletion, substitution, addition, or insertion of one or two or more nucleotides in a nucleotide sequence of a precursor RNA (a premature miRNA) of the sequence of any of SEQ ID NOs: 1 to 243, a nucleotide sequence derived from the nucleotide sequence by the replacement of u with t, or a partial sequence thereof, a variant that exhibits percent (%) identity of approximately 90% or higher, approximately 95% or higher, approximately 97% or higher, approximately 98% or higher, or approximately 99% or higher to each of these nucleotide sequences or the partial sequences thereof, or a nucleic acid hybridizing under the stringent conditions defined above to a polynucleotide or an oligonucleotide comprising each of these nucleotide sequences or the partial sequences thereof.

The term "several" used herein means an integer of approximately 10, 9, 8, 7, 6, 5, 4, 3, or 2.

The variant as used herein can be prepared by a well-known technique such as site-directed mutagenesis or mutagenesis using PCR.

The term "percent (%) identity" used herein can be determined with or without an introduced gap, using a protein or gene search system based on BLAST (https://blast.ncbi.nlm.nih.gov/Blast.cgi) or FASTA (http://www.genome.jp/tools/fasta/) (Zheng Zhang et al., 2000, J. Comput. Biol., Vol. 7, p. 203-214; Altschul, S. F et al., 1990, Journal of Molecular Biology, Vol. 215, p. 403-410; and Pearson, W. R et al., 1988, Proc. Natl. Acad. Sci. U.S.A., Vol. 85, p. 2444-2448).

The term "derivative" used herein is meant to include unlimitedly a modified nucleic acid, for example, a derivative labeled with a fluorophore or the like, a derivative containing a modified nucleotide (e.g., a nucleotide containing a group such as halogen, alkyl such as methyl, alkoxy such as methoxy, thio, or carboxymethyl, and a nucleotide that has undergone base rearrangement, double bond saturation, deamination, replacement of an oxygen molecule with a sulfur molecule, etc.), PNA (peptide nucleic acid; Nielsen, P. E et al., 1991, Science, Vol. 254, p. 1497-500), and LNA (locked nucleic acid; Obika, S et al., 1998, Tetrahedron Lett., Vol. 39, p. 5401-5404).

As used herein, the "nucleic acid" capable of specifically binding to a polynucleotide selected from the bladder cancer marker miRNAs described above or to a complementary strand of the polynucleotide is a synthesized or prepared nucleic acid and, for example, includes a "nucleic acid probe" or a "primer", and is utilized directly or indirectly for detecting the presence or absence of bladder cancer in a subject, for diagnosing the presence or absence or the severity of bladder cancer, the presence or absence or the degree of amelioration of bladder cancer, or the therapeutic sensitivity of bladder cancer, or for screening for a candidate substance useful in the prevention, amelioration, or treatment of bladder cancer. The "nucleic acid" includes a nucleotide, an oligonucleotide, and a polynucleotide capable of specifically recognizing and binding to a transcript represented by any of SEQ ID NOs: 1 to 766 or a synthetic cDNA nucleic acid thereof, or a complementary strand thereto in vivo, particularly, in a sample such as a body fluid (e.g., blood or urine), in relation to the development of bladder cancer. The nucleotide, the oligonucleotide, and the polynucleotide can be effectively used as probes for detecting the aforementioned gene expressed in vivo, in tissues, in cells, or the like on the basis of the properties described above, or as primers for amplifying the aforementioned gene expressed in vivo.

The term "detection" used herein is interchangeable with the term "examination", "measurement", "detection", or "decision support". As used herein, the term "evaluation" is meant to include diagnosis- or evaluation-support on the basis of examination results or measurement results.

The term "subject" used herein means a mammal such as a primate including a human and a chimpanzee, a pet animal including a dog and a cat, a livestock animal including cattle, a horse, sheep, and a goat, a rodent including a mouse and a rat, and animals raised in a zoo. The subject is preferably a human. Meanwhile, the "healthy subject" also means such a mammal, which is an animal without cancer to be detected. The healthy subject is preferably a human.

The term "bladder cancer" used herein is a malignant tumor developed in the bladder, and the term encompasses urothelial carcinoma of the renal pelvis and the urinary tract.

The term "P" or "P value" used herein refers to a probability at which a more extreme statistic than that actually calculated from data under null hypothesis is observed in a statistical test. Thus, a smaller "P" or "P value" is regarded as being a more significant difference between subjects to be compared.

The term "sensitivity" used herein means a value of (the number of true positives)/(the number of true positives+the number of false negatives). High sensitivity allows bladder cancer to be detected early, which leads to complete resection of cancer regions or a lowered recurrence rate.

The term "specificity" used herein means a value of (the number of true negatives)/(the number of true negatives+the number of false positives). High specificity prevents needless extra examination for healthy subjects misjudged as being bladder cancer patients, leading to reduction in burden on patients and reduction in medical expense.

The term "accuracy" used herein means a value of (the number of true positives+the number of true negatives)/(the total number of cases). The accuracy indicates the ratio of samples that are identified correctly to all samples, and serves as a primary index for evaluating detection performance.

As used herein, the "sample" that is subjected to determination, detection, or diagnosis refers to a tissue and a biological material in which the expression of the gene of the present invention varies as bladder cancer develops, as bladder cancer progresses, or as therapeutic effects on bladder cancer are exerted. Specifically, the sample refers to bladder tissue, renal pelvis, urinary tract, lymph node, organs in the vicinity thereof, organs suspected of metastasis, skin, a body fluid such as blood, urine, saliva, sweat, and tissue exudate, serum or plasma prepared from blood, and others such as feces, hair, or the like. The "sample" further refers to a biological sample extracted therefrom, specifically, a gene such as RNA or miRNA.

The term "hsa-miR-6087 gene" or "hsa-miR-6087" used herein includes the hsa-miR-6087 gene (miRBase Accession No. MIMAT0023712) shown in SEQ ID NO: 1, a homolog or an ortholog of a different organism species, and the like. The gene can be obtained by a method described in Yoo J K et al., 2012, Stem Cells Dev., Vol. 21, pp. 2049-2057. Also, "hsa-mir-6087" (miRBase Accession No. MI0020364; SEQ ID NO: 244) having a hairpin-like structure is known as a precursor of "hsa-miR-6087."

The term "hsa-miR-1185-1-3p gene" or "hsa-miR-1185-1-3p" used herein includes the hsa-miR-1185-1-3p gene (miRBase Accession No. MIMAT0022838) shown in SEQ ID NO: 2, a homolog or an ortholog of a different organism species, and the like. The gene can be obtained by a method described in Berezikov E et al., 2006, Genome Res., Vol. 16, pp. 1289-1298. Also, "hsa-mir-1185-1" (miRBase Accession No. MI0003844; SEQ ID NO: 245) having a hairpin-like structure is known as a precursor of "hsa-miR-1185-1-3p."

The term "hsa-miR-1185-2-3p gene" or "hsa-miR-1185-2-3p" used herein includes the hsa-miR-1185-2-3p gene (miRBase Accession No. MIMAT0022713) shown in SEQ ID NO: 3, a homolog or an ortholog of a different organism species, and the like. The gene can be obtained by a method described in Berezikov E et al., 2006, Genome Res., Vol. 16, pp. 1289-1298. Also, "hsa-mir-1185-2" (miRBase Accession No. MI0003821; SEQ ID NO: 246) having a hairpin-like structure is known as a precursor of "hsa-miR-1185-2-3p."

The term "hsa-miR-1193 gene" or "hsa-miR-1193" used herein includes the hsa-miR-1193 gene (miRBase Accession No. MIMAT0015049) shown in SEQ ID NO: 4, a homolog or an ortholog of a different organism species, and the like. The gene can be obtained by a method described in Stark M S et al., 2010, PLoS One, Vol. 5, e9685. Also, "hsa-mir-1193" (miRBase Accession No. MI0014205; SEQ ID NO: 247) having a hairpin-like structure is known as a precursor of "hsa-miR-1193."

The term "hsa-miR-1199-5p gene" or "hsa-miR-1199-5p" used herein includes the hsa-miR-1199-5p gene (miRBase Accession No. MIMAT0031119) shown in SEQ ID NO: 5, a homolog or an ortholog of a different organism species, and the like. The gene can be obtained by a method described in Salvi A et al., 2013, Int. J. Oncol., Vol. 42, pp. 391-402. Also, "hsa-mir-1199" (miRBase Accession No. MI0020340; SEQ ID NO: 248) having a hairpin-like structure is known as a precursor of "hsa-miR-1199-5p."

The term "hsa-miR-1225-5p gene" or "hsa-miR-1225-5p" used herein includes the hsa-miR-1225-5p gene (miRBase Accession No. MIMAT0005572) shown in SEQ ID NO: 6, a homolog or an ortholog of a different organism species, and the like. The gene can be obtained by a method described in Berezikov E et al., 2007, Mol. Cell, Vol. 28, pp. 328-336. Also, "hsa-mir-1225" (miRBase Accession No. MI0006311; SEQ ID NO: 249) having a hairpin-like structure is known as a precursor of "hsa-miR-1225-5p."

The term "hsa-miR-1227-5p gene" or "hsa-miR-1227-5p" used herein includes the hsa-miR-1227-5p gene (miRBase Accession No. MIMAT0022941) shown in SEQ ID NO: 7, a homolog or an ortholog of a different organism species, and the like. The gene can be obtained by a method described in Berezikov E et al., 2007, Mol. Cell, Vol. 28, pp. 328-336. Also, "hsa-mir-1227" (miRBase Accession No. MI0006316; SEQ ID NO: 250) having a hairpin-like structure is known as a precursor of "hsa-miR-1227-5p."

The term "hsa-miR-1228-3p gene" or "hsa-miR-1228-3p" used herein includes the hsa-miR-1228-3p gene (miRBase Accession No. MIMAT0005583) shown in SEQ ID NO: 8, a homolog or an ortholog of a different organism species, and the like. The gene can be obtained by a method described in Berezikov E et al., 2007, Mol. Cell, Vol. 28, pp. 328-336. Also, "hsa-mir-1228" (miRBase Accession No. MI0006318; SEQ ID NO: 251) having a hairpin-like structure is known as a precursor of "hsa-miR-1228-3p."

The term "hsa-miR-1228-5p gene" or "hsa-miR-1228-5p" used herein includes the hsa-miR-1228-5p gene (miRBase Accession No. MIMAT0005582) shown in SEQ ID NO: 9, a homolog or an ortholog of a different organism species, and the like. The gene can be obtained by a method described in Berezikov E et al., 2007, Mol. Cell, Vol. 28, pp. 328-336. Also, "hsa-mir-1228" (miRBase Accession No. MI0006318; SEQ ID NO: 252) having a hairpin-like structure is known as a precursor of "hsa-miR-1228-5p."

The term "hsa-miR-1237-5p gene" or "hsa-miR-1237-5p" used herein includes the hsa-miR-1237-5p gene (miRBase Accession No. MIMAT0022946) shown in SEQ ID NO: 10, a homolog or an ortholog of a different organism species, and the like. The gene can be obtained by a method described in Berezikov E et al., 2007, Mol. Cell, Vol. 28, pp. 328-336. Also, "hsa-mir-1237" (miRBase Accession No. MI0006327; SEQ ID NO: 253) having a hairpin-like structure is known as a precursor of "hsa-miR-1237-5p."

The term "hsa-miR-1238-5p gene" or "hsa-miR-1238-5p" used herein includes the hsa-miR-1238-5p gene (miRBase Accession No. MIMAT0022947) shown in SEQ ID NO: 11, a homolog or an ortholog of a different organism species, and the like. The gene can be obtained by a method described in Berezikov E et al., 2007, Mol. Cell, Vol. 28, pp. 328-336. Also, "hsa-mir-1238" (miRBase Accession No. MI0006328; SEQ ID NO: 254) having a hairpin-like structure is known as a precursor of "hsa-miR-1238-5p."

The term "hsa-miR-1247-3p gene" or "hsa-miR-1247-3p" used herein includes the hsa-miR-1247-3p gene (miRBase Accession No. MIMAT0022721) shown in SEQ ID NO: 12, a homolog or an ortholog of a different organism species, and the like. The gene can be obtained by a method described in Morin R D et al., 2008, Genome Res., Vol. 18, pp. 610-621. Also, "hsa-mir-1247" (miRBase Accession No. MI0006382; SEQ ID NO: 255) having a hairpin-like structure is known as a precursor of "hsa-miR-1247-3p."

The term "hsa-miR-1268a gene" or "hsa-miR-1268a" used herein includes the hsa-miR-1268a gene (miRBase Accession No. MIMAT0005922) shown in SEQ ID NO: 13, a homolog or an ortholog of a different organism species, and the like. The gene can be obtained by a method described in Morin R D et al., 2008, Genome Res., Vol. 18, pp. 610-621. Also, "hsa-mir-1268a" (miRBase Accession No. MI0006405; SEQ ID NO: 256) having a hairpin-like structure is known as a precursor of "hsa-miR-1268a."

The term "hsa-miR-1268b gene" or "hsa-miR-1268b" used herein includes the hsa-miR-1268b gene (miRBase Accession No. MIMAT0018925) shown in SEQ ID NO: 14, a homolog or an ortholog of a different organism species, and the like. The gene can be obtained by a method described in Jima D D et al., 2010, Blood, Vol. 116, e118-e127. Also, "hsa-mir-1268b" (miRBase Accession No. MI0016748; SEQ ID NO: 257) having a hairpin-like structure is known as a precursor of "hsa-miR-1268b."

The term "hsa-miR-1273g-3p gene" or "hsa-miR-1273g-3p" used herein includes the hsa-miR-1273g-3p gene (miRBase Accession No. MIMAT0022742) shown in SEQ ID NO: 15, a homolog or an ortholog of a different organism species, and the like. The gene can be obtained by a method described in Reshmi G et al., 2011, Genomics, Vol. 97, pp. 333-340. Also, "hsa-mir-1273g" (miRBase Accession No. MI0018003; SEQ ID NO: 258) having a hairpin-like structure is known as a precursor of "hsa-miR-1273g-3p."

The term "hsa-miR-128-2-5p gene" or "hsa-miR-128-2-5p" used herein includes the hsa-miR-128-2-5p gene (miRBase Accession No. MIMAT0031095) shown in SEQ ID NO: 16, a homolog or an ortholog of a different organism species, and the like. The gene can be obtained by a method described in Lagos-Quintana M et al., 2002, Curr. Biol., Vol. 12, pp. 735-739. Also, "hsa-mir-128-2" (miRBase Accession No. MI0000727; SEQ ID NO: 259) having a hairpin-like structure is known as a precursor of "hsa-miR-128-2-5p."

The term "hsa-miR-1343-3p gene" or "hsa-miR-1343-3p" used herein includes the hsa-miR-1343-3p gene (miRBase Accession No. MIMAT0019776) shown in SEQ ID NO: 17, a homolog or an ortholog of a different organism species, and the like. The gene can be obtained by a method described in Persson H et al., 2011, Cancer Res., Vol. 71, pp. 78-86. Also, "hsa-mir-1343" (miRBase Accession No. MI0017320; SEQ ID NO: 260) having a hairpin-like structure is known as a precursor of "hsa-miR-1343-3p."

The term "hsa-miR-1343-5p gene" or "hsa-miR-1343-5p" used herein includes the hsa-miR-1343-5p gene (miRBase Accession No. MIMAT0027038) shown in SEQ ID NO: 18, a homolog or an ortholog of a different organism species, and the like. The gene can be obtained by a method described in Persson H et al., 2011, Cancer Res., Vol. 71, pp. 78-86. Also, "hsa-mir-1343" (miRBase Accession No. MI0017320; SEQ ID NO: 261) having a hairpin-like structure is known as a precursor of "hsa-miR-1343-5p."

The term "hsa-miR-1470 gene" or "hsa-miR-1470" used herein includes the hsa-miR-1470 gene (miRBase Accession No. MIMAT0007348) shown in SEQ ID NO: 19, a homolog or an ortholog of a different organism species, and the like. The gene can be obtained by a method described in Kawaji H et al., 2008, BMC Genomics, Vol. 9, p. 157. Also, "hsa-mir-1470" (miRBase Accession No. MI0007075; SEQ ID NO: 262) having a hairpin-like structure is known as a precursor of "hsa-miR-1470."

The term "hsa-miR-17-3p gene" or "hsa-miR-17-3p" used herein includes the hsa-miR-17-3p gene (miRBase Accession No. MIMAT0000071) shown in SEQ ID NO: 20, a homolog or an ortholog of a different organism species, and the like. The gene can be obtained by a method described in Lagos-Quintana M et al., 2001, Science, Vol. 294, pp. 853-858. Also, "hsa-mir-17" (miRBase Accession No. MI0000071; SEQ ID NO: 263) having a hairpin-like structure is known as a precursor of "hsa-miR-17-3p."

The term "hsa-miR-187-5p gene" or "hsa-miR-187-5p" used herein includes the hsa-miR-187-5p gene (miRBase Accession No. MIMAT0004561) shown in SEQ ID NO: 21, a homolog or an ortholog of a different organism species, and the like. The gene can be obtained by a method described in Lim L P et al., 2003, Science, Vol. 299, p. 1540. Also, "hsa-mir-187" (miRBase Accession No. MI0000274; SEQ ID NO: 264) having a hairpin-like structure is known as a precursor of "hsa-miR-187-5p."

The term "hsa-miR-1908-3p gene" or "hsa-miR-1908-3p" used herein includes the hsa-miR-1908-3p gene (miRBase Accession No. MIMAT0026916) shown in SEQ ID NO: 22, a homolog or an ortholog of a different organism species, and the like. The gene can be obtained by a method described in Bar M et al., 2008, Stem Cells, Vol. 26, pp. 2496-2505. Also, "hsa-mir-1908" (miRBase Accession No. MI0008329; SEQ ID NO: 265) having a hairpin-like structure is known as a precursor of "hsa-miR-1908-3p."

The term "hsa-miR-1908-5p gene" or "hsa-miR-1908-5p" used herein includes the hsa-miR-1908-5p gene (miRBase Accession No. MIMAT0007881) shown in SEQ ID NO: 23, a homolog or an ortholog of a different organism species, and the like. The gene can be obtained by a method described in Bar M et al., 2008, Stem Cells, Vol. 26, pp. 2496-2505. Also, "hsa-mir-1908" (miRBase Accession No.

MI0008329; SEQ ID NO: 266) having a hairpin-like structure is known as a precursor of "hsa-miR-1908-5p."

The term "hsa-miR-1909-3p gene" or "hsa-miR-1909-3p" used herein includes the hsa-miR-1909-3p gene (miRBase Accession No. MIMAT0007883) shown in SEQ ID NO: 24, a homolog or an ortholog of a different organism species, and the like. The gene can be obtained by a method described in Bar M et al., 2008, Stem Cells, Vol. 26, pp. 2496-2505. Also, "hsa-mir-1909" (miRBase Accession No. MI0008330; SEQ ID NO: 267) having a hairpin-like structure is known as a precursor of "hsa-miR-1909-3p."

The term "hsa-miR-1915-3p gene" or "hsa-miR-1915-3p" used herein includes the hsa-miR-1915-3p gene (miRBase Accession No. MIMAT0007892) shown in SEQ ID NO: 25, a homolog or an ortholog of a different organism species, and the like. The gene can be obtained by a method described in Bar M et al., 2008, Stem Cells, Vol. 26, pp. 2496-2505. Also, "hsa-mir-1915" (miRBase Accession No. MI0008336; SEQ ID NO: 268) having a hairpin-like structure is known as a precursor of "hsa-miR-1915-3p."

The term "hsa-miR-210-5p gene" or "hsa-miR-210-5p" used herein includes the hsa-miR-210-5p gene (miRBase Accession No. MIMAT0026475) shown in SEQ ID NO: 26, a homolog or an ortholog of a different organism species, and the like. The gene can be obtained by a method described in Lim L P et al., 2003, Science, Vol. 299, p. 1540. Also, "hsa-mir-210" (miRBase Accession No. MI0000286; SEQ ID NO: 269) having a hairpin-like structure is known as a precursor of "hsa-miR-210-5p."

The term "hsa-miR-24-3p gene" or "hsa-miR-24-3p" used herein includes the hsa-miR-24-3p gene (miRBase Accession No. MIMAT0000080) shown in SEQ ID NO: 27, a homolog or an ortholog of a different organism species, and the like. The gene can be obtained by a method described in Lagos-Quintana M et al., 2001, Science, Vol. 294, pp. 853-858. Also, "hsa-mir-24-1" (miRBase Accession No. MI0000080; SEQ ID NO: 472) and "hsa-mir-24-2" (miRBase Accession No. MI0000081; SEQ ID NO: 484) each having a hairpin-like structure are known as precursors of "hsa-miR-24-3p."

The term "hsa-miR-2467-3p gene" or "hsa-miR-2467-3p" used herein includes the hsa-miR-2467-3p gene (miRBase Accession No. MIMAT0019953) shown in SEQ ID NO: 28, a homolog or an ortholog of a different organism species, and the like. The gene can be obtained by a method described in Persson H et al., 2011, Cancer Res., Vol. 71, pp. 78-86. Also, "hsa-mir-2467" (miRBase Accession No. MI0017432; SEQ ID NO: 270) having a hairpin-like structure is known as a precursor of "hsa-miR-2467-3p."

The term "hsa-miR-2861 gene" or "hsa-miR-2861" used herein includes the hsa-miR-2861 gene (miRBase Accession No. MIMAT0013802) shown in SEQ ID NO: 29, a homolog or an ortholog of a different organism species, and the like. The gene can be obtained by a method described in Li H et al., 2009, J. Clin. Invest., Vol. 119, pp. 3666-3677. Also, "hsa-mir-2861" (miRBase Accession No. MI0013006; SEQ ID NO: 271) having a hairpin-like structure is known as a precursor of "hsa-miR-2861."

The term "hsa-miR-296-3p gene" or "hsa-miR-296-3p" used herein includes the hsa-miR-296-3p gene (miRBase Accession No. MIMAT0004679) shown in SEQ ID NO: 30, a homolog or an ortholog of a different organism species, and the like. The gene can be obtained by a method described in Houbaviy H B et al., 2003, Dev. Cell, Vol. 5, pp. 351-358. Also, "hsa-mir-296" (miRBase Accession No. MI0000747; SEQ ID NO: 272) having a hairpin-like structure is known as a precursor of "hsa-miR-296-3p."

The term "hsa-miR-29b-3p gene" or "hsa-miR-29b-3p" used herein includes the hsa-miR-29b-3p gene (miRBase Accession No. MIMAT0000100) shown in SEQ ID NO: 31, a homolog or an ortholog of a different organism species, and the like. The gene can be obtained by a method described in Mourelatos Z et al., 2002, Genes Dev., Vol. 16, pp. 720-728. Also, "hsa-mir-29b-1" (miRBase Accession No. MI0000105; SEQ ID NO: 473) and "hsa-mir-29b-2" (miRBase Accession No. MI0000107; SEQ ID NO: 485) each having a hairpin-like structure are known as precursors of "hsa-miR-29b-3p."

The term "hsa-miR-3131 gene" or "hsa-miR-3131" used herein includes the hsa-miR-3131 gene (miRBase Accession No. MIMAT0014996) shown in SEQ ID NO: 32, a homolog or an ortholog of a different organism species, and the like. The gene can be obtained by a method described in Stark M S et al., 2010, PLoS One, Vol. 5, e9685. Also, "hsa-mir-3131" (miRBase Accession No. MI0014151; SEQ ID NO: 273) having a hairpin-like structure is known as a precursor of "hsa-miR-3131."

The term "hsa-miR-3154 gene" or "hsa-miR-3154" used herein includes the hsa-miR-3154 gene (miRBase Accession No. MIMAT0015028) shown in SEQ ID NO: 33, a homolog or an ortholog of a different organism species, and the like. The gene can be obtained by a method described in Berezikov E et al., 2006, Genome Res., Vol. 16, pp. 1289-1298. Also, "hsa-mir-3154" (miRBase Accession No. MI0014182; SEQ ID NO: 274) having a hairpin-like structure is known as a precursor of "hsa-miR-3154."

The term "hsa-miR-3158-5p gene" or "hsa-miR-3158-5p" used herein includes the hsa-miR-3158-5p gene (miRBase Accession No. MIMAT0019211) shown in SEQ ID NO: 34, a homolog or an ortholog of a different organism species, and the like. The gene can be obtained by a method described in Creighton C J et al., 2010, PLoS One., Vol. 5, e9637. Also, "hsa-mir-3158-1" (miRBase Accession No. MI0014186; SEQ ID NO: 474) and "hsa-mir-3158-2" (miRBase Accession No. MI0014187; SEQ ID NO: 486) each having a hairpin-like structure are known as precursors of "hsa-miR-3158-5p."

The term "hsa-miR-3160-5p gene" or "hsa-miR-3160-5p" used herein includes the hsa-miR-3160-5p gene (miRBase Accession No. MIMAT0019212) shown in SEQ ID NO: 35, a homolog or an ortholog of a different organism species, and the like. The gene can be obtained by a method described in Stark M S et al., 2010, PLoS One, Vol. 5, e9685. Also, "hsa-mir-3160-1" (miRBase Accession No. MI0014189; SEQ ID NO: 475) and "hsa-mir-3160-2" (miRBase Accession No. MI0014190; SEQ ID NO: 487) each having a hairpin-like structure are known as precursors of "hsa-miR-3160-5p."

The term "hsa-miR-3162-5p gene" or "hsa-miR-3162-5p" used herein includes the hsa-miR-3162-5p gene (miRBase Accession No. MIMAT0015036) shown in SEQ ID NO: 36, a homolog or an ortholog of a different organism species, and the like. The gene can be obtained by a method described in Stark M S et al., 2010, PLoS One, Vol. 5, e9685. Also, "hsa-mir-3162" (miRBase Accession No. MI0014192; SEQ ID NO: 275) having a hairpin-like structure is known as a precursor of "hsa-miR-3162-5p."

The term "hsa-miR-3178 gene" or "hsa-miR-3178" used herein includes the hsa-miR-3178 gene (miRBase Accession No. MIMAT0015055) shown in SEQ ID NO: 37, a homolog or an ortholog of a different organism species, and the like. The gene can be obtained by a method described in Stark M S et al., 2010, PLoS One, Vol. 5, e9685. Also, "hsa-mir- 3178" (miRBase Accession No. MI0014212; SEQ ID NO: 276) having a hairpin-like structure is known as a precursor of "hsa-miR-3178."

The term "hsa-miR-3180-3p gene" or "hsa-miR-3180-3p" used herein includes the hsa-miR-3180-3p gene (miRBase Accession No. MIMAT0015058) shown in SEQ ID NO: 38, a homolog or an ortholog of a different organism species, and the like. The gene can be obtained by a method described in Creighton C J et al., 2010, PLoS One., Vol. 5, e9637. Also, "hsa-mir-3180-1" (miRBase Accession No. MI0014214; SEQ ID NO: 496), "hsa-mir-3180-2" (miRBase Accession No. MI0014215; SEQ ID NO: 497), and "hsa-mir-3180-3" (miRBase Accession No. MI0014217; SEQ ID NO: 498) each having a hairpin-like structure are known as precursors of "hsa-miR-3180-3p."

The term "hsa-miR-3184-5p gene" or "hsa-miR-3184-5p" used herein includes the hsa-miR-3184-5p gene (miRBase Accession No. MIMAT0015064) shown in SEQ ID NO: 39, a homolog or an ortholog of a different organism species, and the like. The gene can be obtained by a method described in Stark M S et al., 2010, PLoS One, Vol. 5, e9685. Also, "hsa-mir-3184" (miRBase Accession No. MI0014226; SEQ ID NO: 277) having a hairpin-like structure is known as a precursor of "hsa-miR-3184-5p."

The term "hsa-miR-3185 gene" or "hsa-miR-3185" used herein includes the hsa-miR-3185 gene (miRBase Accession No. MIMAT0015065) shown in SEQ ID NO: 40, a homolog or an ortholog of a different organism species, and the like. The gene can be obtained by a method described in Stark M S et al., 2010, PLoS One, Vol. 5, e9685. Also, "hsa-mir-3185" (miRBase Accession No. MI0014227; SEQ ID NO: 278) having a hairpin-like structure is known as a precursor of "hsa-miR-3185."

The term "hsa-miR-3194-3p gene" or "hsa-miR-3194-3p" used herein includes the hsa-miR-3194-3p gene (miRBase Accession No. MIMAT0019218) shown in SEQ ID NO: 41, a homolog or an ortholog of a different organism species, and the like. The gene can be obtained by a method described in Stark M S et al., 2010, PLoS One, Vol. 5, e9685. Also, "hsa-mir-3194" (miRBase Accession No. MI0014239; SEQ ID NO: 279) having a hairpin-like structure is known as a precursor of "hsa-miR-3194-3p."

The term "hsa-miR-3195 gene" or "hsa-miR-3195" used herein includes the hsa-miR-3195 gene (miRBase Accession No. MIMAT0015079) shown in SEQ ID NO: 42, a homolog or an ortholog of a different organism species, and the like. The gene can be obtained by a method described in Stark M S et al., 2010, PLoS One, Vol. 5, e9685. Also, "hsa-mir-3195" (miRBase Accession No. MI0014240; SEQ ID NO: 280) having a hairpin-like structure is known as a precursor of "hsa-miR-3195."

The term "hsa-miR-3197 gene" or "hsa-miR-3197" used herein includes the hsa-miR-3197 gene (miRBase Accession No. MIMAT0015082) shown in SEQ ID NO: 43, a homolog or an ortholog of a different organism species, and the like. The gene can be obtained by a method described in Stark M S et al., 2010, PLoS One, Vol. 5, e9685. Also, "hsa-mir-3197" (miRBase Accession No. MI0014245; SEQ ID NO: 281) having a hairpin-like structure is known as a precursor of "hsa-miR-3197."

The term "hsa-miR-320a gene" or "hsa-miR-320a" used herein includes the hsa-miR-320a gene (miRBase Accession No. MIMAT0000510) shown in SEQ ID NO: 44, a homolog or an ortholog of a different organism species, and the like. The gene can be obtained by a method described in Michael M Z et al., 2003, Mol. Cancer Res., Vol. 1, pp. 882-891. Also, "hsa-mir-320a" (miRBase Accession No. MI0000542; SEQ ID NO: 282) having a hairpin-like structure is known as a precursor of "hsa-miR-320a."

The term "hsa-miR-320b gene" or "hsa-miR-320b" used herein includes the hsa-miR-320b gene (miRBase Accession No. MIMAT0005792) shown in SEQ ID NO: 45, a homolog or an ortholog of a different organism species, and the like. The gene can be obtained by a method described in Berezikov E et al., 2006, Genome Res., Vol. 16, pp. 1289-1298. Also, "hsa-mir-320b-1" (miRBase Accession No. MI0003776; SEQ ID NO: 476) and "hsa-mir-320b-2" (miRBase Accession No. MI0003839; SEQ ID NO: 488) each having a hairpin-like structure are known as precursors of "hsa-miR-320b."

The term "hsa-miR-328-5p gene" or "hsa-miR-328-5p" used herein includes the hsa-miR-328-5p gene (miRBase Accession No. MIMAT0026486) shown in SEQ ID NO: 46, a homolog or an ortholog of a different organism species, and the like. The gene can be obtained by a method described in Kim J et al., 2004, Proc. Natl. Acad. Sci., U.S.A., Vol. 101, pp. 360-365. Also, "hsa-mir-328" (miRBase Accession No. MI0000804; SEQ ID NO: 283) having a hairpin-like structure is known as a precursor of "hsa-miR-328-5p."

The term "hsa-miR-342-5p gene" or "hsa-miR-342-5p" used herein includes the hsa-miR-342-5p gene (miRBase Accession No. MIMAT0004694) shown in SEQ ID NO: 47, a homolog or an ortholog of a different organism species, and the like. The gene can be obtained by a method described in Kim J et al., 2004, Proc. Natl. Acad. Sci., U.S.A., Vol. 101, pp. 360-365. Also, "hsa-mir-342" (miRBase Accession No. MI0000805; SEQ ID NO: 284) having a hairpin-like structure is known as a precursor of "hsa-miR-342-5p."

The term "hsa-miR-345-3p gene" or "hsa-miR-345-3p" used herein includes the hsa-miR-345-3p gene (miRBase Accession No. MIMAT0022698) shown in SEQ ID NO: 48, a homolog or an ortholog of a different organism species, and the like. The gene can be obtained by a method described in Kim J et al., 2004, Proc. Natl. Acad. Sci., U.S.A., Vol. 101, pp. 360-365. Also, "hsa-mir-345" (miRBase Accession No. MI0000825; SEQ ID NO: 285) having a hairpin-like structure is known as a precursor of "hsa-miR-345-3p."

The term "hsa-miR-3616-3p gene" or "hsa-miR-3616-3p" used herein includes the hsa-miR-3616-3p gene (miRBase Accession No. MIMAT0017996) shown in SEQ ID NO: 49, a homolog or an ortholog of a different organism species, and the like. The gene can be obtained by a method described in Witten D et al., 2010, BMC Biol., Vol. 8, p. 58. Also, "hsa-mir-3616" (miRBase Accession No. MI0016006; SEQ ID NO: 286) having a hairpin-like structure is known as a precursor of "hsa-miR-3616-3p."

The term "hsa-miR-3619-3p gene" or "hsa-miR-3619-3p" used herein includes the hsa-miR-3619-3p gene (miRBase Accession No. MIMAT0019219) shown in SEQ ID NO: 50, a homolog or an ortholog of a different organism species, and the like. The gene can be obtained by a method described in Witten D et al., 2010, BMC Biol., Vol. 8, p. 58. Also, "hsa-mir-3619" (miRBase Accession No. MI0016009; SEQ ID NO: 287) having a hairpin-like structure is known as a precursor of "hsa-miR-3619-3p."

The term "hsa-miR-3620-5p gene" or "hsa-miR-3620-5p" used herein includes the hsa-miR-3620-5p gene (miRBase Accession No. MIMAT0022967) shown in SEQ ID NO: 51, a homolog or an ortholog of a different organism species, and the like. The gene can be obtained by a method described in Witten D et al., 2010, BMC Biol., Vol. 8, p. 58.

Also, "hsa-mir-3620" (miRBase Accession No. MI0016011; SEQ ID NO: 288) having a hairpin-like structure is known as a precursor of "hsa-miR-3620-5p."

The term "hsa-miR-3621 gene" or "hsa-miR-3621" used herein includes the hsa-miR-3621 gene (miRBase Accession No. MIMAT0018002) shown in SEQ ID NO: 52, a homolog or an ortholog of a different organism species, and the like. The gene can be obtained by a method described in Witten D et al., 2010, BMC Biol., Vol. 8, p. 58. Also, "hsa-mir-3621" (miRBase Accession No. MI0016012; SEQ ID NO: 289) having a hairpin-like structure is known as a precursor of "hsa-miR-3621."

The term "hsa-miR-3622a-5p gene" or "hsa-miR-3622a-5p" used herein includes the hsa-miR-3622a-5p gene (miRBase Accession No. MIMAT0018003) shown in SEQ ID NO: 53, a homolog or an ortholog of a different organism species, and the like. The gene can be obtained by a method described in Witten D et al., 2010, BMC Biol., Vol. 8, p. 58. Also, "hsa-mir-3622a" (miRBase Accession No. MI0016013; SEQ ID NO: 290) having a hairpin-like structure is known as a precursor of "hsa-miR-3622a-5p."

The term "hsa-miR-3648 gene" or "hsa-miR-3648" used herein includes the hsa-miR-3648 gene (miRBase Accession No. MIMAT0018068) shown in SEQ ID NO: 54, a homolog or an ortholog of a different organism species, and the like. The gene can be obtained by a method described in Meiri E et al., 2010, Nucleic Acids Res., Vol. 38, pp. 6234-6246. Also, "hsa-mir-3648-1" (miRBase Accession No. MI0016048; SEQ ID NO: 477) and "hsa-mir-3648-2" (miRBase Accession No. MI0031512; SEQ ID NO: 489) each having a hairpin-like structure are known as precursors of "hsa-miR-3648."

The term "hsa-miR-3652 gene" or "hsa-miR-3652" used herein includes the hsa-miR-3652 gene (miRBase Accession No. MIMAT0018072) shown in SEQ ID NO: 55, a homolog or an ortholog of a different organism species, and the like. The gene can be obtained by a method described in Meiri E et al., 2010, Nucleic Acids Res., Vol. 38, pp. 6234-6246. Also, "hsa-mir-3652" (miRBase Accession No. MI0016052; SEQ ID NO: 291) having a hairpin-like structure is known as a precursor of "hsa-miR-3652."

The term "hsa-miR-3656 gene" or "hsa-miR-3656" used herein includes the hsa-miR-3656 gene (miRBase Accession No. MIMAT0018076) shown in SEQ ID NO: 56, a homolog or an ortholog of a different organism species, and the like. The gene can be obtained by a method described in Meiri E et al., 2010, Nucleic Acids Res., Vol. 38, pp. 6234-6246. Also, "hsa-mir-3656" (miRBase Accession No. MI0016056; SEQ ID NO: 292) having a hairpin-like structure is known as a precursor of "hsa-miR-3656."

The term "hsa-miR-3663-3p gene" or "hsa-miR-3663-3p" used herein includes the hsa-miR-3663-3p gene (miRBase Accession No. MIMAT0018085) shown in SEQ ID NO: 57, a homolog or an ortholog of a different organism species, and the like. The gene can be obtained by a method described in Liao J Y et al., 2010, PLoS One, Vol. 5, e10563. Also, "hsa-mir-3663" (miRBase Accession No. MI0016064; SEQ ID NO: 293) having a hairpin-like structure is known as a precursor of "hsa-miR-3663-3p."

The term "hsa-miR-3679-5p gene" or "hsa-miR-3679-5p" used herein includes the hsa-miR-3679-5p gene (miRBase Accession No. MIMAT0018104) shown in SEQ ID NO: 58, a homolog or an ortholog of a different organism species, and the like. The gene can be obtained by a method described in Creighton C J et al., 2010, PLoS One., Vol. 5, e9637. Also, "hsa-mir-3679" (miRBase Accession No. MI0016080; SEQ ID NO: 294) having a hairpin-like structure is known as a precursor of "hsa-miR-3679-5p."

The term "hsa-miR-371b-5p gene" or "hsa-miR-371b-5p" used herein includes the hsa-miR-371b-5p gene (miRBase Accession No. MIMAT0019892) shown in SEQ ID NO: 59, a homolog or an ortholog of a different organism species, and the like. The gene can be obtained by a method described in Persson H et al., 2011, Cancer Res., Vol. 71, pp. 78-86. Also, "hsa-mir-371b" (miRBase Accession No. MI0017393; SEQ ID NO: 295) having a hairpin-like structure is known as a precursor of "hsa-miR-371b-5p."

The term "hsa-miR-373-5p gene" or "hsa-miR-373-5p" used herein includes the hsa-miR-373-5p gene (miRBase Accession No. MIMAT0000725) shown in SEQ ID NO: 60, a homolog or an ortholog of a different organism species, and the like. The gene can be obtained by a method described in Suh M R et al., 2004, Dev. Biol., Vol. 270, pp. 488-498. Also, "hsa-mir-373" (miRBase Accession No. MI0000781; SEQ ID NO: 296) having a hairpin-like structure is known as a precursor of "hsa-miR-373-5p."

The term "hsa-miR-3917 gene" or "hsa-miR-3917" used herein includes the hsa-miR-3917 gene (miRBase Accession No. MIMAT0018191) shown in SEQ ID NO: 61, a homolog or an ortholog of a different organism species, and the like. The gene can be obtained by a method described in Creighton C J et al., 2010, PLoS One., Vol. 5, e9637. Also, "hsa-mir-3917" (miRBase Accession No. MI0016423; SEQ ID NO: 297) having a hairpin-like structure is known as a precursor of "hsa-miR-3917."

The term "hsa-miR-3940-5p gene" or "hsa-miR-3940-5p" used herein includes the hsa-miR-3940-5p gene (miRBase Accession No. MIMAT0019229) shown in SEQ ID NO: 62, a homolog or an ortholog of a different organism species, and the like. The gene can be obtained by a method described in Liao J Y et al., 2010, PLoS One, Vol. 5, e10563. Also, "hsa-mir-3940" (miRBase Accession No. MI0016597; SEQ ID NO: 298) having a hairpin-like structure is known as a precursor of "hsa-miR-3940-5p."

The term "hsa-miR-3960 gene" or "hsa-miR-3960" used herein includes the hsa-miR-3960 gene (miRBase Accession No. MIMAT0019337) shown in SEQ ID NO: 63, a homolog or an ortholog of a different organism species, and the like. The gene can be obtained by a method described in Hu R et al., 2011, J. Biol. Chem., Vol. 286, pp. 12328-12339. Also, "hsa-mir-3960" (miRBase Accession No. MI0016964; SEQ ID NO: 299) having a hairpin-like structure is known as a precursor of "hsa-miR-3960."

The term "hsa-miR-4258 gene" or "hsa-miR-4258" used herein includes the hsa-miR-4258 gene (miRBase Accession No. MIMAT0016879) shown in SEQ ID NO: 64, a homolog or an ortholog of a different organism species, and the like. The gene can be obtained by a method described in Goff L A et al., 2009, PLoS One, Vol. 4, e7192. Also, "hsa-mir-4258" (miRBase Accession No. MI0015857; SEQ ID NO: 300) having a hairpin-like structure is known as a precursor of "hsa-miR-4258."

The term "hsa-miR-4259 gene" or "hsa-miR-4259" used herein includes the hsa-miR-4259 gene (miRBase Accession No. MIMAT0016880) shown in SEQ ID NO: 65, a homolog or an ortholog of a different organism species, and the like. The gene can be obtained by a method described in Goff L A et al., 2009, PLoS One, Vol. 4, e7192. Also, "hsa-mir-4259" (miRBase Accession No. MI0015858; SEQ ID NO: 301) having a hairpin-like structure is known as a precursor of "hsa-miR-4259."

The term "hsa-miR-4270 gene" or "hsa-miR-4270" used herein includes the hsa-miR-4270 gene (miRBase Accession No. MIMAT0016900) shown in SEQ ID NO: 66, a homolog or an ortholog of a different organism species, and the like. The gene can be obtained by a method described in Goff L A et al., 2009, PLoS One, Vol. 4, e7192. Also, "hsa-mir-4270" (miRBase Accession No. MI0015878; SEQ ID NO: 302) having a hairpin-like structure is known as a precursor of "hsa-miR-4270."

The term "hsa-miR-4286 gene" or "hsa-miR-4286" used herein includes the hsa-miR-4286 gene (miRBase Accession No. MIMAT0016916) shown in SEQ ID NO: 67, a homolog or an ortholog of a different organism species, and the like. The gene can be obtained by a method described in Goff L A et al., 2009, PLoS One, Vol. 4, e7192. Also, "hsa-mir-4286" (miRBase Accession No. MI0015894; SEQ ID NO: 303) having a hairpin-like structure is known as a precursor of "hsa-miR-4286."

The term "hsa-miR-4298 gene" or "hsa-miR-4298" used herein includes the hsa-miR-4298 gene (miRBase Accession No. MIMAT0016852) shown in SEQ ID NO: 68, a homolog or an ortholog of a different organism species, and the like. The gene can be obtained by a method described in Goff L A et al., 2009, PLoS One, Vol. 4, e7192. Also, "hsa-mir-4298" (miRBase Accession No. MI0015830; SEQ ID NO: 304) having a hairpin-like structure is known as a precursor of "hsa-miR-4298."

The term "hsa-miR-4322 gene" or "hsa-miR-4322" used herein includes the hsa-miR-4322 gene (miRBase Accession No. MIMAT0016873) shown in SEQ ID NO: 69, a homolog or an ortholog of a different organism species, and the like. The gene can be obtained by a method described in Goff L A et al., 2009, PLoS One, Vol. 4, e7192. Also, "hsa-mir-4322" (miRBase Accession No. MI0015851; SEQ ID NO: 305) having a hairpin-like structure is known as a precursor of "hsa-miR-4322."

The term "hsa-miR-4327 gene" or "hsa-miR-4327" used herein includes the hsa-miR-4327 gene (miRBase Accession No. MIMAT0016889) shown in SEQ ID NO: 70, a homolog or an ortholog of a different organism species, and the like. The gene can be obtained by a method described in Goff L A et al., 2009, PLoS One, Vol. 4, e7192. Also, "hsa-mir-4327" (miRBase Accession No. MI0015867; SEQ ID NO: 306) having a hairpin-like structure is known as a precursor of "hsa-miR-4327."

The term "hsa-miR-4417 gene" or "hsa-miR-4417" used herein includes the hsa-miR-4417 gene (miRBase Accession No. MIMAT0018929) shown in SEQ ID NO: 71, a homolog or an ortholog of a different organism species, and the like. The gene can be obtained by a method described in Jima D D et al., 2010, Blood, Vol. 116, e118-e127. Also, "hsa-mir-4417" (miRBase Accession No. MI0016753; SEQ ID NO: 307) having a hairpin-like structure is known as a precursor of "hsa-miR-4417."

The term "hsa-miR-4419b gene" or "hsa-miR-4419b" used herein includes the hsa-miR-4419b gene (miRBase Accession No. MIMAT0019034) shown in SEQ ID NO: 72, a homolog or an ortholog of a different organism species, and the like. The gene can be obtained by a method described in Jima D D et al., 2010, Blood, Vol. 116, e118-e127. Also, "hsa-mir-4419b" (miRBase Accession No. MI0016861; SEQ ID NO: 308) having a hairpin-like structure is known as a precursor of "hsa-miR-4419b."

The term "hsa-miR-4429 gene" or "hsa-miR-4429" used herein includes the hsa-miR-4429 gene (miRBase Accession No. MIMAT0018944) shown in SEQ ID NO: 73, a homolog or an ortholog of a different organism species, and the like. The gene can be obtained by a method described in Jima D D et al., 2010, Blood, Vol. 116, e118-e127. Also, "hsa-mir-4429" (miRBase Accession No. MI0016768; SEQ ID NO: 309) having a hairpin-like structure is known as a precursor of "hsa-miR-4429."

The term "hsa-miR-4430 gene" or "hsa-miR-4430" used herein includes the hsa-miR-4430 gene (miRBase Accession No. MIMAT0018945) shown in SEQ ID NO: 74, a homolog or an ortholog of a different organism species, and the like. The gene can be obtained by a method described in Jima D D et al., 2010, Blood, Vol. 116, e118-e127. Also, "hsa-mir-4430" (miRBase Accession No. MI0016769; SEQ ID NO: 310) having a hairpin-like structure is known as a precursor of "hsa-miR-4430."

The term "hsa-miR-4433a-3p gene" or "hsa-miR-4433a-3p" used herein includes the hsa-miR-4433a-3p gene (miRBase Accession No. MIMAT0018949) shown in SEQ ID NO: 75, a homolog or an ortholog of a different organism species, and the like. The gene can be obtained by a method described in Jima D D et al., 2010, Blood, Vol. 116, e118-e127. Also, "hsa-mir-4433a" (miRBase Accession No. MI0016773; SEQ ID NO: 311) having a hairpin-like structure is known as a precursor of "hsa-miR-4433a-3p."

The term "hsa-miR-4436b-5p gene" or "hsa-miR-4436b-5p" used herein includes the hsa-miR-4436b-5p gene (miRBase Accession No. MIMAT0019940) shown in SEQ ID NO: 76, a homolog or an ortholog of a different organism species, and the like. The gene can be obtained by a method described in Persson H et al., 2011, Cancer Res., Vol. 71, pp. 78-86. Also, "hsa-mir-4436b-1" (miRBase Accession No. MI0017425; SEQ ID NO: 478) and "hsa-mir-4436b-2" (miRBase Accession No. MI0019110; SEQ ID NO: 490) each having a hairpin-like structure are known as precursors of "hsa-miR-4436b-5p."

The term "hsa-miR-4443 gene" or "hsa-miR-4443" used herein includes the hsa-miR-4443 gene (miRBase Accession No. MIMAT0018961) shown in SEQ ID NO: 77, a homolog or an ortholog of a different organism species, and the like. The gene can be obtained by a method described in Jima D D et al., 2010, Blood, Vol. 116, e118-e127. Also, "hsa-mir-4443" (miRBase Accession No. MI0016786; SEQ ID NO: 312) having a hairpin-like structure is known as a precursor of "hsa-miR-4443."

The term "hsa-miR-4446-3p gene" or "hsa-miR-4446-3p" used herein includes the hsa-miR-4446-3p gene (miRBase Accession No. MIMAT0018965) shown in SEQ ID NO: 78, a homolog or an ortholog of a different organism species, and the like. The gene can be obtained by a method described in Jima D D et al., 2010, Blood, Vol. 116, e118-e127. Also, "hsa-mir-4446" (miRBase Accession No. MI0016789; SEQ ID NO: 313) having a hairpin-like structure is known as a precursor of "hsa-miR-4446-3p."

The term "hsa-miR-4447 gene" or "hsa-miR-4447" used herein includes the hsa-miR-4447 gene (miRBase Accession No. MIMAT0018966) shown in SEQ ID NO: 79, a homolog or an ortholog of a different organism species, and the like. The gene can be obtained by a method described in Jima D D et al., 2010, Blood, Vol. 116, e118-e127. Also, "hsa-mir-4447" (miRBase Accession No. MI0016790; SEQ ID NO: 314) having a hairpin-like structure is known as a precursor of "hsa-miR-4447."

The term "hsa-miR-4448 gene" or "hsa-miR-4448" used herein includes the hsa-miR-4448 gene (miRBase Accession No. MIMAT0018967) shown in SEQ ID NO: 80, a homolog or an ortholog of a different organism species, and the like. The gene can be obtained by a method described in Jima D D et al., 2010, Blood, Vol. 116, e118-e127. Also, "hsa-mir- 4448" (miRBase Accession No. MI0016791; SEQ ID NO: 315) having a hairpin-like structure is known as a precursor of "hsa-miR-4448."

The term "hsa-miR-4449 gene" or "hsa-miR-4449" used herein includes the hsa-miR-4449 gene (miRBase Accession No. MIMAT0018968) shown in SEQ ID NO: 81, a homolog or an ortholog of a different organism species, and the like. The gene can be obtained by a method described in Jima D D et al., 2010, Blood, Vol. 116, e118-e127. Also, "hsa-mir-4449" (miRBase Accession No. MI0016792; SEQ ID NO: 316) having a hairpin-like structure is known as a precursor of "hsa-miR-4449."

The term "hsa-miR-4454 gene" or "hsa-miR-4454" used herein includes the hsa-miR-4454 gene (miRBase Accession No. MIMAT0018976) shown in SEQ ID NO: 82, a homolog or an ortholog of a different organism species, and the like. The gene can be obtained by a method described in Jima D D et al., 2010, Blood, Vol. 116, e118-e127. Also, "hsa-mir-4454" (miRBase Accession No. MI0016800; SEQ ID NO: 317) having a hairpin-like structure is known as a precursor of "hsa-miR-4454."

The term "hsa-miR-4455 gene" or "hsa-miR-4455" used herein includes the hsa-miR-4455 gene (miRBase Accession No. MIMAT0018977) shown in SEQ ID NO: 83, a homolog or an ortholog of a different organism species, and the like. The gene can be obtained by a method described in Jima D D et al., 2010, Blood, Vol. 116, e118-e127. Also, "hsa-mir-4455" (miRBase Accession No. MI0016801; SEQ ID NO: 318) having a hairpin-like structure is known as a precursor of "hsa-miR-4455."

The term "hsa-miR-4459 gene" or "hsa-miR-4459" used herein includes the hsa-miR-4459 gene (miRBase Accession No. MIMAT0018981) shown in SEQ ID NO: 84, a homolog or an ortholog of a different organism species, and the like. The gene can be obtained by a method described in Jima D D et al., 2010, Blood, Vol. 116, e118-e127. Also, "hsa-mir-4459" (miRBase Accession No. MI0016805; SEQ ID NO: 319) having a hairpin-like structure is known as a precursor of "hsa-miR-4459."

The term "hsa-miR-4462 gene" or "hsa-miR-4462" used herein includes the hsa-miR-4462 gene (miRBase Accession No. MIMAT0018986) shown in SEQ ID NO: 85, a homolog or an ortholog of a different organism species, and the like. The gene can be obtained by a method described in Jima D D et al., 2010, Blood, Vol. 116, e118-e127. Also, "hsa-mir-4462" (miRBase Accession No. MI0016810; SEQ ID NO: 320) having a hairpin-like structure is known as a precursor of "hsa-miR-4462."

The term "hsa-miR-4466 gene" or "hsa-miR-4466" used herein includes the hsa-miR-4466 gene (miRBase Accession No. MIMAT0018993) shown in SEQ ID NO: 86, a homolog or an ortholog of a different organism species, and the like. The gene can be obtained by a method described in Jima D D et al., 2010, Blood, Vol. 116, e118-e127. Also, "hsa-mir-4466" (miRBase Accession No. MI0016817; SEQ ID NO: 321) having a hairpin-like structure is known as a precursor of "hsa-miR-4466."

The term "hsa-miR-4467 gene" or "hsa-miR-4467" used herein includes the hsa-miR-4467 gene (miRBase Accession No. MIMAT0018994) shown in SEQ ID NO: 87, a homolog or an ortholog of a different organism species, and the like. The gene can be obtained by a method described in Jima D D et al., 2010, Blood, Vol. 116, e118-e127. Also, "hsa-mir-4467" (miRBase Accession No. MI0016818; SEQ ID NO: 322) having a hairpin-like structure is known as a precursor of "hsa-miR-4467."

The term "hsa-miR-4480 gene" or "hsa-miR-4480" used herein includes the hsa-miR-4480 gene (miRBase Accession No. MIMAT0019014) shown in SEQ ID NO: 88, a homolog or an ortholog of a different organism species, and the like. The gene can be obtained by a method described in Jima D D et al., 2010, Blood, Vol. 116, e118-e127. Also, "hsa-mir-4480" (miRBase Accession No. MI0016841; SEQ ID NO: 323) having a hairpin-like structure is known as a precursor of "hsa-miR-4480."

The term "hsa-miR-4483 gene" or "hsa-miR-4483" used herein includes the hsa-miR-4483 gene (miRBase Accession No. MIMAT0019017) shown in SEQ ID NO: 89, a homolog or an ortholog of a different organism species, and the like. The gene can be obtained by a method described in Jima D D et al., 2010, Blood, Vol. 116, e118-e127. Also, "hsa-mir-4483" (miRBase Accession No. MI0016844; SEQ ID NO: 324) having a hairpin-like structure is known as a precursor of "hsa-miR-4483."

The term "hsa-miR-4484 gene" or "hsa-miR-4484" used herein includes the hsa-miR-4484 gene (miRBase Accession No. MIMAT0019018) shown in SEQ ID NO: 90, a homolog or an ortholog of a different organism species, and the like. The gene can be obtained by a method described in Jima D D et al., 2010, Blood, Vol. 116, e118-e127. Also, "hsa-mir-4484" (miRBase Accession No. MI0016845; SEQ ID NO: 325) having a hairpin-like structure is known as a precursor of "hsa-miR-4484."

The term "hsa-miR-4485-5p gene" or "hsa-miR-4485-5p" used herein includes the hsa-miR-4485-5p gene (miRBase Accession No. MIMAT0032116) shown in SEQ ID NO: 91, a homolog or an ortholog of a different organism species, and the like. The gene can be obtained by a method described in Jima D D et al., 2010, Blood, Vol. 116, e118-e127. Also, "hsa-mir-4485" (miRBase Accession No. MI0016846; SEQ ID NO: 326) having a hairpin-like structure is known as a precursor of "hsa-miR-4485-5p."

The term "hsa-miR-4488 gene" or "hsa-miR-4488" used herein includes the hsa-miR-4488 gene (miRBase Accession No. MIMAT0019022) shown in SEQ ID NO: 92, a homolog or an ortholog of a different organism species, and the like. The gene can be obtained by a method described in Jima D D et al., 2010, Blood, Vol. 116, e118-e127. Also, "hsa-mir-4488" (miRBase Accession No. MI0016849; SEQ ID NO: 327) having a hairpin-like structure is known as a precursor of "hsa-miR-4488."

The term "hsa-miR-4492 gene" or "hsa-miR-4492" used herein includes the hsa-miR-4492 gene (miRBase Accession No. MIMAT0019027) shown in SEQ ID NO: 93, a homolog or an ortholog of a different organism species, and the like. The gene can be obtained by a method described in Jima D D et al., 2010, Blood, Vol. 116, e118-e127. Also, "hsa-mir-4492" (miRBase Accession No. MI0016854; SEQ ID NO: 328) having a hairpin-like structure is known as a precursor of "hsa-miR-4492."

The term "hsa-miR-4505 gene" or "hsa-miR-4505" used herein includes the hsa-miR-4505 gene (miRBase Accession No. MIMAT0019041) shown in SEQ ID NO: 94, a homolog or an ortholog of a different organism species, and the like. The gene can be obtained by a method described in Jima D D et al., 2010, Blood, Vol. 116, e118-e127. Also, "hsa-mir-4505" (miRBase Accession No. MI0016868; SEQ ID NO: 329) having a hairpin-like structure is known as a precursor of "hsa-miR-4505."

The term "hsa-miR-4515 gene" or "hsa-miR-4515" used herein includes the hsa-miR-4515 gene (miRBase Accession No. MIMAT0019052) shown in SEQ ID NO: 95, a homolog or an ortholog of a different organism species, and the like.

The gene can be obtained by a method described in Jima D D et al., 2010, Blood, Vol. 116, e118-e127. Also, "hsa-mir-4515" (miRBase Accession No. MI0016881; SEQ ID NO: 330) having a hairpin-like structure is known as a precursor of "hsa-miR-4515."

The term "hsa-miR-4525 gene" or "hsa-miR-4525" used herein includes the hsa-miR-4525 gene (miRBase Accession No. MIMAT0019064) shown in SEQ ID NO: 96, a homolog or an ortholog of a different organism species, and the like. The gene can be obtained by a method described in Jima D D et al., 2010, Blood, Vol. 116, e118-e127. Also, "hsa-mir-4525" (miRBase Accession No. MI0016892; SEQ ID NO: 331) having a hairpin-like structure is known as a precursor of "hsa-miR-4525."

The term "hsa-miR-4534 gene" or "hsa-miR-4534" used herein includes the hsa-miR-4534 gene (miRBase Accession No. MIMAT0019073) shown in SEQ ID NO: 97, a homolog or an ortholog of a different organism species, and the like. The gene can be obtained by a method described in Jima D D et al., 2010, Blood, Vol. 116, e118-e127. Also, "hsa-mir-4534" (miRBase Accession No. MI0016901; SEQ ID NO: 332) having a hairpin-like structure is known as a precursor of "hsa-miR-4534."

The term "hsa-miR-4535 gene" or "hsa-miR-4535" used herein includes the hsa-miR-4535 gene (miRBase Accession No. MIMAT0019075) shown in SEQ ID NO: 98, a homolog or an ortholog of a different organism species, and the like. The gene can be obtained by a method described in Jima D D et al., 2010, Blood, Vol. 116, e118-e127. Also, "hsa-mir-4535" (miRBase Accession No. MI0016903; SEQ ID NO: 333) having a hairpin-like structure is known as a precursor of "hsa-miR-4535."

The term "hsa-miR-4633-3p gene" or "hsa-miR-4633-3p" used herein includes the hsa-miR-4633-3p gene (miRBase Accession No. MIMAT0019690) shown in SEQ ID NO: 99, a homolog or an ortholog of a different organism species, and the like. The gene can be obtained by a method described in Persson H et al., 2011, Cancer Res., Vol. 71, pp. 78-86. Also, "hsa-mir-4633" (miRBase Accession No. MI0017260; SEQ ID NO: 334) having a hairpin-like structure is known as a precursor of "hsa-miR-4633-3p."

The term "hsa-miR-4634 gene" or "hsa-miR-4634" used herein includes the hsa-miR-4634 gene (miRBase Accession No. MIMAT0019691) shown in SEQ ID NO: 100, a homolog or an ortholog of a different organism species, and the like. The gene can be obtained by a method described in Persson H et al., 2011, Cancer Res., Vol. 71, pp. 78-86. Also, "hsa-mir-4634" (miRBase Accession No. MI0017261; SEQ ID NO: 335) having a hairpin-like structure is known as a precursor of "hsa-miR-4634."

The term "hsa-miR-4640-5p gene" or "hsa-miR-4640-5p" used herein includes the hsa-miR-4640-5p gene (miRBase Accession No. MIMAT0019699) shown in SEQ ID NO: 101, a homolog or an ortholog of a different organism species, and the like. The gene can be obtained by a method described in Persson H et al., 2011, Cancer Res., Vol. 71, pp. 78-86. Also, "hsa-mir-4640" (miRBase Accession No. MI0017267; SEQ ID NO: 336) having a hairpin-like structure is known as a precursor of "hsa-miR-4640-5p."

The term "hsa-miR-4649-5p gene" or "hsa-miR-4649-5p" used herein includes the hsa-miR-4649-5p gene (miRBase Accession No. MIMAT0019711) shown in SEQ ID NO: 102, a homolog or an ortholog of a different organism species, and the like. The gene can be obtained by a method described in Persson H et al., 2011, Cancer Res., Vol. 71, pp. 78-86. Also, "hsa-mir-4649" (miRBase Accession No. MI0017276; SEQ ID NO: 337) having a hairpin-like structure is known as a precursor of "hsa-miR-4649-5p."

The term "hsa-miR-4651 gene" or "hsa-miR-4651" used herein includes the hsa-miR-4651 gene (miRBase Accession No. MIMAT0019715) shown in SEQ ID NO: 103, a homolog or an ortholog of a different organism species, and the like. The gene can be obtained by a method described in Persson H et al., 2011, Cancer Res., Vol. 71, pp. 78-86. Also, "hsa-mir-4651" (miRBase Accession No. MI0017279; SEQ ID NO: 338) having a hairpin-like structure is known as a precursor of "hsa-miR-4651."

The term "hsa-miR-4652-5p gene" or "hsa-miR-4652-5p" used herein includes the hsa-miR-4652-5p gene (miRBase Accession No. MIMAT0019716) shown in SEQ ID NO: 104, a homolog or an ortholog of a different organism species, and the like. The gene can be obtained by a method described in Persson H et al., 2011, Cancer Res., Vol. 71, pp. 78-86. Also, "hsa-mir-4652" (miRBase Accession No. MI0017280; SEQ ID NO: 339) having a hairpin-like structure is known as a precursor of "hsa-miR-4652-5p."

The term "hsa-miR-4655-5p gene" or "hsa-miR-4655-5p" used herein includes the hsa-miR-4655-5p gene (miRBase Accession No. MIMAT0019721) shown in SEQ ID NO: 105, a homolog or an ortholog of a different organism species, and the like. The gene can be obtained by a method described in Persson H et al., 2011, Cancer Res., Vol. 71, pp. 78-86. Also, "hsa-mir-4655" (miRBase Accession No. MI0017283; SEQ ID NO: 340) having a hairpin-like structure is known as a precursor of "hsa-miR-4655-5p."

The term "hsa-miR-4656 gene" or "hsa-miR-4656" used herein includes the hsa-miR-4656 gene (miRBase Accession No. MIMAT0019723) shown in SEQ ID NO: 106, a homolog or an ortholog of a different organism species, and the like. The gene can be obtained by a method described in Persson H et al., 2011, Cancer Res., Vol. 71, pp. 78-86. Also, "hsa-mir-4656" (miRBase Accession No. MI0017284; SEQ ID NO: 341) having a hairpin-like structure is known as a precursor of "hsa-miR-4656."

The term "hsa-miR-4658 gene" or "hsa-miR-4658" used herein includes the hsa-miR-4658 gene (miRBase Accession No. MIMAT0019725) shown in SEQ ID NO: 107, a homolog or an ortholog of a different organism species, and the like. The gene can be obtained by a method described in Persson H et al., 2011, Cancer Res., Vol. 71, pp. 78-86. Also, "hsa-mir-4658" (miRBase Accession No. MI0017286; SEQ ID NO: 342) having a hairpin-like structure is known as a precursor of "hsa-miR-4658."

The term "hsa-miR-4663 gene" or "hsa-miR-4663" used herein includes the hsa-miR-4663 gene (miRBase Accession No. MIMAT0019735) shown in SEQ ID NO: 108, a homolog or an ortholog of a different organism species, and the like. The gene can be obtained by a method described in Persson H et al., 2011, Cancer Res., Vol. 71, pp. 78-86. Also, "hsa-mir-4663" (miRBase Accession No. MI0017292; SEQ ID NO: 343) having a hairpin-like structure is known as a precursor of "hsa-miR-4663."

The term "hsa-miR-4673 gene" or "hsa-miR-4673" used herein includes the hsa-miR-4673 gene (miRBase Accession No. MIMAT0019755) shown in SEQ ID NO: 109, a homolog or an ortholog of a different organism species, and the like. The gene can be obtained by a method described in Persson H et al., 2011, Cancer Res., Vol. 71, pp. 78-86. Also, "hsa-mir-4673" (miRBase Accession No. MI0017304; SEQ ID NO: 344) having a hairpin-like structure is known as a precursor of "hsa-miR-4673."

The term "hsa-miR-4675 gene" or "hsa-miR-4675" used herein includes the hsa-miR-4675 gene (miRBase Accession No. MIMAT0019757) shown in SEQ ID NO: 110, a homolog or an ortholog of a different organism species, and the like. The gene can be obtained by a method described in Persson H et al., 2011, Cancer Res., Vol. 71, pp. 78-86. Also, "hsa-mir-4675" (miRBase Accession No. MI0017306; SEQ ID NO: 345) having a hairpin-like structure is known as a precursor of "hsa-miR-4675."

The term "hsa-miR-4687-3p gene" or "hsa-miR-4687-3p" used herein includes the hsa-miR-4687-3p gene (miRBase Accession No. MIMAT0019775) shown in SEQ ID NO: 111, a homolog or an ortholog of a different organism species, and the like. The gene can be obtained by a method described in Persson H et al., 2011, Cancer Res., Vol. 71, pp. 78-86. Also, "hsa-mir-4687" (miRBase Accession No. MI0017319; SEQ ID NO: 346) having a hairpin-like structure is known as a precursor of "hsa-miR-4687-3p."

The term "hsa-miR-4687-5p gene" or "hsa-miR-4687-5p" used herein includes the hsa-miR-4687-5p gene (miRBase Accession No. MIMAT0019774) shown in SEQ ID NO: 112, a homolog or an ortholog of a different organism species, and the like. The gene can be obtained by a method described in Persson H et al., 2011, Cancer Res., Vol. 71, pp. 78-86. Also, "hsa-mir-4687" (miRBase Accession No. MI0017319; SEQ ID NO: 347) having a hairpin-like structure is known as a precursor of "hsa-miR-4687-5p."

The term "hsa-miR-4690-5p gene" or "hsa-miR-4690-5p" used herein includes the hsa-miR-4690-5p gene (miRBase Accession No. MIMAT0019779) shown in SEQ ID NO: 113, a homolog or an ortholog of a different organism species, and the like. The gene can be obtained by a method described in Persson H et al., 2011, Cancer Res., Vol. 71, pp. 78-86. Also, "hsa-mir-4690" (miRBase Accession No. MI0017323; SEQ ID NO: 348) having a hairpin-like structure is known as a precursor of "hsa-miR-4690-5p."

The term "hsa-miR-4695-5p gene" or "hsa-miR-4695-5p" used herein includes the hsa-miR-4695-5p gene (miRBase Accession No. MIMAT0019788) shown in SEQ ID NO: 114, a homolog or an ortholog of a different organism species, and the like. The gene can be obtained by a method described in Persson H et al., 2011, Cancer Res., Vol. 71, pp. 78-86. Also, "hsa-mir-4695" (miRBase Accession No. MI0017328; SEQ ID NO: 349) having a hairpin-like structure is known as a precursor of "hsa-miR-4695-5p."

The term "hsa-miR-4697-5p gene" or "hsa-miR-4697-5p" used herein includes the hsa-miR-4697-5p gene (miRBase Accession No. MIMAT0019791) shown in SEQ ID NO: 115, a homolog or an ortholog of a different organism species, and the like. The gene can be obtained by a method described in Persson H et al., 2011, Cancer Res., Vol. 71, pp. 78-86. Also, "hsa-mir-4697" (miRBase Accession No. MI0017330; SEQ ID NO: 350) having a hairpin-like structure is known as a precursor of "hsa-miR-4697-5p."

The term "hsa-miR-4706 gene" or "hsa-miR-4706" used herein includes the hsa-miR-4706 gene (miRBase Accession No. MIMAT0019806) shown in SEQ ID NO: 116, a homolog or an ortholog of a different organism species, and the like. The gene can be obtained by a method described in Persson H et al., 2011, Cancer Res., Vol. 71, pp. 78-86. Also, "hsa-mir-4706" (miRBase Accession No. MI0017339; SEQ ID NO: 351) having a hairpin-like structure is known as a precursor of "hsa-miR-4706."

The term "hsa-miR-4707-3p gene" or "hsa-miR-4707-3p" used herein includes the hsa-miR-4707-3p gene (miRBase Accession No. MIMAT0019808) shown in SEQ ID NO: 117, a homolog or an ortholog of a different organism species, and the like. The gene can be obtained by a method described in Persson H et al., 2011, Cancer Res., Vol. 71, pp. 78-86. Also, "hsa-mir-4707" (miRBase Accession No. MI0017340; SEQ ID NO: 352) having a hairpin-like structure is known as a precursor of "hsa-miR-4707-3p."

The term "hsa-miR-4707-5p gene" or "hsa-miR-4707-5p" used herein includes the hsa-miR-4707-5p gene (miRBase Accession No. MIMAT0019807) shown in SEQ ID NO: 118, a homolog or an ortholog of a different organism species, and the like. The gene can be obtained by a method described in Persson H et al., 2011, Cancer Res., Vol. 71, pp. 78-86. Also, "hsa-mir-4707" (miRBase Accession No. MI0017340; SEQ ID NO: 353) having a hairpin-like structure is known as a precursor of "hsa-miR-4707-5p."

The term "hsa-miR-4708-3p gene" or "hsa-miR-4708-3p" used herein includes the hsa-miR-4708-3p gene (miRBase Accession No. MIMAT0019810) shown in SEQ ID NO: 119, a homolog or an ortholog of a different organism species, and the like. The gene can be obtained by a method described in Persson H et al., 2011, Cancer Res., Vol. 71, pp. 78-86. Also, "hsa-mir-4708" (miRBase Accession No. MI0017341; SEQ ID NO: 354) having a hairpin-like structure is known as a precursor of "hsa-miR-4708-3p."

The term "hsa-miR-4710 gene" or "hsa-miR-4710" used herein includes the hsa-miR-4710 gene (miRBase Accession No. MIMAT0019815) shown in SEQ ID NO: 120, a homolog or an ortholog of a different organism species, and the like. The gene can be obtained by a method described in Persson H et al., 2011, Cancer Res., Vol. 71, pp. 78-86. Also, "hsa-mir-4710" (miRBase Accession No. MI0017344; SEQ ID NO: 355) having a hairpin-like structure is known as a precursor of "hsa-miR-4710."

The term "hsa-miR-4718 gene" or "hsa-miR-4718" used herein includes the hsa-miR-4718 gene (miRBase Accession No. MIMAT0019831) shown in SEQ ID NO: 121, a homolog or an ortholog of a different organism species, and the like. The gene can be obtained by a method described in Persson H et al., 2011, Cancer Res., Vol. 71, pp. 78-86. Also, "hsa-mir-4718" (miRBase Accession No. MI0017353; SEQ ID NO: 356) having a hairpin-like structure is known as a precursor of "hsa-miR-4718."

The term "hsa-miR-4722-5p gene" or "hsa-miR-4722-5p" used herein includes the hsa-miR-4722-5p gene (miRBase Accession No. MIMAT0019836) shown in SEQ ID NO: 122, a homolog or an ortholog of a different organism species, and the like. The gene can be obtained by a method described in Persson H et al., 2011, Cancer Res., Vol. 71, pp. 78-86. Also, "hsa-mir-4722" (miRBase Accession No. MI0017357; SEQ ID NO: 357) having a hairpin-like structure is known as a precursor of "hsa-miR-4722-5p."

The term "hsa-miR-4725-3p gene" or "hsa-miR-4725-3p" used herein includes the hsa-miR-4725-3p gene (miRBase Accession No. MIMAT0019844) shown in SEQ ID NO: 123, a homolog or an ortholog of a different organism species, and the like. The gene can be obtained by a method described in Persson H et al., 2011, Cancer Res., Vol. 71, pp. 78-86. Also, "hsa-mir-4725" (miRBase Accession No. MI0017362; SEQ ID NO: 358) having a hairpin-like structure is known as a precursor of "hsa-miR-4725-3p."

The term "hsa-miR-4726-5p gene" or "hsa-miR-4726-5p" used herein includes the hsa-miR-4726-5p gene (miRBase Accession No. MIMAT0019845) shown in SEQ ID NO: 124, a homolog or an ortholog of a different organism species, and the like. The gene can be obtained by a method described in Persson H et al., 2011, Cancer Res., Vol. 71, pp. 78-86. Also, "hsa-mir-4726" (miRBase Accession No. MI0017363; SEQ ID NO: 359) having a hairpin-like structure is known as a precursor of "hsa-miR-4726-5p."

The term "hsa-miR-4727-3p gene" or "hsa-miR-4727-3p" used herein includes the hsa-miR-4727-3p gene (miRBase Accession No. MIMAT0019848) shown in SEQ ID NO: 125, a homolog or an ortholog of a different organism species, and the like. The gene can be obtained by a method described in Persson H et al., 2011, Cancer Res., Vol. 71, pp. 78-86. Also, "hsa-mir-4727" (miRBase Accession No. MI0017364; SEQ ID NO: 360) having a hairpin-like structure is known as a precursor of "hsa-miR-4727-3p."

The term "hsa-miR-4728-5p gene" or "hsa-miR-4728-5p" used herein includes the hsa-miR-4728-5p gene (miRBase Accession No. MIMAT0019849) shown in SEQ ID NO: 126, a homolog or an ortholog of a different organism species, and the like. The gene can be obtained by a method described in Persson H et al., 2011, Cancer Res., Vol. 71, pp. 78-86. Also, "hsa-mir-4728" (miRBase Accession No. MI0017365; SEQ ID NO: 361) having a hairpin-like structure is known as a precursor of "hsa-miR-4728-5p."

The term "hsa-miR-4731-5p gene" or "hsa-miR-4731-5p" used herein includes the hsa-miR-4731-5p gene (miRBase Accession No. MIMAT0019853) shown in SEQ ID NO: 127, a homolog or an ortholog of a different organism species, and the like. The gene can be obtained by a method described in Persson H et al., 2011, Cancer Res., Vol. 71, pp. 78-86. Also, "hsa-mir-4731" (miRBase Accession No. MI0017368; SEQ ID NO: 362) having a hairpin-like structure is known as a precursor of "hsa-miR-4731-5p."

The term "hsa-miR-4736 gene" or "hsa-miR-4736" used herein includes the hsa-miR-4736 gene (miRBase Accession No. MIMAT0019862) shown in SEQ ID NO: 128, a homolog or an ortholog of a different organism species, and the like. The gene can be obtained by a method described in Persson H et al., 2011, Cancer Res., Vol. 71, pp. 78-86. Also, "hsa-mir-4736" (miRBase Accession No. MI0017373; SEQ ID NO: 363) having a hairpin-like structure is known as a precursor of "hsa-miR-4736."

The term "hsa-miR-4739 gene" or "hsa-miR-4739" used herein includes the hsa-miR-4739 gene (miRBase Accession No. MIMAT0019868) shown in SEQ ID NO: 129, a homolog or an ortholog of a different organism species, and the like. The gene can be obtained by a method described in Persson H et al., 2011, Cancer Res., Vol. 71, pp. 78-86. Also, "hsa-mir-4739" (miRBase Accession No. MI0017377; SEQ ID NO: 364) having a hairpin-like structure is known as a precursor of "hsa-miR-4739."

The term "hsa-miR-4740-5p gene" or "hsa-miR-4740-5p" used herein includes the hsa-miR-4740-5p gene (miRBase Accession No. MIMAT0019869) shown in SEQ ID NO: 130, a homolog or an ortholog of a different organism species, and the like. The gene can be obtained by a method described in Persson H et al., 2011, Cancer Res., Vol. 71, pp. 78-86. Also, "hsa-mir-4740" (miRBase Accession No. MI0017378; SEQ ID NO: 365) having a hairpin-like structure is known as a precursor of "hsa-miR-4740-5p."

The term "hsa-miR-4741 gene" or "hsa-miR-4741" used herein includes the hsa-miR-4741 gene (miRBase Accession No. MIMAT0019871) shown in SEQ ID NO: 131, a homolog or an ortholog of a different organism species, and the like. The gene can be obtained by a method described in Persson H et al., 2011, Cancer Res., Vol. 71, pp. 78-86. Also, "hsa-mir-4741" (miRBase Accession No. MI0017379; SEQ ID NO: 366) having a hairpin-like structure is known as a precursor of "hsa-miR-4741."

The term "hsa-miR-4750-5p gene" or "hsa-miR-4750-5p" used herein includes the hsa-miR-4750-5p gene (miRBase Accession No. MIMAT0019887) shown in SEQ ID NO: 132, a homolog or an ortholog of a different organism species, and the like. The gene can be obtained by a method described in Persson H et al., 2011, Cancer Res., Vol. 71, pp. 78-86. Also, "hsa-mir-4750" (miRBase Accession No. MI0017389; SEQ ID NO: 367) having a hairpin-like structure is known as a precursor of "hsa-miR-4750-5p."

The term "hsa-miR-4755-3p gene" or "hsa-miR-4755-3p" used herein includes the hsa-miR-4755-3p gene (miRBase Accession No. MIMAT0019896) shown in SEQ ID NO: 133, a homolog or an ortholog of a different organism species, and the like. The gene can be obtained by a method described in Persson H et al., 2011, Cancer Res., Vol. 71, pp. 78-86. Also, "hsa-mir-4755" (miRBase Accession No. MI0017395; SEQ ID NO: 368) having a hairpin-like structure is known as a precursor of "hsa-miR-4755-3p."

The term "hsa-miR-4763-3p gene" or "hsa-miR-4763-3p" used herein includes the hsa-miR-4763-3p gene (miRBase Accession No. MIMAT0019913) shown in SEQ ID NO: 134, a homolog or an ortholog of a different organism species, and the like. The gene can be obtained by a method described in Persson H et al., 2011, Cancer Res., Vol. 71, pp. 78-86. Also, "hsa-mir-4763" (miRBase Accession No. MI0017404; SEQ ID NO: 369) having a hairpin-like structure is known as a precursor of "hsa-miR-4763-3p."

The term "hsa-miR-4771 gene" or "hsa-miR-4771" used herein includes the hsa-miR-4771 gene (miRBase Accession No. MIMAT0019925) shown in SEQ ID NO: 135, a homolog or an ortholog of a different organism species, and the like. The gene can be obtained by a method described in Persson H et al., 2011, Cancer Res., Vol. 71, pp. 78-86. Also, "hsa-mir-4771-1" (miRBase Accession No. MI0017412; SEQ ID NO: 479) and "hsa-mir-4771-2" (miRBase Accession No. MI0017413; SEQ ID NO: 491) each having a hairpin-like structure are known as precursors of "hsa-miR-4771."

The term "hsa-miR-4783-3p gene" or "hsa-miR-4783-3p" used herein includes the hsa-miR-4783-3p gene (miRBase Accession No. MIMAT0019947) shown in SEQ ID NO: 136, a homolog or an ortholog of a different organism species, and the like. The gene can be obtained by a method described in Persson H et al., 2011, Cancer Res., Vol. 71, pp. 78-86. Also, "hsa-mir-4783" (miRBase Accession No. MI0017428; SEQ ID NO: 370) having a hairpin-like structure is known as a precursor of "hsa-miR-4783-3p."

The term "hsa-miR-4783-5p gene" or "hsa-miR-4783-5p" used herein includes the hsa-miR-4783-5p gene (miRBase Accession No. MIMAT0019946) shown in SEQ ID NO: 137, a homolog or an ortholog of a different organism species, and the like. The gene can be obtained by a method described in Persson H et al., 2011, Cancer Res., Vol. 71, pp. 78-86. Also, "hsa-mir-4783" (miRBase Accession No. MI0017428; SEQ ID NO: 371) having a hairpin-like structure is known as a precursor of "hsa-miR-4783-5p."

The term "hsa-miR-4787-3p gene" or "hsa-miR-4787-3p" used herein includes the hsa-miR-4787-3p gene (miRBase Accession No. MIMAT0019957) shown in SEQ ID NO: 138, a homolog or an ortholog of a different organism species, and the like. The gene can be obtained by a method described in Persson H et al., 2011, Cancer Res., Vol. 71, pp. 78-86. Also, "hsa-mir-4787" (miRBase Accession No. MI0017434; SEQ ID NO: 372) having a hairpin-like structure is known as a precursor of "hsa-miR-4787-3p."

The term "hsa-miR-4792 gene" or "hsa-miR-4792" used herein includes the hsa-miR-4792 gene (miRBase Accession No. MIMAT0019964) shown in SEQ ID NO: 139, a homolog or an ortholog of a different organism species, and the like. The gene can be obtained by a method described in Persson H et al., 2011, Cancer Res., Vol. 71, pp. 78-86. Also, "hsa-mir-4792" (miRBase Accession No. MI0017439; SEQ ID NO: 373) having a hairpin-like structure is known as a precursor of "hsa-miR-4792."

The term "hsa-miR-498 gene" or "hsa-miR-498" used herein includes the hsa-miR-498 gene (miRBase Accession No. MIMAT0002824) shown in SEQ ID NO: 140, a homolog or an ortholog of a different organism species, and the like. The gene can be obtained by a method described in Bentwich I et al., 2005, Nat. Genet., Vol. 37, pp. 766-770. Also, "hsa-mir-498" (miRBase Accession No. MI0003142; SEQ ID NO: 374) having a hairpin-like structure is known as a precursor of "hsa-miR-498."

The term "hsa-miR-5008-5p gene" or "hsa-miR-5008-5p" used herein includes the hsa-miR-5008-5p gene (miRBase Accession No. MIMAT0021039) shown in SEQ ID NO: 141, a homolog or an ortholog of a different organism species, and the like. The gene can be obtained by a method described in Hansen T B et al., 2011, RNA Biol., Vol. 8, pp. 378-383. Also, "hsa-mir-5008" (miRBase Accession No. MI0017876; SEQ ID NO: 375) having a hairpin-like structure is known as a precursor of "hsa-miR-5008-5p."

The term "hsa-miR-5010-5p gene" or "hsa-miR-5010-5p" used herein includes the hsa-miR-5010-5p gene (miRBase Accession No. MIMAT0021043) shown in SEQ ID NO: 142, a homolog or an ortholog of a different organism species, and the like. The gene can be obtained by a method described in Hansen T B et al., 2011, RNA Biol., Vol. 8, pp. 378-383. Also, "hsa-mir-5010" (miRBase Accession No. MI0017878; SEQ ID NO: 376) having a hairpin-like structure is known as a precursor of "hsa-miR-5010-5p."

The term "hsa-miR-504-3p gene" or "hsa-miR-504-3p" used herein includes the hsa-miR-504-3p gene (miRBase Accession No. MIMAT0026612) shown in SEQ ID NO: 143, a homolog or an ortholog of a different organism species, and the like. The gene can be obtained by a method described in Bentwich I et al., 2005, Nat. Genet., Vol. 37, pp. 766-770. Also, "hsa-mir-504" (miRBase Accession No. MI0003189; SEQ ID NO: 377) having a hairpin-like structure is known as a precursor of "hsa-miR-504-3p."

The term "hsa-miR-5195-3p gene" or "hsa-miR-5195-3p" used herein includes the hsa-miR-5195-3p gene (miRBase Accession No. MIMAT0021127) shown in SEQ ID NO: 144, a homolog or an ortholog of a different organism species, and the like. The gene can be obtained by a method described in Schotte D et al., 2011, Leukemia, Vol. 25, pp. 1389-1399. Also, "hsa-mir-5195" (miRBase Accession No. MI0018174; SEQ ID NO: 378) having a hairpin-like structure is known as a precursor of "hsa-miR-5195-3p."

The term "hsa-miR-550a-5p gene" or "hsa-miR-550a-5p" used herein includes the hsa-miR-550a-5p gene (miRBase Accession No. MIMAT0004800) shown in SEQ ID NO: 145, a homolog or an ortholog of a different organism species, and the like. The gene can be obtained by a method described in Cummins J M et al., 2006, Proc. Natl. Acad. Sci. U.S.A., Vol. 103, pp. 3687-3692. Also, "hsa-mir-550a-1" (miRBase Accession No. MI0003600; SEQ ID NO: 480) and "hsa-mir-550a-2" (miRBase Accession No. MI0003601; SEQ ID NO: 492) each having a hairpin-like structure are known as precursors of "hsa-miR-550a-5p."

The term "hsa-miR-5572 gene" or "hsa-miR-5572" used herein includes the hsa-miR-5572 gene (miRBase Accession No. MIMAT0022260) shown in SEQ ID NO: 146, a homolog or an ortholog of a different organism species, and the like. The gene can be obtained by a method described in Tandon M et al., 2012, Oral Dis., Vol. 18, pp. 127-131. Also, "hsa-mir-5572" (miRBase Accession No. MI0019117; SEQ ID NO: 379) having a hairpin-like structure is known as a precursor of "hsa-miR-5572."

The term "hsa-miR-5739 gene" or "hsa-miR-5739" used herein includes the hsa-miR-5739 gene (miRBase Accession No. MIMAT0023116) shown in SEQ ID NO: 147, a homolog or an ortholog of a different organism species, and the like. The gene can be obtained by a method described in Yoo J K et al., 2011, Biochem. Biophys. Res. Commun., Vol. 415, pp. 258-262. Also, "hsa-mir-5739" (miRBase Accession No. MI0019412; SEQ ID NO: 380) having a hairpin-like structure is known as a precursor of "hsa-miR-5739."

The term "hsa-miR-6075 gene" or "hsa-miR-6075" used herein includes the hsa-miR-6075 gene (miRBase Accession No. MIMAT0023700) shown in SEQ ID NO: 148, a homolog or an ortholog of a different organism species, and the like. The gene can be obtained by a method described in Voellenkle C et al., 2012, RNA, Vol. 18, pp. 472-484. Also, "hsa-mir-6075" (miRBase Accession No. MI0020352; SEQ ID NO: 381) having a hairpin-like structure is known as a precursor of "hsa-miR-6075."

The term "hsa-miR-6076 gene" or "hsa-miR-6076" used herein includes the hsa-miR-6076 gene (miRBase Accession No. MIMAT0023701) shown in SEQ ID NO: 149, a homolog or an ortholog of a different organism species, and the like. The gene can be obtained by a method described in Voellenkle C et al., 2012, RNA, Vol. 18, pp. 472-484. Also, "hsa-mir-6076" (miRBase Accession No. MI0020353; SEQ ID NO: 382) having a hairpin-like structure is known as a precursor of "hsa-miR-6076."

The term "hsa-miR-6088 gene" or "hsa-miR-6088" used herein includes the hsa-miR-6088 gene (miRBase Accession No. MIMAT0023713) shown in SEQ ID NO: 150, a homolog or an ortholog of a different organism species, and the like. The gene can be obtained by a method described in Yoo J K et al., 2012, Stem Cells Dev., Vol. 21, pp. 2049-2057. Also, "hsa-mir-6088" (miRBase Accession No. MI0020365; SEQ ID NO: 383) having a hairpin-like structure is known as a precursor of "hsa-miR-6088."

The term "hsa-miR-6124 gene" or "hsa-miR-6124" used herein includes the hsa-miR-6124 gene (miRBase Accession No. MIMAT0024597) shown in SEQ ID NO: 151, a homolog or an ortholog of a different organism species, and the like. The gene can be obtained by a method described in Smith J L et al., 2012, J. Virol., Vol. 86, pp. 5278-5287. Also, "hsa-mir-6124" (miRBase Accession No. MI0021258; SEQ ID NO: 384) having a hairpin-like structure is known as a precursor of "hsa-miR-6124."

The term "hsa-miR-6131 gene" or "hsa-miR-6131" used herein includes the hsa-miR-6131 gene (miRBase Accession No. MIMAT0024615) shown in SEQ ID NO: 152, a homolog or an ortholog of a different organism species, and the like. The gene can be obtained by a method described in Dannemann M et al., 2012, Genome Biol. Evol., Vol. 4, pp. 552-564. Also, "hsa-mir-6131" (miRBase Accession No. MI0021276; SEQ ID NO: 385) having a hairpin-like structure is known as a precursor of "hsa-miR-6131."

The term "hsa-miR-6132 gene" or "hsa-miR-6132" used herein includes the hsa-miR-6132 gene (miRBase Accession No. MIMAT0024616) shown in SEQ ID NO: 153, a homolog or an ortholog of a different organism species, and the like. The gene can be obtained by a method described in Dannemann M et al., 2012, Genome Biol. Evol., Vol. 4, pp. 552-564. Also, "hsa-mir-6132" (miRBase Accession No. MI0021277; SEQ ID NO: 386) having a hairpin-like structure is known as a precursor of "hsa-miR-6132."

The term "hsa-miR-614 gene" or "hsa-miR-614" used herein includes the hsa-miR-614 gene (miRBase Accession No. MIMAT0003282) shown in SEQ ID NO: 154, a homolog or an ortholog of a different organism species, and the like. The gene can be obtained by a method described in Cummins J M et al., 2006, Proc. Natl. Acad. Sci. U.S.A., Vol. 103, pp. 3687-3692. Also, "hsa-mir-614" (miRBase Accession No. MI0003627; SEQ ID NO: 387) having a hairpin-like structure is known as a precursor of "hsa-miR-614."

The term "hsa-miR-615-5p gene" or "hsa-miR-615-5p" used herein includes the hsa-miR-615-5p gene (miRBase Accession No. MIMAT0004804) shown in SEQ ID NO: 155, a homolog or an ortholog of a different organism species, and the like. The gene can be obtained by a method described in Cummins J M et al., 2006, Proc. Natl. Acad. Sci. U.S.A., Vol. 103, pp. 3687-3692. Also, "hsa-mir-615" (miRBase Accession No. MI0003628; SEQ ID NO: 388) having a hairpin-like structure is known as a precursor of "hsa-miR-615-5p."

The term "hsa-miR-619-5p gene" or "hsa-miR-619-5p" used herein includes the hsa-miR-619-5p gene (miRBase Accession No. MIMAT0026622) shown in SEQ ID NO: 156, a homolog or an ortholog of a different organism species, and the like. The gene can be obtained by a method described in Cummins J M et al., 2006, Proc. Natl. Acad. Sci. U.S.A., Vol. 103, pp. 3687-3692. Also, "hsa-mir-619" (miRBase Accession No. MI0003633; SEQ ID NO: 389) having a hairpin-like structure is known as a precursor of "hsa-miR-619-5p."

The term "hsa-miR-642b-3p gene" or "hsa-miR-642b-3p" used herein includes the hsa-miR-642b-3p gene (miRBase Accession No. MIMAT0018444) shown in SEQ ID NO: 157, a homolog or an ortholog of a different organism species, and the like. The gene can be obtained by a method described in Witten D et al., 2010, BMC Biol., Vol. 8, p. 58. Also, "hsa-mir-642b" (miRBase Accession No. MI0016685; SEQ ID NO: 390) having a hairpin-like structure is known as a precursor of "hsa-miR-642b-3p."

The term "hsa-miR-6510-5p gene" or "hsa-miR-6510-5p" used herein includes the hsa-miR-6510-5p gene (miRBase Accession No. MIMAT0025476) shown in SEQ ID NO: 158, a homolog or an ortholog of a different organism species, and the like. The gene can be obtained by a method described in Joyce C E et al., 2011, Hum. Mol. Genet., Vol. 20, pp. 4025-4040. Also, "hsa-mir-6510" (miRBase Accession No. MI0022222; SEQ ID NO: 391) having a hairpin-like structure is known as a precursor of "hsa-miR-6510-5p."

The term "hsa-miR-6511a-5p gene" or "hsa-miR-6511a-5p" used herein includes the hsa-miR-6511a-5p gene (miRBase Accession No. MIMAT0025478) shown in SEQ ID NO: 159, a homolog or an ortholog of a different organism species, and the like. The gene can be obtained by a method described in Joyce C E et al., 2011, Hum. Mol. Genet., Vol. 20, pp. 4025-4040. Also, "hsa-mir-6511a-1" (miRBase Accession No. MI0022223; SEQ ID NO: 499), "hsa-mir-6511a-2" (miRBase Accession No. MI0023564; SEQ ID NO: 501), "hsa-mir-6511a-3" (miRBase Accession No. MI0023565; SEQ ID NO: 503), and "hsa-mir-6511a-4" (miRBase Accession No. MI0023566; SEQ ID NO: 505) each having a hairpin-like structure are known as precursors of "hsa-miR-6511a-5p."

The term "hsa-miR-6515-3p gene" or "hsa-miR-6515-3p" used herein includes the hsa-miR-6515-3p gene (miRBase Accession No. MIMAT0025487) shown in SEQ ID NO: 160, a homolog or an ortholog of a different organism species, and the like. The gene can be obtained by a method described in Joyce C E et al., 2011, Hum. Mol. Genet., Vol. 20, pp. 4025-4040. Also, "hsa-mir-6515" (miRBase Accession No. MI0022227; SEQ ID NO: 392) having a hairpin-like structure is known as a precursor of "hsa-miR-6515-3p."

The term "hsa-miR-6515-5p gene" or "hsa-miR-6515-5p" used herein includes the hsa-miR-6515-5p gene (miRBase Accession No. MIMAT0025486) shown in SEQ ID NO: 161, a homolog or an ortholog of a different organism species, and the like. The gene can be obtained by a method described in Joyce C E et al., 2011, Hum. Mol. Genet., Vol. 20, pp. 4025-4040. Also, "hsa-mir-6515" (miRBase Accession No. MI0022227; SEQ ID NO: 393) having a hairpin-like structure is known as a precursor of "hsa-miR-6515-5p."

The term "hsa-miR-663b gene" or "hsa-miR-663b" used herein includes the hsa-miR-663b gene (miRBase Accession No. MIMAT0005867) shown in SEQ ID NO: 162, a homolog or an ortholog of a different organism species, and the like. The gene can be obtained by a method described in Takada S et al., 2008, Leukemia, Vol. 22, pp. 1274-1278. Also, "hsa-mir-663b" (miRBase Accession No. MI0006336; SEQ ID NO: 394) having a hairpin-like structure is known as a precursor of "hsa-miR-663b."

The term "hsa-miR-6716-5p gene" or "hsa-miR-6716-5p" used herein includes the hsa-miR-6716-5p gene (miRBase Accession No. MIMAT0025844) shown in SEQ ID NO: 163, a homolog or an ortholog of a different organism species, and the like. The gene can be obtained by a method described in Li Y et al., 2012, Gene, Vol. 497, pp. 330-335. Also, "hsa-mir-6716" (miRBase Accession No. MI0022550; SEQ ID NO: 395) having a hairpin-like structure is known as a precursor of "hsa-miR-6716-5p."

The term "hsa-miR-6717-5p gene" or "hsa-miR-6717-5p" used herein includes the hsa-miR-6717-5p gene (miRBase Accession No. MIMAT0025846) shown in SEQ ID NO: 164, a homolog or an ortholog of a different organism species, and the like. The gene can be obtained by a method described in Li Y et al., 2012, Gene, Vol. 497, pp. 330-335. Also, "hsa-mir-6717" (miRBase Accession No. MI0022551; SEQ ID NO: 396) having a hairpin-like structure is known as a precursor of "hsa-miR-6717-5p."

The term "hsa-miR-6722-3p gene" or "hsa-miR-6722-3p" used herein includes the hsa-miR-6722-3p gene (miRBase Accession No. MIMAT0025854) shown in SEQ ID NO: 165, a homolog or an ortholog of a different organism species, and the like. The gene can be obtained by a method described in Li Y et al., 2012, Gene, Vol. 497, pp. 330-335. Also, "hsa-mir-6722" (miRBase Accession No. MI0022557; SEQ ID NO: 397) having a hairpin-like structure is known as a precursor of "hsa-miR-6722-3p."

The term "hsa-miR-6724-5p gene" or "hsa-miR-6724-5p" used herein includes the hsa-miR-6724-5p gene (miRBase Accession No. MIMAT0025856) shown in SEQ ID NO: 166, a homolog or an ortholog of a different organism species, and the like. The gene can be obtained by a method described in Li Y et al., 2012, Gene, Vol. 497, pp. 330-335. Also, "hsa-mir-6724-1" (miRBase Accession No. MI0022559; SEQ ID NO: 500), "hsa-mir-6724-2" (miRBase Accession No. MI0031516; SEQ ID NO: 502), "hsa-mir-6724-3" (miRBase Accession No. MI0031517; SEQ ID NO: 504), and "hsa-mir-6724-4" (miRBase Accession No. MI0031518; SEQ ID NO: 506) each having a hairpin-like structure are known as precursors of "hsa-miR-6724-5p."

The term "hsa-miR-6726-5p gene" or "hsa-miR-6726-5p" used herein includes the hsa-miR-6726-5p gene (miRBase Accession No. MIMAT0027353) shown in SEQ ID NO: 167, a homolog or an ortholog of a different organism species, and the like. The gene can be obtained by a method described in Ladewig E et al., 2012, Genome Res., Vol. 22, pp. 1634-1645. Also, "hsa-mir-6726" (miRBase Accession No. MI0022571; SEQ ID NO: 398) having a hairpin-like structure is known as a precursor of "hsa-miR-6726-5p."

The term "hsa-miR-6737-5p gene" or "hsa-miR-6737-5p" used herein includes the hsa-miR-6737-5p gene (miRBase Accession No. MIMAT0027375) shown in SEQ ID NO: 168, a homolog or an ortholog of a different organism species, and the like. The gene can be obtained by a method described in Ladewig E et al., 2012, Genome Res., Vol. 22, pp. 1634-1645. Also, "hsa-mir-6737" (miRBase Accession No. MI0022582; SEQ ID NO: 399) having a hairpin-like structure is known as a precursor of "hsa-miR-6737-5p."

The term "hsa-miR-6741-5p gene" or "hsa-miR-6741-5p" used herein includes the hsa-miR-6741-5p gene (miRBase Accession No. MIMAT0027383) shown in SEQ ID NO: 169, a homolog or an ortholog of a different organism species, and the like. The gene can be obtained by a method described in Ladewig E et al., 2012, Genome Res., Vol. 22, pp. 1634-1645. Also, "hsa-mir-6741" (miRBase Accession No. MI0022586; SEQ ID NO: 400) having a hairpin-like structure is known as a precursor of "hsa-miR-6741-5p."

The term "hsa-miR-6742-5p gene" or "hsa-miR-6742-5p" used herein includes the hsa-miR-6742-5p gene (miRBase Accession No. MIMAT0027385) shown in SEQ ID NO: 170, a homolog or an ortholog of a different organism species, and the like. The gene can be obtained by a method described in Ladewig E et al., 2012, Genome Res., Vol. 22, pp. 1634-1645. Also, "hsa-mir-6742" (miRBase Accession No. MI0022587; SEQ ID NO: 401) having a hairpin-like structure is known as a precursor of "hsa-miR-6742-5p."

The term "hsa-miR-6743-5p gene" or "hsa-miR-6743-5p" used herein includes the hsa-miR-6743-5p gene (miRBase Accession No. MIMAT0027387) shown in SEQ ID NO: 171, a homolog or an ortholog of a different organism species, and the like. The gene can be obtained by a method described in Ladewig E et al., 2012, Genome Res., Vol. 22, pp. 1634-1645. Also, "hsa-mir-6743" (miRBase Accession No. MI0022588; SEQ ID NO: 402) having a hairpin-like structure is known as a precursor of "hsa-miR-6743-5p."

The term "hsa-miR-6746-5p gene" or "hsa-miR-6746-5p" used herein includes the hsa-miR-6746-5p gene (miRBase Accession No. MIMAT0027392) shown in SEQ ID NO: 172, a homolog or an ortholog of a different organism species, and the like. The gene can be obtained by a method described in Ladewig E et al., 2012, Genome Res., Vol. 22, pp. 1634-1645. Also, "hsa-mir-6746" (miRBase Accession No. MI0022591; SEQ ID NO: 403) having a hairpin-like structure is known as a precursor of "hsa-miR-6746-5p."

The term "hsa-miR-6749-5p gene" or "hsa-miR-6749-5p" used herein includes the hsa-miR-6749-5p gene (miRBase Accession No. MIMAT0027398) shown in SEQ ID NO: 173, a homolog or an ortholog of a different organism species, and the like. The gene can be obtained by a method described in Ladewig E et al., 2012, Genome Res., Vol. 22, pp. 1634-1645. Also, "hsa-mir-6749" (miRBase Accession No. MI0022594; SEQ ID NO: 404) having a hairpin-like structure is known as a precursor of "hsa-miR-6749-5p."

The term "hsa-miR-6760-5p gene" or "hsa-miR-6760-5p" used herein includes the hsa-miR-6760-5p gene (miRBase Accession No. MIMAT0027420) shown in SEQ ID NO: 174, a homolog or an ortholog of a different organism species, and the like. The gene can be obtained by a method described in Ladewig E et al., 2012, Genome Res., Vol. 22, pp. 1634-1645. Also, "hsa-mir-6760" (miRBase Accession No. MI0022605; SEQ ID NO: 405) having a hairpin-like structure is known as a precursor of "hsa-miR-6760-5p."

The term "hsa-miR-6762-5p gene" or "hsa-miR-6762-5p" used herein includes the hsa-miR-6762-5p gene (miRBase Accession No. MIMAT0027424) shown in SEQ ID NO: 175, a homolog or an ortholog of a different organism species, and the like. The gene can be obtained by a method described in Ladewig E et al., 2012, Genome Res., Vol. 22, pp. 1634-1645. Also, "hsa-mir-6762" (miRBase Accession No. MI0022607; SEQ ID NO: 406) having a hairpin-like structure is known as a precursor of "hsa-miR-6762-5p."

The term "hsa-miR-6765-3p gene" or "hsa-miR-6765-3p" used herein includes the hsa-miR-6765-3p gene (miRBase Accession No. MIMAT0027431) shown in SEQ ID NO: 176, a homolog or an ortholog of a different organism species, and the like. The gene can be obtained by a method described in Ladewig E et al., 2012, Genome Res., Vol. 22, pp. 1634-1645. Also, "hsa-mir-6765" (miRBase Accession No. MI0022610; SEQ ID NO: 407) having a hairpin-like structure is known as a precursor of "hsa-miR-6765-3p."

The term "hsa-miR-6765-5p gene" or "hsa-miR-6765-5p" used herein includes the hsa-miR-6765-5p gene (miRBase Accession No. MIMAT0027430) shown in SEQ ID NO: 177, a homolog or an ortholog of a different organism species, and the like. The gene can be obtained by a method described in Ladewig E et al., 2012, Genome Res., Vol. 22, pp. 1634-1645. Also, "hsa-mir-6765" (miRBase Accession No. MI0022610; SEQ ID NO: 408) having a hairpin-like structure is known as a precursor of "hsa-miR-6765-5p."

The term "hsa-miR-6766-3p gene" or "hsa-miR-6766-3p" used herein includes the hsa-miR-6766-3p gene (miRBase Accession No. MIMAT0027433) shown in SEQ ID NO: 178, a homolog or an ortholog of a different organism species, and the like. The gene can be obtained by a method described in Ladewig E et al., 2012, Genome Res., Vol. 22, pp. 1634-1645. Also, "hsa-mir-6766" (miRBase Accession No. MI0022611; SEQ ID NO: 409) having a hairpin-like structure is known as a precursor of "hsa-miR-6766-3p."

The term "hsa-miR-6766-5p gene" or "hsa-miR-6766-5p" used herein includes the hsa-miR-6766-5p gene (miRBase Accession No. MIMAT0027432) shown in SEQ ID NO: 179, a homolog or an ortholog of a different organism species, and the like. The gene can be obtained by a method described in Ladewig E et al., 2012, Genome Res., Vol. 22, pp. 1634-1645. Also, "hsa-mir-6766" (miRBase Accession No. MI0022611; SEQ ID NO: 410) having a hairpin-like structure is known as a precursor of "hsa-miR-6766-5p."

The term "hsa-miR-6771-5p gene" or "hsa-miR-6771-5p" used herein includes the hsa-miR-6771-5p gene (miRBase Accession No. MIMAT0027442) shown in SEQ ID NO: 180, a homolog or an ortholog of a different organism species, and the like. The gene can be obtained by a method described in Ladewig E et al., 2012, Genome Res., Vol. 22, pp. 1634-1645. Also, "hsa-mir-6771" (miRBase Accession No. MI0022616; SEQ ID NO: 411) having a hairpin-like structure is known as a precursor of "hsa-miR-6771-5p."

The term "hsa-miR-6774-5p gene" or "hsa-miR-6774-5p" used herein includes the hsa-miR-6774-5p gene (miRBase Accession No. MIMAT0027448) shown in SEQ ID NO: 181, a homolog or an ortholog of a different organism species, and the like. The gene can be obtained by a method described in Ladewig E et al., 2012, Genome Res., Vol. 22, pp. 1634-1645. Also, "hsa-mir-6774" (miRBase Accession No. MI0022619; SEQ ID NO: 412) having a hairpin-like structure is known as a precursor of "hsa-miR-6774-5p."

The term "hsa-miR-6777-5p gene" or "hsa-miR-6777-5p" used herein includes the hsa-miR-6777-5p gene (miRBase Accession No. MIMAT0027454) shown in SEQ ID NO: 182, a homolog or an ortholog of a different organism species, and the like. The gene can be obtained by a method described in Ladewig E et al., 2012, Genome Res., Vol. 22, pp. 1634-1645. Also, "hsa-mir-6777" (miRBase Accession No. MI0022622; SEQ ID NO: 413) having a hairpin-like structure is known as a precursor of "hsa-miR-6777-5p."

The term "hsa-miR-6778-5p gene" or "hsa-miR-6778-5p" used herein includes the hsa-miR-6778-5p gene (miRBase Accession No. MIMAT0027456) shown in SEQ ID NO: 183, a homolog or an ortholog of a different organism species, and the like. The gene can be obtained by a method described in Ladewig E et al., 2012, Genome Res., Vol. 22, pp. 1634-1645. Also, "hsa-mir-6778" (miRBase Accession No. MI0022623; SEQ ID NO: 414) having a hairpin-like structure is known as a precursor of "hsa-miR-6778-5p."

The term "hsa-miR-6780b-5p gene" or "hsa-miR-6780b-5p" used herein includes the hsa-miR-6780b-5p gene (miRBase Accession No. MIMAT0027572) shown in SEQ ID NO: 184, a homolog or an ortholog of a different organism species, and the like. The gene can be obtained by a method described in Ladewig E et al., 2012, Genome Res., Vol. 22, pp. 1634-1645. Also, "hsa-mir-6780b" (miRBase Accession No. MI0022681; SEQ ID NO: 415) having a hairpin-like structure is known as a precursor of "hsa-miR-6780b-5p."

The term "hsa-miR-6781-5p gene" or "hsa-miR-6781-5p" used herein includes the hsa-miR-6781-5p gene (miRBase Accession No. MIMAT0027462) shown in SEQ ID NO: 185, a homolog or an ortholog of a different organism species, and the like. The gene can be obtained by a method described in Ladewig E et al., 2012, Genome Res., Vol. 22, pp. 1634-1645. Also, "hsa-mir-6781" (miRBase Accession No. MI0022626; SEQ ID NO: 416) having a hairpin-like structure is known as a precursor of "hsa-miR-6781-5p."

The term "hsa-miR-6782-5p gene" or "hsa-miR-6782-5p" used herein includes the hsa-miR-6782-5p gene (miRBase Accession No. MIMAT0027464) shown in SEQ ID NO: 186, a homolog or an ortholog of a different organism species, and the like. The gene can be obtained by a method described in Ladewig E et al., 2012, Genome Res., Vol. 22, pp. 1634-1645. Also, "hsa-mir-6782" (miRBase Accession No. MI0022627; SEQ ID NO: 417) having a hairpin-like structure is known as a precursor of "hsa-miR-6782-5p."

The term "hsa-miR-6784-5p gene" or "hsa-miR-6784-5p" used herein includes the hsa-miR-6784-5p gene (miRBase Accession No. MIMAT0027468) shown in SEQ ID NO: 187, a homolog or an ortholog of a different organism species, and the like. The gene can be obtained by a method described in Ladewig E et al., 2012, Genome Res., Vol. 22, pp. 1634-1645. Also, "hsa-mir-6784" (miRBase Accession No. MI0022629; SEQ ID NO: 418) having a hairpin-like structure is known as a precursor of "hsa-miR-6784-5p."

The term "hsa-miR-6785-5p gene" or "hsa-miR-6785-5p" used herein includes the hsa-miR-6785-5p gene (miRBase Accession No. MIMAT0027470) shown in SEQ ID NO: 188, a homolog or an ortholog of a different organism species, and the like. The gene can be obtained by a method described in Ladewig E et al., 2012, Genome Res., Vol. 22, pp. 1634-1645. Also, "hsa-mir-6785" (miRBase Accession No. MI0022630; SEQ ID NO: 419) having a hairpin-like structure is known as a precursor of "hsa-miR-6785-5p."

The term "hsa-miR-6787-5p gene" or "hsa-miR-6787-5p" used herein includes the hsa-miR-6787-5p gene (miRBase Accession No. MIMAT0027474) shown in SEQ ID NO: 189, a homolog or an ortholog of a different organism species, and the like. The gene can be obtained by a method described in Ladewig E et al., 2012, Genome Res., Vol. 22, pp. 1634-1645. Also, "hsa-mir-6787" (miRBase Accession No. MI0022632; SEQ ID NO: 420) having a hairpin-like structure is known as a precursor of "hsa-miR-6787-5p."

The term "hsa-miR-6789-5p gene" or "hsa-miR-6789-5p" used herein includes the hsa-miR-6789-5p gene (miRBase Accession No. MIMAT0027478) shown in SEQ ID NO: 190, a homolog or an ortholog of a different organism species, and the like. The gene can be obtained by a method described in Ladewig E et al., 2012, Genome Res., Vol. 22, pp. 1634-1645. Also, "hsa-mir-6789" (miRBase Accession No. MI0022634; SEQ ID NO: 421) having a hairpin-like structure is known as a precursor of "hsa-miR-6789-5p."

The term "hsa-miR-6791-5p gene" or "hsa-miR-6791-5p" used herein includes the hsa-miR-6791-5p gene (miRBase Accession No. MIMAT0027482) shown in SEQ ID NO: 191, a homolog or an ortholog of a different organism species, and the like. The gene can be obtained by a method described in Ladewig E et al., 2012, Genome Res., Vol. 22, pp. 1634-1645. Also, "hsa-mir-6791" (miRBase Accession No. MI0022636; SEQ ID NO: 422) having a hairpin-like structure is known as a precursor of "hsa-miR-6791-5p."

The term "hsa-miR-6794-5p gene" or "hsa-miR-6794-5p" used herein includes the hsa-miR-6794-5p gene (miRBase Accession No. MIMAT0027488) shown in SEQ ID NO: 192, a homolog or an ortholog of a different organism species, and the like. The gene can be obtained by a method described in Ladewig E et al., 2012, Genome Res., Vol. 22, pp. 1634-1645. Also, "hsa-mir-6794" (miRBase Accession No. MI0022639; SEQ ID NO: 423) having a hairpin-like structure is known as a precursor of "hsa-miR-6794-5p."

The term "hsa-miR-6800-5p gene" or "hsa-miR-6800-5p" used herein includes the hsa-miR-6800-5p gene (miRBase Accession No. MIMAT0027500) shown in SEQ ID NO: 193, a homolog or an ortholog of a different organism species, and the like. The gene can be obtained by a method described in Ladewig E et al., 2012, Genome Res., Vol. 22, pp. 1634-1645. Also, "hsa-mir-6800" (miRBase Accession No. MI0022645; SEQ ID NO: 424) having a hairpin-like structure is known as a precursor of "hsa-miR-6800-5p."

The term "hsa-miR-6802-5p gene" or "hsa-miR-6802-5p" used herein includes the hsa-miR-6802-5p gene (miRBase Accession No. MIMAT0027504) shown in SEQ ID NO: 194, a homolog or an ortholog of a different organism species, and the like. The gene can be obtained by a method described in Ladewig E et al., 2012, Genome Res., Vol. 22, pp. 1634-1645. Also, "hsa-mir-6802" (miRBase Accession No. MI0022647; SEQ ID NO: 425) having a hairpin-like structure is known as a precursor of "hsa-miR-6802-5p."

The term "hsa-miR-6803-5p gene" or "hsa-miR-6803-5p" used herein includes the hsa-miR-6803-5p gene (miRBase Accession No. MIMAT0027506) shown in SEQ ID NO: 195, a homolog or an ortholog of a different organism species, and the like. The gene can be obtained by a method described in Ladewig E et al., 2012, Genome Res., Vol. 22, pp. 1634-1645. Also, "hsa-mir-6803" (miRBase Accession No. MI0022648; SEQ ID NO: 426) having a hairpin-like structure is known as a precursor of "hsa-miR-6803-5p."

The term "hsa-miR-6812-5p gene" or "hsa-miR-6812-5p" used herein includes the hsa-miR-6812-5p gene (miRBase Accession No. MIMAT0027524) shown in SEQ ID NO: 196, a homolog or an ortholog of a different organism species, and the like. The gene can be obtained by a method described in Ladewig E et al., 2012, Genome Res., Vol. 22, pp. 1634-1645. Also, "hsa-mir-6812" (miRBase Accession No. MI0022657; SEQ ID NO: 427) having a hairpin-like structure is known as a precursor of "hsa-miR-6812-5p."

The term "hsa-miR-6816-5p gene" or "hsa-miR-6816-5p" used herein includes the hsa-miR-6816-5p gene (miRBase Accession No. MIMAT0027532) shown in SEQ ID NO: 197, a homolog or an ortholog of a different organism species, and the like. The gene can be obtained by a method described in Ladewig E et al., 2012, Genome Res., Vol. 22, pp. 1634-1645. Also, "hsa-mir-6816" (miRBase Accession No. MI0022661; SEQ ID NO: 428) having a hairpin-like structure is known as a precursor of "hsa-miR-6816-5p."

The term "hsa-miR-6819-5p gene" or "hsa-miR-6819-5p" used herein includes the hsa-miR-6819-5p gene (miRBase Accession No. MIMAT0027538) shown in SEQ ID NO: 198, a homolog or an ortholog of a different organism species, and the like. The gene can be obtained by a method described in Ladewig E et al., 2012, Genome Res., Vol. 22, pp. 1634-1645. Also, "hsa-mir-6819" (miRBase Accession No. MI0022664; SEQ ID NO: 429) having a hairpin-like structure is known as a precursor of "hsa-miR-6819-5p."

The term "hsa-miR-6821-5p gene" or "hsa-miR-6821-5p" used herein includes the hsa-miR-6821-5p gene (miRBase Accession No. MIMAT0027542) shown in SEQ ID NO: 199, a homolog or an ortholog of a different organism species, and the like. The gene can be obtained by a method described in Ladewig E et al., 2012, Genome Res., Vol. 22, pp. 1634-1645. Also, "hsa-mir-6821" (miRBase Accession No. MI0022666; SEQ ID NO: 430) having a hairpin-like structure is known as a precursor of "hsa-miR-6821-5p."

The term "hsa-miR-6826-5p gene" or "hsa-miR-6826-5p" used herein includes the hsa-miR-6826-5p gene (miRBase Accession No. MIMAT0027552) shown in SEQ ID NO: 200, a homolog or an ortholog of a different organism species, and the like. The gene can be obtained by a method described in Ladewig E et al., 2012, Genome Res., Vol. 22, pp. 1634-1645. Also, "hsa-mir-6826" (miRBase Accession No. MI0022671; SEQ ID NO: 431) having a hairpin-like structure is known as a precursor of "hsa-miR-6826-5p."

The term "hsa-miR-6831-5p gene" or "hsa-miR-6831-5p" used herein includes the hsa-miR-6831-5p gene (miRBase Accession No. MIMAT0027562) shown in SEQ ID NO: 201, a homolog or an ortholog of a different organism species, and the like. The gene can be obtained by a method described in Ladewig E et al., 2012, Genome Res., Vol. 22, pp. 1634-1645. Also, "hsa-mir-6831" (miRBase Accession No. MI0022676; SEQ ID NO: 432) having a hairpin-like structure is known as a precursor of "hsa-miR-6831-5p."

The term "hsa-miR-6836-3p gene" or "hsa-miR-6836-3p" used herein includes the hsa-miR-6836-3p gene (miRBase Accession No. MIMAT0027575) shown in SEQ ID NO: 202, a homolog or an ortholog of a different organism species, and the like. The gene can be obtained by a method described in Ladewig E et al., 2012, Genome Res., Vol. 22, pp. 1634-1645. Also, "hsa-mir-6836" (miRBase Accession No. MI0022682; SEQ ID NO: 433) having a hairpin-like structure is known as a precursor of "hsa-miR-6836-3p."

The term "hsa-miR-6840-3p gene" or "hsa-miR-6840-3p" used herein includes the hsa-miR-6840-3p gene (miRBase Accession No. MIMAT0027583) shown in SEQ ID NO: 203, a homolog or an ortholog of a different organism species, and the like. The gene can be obtained by a method described in Ladewig E et al., 2012, Genome Res., Vol. 22, pp. 1634-1645. Also, "hsa-mir-6840" (miRBase Accession No. MI0022686; SEQ ID NO: 434) having a hairpin-like structure is known as a precursor of "hsa-miR-6840-3p."

The term "hsa-miR-6842-5p gene" or "hsa-miR-6842-5p" used herein includes the hsa-miR-6842-5p gene (miRBase Accession No. MIMAT0027586) shown in SEQ ID NO: 204, a homolog or an ortholog of a different organism species, and the like. The gene can be obtained by a method described in Ladewig E et al., 2012, Genome Res., Vol. 22, pp. 1634-1645. Also, "hsa-mir-6842" (miRBase Accession No. MI0022688; SEQ ID NO: 435) having a hairpin-like structure is known as a precursor of "hsa-miR-6842-5p."

The term "hsa-miR-6850-5p gene" or "hsa-miR-6850-5p" used herein includes the hsa-miR-6850-5p gene (miRBase Accession No. MIMAT0027600) shown in SEQ ID NO: 205, a homolog or an ortholog of a different organism species, and the like. The gene can be obtained by a method described in Ladewig E et al., 2012, Genome Res., Vol. 22, pp. 1634-1645. Also, "hsa-mir-6850" (miRBase Accession No. MI0022696; SEQ ID NO: 436) having a hairpin-like structure is known as a precursor of "hsa-miR-6850-5p."

The term "hsa-miR-6861-5p gene" or "hsa-miR-6861-5p" used herein includes the hsa-miR-6861-5p gene (miRBase Accession No. MIMAT0027623) shown in SEQ ID NO: 206, a homolog or an ortholog of a different organism species, and the like. The gene can be obtained by a method described in Ladewig E et al., 2012, Genome Res., Vol. 22, pp. 1634-1645. Also, "hsa-mir-6861" (miRBase Accession No. MI0022708; SEQ ID NO: 437) having a hairpin-like structure is known as a precursor of "hsa-miR-6861-5p."

The term "hsa-miR-6869-5p gene" or "hsa-miR-6869-5p" used herein includes the hsa-miR-6869-5p gene (miRBase Accession No. MIMAT0027638) shown in SEQ ID NO: 207, a homolog or an ortholog of a different organism species, and the like. The gene can be obtained by a method described in Ladewig E et al., 2012, Genome Res., Vol. 22, pp. 1634-1645. Also, "hsa-mir-6869" (miRBase Accession No. MI0022716; SEQ ID NO: 438) having a hairpin-like structure is known as a precursor of "hsa-miR-6869-5p."

The term "hsa-miR-6870-5p gene" or "hsa-miR-6870-5p" used herein includes the hsa-miR-6870-5p gene (miRBase Accession No. MIMAT0027640) shown in SEQ ID NO: 208, a homolog or an ortholog of a different organism species, and the like. The gene can be obtained by a method described in Ladewig E et al., 2012, Genome Res., Vol. 22, pp. 1634-1645. Also, "hsa-mir-6870" (miRBase Accession No. MI0022717; SEQ ID NO: 439) having a hairpin-like structure is known as a precursor of "hsa-miR-6870-5p."

The term "hsa-miR-6877-5p gene" or "hsa-miR-6877-5p" used herein includes the hsa-miR-6877-5p gene (miRBase Accession No. MIMAT0027654) shown in SEQ ID NO: 209, a homolog or an ortholog of a different organism species, and the like. The gene can be obtained by a method described in Ladewig E et al., 2012, Genome Res., Vol. 22, pp. 1634-1645. Also, "hsa-mir-6877" (miRBase Accession No. MI0022724; SEQ ID NO: 440) having a hairpin-like structure is known as a precursor of "hsa-miR-6877-5p."

The term "hsa-miR-6879-5p gene" or "hsa-miR-6879-5p" used herein includes the hsa-miR-6879-5p gene (miRBase Accession No. MIMAT0027658) shown in SEQ ID NO: 210, a homolog or an ortholog of a different organism species, and the like. The gene can be obtained by a method described in Ladewig E et al., 2012, Genome Res., Vol. 22, pp. 1634-1645. Also, "hsa-mir-6879" (miRBase Accession No. MI0022726; SEQ ID NO: 441) having a hairpin-like structure is known as a precursor of "hsa-miR-6879-5p."

The term "hsa-miR-6880-3p gene" or "hsa-miR-6880-3p" used herein includes the hsa-miR-6880-3p gene (miRBase Accession No. MIMAT0027661) shown in SEQ ID NO: 211, a homolog or an ortholog of a different organism species, and the like. The gene can be obtained by a method described in Ladewig E et al., 2012, Genome Res., Vol. 22, pp. 1634-1645. Also, "hsa-mir-6880" (miRBase Accession No. MI0022727; SEQ ID NO: 442) having a hairpin-like structure is known as a precursor of "hsa-miR-6880-3p."

The term "hsa-miR-6880-5p gene" or "hsa-miR-6880-5p" used herein includes the hsa-miR-6880-5p gene (miRBase Accession No. MIMAT0027660) shown in SEQ ID NO: 212, a homolog or an ortholog of a different organism species, and the like. The gene can be obtained by a method described in Ladewig E et al., 2012, Genome Res., Vol. 22, pp. 1634-1645. Also, "hsa-mir-6880" (miRBase Accession No. MI0022727; SEQ ID NO: 443) having a hairpin-like structure is known as a precursor of "hsa-miR-6880-5p."

The term "hsa-miR-6885-5p gene" or "hsa-miR-6885-5p" used herein includes the hsa-miR-6885-5p gene (miRBase Accession No. MIMAT0027670) shown in SEQ ID NO: 213, a homolog or an ortholog of a different organism species, and the like. The gene can be obtained by a method described in Ladewig E et al., 2012, Genome Res., Vol. 22, pp. 1634-1645. Also, "hsa-mir-6885" (miRBase Accession No. MI0022732; SEQ ID NO: 444) having a hairpin-like structure is known as a precursor of "hsa-miR-6885-5p."

The term "hsa-miR-6887-5p gene" or "hsa-miR-6887-5p" used herein includes the hsa-miR-6887-5p gene (miRBase Accession No. MIMAT0027674) shown in SEQ ID NO: 214, a homolog or an ortholog of a different organism species, and the like. The gene can be obtained by a method described in Ladewig E et al., 2012, Genome Res., Vol. 22, pp. 1634-1645. Also, "hsa-mir-6887" (miRBase Accession No. MI0022734; SEQ ID NO: 445) having a hairpin-like structure is known as a precursor of "hsa-miR-6887-5p."

The term "hsa-miR-7107-5p gene" or "hsa-miR-7107-5p" used herein includes the hsa-miR-7107-5p gene (miRBase Accession No. MIMAT0028111) shown in SEQ ID NO: 215, a homolog or an ortholog of a different organism species, and the like. The gene can be obtained by a method described in Ladewig E et al., 2012, Genome Res., Vol. 22, pp. 1634-1645. Also, "hsa-mir-7107" (miRBase Accession No. MI0022958; SEQ ID NO: 446) having a hairpin-like structure is known as a precursor of "hsa-miR-7107-5p."

The term "hsa-miR-7108-3p gene" or "hsa-miR-7108-3p" used herein includes the hsa-miR-7108-3p gene (miRBase Accession No. MIMAT0028114) shown in SEQ ID NO: 216, a homolog or an ortholog of a different organism species, and the like. The gene can be obtained by a method described in Ladewig E et al., 2012, Genome Res., Vol. 22, pp. 1634-1645. Also, "hsa-mir-7108" (miRBase Accession No. MI0022959; SEQ ID NO: 447) having a hairpin-like structure is known as a precursor of "hsa-miR-7108-3p."

The term "hsa-miR-7109-5p gene" or "hsa-miR-7109-5p" used herein includes the hsa-miR-7109-5p gene (miRBase Accession No. MIMAT0028115) shown in SEQ ID NO: 217, a homolog or an ortholog of a different organism species, and the like. The gene can be obtained by a method described in Ladewig E et al., 2012, Genome Res., Vol. 22, pp. 1634-1645. Also, "hsa-mir-7109" (miRBase Accession No. MI0022960; SEQ ID NO: 448) having a hairpin-like structure is known as a precursor of "hsa-miR-7109-5p."

The term "hsa-miR-711 gene" or "hsa-miR-711" used herein includes the hsa-miR-711 gene (miRBase Accession No. MIMAT0012734) shown in SEQ ID NO: 218, a homolog or an ortholog of a different organism species, and the like. The gene can be obtained by a method described in Artzi S et al., 2008, BMC Bioinformatics, Vol. 9, p. 39. Also, "hsa-mir-711" (miRBase Accession No. MI0012488; SEQ ID NO: 449) having a hairpin-like structure is known as a precursor of "hsa-miR-711."

The term "hsa-miR-7113-3p gene" or "hsa-miR-7113-3p" used herein includes the hsa-miR-7113-3p gene (miRBase Accession No. MIMAT0028124) shown in SEQ ID NO: 219, a homolog or an ortholog of a different organism species, and the like. The gene can be obtained by a method described in Ladewig E et al., 2012, Genome Res., Vol. 22, pp. 1634-1645. Also, "hsa-mir-7113" (miRBase Accession No. MI0022964; SEQ ID NO: 450) having a hairpin-like structure is known as a precursor of "hsa-miR-7113-3p."

The term "hsa-miR-7150 gene" or "hsa-miR-7150" used herein includes the hsa-miR-7150 gene (miRBase Accession No. MIMAT0028211) shown in SEQ ID NO: 220, a homolog or an ortholog of a different organism species, and the like. The gene can be obtained by a method described in Oulas A et al., 2009, Nucleic Acids Res., Vol. 37, pp. 3276-3287. Also, "hsa-mir-7150" (miRBase Accession No. MI0023610; SEQ ID NO: 451) having a hairpin-like structure is known as a precursor of "hsa-miR-7150."

The term "hsa-miR-744-5p gene" or "hsa-miR-744-5p" used herein includes the hsa-miR-744-5p gene (miRBase Accession No. MIMAT0004945) shown in SEQ ID NO: 221, a homolog or an ortholog of a different organism species, and the like. The gene can be obtained by a method described in Berezikov E et al., 2006, Genome Res., Vol. 16, pp. 1289-1298. Also, "hsa-mir-744" (miRBase Accession No. MI0005559; SEQ ID NO: 452) having a hairpin-like structure is known as a precursor of "hsa-miR-744-5p."

The term "hsa-miR-7975 gene" or "hsa-miR-7975" used herein includes the hsa-miR-7975 gene (miRBase Accession No. MIMAT0031178) shown in SEQ ID NO: 222, a homolog or an ortholog of a different organism species, and the like. The gene can be obtained by a method described in Velthut-Meikas A et al., 2013, Mol. Endocrinol., Vol. 27, pp. 1128-1141. Also, "hsa-mir-7975" (miRBase Accession No. MI0025751; SEQ ID NO: 453) having a hairpin-like structure is known as a precursor of "hsa-miR-7975."

The term "hsa-miR-7977 gene" or "hsa-miR-7977" used herein includes the hsa-miR-7977 gene (miRBase Accession No. MIMAT0031180) shown in SEQ ID NO: 223, a homolog or an ortholog of a different organism species, and the like. The gene can be obtained by a method described in Velthut-Meikas A et al., 2013, Mol. Endocrinol., Vol. 27, pp. 1128-1141. Also, "hsa-mir-7977" (miRBase Accession No. MI0025753; SEQ ID NO: 454) having a hairpin-like structure is known as a precursor of "hsa-miR-7977."

The term "hsa-miR-8052 gene" or "hsa-miR-8052" used herein includes the hsa-miR-8052 gene (miRBase Accession No. MIMAT0030979) shown in SEQ ID NO: 224, a homolog or an ortholog of a different organism species, and the like. The gene can be obtained by a method described in Wang H J et al., 2013, Shock, Vol. 39, pp. 480-487. Also, "hsa-mir-8052" (miRBase Accession No. MI0025888; SEQ ID NO: 455) having a hairpin-like structure is known as a precursor of "hsa-miR-8052."

The term "hsa-miR-8069 gene" or "hsa-miR-8069" used herein includes the hsa-miR-8069 gene (miRBase Accession No. MIMAT0030996) shown in SEQ ID NO: 225, a homolog or an ortholog of a different organism species, and the like. The gene can be obtained by a method described in Wang H J et al., 2013, Shock, Vol. 39, pp. 480-487. Also, "hsa-mir-8069-1" (miRBase Accession No. MI0025905; SEQ ID NO: 481) and "hsa-mir-8069-2" (miRBase Accession No. MI0031519; SEQ ID NO: 493) each having a hairpin-like structure are known as precursors of "hsa-miR-8069."

The term "hsa-miR-8073 gene" or "hsa-miR-8073" used herein includes the hsa-miR-8073 gene (miRBase Accession No. MIMAT0031000) shown in SEQ ID NO: 226, a homolog or an ortholog of a different organism species, and the like. The gene can be obtained by a method described in Wang H J et al., 2013, Shock, Vol. 39, pp. 480-487. Also, "hsa-mir-8073" (miRBase Accession No. MI0025909; SEQ ID NO: 456) having a hairpin-like structure is known as a precursor of "hsa-miR-8073."

The term "hsa-miR-887-3p gene" or "hsa-miR-887-3p" used herein includes the hsa-miR-887-3p gene (miRBase Accession No. MIMAT0004951) shown in SEQ ID NO: 227, a homolog or an ortholog of a different organism species, and the like. The gene can be obtained by a method described in Berezikov E et al., 2006, Genome Res., Vol. 16, pp. 1289-1298. Also, "hsa-mir-887" (miRBase Accession No. MI0005562; SEQ ID NO: 457) having a hairpin-like structure is known as a precursor of "hsa-miR-887-3p."

The term "hsa-miR-937-5p gene" or "hsa-miR-937-5p" used herein includes the hsa-miR-937-5p gene (miRBase Accession No. MIMAT0022938) shown in SEQ ID NO: 228, a homolog or an ortholog of a different organism species, and the like. The gene can be obtained by a method described in Lui W O et al., 2007, Cancer Res., Vol. 67, pp. 6031-6043. Also, "hsa-mir-937" (miRBase Accession No. MI0005759; SEQ ID NO: 458) having a hairpin-like structure is known as a precursor of "hsa-miR-937-5p."

The term "hsa-miR-1202 gene" or "hsa-miR-1202" used herein includes the hsa-miR-1202 gene (miRBase Accession No. MIMAT0005865) shown in SEQ ID NO: 229, a homolog or an ortholog of a different organism species, and the like. The gene can be obtained by a method described in Marton S et al., 2008, Leukemia, Vol. 22, pp. 330-338. Also, "hsa-mir-1202" (miRBase Accession No. MI0006334; SEQ ID NO: 459) having a hairpin-like structure is known as a precursor of "hsa-miR-1202."

The term "hsa-miR-1207-5p gene" or "hsa-miR-1207-5p" used herein includes the hsa-miR-1207-5p gene (miRBase Accession No. MIMAT0005871) shown in SEQ ID NO: 230, a homolog or an ortholog of a different organism species, and the like. The gene can be obtained by a method described in Huppi K et al., 2008, Mol. Cancer Res., Vol. 6, pp. 212-221. Also, "hsa-mir-1207" (miRBase Accession No. MI0006340; SEQ ID NO: 460) having a hairpin-like structure is known as a precursor of "hsa-miR-1207-5p."

The term "hsa-miR-1246 gene" or "hsa-miR-1246" used herein includes the hsa-miR-1246 gene (miRBase Accession No. MIMAT0005898) shown in SEQ ID NO: 231, a homolog or an ortholog of a different organism species, and the like. The gene can be obtained by a method described in Morin R D et al., 2008, Genome Res., Vol. 18, pp. 610-621. Also, "hsa-mir-1246" (miRBase Accession No. MI0006381; SEQ ID NO: 461) having a hairpin-like structure is known as a precursor of "hsa-miR-1246."

The term "hsa-miR-1254 gene" or "hsa-miR-1254" used herein includes the hsa-miR-1254 gene (miRBase Accession No. MIMAT0005905) shown in SEQ ID NO: 232, a homolog or an ortholog of a different organism species, and the like. The gene can be obtained by a method described in Morin R D et al., 2008, Genome Res., Vol. 18, pp. 610-621. Also, "hsa-mir-1254-1" (miRBase Accession No. MI0006388; SEQ ID NO: 482) and "hsa-mir-1254-2" (miRBase Accession No. MI0016747; SEQ ID NO: 494) each having a hairpin-like structure are known as precursors of "hsa-miR-1254."

The term "hsa-miR-135a-3p gene" or "hsa-miR-135a-3p" used herein includes the hsa-miR-135a-3p gene (miRBase Accession No. MIMAT0004595) shown in SEQ ID NO: 233, a homolog or an ortholog of a different organism species, and the like. The gene can be obtained by a method described in Lagos-Quintana M et al., 2002, Curr. Biol., Vol. 12, pp. 735-739. Also, "hsa-mir-135a-1" (miRBase Accession No. MI0000452; SEQ ID NO: 462) having a hairpin-like structure is known as a precursor of "hsa-miR-135a-3p."

The term "hsa-miR-1469 gene" or "hsa-miR-1469" used herein includes the hsa-miR-1469 gene (miRBase Accession No. MIMAT0007347) shown in SEQ ID NO: 234, a homolog or an ortholog of a different organism species, and the like. The gene can be obtained by a method described in Kawaji H et al., 2008, BMC Genomics, Vol. 9, p. 157. Also, "hsa-mir-1469" (miRBase Accession No. MI0007074; SEQ ID NO: 463) having a hairpin-like structure is known as a precursor of "hsa-miR-1469."

The term "hsa-miR-149-3p gene" or "hsa-miR-149-3p" used herein includes the hsa-miR-149-3p gene (miRBase Accession No. MIMAT0004609) shown in SEQ ID NO: 235, a homolog or an ortholog of a different organism species, and the like. The gene can be obtained by a method described in Lagos-Quintana M et al., 2002, Curr. Biol., Vol. 12, pp. 735-739. Also, "hsa-mir-149" (miRBase Accession No. MI0000478; SEQ ID NO: 464) having a hairpin-like structure is known as a precursor of "hsa-miR-149-3p."

The term "hsa-miR-150-3p gene" or "hsa-miR-150-3p" used herein includes the hsa-miR-150-3p gene (miRBase Accession No. MIMAT0004610) shown in SEQ ID NO: 236, a homolog or an ortholog of a different organism species, and the like. The gene can be obtained by a method described in Lagos-Quintana M et al., 2002, Curr. Biol., Vol. 12, pp. 735-739. Also, "hsa-mir-150" (miRBase Accession No. MI0000479; SEQ ID NO: 465) having a hairpin-like structure is known as a precursor of "hsa-miR-150-3p."

The term "hsa-miR-1914-3p gene" or "hsa-miR-1914-3p" used herein includes the hsa-miR-1914-3p gene (miRBase Accession No. MIMAT0007890) shown in SEQ ID NO: 237, a homolog or an ortholog of a different organism species, and the like. The gene can be obtained by a method described in Bar M et al., 2008, Stem Cells, Vol. 26, pp. 2496-2505. Also, "hsa-mir-1914" (miRBase Accession No. MI0008335; SEQ ID NO: 466) having a hairpin-like structure is known as a precursor of "hsa-miR-1914-3p."

The term "hsa-miR-191-5p gene" or "hsa-miR-191-5p" used herein includes the hsa-miR-191-5p gene (miRBase Accession No. MIMAT0000440) shown in SEQ ID NO: 238, a homolog or an ortholog of a different organism species, and the like. The gene can be obtained by a method described in Lagos-Quintana M et al., 2003, RNA, Vol. 9, pp. 175-179. Also, "hsa-mir-191" (miRBase Accession No. MI0000465; SEQ ID NO: 467) having a hairpin-like structure is known as a precursor of "hsa-miR-191-5p."

The term "hsa-miR-423-5p gene" or "hsa-miR-423-5p" used herein includes the hsa-miR-423-5p gene (miRBase Accession No. MIMAT0004748) shown in SEQ ID NO: 239, a homolog or an ortholog of a different organism species, and the like. The gene can be obtained by a method described in Kasashima K et al., 2004, Biochem. Biophys. Res. Commun., Vol. 322, pp. 403-410. Also, "hsa-mir-423" (miRBase Accession No. MI0001445; SEQ ID NO: 468) having a hairpin-like structure is known as a precursor of "hsa-miR-423-5p."

The term "hsa-miR-663a gene" or "hsa-miR-663a" used herein includes the hsa-miR-663a gene (miRBase Accession No. MIMAT0003326) shown in SEQ ID NO: 240, a homolog or an ortholog of a different organism species, and the like. The gene can be obtained by a method described in Cummins J M et al., 2006, Proc. Natl. Acad. Sci. U.S.A., Vol. 103, pp. 3687-3692. Also, "hsa-mir-663a" (miRBase Accession No. MI0003672; SEQ ID NO: 469) having a hairpin-like structure is known as a precursor of "hsa-miR-663a."

The term "hsa-miR-92a-2-5p gene" or "hsa-miR-92a-2-5p" used herein includes the hsa-miR-92a-2-5p gene (miRBase Accession No. MIMAT0004508) shown in SEQ ID NO: 241, a homolog or an ortholog of a different organism species, and the like. The gene can be obtained by a method described in Mourelatos Z et al., 2002, Genes Dev., Vol. 16, pp. 720-728. Also, "hsa-mir-92a-2" (miRBase Accession No. MI0000094; SEQ ID NO: 470) having a hairpin-like structure is known as a precursor of "hsa-miR-92a-2-5p."

The term "hsa-miR-92a-3p gene" or "hsa-miR-92a-3p" used herein includes the hsa-miR-92a-3p gene (miRBase Accession No. MIMAT0000092) shown in SEQ ID NO: 242, a homolog or an ortholog of a different organism species, and the like. The gene can be obtained by a method described in Mourelatos Z et al., 2002, Genes Dev., Vol. 16, pp. 720-728. Also, "hsa-mir-92a-1" (miRBase Accession No. MI0000093; SEQ ID NO: 483) and "hsa-mir-92a-2" (miRBase Accession No. MI0000094; SEQ ID NO: 495) each having a hairpin-like structure are known as precursors of "hsa-miR-92a-3p."

The term "hsa-miR-940 gene" or "hsa-miR-940" used herein includes the hsa-miR-940 gene (miRBase Accession No. MIMAT0004983) shown in SEQ ID NO: 243, a homolog or an ortholog of a different organism species, and the like. The gene can be obtained by a method described in Lui W O et al., 2007, Cancer Res., Vol. 67, pp. 6031-6043. Also, "hsa-mir-940" (miRBase Accession No. MI0005762; SEQ ID NO: 471) having a hairpin-like structure is known as a precursor of "hsa-miR-940."

A mature miRNA may become a variant due to the sequence cleaved shorter or longer by one to several flanking nucleotides or due to substitution of nucleotides, when it is cleaved as the mature miRNA from its RNA precursor having a hairpin-like structure. This variant is referred to as isomiR (Morin R D et al., 2008, Genome Res., Vol. 18, pp. 610-621). The miRBase Release 21 shows the nucleotide sequences represented by any of SEQ ID NOs: 1 to 243 as well as a large number of the nucleotide sequence variants and fragments represented by any of SEQ ID NOs: 507 to 766, referred to as isomiRs. These variants can also be obtained as miRNAs having a nucleotide sequence represented by any of SEQ ID NOs: 1 to 243. Among the variants of polynucleotides comprising the nucleotide sequence represented by any of SEQ ID NOs: 1, 2, 3, 8, 9, 10, 12, 13, 14, 15, 16, 17, 20, 21, 22, 24, 25, 26, 27, 28, 29, 30, 31, 32, 33, 34, 36, 37, 38, 42, 43, 44, 45, 46, 47, 48, 49, 51, 54, 55, 56, 58, 61, 62, 63, 67, 68, 69, 71, 72, 73, 74, 75, 77, 78, 80, 81, 82, 84, 86, 87, 89, 90, 91, 92, 93, 94, 95, 96, 101, 103, 105, 109, 111, 113, 114, 116, 117, 118, 119, 123, 124, 126, 127, 129, 131, 132, 133, 134, 135, 136, 139, 142, 143, 146, 150, 151, 152, 153, 154, 155, 156, 157, 158, 159, 161, 162, 163, 164, 166, 218, 221, 227, 228, 231, 232, 233, 235, 236, 237, 238, 239, 240, 241, 242, and 243 or a nucleotide sequence derived from any of the nucleotide sequences mentioned above by the replacement of u with t according to the present invention, specific examples of the longest variants registered in the miRBase Release 21 include polynucleotides represented by SEQ ID NOs: 507 to 632. Among the variants of polynucleotides comprising the nucleotide sequence represented by any of SEQ ID NOs: 1, 2, 3, 4, 8, 9, 10, 12, 13, 14, 15, 16, 17, 19, 20, 21, 22, 24, 25, 26, 27, 28, 29, 30, 31, 32, 33, 34, 36, 37, 38, 40, 41, 42, 43, 44, 45, 46, 47, 48, 49, 51, 53, 54, 55, 56, 58, 61, 62, 63, 67, 68, 71, 72, 73, 74, 75, 77, 78, 80, 81, 82, 84, 86, 90, 91, 92, 93, 95, 96, 101, 105, 107, 109, 111, 112, 113, 114, 116, 117, 118, 119, 120, 122, 123, 124, 125, 126, 127, 129, 131, 132, 133, 134, 135, 136, 138, 139, 142, 143, 145, 146, 150, 151, 152, 154, 155, 156, 157, 158, 159, 161, 162, 163, 164, 166, 218, 221, 222, 227, 228, 229, 231, 232, 233, and 235 or a nucleotide sequence derived from any of the nucleotide sequences mentioned above by the replacement of u with t according to the present invention, examples of the shortest variants registered in the miRBase Release 21 include polynucleotides represented by SEQ ID NOs: 633 to 766. In addition to these variants and fragments, a large number of isomiR polynucleotides of SEQ ID NOs: 1 to 243 registered in the miRBase are included. Further examples of polynucleotides each comprising a nucleotide sequence represented by any of SEQ ID NOs: 1 to 243 include precursors thereof, which are polynucleotides each represented by any of SEQ ID NOs: 507 to 766.

The names and miRBase Accession Nos. (registration numbers) of the genes represented by SEQ ID NOs: 1 to 766 are shown in Table 1.

As used herein, the expression "capable of specifically binding" refers to a situation in which the nucleic acid probe or the primer used in the present invention binds to a specific target nucleic acid and it cannot substantially bind to other nucleic acids.

TABLE 1

| SEQ ID NO | Name of gene | MIMAT No. |
|---|---|---|
| 1 | hsa-miR-6087 | MIMAT0023712 |
| 2 | hsa-miR-1185-1-3p | MIMAT0022838 |
| 3 | hsa-miR-1185-2-3p | MIMAT0022713 |
| 4 | hsa-miR-1193 | MIMAT0015049 |
| 5 | hsa-miR-1199-5p | MIMAT0031119 |
| 6 | hsa-miR-1225-5p | MIMAT0005572 |
| 7 | hsa-miR-1227-5p | MIMAT0022941 |
| 8 | hsa-miR-1228-3p | MIMAT0005583 |
| 9 | hsa-miR-1228-5p | MIMAT0005582 |
| 10 | hsa-miR-1237-5p | MIMAT0022946 |
| 11 | hsa-miR-1238-5p | MIMAT0022947 |
| 12 | hsa-miR-1247-3p | MIMAT0022721 |
| 13 | hsa-miR-1268a | MIMAT0005922 |
| 14 | hsa-miR-1268b | MIMAT0018925 |
| 15 | hsa-miR-1273g-3p | MIMAT0022742 |
| 16 | hsa-miR-128-2-5p | MIMAT0031095 |
| 17 | hsa-miR-1343-3p | MIMAT0019776 |
| 18 | hsa-miR-1343-5p | MIMAT0027038 |
| 19 | hsa-miR-1470 | MIMAT0007348 |
| 20 | hsa-miR-17-3p | MIMAT0000071 |
| 21 | hsa-miR-187-5p | MIMAT0004561 |
| 22 | hsa-miR-1908-3p | MIMAT0026916 |
| 23 | hsa-miR-1908-5p | MIMAT0007881 |
| 24 | hsa-miR-1909-3p | MIMAT0007883 |
| 25 | hsa-miR-1915-3p | MIMAT0007892 |
| 26 | hsa-miR-210-5p | MIMAT0026475 |
| 27 | hsa-miR-24-3p | MIMAT0000080 |
| 28 | hsa-miR-2467-3p | MIMAT0019953 |
| 29 | hsa-miR-2861 | MIMAT0013802 |
| 30 | hsa-miR-296-3p | MIMAT0004679 |
| 31 | hsa-miR-29b-3p | MIMAT0000100 |
| 32 | hsa-miR-3131 | MIMAT0014996 |
| 33 | hsa-miR-3154 | MIMAT0015028 |
| 34 | hsa-miR-3158-5p | MIMAT0019211 |
| 35 | hsa-miR-3160-5p | MIMAT0019212 |
| 36 | hsa-miR-3162-5p | MIMAT0015036 |
| 37 | hsa-miR-3178 | MIMAT0015055 |
| 38 | hsa-miR-3180-3p | MIMAT0015058 |
| 39 | hsa-miR-3184-5p | MIMAT0015064 |
| 40 | hsa-miR-3185 | MIMAT0015065 |
| 41 | hsa-miR-3194-3p | MIMAT0019218 |
| 42 | hsa-miR-3195 | MIMAT0015079 |
| 43 | hsa-miR-3197 | MIMAT0015082 |

TABLE 1-continued

| SEQ ID NO | Name of gene | MIMAT No. |
|---|---|---|
| 44 | hsa-miR-320a | MIMAT0000510 |
| 45 | hsa-miR-320b | MIMAT0005792 |
| 46 | hsa-miR-328-5p | MIMAT0026486 |
| 47 | hsa-miR-342-5p | MIMAT0004694 |
| 48 | hsa-miR-345-3p | MIMAT0022698 |
| 49 | hsa-miR-3616-3p | MIMAT0017996 |
| 50 | hsa-miR-3619-3p | MIMAT0019219 |
| 51 | hsa-miR-3620-5p | MIMAT0022967 |
| 52 | hsa-miR-3621 | MIMAT0018002 |
| 53 | hsa-miR-3622a-5p | MIMAT0018003 |
| 54 | hsa-miR-3648 | MIMAT0018068 |
| 55 | hsa-miR-3652 | MIMAT0018072 |
| 56 | hsa-miR-3656 | MIMAT0018076 |
| 57 | hsa-miR-3663-3p | MIMAT0018085 |
| 58 | hsa-miR-3679-5p | MIMAT0018104 |
| 59 | hsa-miR-371b-5p | MIMAT0019892 |
| 60 | hsa-miR-373-5p | MIMAT0000725 |
| 61 | hsa-miR-3917 | MIMAT0018191 |
| 62 | hsa-miR-3940-5p | MIMAT0019229 |
| 63 | hsa-miR-3960 | MIMAT0019337 |
| 64 | hsa-miR-4258 | MIMAT0016879 |
| 65 | hsa-miR-4259 | MIMAT0016880 |
| 66 | hsa-miR-4270 | MIMAT0016900 |
| 67 | hsa-miR-4286 | MIMAT0016916 |
| 68 | hsa-miR-4298 | MIMAT0016852 |
| 69 | hsa-miR-4322 | MIMAT0016873 |
| 70 | hsa-miR-4327 | MIMAT0016889 |
| 71 | hsa-miR-4417 | MIMAT0018929 |
| 72 | hsa-miR-4419b | MIMAT0019034 |
| 73 | hsa-miR-4429 | MIMAT0018944 |
| 74 | hsa-miR-4430 | MIMAT0018945 |
| 75 | hsa-miR-4433a-3p | MIMAT0018949 |
| 76 | hsa-miR-4436b-5p | MIMAT0019940 |
| 77 | hsa-miR-4443 | MIMAT0018961 |
| 78 | hsa-miR-4446-3p | MIMAT0018965 |
| 79 | hsa-miR-4447 | MIMAT0018966 |
| 80 | hsa-miR-4448 | MIMAT0018967 |
| 81 | hsa-miR-4449 | MIMAT0018968 |
| 82 | hsa-miR-4454 | MIMAT0018976 |
| 83 | hsa-miR-4455 | MIMAT0018977 |
| 84 | hsa-miR-4459 | MIMAT0018981 |
| 85 | hsa-miR-4462 | MIMAT0018986 |
| 86 | hsa-miR-4466 | MIMAT0018993 |
| 87 | hsa-miR-4467 | MIMAT0018994 |
| 88 | hsa-miR-4480 | MIMAT0019014 |
| 89 | hsa-miR-4483 | MIMAT0019017 |
| 90 | hsa-miR-4484 | MIMAT0019018 |
| 91 | hsa-miR-4485-5p | MIMAT0032116 |
| 92 | hsa-miR-4488 | MIMAT0019022 |
| 93 | hsa-miR-4492 | MIMAT0019027 |
| 94 | hsa-miR-4505 | MIMAT0019041 |
| 95 | hsa-miR-4515 | MIMAT0019052 |
| 96 | hsa-miR-4525 | MIMAT0019064 |
| 97 | hsa-miR-4534 | MIMAT0019073 |
| 98 | hsa-miR-4535 | MIMAT0019075 |
| 99 | hsa-miR-4633-3p | MIMAT0019690 |
| 100 | hsa-miR-4634 | MIMAT0019691 |
| 101 | hsa-miR-4640-5p | MIMAT0019699 |
| 102 | hsa-miR-4649-5p | MIMAT0019711 |
| 103 | hsa-miR-4651 | MIMAT0019715 |
| 104 | hsa-miR-4652-5p | MIMAT0019716 |
| 105 | hsa-miR-4655-5p | MIMAT0019721 |
| 106 | hsa-miR-4656 | MIMAT0019723 |
| 107 | hsa-miR-4658 | MIMAT0019725 |
| 108 | hsa-miR-4663 | MIMAT0019735 |
| 109 | hsa-miR-4673 | MIMAT0019755 |
| 110 | hsa-miR-4675 | MIMAT0019757 |
| 111 | hsa-miR-4687-3p | MIMAT0019775 |
| 112 | hsa-miR-4687-5p | MIMAT0019774 |
| 113 | hsa-miR-4690-5p | MIMAT0019779 |
| 114 | hsa-miR-4695-5p | MIMAT0019788 |
| 115 | hsa-miR-4697-5p | MIMAT0019791 |
| 116 | hsa-miR-4706 | MIMAT0019806 |
| 117 | hsa-miR-4707-3p | MIMAT0019808 |
| 118 | hsa-miR-4707-5p | MIMAT0019807 |
| 119 | hsa-miR-4708-3p | MIMAT0019810 |
| 120 | hsa-miR-4710 | MIMAT0019815 |
| 121 | hsa-miR-4718 | MIMAT0019831 |
| 122 | hsa-miR-4722-5p | MIMAT0019836 |
| 123 | hsa-miR-4725-3p | MIMAT0019844 |
| 124 | hsa-miR-4726-5p | MIMAT0019845 |
| 125 | hsa-miR-4727-3p | MIMAT0019848 |
| 126 | hsa-miR-4728-5p | MIMAT0019849 |
| 127 | hsa-miR-4731-5p | MIMAT0019853 |
| 128 | hsa-miR-4736 | MIMAT0019862 |
| 129 | hsa-miR-4739 | MIMAT0019868 |
| 130 | hsa-miR-4740-5p | MIMAT0019869 |
| 131 | hsa-miR-4741 | MIMAT0019871 |
| 132 | hsa-miR-4750-5p | MIMAT0019887 |
| 133 | hsa-miR-4755-3p | MIMAT0019896 |
| 134 | hsa-miR-4763-3p | MIMAT0019913 |
| 135 | hsa-miR-4771 | MIMAT0019925 |
| 136 | hsa-miR-4783-3p | MIMAT0019947 |
| 137 | hsa-miR-4783-5p | MIMAT0019946 |
| 138 | hsa-miR-4787-3p | MIMAT0019957 |
| 139 | hsa-miR-4792 | MIMAT0019964 |
| 140 | hsa-miR-498 | MIMAT0002824 |
| 141 | hsa-miR-5008-5p | MIMAT0021039 |
| 142 | hsa-miR-5010-5p | MIMAT0021043 |
| 143 | hsa-miR-504-3p | MIMAT0026612 |
| 144 | hsa-miR-5195-3p | MIMAT0021127 |
| 145 | hsa-miR-550a-5p | MIMAT0004800 |
| 146 | hsa-miR-5572 | MIMAT0022260 |
| 147 | hsa-miR-5739 | MIMAT0023116 |
| 148 | hsa-miR-6075 | MIMAT0023700 |
| 149 | hsa-miR-6076 | MIMAT0023701 |
| 150 | hsa-miR-6088 | MIMAT0023713 |
| 151 | hsa-miR-6124 | MIMAT0024597 |
| 152 | hsa-miR-6131 | MIMAT0024615 |
| 153 | hsa-miR-6132 | MIMAT0024616 |
| 154 | hsa-miR-614 | MIMAT0003282 |
| 155 | hsa-miR-615-5p | MIMAT0004804 |
| 156 | hsa-miR-619-5p | MIMAT0026622 |
| 157 | hsa-miR-642b-3p | MIMAT0018444 |
| 158 | hsa-miR-6510-5p | MIMAT0025476 |
| 159 | hsa-miR-6511a-5p | MIMAT0025478 |
| 160 | hsa-miR-6515-3p | MIMAT0025487 |
| 161 | hsa-miR-6515-5p | MIMAT0025486 |
| 162 | hsa-miR-663b | MIMAT0005867 |
| 163 | hsa-miR-6716-5p | MIMAT0025844 |
| 164 | hsa-miR-6717-5p | MIMAT0025846 |
| 165 | hsa-miR-6722-3p | MIMAT0025854 |
| 166 | hsa-miR-6724-5p | MIMAT0025856 |
| 167 | hsa-miR-6726-5p | MIMAT0027353 |
| 168 | hsa-miR-6737-5p | MIMAT0027375 |
| 169 | hsa-miR-6741-5p | MIMAT0027383 |
| 170 | hsa-miR-6742-5p | MIMAT0027385 |
| 171 | hsa-miR-6743-5p | MIMAT0027387 |
| 172 | hsa-miR-6746-5p | MIMAT0027392 |
| 173 | hsa-miR-6749-5p | MIMAT0027398 |
| 174 | hsa-miR-6760-5p | MIMAT0027420 |
| 175 | hsa-miR-6762-5p | MIMAT0027424 |
| 176 | hsa-miR-6765-3p | MIMAT0027431 |
| 177 | hsa-miR-6765-5p | MIMAT0027430 |
| 178 | hsa-miR-6766-3p | MIMAT0027433 |
| 179 | hsa-miR-6766-5p | MIMAT0027432 |
| 180 | hsa-miR-6771-5p | MIMAT0027442 |
| 181 | hsa-miR-6774-5p | MIMAT0027448 |
| 182 | hsa-miR-6777-5p | MIMAT0027454 |
| 183 | hsa-miR-6778-5p | MIMAT0027456 |
| 184 | hsa-miR-6780b-5p | MIMAT0027572 |
| 185 | hsa-miR-6781-5p | MIMAT0027462 |
| 186 | hsa-miR-6782-5p | MIMAT0027464 |
| 187 | hsa-miR-6784-5p | MIMAT0027468 |
| 188 | hsa-miR-6785-5p | MIMAT0027470 |
| 189 | hsa-miR-6787-5p | MIMAT0027474 |
| 190 | hsa-miR-6789-5p | MIMAT0027478 |
| 191 | hsa-miR-6791-5p | MIMAT0027482 |
| 192 | hsa-miR-6794-5p | MIMAT0027488 |
| 193 | hsa-miR-6800-5p | MIMAT0027500 |
| 194 | hsa-miR-6802-5p | MIMAT0027504 |
| 195 | hsa-miR-6803-5p | MIMAT0027506 |

TABLE 1-continued

| SEQ ID NO | Name of gene | MIMAT No. |
|---|---|---|
| 196 | hsa-miR-6812-5p | MIMAT0027524 |
| 197 | hsa-miR-6816-5p | MIMAT0027532 |
| 198 | hsa-miR-6819-5p | MIMAT0027538 |
| 199 | hsa-miR-6821-5p | MIMAT0027542 |
| 200 | hsa-miR-6826-5p | MIMAT0027552 |
| 201 | hsa-miR-6831-5p | MIMAT0027562 |
| 202 | hsa-miR-6836-3p | MIMAT0027575 |
| 203 | hsa-miR-6840-3p | MIMAT0027583 |
| 204 | hsa-miR-6842-5p | MIMAT0027586 |
| 205 | hsa-miR-6850-5p | MIMAT0027600 |
| 206 | hsa-miR-6861-5p | MIMAT0027623 |
| 207 | hsa-miR-6869-5p | MIMAT0027638 |
| 208 | hsa-miR-6870-5p | MIMAT0027640 |
| 209 | hsa-miR-6877-5p | MIMAT0027654 |
| 210 | hsa-miR-6879-5p | MIMAT0027658 |
| 211 | hsa-miR-6880-3p | MIMAT0027661 |
| 212 | hsa-miR-6880-5p | MIMAT0027660 |
| 213 | hsa-miR-6885-5p | MIMAT0027670 |
| 214 | hsa-miR-6887-5p | MIMAT0027674 |
| 215 | hsa-miR-7107-5p | MIMAT0028111 |
| 216 | hsa-miR-7108-3p | MIMAT0028114 |
| 217 | hsa-miR-7109-5p | MIMAT0028115 |
| 218 | hsa-miR-711 | MIMAT0012734 |
| 219 | hsa-miR-7113-3p | MIMAT0028124 |
| 220 | hsa-miR-7150 | MIMAT0028211 |
| 221 | hsa-miR-744-5p | MIMAT0004945 |
| 222 | hsa-miR-7975 | MIMAT0031178 |
| 223 | hsa-miR-7977 | MIMAT0031180 |
| 224 | hsa-miR-8052 | MIMAT0030979 |
| 225 | hsa-miR-8069 | MIMAT0030996 |
| 226 | hsa-miR-8073 | MIMAT0031000 |
| 227 | hsa-miR-887-3p | MIMAT0004951 |
| 228 | hsa-miR-937-5p | MIMAT0022938 |
| 229 | hsa-miR-1202 | MIMAT0005865 |
| 230 | hsa-miR-1207-5p | MIMAT0005871 |
| 231 | hsa-miR-1246 | MIMAT0005898 |
| 232 | hsa-miR-1254 | MIMAT0005905 |
| 233 | hsa-miR-135a-3p | MIMAT0004595 |
| 234 | hsa-miR-1469 | MIMAT0007347 |
| 235 | hsa-miR-149-3p | MIMAT0004609 |
| 236 | hsa-miR-150-3p | MIMAT0004610 |
| 237 | hsa-miR-1914-3p | MIMAT0007890 |
| 238 | hsa-miR-191-5p | MIMAT0000440 |
| 239 | hsa-miR-423-5p | MIMAT0004748 |
| 240 | hsa-miR-663a | MIMAT0003326 |
| 241 | hsa-miR-92a-2-5p | MIMAT0004508 |
| 242 | hsa-miR-92a-3p | MIMAT0000092 |
| 243 | hsa-miR-940 | MIMAT0004983 |
| 244 | hsa-mir-6087 | MI0020364 |
| 245 | hsa-mir-1185-1 | MI0003844 |
| 246 | hsa-mir-1185-2 | MI0003821 |
| 247 | hsa-mir-1193 | MI0014205 |
| 248 | hsa-mir-1199 | MI0020340 |
| 249 | hsa-mir-1225 | MI0006311 |
| 250 | hsa-mir-1227 | MI0006316 |
| 251 | hsa-mir-1228 | MI0006318 |
| 252 | hsa-mir-1228 | MI0006318 |
| 253 | hsa-mir-1237 | MI0006327 |
| 254 | hsa-mir-1238 | MI0006328 |
| 255 | hsa-mir-1247 | MI0006382 |
| 256 | hsa-mir-1268a | MI0006405 |
| 257 | hsa-mir-1268b | MI0016748 |
| 258 | hsa-mir-1273g | MI0018003 |
| 259 | hsa-mir-128-2 | MI0000727 |
| 260 | hsa-mir-1343 | MI0017320 |
| 261 | hsa-mir-1343 | MI0017320 |
| 262 | hsa-mir-1470 | MI0007075 |
| 263 | hsa-mir-17 | MI0000071 |
| 264 | hsa-mir-187 | MI0000274 |
| 265 | hsa-mir-1908 | MI0008329 |
| 266 | hsa-mir-1908 | MI0008329 |
| 267 | hsa-mir-1909 | MI0008330 |
| 268 | hsa-mir-1915 | MI0008336 |
| 269 | hsa-mir-210 | MI0000286 |
| 270 | hsa-mir-2467 | MI0017432 |
| 271 | hsa-mir-2861 | MI0013006 |
| 272 | hsa-mir-296 | MI0000747 |
| 273 | hsa-mir-3131 | MI0014151 |
| 274 | hsa-mir-3154 | MI0014182 |
| 275 | hsa-mir-3162 | MI0014192 |
| 276 | hsa-mir-3178 | MI0014212 |
| 277 | hsa-mir-3184 | MI0014226 |
| 278 | hsa-mir-3185 | MI0014227 |
| 279 | hsa-mir-3194 | MI0014239 |
| 280 | hsa-mir-3195 | MI0014240 |
| 281 | hsa-mir-3197 | MI0014245 |
| 282 | hsa-mir-320a | MI0000542 |
| 283 | hsa-mir-328 | MI0000804 |
| 284 | hsa-mir-342 | MI0000805 |
| 285 | hsa-mir-345 | MI0000825 |
| 286 | hsa-mir-3616 | MI0016006 |
| 287 | hsa-mir-3619 | MI0016009 |
| 288 | hsa-mir-3620 | MI0016011 |
| 289 | hsa-mir-3621 | MI0016012 |
| 290 | hsa-mir-3622a | MI0016013 |
| 291 | hsa-mir-3652 | MI0016052 |
| 292 | hsa-mir-3656 | MI0016056 |
| 293 | hsa-mir-3663 | MI0016064 |
| 294 | hsa-mir-3679 | MI0016080 |
| 295 | hsa-mir-371b | MI0017393 |
| 296 | hsa-mir-373 | MI0000781 |
| 297 | hsa-mir-3917 | MI0016423 |
| 298 | hsa-mir-3940 | MI0016597 |
| 299 | hsa-mir-3960 | MI0016964 |
| 300 | hsa-mir-4258 | MI0015857 |
| 301 | hsa-mir-4259 | MI0015858 |
| 302 | hsa-mir-4270 | MI0015878 |
| 303 | hsa-mir-4286 | MI0015894 |
| 304 | hsa-mir-4298 | MI0015830 |
| 305 | hsa-mir-4322 | MI0015851 |
| 306 | hsa-mir-4327 | MI0015867 |
| 307 | hsa-mir-4417 | MI0016753 |
| 308 | hsa-mir-4419b | MI0016861 |
| 309 | hsa-mir-4429 | MI0016768 |
| 310 | hsa-mir-4430 | MI0016769 |
| 311 | hsa-mir-4433a | MI0016773 |
| 312 | hsa-mir-4443 | MI0016786 |
| 313 | hsa-mir-4446 | MI0016789 |
| 314 | hsa-mir-4447 | MI0016790 |
| 315 | hsa-mir-4448 | MI0016791 |
| 316 | hsa-mir-4449 | MI0016792 |
| 317 | hsa-mir-4454 | MI0016800 |
| 318 | hsa-mir-4455 | MI0016801 |
| 319 | hsa-mir-4459 | MI0016805 |
| 320 | hsa-mir-4462 | MI0016810 |
| 321 | hsa-mir-4466 | MI0016817 |
| 322 | hsa-mir-4467 | MI0016818 |
| 323 | hsa-mir-4480 | MI0016841 |
| 324 | hsa-mir-4483 | MI0016844 |
| 325 | hsa-mir-4484 | MI0016845 |
| 326 | hsa-mir-4485 | MI0016846 |
| 327 | hsa-mir-4488 | MI0016849 |
| 328 | hsa-mir-4492 | MI0016854 |
| 329 | hsa-mir-4505 | MI0016868 |
| 330 | hsa-mir-4515 | MI0016881 |
| 331 | hsa-mir-4525 | MI0016892 |
| 332 | hsa-mir-4534 | MI0016901 |
| 333 | hsa-mir-4535 | MI0016903 |
| 334 | hsa-mir-4633 | MI0017260 |
| 335 | hsa-mir-4634 | MI0017261 |
| 336 | hsa-mir-4640 | MI0017267 |
| 337 | hsa-mir-4649 | MI0017276 |
| 338 | hsa-mir-4651 | MI0017279 |
| 339 | hsa-mir-4652 | MI0017280 |
| 340 | hsa-mir-4655 | MI0017283 |
| 341 | hsa-mir-4656 | MI0017284 |
| 342 | hsa-mir-4658 | MI0017286 |
| 343 | hsa-mir-4663 | MI0017292 |
| 344 | hsa-mir-4673 | MI0017304 |
| 345 | hsa-mir-4675 | MI0017306 |
| 346 | hsa-mir-4687 | MI0017319 |
| 347 | hsa-mir-4687 | MI0017319 |

TABLE 1-continued

| SEQ ID NO | Name of gene | MIMAT No. |
|---|---|---|
| 348 | hsa-mir-4690 | MI0017323 |
| 349 | hsa-mir-4695 | MI0017328 |
| 350 | hsa-mir-4697 | MI0017330 |
| 351 | hsa-mir-4706 | MI0017339 |
| 352 | hsa-mir-4707 | MI0017340 |
| 353 | hsa-mir-4707 | MI0017340 |
| 354 | hsa-mir-4708 | MI0017341 |
| 355 | hsa-mir-4710 | MI0017344 |
| 356 | hsa-mir-4718 | MI0017353 |
| 357 | hsa-mir-4722 | MI0017357 |
| 358 | hsa-mir-4725 | MI0017362 |
| 359 | hsa-mir-4726 | MI0017363 |
| 360 | hsa-mir-4727 | MI0017364 |
| 361 | hsa-mir-4728 | MI0017365 |
| 362 | hsa-mir-4731 | MI0017368 |
| 363 | hsa-mir-4736 | MI0017373 |
| 364 | hsa-mir-4739 | MI0017377 |
| 365 | hsa-mir-4740 | MI0017378 |
| 366 | hsa-mir-4741 | MI0017379 |
| 367 | hsa-mir-4750 | MI0017389 |
| 368 | hsa-mir-4755 | MI0017395 |
| 369 | hsa-mir-4763 | MI0017404 |
| 370 | hsa-mir-4783 | MI0017428 |
| 371 | hsa-mir-4783 | MI0017428 |
| 372 | hsa-mir-4787 | MI0017434 |
| 373 | hsa-mir-4792 | MI0017439 |
| 374 | hsa-mir-498 | MI0003142 |
| 375 | hsa-mir-5008 | MI0017876 |
| 376 | hsa-mir-5010 | MI0017878 |
| 377 | hsa-mir-504 | MI0003189 |
| 378 | hsa-mir-5195 | MI0018174 |
| 379 | hsa-mir-5572 | MI0019117 |
| 380 | hsa-mir-5739 | MI0019412 |
| 381 | hsa-mir-6075 | MI0020352 |
| 382 | hsa-mir-6076 | MI0020353 |
| 383 | hsa-mir-6088 | MI0020365 |
| 384 | hsa-mir-6124 | MI0021258 |
| 385 | hsa-mir-6131 | MI0021276 |
| 386 | hsa-mir-6132 | MI0021277 |
| 387 | hsa-mir-614 | MI0003627 |
| 388 | hsa-mir-615 | MI0003628 |
| 389 | hsa-mir-619 | MI0003633 |
| 390 | hsa-mir-642b | MI0016685 |
| 391 | hsa-mir-6510 | MI0022222 |
| 392 | hsa-mir-6515 | MI0022227 |
| 393 | hsa-mir-6515 | MI0022227 |
| 394 | hsa-mir-663b | MI0006336 |
| 395 | hsa-mir-6716 | MI0022550 |
| 396 | hsa-mir-6717 | MI0022551 |
| 397 | hsa-mir-6722 | MI0022557 |
| 398 | hsa-mir-6726 | MI0022571 |
| 399 | hsa-mir-6737 | MI0022582 |
| 400 | hsa-mir-6741 | MI0022586 |
| 401 | hsa-mir-6742 | MI0022587 |
| 402 | hsa-mir-6743 | MI0022588 |
| 403 | hsa-mir-6746 | MI0022591 |
| 404 | hsa-mir-6749 | MI0022594 |
| 405 | hsa-mir-6760 | MI0022605 |
| 406 | hsa-mir-6762 | MI0022607 |
| 407 | hsa-mir-6765 | MI0022610 |
| 408 | hsa-mir-6765 | MI0022610 |
| 409 | hsa-mir-6766 | MI0022611 |
| 410 | hsa-mir-6766 | MI0022611 |
| 411 | hsa-mir-6771 | MI0022616 |
| 412 | hsa-mir-6774 | MI0022619 |
| 413 | hsa-mir-6777 | MI0022622 |
| 414 | hsa-mir-6778 | MI0022623 |
| 415 | hsa-mir-6780b | MI0022681 |
| 416 | hsa-mir-6781 | MI0022626 |
| 417 | hsa-mir-6782 | MI0022627 |
| 418 | hsa-mir-6784 | MI0022629 |
| 419 | hsa-mir-6785 | MI0022630 |
| 420 | hsa-mir-6787 | MI0022632 |
| 421 | hsa-mir-6789 | MI0022634 |
| 422 | hsa-mir-6791 | MI0022636 |
| 423 | hsa-mir-6794 | MI0022639 |
| 424 | hsa-mir-6800 | MI0022645 |
| 425 | hsa-mir-6802 | MI0022647 |
| 426 | hsa-mir-6803 | MI0022648 |
| 427 | hsa-mir-6812 | MI0022657 |
| 428 | hsa-mir-6816 | MI0022661 |
| 429 | hsa-mir-6819 | MI0022664 |
| 430 | hsa-mir-6821 | MI0022666 |
| 431 | hsa-mir-6826 | MI0022671 |
| 432 | hsa-mir-6831 | MI0022676 |
| 433 | hsa-mir-6836 | MI0022682 |
| 434 | hsa-mir-6840 | MI0022686 |
| 435 | hsa-mir-6842 | MI0022688 |
| 436 | hsa-mir-6850 | MI0022696 |
| 437 | hsa-mir-6861 | MI0022708 |
| 438 | hsa-mir-6869 | MI0022716 |
| 439 | hsa-mir-6870 | MI0022717 |
| 440 | hsa-mir-6877 | MI0022724 |
| 441 | hsa-mir-6879 | MI0022726 |
| 442 | hsa-mir-6880 | MI0022727 |
| 443 | hsa-mir-6880 | MI0022727 |
| 444 | hsa-mir-6885 | MI0022732 |
| 445 | hsa-mir-6887 | MI0022734 |
| 446 | hsa-mir-7107 | MI0022958 |
| 447 | hsa-mir-7108 | MI0022959 |
| 448 | hsa-mir-7109 | MI0022960 |
| 449 | hsa-mir-711 | MI0012488 |
| 450 | hsa-mir-7113 | MI0022964 |
| 451 | hsa-mir-7150 | MI0023610 |
| 452 | hsa-mir-744 | MI0005559 |
| 453 | hsa-mir-7975 | MI0025751 |
| 454 | hsa-mir-7977 | MI0025753 |
| 455 | hsa-mir-8052 | MI0025888 |
| 456 | hsa-mir-8073 | MI0025909 |
| 457 | hsa-mir-887 | MI0005562 |
| 458 | hsa-mir-937 | MI0005759 |
| 459 | hsa-mir-1202 | MI0006334 |
| 460 | hsa-mir-1207 | MI0006340 |
| 461 | hsa-mir-1246 | MI0006381 |
| 462 | hsa-mir-135a-1 | MI0000452 |
| 463 | hsa-mir-1469 | MI0007074 |
| 464 | hsa-mir-149 | MI0000478 |
| 465 | hsa-mir-150 | MI0000479 |
| 466 | hsa-mir-1914 | MI0008335 |
| 467 | hsa-mir-191 | MI0000465 |
| 468 | hsa-mir-423 | MI0001445 |
| 469 | hsa-mir-663a | MI0003672 |
| 470 | hsa-mir-92a-2 | MI0000094 |
| 471 | hsa-mir-940 | MI0005762 |
| 472 | hsa-mir-24-1 | MI0000080 |
| 473 | hsa-mir-29b-1 | MI0000105 |
| 474 | hsa-mir-3158-1 | MI0014186 |
| 475 | hsa-mir-3160-1 | MI0014189 |
| 476 | hsa-mir-320b-1 | MI0003776 |
| 477 | hsa-mir-3648-1 | MI0016048 |
| 478 | hsa-mir-4436b-1 | MI0017425 |
| 479 | hsa-mir-4771-1 | MI0017412 |
| 480 | hsa-mir-550a-1 | MI0003600 |
| 481 | hsa-mir-8069-1 | MI0025905 |
| 482 | hsa-mir-1254-1 | MI0006388 |
| 483 | hsa-mir-92a-1 | MI0000093 |
| 484 | hsa-mir-24-2 | MI0000081 |
| 485 | hsa-mir-29b-2 | MI0000107 |
| 486 | hsa-mir-3158-2 | MI0014187 |
| 487 | hsa-mir-3160-2 | MI0014190 |
| 488 | hsa-mir-320b-2 | MI0003839 |
| 489 | hsa-mir-3648-2 | MI0031512 |
| 490 | hsa-mir-4436b-2 | MI0019110 |
| 491 | hsa-mir-4771-2 | MI0017413 |
| 492 | hsa-mir-550a-2 | MI0003601 |
| 493 | hsa-mir-8069-2 | MI0031519 |
| 494 | hsa-mir-1254-2 | MI0016747 |
| 495 | hsa-mir-92a-2 | MI0000094 |
| 496 | hsa-mir-3180-1 | MI0014214 |
| 497 | hsa-mir-3180-2 | MI0014215 |
| 498 | hsa-mir-3180-3 | MI0014217 |
| 499 | hsa-mir-6511a-1 | MI0022223 |

TABLE 1-continued

| SEQ ID NO | Name of gene | MIMAT No. |
|---|---|---|
| 500 | hsa-mir-6724-1 | MI0022559 |
| 501 | hsa-mir-6511a-2 | MI0023564 |
| 502 | hsa-mir-6724-2 | MI0031516 |
| 503 | hsa-mir-6511a-3 | MI0023565 |
| 504 | hsa-mir-6724-3 | MI0031517 |
| 505 | hsa-mir-6511a-4 | MI0023566 |
| 506 | hsa-mir-6724-4 | MI0031518 |
| 507 | isomiR example 1 of SEQ ID NO: 1 | — |
| 508 | isomiR example 2 of SEQ ID NO: 2 | — |
| 509 | isomiR example 3 of SEQ ID NO: 3 | — |
| 510 | isomiR example 4 of SEQ ID NO: 8 | — |
| 511 | isomiR example 5 of SEQ ID NO: 9 | — |
| 512 | isomiR example 6 of SEQ ID NO: 10 | — |
| 513 | isomiR example 7 of SEQ ID NO: 12 | — |
| 514 | isomiR example 8 of SEQ ID NO: 13 | — |
| 515 | isomiR example 9 of SEQ ID NO: 14 | — |
| 516 | isomiR example 10 of SEQ ID NO: 15 | — |
| 517 | isomiR example 11 of SEQ ID NO: 16 | — |
| 518 | isomiR example 12 of SEQ ID NO: 17 | — |
| 519 | isomiR example 13 of SEQ ID NO: 20 | — |
| 520 | isomiR example 14 of SEQ ID NO: 21 | — |
| 521 | isomiR example 15 of SEQ ID NO: 22 | — |
| 522 | isomiR example 16 of SEQ ID NO: 24 | — |
| 523 | isomiR example 17 of SEQ ID NO: 25 | — |
| 524 | isomiR example 18 of SEQ ID NO: 26 | — |
| 525 | isomiR example 19 of SEQ ID NO: 27 | — |
| 526 | isomiR example 20 of SEQ ID NO: 28 | — |
| 527 | isomiR example 21 of SEQ ID NO: 29 | — |
| 528 | isomiR example 22 of SEQ ID NO: 30 | — |
| 529 | isomiR example 23 of SEQ ID NO: 31 | — |
| 530 | isomiR example 24 of SEQ ID NO: 32 | — |
| 531 | isomiR example 25 of SEQ ID NO: 33 | — |
| 532 | isomiR example 26 of SEQ ID NO: 34 | — |
| 533 | isomiR example 27 of SEQ ID NO: 36 | — |
| 534 | isomiR example 28 of SEQ ID NO: 37 | — |
| 535 | isomiR example 29 of SEQ ID NO: 38 | — |
| 536 | isomiR example 30 of SEQ ID NO: 42 | — |
| 537 | isomiR example 31 of SEQ ID NO: 43 | — |
| 538 | isomiR example 32 of SEQ ID NO: 44 | — |
| 539 | isomiR example 33 of SEQ ID NO: 45 | — |
| 540 | isomiR example 34 of SEQ ID NO: 46 | — |
| 541 | isomiR example 35 of SEQ ID NO: 47 | — |
| 542 | isomiR example 36 of SEQ ID NO: 48 | — |
| 543 | isomiR example 37 of SEQ ID NO: 49 | — |
| 544 | isomiR example 38 of SEQ ID NO: 51 | — |
| 545 | isomiR example 39 of SEQ ID NO: 54 | — |
| 546 | isomiR example 40 of SEQ ID NO: 55 | — |
| 547 | isomiR example 41 of SEQ ID NO: 56 | — |
| 548 | isomiR example 42 of SEQ ID NO: 58 | — |
| 549 | isomiR example 43 of SEQ ID NO: 61 | — |
| 550 | isomiR example 44 of SEQ ID NO: 62 | — |
| 551 | isomiR example 45 of SEQ ID NO: 63 | — |
| 552 | isomiR example 46 of SEQ ID NO: 67 | — |
| 553 | isomiR example 47 of SEQ ID NO: 68 | — |
| 554 | isomiR example 48 of SEQ ID NO: 69 | — |
| 555 | isomiR example 49 of SEQ ID NO: 71 | — |
| 556 | isomiR example 50 of SEQ ID NO: 72 | — |
| 557 | isomiR example 51 of SEQ ID NO: 73 | — |
| 558 | isomiR example 52 of SEQ ID NO: 74 | — |
| 559 | isomiR example 53 of SEQ ID NO: 75 | — |
| 560 | isomiR example 54 of SEQ ID NO: 77 | — |
| 561 | isomiR example 55 of SEQ ID NO: 78 | — |
| 562 | isomiR example 56 of SEQ ID NO: 80 | — |
| 563 | isomiR example 57 of SEQ ID NO: 81 | — |
| 564 | isomiR example 58 of SEQ ID NO: 82 | — |
| 565 | isomiR example 59 of SEQ ID NO: 84 | — |
| 566 | isomiR example 60 of SEQ ID NO: 86 | — |
| 567 | isomiR example 61 of SEQ ID NO: 87 | — |
| 568 | isomiR example 62 of SEQ ID NO: 89 | — |
| 569 | isomiR example 63 of SEQ ID NO: 90 | — |
| 570 | isomiR example 64 of SEQ ID NO: 91 | — |
| 571 | isomiR example 65 of SEQ ID NO: 92 | — |
| 572 | isomiR example 66 of SEQ ID NO: 93 | — |
| 573 | isomiR example 67 of SEQ ID NO: 94 | — |
| 574 | isomiR example 68 of SEQ ID NO: 95 | — |
| 575 | isomiR example 69 of SEQ ID NO: 96 | — |
| 576 | isomiR example 70 of SEQ ID NO: 101 | — |
| 577 | isomiR example 71 of SEQ ID NO: 103 | — |
| 578 | isomiR example 72 of SEQ ID NO: 105 | — |
| 579 | isomiR example 73 of SEQ ID NO: 109 | — |
| 580 | isomiR example 74 of SEQ ID NO: 111 | — |
| 581 | isomiR example 75 of SEQ ID NO: 113 | — |
| 582 | isomiR example 76 of SEQ ID NO: 114 | — |
| 583 | isomiR example 77 of SEQ ID NO: 116 | — |
| 584 | isomiR example 78 of SEQ ID NO: 117 | — |
| 585 | isomiR example 79 of SEQ ID NO: 118 | — |
| 586 | isomiR example 80 of SEQ ID NO: 119 | — |
| 587 | isomiR example 81 of SEQ ID NO: 123 | — |
| 588 | isomiR example 82 of SEQ ID NO: 124 | — |
| 589 | isomiR example 83 of SEQ ID NO: 126 | — |
| 590 | isomiR example 84 of SEQ ID NO: 127 | — |
| 591 | isomiR example 85 of SEQ ID NO: 129 | — |
| 592 | isomiR example 86 of SEQ ID NO: 131 | — |
| 593 | isomiR example 87 of SEQ ID NO: 132 | — |
| 594 | isomiR example 88 of SEQ ID NO: 133 | — |
| 595 | isomiR example 89 of SEQ ID NO: 134 | — |
| 596 | isomiR example 90 of SEQ ID NO: 135 | — |
| 597 | isomiR example 91 of SEQ ID NO: 136 | — |
| 598 | isomiR example 92 of SEQ ID NO: 139 | — |
| 599 | isomiR example 93 of SEQ ID NO: 142 | — |
| 600 | isomiR example 94 of SEQ ID NO: 143 | — |
| 601 | isomiR example 95 of SEQ ID NO: 146 | — |
| 602 | isomiR example 96 of SEQ ID NO: 150 | — |
| 603 | isomiR example 97 of SEQ ID NO: 151 | — |
| 604 | isomiR example 98 of SEQ ID NO: 152 | — |
| 605 | isomiR example 99 of SEQ ID NO: 153 | — |
| 606 | isomiR example 100 of SEQ ID NO: 154 | — |
| 607 | isomiR example 101 of SEQ ID NO: 155 | — |
| 608 | isomiR example 102 of SEQ ID NO: 156 | — |
| 609 | isomiR example 103 of SEQ ID NO: 157 | — |
| 610 | isomiR example 104 of SEQ ID NO: 158 | — |
| 611 | isomiR example 105 of SEQ ID NO: 159 | — |
| 612 | isomiR example 106 of SEQ ID NO: 161 | — |
| 613 | isomiR example 107 of SEQ ID NO: 162 | — |
| 614 | isomiR example 108 of SEQ ID NO: 163 | — |
| 615 | isomiR example 109 of SEQ ID NO: 164 | — |
| 616 | isomiR example 110 of SEQ ID NO: 166 | — |
| 617 | isomiR example 111 of SEQ ID NO: 218 | — |
| 618 | isomiR example 112 of SEQ ID NO: 221 | — |
| 619 | isomiR example 113 of SEQ ID NO: 227 | — |
| 620 | isomiR example 114 of SEQ ID NO: 228 | — |
| 621 | isomiR example 115 of SEQ ID NO: 231 | — |
| 622 | isomiR example 116 of SEQ ID NO: 232 | — |
| 623 | isomiR example 117 of SEQ ID NO: 233 | — |
| 624 | isomiR example 118 of SEQ ID NO: 235 | — |
| 625 | isomiR example 119 of SEQ ID NO: 236 | — |
| 626 | isomiR example 120 of SEQ ID NO: 237 | — |
| 627 | isomiR example 121 of SEQ ID NO: 238 | — |
| 628 | isomiR example 122 of SEQ ID NO: 239 | — |
| 629 | isomiR example 123 of SEQ ID NO: 240 | — |
| 630 | isomiR example 124 of SEQ ID NO: 241 | — |
| 631 | isomiR example 125 of SEQ ID NO: 242 | — |
| 632 | isomiR example 126 of SEQ ID NO: 243 | — |
| 633 | isomiR example 1 of SEQ ID NO: 1 | — |
| 634 | isomiR example 2 of SEQ ID NO: 2 | — |
| 635 | isomiR example 3 of SEQ ID NO: 3 | — |
| 636 | isomiR example 4 of SEQ ID NO: 4 | — |
| 637 | isomiR example 5 of SEQ ID NO: 8 | — |
| 638 | isomiR example 6 of SEQ ID NO: 9 | — |
| 639 | isomiR example 7 of SEQ ID NO: 10 | — |
| 640 | isomiR example 8 of SEQ ID NO: 12 | — |
| 641 | isomiR example 9 of SEQ ID NO: 13 | — |
| 642 | isomiR example 10 of SEQ ID NO: 14 | — |
| 643 | isomiR example 11 of SEQ ID NO: 15 | — |
| 644 | isomiR example 12 of SEQ ID NO: 16 | — |
| 645 | isomiR example 13 of SEQ ID NO: 17 | — |
| 646 | isomiR example 14 of SEQ ID NO: 19 | — |
| 647 | isomiR example 15 of SEQ ID NO: 20 | — |
| 648 | isomiR example 16 of SEQ ID NO: 21 | — |
| 649 | isomiR example 17 of SEQ ID NO: 22 | — |
| 650 | isomiR example 18 of SEQ ID NO: 24 | — |
| 651 | isomiR example 19 of SEQ ID NO: 25 | — |

TABLE 1-continued

| SEQ ID NO | Name of gene | MIMAT No. |
|---|---|---|
| 652 | isomiR example 20 of SEQ ID NO: 26 | — |
| 653 | isomiR example 21 of SEQ ID NO: 27 | — |
| 654 | isomiR example 22 of SEQ ID NO: 28 | — |
| 655 | isomiR example 23 of SEQ ID NO: 29 | — |
| 656 | isomiR example 24 of SEQ ID NO: 30 | — |
| 657 | isomiR example 25 of SEQ ID NO: 31 | — |
| 658 | isomiR example 26 of SEQ ID NO: 32 | — |
| 659 | isomiR example 27 of SEQ ID NO: 33 | — |
| 660 | isomiR example 28 of SEQ ID NO: 34 | — |
| 661 | isomiR example 29 of SEQ ID NO: 36 | — |
| 662 | isomiR example 30 of SEQ ID NO: 37 | — |
| 663 | isomiR example 31 of SEQ ID NO: 38 | — |
| 664 | isomiR example 32 of SEQ ID NO: 40 | — |
| 665 | isomiR example 33 of SEQ ID NO: 41 | — |
| 666 | isomiR example 34 of SEQ ID NO: 42 | — |
| 667 | isomiR example 35 of SEQ ID NO: 43 | — |
| 668 | isomiR example 36 of SEQ ID NO: 44 | — |
| 669 | isomiR example 37 of SEQ ID NO: 45 | — |
| 670 | isomiR example 38 of SEQ ID NO: 46 | — |
| 671 | isomiR example 39 of SEQ ID NO: 47 | — |
| 672 | isomiR example 40 of SEQ ID NO: 48 | — |
| 673 | isomiR example 41 of SEQ ID NO: 49 | — |
| 674 | isomiR example 42 of SEQ ID NO: 51 | — |
| 675 | isomiR example 43 of SEQ ID NO: 53 | — |
| 676 | isomiR example 44 of SEQ ID NO: 54 | — |
| 677 | isomiR example 45 of SEQ ID NO: 55 | — |
| 678 | isomiR example 46 of SEQ ID NO: 56 | — |
| 679 | isomiR example 47 of SEQ ID NO: 58 | — |
| 680 | isomiR example 48 of SEQ ID NO: 61 | — |
| 681 | isomiR example 49 of SEQ ID NO: 62 | — |
| 682 | isomiR example 50 of SEQ ID NO: 63 | — |
| 683 | isomiR example 51 of SEQ ID NO: 67 | — |
| 684 | isomiR example 52 of SEQ ID NO: 68 | — |
| 685 | isomiR example 53 of SEQ ID NO: 71 | — |
| 686 | isomiR example 54 of SEQ ID NO: 72 | — |
| 687 | isomiR example 55 of SEQ ID NO: 73 | — |
| 688 | isomiR example 56 of SEQ ID NO: 74 | — |
| 689 | isomiR example 57 of SEQ ID NO: 75 | — |
| 690 | isomiR example 58 of SEQ ID NO: 77 | — |
| 691 | isomiR example 59 of SEQ ID NO: 78 | — |
| 692 | isomiR example 60 of SEQ ID NO: 80 | — |
| 693 | isomiR example 61 of SEQ ID NO: 81 | — |
| 694 | isomiR example 62 of SEQ ID NO: 82 | — |
| 695 | isomiR example 63 of SEQ ID NO: 84 | — |
| 696 | isomiR example 64 of SEQ ID NO: 86 | — |
| 697 | isomiR example 65 of SEQ ID NO: 90 | — |
| 698 | isomiR example 66 of SEQ ID NO: 91 | — |
| 699 | isomiR example 67 of SEQ ID NO: 92 | — |
| 700 | isomiR example 68 of SEQ ID NO: 93 | — |
| 701 | isomiR example 69 of SEQ ID NO: 95 | — |
| 702 | isomiR example 70 of SEQ ID NO: 96 | — |
| 703 | isomiR example 71 of SEQ ID NO: 101 | — |
| 704 | isomiR example 72 of SEQ ID NO: 105 | — |
| 705 | isomiR example 73 of SEQ ID NO: 107 | — |
| 706 | isomiR example 74 of SEQ ID NO: 109 | — |
| 707 | isomiR example 75 of SEQ ID NO: 111 | — |
| 708 | isomiR example 76 of SEQ ID NO: 112 | — |
| 709 | isomiR example 77 of SEQ ID NO: 113 | — |
| 710 | isomiR example 78 of SEQ ID NO: 114 | — |
| 711 | isomiR example 79 of SEQ ID NO: 116 | — |
| 712 | isomiR example 80 of SEQ ID NO: 117 | — |
| 713 | isomiR example 81 of SEQ ID NO: 118 | — |
| 714 | isomiR example 82 of SEQ ID NO: 119 | — |
| 715 | isomiR example 83 of SEQ ID NO: 120 | — |
| 716 | isomiR example 84 of SEQ ID NO: 122 | — |
| 717 | isomiR example 85 of SEQ ID NO: 123 | — |
| 718 | isomiR example 86 of SEQ ID NO: 124 | — |
| 719 | isomiR example 87 of SEQ ID NO: 125 | — |
| 720 | isomiR example 88 of SEQ ID NO: 126 | — |
| 721 | isomiR example 89 of SEQ ID NO: 127 | — |
| 722 | isomiR example 90 of SEQ ID NO: 129 | — |
| 723 | isomiR example 91 of SEQ ID NO: 131 | — |
| 724 | isomiR example 92 of SEQ ID NO: 132 | — |
| 725 | isomiR example 93 of SEQ ID NO: 133 | — |
| 726 | isomiR example 94 of SEQ ID NO: 134 | — |
| 727 | isomiR example 95 of SEQ ID NO: 135 | — |
| 728 | isomiR example 96 of SEQ ID NO: 136 | — |
| 729 | isomiR example 97 of SEQ ID NO: 138 | — |
| 730 | isomiR example 98 of SEQ ID NO: 139 | — |
| 731 | isomiR example 99 of SEQ ID NO: 142 | — |
| 732 | isomiR example 100 of SEQ ID NO: 143 | — |
| 733 | isomiR example 101 of SEQ ID NO: 145 | — |
| 734 | isomiR example 102 of SEQ ID NO: 146 | — |
| 735 | isomiR example 103 of SEQ ID NO: 150 | — |
| 736 | isomiR example 104 of SEQ ID NO: 151 | — |
| 737 | isomiR example 105 of SEQ ID NO: 152 | — |
| 738 | isomiR example 106 of SEQ ID NO: 154 | — |
| 739 | isomiR example 107 of SEQ ID NO: 155 | — |
| 740 | isomiR example 108 of SEQ ID NO: 156 | — |
| 741 | isomiR example 109 of SEQ ID NO: 157 | — |
| 742 | isomiR example 110 of SEQ ID NO: 158 | — |
| 743 | isomiR example 111 of SEQ ID NO: 159 | — |
| 744 | isomiR example 112 of SEQ ID NO: 161 | — |
| 745 | isomiR example 113 of SEQ ID NO: 162 | — |
| 746 | isomiR example 114 of SEQ ID NO: 163 | — |
| 747 | isomiR example 115 of SEQ ID NO: 164 | — |
| 748 | isomiR example 116 of SEQ ID NO: 166 | — |
| 749 | isomiR example 117 of SEQ ID NO: 218 | — |
| 750 | isomiR example 118 of SEQ ID NO: 221 | — |
| 751 | isomiR example 119 of SEQ ID NO: 222 | — |
| 752 | isomiR example 120 of SEQ ID NO: 227 | — |
| 753 | isomiR example 121 of SEQ ID NO: 228 | — |
| 754 | isomiR example 122 of SEQ ID NO: 229 | — |
| 755 | isomiR example 123 of SEQ ID NO: 231 | — |
| 756 | isomiR example 124 of SEQ ID NO: 232 | — |
| 757 | isomiR example 125 of SEQ ID NO: 233 | — |
| 758 | isomiR example 126 of SEQ ID NO: 235 | — |
| 759 | isomiR example 127 of SEQ ID NO: 236 | — |
| 760 | isomiR example 128 of SEQ ID NO: 237 | — |
| 761 | isomiR example 129 of SEQ ID NO: 238 | — |
| 762 | isomiR example 130 of SEQ ID NO: 239 | — |
| 763 | isomiR example 131 of SEQ ID NO: 240 | — |
| 764 | isomiR example 132 of SEQ ID NO: 241 | — |
| 765 | isomiR example 133 of SEQ ID NO: 242 | — |
| 766 | isomiR example 134 of SEQ ID NO: 243 | — |

The present specification encompasses the contents disclosed in Japanese Patent Application No. 2018-084416 from which the present application claims priority.

Advantageous Effect of Invention

The present invention enables easy detection of bladder cancer with high accuracy. For example, whether or not a subject has bladder cancer can be detected easily with the use of the measured expression level(s) of one or several miRNAs in the blood, serum, and/or plasma that can be collected less invasively from the subject as an indicator(s).

DESCRIPTION OF EMBODIMENTS

Figure 1:
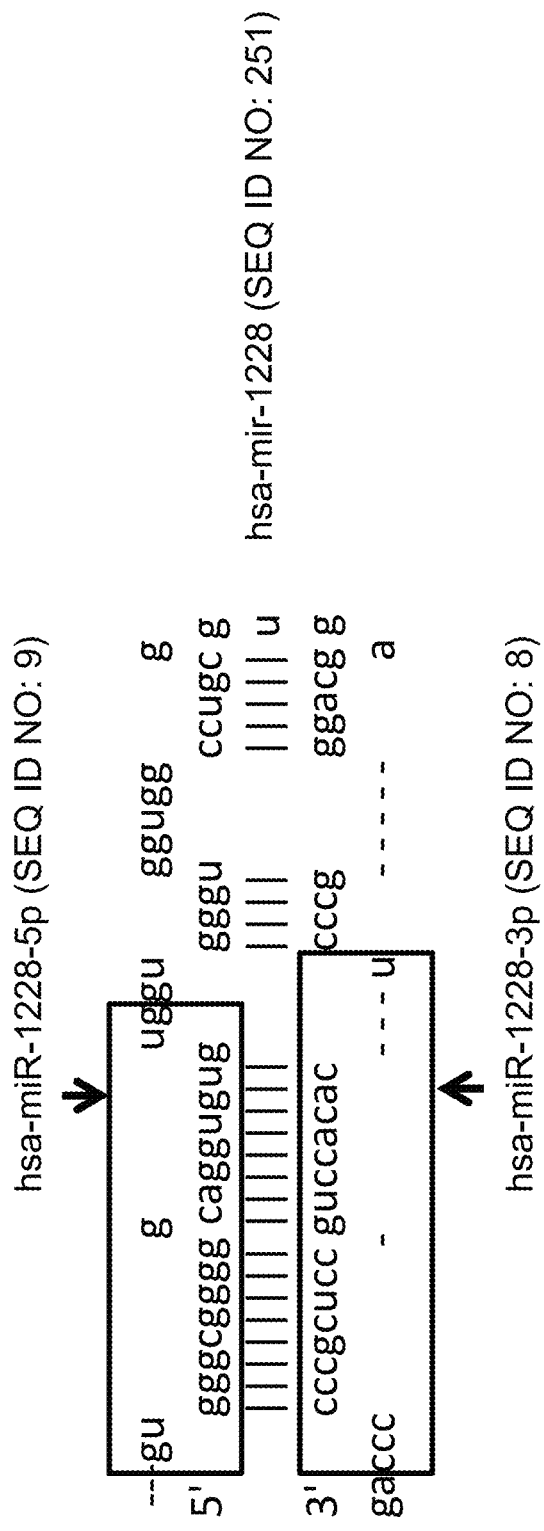
FIG. 1 illustrates the relationship between the nucleotide sequences of hsa-miR-1228-5p represented by SEQ ID NO: 9 and hsa-miR-1228-3p represented by SEQ ID NO: 8, which are generated from a precursor hsa-mir-1228 represented by SEQ ID NO: 251.

Hereinafter, the present invention will be further described in detail.

1. Target Nucleic Acid(s) for Bladder Cancer

The major target nucleic acids as bladder cancer markers for detecting bladder cancer or the presence and/or absence of bladder cancer cells by using the nucleic acid probes or primers for detection of bladder cancer as defined above according to the present invention include at least one miRNA selected from the group consisting of miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR- 504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, and miR-937-5p. Further, it is possible to preferably use, as target nucleic acid(s), other bladder cancer markers that can be combined with these miRNAs, specifically at least one miRNA selected from the group consisting of miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940.

Examples of the above miRNAs include any human gene containing any nucleotide sequence represented by any of SEQ ID NOs: 1 to 243 (i.e., respective miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, miR-937-5p, miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, miR-940), any congener thereof, any transcript thereof, and any variant or derivative thereof. Here, the gene, congener, transcript, variant, and derivative are as defined above.

Preferable target nucleic acid(s) is any human gene containing any nucleotide sequence represented by any of SEQ ID NOs: 1 to 243 or any transcript thereof, and more preferably is the corresponding transcript, namely miRNA and any precursor RNA such as pri-miRNA or pre-miRNA thereof.

The 1st target gene is the hsa-miR-6087 gene, a congener thereof, a transcript thereof, or a variant or derivative thereof. None of the previously known reports show that change in the expression of the gene or the transcript thereof can serve as a marker for bladder cancer.

The 2nd target gene is the hsa-miR-1185-1-3p gene, a congener thereof, a transcript thereof, or a variant or derivative thereof. None of the previously known reports show that change in the expression of the gene or the transcript thereof can serve as a marker for bladder cancer.

The 3rd target gene is the hsa-miR-1185-2-3p gene, a congener thereof, a transcript thereof, or a variant or derivative thereof. None of the previously known reports show that change in the expression of the gene or the transcript thereof can serve as a marker for bladder cancer.

The 4th target gene is the hsa-miR-1193 gene, a congener thereof, a transcript thereof, or a variant or derivative thereof. None of the previously known reports show that change in the expression of the gene or the transcript thereof can serve as a marker for bladder cancer.

The 5th target gene is the hsa-miR-1199-5p gene, a congener thereof, a transcript thereof, or a variant or derivative thereof. None of the previously known reports show that change in the expression of the gene or the transcript thereof can serve as a marker for bladder cancer.

The 6th target gene is the hsa-miR-1225-5p gene, a congener thereof, a transcript thereof, or a variant or derivative thereof. None of the previously known reports show that change in the expression of the gene or the transcript thereof can serve as a marker for bladder cancer.

The 7th target gene is the hsa-miR-1227-5p gene, a congener thereof, a transcript thereof, or a variant or derivative thereof. None of the previously known reports show that change in the expression of the gene or the transcript thereof can serve as a marker for bladder cancer.

The 8th target gene is the hsa-miR-1228-3p gene, a congener thereof, a transcript thereof, or a variant or derivative thereof. None of the previously known reports show that change in the expression of the gene or the transcript thereof can serve as a marker for bladder cancer.

The 9th target gene is the hsa-miR-1228-5p gene, a congener thereof, a transcript thereof, or a variant or derivative thereof. None of the previously known reports show that change in the expression of the gene or the transcript thereof can serve as a marker for bladder cancer.

The 10th target gene is the hsa-miR-1237-5p gene, a congener thereof, a transcript thereof, or a variant or derivative thereof. None of the previously known reports show that change in the expression of the gene or the transcript thereof can serve as a marker for bladder cancer.

The 11th target gene is the hsa-miR-1238-5p gene, a congener thereof, a transcript thereof, or a variant or derivative thereof. None of the previously known reports show that change in the expression of the gene or the transcript thereof can serve as a marker for bladder cancer.

The 12th target gene is the hsa-miR-1247-3p gene, a congener thereof, a transcript thereof, or a variant or derivative thereof. None of the previously known reports show that change in the expression of the gene or the transcript thereof can serve as a marker for bladder cancer.

The 13th target gene is the hsa-miR-1268a gene, a congener thereof, a transcript thereof, or a variant or derivative thereof. None of the previously known reports show that change in the expression of the gene or the transcript thereof can serve as a marker for bladder cancer.

The 14th target gene is the hsa-miR-1268b gene, a congener thereof, a transcript thereof, or a variant or derivative thereof. None of the previously known reports show that change in the expression of the gene or the transcript thereof can serve as a marker for bladder cancer.

The 15th target gene is the hsa-miR-1273g-3p gene, a congener thereof, a transcript thereof, or a variant or derivative thereof. None of the previously known reports show that change in the expression of the gene or the transcript thereof can serve as a marker for bladder cancer.

The 16th target gene is the hsa-miR-128-2-5p gene, a congener thereof, a transcript thereof, or a variant or derivative thereof. None of the previously known reports show that change in the expression of the gene or the transcript thereof can serve as a marker for bladder cancer.

The 17th target gene is the hsa-miR-1343-3p gene, a congener thereof, a transcript thereof, or a variant or derivative thereof. None of the previously known reports show that change in the expression of the gene or the transcript thereof can serve as a marker for bladder cancer.

The 18th target gene is the hsa-miR-1343-5p gene, a congener thereof, a transcript thereof, or a variant or derivative thereof. None of the previously known reports show that change in the expression of the gene or the transcript thereof can serve as a marker for bladder cancer.

The 19th target gene is the hsa-miR-1470 gene, a congener thereof, a transcript thereof, or a variant or derivative thereof. None of the previously known reports show that change in the expression of the gene or the transcript thereof can serve as a marker for bladder cancer.

The 20th target gene is the hsa-miR-17-3p gene, a congener thereof, a transcript thereof, or a variant or derivative thereof. None of the previously known reports show that change in the expression of the gene or the transcript thereof can serve as a marker for bladder cancer.

The 21st target gene is the hsa-miR-187-5p gene, a congener thereof, a transcript thereof, or a variant or derivative thereof. None of the previously known reports show that change in the expression of the gene or the transcript thereof can serve as a marker for bladder cancer.

The 22nd target gene is the hsa-miR-1908-3p gene, a congener thereof, a transcript thereof, or a variant or derivative thereof. None of the previously known reports show that change in the expression of the gene or the transcript thereof can serve as a marker for bladder cancer.

The 23rd target gene is the hsa-miR-1908-5p gene, a congener thereof, a transcript thereof, or a variant or derivative thereof. None of the previously known reports show that change in the expression of the gene or the transcript thereof can serve as a marker for bladder cancer.

The 24th target gene is the hsa-miR-1909-3p gene, a congener thereof, a transcript thereof, or a variant or derivative thereof. None of the previously known reports show that change in the expression of the gene or the transcript thereof can serve as a marker for bladder cancer.

The 25th target gene is the hsa-miR-1915-3p gene, a congener thereof, a transcript thereof, or a variant or derivative thereof. None of the previously known reports show that change in the expression of the gene or the transcript thereof can serve as a marker for bladder cancer.

The 26th target gene is the hsa-miR-210-5p gene, a congener thereof, a transcript thereof, or a variant or derivative thereof. None of the previously known reports show that change in the expression of the gene or the transcript thereof can serve as a marker for bladder cancer.

The 27th target gene is the hsa-miR-24-3p gene, a congener thereof, a transcript thereof, or a variant or derivative thereof. None of the previously known reports show that change in the expression of the gene or the transcript thereof can serve as a marker for bladder cancer.

The 28th target gene is the hsa-miR-2467-3p gene, a congener thereof, a transcript thereof, or a variant or derivative thereof. None of the previously known reports show that change in the expression of the gene or the transcript thereof can serve as a marker for bladder cancer.

The 29th target gene is the hsa-miR-2861 gene, a congener thereof, a transcript thereof, or a variant or derivative thereof. None of the previously known reports show that change in the expression of the gene or the transcript thereof can serve as a marker for bladder cancer.

The 30th target gene is the hsa-miR-296-3p gene, a congener thereof, a transcript thereof, or a variant or derivative thereof. None of the previously known reports show that change in the expression of the gene or the transcript thereof can serve as a marker for bladder cancer.

The 31st target gene is the hsa-miR-29b-3p gene, a congener thereof, a transcript thereof, or a variant or derivative thereof. None of the previously known reports show that change in the expression of the gene or the transcript thereof can serve as a marker for bladder cancer.

The 32nd target gene is the hsa-miR-3131 gene, a congener thereof, a transcript thereof, or a variant or derivative thereof. None of the previously known reports show that change in the expression of the gene or the transcript thereof can serve as a marker for bladder cancer.

The 33rd target gene is the hsa-miR-3154 gene, a congener thereof, a transcript thereof, or a variant or derivative thereof. None of the previously known reports show that change in the expression of the gene or the transcript thereof can serve as a marker for bladder cancer.

The 34th target gene is the hsa-miR-3158-5p gene, a congener thereof, a transcript thereof, or a variant or derivative thereof. None of the previously known reports show that change in the expression of the gene or the transcript thereof can serve as a marker for bladder cancer.

The 35th target gene is the hsa-miR-3160-5p gene, a congener thereof, a transcript thereof, or a variant or derivative thereof. None of the previously known reports show that change in the expression of the gene or the transcript thereof can serve as a marker for bladder cancer.

The 36th target gene is the hsa-miR-3162-5p gene, a congener thereof, a transcript thereof, or a variant or derivative thereof. None of the previously known reports show that change in the expression of the gene or the transcript thereof can serve as a marker for bladder cancer.

The 37th target gene is the hsa-miR-3178 gene, a congener thereof, a transcript thereof, or a variant or derivative thereof. None of the previously known reports show that change in the expression of the gene or the transcript thereof can serve as a marker for bladder cancer.

The 38th target gene is the hsa-miR-3180-3p gene, a congener thereof, a transcript thereof, or a variant or derivative thereof. None of the previously known reports show that change in the expression of the gene or the transcript thereof can serve as a marker for bladder cancer.

The 39th target gene is the hsa-miR-3184-5p gene, a congener thereof, a transcript thereof, or a variant or derivative thereof. None of the previously known reports show that change in the expression of the gene or the transcript thereof can serve as a marker for bladder cancer.

The 40th target gene is the hsa-miR-3185 gene, a congener thereof, a transcript thereof, or a variant or derivative thereof. None of the previously known reports show that change in the expression of the gene or the transcript thereof can serve as a marker for bladder cancer.

The 41st target gene is the hsa-miR-3194-3p gene, a congener thereof, a transcript thereof, or a variant or derivative thereof. None of the previously known reports show that change in the expression of the gene or the transcript thereof can serve as a marker for bladder cancer.

The 42nd target gene is the hsa-miR-3195 gene, a congener thereof, a transcript thereof, or a variant or derivative thereof. None of the previously known reports show that change in the expression of the gene or the transcript thereof can serve as a marker for bladder cancer.

The 43rd target gene is the hsa-miR-3197 gene, a congener thereof, a transcript thereof, or a variant or derivative thereof. None of the previously known reports show that change in the expression of the gene or the transcript thereof can serve as a marker for bladder cancer.

The 44th target gene is the hsa-miR-320a gene, a congener thereof, a transcript thereof, or a variant or derivative thereof. None of the previously known reports show that change in the expression of the gene or the transcript thereof can serve as a marker for bladder cancer.

The 45th target gene is the hsa-miR-320b gene, a congener thereof, a transcript thereof, or a variant or derivative thereof. None of the previously known reports show that change in the expression of the gene or the transcript thereof can serve as a marker for bladder cancer.

The 46th target gene is the hsa-miR-328-5p gene, a congener thereof, a transcript thereof, or a variant or derivative thereof. None of the previously known reports show that change in the expression of the gene or the transcript thereof can serve as a marker for bladder cancer.

The 47th target gene is the hsa-miR-342-5p gene, a congener thereof, a transcript thereof, or a variant or derivative thereof. None of the previously known reports show that change in the expression of the gene or the transcript thereof can serve as a marker for bladder cancer.

The 48th target gene is the hsa-miR-345-3p gene, a congener thereof, a transcript thereof, or a variant or derivative thereof. None of the previously known reports show that change in the expression of the gene or the transcript thereof can serve as a marker for bladder cancer.

The 49th target gene is the hsa-miR-3616-3p gene, a congener thereof, a transcript thereof, or a variant or derivative thereof. None of the previously known reports show that change in the expression of the gene or the transcript thereof can serve as a marker for bladder cancer.

The 50th target gene is the hsa-miR-3619-3p gene, a congener thereof, a transcript thereof, or a variant or derivative thereof. None of the previously known reports show that change in the expression of the gene or the transcript thereof can serve as a marker for bladder cancer.

The 51st target gene is the hsa-miR-3620-5p gene, a congener thereof, a transcript thereof, or a variant or derivative thereof. None of the previously known reports show that change in the expression of the gene or the transcript thereof can serve as a marker for bladder cancer.

The 52nd target gene is the hsa-miR-3621 gene, a congener thereof, a transcript thereof, or a variant or derivative thereof. None of the previously known reports show that change in the expression of the gene or the transcript thereof can serve as a marker for bladder cancer.

The 53rd target gene is the hsa-miR-3622a-5p gene, a congener thereof, a transcript thereof, or a variant or derivative thereof. None of the previously known reports show that change in the expression of the gene or the transcript thereof can serve as a marker for bladder cancer.

The 54th target gene is the hsa-miR-3648 gene, a congener thereof, a transcript thereof, or a variant or derivative thereof. None of the previously known reports show that change in the expression of the gene or the transcript thereof can serve as a marker for bladder cancer.

The 55th target gene is the hsa-miR-3652 gene, a congener thereof, a transcript thereof, or a variant or derivative thereof. None of the previously known reports show that change in the expression of the gene or the transcript thereof can serve as a marker for bladder cancer.

The 56th target gene is the hsa-miR-3656 gene, a congener thereof, a transcript thereof, or a variant or derivative thereof. None of the previously known reports show that change in the expression of the gene or the transcript thereof can serve as a marker for bladder cancer.

The 57th target gene is the hsa-miR-3663-3p gene, a congener thereof, a transcript thereof, or a variant or derivative thereof. None of the previously known reports show that change in the expression of the gene or the transcript thereof can serve as a marker for bladder cancer.

The 58th target gene is the hsa-miR-3679-5p gene, a congener thereof, a transcript thereof, or a variant or derivative thereof. None of the previously known reports show that change in the expression of the gene or the transcript thereof can serve as a marker for bladder cancer.

The 59th target gene is the hsa-miR-371b-5p gene, a congener thereof, a transcript thereof, or a variant or derivative thereof. None of the previously known reports show that change in the expression of the gene or the transcript thereof can serve as a marker for bladder cancer.

The 60th target gene is the hsa-miR-373-5p gene, a congener thereof, a transcript thereof, or a variant or derivative thereof. None of the previously known reports show that change in the expression of the gene or the transcript thereof can serve as a marker for bladder cancer.

The 61st target gene is the hsa-miR-3917 gene, a congener thereof, a transcript thereof, or a variant or derivative thereof. None of the previously known reports show that change in the expression of the gene or the transcript thereof can serve as a marker for bladder cancer.

The 62nd target gene is the hsa-miR-3940-5p gene, a congener thereof, a transcript thereof, or a variant or derivative thereof. None of the previously known reports show that change in the expression of the gene or the transcript thereof can serve as a marker for bladder cancer.

The 63rd target gene is the hsa-miR-3960 gene, a congener thereof, a transcript thereof, or a variant or derivative thereof. None of the previously known reports show that change in the expression of the gene or the transcript thereof can serve as a marker for bladder cancer.

The 64th target gene is the hsa-miR-4258 gene, a congener thereof, a transcript thereof, or a variant or derivative thereof. None of the previously known reports show that change in the expression of the gene or the transcript thereof can serve as a marker for bladder cancer.

The 65th target gene is the hsa-miR-4259 gene, a congener thereof, a transcript thereof, or a variant or derivative thereof. None of the previously known reports show that change in the expression of the gene or the transcript thereof can serve as a marker for bladder cancer.

The 66th target gene is the hsa-miR-4270 gene, a congener thereof, a transcript thereof, or a variant or derivative thereof. None of the previously known reports show that change in the expression of the gene or the transcript thereof can serve as a marker for bladder cancer.

The 67th target gene is the hsa-miR-4286 gene, a congener thereof, a transcript thereof, or a variant or derivative thereof. None of the previously known reports show that change in the expression of the gene or the transcript thereof can serve as a marker for bladder cancer.

The 68th target gene is the hsa-miR-4298 gene, a congener thereof, a transcript thereof, or a variant or derivative thereof. None of the previously known reports show that change in the expression of the gene or the transcript thereof can serve as a marker for bladder cancer.

The 69th target gene is the hsa-miR-4322 gene, a congener thereof, a transcript thereof, or a variant or derivative thereof. None of the previously known reports show that change in the expression of the gene or the transcript thereof can serve as a marker for bladder cancer.

The 70th target gene is the hsa-miR-4327 gene, a congener thereof, a transcript thereof, or a variant or derivative thereof. None of the previously known reports show that change in the expression of the gene or the transcript thereof can serve as a marker for bladder cancer.

The 71st target gene is the hsa-miR-4417 gene, a congener thereof, a transcript thereof, or a variant or derivative thereof. None of the previously known reports show that change in the expression of the gene or the transcript thereof can serve as a marker for bladder cancer.

The 72nd target gene is the hsa-miR-4419b gene, a congener thereof, a transcript thereof, or a variant or derivative thereof. None of the previously known reports show that change in the expression of the gene or the transcript thereof can serve as a marker for bladder cancer.

The 73rd target gene is the hsa-miR-4429 gene, a congener thereof, a transcript thereof, or a variant or derivative thereof. None of the previously known reports show that change in the expression of the gene or the transcript thereof can serve as a marker for bladder cancer.

The 74th target gene is the hsa-miR-4430 gene, a congener thereof, a transcript thereof, or a variant or derivative thereof. None of the previously known reports show that change in the expression of the gene or the transcript thereof can serve as a marker for bladder cancer.

The 75th target gene is the hsa-miR-4433a-3p gene, a congener thereof, a transcript thereof, or a variant or derivative thereof. None of the previously known reports show that change in the expression of the gene or the transcript thereof can serve as a marker for bladder cancer.

The 76th target gene is the hsa-miR-4436b-5p gene, a congener thereof, a transcript thereof, or a variant or derivative thereof. None of the previously known reports show that change in the expression of the gene or the transcript thereof can serve as a marker for bladder cancer.

The 77th target gene is the hsa-miR-4443 gene, a congener thereof, a transcript thereof, or a variant or derivative thereof. None of the previously known reports show that change in the expression of the gene or the transcript thereof can serve as a marker for bladder cancer.

The 78th target gene is the hsa-miR-4446-3p gene, a congener thereof, a transcript thereof, or a variant or derivative thereof. None of the previously known reports show that change in the expression of the gene or the transcript thereof can serve as a marker for bladder cancer.

The 79th target gene is the hsa-miR-4447 gene, a congener thereof, a transcript thereof, or a variant or derivative thereof. None of the previously known reports show that change in the expression of the gene or the transcript thereof can serve as a marker for bladder cancer.

The 80th target gene is the hsa-miR-4448 gene, a congener thereof, a transcript thereof, or a variant or derivative thereof. None of the previously known reports show that change in the expression of the gene or the transcript thereof can serve as a marker for bladder cancer.

The 81st target gene is the hsa-miR-4449 gene, a congener thereof, a transcript thereof, or a variant or derivative thereof. None of the previously known reports show that change in the expression of the gene or the transcript thereof can serve as a marker for bladder cancer.

The 82nd target gene is the hsa-miR-4454 gene, a congener thereof, a transcript thereof, or a variant or derivative thereof. None of the previously known reports show that change in the expression of the gene or the transcript thereof can serve as a marker for bladder cancer.

The 83rd target gene is the hsa-miR-4455 gene, a congener thereof, a transcript thereof, or a variant or derivative thereof. None of the previously known reports show that change in the expression of the gene or the transcript thereof can serve as a marker for bladder cancer.

The 84th target gene is the hsa-miR-4459 gene, a congener thereof, a transcript thereof, or a variant or derivative thereof. None of the previously known reports show that change in the expression of the gene or the transcript thereof can serve as a marker for bladder cancer.

The 85th target gene is the hsa-miR-4462 gene, a congener thereof, a transcript thereof, or a variant or derivative thereof. None of the previously known reports show that change in the expression of the gene or the transcript thereof can serve as a marker for bladder cancer.

The 86th target gene is the hsa-miR-4466 gene, a congener thereof, a transcript thereof, or a variant or derivative thereof. None of the previously known reports show that change in the expression of the gene or the transcript thereof can serve as a marker for bladder cancer.

The 87th target gene is the hsa-miR-4467 gene, a congener thereof, a transcript thereof, or a variant or derivative thereof. None of the previously known reports show that change in the expression of the gene or the transcript thereof can serve as a marker for bladder cancer.

The 88th target gene is the hsa-miR-4480 gene, a congener thereof, a transcript thereof, or a variant or derivative thereof. None of the previously known reports show that change in the expression of the gene or the transcript thereof can serve as a marker for bladder cancer.

The 89th target gene is the hsa-miR-4483 gene, a congener thereof, a transcript thereof, or a variant or derivative thereof. None of the previously known reports show that change in the expression of the gene or the transcript thereof can serve as a marker for bladder cancer.

The 90th target gene is the hsa-miR-4484 gene, a congener thereof, a transcript thereof, or a variant or derivative thereof. None of the previously known reports show that change in the expression of the gene or the transcript thereof can serve as a marker for bladder cancer.

The 91st target gene is the hsa-miR-4485-5p gene, a congener thereof, a transcript thereof, or a variant or derivative thereof. None of the previously known reports show that change in the expression of the gene or the transcript thereof can serve as a marker for bladder cancer.

The 92nd target gene is the hsa-miR-4488 gene, a congener thereof, a transcript thereof, or a variant or derivative thereof. None of the previously known reports show that change in the expression of the gene or the transcript thereof can serve as a marker for bladder cancer.

The 93rd target gene is the hsa-miR-4492 gene, a congener thereof, a transcript thereof, or a variant or derivative thereof. None of the previously known reports show that change in the expression of the gene or the transcript thereof can serve as a marker for bladder cancer.

The 94th target gene is the hsa-miR-4505 gene, a congener thereof, a transcript thereof, or a variant or derivative thereof. None of the previously known reports show that change in the expression of the gene or the transcript thereof can serve as a marker for bladder cancer.

The 95th target gene is the hsa-miR-4515 gene, a congener thereof, a transcript thereof, or a variant or derivative thereof. None of the previously known reports show that change in the expression of the gene or the transcript thereof can serve as a marker for bladder cancer.

The 96th target gene is the hsa-miR-4525 gene, a congener thereof, a transcript thereof, or a variant or derivative thereof. None of the previously known reports show that change in the expression of the gene or the transcript thereof can serve as a marker for bladder cancer.

The 97th target gene is the hsa-miR-4534 gene, a congener thereof, a transcript thereof, or a variant or derivative thereof. None of the previously known reports show that change in the expression of the gene or the transcript thereof can serve as a marker for bladder cancer.

The 98th target gene is the hsa-miR-4535 gene, a congener thereof, a transcript thereof, or a variant or derivative thereof. None of the previously known reports show that change in the expression of the gene or the transcript thereof can serve as a marker for bladder cancer.

The 99th target gene is the hsa-miR-4633-3p gene, a congener thereof, a transcript thereof, or a variant or derivative thereof. None of the previously known reports show that change in the expression of the gene or the transcript thereof can serve as a marker for bladder cancer.

The 100th target gene is the hsa-miR-4634 gene, a congener thereof, a transcript thereof, or a variant or derivative thereof. None of the previously known reports show that change in the expression of the gene or the transcript thereof can serve as a marker for bladder cancer.

The 101st target gene is the hsa-miR-4640-5p gene, a congener thereof, a transcript thereof, or a variant or derivative thereof. None of the previously known reports show that change in the expression of the gene or the transcript thereof can serve as a marker for bladder cancer.

The 102nd target gene is the hsa-miR-4649-5p gene, a congener thereof, a transcript thereof, or a variant or derivative thereof. None of the previously known reports show that change in the expression of the gene or the transcript thereof can serve as a marker for bladder cancer.

The 103rd target gene is the hsa-miR-4651 gene, a congener thereof, a transcript thereof, or a variant or derivative thereof. None of the previously known reports show that change in the expression of the gene or the transcript thereof can serve as a marker for bladder cancer.

The 104th target gene is the hsa-miR-4652-5p gene, a congener thereof, a transcript thereof, or a variant or derivative thereof. None of the previously known reports show that change in the expression of the gene or the transcript thereof can serve as a marker for bladder cancer.

The 105th target gene is the hsa-miR-4655-5p gene, a congener thereof, a transcript thereof, or a variant or derivative thereof. None of the previously known reports show that change in the expression of the gene or the transcript thereof can serve as a marker for bladder cancer.

The 106th target gene is the hsa-miR-4656 gene, a congener thereof, a transcript thereof, or a variant or derivative thereof. None of the previously known reports show that change in the expression of the gene or the transcript thereof can serve as a marker for bladder cancer.

The 107th target gene is the hsa-miR-4658 gene, a congener thereof, a transcript thereof, or a variant or derivative thereof. None of the previously known reports show that change in the expression of the gene or the transcript thereof can serve as a marker for bladder cancer.

The 108th target gene is the hsa-miR-4663 gene, a congener thereof, a transcript thereof, or a variant or derivative thereof. None of the previously known reports show that change in the expression of the gene or the transcript thereof can serve as a marker for bladder cancer.

The 109th target gene is the hsa-miR-4673 gene, a congener thereof, a transcript thereof, or a variant or derivative thereof. None of the previously known reports show that change in the expression of the gene or the transcript thereof can serve as a marker for bladder cancer.

The 110th target gene is the hsa-miR-4675 gene, a congener thereof, a transcript thereof, or a variant or derivative thereof. None of the previously known reports show that change in the expression of the gene or the transcript thereof can serve as a marker for bladder cancer.

The 111th target gene is the hsa-miR-4687-3p gene, a congener thereof, a transcript thereof, or a variant or derivative thereof. None of the previously known reports show that change in the expression of the gene or the transcript thereof can serve as a marker for bladder cancer.

The 112th target gene is the hsa-miR-4687-5p gene, a congener thereof, a transcript thereof, or a variant or derivative thereof. None of the previously known reports show that change in the expression of the gene or the transcript thereof can serve as a marker for bladder cancer.

The 113th target gene is the hsa-miR-4690-5p gene, a congener thereof, a transcript thereof, or a variant or derivative thereof. None of the previously known reports show that change in the expression of the gene or the transcript thereof can serve as a marker for bladder cancer.

The 114th target gene is the hsa-miR-4695-5p gene, a congener thereof, a transcript thereof, or a variant or derivative thereof. None of the previously known reports show that change in the expression of the gene or the transcript thereof can serve as a marker for bladder cancer.

The 115th target gene is the hsa-miR-4697-5p gene, a congener thereof, a transcript thereof, or a variant or deriva- The 116th target gene is the hsa-miR-4706 gene, a congener thereof, a transcript thereof, or a variant or derivative thereof. None of the previously known reports show that change in the expression of the gene or the transcript thereof can serve as a marker for bladder cancer.

The 117th target gene is the hsa-miR-4707-3p gene, a congener thereof, a transcript thereof, or a variant or derivative thereof. None of the previously known reports show that change in the expression of the gene or the transcript thereof can serve as a marker for bladder cancer.

The 118th target gene is the hsa-miR-4707-5p gene, a congener thereof, a transcript thereof, or a variant or derivative thereof. None of the previously known reports show that change in the expression of the gene or the transcript thereof can serve as a marker for bladder cancer.

The 119th target gene is the hsa-miR-4708-3p gene, a congener thereof, a transcript thereof, or a variant or derivative thereof. None of the previously known reports show that change in the expression of the gene or the transcript thereof can serve as a marker for bladder cancer.

The 120th target gene is the hsa-miR-4710 gene, a congener thereof, a transcript thereof, or a variant or derivative thereof. None of the previously known reports show that change in the expression of the gene or the transcript thereof can serve as a marker for bladder cancer.

The 121st target gene is the hsa-miR-4718 gene, a congener thereof, a transcript thereof, or a variant or derivative thereof. None of the previously known reports show that change in the expression of the gene or the transcript thereof can serve as a marker for bladder cancer.

The 122nd target gene is the hsa-miR-4722-5p gene, a congener thereof, a transcript thereof, or a variant or derivative thereof. None of the previously known reports show that change in the expression of the gene or the transcript thereof can serve as a marker for bladder cancer.

The 123rd target gene is the hsa-miR-4725-3p gene, a congener thereof, a transcript thereof, or a variant or derivative thereof. None of the previously known reports show that change in the expression of the gene or the transcript thereof can serve as a marker for bladder cancer.

The 124th target gene is the hsa-miR-4726-5p gene, a congener thereof, a transcript thereof, or a variant or derivative thereof. None of the previously known reports show that change in the expression of the gene or the transcript thereof can serve as a marker for bladder cancer.

The 125th target gene is the hsa-miR-4727-3p gene, a congener thereof, a transcript thereof, or a variant or derivative thereof. None of the previously known reports show that change in the expression of the gene or the transcript thereof can serve as a marker for bladder cancer.

The 126th target gene is the hsa-miR-4728-5p gene, a congener thereof, a transcript thereof, or a variant or derivative thereof. None of the previously known reports show that change in the expression of the gene or the transcript thereof can serve as a marker for bladder cancer.

The 127th target gene is the hsa-miR-4731-5p gene, a congener thereof, a transcript thereof, or a variant or derivative thereof. None of the previously known reports show that change in the expression of the gene or the transcript thereof can serve as a marker for bladder cancer.

The 128th target gene is the hsa-miR-4736 gene, a congener thereof, a transcript thereof, or a variant or derivative thereof. None of the previously known reports show that change in the expression of the gene or the transcript thereof can serve as a marker for bladder cancer.

The 129th target gene is the hsa-miR-4739 gene, a congener thereof, a transcript thereof, or a variant or derivative thereof. None of the previously known reports show that change in the expression of the gene or the transcript thereof can serve as a marker for bladder cancer.

The 130th target gene is the hsa-miR-4740-5p gene, a congener thereof, a transcript thereof, or a variant or derivative thereof. None of the previously known reports show that change in the expression of the gene or the transcript thereof can serve as a marker for bladder cancer.

The 131st target gene is the hsa-miR-4741 gene, a congener thereof, a transcript thereof, or a variant or derivative thereof. None of the previously known reports show that change in the expression of the gene or the transcript thereof can serve as a marker for bladder cancer.

The 132nd target gene is the hsa-miR-4750-5p gene, a congener thereof, a transcript thereof, or a variant or derivative thereof. None of the previously known reports show that change in the expression of the gene or the transcript thereof can serve as a marker for bladder cancer.

The 133rd target gene is the hsa-miR-4755-3p gene, a congener thereof, a transcript thereof, or a variant or derivative thereof. None of the previously known reports show that change in the expression of the gene or the transcript thereof can serve as a marker for bladder cancer.

The 134th target gene is the hsa-miR-4763-3p gene, a congener thereof, a transcript thereof, or a variant or derivative thereof. None of the previously known reports show that change in the expression of the gene or the transcript thereof can serve as a marker for bladder cancer.

The 135th target gene is the hsa-miR-4771 gene, a congener thereof, a transcript thereof, or a variant or derivative thereof. None of the previously known reports show that change in the expression of the gene or the transcript thereof can serve as a marker for bladder cancer.

The 136th target gene is the hsa-miR-4783-3p gene, a congener thereof, a transcript thereof, or a variant or derivative thereof. None of the previously known reports show that change in the expression of the gene or the transcript thereof can serve as a marker for bladder cancer.

The 137th target gene is the hsa-miR-4783-5p gene, a congener thereof, a transcript thereof, or a variant or derivative thereof. None of the previously known reports show that change in the expression of the gene or the transcript thereof can serve as a marker for bladder cancer.

The 138th target gene is the hsa-miR-4787-3p gene, a congener thereof, a transcript thereof, or a variant or derivative thereof. None of the previously known reports show that change in the expression of the gene or the transcript thereof can serve as a marker for bladder cancer.

The 139th target gene is the hsa-miR-4792 gene, a congener thereof, a transcript thereof, or a variant or derivative thereof. None of the previously known reports show that change in the expression of the gene or the transcript thereof can serve as a marker for bladder cancer.

The 140th target gene is the hsa-miR-498 gene, a congener thereof, a transcript thereof, or a variant or derivative thereof. None of the previously known reports show that change in the expression of the gene or the transcript thereof can serve as a marker for bladder cancer.

The 141st target gene is the hsa-miR-5008-5p gene, a congener thereof, a transcript thereof, or a variant or derivative thereof. None of the previously known reports show that change in the expression of the gene or the transcript thereof can serve as a marker for bladder cancer.

The 142nd target gene is the hsa-miR-5010-5p gene, a congener thereof, a transcript thereof, or a variant or derivative thereof. None of the previously known reports show that change in the expression of the gene or the transcript thereof can serve as a marker for bladder cancer.

The 143rd target gene is the hsa-miR-504-3p gene, a congener thereof, a transcript thereof, or a variant or derivative thereof. None of the previously known reports show that change in the expression of the gene or the transcript thereof can serve as a marker for bladder cancer.

The 144th target gene is the hsa-miR-5195-3p gene, a congener thereof, a transcript thereof, or a variant or derivative thereof. None of the previously known reports show that change in the expression of the gene or the transcript thereof can serve as a marker for bladder cancer.

The 145th target gene is the hsa-miR-550a-5p gene, a congener thereof, a transcript thereof, or a variant or derivative thereof. None of the previously known reports show that change in the expression of the gene or the transcript thereof can serve as a marker for bladder cancer.

The 146th target gene is the hsa-miR-5572 gene, a congener thereof, a transcript thereof, or a variant or derivative thereof. None of the previously known reports show that change in the expression of the gene or the transcript thereof can serve as a marker for bladder cancer.

The 147th target gene is the hsa-miR-5739 gene, a congener thereof, a transcript thereof, or a variant or derivative thereof. None of the previously known reports show that change in the expression of the gene or the transcript thereof can serve as a marker for bladder cancer.

The 148th target gene is the hsa-miR-6075 gene, a congener thereof, a transcript thereof, or a variant or derivative thereof. None of the previously known reports show that change in the expression of the gene or the transcript thereof can serve as a marker for bladder cancer.

The 149th target gene is the hsa-miR-6076 gene, a congener thereof, a transcript thereof, or a variant or derivative thereof. None of the previously known reports show that change in the expression of the gene or the transcript thereof can serve as a marker for bladder cancer.

The 150th target gene is the hsa-miR-6088 gene, a congener thereof, a transcript thereof, or a variant or derivative thereof. None of the previously known reports show that change in the expression of the gene or the transcript thereof can serve as a marker for bladder cancer.

The 151st target gene is the hsa-miR-6124 gene, a congener thereof, a transcript thereof, or a variant or derivative thereof. None of the previously known reports show that change in the expression of the gene or the transcript thereof can serve as a marker for bladder cancer.

The 152nd target gene is the hsa-miR-6131 gene, a congener thereof, a transcript thereof, or a variant or derivative thereof. None of the previously known reports show that change in the expression of the gene or the transcript thereof can serve as a marker for bladder cancer.

The 153rd target gene is the hsa-miR-6132 gene, a congener thereof, a transcript thereof, or a variant or derivative thereof. None of the previously known reports show that change in the expression of the gene or the transcript thereof can serve as a marker for bladder cancer.

The 154th target gene is the hsa-miR-614 gene, a congener thereof, a transcript thereof, or a variant or derivative thereof. None of the previously known reports show that change in the expression of the gene or the transcript thereof can serve as a marker for bladder cancer.

The 155th target gene is the hsa-miR-615-5p gene, a congener thereof, a transcript thereof, or a variant or derivative thereof. None of the previously known reports show that change in the expression of the gene or the transcript thereof can serve as a marker for bladder cancer.

The 156th target gene is the hsa-miR-619-5p gene, a congener thereof, a transcript thereof, or a variant or derivative thereof. None of the previously known reports show that change in the expression of the gene or the transcript thereof can serve as a marker for bladder cancer.

The 157th target gene is the hsa-miR-642b-3p gene, a congener thereof, a transcript thereof, or a variant or derivative thereof. None of the previously known reports show that change in the expression of the gene or the transcript thereof can serve as a marker for bladder cancer.

The 158th target gene is the hsa-miR-6510-5p gene, a congener thereof, a transcript thereof, or a variant or derivative thereof. None of the previously known reports show that change in the expression of the gene or the transcript thereof can serve as a marker for bladder cancer.

The 159th target gene is the hsa-miR-6511a-5p gene, a congener thereof, a transcript thereof, or a variant or derivative thereof. None of the previously known reports show that change in the expression of the gene or the transcript thereof can serve as a marker for bladder cancer.

The 160th target gene is the hsa-miR-6515-3p gene, a congener thereof, a transcript thereof, or a variant or derivative thereof. None of the previously known reports show that change in the expression of the gene or the transcript thereof can serve as a marker for bladder cancer.

The 161st target gene is the hsa-miR-6515-5p gene, a congener thereof, a transcript thereof, or a variant or derivative thereof. None of the previously known reports show that change in the expression of the gene or the transcript thereof can serve as a marker for bladder cancer.

The 162nd target gene is the hsa-miR-663b gene, a congener thereof, a transcript thereof, or a variant or derivative thereof. None of the previously known reports show that change in the expression of the gene or the transcript thereof can serve as a marker for bladder cancer.

The 163rd target gene is the hsa-miR-6716-5p gene, a congener thereof, a transcript thereof, or a variant or derivative thereof. None of the previously known reports show that change in the expression of the gene or the transcript thereof can serve as a marker for bladder cancer.

The 164th target gene is the hsa-miR-6717-5p gene, a congener thereof, a transcript thereof, or a variant or derivative thereof. None of the previously known reports show that change in the expression of the gene or the transcript thereof can serve as a marker for bladder cancer.

The 165th target gene is the hsa-miR-6722-3p gene, a congener thereof, a transcript thereof, or a variant or derivative thereof. None of the previously known reports show that change in the expression of the gene or the transcript thereof can serve as a marker for bladder cancer.

The 166th target gene is the hsa-miR-6724-5p gene, a congener thereof, a transcript thereof, or a variant or derivative thereof. None of the previously known reports show that change in the expression of the gene or the transcript thereof can serve as a marker for bladder cancer.

The 167th target gene is the hsa-miR-6726-5p gene, a congener thereof, a transcript thereof, or a variant or derivative thereof. None of the previously known reports show that change in the expression of the gene or the transcript thereof can serve as a marker for bladder cancer.

The 168th target gene is the hsa-miR-6737-5p gene, a congener thereof, a transcript thereof, or a variant or derivative thereof. None of the previously known reports show that The 169th target gene is the hsa-miR-6741-5p gene, a congener thereof, a transcript thereof, or a variant or derivative thereof. None of the previously known reports show that change in the expression of the gene or the transcript thereof can serve as a marker for bladder cancer.

The 170th target gene is the hsa-miR-6742-5p gene, a congener thereof, a transcript thereof, or a variant or derivative thereof. None of the previously known reports show that change in the expression of the gene or the transcript thereof can serve as a marker for bladder cancer.

The 171st target gene is the hsa-miR-6743-5p gene, a congener thereof, a transcript thereof, or a variant or derivative thereof. None of the previously known reports show that change in the expression of the gene or the transcript thereof can serve as a marker for bladder cancer.

The 172nd target gene is the hsa-miR-6746-5p gene, a congener thereof, a transcript thereof, or a variant or derivative thereof. None of the previously known reports show that change in the expression of the gene or the transcript thereof can serve as a marker for bladder cancer.

The 173rd target gene is the hsa-miR-6749-5p gene, a congener thereof, a transcript thereof, or a variant or derivative thereof. None of the previously known reports show that change in the expression of the gene or the transcript thereof can serve as a marker for bladder cancer.

The 174th target gene is the hsa-miR-6760-5p gene, a congener thereof, a transcript thereof, or a variant or derivative thereof. None of the previously known reports show that change in the expression of the gene or the transcript thereof can serve as a marker for bladder cancer.

The 175th target gene is the hsa-miR-6762-5p gene, a congener thereof, a transcript thereof, or a variant or derivative thereof. None of the previously known reports show that change in the expression of the gene or the transcript thereof can serve as a marker for bladder cancer.

The 176th target gene is the hsa-miR-6765-3p gene, a congener thereof, a transcript thereof, or a variant or derivative thereof. None of the previously known reports show that change in the expression of the gene or the transcript thereof can serve as a marker for bladder cancer.

The 177th target gene is the hsa-miR-6765-5p gene, a congener thereof, a transcript thereof, or a variant or derivative thereof. None of the previously known reports show that change in the expression of the gene or the transcript thereof can serve as a marker for bladder cancer.

The 178th target gene is the hsa-miR-6766-3p gene, a congener thereof, a transcript thereof, or a variant or derivative thereof. None of the previously known reports show that change in the expression of the gene or the transcript thereof can serve as a marker for bladder cancer.

The 179th target gene is the hsa-miR-6766-5p gene, a congener thereof, a transcript thereof, or a variant or derivative thereof. None of the previously known reports show that change in the expression of the gene or the transcript thereof can serve as a marker for bladder cancer.

The 180th target gene is the hsa-miR-6771-5p gene, a congener thereof, a transcript thereof, or a variant or derivative thereof. None of the previously known reports show that change in the expression of the gene or the transcript thereof can serve as a marker for bladder cancer.

The 181st target gene is the hsa-miR-6774-5p gene, a congener thereof, a transcript thereof, or a variant or derivative thereof. None of the previously known reports show that change in the expression of the gene or the transcript thereof can serve as a marker for bladder cancer.

The 182nd target gene is the hsa-miR-6777-5p gene, a congener thereof, a transcript thereof, or a variant or derivative thereof. None of the previously known reports show that change in the expression of the gene or the transcript thereof can serve as a marker for bladder cancer.

The 183rd target gene is the hsa-miR-6778-5p gene, a congener thereof, a transcript thereof, or a variant or derivative thereof. None of the previously known reports show that change in the expression of the gene or the transcript thereof can serve as a marker for bladder cancer.

The 184th target gene is the hsa-miR-6780b-5p gene, a congener thereof, a transcript thereof, or a variant or derivative thereof. None of the previously known reports show that change in the expression of the gene or the transcript thereof can serve as a marker for bladder cancer.

The 185th target gene is the hsa-miR-6781-5p gene, a congener thereof, a transcript thereof, or a variant or derivative thereof. None of the previously known reports show that change in the expression of the gene or the transcript thereof can serve as a marker for bladder cancer.

The 186th target gene is the hsa-miR-6782-5p gene, a congener thereof, a transcript thereof, or a variant or derivative thereof. None of the previously known reports show that change in the expression of the gene or the transcript thereof can serve as a marker for bladder cancer.

The 187th target gene is the hsa-miR-6784-5p gene, a congener thereof, a transcript thereof, or a variant or derivative thereof. None of the previously known reports show that change in the expression of the gene or the transcript thereof can serve as a marker for bladder cancer.

The 188th target gene is the hsa-miR-6785-5p gene, a congener thereof, a transcript thereof, or a variant or derivative thereof. None of the previously known reports show that change in the expression of the gene or the transcript thereof can serve as a marker for bladder cancer.

The 189th target gene is the hsa-miR-6787-5p gene, a congener thereof, a transcript thereof, or a variant or derivative thereof. None of the previously known reports show that change in the expression of the gene or the transcript thereof can serve as a marker for bladder cancer.

The 190th target gene is the hsa-miR-6789-5p gene, a congener thereof, a transcript thereof, or a variant or derivative thereof. None of the previously known reports show that change in the expression of the gene or the transcript thereof can serve as a marker for bladder cancer.

The 191st target gene is the hsa-miR-6791-5p gene, a congener thereof, a transcript thereof, or a variant or derivative thereof. None of the previously known reports show that change in the expression of the gene or the transcript thereof can serve as a marker for bladder cancer.

The 192nd target gene is the hsa-miR-6794-5p gene, a congener thereof, a transcript thereof, or a variant or derivative thereof. None of the previously known reports show that change in the expression of the gene or the transcript thereof can serve as a marker for bladder cancer.

The 193rd target gene is the hsa-miR-6800-5p gene, a congener thereof, a transcript thereof, or a variant or derivative thereof. None of the previously known reports show that change in the expression of the gene or the transcript thereof can serve as a marker for bladder cancer.

The 194th target gene is the hsa-miR-6802-5p gene, a congener thereof, a transcript thereof, or a variant or derivative thereof. None of the previously known reports show that change in the expression of the gene or the transcript thereof can serve as a marker for bladder cancer.

The 195th target gene is the hsa-miR-6803-5p gene, a congener thereof, a transcript thereof, or a variant or deriva- The 196th target gene is the hsa-miR-6812-5p gene, a congener thereof, a transcript thereof, or a variant or derivative thereof. None of the previously known reports show that change in the expression of the gene or the transcript thereof can serve as a marker for bladder cancer.

The 197th target gene is the hsa-miR-6816-5p gene, a congener thereof, a transcript thereof, or a variant or derivative thereof. None of the previously known reports show that change in the expression of the gene or the transcript thereof can serve as a marker for bladder cancer.

The 198th target gene is the hsa-miR-6819-5p gene, a congener thereof, a transcript thereof, or a variant or derivative thereof. None of the previously known reports show that change in the expression of the gene or the transcript thereof can serve as a marker for bladder cancer.

The 199th target gene is the hsa-miR-6821-5p gene, a congener thereof, a transcript thereof, or a variant or derivative thereof. None of the previously known reports show that change in the expression of the gene or the transcript thereof can serve as a marker for bladder cancer.

The 200th target gene is the hsa-miR-6826-5p gene, a congener thereof, a transcript thereof, or a variant or derivative thereof. None of the previously known reports show that change in the expression of the gene or the transcript thereof can serve as a marker for bladder cancer.

The 201st target gene is the hsa-miR-6831-5p gene, a congener thereof, a transcript thereof, or a variant or derivative thereof. None of the previously known reports show that change in the expression of the gene or the transcript thereof can serve as a marker for bladder cancer.

The 202nd target gene is the hsa-miR-6836-3p gene, a congener thereof, a transcript thereof, or a variant or derivative thereof. None of the previously known reports show that change in the expression of the gene or the transcript thereof can serve as a marker for bladder cancer.

The 203rd target gene is the hsa-miR-6840-3p gene, a congener thereof, a transcript thereof, or a variant or derivative thereof. None of the previously known reports show that change in the expression of the gene or the transcript thereof can serve as a marker for bladder cancer.

The 204th target gene is the hsa-miR-6842-5p gene, a congener thereof, a transcript thereof, or a variant or derivative thereof. None of the previously known reports show that change in the expression of the gene or the transcript thereof can serve as a marker for bladder cancer.

The 205th target gene is the hsa-miR-6850-5p gene, a congener thereof, a transcript thereof, or a variant or derivative thereof. None of the previously known reports show that change in the expression of the gene or the transcript thereof can serve as a marker for bladder cancer.

The 206th target gene is the hsa-miR-6861-5p gene, a congener thereof, a transcript thereof, or a variant or derivative thereof. None of the previously known reports show that change in the expression of the gene or the transcript thereof can serve as a marker for bladder cancer.

The 207th target gene is the hsa-miR-6869-5p gene, a congener thereof, a transcript thereof, or a variant or derivative thereof. None of the previously known reports show that change in the expression of the gene or the transcript thereof can serve as a marker for bladder cancer.

The 208th target gene is the hsa-miR-6870-5p gene, a congener thereof, a transcript thereof, or a variant or derivative thereof. None of the previously known reports show that change in the expression of the gene or the transcript thereof can serve as a marker for bladder cancer.

The 209th target gene is the hsa-miR-6877-5p gene, a congener thereof, a transcript thereof, or a variant or derivative thereof. None of the previously known reports show that change in the expression of the gene or the transcript thereof can serve as a marker for bladder cancer.

The 210th target gene is the hsa-miR-6879-5p gene, a congener thereof, a transcript thereof, or a variant or derivative thereof. None of the previously known reports show that change in the expression of the gene or the transcript thereof can serve as a marker for bladder cancer.

The 211st target gene is the hsa-miR-6880-3p gene, a congener thereof, a transcript thereof, or a variant or derivative thereof. None of the previously known reports show that change in the expression of the gene or the transcript thereof can serve as a marker for bladder cancer.

The 212nd target gene is the hsa-miR-6880-5p gene, a congener thereof, a transcript thereof, or a variant or derivative thereof. None of the previously known reports show that change in the expression of the gene or the transcript thereof can serve as a marker for bladder cancer.

The 213rd target gene is the hsa-miR-6885-5p gene, a congener thereof, a transcript thereof, or a variant or derivative thereof. None of the previously known reports show that change in the expression of the gene or the transcript thereof can serve as a marker for bladder cancer.

The 214th target gene is the hsa-miR-6887-5p gene, a congener thereof, a transcript thereof, or a variant or derivative thereof. None of the previously known reports show that change in the expression of the gene or the transcript thereof can serve as a marker for bladder cancer.

The 215th target gene is the hsa-miR-7107-5p gene, a congener thereof, a transcript thereof, or a variant or derivative thereof. None of the previously known reports show that change in the expression of the gene or the transcript thereof can serve as a marker for bladder cancer.

The 216th target gene is the hsa-miR-7108-3p gene, a congener thereof, a transcript thereof, or a variant or derivative thereof. None of the previously known reports show that change in the expression of the gene or the transcript thereof can serve as a marker for bladder cancer.

The 217th target gene is the hsa-miR-7109-5p gene, a congener thereof, a transcript thereof, or a variant or derivative thereof. None of the previously known reports show that change in the expression of the gene or the transcript thereof can serve as a marker for bladder cancer.

The 218th target gene is the hsa-miR-711 gene, a congener thereof, a transcript thereof, or a variant or derivative thereof. None of the previously known reports show that change in the expression of the gene or the transcript thereof can serve as a marker for bladder cancer.

The 219th target gene is the hsa-miR-7113-3p gene, a congener thereof, a transcript thereof, or a variant or derivative thereof. None of the previously known reports show that change in the expression of the gene or the transcript thereof can serve as a marker for bladder cancer.

The 220th target gene is the hsa-miR-7150 gene, a congener thereof, a transcript thereof, or a variant or derivative thereof. None of the previously known reports show that change in the expression of the gene or the transcript thereof can serve as a marker for bladder cancer.

The 221st target gene is the hsa-miR-744-5p gene, a congener thereof, a transcript thereof, or a variant or derivative thereof. None of the previously known reports show that change in the expression of the gene or the transcript thereof can serve as a marker for bladder cancer.

The 222nd target gene is the hsa-miR-7975 gene, a congener thereof, a transcript thereof, or a variant or derivative thereof. None of the previously known reports show that change in the expression of the gene or the transcript thereof can serve as a marker for bladder cancer.

The 223rd target gene is the hsa-miR-7977 gene, a congener thereof, a transcript thereof, or a variant or derivative thereof. None of the previously known reports show that change in the expression of the gene or the transcript thereof can serve as a marker for bladder cancer.

The 224th target gene is the hsa-miR-8052 gene, a congener thereof, a transcript thereof, or a variant or derivative thereof. None of the previously known reports show that change in the expression of the gene or the transcript thereof can serve as a marker for bladder cancer.

The 225th target gene is the hsa-miR-8069 gene, a congener thereof, a transcript thereof, or a variant or derivative thereof. None of the previously known reports show that change in the expression of the gene or the transcript thereof can serve as a marker for bladder cancer.

The 226th target gene is the hsa-miR-8073 gene, a congener thereof, a transcript thereof, or a variant or derivative thereof. None of the previously known reports show that change in the expression of the gene or the transcript thereof can serve as a marker for bladder cancer.

The 227th target gene is the hsa-miR-887-3p gene, a congener thereof, a transcript thereof, or a variant or derivative thereof. None of the previously known reports show that change in the expression of the gene or the transcript thereof can serve as a marker for bladder cancer.

The 228th target gene is the hsa-miR-937-5p gene, a congener thereof, a transcript thereof, or a variant or derivative thereof. None of the previously known reports show that change in the expression of the gene or the transcript thereof can serve as a marker for bladder cancer.

The 229th target gene is the miR-1202 gene, a congener thereof, a transcript thereof, or a variant or derivative thereof. The previously known report shows that change in the expression of the gene or the transcript thereof can serve as a marker for bladder cancer (Patent Literature 1).

The 230th target gene is the miR-1207-5p gene, a congener thereof, a transcript thereof, or a variant or derivative thereof. The previously known report shows that change in the expression of the gene or the transcript thereof can serve as a marker for bladder cancer (Patent Literature 1).

The 231st target gene is the miR-1246 gene, a congener thereof, a transcript thereof, or a variant or derivative thereof. The previously known report shows that change in the expression of the gene or the transcript thereof can serve as a marker for bladder cancer (Patent Literature 2).

The 232nd target gene is the miR-1254 gene, a congener thereof, a transcript thereof, or a variant or derivative thereof. The previously known report shows that change in the expression of the gene or the transcript thereof can serve as a marker for bladder cancer (Patent Literature 2).

The 233rd target gene is the miR-135a-3p gene, a congener thereof, a transcript thereof, or a variant or derivative thereof. The previously known report shows that change in the expression of the gene or the transcript thereof can serve as a marker for bladder cancer (Patent Literature 1).

The 234th target gene is the miR-1469 gene, a congener thereof, a transcript thereof, or a variant or derivative thereof. The previously known report shows that change in the expression of the gene or the transcript thereof can serve as a marker for bladder cancer (Patent Literature 1).

The 235th target gene is the miR-149-3p gene, a congener thereof, a transcript thereof, or a variant or derivative thereof. The previously known report shows that change in the expression of the gene or the transcript thereof can serve as a marker for bladder cancer (Patent Literature 1).

The 236th target gene is the miR-150-3p gene, a congener thereof, a transcript thereof, or a variant or derivative thereof. The previously known report shows that change in the expression of the gene or the transcript thereof can serve as a marker for bladder cancer (Patent Literature 1).

The 237th target gene is the miR-1914-3p gene, a congener thereof, a transcript thereof, or a variant or derivative thereof. The previously known report shows that change in the expression of the gene or the transcript thereof can serve as a marker for bladder cancer (Patent Literature 1).

The 238th target gene is the miR-191-5p gene, a congener thereof, a transcript thereof, or a variant or derivative thereof. The previously known report shows that change in the expression of the gene or the transcript thereof can serve as a marker for bladder cancer (Non Patent Literature 2).

The 239th target gene is the miR-423-5p gene, a congener thereof, a transcript thereof, or a variant or derivative thereof. The previously known report shows that change in the expression of the gene or the transcript thereof can serve as a marker for bladder cancer (Non Patent Literature 3).

The 240th target gene is the miR-663a gene, a congener thereof, a transcript thereof, or a variant or derivative thereof. The previously known report shows that change in the expression of the gene or the transcript thereof can serve as a marker for bladder cancer (Patent Literature 1).

The 241st target gene is the miR-92a-2-5p gene, a congener thereof, a transcript thereof, or a variant or derivative thereof. The previously known report shows that change in the expression of the gene or the transcript thereof can serve as a marker for bladder cancer (Patent Literature 1).

The 242nd target gene is the miR-92a-3p gene, a congener thereof, a transcript thereof, or a variant or derivative thereof. The previously known report shows that change in the expression of the gene or the transcript thereof can serve as a marker for bladder cancer (Patent Literature 2).

The 243rd target gene is the miR-940 gene, a congener thereof, a transcript thereof, or a variant or derivative thereof. The previously known report shows that change in the expression of the gene or the transcript thereof can serve as a marker for bladder cancer (Non Patent Literature 2).

In one aspect, the present invention relates to a marker(s) for detecting bladder cancer or diagnosing bladder cancer, which comprises at least one selected from the above target nucleic acid(s).

In one aspect, the present invention relates to use of at least one selected from the above target nucleic acid(s) for detecting bladder cancer or diagnosing bladder cancer.

2. Nucleic Acid Probe(s) or Primer(s) for Detection of Bladder Cancer

A nucleic acid probe(s) or primer(s) capable of being used for detection of bladder cancer or diagnosis of bladder cancer according to the present invention enable(s) qualitative and/or quantitative measurement of the presence, expression level(s), or abundance of the following target nucleic acid(s) for bladder cancer: human-derived miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR- 3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, or miR-937-5p, or any combination thereof, any congener thereof, any transcript thereof, or any variant or derivative thereof.

The expression level(s) of the above target nucleic acid(s) in subjects having bladder cancer may be increased or decreased (hereinafter, also referred to as an "increase/decrease"), depending on the kind(s) of the target nucleic acid(s), than healthy subjects, benign disease patients and subjects having a cancer other than bladder cancer. Thus, a kit or device of the present invention can be effectively used for detection of bladder cancer by measuring the expression level(s) of the above target nucleic acid(s) in body fluid derived from a subject (e.g., a human) suspected of having bladder cancer and in body fluids derived from healthy subjects, benign disease patients and patients with a cancer other than bladder cancer and then comparing the expression level(s) therebetween.

A nucleic acid probe(s) or primer(s) capable of being used in the present invention is a nucleic acid probe(s) capable of specifically binding to a polynucleotide(s) consisting of a nucleotide sequence(s) represented by at least one selected from SEQ ID NOs: 1 to 228 or to a complementary strand(s) of the polynucleotide(s), or a primer(s) for amplifying a polynucleotide(s) consisting of a nucleotide sequence(s) represented by at least one selected from SEQ ID NOs: 1 to 228.

The nucleic acid probes or primers capable of being used in the present invention may further comprise a nucleic acid probe(s) capable of specifically binding to a polynucleotide(s) consisting of a nucleotide sequence(s) represented by at least one selected from SEQ ID NOs: 229 to 243 or to a complementary strand(s) of the polynucleotide(s), or a primer(s) for amplifying a polynucleotide(s) consisting of a nucleotide sequence(s) represented by at least one selected from SEQ ID NOs: 229 to 243.

In a preferred embodiment of the method of the present invention, the above nucleic acid probe(s) or primer(s) includes any combination of one or more polynucleotides selected from a group of polynucleotides comprising a nucleotide sequence(s) represented by any of SEQ ID NOs: 1 to 766 and a nucleotide sequence(s) derived from the nucleotide sequence(s) by the replacement of u with t and a group of polynucleotides complementary thereto, a group of polynucleotides hybridizing under stringent conditions (described below) to DNA comprising a nucleotide sequence(s) complementary to the former nucleotide sequence(s) and a group of polynucleotides complementary thereto, and a group of polynucleotides comprising 15 or more, preferably 17 or more consecutive nucleotides in the nucleotide sequence(s) of these polynucleotide groups. These polynucleotides can be used as nucleic acid probes and primers for detecting target nucleic acids, namely the above bladder cancer markers.

Further, specific examples of the nucleic acid probe(s) or primer(s) capable of being used in the present invention include one or more polynucleotides selected from the group consisting of any of the following polynucleotides (a) to (e):
  (a) a polynucleotide consisting of a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;
  (b) a polynucleotide comprising a nucleotide sequence represented by any of SEQ ID NOs: 1 to 228;
  (c) a polynucleotide consisting of a nucleotide sequence complementary to a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;
  (d) a polynucleotide comprising a nucleotide sequence complementary to a nucleotide sequence represented by any of SEQ ID NOs: 1 to 228 or a nucleotide sequence derived from the nucleotide sequence by the replacement of u with t; and
  (e) a polynucleotide hybridizing under stringent conditions to any of the polynucleotides (a) to (d).

In addition to at least one polynucleotide selected from any of the above polynucleotides (a) to (e), the nucleic acid probe(s) or primer(s) capable of being used in the present invention can further comprise a polynucleotide represented by any of the following (f) to (j):
  (f) a polynucleotide consisting of a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;

(g) a polynucleotide comprising a nucleotide sequence represented by any of SEQ ID NOs: 229 to 243;
(h) a polynucleotide consisting of a nucleotide sequence complementary to a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;
(i) a polynucleotide comprising a nucleotide sequence complementary to a nucleotide sequence represented by any of SEQ ID NOs: 229 to 243 or a nucleotide sequence derived from the nucleotide sequence by the replacement of u with t; and
(j) a polynucleotide hybridizing under stringent conditions to any of the polynucleotides (f) to (i).

The above polynucleotides or fragments thereof used in the present invention may each be DNA or RNA.

The above polynucleotide(s) capable of being used in the present invention may be prepared using a general technique such as DNA recombination technology, a PCR method, or a method using an automated DNA/RNA synthesizer.

As the DNA recombination technology or the PCR method, it is possible to use techniques described in, for instance, Ausubel et al., Current Protocols in Molecular Biology, John Willey & Sons, US(1993); and Sambrook et al., Molecular Cloning A Laboratory Manual, Cold Spring Harbor Laboratory Press, US (1989).

The human-derived miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, miR-937-5p, miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940, which are represented by SEQ ID NOs: 1 to 243, are known, and methods for obtaining them are also known, as described above. Therefore, a polynucleotide that can be used as a nucleic acid probe or a primer in the present invention can be produced via cloning the gene.

Such a nucleic acid probe(s) or primer(s) may be chemically synthesized using an automated DNA synthesizer. A phosphoramidite process is commonly used for this synthesis, and this process can be used to automatically synthesize a single-stranded DNA with up to about 100 nucleotides in length. The automated DNA synthesizer is commercially available from, for instance, Polygen, Inc., ABI, Inc., or Applied BioSystems, Inc.

Alternatively, a polynucleotide(s) of the present invention may be prepared by cDNA cloning. For the cDNA cloning technology, a microRNA Cloning Kit Wako, for instance, can be utilized.

The sequence of a nucleic acid probe or primer for detection of a polynucleotide consisting of a nucleotide sequence represented by any of SEQ ID NOs: 1 to 243 is not present in vivo as an miRNA or any precursor thereof. For instance, the nucleotide sequences represented by SEQ ID NO: 9 and SEQ ID NO: 8 are generated from the precursor represented by SEQ ID NO: 251. This precursor has a hairpin-like structure as shown in FIG. 1, and the nucleotide sequences represented by SEQ ID NO: 9 and SEQ ID NO: 8 have mismatch sequences therebetween. Accordingly, a nucleotide sequence perfectly complementary to the nucleotide sequence represented by SEQ ID NO: 9 or SEQ ID NO: 8 is not naturally occurring in vivo. Thus, the nucleic acid probe(s) or primer(s) for detecting a nucleotide sequence represented by any of SEQ ID NOs: 1 to 243 may have an artificial nucleotide sequence not present in vivo.

3. Kit or Device for Detection of Bladder Cancer

The present invention provides a kit or device for detection of bladder cancer, comprising one or more polynucleotide(s) (which may include any variant(s), fragment(s), or derivative(s)) capable of being used as a nucleic acid probe (s) or primer(s) for measuring a target nucleic acid(s) as a bladder cancer marker(s) in the present invention.

A target nucleic acid(s) as a bladder cancer marker(s) according to the present invention is preferably selected from the following group A.

Group A:
miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR- 187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, and miR-937-5p.

An additional target nucleic acid(s) capable of being optionally used for the measurement is preferably selected from the following group B.

Group B:
miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940.

A kit or device of the present invention comprises a nucleic acid(s) capable of specifically binding to the above target nucleic acid(s) as bladder cancer marker(s), preferably, one or more polynucleotides selected from the polynucleotides described in Section 2 above or a variant thereof.

Specifically, a kit or device of the present invention may comprise at least one of a polynucleotide comprising (or consisting of) a nucleotide sequence represented by any of SEQ ID NOs: 1 to 228 or a nucleotide sequence derived from the nucleotide sequence by the replacement of u with t or a polynucleotide comprising (or consisting of) a complementary sequence thereof, or a polynucleotide hybridizing under stringent conditions to any of the polynucleotides, or a variant or fragment thereof comprising 15 or more consecutive nucleotides of any of the polynucleotide sequences.

A kit or device of the present invention may further comprise one or more of a polynucleotide comprising (or consisting of) a nucleotide sequence represented by any of SEQ ID NOs: 229 to 243 or a nucleotide sequence derived from the nucleotide sequence by the replacement of u with t or a polynucleotide comprising (or consisting of) a complementary sequence thereof, or a polynucleotide hybridizing under stringent conditions to any of the polynucleotides, or a variant or fragment thereof comprising 15 or more consecutive nucleotides of any of the polynucleotide sequences.

A fragment(s) that can be comprised in a kit or device of the present invention may be, for instance, one or more polynucleotides and preferably two or more polynucleotides selected from the group consisting of the following (1) and (2):

(1) a polynucleotide comprising 15 or more consecutive nucleotides in a nucleotide sequence derived from the nucleotide sequence represented by any of SEQ ID NOs: 1 to 228 by the replacement of u with t or in a complementary sequence thereof; and (2) a polynucleotide comprising 15 or more consecutive nucleotides in a nucleotide sequence derived from the nucleotide sequence represented by any of SEQ ID NOs: 229 to 243 by the replacement of u with t or in a complementary sequence thereof.

In a preferred embodiment, the polynucleotide is a polynucleotide consisting of a nucleotide sequence represented by any of SEQ ID NOs: 1 to 228 or a nucleotide sequence derived from the nucleotide sequence by the replacement of u with t or a polynucleotide consisting of a complementary sequence thereof, or a polynucleotide hybridizing under stringent conditions to any of the polynucleotides, or a variant comprising 15 or more, preferably 17 or more, and more preferably 19 or more consecutive nucleotides of any of the polynucleotides.

In addition, in a preferred embodiment, the polynucleotide is a polynucleotide consisting of a nucleotide sequence represented by any of SEQ ID NOs: 229 to 243 or a nucleotide sequence derived from the nucleotide sequence by the replacement of u with t or a polynucleotide consisting of a complementary sequence thereof, or a polynucleotide hybridizing under stringent conditions to any of the polynucleotides, or a variant comprising 15 or more, preferably 17 or more, and more preferably 19 or more consecutive nucleotides of any of the polynucleotides.

In a preferred embodiment, the fragment may be a polynucleotide comprising 15 or more, preferably 17 or more, and more preferably 19 or more consecutive nucleotides.

In the present invention, the size of the polynucleotide fragment is represented by the number of nucleotides in a range of, for instance, from 15 to less than the total number of consecutive nucleotides in the nucleotide sequence of each polynucleotide, from 17 to less than the total number of nucleotides in the sequence, or from 19 to less than the total number of nucleotides in the sequence.

Specific examples of the above polynucleotide(s) as target nucleic acid(s) in a kit or device of the present invention include 1 or a combination of 2, 3, 4, 5, 6, 7, 8, 9, 10, or more of the above polynucleotides consisting of nucleotide sequences represented by SEQ ID NOs: 1 to 243 listed in above Table 1. This is just an example and all the other various possible combinations are included in the present invention.

Examples of a combination of target nucleic acids in a kit or device for discriminating between bladder cancer patients and subjects without bladder cancer such as healthy subjects, benign bone and soft tissue tumor and benign breast disease patients, and patients with a cancer other than bladder cancer in the present invention include a combination of two or more of the above polynucleotides consisting of nucleotide sequences represented by SEQ ID NOs listed in Table 1. Specifically, any two or more of the above polynucleotides consisting of nucleotide sequences represented by SEQ ID NOs: 1 to 243 can be combined. Among them, at least one of the newly found polynucleotides consisting of nucleotide sequences represented by SEQ ID NOs: 1 to 228 is preferably selected. In particular, a combination comprising at least one polynucleotide selected from the group consisting of polynucleotides described in any of Tables 20 to 22, further desirably the group consisting of polynucleotides described in Table 23, is more preferred.

The following shows 253 non-limiting examples listed in Table 7-Nos. 1 to 11, Tables 13 to 16, and Table 26-Nos. 2 to 9, which are shown later in Examples, as a polynucleotide comprising a nucleotide sequence represented by SEQ ID NO: 1 (miR-6087) or a complementary sequence thereof, or a combination comprising the polynucleotide (the tables show 256 discriminants).

A kit or device of the present invention may comprise, in addition to the above-described polynucleotide(s) in the present invention (which may include any variant(s), fragment(s), or derivative(s)), a polynucleotide(s) known to be able to detect bladder cancer or a polynucleotide(s) that will be discovered in the future.

The kit or device of the present invention may be used in combination with, in addition to the above-described polynucleotides according to the present invention, an antibody (or antibodies) for measuring a known marker(s) for detection of bladder cancer, such as NMP22 test to detect nuclear matrix protein NuMA, or BTAtrak test to detect a specific basement membrane fragment complex.

These polynucleotides, or variants thereof or fragments thereof contained in the kit of the present invention may be packaged in different containers either individually or in any combination.

The kit of the present invention may comprise a kit for extracting nucleic acids (e.g., total RNA) from body fluids, cells, or tissues, a fluorescent material for labeling, an enzyme and a medium for nucleic acid amplification, an instruction manual, etc.

The device of the present invention may be a device for measuring a cancer marker(s), in which nucleic acids such as the above-described polynucleotide(s), variant(s), derivative(s), or fragment(s) thereof according to the present invention are, for instance, bonded or attached onto a solid phase. Examples of the material for the solid phase include plastics, paper, glass, and silicone. The material for the solid phase is preferably a plastic from the viewpoint of easy processability. The solid phase has any shape and is, for example, square, round, reed-shaped, or film-shaped. The device of the present invention includes, for example, a device for measurement by a hybridization technique. Specific examples thereof include blotting devices and nucleic acid arrays (e.g., microarrays, DNA chips, and RNA chips).

The nucleic acid array technique is a technique which involves bonding or attaching the nucleic acids one by one by use of a method [e.g., a method of spotting the nucleic acids using a high-density dispenser called spotter or arrayer onto the surface of the solid phase surface-treated, if necessary, by coating with L-lysine or the introduction of a functional group such as an amino group or a carboxyl group, a method of spraying the nucleic acids onto the solid phase using an inkjet which injects very small liquid droplets by a piezoelectric element or the like from a nozzle, or a method of sequentially synthesizing nucleotides on the solid phase] to prepare an array such as a chip and measuring target nucleic acids through the use of hybridization using this array.

The kit or device of the present invention comprises nucleic acids capable of specifically binding to at least one, preferably at least two, more preferably at least three, most preferably at least five to all polynucleotides selected from the above-mentioned bladder cancer marker miRNAs of the group A, or to a complementary strand(s) of the polynucleotide(s), respectively. The kit or device of the present invention can optionally further comprise nucleic acids capable of specifically binding to at least one, preferably at least two, more preferably at least three, most preferably at least five to all polynucleotides selected from the above-mentioned bladder cancer marker miRNAs of the group B, or to a complementary strand(s) of the polynucleotide(s), respectively.

The kit or device of the present invention can be used for detecting bladder cancer as described in Section 4 below.

4. Method for Detecting Bladder Cancer

The present invention further relates to a method for detecting bladder cancer, comprising measuring, in vitro, 1 or more (e.g., expression profile(s)) of expression levels of bladder cancer-derived genes represented by miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, and miR-937-5p, and optionally expression levels of bladder cancer-derived genes represented by miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940 in a sample; and evaluating in vitro whether or not a subject has bladder cancer using the measured expression level(s) (and optionally a control expression level(s) in a healthy subject (s) as likewise measured). In the method, it is possible to determine that a subject has bladder cancer by using the expression level(s) of the above-mentioned genes in a sample from a subject suspected of having bladder cancer and control expression levels of the genes in samples from subjects without bladder cancer, if there is a difference in the expression level(s) of the target nucleic acid(s) in the samples (e.g., when comparing the expression level(s) between the subjects), in which the sample(s) may be, for instance, blood, serum, plasma or the like collected from the subject suspected of having bladder cancer and subjects without bladder cancer.

The above-mentioned method of the present invention enables less-invasive, highly sensitive and specific early diagnosis of bladder cancer. This allows for an early treatment and improvement in prognosis and further makes it possible to monitor exacerbation of the disease and monitor effectiveness of surgical, radiotherapeutic, and chemotherapeutic treatment.

For the method for extracting the bladder cancer-derived gene(s) from the sample such as blood, serum, or plasma according to the present invention, it is particularly preferred to add a reagent for RNA extraction in 3D-Gene (registered trademark) RNA extraction reagent from liquid sample kit (Toray Industries, Inc., Japan) for preparation of a sample. Alternatively, a general acidic phenol method (acid guanidinium-phenol-chloroform (AGPC)) may be used, or Trizol (registered trademark) (Life Technologies Corp.) may be used. Alternatively, for preparation of a sample, a reagent for RNA extraction containing acidic phenol, such as Trizol (Life Technologies Corp.) or Isogen (Nippon Gene Co., Ltd., Japan) may be added. Alternatively, a kit such as miRNeasy (registered trademark) Mini Kit (Qiagen N.V.) may be used. However, the method according to the present invention is not limited thereto.

The present invention also provides use of a bladder cancer-derived miRNA gene(s) in a sample from a subject for in vitro detection of an expression product(s) thereof.

A technique to be used for carrying out the method of the present invention is not limited and, for instance, the kit or device of the present invention (comprising the above nucleic acid(s) capable of being used in the present invention) as described in the above Section 3 may be used for carrying out the method. In the method of the present invention, the kit or device described above comprising a single polynucleotide or any possible combination of polynucleotides that can be used in the present invention as described above, can be used.

In the detection or (genetic) diagnosis of bladder cancer according to the present invention, a polynucleotide(s) contained in the kit or device of the present invention can be used as a probe(s) or a primer(s). In the case of using the polynucleotide(s) as a primer(s), TaqMan (registered trademark) MicroRNA Assays from Life Technologies Corp., miScript PCR System from Qiagen N.V., or the like can be used. However, the method according to the present invention is not limited thereto.

In the method of the present invention, measurement of the gene expression levels can be performed according to a routine technique of a method known in the art for specifically detecting particular genes, for example, a hybridization technique such as Northern blot, Southern blot, in situ hybridization, Northern hybridization, or Southern hybridization; a quantitative amplification technique such as quantitative RT-PCR; or a method with a next-generation sequencer. A body fluid such as blood, serum, plasma, or urine from a subject is collected as a sample to be assayed depending on the type of the detection method to be used. Alternatively, total RNA prepared from such a body fluid by the method described above may be used, and various polynucleotides including cDNA prepared from the RNA may be used.

The method of the present invention is useful for the diagnosis of bladder cancer or the detection of the presence or absence of bladder cancer. Specifically, the detection of bladder cancer according to the present invention can be performed by detecting in vitro an expression level(s) of a gene(s) which is detected using the nucleic acid probe(s) or the primer(s) contained in the kit or the device according to the present invention, in a sample such as blood, serum, plasma, or urine from a subject suspected of having bladder cancer. If the expression level(s) of a polynucleotide(s) consisting of a nucleotide sequence(s) represented by at least one of SEQ ID NOs: 1 to 228 and optionally a nucleotide sequence(s) represented by one or more of SEQ ID NOs: 229 to 243 in a sample such as blood, serum, plasma, or urine of a subject suspected of having bladder cancer, is statistically significantly higher compared to an expression level(s) thereof in a sample such as blood, serum, or plasma, or urine of a subject without bladder cancer, the former subject can be evaluated as having bladder cancer.

Regarding the method of the present invention, the method for detecting the absence of bladder cancer or the presence of bladder cancer for a sample from a subject comprises collecting a body fluid such as blood, serum, plasma, or urine of the subject, and measuring the expression level(s) of the target gene(s) (or target nucleic acid(s)) contained therein using one or more polynucleotides (including variant(s), fragment(s), or derivative(s)) selected from the groups of polynucleotides according to the present invention, thereby evaluating the presence or absence of bladder cancer or detecting bladder cancer. The method for detecting bladder cancer according to the present invention can also be used to evaluate or diagnose, for example, the presence or absence of amelioration of the disease or the degree of amelioration thereof in a bladder cancer patient when a bladder cancer-related therapeutic drug which is known in the art or on a development stage (including gemcitabine, a platinum-containing drug (cisplatin/carboplatin), paclitaxel, methotrexate, vinblastine, adriamycin, cisplatin, taxane (docetaxel), ifosfamide, other platinum-containing drugs (nedaplatin), and combination drugs thereof, as non-limiting examples) is administered to the patient for treatment or amelioration of the disease.

The method of the present invention may comprise, for example, the following steps (a), (b), and (c):
(a) contacting in vitro a sample from a subject with a polynucleotide(s) contained in a kit or device of the present invention;
(b) measuring an expression level(s) of target nucleic acid(s) in the sample using the polynucleotide(s) as a nucleic acid probe(s) or primer(s); and
(c) evaluating the presence or absence of bladder cancer (cells) in the subject on the basis of the measurement results in step (b).

In one embodiment, the present invention provides a method for detecting bladder cancer, comprising measuring an expression level(s) of a target nucleic acid(s) in a sample from a subject using a nucleic acid(s) capable of specifically binding to at least one, preferably at least two polynucleotides selected from miR-6087, miR-1185-1-3p, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4652-5p, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p, and miR-937-5p, or to a complementary strand(s) of the polynucleotide(s); and evaluating in vitro whether or not the subject has bladder cancer by using the measured expression level(s) and a control expression level(s) in a subject(s) without bladder cancer as likewise measured.

The term "evaluating" as used herein is evaluation support based on results of in vitro examination, not physician's judgment.

As described above, in the method of the present invention, specifically, miR-6087 is hsa-miR-6087, miR-1185-1-3p is hsa-miR-1185-1-3p, miR-1185-2-3p is hsa-miR-1185-2-3p, miR-1193 is hsa-miR-1193, miR-1199-5p is hsa-miR-1199-5p, miR-1225-5p is hsa-miR-1225-5p, miR-1227-5p is hsa-miR-1227-5p, miR-1228-3p is hsa-miR-1228-3p, miR-1228-5p is hsa-miR-1228-5p, miR-1237-5p is hsa-miR-1237-5p, miR-1238-5p is hsa-miR-1238-5p, miR-1247-3p is hsa-miR-1247-3p, miR-1268a is hsa-miR-1268a, miR-1268b is hsa-miR-1268b, miR-1273g-3p is hsa-miR-1273g-3p, miR-128-2-5p is hsa-miR-128-2-5p, miR-1343-3p is hsa-miR-1343-3p, miR-1343-5p is hsa-miR-1343-5p, miR-1470 is hsa-miR-1470, miR-17-3p is hsa-miR-17-3p, miR-187-5p is hsa-miR-187-5p, miR-1908-3p is hsa-miR-1908-3p, miR-1908-5p is hsa-miR-1908-5p, miR-1909-3p is hsa-miR-1909-3p, miR-1915-3p is hsa-miR-1915-3p, miR-210-5p is hsa-miR-210-5p, miR-24-3p is hsa-miR-24-3p, miR-2467-3p is hsa-miR-2467-3p, miR-2861 is hsa-miR-2861, miR-296-3p is hsa-miR-296-3p, miR-29b-3p is hsa-miR-29b-3p, miR-3131 is hsa-miR-3131, miR-3154 is hsa-miR-3154, miR-3158-5p is hsa-miR-3158-5p, miR-3160-5p is hsa-miR-3160-5p, miR-3162-5p is hsa-miR-3162-5p, miR-3178 is hsa-miR-3178, miR-3180-3p is hsa-miR-3180-3p, miR-3184-5p is hsa-miR-3184-5p, miR-3185 is hsa-miR-3185, miR-3194-3p is hsa-miR-3194-3p, miR-3195 is hsa-miR-3195, miR-3197 is hsa-miR-3197, miR-320a is hsa-miR-320a, miR-320b is hsa-miR-320b, miR-328-5p is hsa-miR-328-5p, miR-342-5p is hsa-miR-342-5p, miR-345-3p is hsa-miR-345-3p, miR-3616-3p is hsa-miR-3616-3p, miR-3619-3p is hsa-miR-3619-3p, miR-3620-5p is hsa-miR-3620-5p, miR-3621 is hsa-miR-3621, miR-3622a-5p is hsa-miR-3622a-5p, miR-3648 is hsa-miR-3648, miR-3652 is hsa-miR-3652, miR-3656 is hsa-miR-3656, miR-3663-3p is hsa-miR-3663-3p, miR-3679-5p is hsa-miR-3679-5p, miR-371b-5p is hsa-miR-371b-5p, miR-373-5p is hsa-miR-373-5p, miR-3917 is hsa-miR-3917, miR-3940-5p is hsa-miR-3940-5p, miR-3960 is hsa-miR-3960, miR-4258 is hsa-miR-4258, miR-4259 is hsa-miR-4259, miR-4270 is hsa-miR-4270, miR-4286 is hsa-miR-4286, miR-4298 is hsa-miR-4298, miR-4322 is hsa-miR-4322, miR-4327 is hsa-miR-4327, miR-4417 is hsa-miR-4417, miR-4419b is hsa-miR-4419b, miR-4429 is hsa-miR-4429, miR-4430 is hsa-miR-4430, miR-4433a-3p is hsa-miR-4433a-3p, miR-4436b-5p is hsa-miR-4436b-5p, miR-4443 is hsa-miR-4443, miR-4446-3p is hsa-miR-4446-3p, miR-4447 is hsa-miR-4447, miR-4448 is hsa-miR-4448, miR-4449 is hsa-miR-4449, miR-4454 is hsa-miR-4454, miR-4455 is hsa-miR-4455, miR-4459 is hsa-miR-4459, miR-4462 is hsa-miR-4462, miR-4466 is hsa-miR-4466, miR-4467 is hsa-miR-4467, miR-4480 is hsa-miR-4480, miR-4483 is hsa-miR-4483, miR-4484 is hsa-miR-4484, miR-4485-5p is hsa-miR-4485-5p, miR-4488 is hsa-miR-4488, miR-4492 is hsa-miR-4492, miR-4505 is hsa-miR-4505, miR-4515 is hsa-miR-4515, miR-4525 is hsa-miR-4525, miR-4534 is hsa-miR-4534, miR-4535 is hsa-miR-4535, miR-4633-3p is hsa-miR-4633-

3p, miR-4634 is hsa-miR-4634, miR-4640-5p is hsa-miR-4640-5p, miR-4649-5p is hsa-miR-4649-5p, miR-4651 is hsa-miR-4651, miR-4652-5p is hsa-miR-4652-5p, miR-4655-5p is hsa-miR-4655-5p, miR-4656 is hsa-miR-4656, miR-4658 is hsa-miR-4658, miR-4663 is hsa-miR-4663, miR-4673 is hsa-miR-4673, miR-4675 is hsa-miR-4675, miR-4687-3p is hsa-miR-4687-3p, miR-4687-5p is hsa-miR-4687-5p, miR-4690-5p is hsa-miR-4690-5p, miR-4695-5p is hsa-miR-4695-5p, miR-4697-5p is hsa-miR-4697-5p, miR-4706 is hsa-miR-4706, miR-4707-3p is hsa-miR-4707-3p, miR-4707-5p is hsa-miR-4707-5p, miR-4708-3p is hsa-miR-4708-3p, miR-4710 is hsa-miR-4710, miR-4718 is hsa-miR-4718, miR-4722-5p is hsa-miR-4722-5p, miR-4725-3p is hsa-miR-4725-3p, miR-4726-5p is hsa-miR-4726-5p, miR-4727-3p is hsa-miR-4727-3p, miR-4728-5p is hsa-miR-4728-5p, miR-4731-5p is hsa-miR-4731-5p, miR-4736 is hsa-miR-4736, miR-4739 is hsa-miR-4739, miR-4740-5p is hsa-miR-4740-5p, miR-4741 is hsa-miR-4741, miR-4750-5p is hsa-miR-4750-5p, miR-4755-3p is hsa-miR-4755-3p, miR-4763-3p is hsa-miR-4763-3p, miR-4771 is hsa-miR-4771, miR-4783-3p is hsa-miR-4783-3p, miR-4783-5p is hsa-miR-4783-5p, miR-4787-3p is hsa-miR-4787-3p, miR-4792 is hsa-miR-4792, miR-498 is hsa-miR-498, miR-5008-5p is hsa-miR-5008-5p, miR-5010-5p is hsa-miR-5010-5p, miR-504-3p is hsa-miR-504-3p, miR-5195-3p is hsa-miR-5195-3p, miR-550a-5p is hsa-miR-550a-5p, miR-5572 is hsa-miR-5572, miR-5739 is hsa-miR-5739, miR-6075 is hsa-miR-6075, miR-6076 is hsa-miR-6076, miR-6088 is hsa-miR-6088, miR-6124 is hsa-miR-6124, miR-6131 is hsa-miR-6131, miR-6132 is hsa-miR-6132, miR-614 is hsa-miR-614, miR-615-5p is hsa-miR-615-5p, miR-619-5p is hsa-miR-619-5p, miR-642b-3p is hsa-miR-642b-3p, miR-6510-5p is hsa-miR-6510-5p, miR-6511a-5p is hsa-miR-6511a-5p, miR-6515-3p is hsa-miR-6515-3p, miR-6515-5p is hsa-miR-6515-5p, miR-663b is hsa-miR-663b, miR-6716-5p is hsa-miR-6716-5p, miR-6717-5p is hsa-miR-6717-5p, miR-6722-3p is hsa-miR-6722-3p, miR-6724-5p is hsa-miR-6724-5p, miR-6726-5p is hsa-miR-6726-5p, miR-6737-5p is hsa-miR-6737-5p, miR-6741-5p is hsa-miR-6741-5p, miR-6742-5p is hsa-miR-6742-5p, miR-6743-5p is hsa-miR-6743-5p, miR-6746-5p is hsa-miR-6746-5p, miR-6749-5p is hsa-miR-6749-5p, miR-6760-5p is hsa-miR-6760-5p, miR-6762-5p is hsa-miR-6762-5p, miR-6765-3p is hsa-miR-6765-3p, miR-6765-5p is hsa-miR-6765-5p, miR-6766-3p is hsa-miR-6766-3p, miR-6766-5p is hsa-miR-6766-5p, miR-6771-5p is hsa-miR-6771-5p, miR-6774-5p is hsa-miR-6774-5p, miR-6777-5p is hsa-miR-6777-5p, miR-6778-5p is hsa-miR-6778-5p, miR-6780b-5p is hsa-miR-6780b-5p, miR-6781-5p is hsa-miR-6781-5p, miR-6782-5p is hsa-miR-6782-5p, miR-6784-5p is hsa-miR-6784-5p, miR-6785-5p is hsa-miR-6785-5p, miR-6787-5p is hsa-miR-6787-5p, miR-6789-5p is hsa-miR-6789-5p, miR-6791-5p is hsa-miR-6791-5p, miR-6794-5p is hsa-miR-6794-5p, miR-6800-5p is hsa-miR-6800-5p, miR-6802-5p is hsa-miR-6802-5p, miR-6803-5p is hsa-miR-6803-5p, miR-6812-5p is hsa-miR-6812-5p, miR-6816-5p is hsa-miR-6816-5p, miR-6819-5p is hsa-miR-6819-5p, miR-6821-5p is hsa-miR-6821-5p, miR-6826-5p is hsa-miR-6826-5p, miR-6831-5p is hsa-miR-6831-5p, miR-6836-3p is hsa-miR-6836-3p, miR-6840-3p is hsa-miR-6840-3p, miR-6842-5p is hsa-miR-6842-5p, miR-6850-5p is hsa-miR-6850-5p, miR-6861-5p is hsa-miR-6861-5p, miR-6869-5p is hsa-miR-6869-5p, miR-6870-5p is hsa-miR-6870-5p, miR-6877-5p is hsa-miR-6877-5p, miR-6879-5p is hsa-miR-6879-5p, miR-6880-3p is hsa-miR-6880-3p, miR-6880-5p is hsa-miR-6880-5p, miR-6885-5p is hsa-miR-6885-5p, miR-6887-5p is hsa-miR-6887-5p, miR-7107-5p is hsa-miR-7107-5p, miR-7108-3p is hsa-miR-7108-3p, miR-7109-5p is hsa-miR-7109-5p, miR-711 is hsa-miR-711, miR-7113-3p is hsa-miR-7113-3p, miR-7150 is hsa-miR-7150, miR-744-5p is hsa-miR-744-5p, miR-7975 is hsa-miR-7975, miR-7977 is hsa-miR-7977, miR-8052 is hsa-miR-8052, miR-8069 is hsa-miR-8069, miR-8073 is hsa-miR-8073, miR-887-3p is hsa-miR-887-3p, and miR-937-5p is hsa-miR-937-5p.

In addition, in one embodiment, a nucleic acid(s) (specifically, a probe(s) or primer(s)) in the method of the present invention, is selected from polynucleotides shown in any of the following group (a) to (e):
 (a) a polynucleotide consisting of a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;
 (b) a polynucleotide comprising a nucleotide sequence represented by any of SEQ ID NOs: 1 to 228;
 (c) a polynucleotide consisting of a nucleotide sequence complementary to a nucleotide sequence represented by any of SEQ ID NOs: 1 to 228 or a nucleotide sequence derived from the nucleotide sequence by the replacement of u with t, a variant thereof, a derivative thereof, or a fragment thereof comprising 15 or more consecutive nucleotides;
 (d) a polynucleotide comprising a nucleotide sequence complementary to a nucleotide sequence represented by any of SEQ ID NOs: 1 to 228 or a nucleotide sequence derived from the nucleotide sequence by the replacement of u with t; and
 (e) a polynucleotide hybridizing under stringent conditions to any of the polynucleotides (a) to (d).

In the method of the present invention, further, the expression level(s) of at least one polynucleotide selected from miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940 can be measured.

Specifically, miR-1202 is hsa-miR-1202, miR-1207-5p is hsa-miR-1207-5p, miR-1246 is hsa-miR-1246, miR-1254 is hsa-miR-1254, miR-135a-3p is hsa-miR-135a-3p, miR-1469 is hsa-miR-1469, miR-149-3p is hsa-miR-149-3p, miR-150-3p is hsa-miR-150-3p, miR-1914-3p is hsa-miR-1914-3p, miR-191-5p is hsa-miR-191-5p, miR-423-5p is hsa-miR-423-5p, miR-663a is hsa-miR-663a, miR-92a-2-5p is hsa-miR-92a-2-5p, miR-92a-3p is hsa-miR-92a-3p, and miR-940 is hsa-miR-940.

Further, in one embodiment, the expression level(s) of the polynucleotide(s) are measured by using nucleic acid(s) capable of specifically binding to the polynucleotide(s) or to the complementary strand(s) of the polynucleotide(s), and the nucleic acid(s) are polynucleotide(s) selected from the following polynucleotides (f) to (j):
 (f) a polynucleotide consisting of a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;
 (g) a polynucleotide comprising a nucleotide sequence represented by any of SEQ ID NOs: 229 to 243;
 (h) a polynucleotide consisting of a nucleotide sequence complementary to a nucleotide sequence represented by any of SEQ ID NOs: 229 to 243 or a nucleotide sequence derived from the nucleotide sequence by the replacement of u with t, a variant thereof, a derivative thereof, or a fragment thereof comprising 15 or more consecutive nucleotides;
(i) a polynucleotide comprising a nucleotide sequence complementary to a nucleotide sequence represented by any of SEQ ID NOs: 229 to 243 or a nucleotide sequence derived from the nucleotide sequence by the replacement of u with t; and
j) a polynucleotide hybridizing under stringent conditions to any of the polynucleotides (f) to (i).

Examples of the sample used in the method of the present invention can include samples prepared from living tissues (preferably bladder tissues or renal pelvis or urinary tract tissues) or body fluids such as blood, serum, plasma, and urine from subjects. Specifically, for example, an RNA-containing sample prepared from the tissue, a polynucleotide-containing sample further prepared therefrom, a body fluid such as blood, serum, plasma, or urine, a portion or the whole of a living tissue collected from the subject by biopsy or the like, or a living tissue excised by surgery can be used, and the sample for measurement can be prepared therefrom.

As used herein, the subject refers to a mammal, for example, a human, a monkey, a mouse, or a rat, without any limitation, and is preferably a human.

The steps of the method of the present invention can be changed depending on the type of the sample to be measured.

In the case of using RNA as an analyte, the method for detecting bladder cancer (cells) can comprise, for example, the following steps (a), (b), and (c):
(a) binding RNA prepared from a sample from a subject (wherein, for example, the 3' end of the RNA may be polyadenylated for quantitative RT-PCR in step (b) or any sequence may be added to one or both ends of the RNA by ligation, etc.) or a complementary polynucleotides (cDNA) transcribed from the RNA to a polynucleotide(s) in the kit of the present invention;
(b) measuring the sample-derived RNA or the cDNA synthesized from the RNA, which has been bound to the polynucleotide(s), by hybridization using the polynucleotide(s) as a nucleic acid probe(s) or by quantitative RT-PCR using the polynucleotide(s) as a primer (s); and
(c) evaluating the presence or absence of bladder cancer (or bladder cancer-derived gene(s)) on the basis of the measurement results of step (b).

For example, various hybridization methods can be used for measuring the expression level(s) of a target gene(s) according to the present invention. For example, Northern blot, Southern blot, DNA chip analysis, in situ hybridization, Northern hybridization, or Southern hybridization can be used as such a hybridization method. PCR such as quantitative RT-PCR or next-generation sequencing can also be used in combination with a hybridization method, or as an alternative thereof.

In the case of using the Northern blot, the presence or absence of expression of each gene or the expression level thereof in the RNA can be detected or measured by using, for example, the nucleic acid probe(s) that can be used in the present invention. Specific examples thereof can include a method which comprises labeling the nucleic acid probe (or a complementary strand) with a radioisotope ($^{32}P$, $^{33}P$, $^{35}S$, etc.), a fluorescent material, or the like, hybridizing the labeled product with the living tissue-derived RNA from a subject, which is transferred to a nylon membrane or the like according to a routine method, and then detecting and measuring a signal derived from the label (radioisotope or fluorescent material) on the formed DNA/RNA duplex using a radiation detector (examples thereof can include BAS-1800 II (Fujifilm Corp.)) or a fluorescence detector (examples thereof can include STORM 865 (GE Healthcare Japan Corp.)).

In the case of using the quantitative RT-PCR, the presence or absence of expression of each gene or the expression level thereof in the RNA can be detected or measured by using, for example, the primer(s) that can be used in the present invention. Specific examples thereof can include a method which comprises recovering the living tissue-derived RNA from a subject, polyadenylating the 3'-end, preparing cDNAs from the polyadenylated RNA according to a routine method, and performing PCR according to a routine method by hybridizing a pair of primers (consisting of a positive strand and a reverse strand each binding to the cDNA) which could be contained in the kit or device for detection of the present invention with the cDNA such that the region of each target gene marker can be amplified with the cDNA as a template, to detect the obtained single-stranded or double-stranded DNA. The method for detecting the single-stranded or double-stranded DNA can include a method of performing the PCR using the primers labeled in advance with a radioisotope or a fluorescent material, a method of electrophoresing the PCR product on an agarose gel and staining the double-stranded DNA with ethidium bromide or the like for detection, and a method of transferring the produced single-stranded or double-stranded DNA to a nylon membrane or the like according to a routine method and hybridizing the single-stranded or double-stranded DNA with a labeled nucleic acid probe for detection.

In the case of using the nucleic acid array analysis, an RNA chip or a DNA chip in which the kit or device for detection in the present invention is attached as nucleic acid probes (single-stranded or double-stranded) to a substrate (solid phase), for example, is used. Regions having the attached nucleic acid probes are referred to as probe spots, and regions having no attached nucleic acid probe are referred to as blank spots. A group of genes immobilized on a solid-phase substrate is generally called a nucleic acid chip, a nucleic acid array, a microarray, or the like. The DNA or RNA array includes a DNA or RNA macroarray and a DNA or RNA microarray. In the present specification, the term "chip" includes these arrays. 3D-Gene (registered trademark) Human miRNA Oligo chip (Toray Industries, Inc., Japan) can be used as the DNA chip, though the DNA chip is not limited thereto.

Examples of the measurement using the DNA chip can include, but are not limited to, a method of detecting and measuring a signal derived from the label on the kit or device for detection using an image detector (examples thereof can include Typhoon 9410 (GE Healthcare) and 3D-Gene (registered trademark) scanner (Toray Industries, Inc., Japan)).

The "stringent conditions" used herein are, as mentioned above, conditions under which a nucleic acid probe hybridizes to its target sequence to a detectably larger extent (e.g., a measurement value equal to or larger than "(a mean of background measurement values)+(a standard error of the background measurement values)×2)") than that for other sequences.

The stringent conditions are defined by hybridization and subsequent washing. Examples of the hybridization conditions include, but not limited to, 30° C. to 60° C. for 1 to 24 hours in a solution containing SSC, a surfactant, formamide, dextran sulfate, a blocking agent(s), etc. In this context, 1×SSC is an aqueous solution (pH 7.0) containing 150 mM sodium chloride and 15 mM sodium citrate. The surfactant includes, for example, SDS (sodium dodecyl sulfate), Triton, or Tween. The hybridization conditions more preferably comprise 3-10×SSC and 0.1-1% SDS. Examples of the conditions for the washing, following the hybridization, which is another condition to define the stringent conditions, can include conditions comprising continuous washing at 30° C. in a solution containing 0.5×SSC and 0.1% SDS, at 30° C. in a solution containing 0.2×SSC and 0.1% SDS, and at 30° C. in a 0.05×SSC solution. It is desirable that the complementary strand should maintain its hybridized state with a target plus strand even by washing under such conditions. Specifically, examples of such a complementary strand can include a strand consisting of a nucleotide sequence in a completely complementary relationship with the nucleotide sequence of the target plus (+) strand, and a strand consisting of a nucleotide sequence having at least 80%, preferably at least 85%, more preferably at least 90% or at least 95% homology to the strand.

Other examples of the "stringent conditions" for the hybridization are described in, for example, Sambrook, J. & Russel, D., Molecular Cloning, A LABORATORY MANUAL, Cold Spring Harbor Laboratory Press, published on Jan. 15, 2001, Vol. 1, 7.42 to 7.45 and Vol. 2, 8.9 to 8.17, and can be used in the present invention.

Examples of the conditions for carrying out PCR using polynucleotide fragments in the kit of the present invention as primers include treatment for approximately 15 seconds to 1 minute at 5 to 10° C. plus a Tm value calculated from the sequences of the primers, using a PCR buffer having composition such as 10 mM Tris-HCL (pH 8.3), 50 mM KCl, and 1 to 2 mM MgCl$_2$. Examples of the method for calculating such a Tm value include Tm value=2×(the number of adenine residues+the number of thymine residues)+4×(the number of guanine residues+the number of cytosine residues).

In the case of using the quantitative RT-PCR, a commercially available kit for measurement specially designed for quantitatively measuring miRNA, such as TaqMan (registered trademark) MicroRNA Assays (Life Technologies Corp.), LNA (registered trademark)-based MicroRNA PCR (Exiqon), or Ncode (registered trademark) miRNA qRT-PCT kit (Invitrogen Corp.) may be used.

In the method of the present invention, measurement of the gene expression level(s) may be performed with a sequencer, in addition to hybridization methods described above. In use of a sequencer, any of DNA sequencers of the first generation based on Sanger method, the second generation with shorter read size, and the third generation with longer read size can be used (herein referred to as "next-generation sequencer", including sequencers of the second generation and the third generation). For example, a commercially available measurement kit specially designed for measuring miRNA using Miseq, Hiseq, or NexSeq (Illumina, Inc.); Ion Proton, Ion PGM, or Ion S5/S5 XL (Thermo Fisher Scientific Inc.); PacBio RS II or Sequel (Pacific Biosciences of California, Inc.); MinION (Oxford Nanopore Technologies Ltd.) exemplified in use of a Nanopore sequencer; or the like may be used.

Next-generation sequencing is a method of obtaining sequence information using a next-generation sequencer, and characterized by being capable of simultaneously performing a huge number of sequencing reactions compared to Sanger method (e.g., Rick Kamps et al., Int. J. Mol. Sci., 2017, 18(2), p. 308 and Int. Neurourol. J., 2016, 20 (Suppl.2), S76-83). Examples of next-generation sequencing steps for miRNA include, but not limited to, the following steps: at first, adaptor sequences having predetermined nucleotide sequences are attached, and all RNAs are reverse-transcribed into cDNAs before or after attachment of the sequences. After the reverse transcription, cDNAs derived from specific target miRNAs may be amplified or concentrated by PCR or the like or with a probe or the like, for analyzing the target miRNA before sequencing steps. Subsequent sequencing steps varies in detail depending on the type of a next-generation sequencer, but typically, a sequencing reaction is performed by linking to a substrate via an adaptor sequence and further using the adaptor sequence as a priming site. See details of the sequencing reaction, for example, in Rick Kamps et al. (see supra). Finally, the data are outputted. This step provides a collection of sequence information (reads) obtained by the sequencing reaction. For example, next-generation sequencing can identify a target miRNA(s) based on the sequence information, and measure the expression level thereof based on the number of reads having the sequences of the target miRNA(s).

For the calculation of gene expression levels, statistical treatment described in, for example, Statistical analysis of gene expression microarray data (Speed T., Chapman and Hall/CRC), and A beginner's guide Microarray gene expression data analysis (Causton H. C. et al., Blackwell publishing) can be used in the present invention, though the calculation method is not limited thereto. For example, twice, preferably 3 times, more preferably 6 times the standard deviation of the measurement values of the blank spots are added to the average measurement value of the blank spots on the DNA chip, and probe spots having a signal value equal to or larger than the resulting value can be regarded as detection spots. Alternatively, the average measurement value of the blank spots is regarded as a background and can be subtracted from the measurement values of the probe spots to determine gene expression levels. A missing value for a gene expression level can be excluded from the analyte, preferably replaced with the smallest value of the gene expression level in each DNA chip, or more preferably replaced with a value obtained by subtracting 0.1 from a logarithmic value of the smallest value of the gene expression level. In order to eliminate low-signal genes, only a gene(s) having a gene expression level of $2^6$, preferably $2^8$, more preferably $2^{10}$ or larger in 20% or more, preferably 50% or more, more preferably 80% or more of the number of measurement samples can be selected as the analyte(s). Examples of the normalization of the gene expression level include, but are not limited to, global normalization and quantile normalization (Bolstad, B. M. et al., 2003, Bioinformatics, Vol. 19, p. 185-193).

The present invention also provides a method for detecting bladder cancer (or assisting the detection thereof) in a subject, comprising measuring a target genes or gene expression levels in a sample from the subject; and assigning the expression levels of the target genes in the sample from the subject to a discriminant (discriminant function), which is prepared using gene expression levels of a sample(s) from a subject(s) (or a patient(s)) known to have bladder cancer and a sample(s) from a subject(s) without bladder cancer, as a training sample(s), and which can distinguishably discriminate the presence or absence of bladder cancer, thereby evaluating the presence or absence of bladder cancer.

Specifically, the present invention further provides the method comprising a first step of measuring in vitro expression levels of target genes, which are known to determine or evaluate whether a subject has bladder cancer and/or not, in a plurality of samples; a second step of preparing a discriminant using the measurement values of the expression levels of the target genes obtained in the first step as training samples; a third step of measuring in vitro the expression levels of the target genes in a sample from the subject in the same manner as in the first step; and a fourth step of assigning the measurement values of the expression levels of the target genes obtained in the third step to the discriminant obtained in the second step, and determining or evaluating whether or not the subject has bladder cancer on the basis of the results obtained from the discriminant. The above target genes are those that can be detected, for example, by the polynucleotides, the polynucleotides contained in the kit or chip, and variants thereof or fragments thereof.

The discriminant herein can be prepared by use of any discriminant analysis method, based on which a discriminant that distinguishably discriminates the presence or absence of bladder cancer can be prepared, such as Fisher's discriminant analysis, nonlinear discriminant analysis based on the Mahalanobis' distance, neural network, Support Vector Machine (SVM), logistic regression analysis (especially, logistic regression analysis using the LASSO (Least Absolute Shrinkage and Selection Operator)), k-nearest neighbor method, or decision tree, though the analysis method is not limited to these specific examples.

When a clustering boundary is a straight line or a hyperplane, the linear discriminant analysis is a method for determining the belonging of a cluster using Formula 1 as a discriminant. In Formula 1, x represents an explanatory variable, w represents a coefficient of the explanatory variable, and wo represents a constant term.

$$f(x) = w_0 + \sum_{i=1}^{n} w_i x_i \qquad \text{Formula 1}$$

Values obtained from the discriminant are referred to as discriminant scores. The measurement values of a newly offered data set can be assigned as explanatory variables to the discriminant to determine clusters by the signs of the discriminant scores.

The Fisher's discriminant analysis, a type of linear discriminant analysis, is a dimensionality reduction method for selecting a dimension suitable for discriminating classes, and constructs a highly discriminating synthetic variable by focusing on the variance of the synthetic variables and minimizing the variance of data having the same label (Venables, W. N. et al., Modern Applied Statistics with S. Fourth edition. Springer, 2002). In the Fisher's discriminant analysis, direction w of projection is determined so as to maximize Formula 2. In this formula, μ represents an average input, $n_g$ represents the number of data belonging to class g, and $\mu_g$ represents an average input of the data belonging to class g. The numerator and the denominator are the interclass variance and the intraclass variance, respectively, when each of data is projected in the direction of the vector w. Discriminant coefficient wi is determined by maximizing this ratio (Takafumi Kanamori et al., "Pattern Recognition", KYORITSU SHUPPAN CO., LTD. (Tokyo, Japan) (2009); Richard O. et al., Pattern Classification, Second Edition, Wiley-Interscience, 2000).

$$J(w) = \frac{\sum_{g=1}^{G} n_g (w^T \mu_g - w^T \mu)(w^T \mu_g - w^T \mu)^T}{\sum_{g=1}^{G} \sum_{i:\ y_i=g} (w^T x_i - w^T \mu_g)(w^T x_i - w^T \mu_g)} \qquad \text{Formula 2}$$

-continued $$\text{subject to } \mu = \sum_{i=1}^{n} \frac{x_i}{n}, \mu_g = \sum_{i:\ u_i=g}^{n} \frac{x_i}{n_g}$$

The Mahalanobis' distance is calculated according to Formula 3 in consideration of data correlation and can be used as nonlinear discriminant analysis for determining a cluster in which a data point belongs to, based on a short Mahalanobis' distance from the data point to that cluster. In Formula 3, μ represents a central vector of each cluster, and $S^{-1}$ represents an inverse matrix of the variance-covariance matrix of the cluster. The central vector is calculated from explanatory variable x, and an average vector, a median value vector, or the like can be used.

$$D(x, \mu) = \{(x-\mu)^t S^{-1}(x-\mu)\}^{\frac{1}{2}} \qquad \text{Formula 3}$$

SVM is a discriminant analysis method devised by V. Vapnik (The Nature of Statistical Leaning Theory, Springer, 1995). Particular data points of a data set having known classes are defined as explanatory variables, and classes are defined as objective variables. A boundary plane called hyperplane for correctly classifying the data set into the known classes is determined, and a discriminant for data classification is determined using the boundary plane. Then, the measurement values of a newly offered data set can be assigned as explanatory variables to the discriminant to determine classes. In this respect, the result of the discriminant analysis may be classes, may be a probability of being classified into correct classes, or may be the distance from the hyperplane. In SVM, a method of nonlinearly converting a feature vector to a high dimension and performing linear discriminant analysis in the space is known as a method for tackling nonlinear problems. An expression in which an inner product of two factors in a nonlinearly mapped space is expressed only by inputs in their original spaces is called kernel. Examples of the kernel can include a linear kernel, an RBF (Radial Basis Function) kernel, and a Gaussian kernel. While highly dimensional mapping is performed according to the kernel, the optimum discriminant, i.e., a discriminant, can be actually constructed by mere calculation according to the kernel, which avoids calculating features in the mapped space (e.g., Hideki Aso et al., Frontier of Statistical Science 6 "Statistics of pattern recognition and learning—New concepts and approaches", Iwanami Shoten, Publishers (Tokyo, Japan) (2004); Nello Cristianini et al., Introduction to SVM, Kyoritsu Shuppan Co., Ltd. (Tokyo, Japan) (2008)).

C-support vector classification (C-SVC), a type of SVM, comprises preparing a hyperplane by training a data set with the explanatory variables of two groups and classifying an unknown data set into either of the groups (C. Cortes et al., 1995, Machine Learning, Vol. 20, p. 273-297).

Exemplary calculation of the C-SVC discriminant that can be used in the method of the present invention will be given below. First, all subjects are divided into two groups, i.e., a group of bladder cancer patients and a group of subjects without bladder cancer. A bladder tissue test can be used as a reference of determining whether or not a subject has bladder cancer.

Next, a data set consisting of comprehensive gene expression levels of serum-derived samples of the two divided groups (hereinafter, this data set is referred to as a training cohort) is prepared, and a C-SVC discriminant is determined by using genes found to differ clearly in their gene expression levels between the two groups as explanatory variables and this grouping as objective variables (e.g., −1 and +1). An optimizing objective function is represented by Formula 4 wherein e represents all input vectors, y represents an objective variable, a represents a Lagrange's undetermined multiplier vector, Q represents a positive definite matrix, and C represents a parameter for adjusting constrained conditions.

$$\min_a \frac{1}{2} a^T Q a - e^T a \qquad \text{Formula 4}$$

subject to $y^T a = 0, 0 \le a_i \le C, i = 1, \ldots, l$,

Formula 5 is a finally obtained discriminant, and a group in which the data point belongs to can be determined on the basis of the sign of a value obtained according to the discriminant. In this formula, x represents a support vector, y represents a label indicating the belonging of a group, a represents the corresponding coefficient, b represents a constant term, and K represents a kernel function.

$$f(x) = \text{sgn}\left(\sum_{i=1}^{l} y_i a_i K(x_i, x) + b\right) \qquad \text{Formula 5}$$

For example, an RBF kernel defined by Formula 6 can be used as the kernel function. In this formula, x represents a support vector, and y represents a kernel parameter for adjusting the complexity of the hyperplane.

$$K(x_i, x_j) = \exp(-r\|x_i - x_j\|^2), r < 0 \qquad \text{Formula 6}$$

Logistic regression is a multivariate analysis method in which one category variable (binary variable) is used as an objective variable to predict the probability of occurrence by using multiple explanatory variables, and is expressed in the following formula 7.

$$\text{logit}(\text{prob}(y_i = 1)) = \beta_0 + \Sigma_{j=1}^{P} \beta_j \chi_j \qquad \text{Formula 7}$$

The LASSO (Least Absolute Shrinkage and Selection Operator) method is one of techniques for selecting and adjusting variables when multiple observed variables are present, and was proposed by Tibshirani (Tibshirani R., 1996, J R Stat Soc Ser B, vol. 58, p267-88). The LASSO method is characterized in that when regression coefficients are estimated, penalties are imposed, so that overfitting to a model is reduced and some of the regression coefficients are then estimated as 0. In logistic regression using the LASSO method, regression coefficients are estimated so as to maximize a log-likelihood function expressed in Formula 8.

$$\frac{1}{N}\sum_{i=1}^{N}\left(y_i(\beta_0 + \chi_j^T \beta) - \log\left(1 + e^{(\beta_0 + \chi_j^T \beta)}\right)\right) - \lambda \sum_{j=1}^{P}|\beta_j| \qquad \text{Formula 8}$$

The value y of the discriminant formula obtained in analysis by the LASSO method is assigned to the logistic function represented by the following formula 9, and the group to which the subject belongs can be determined on the basis of the obtained value.

$$\text{Exp}(y)/(1+\exp(y)) \qquad \text{Formula 9}$$

In addition to these methods, an approach such as neural network, k-nearest neighbor method, decision tree, or logistic regression analysis can be selected as a method for determining or evaluating whether or not the sample derived from the subject contains bladder cancer.

The method of the present invention can comprise, for example, the following steps (a), (b), and (c):

(a) measuring an expression level(s) of a target gene(s) in samples already known to be from bladder cancer patients and to be from subjects without bladder cancer, using polynucleotide(s), a kit, or a DNA chip for detection according to the present invention;

(b) preparing the discriminants of Formulas 1 to 3, 5 and 6 described above from the measurement values of the expression level(s) measured in step (a); and (c) measuring an expression level(s) of the target gene(s) in a sample from a subject using the polynucleotide(s), the kit, or the DNA chip for diagnosis (detection) according to the present invention, and assigning the obtained measurement value(s) to the discriminants prepared in step (b), and determining or evaluating whether or not the subject has bladder cancer on the basis of the obtained results, or evaluating the expression level(s) derived from a bladder cancer patient by comparison with a control from a subject(s) without bladder cancer.

In this context, in the discriminants of Formulas 1 to 3, 5 and 6, x represents an explanatory variable and includes a value obtained by measuring a polynucleotide(s) selected from the polynucleotides described in Section 2 above, or a fragment thereof. Specifically, the explanatory variable of the present invention for discriminating between a bladder cancer patient(s) and subject(s) without bladder cancer is a gene expression level(s) selected from, for example, the following (1) and (2):

(1) gene expression level(s) in sera of a bladder cancer patient and a subject without bladder cancer as measured by any DNA comprising 15 or more consecutive nucleotides in the nucleotide sequence represented by any of SEQ ID NOs: 1 to 228 or in a complementary sequence thereof; and (2) gene expression level(s) in sera of a bladder cancer patient and a subject without bladder cancer as measured by any DNA comprising 15 or more consecutive nucleotides in the nucleotide sequence represented by any of SEQ ID NOs: 229 to 243 or in a complementary sequence thereof.

As described above, for the method for determining or evaluating whether or not a subject has bladder cancer using a sample from the subject, it is necessary to use a discriminant employing one or more gene expression levels as an explanatory variable(s). In particular, for enhancing the accuracy of the discriminant using a single gene expression level alone, it is necessary to use a gene having a clear difference in the expression level between two groups consisting of a group of bladder cancer patients and a group of subjects with normal cognitive functions, in a discriminant.

Specifically, the gene that is used for an explanatory variable of a discriminant is preferably determined as follows. First, using comprehensive gene expression levels of a group of bladder cancer patients and comprehensive gene expression levels of a group of test subjects without bladder cancer, both of which are in a training cohort, as a data set, the degree of difference in the expression level of each gene between the two groups is obtained by use of, for example, the P value of a parametric analysis such as t-test, the P value of a nonparametric analysis such as the Mann-Whitney's U test or the P value of the Wilcoxon test.

The gene can be regarded as being statistically significant when the critical rate (significance level) as the P value obtained by the test is smaller than, for example, 5%, 1%, or 0.01%.

In order to correct an increased probability of type I error attributed to the repetition of a test, a method known in the art, for example, Bonferroni or Holm method, can be used for the correction (e.g., Yasushi Nagata et al., "Basics of statistical multiple comparison methods", Scientist Press Co., Ltd. (Tokyo, Japan) (2007)). As an example of the Bonferroni correction, for example, the P value obtained by a test is multiplied by the number of repetitions of the test, i.e., the number of genes used in the analysis, and the obtained value can be compared with a desired significance level to suppress a probability of causing type I error in the whole test.

Instead of the test, the absolute value (fold change) of an expression ratio of a median value of each gene expression level between gene expression levels of a group of bladder cancer patients and gene expression levels of a group of test subjects without bladder cancer may be calculated to select a gene that is used for an explanatory variable in a discriminant. Alternatively, ROC curves may be prepared using gene expression levels of a group of bladder cancer patients and a group of test subjects without bladder cancer, and a gene that is used for an explanatory variable in a discriminant can be selected on the basis of an AUROC value.

Next, a discriminant that can be calculated by various methods described above is prepared using any number of genes having large difference in their gene expression levels determined here. Examples of the method for constructing a discriminant that produces the largest discrimination accuracy include a method of constructing a discriminant in every combination of genes that satisfy the significance level being P value, and a method of repetitively evaluating the genes for use in the preparation of a discriminant while increasing the number of genes one by one in a descending order of difference in gene expression level (Furey T S. et al., 2000, Bioinformatics, Vol. 16, p. 906-14). To the discriminant, the gene expression level of another independent bladder cancer patient or a test subject without bladder cancer is assigned as an explanatory variable to calculate discrimination results of the group to which the independent bladder cancer patient or the test subject without bladder cancer belongs. Specifically, the gene set for diagnosis found and the discriminant constructed using the gene set for diagnosis can be evaluated in an independent sample cohort to find more universal gene set for diagnosis that can detect bladder cancer and a more universal method for discriminating bladder cancer.

In preparing a discriminant using expression levels of a plurality of genes as an explanatory variable, it is not necessary to select a gene having a clear difference in expression level between the group of bladder cancer patients and the group of test subjects without bladder cancer as described above. Specifically, if expression levels of a plurality of genes are used in combination even though the expression levels of individual genes do not clearly differ, a discriminant having high discriminant performance can be obtained, as the case may be. Because of this, it is possible to utilize a method of directly searching for a discriminant having high discriminant performance without beforehand selecting the gene to be employed in the discriminant.

Split-sample method is preferably used for evaluating the performance (generality) of the discriminant. Specifically, a data set is divided into a training cohort and a validation cohort, and gene selection by a statistical test and discriminant preparation are performed using the training cohort. Accuracy, sensitivity, and specificity are calculated using a result of discriminating a validation cohort according to the discriminant, and a true group to which the validation cohort belongs, to evaluate the performance of the discriminant. On the other hand, instead of dividing a data set, the gene selection by a statistical test and discriminant preparation may be performed using all of samples, and accuracy, sensitivity, and specificity can be calculated by the discriminant using a newly prepared sample cohort for evaluation of the performance of the discriminant.

The present invention provides a polynucleotide(s) for diagnosis or detection of a disease as being useful for diagnosing and treating bladder cancer, a method for detecting bladder cancer using the polynucleotide(s), and a kit and device for detecting bladder cancer, comprising the polynucleotide(s). In particular, existing diagnosis might cause needless extra examination for non-bladder cancer patients misjudged as being bladder cancer patients, or loss of treatment opportunities because of oversight of bladder cancer patients. By contrast, according to the present invention, bladder cancer can be accurately determined in a non-invasive manner and in a small amount of a sample, irrespective of stage, the degree of infiltration, histological grade, and primary/recurrent tumor. Specifically, the present invention provides a kit or device for diagnosis of a disease useful in diagnosis and treatment of bladder cancer from highly accurate bladder cancer markers, and a method for determining (or detecting) bladder cancer.

A gene set for diagnosis may be set as, for instance, any combination selected from one or two or more of the above polynucleotides based on a nucleotide sequence(s) represented by any of SEQ ID NOs: 1 to 228 as described above, and optionally further comprising one or two or more of the above polynucleotide based on a nucleotide sequence(s) represented by any of SEQ ID NOs: 229 to 243. Then, a discriminant is constructed using the expression levels of the gene set for diagnosis in samples from patients diagnosed with bladder cancer as a result of tissue diagnosis and samples from subjects without bladder cancer. As a result, whether or not a subject, from which an unknown sample is provided, has bladder cancer can be discriminated with 96% accuracy at the highest by measuring expression levels of the gene set for diagnosis in the unknown sample.

The kit and the method, etc. of the present invention can detect bladder cancer with good sensitivity and therefore enables bladder cancer to be detected early. As a result, early treatment is achieved, probably leading to drastic improvement in survival rate. Furthermore, it becomes possible to avoid losing treatment opportunities because of oversight of bladder cancer patients, or carrying out needless extra examination for non-bladder cancer patients misjudged as being bladder cancer patients, due to high variability found among observers of urinary cytology or different results based on the subjective views of operators of bladder endoscopy.

EXAMPLES

The present invention is described further specifically with reference to Examples below. However, the scope of the present invention is not intended to be limited by these Examples.

Reference Example

<Collection of Samples>

Sera were collected using VENOJECT II vacuum blood collecting tube VP-AS109K63 (Terumo Corp. (Japan)) from a total of 1,303 people (Table 2) including 392 bladder cancer patients, 50 lung cancer patients, 50 colorectal cancer patients, 50 esophageal cancer patients, 50 stomach cancer patients, 50 liver cancer patients, 50 biliary tract cancer patients, 50 pancreatic cancer patients, 50 prostate cancer patients, 50 breast cancer patients, 50 ovarian cancer patients, 11 uterine sarcoma patients, 50 malignant brain tumor patients, 50 malignant bone and soft tissue tumor patients, 50 benign bone and soft tissue tumor patients, 28 benign breast disease patients, 28 benign ovarian tumor patients, 50 benign prostate disease patients, 18 uterine fibroid patients, 26 benign brain tumor patients, and 100 healthy subjects after obtainment of informed consent.

For the stage of the bladder cancer patients, 57 people were in stage 0a, 10 people were in stage 0 is, 121 people were in stage I, 15 people were in stage II, 2 people were in stage III, 14 people were in stage IV, and 97 people were unknown. For the T classification that shows the depth of in-wall invasion of the primary tumor in the TNM classification, 300 people were of below T2, 90 people were of T2 or higher, and 2 people were unknown. For the histological grade of bladder cancer, 315 people were in the High grade, and 77 people were in the Low grade. Further, 178 patients had the primary bladder cancer, and 214 patients had recurrence (Table 3).

<Extraction of Total RNA>

Total RNA was obtained, using a reagent for RNA extraction in 3D-Gene (registered trademark) RNA extraction reagent from liquid sample kit (Toray Industries, Inc., Japan) according to the protocol provided by the manufacturer, from 300 μL of the serum sample obtained from each of the total of 1,303 people.

<Measurement of Gene Expression Level> miRNA in the total RNA, which was obtained from the serum sample of each of the total of 1,303 people was fluorescently labeled by use of 3D-Gene (registered trademark) miRNA Labeling kit (Toray Industries, Inc.) according to the protocol provided by the manufacturer. The oligo DNA chip used was 3D-Gene (registered trademark) Human miRNA Oligo chip (Toray Industries, Inc.) with attached probes having sequences complementary to 2,565 miRNAs among the miRNAs registered in miRBase Release 21. Hybridization under stringent conditions and washing following the hybridization were performed according to the protocol provided by the manufacturer. The DNA chip was scanned using 3D-Gene (registered trademark) scanner (Toray Industries, Inc.) to obtain images. Fluorescence intensity was digitized using 3D-Gene (registered trademark) Extraction (Toray Industries, Inc.). The digitized fluorescence intensity was converted to a logarithmic value having a base of 2 and used as a gene expression level, from which a blank value was subtracted. A missing value was replaced with a signal value 0.1. As a result, the comprehensive gene expression levels of the miRNAs in the sera were obtained for the above 1,303 people.

Samples to be used for discriminant analysis (Examples 1, 2, and 3) of bladder cancer were extracted as follows. In the following description, benign bone and soft tissue tumor, benign breast disease, benign ovarian tumor, prostate benign disease, uterine fibroid, and benign brain tumor patients are collectively referred to as "benign disease patients", and lung cancer, colorectal cancer, esophageal cancer, stomach cancer, liver cancer, biliary tract cancer, pancreatic cancer, prostate cancer, breast cancer, ovarian cancer, uterine sarcoma, malignant brain tumor, and malignant bone and soft tissue tumor patients are collectively referred to as "patients of cancers other than bladder cancer" (Table 2). First, 392 bladder cancer patients were assigned to a positive sample group, and a total of 911 people including 611 cancer patients other than the aforementioned bladder cancer patients, 200 benign disease patients, and 100 healthy subjects were assigned to a negative sample group (Table 2). ⅔ of the samples of each group were sorted into a training cohort, and rest ⅓ of the samples were sorted into a validation cohort (Table 4). That is, 261 bladder cancer patients, 408 patients of cancers other than bladder cancer, 133 benign disease patients, and 67 healthy subjects were assigned to a training cohort, and 131 bladder cancer patients, 203 patients of cancers other than bladder cancer, 67 benign disease patients, and 33 healthy subjects were assigned to a validation cohort (Table 4).

The samples to be used for discriminant analysis (Example 4) of bladder cancer patients of T2 or higher and bladder cancer patients of below T2 in the TNM classification were extracted as follows. First, 90 bladder cancer patients of below T2 were assigned to a positive sample group, and 300 bladder cancer patients of T2 or higher were assigned to a negative sample group. Further, 58 bladder cancer patients of below T2 and 137 bladder cancer patients of T2 or higher were sorted into a training cohort, and 32 bladder cancer patients of below T2 and 163 bladder cancer patients of T2 or higher were sorted into a validation cohort (Table 5).

Calculation and statistical analysis using the digitized gene expression levels of the miRNAs were carried out using R language 3.3.1 (R Core Team (2016). R: A language and environment for statistical computing. R Foundation for Statistical Computing, Vienna, Austria. URL https://www.R-project.org/.) and MASS package 7.3.45 (Venables, W. N. & Ripley, B. D. (2002) Modem Applied Statistics with S. Fourth Edition. Springer, New York. ISBN 0-387-95457-0).

TABLE 2

| Generic term | Disease type of subjects | Number of samples | Total |
|---|---|---|---|
| Bladder cancer patients | Bladder cancer patients | 392 | 392 |
| Other cancer patients | Lung cancer patients | 50 | 611 |
| | Colorectal cancer patients | 50 | |
| | Esophageal cancer patients | 50 | |
| | Stomach cancer patients | 50 | |
| | Liver cancer patients | 50 | |
| | Biliary tract cancer patients | 50 | |
| | Pancreatic cancer patients | 50 | |
| | Prostate cancer patients | 50 | |
| | Breast cancer patients | 50 | |
| | Ovarian cancer patients | 50 | |
| | Uterine sarcoma cancer | 11 | |
| | Malignant brain tumor patients | 50 | |
| | Malignant bone and soft tissue tumor patients | 50 | |
| Benign disease patients | Benign bone and soft tissue tumor patients | 50 | 200 |
| | Benign breast disease patients | 28 | |
| | Benign ovarian tumor patients | 28 | |
| | Prostatic hypertrophy patients | 50 | |
| | Uterine fibroid patients | 18 | |
| | Benign brain tumor patients | 26 | |
| Heathy subjects | Healthy subjects | 100 | 100 |
| Total | | | 1303 |

TABLE 3

| Generic term | Class | Number of Samples |
|---|---|---|
| Bladder cancer stage | 0a | 57 |
| | 0is | 10 |
| | I | 121 |
| | II | 15 |
| | III | 2 |
| | IV | 14 |
| | Unknown | 97 |
| Bladder cancer T classification | Below T2 | 300 |
| | T2 or higher | 90 |
| | Unknown | 2 |
| Histological grade of bladder cancer | High grade | 315 |
| | Low grade | 77 |
| Bladder cancer Primary/Recurrent | Primary | 178 |
| | Recurrent | 214 |

TABLE 4

| Generic term | Training cohort | Validation cohort | Total |
|---|---|---|---|
| Bladder cancer patients (Positive group) | 261 | 131 | 392 |
| Other cancer patients (Negative Group) | 408 | 203 | 611 |
| Benign disease patients (Negative group) | 133 | 67 | 200 |
| Healthy subjects (Negative group) | 67 | 33 | 100 |
| Total | 869 | 434 | 1303 |

TABLE 5

| T classification | Training cohort | Validation cohort | Total |
|---|---|---|---|
| Below T2 (Positive group) | 58 | 32 | 90 |
| T2 or higher (Negative group) | 137 | 163 | 300 |
| Total | 195 | 195 | 390 |

Example 1

<Discriminant Analysis of Bladder Cancer with 1 or Combination of 2 to 5 miRNAs>

In this Example, discriminant formulas with 1 to 5 gene markers were created using a training cohort (Table 4) including bladder cancer patients and subjects without bladder cancer, and then the discriminant performance was evaluated in a validation cohort (Table 4). Genes to be used for the top 50 discriminant formulas ranked by the discriminant performance with each of 1 to 5 markers, that is, a total of 250 discriminant formulas were extracted to obtain 149 gene markers capable of detecting bladder cancer (Table 6).

Specifically, first, miRNA expression levels in the training cohort and the validation cohort obtained in the above Reference Example were together normalized in accordance with global normalization. Further, in order to acquire more reliable diagnostic markers, only 384 genes with a gene expression level of $2^6$ or larger in 50% or more of the samples were analyzed in either the positive sample group (bladder cancer patients) or the negative sample group (patients of cancers other than bladder cancer, benign disease patients, and healthy subjects).

Next, Fisher's discriminant analysis was performed on the measured values of the expression levels of one or a combination of two to five genes out of the aforementioned 384 genes, to construct discriminant formulas for discriminating the presence or absence of bladder cancer. At this time, discriminant formulas with high discriminant performance were searched for by a modified greedy algorithm. Further, the above-prepared discriminant formulas were used to calculate the accuracy, the sensitivity, and the specificity in the validation cohort. Then, the discriminant performance was validated in independent samples. The results for each number of genes used for discrimination are shown below.

Example 1-1

As a result of the above, the top 50 formulas ranked by the discrimination performance were obtained with number of gene 1. The discriminant formulas and their thresholds (determining positive or negative, where values equal to or higher than the thresholds are positive), the sensitivity, specificity, accuracy, and AUC in the training cohort and the validation cohort, and the genes used for the discriminant formulas are shown in Table 7-1. The genes included in these discriminant formulas were selected as diagnostic markers capable of discriminating between bladder cancer patients and subjects without bladder cancer.

Figure 2A:
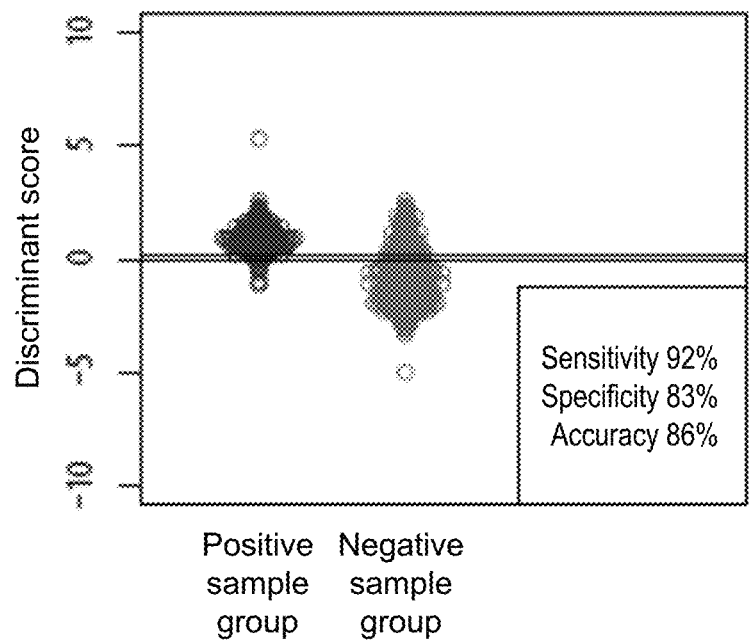
FIG. 2 shows plots of discriminant scores in a training cohort (A) and a validation cohort (B) obtained by a discriminant formula for 1 miRNA.
Figure 2B:
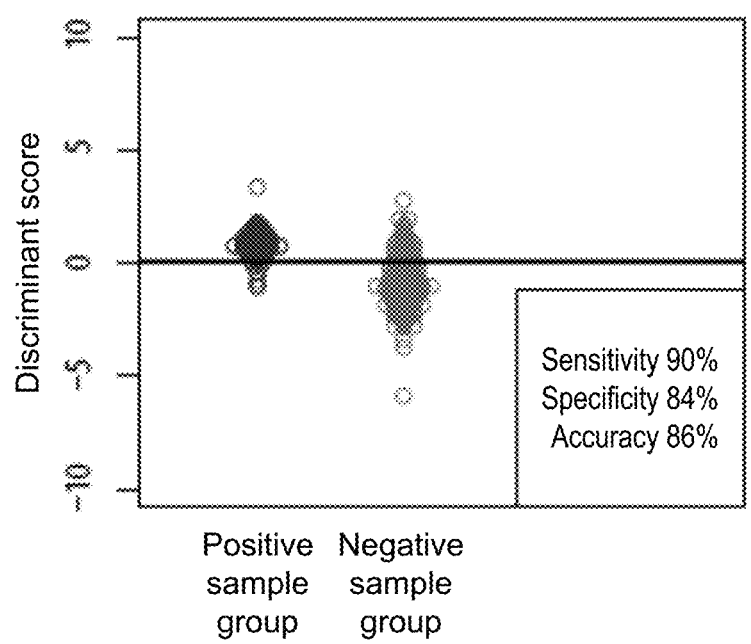
Figure 3:
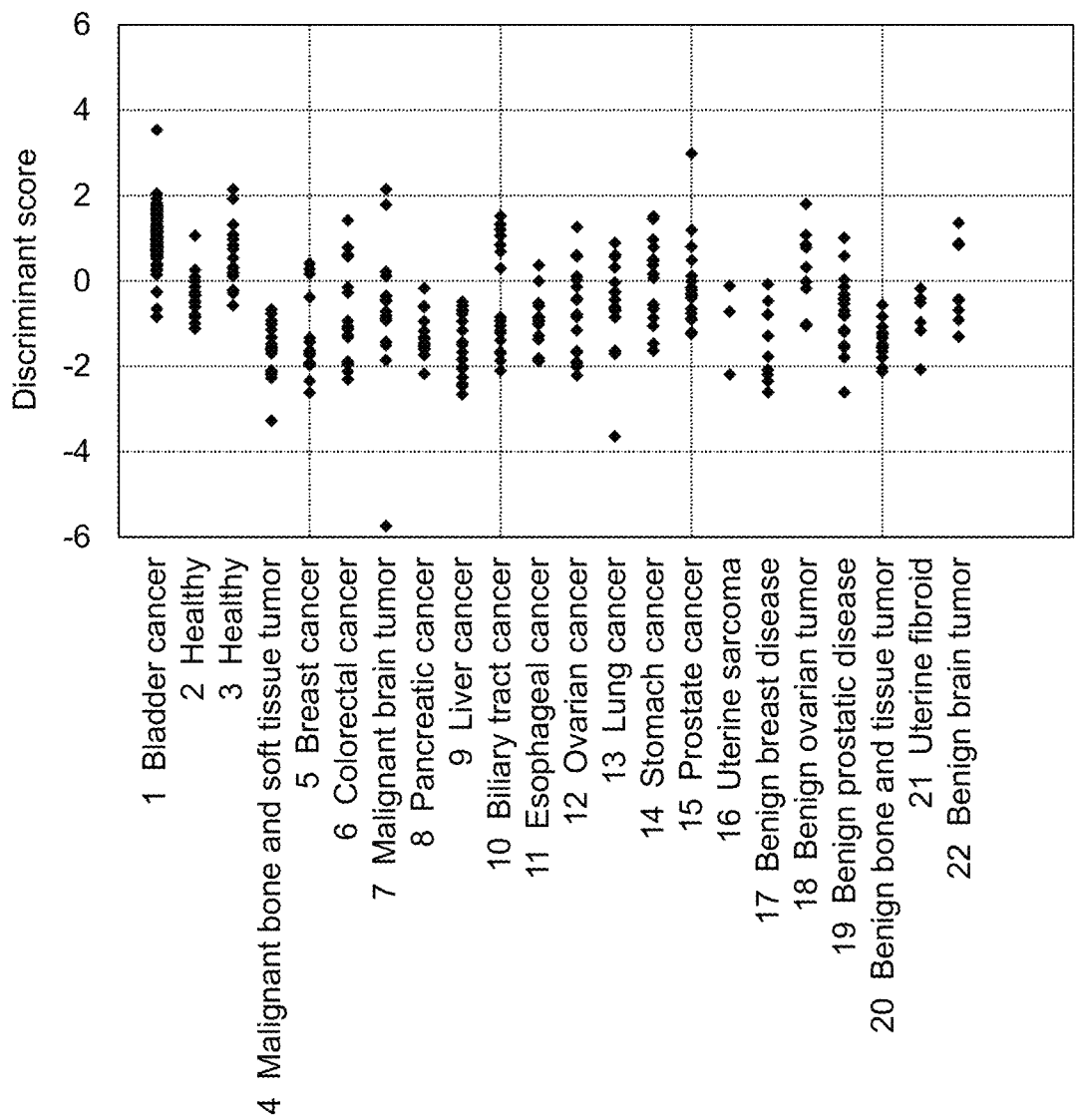
FIG. 3 shows plots of discriminant scores in validation cohorts according to the disease type obtained by a discriminant formula for 1 miRNA.
Figure 4A:
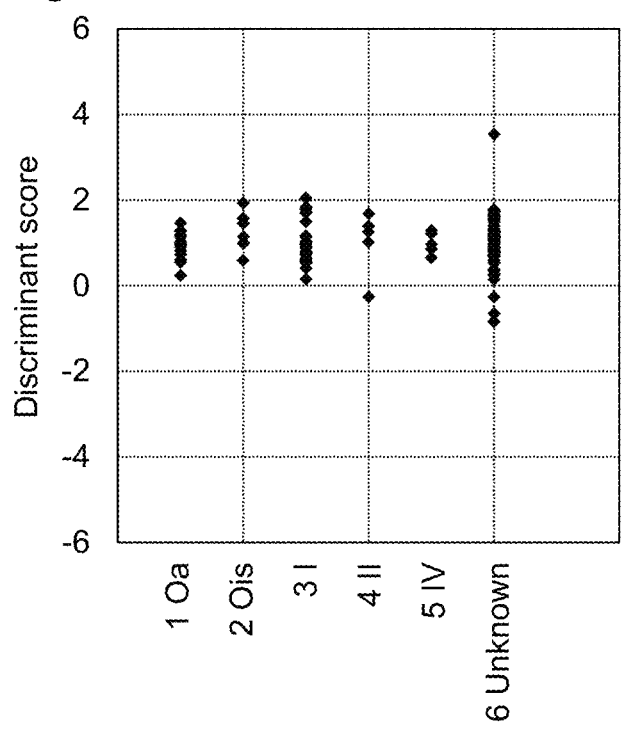
FIG. 4A and FIG. 4B show plots of discriminant scores in validation cohorts according to the stage (A) and according to the depth of intramural invasion (B) obtained by a discriminant formula for 1 miRNA.
Figure 4B:
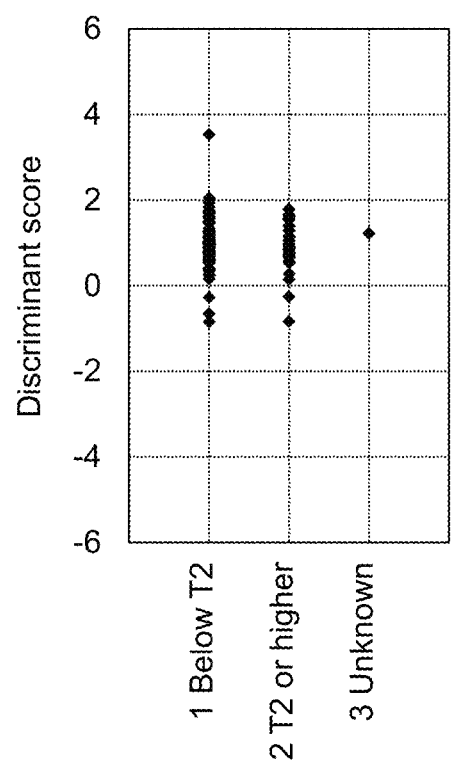
Figure 4C:
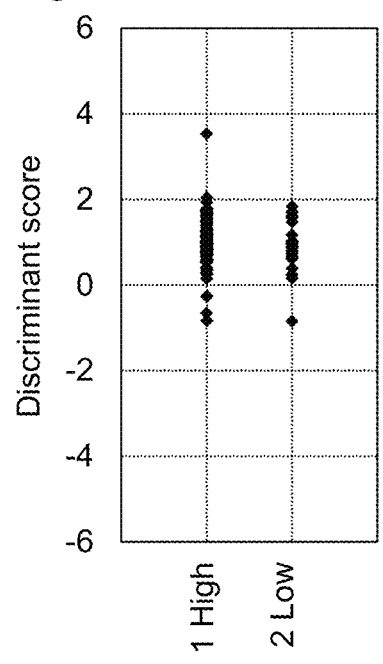
FIG. 4C and FIG. 4D show plots of discriminant scores in validation cohorts according to the histologic tumor grade (C) and primary/recurrence (D) obtained by a discriminant formula for 1 miRNA.
Figure 4D:
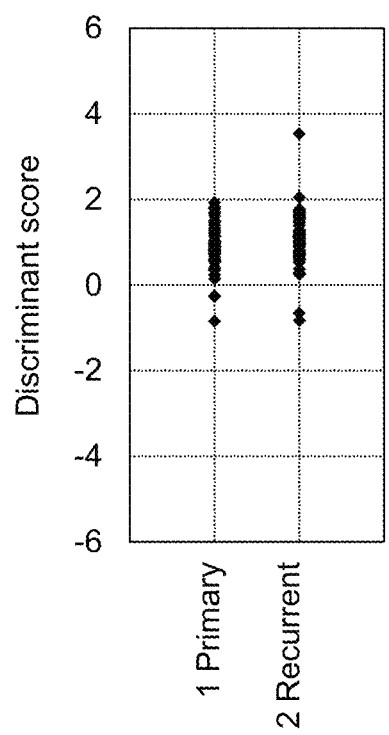

Measured values were plugged into the discriminant formula shown in No. 1 of Table 7-2 to obtain discriminant scores. Then, the discriminant scores of 261 bladder cancer patients (positive sample group) and 608 subjects without bladder cancer (negative sample group) in the training cohort were plotted, thereby showing that both groups were significantly separated, in FIG. 2A. The vertical axis of the figure represents the discriminant scores. As compared to the threshold 0.19, higher scores were determined as having bladder cancer, and lower scores were determined as not having bladder cancer. These results could be reproduced also in the validation cohort (FIG. 2B). Further, the discriminant scores in the validation cohort were plotted for each disease type, thereby showing that bladder cancer was significantly separated regardless of the disease type, in FIG. 3. The vertical axis of the figure represents the discriminant scores. As compared to the threshold 0, higher scores were determined as having bladder cancer, and lower scores were determined as not having bladder cancer.

The discriminant scores of the bladder cancer patients were illustrated separately for each stage, depth of in-wall invasion, histological grade, and primary/recurrence. As a result, it could be confirmed that bladder cancer could be detected with high accuracy in all categories (FIGS. 4A to D). The vertical axis of the figure represents the discriminant scores. As compared to the threshold 0, higher scores were determined as having bladder cancer, and lower scores were determined as not having bladder cancer.

Example 1-2

As a result of the above, the top 50 formulas ranked by the discriminant performance were obtained with number of gene combination 2. These discriminant formulas and their thresholds (determining positive or negative, where values equal to or higher than the thresholds are positive), the sensitivity, specificity, accuracy, and AUC in the training cohort and the validation cohort, and the genes used for the discriminant formulas are shown in Tables 8-1 and 8-2. The genes included in these discriminant formulas were selected as diagnostic markers capable of discriminating between bladder cancer patients and subjects without bladder cancer. The accuracy was 84% to 89%, and the sensitivity to discriminate bladder cancer was 86% to 96%, showing extremely high discrimination performance (Table 8-2). The discriminant formulas and the thresholds for discrimination with number of gene combination 2 are shown in Table 8-3.

Example 1-3

As a result of the above, the top 50 formulas ranked by the discriminant performance were obtained with number of gene combination 3. These discriminant formulas and their thresholds (determining positive or negative, where values equal to or higher than the thresholds are positive), the sensitivity, specificity, accuracy, and AUC in the training cohort and the validation cohort, and the genes used for the discriminant formulas are shown in Tables 9-1 and 9-2. The genes included in these discriminant formulas were selected as diagnostic markers capable of discriminating between bladder cancer patients and subjects without bladder cancer.

Figure 5A:
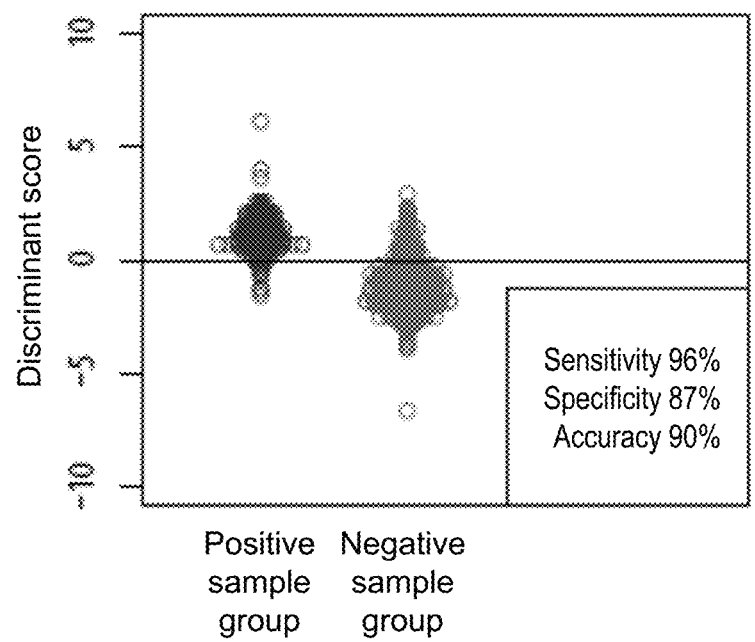
FIG. 5 shows plots of discriminant scores in a training cohort (A) and a validation cohort (B) obtained by a discriminant formula for 3 miRNAs.
Figure 5B:
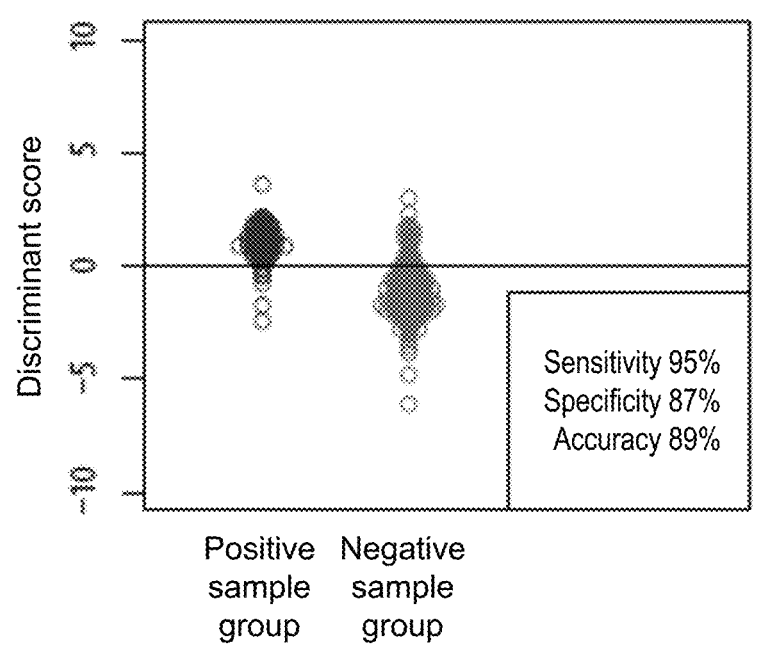
Figure 6:
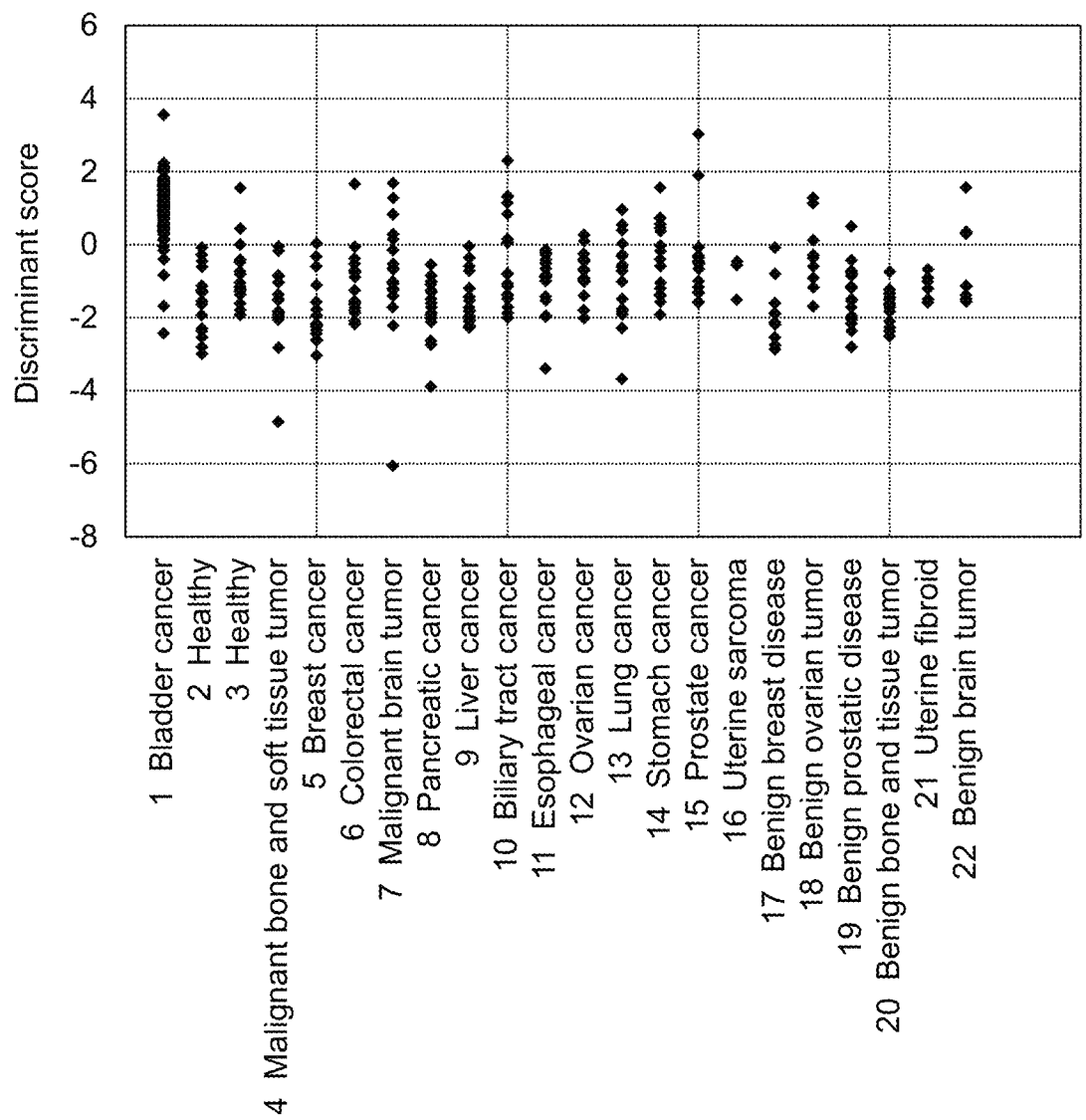
FIG. 6 shows plots of discriminant scores in validation cohorts according to the disease type obtained by a discriminant formula for 3 miRNAs.
Figure 7A:
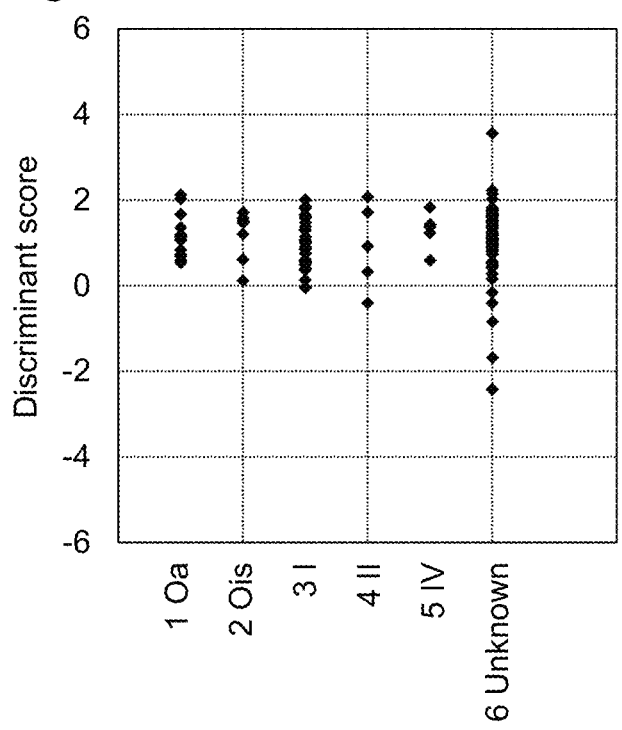
FIG. 7A and FIG. 7B show plots of discriminant scores in validation cohorts according to the stage (A) and according to the depth of intramural invasion (B) obtained by a discriminant formula for 3 miRNAs.
Figure 7B:
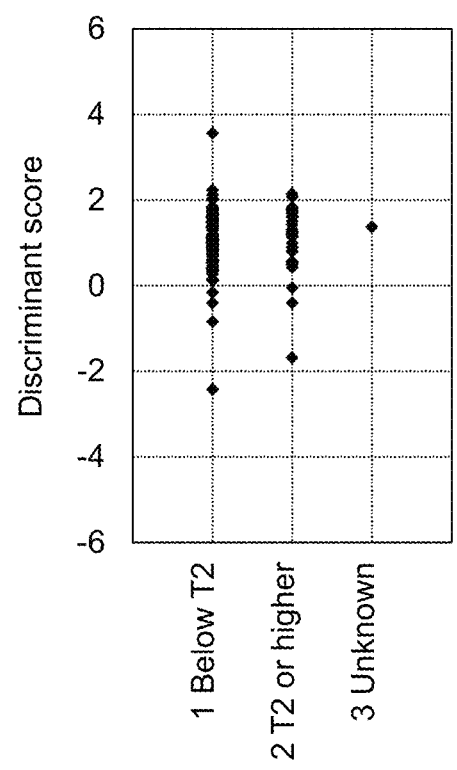
Figure 7C:
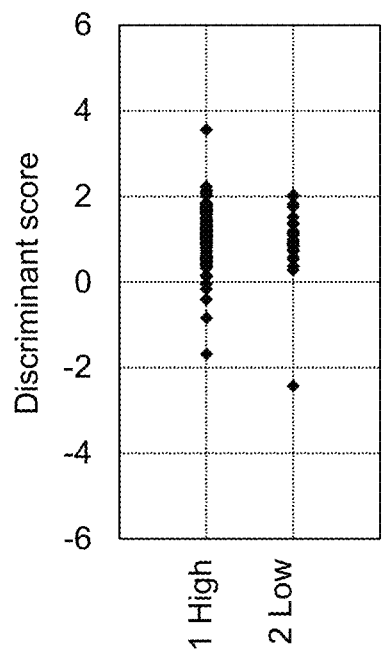
FIG. 7C and FIG. 7D show plots of discriminant scores in validation cohorts according to the histologic tumor grade (C) and primary/recurrence (D) obtained by a discriminant formula for 3 miRNAs.
Figure 7D:
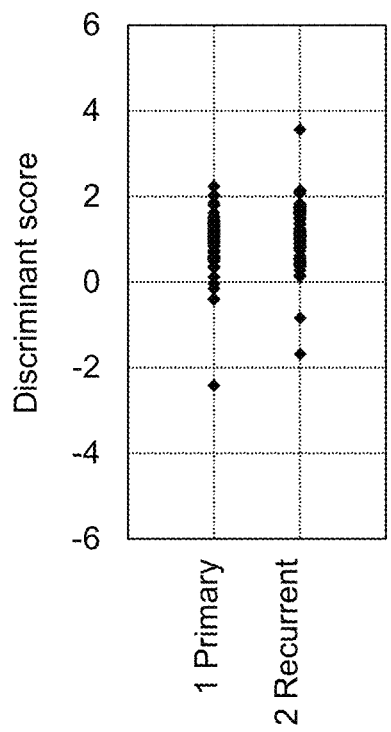

Measured values were plugged into the discriminant formula shown in No. 1 of Table 9-3 to obtain discriminant scores. Then, the discriminant scores of 261 bladder cancer patients (positive sample group) and 608 subjects without bladder cancer (negative sample group) in the training cohort were plotted, thereby showing that both groups were significantly separated, in FIG. 5A. The vertical axis of the figure represents the discriminant scores. As compared to the threshold −0.03, higher scores were determined as having bladder cancer, and lower scores were determined as not having bladder cancer. These results could be reproduced also in the validation cohort (FIG. 5B). Further, the discriminant scores in the validation cohort were plotted for each disease type, thereby showing that bladder cancer was significantly separated regardless of the disease type, in FIG. 6. The vertical axis of the figure represents the discriminant scores. As compared to the threshold 0, higher scores were determined as having bladder cancer, and lower scores were determined as not having bladder cancer.

The discriminant scores of the bladder cancer patients were illustrated separately for each stage, depth of in-wall invasion, histological grade, and primary/recurrence. As a result, it could be confirmed that bladder cancer could be detected with high accuracy in all categories (FIGS. 7A to D). The vertical axis of the figure represents the discriminant scores. As compared to the threshold 0, higher scores were determined as having bladder cancer, and lower scores were determined as not having bladder cancer.

Example 1-4

As a result of the above, the top 50 formulas ranked by the discriminant performance were obtained with number of gene combination 4. These discriminant formulas and their thresholds (determining positive or negative, where values equal to or higher than the thresholds are positive), the sensitivity, specificity, accuracy, and AUC in the training cohort and the validation cohort, and the genes used for the discriminant formulas are shown in Tables 10-1 and 10-2. The genes included in these discriminant formulas were selected as diagnostic markers capable of discriminating between bladder cancer patients and subjects without bladder cancer.

Figure 8A:
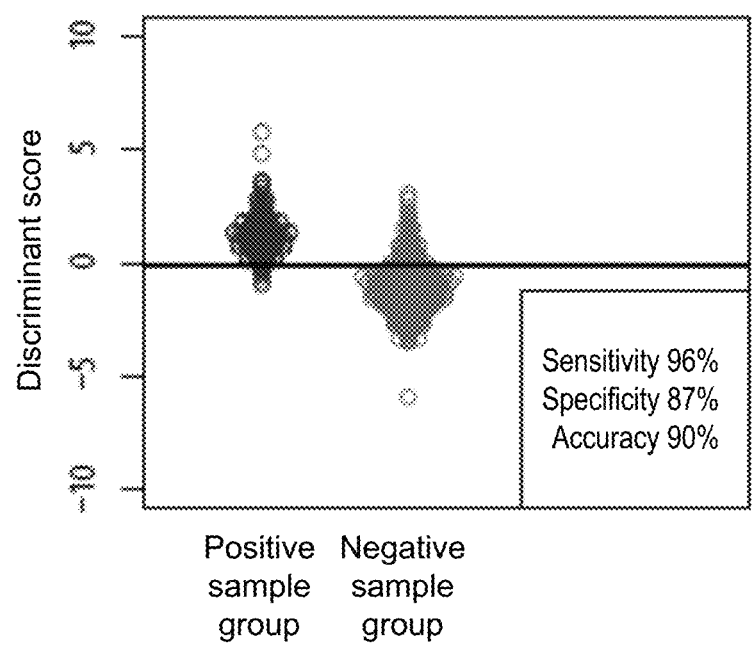
FIG. 8 shows plots of discriminant scores in a training cohort (A) and a validation cohort (B) obtained by a discriminant formula for 4 miRNAs.
Figure 8B:
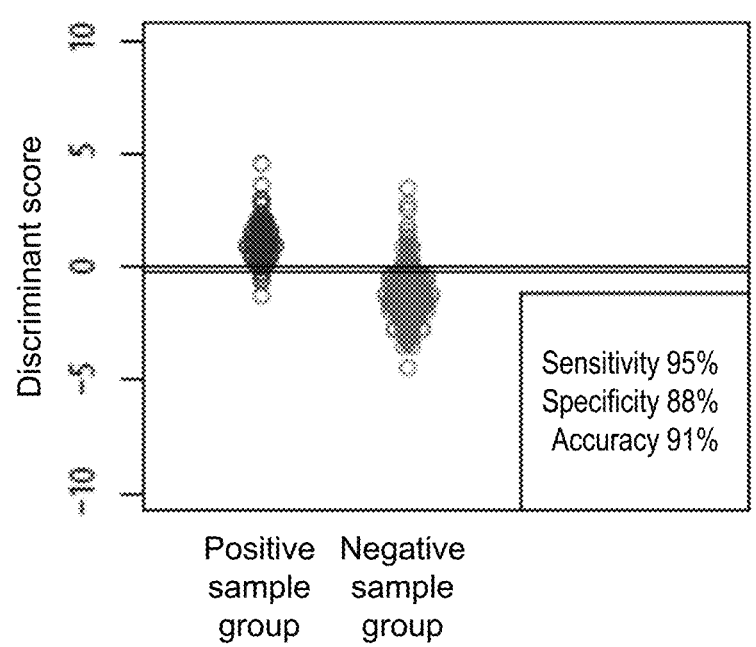
Figure 9:
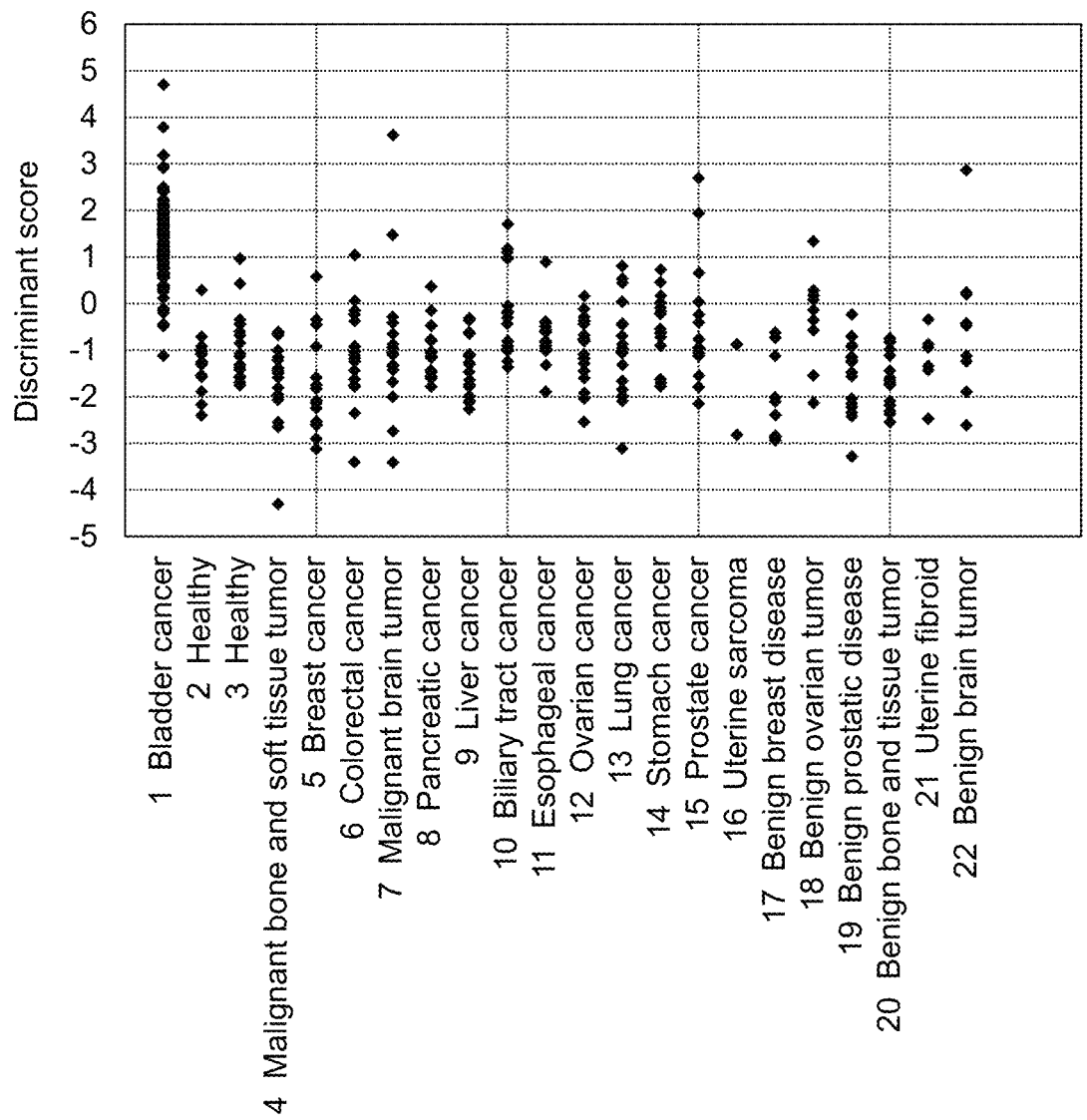
FIG. 9 shows plots of discriminant scores in validation cohorts according to the disease type obtained by a discriminant formula for 4 miRNAs.
Figure 10A:
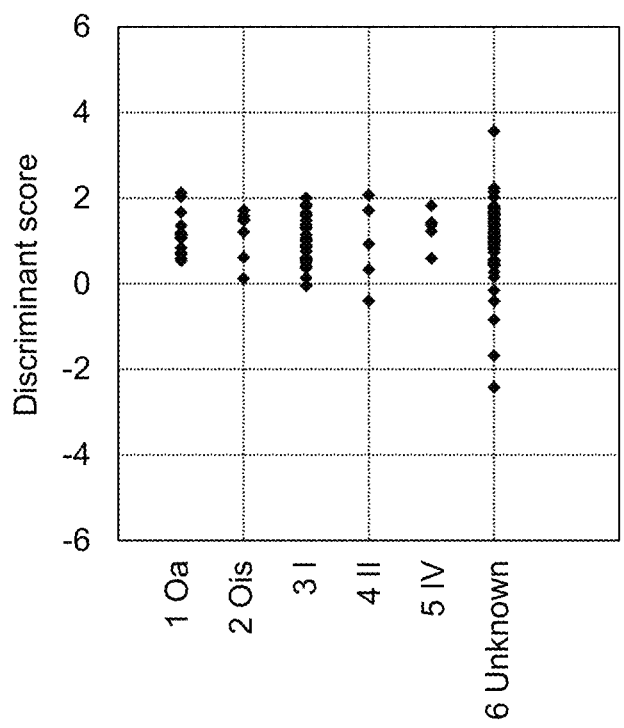
FIG. 10A and FIG. 10B show plots of discriminant scores in validation cohorts according to the stage (A) and according to the depth of intramural invasion (B) obtained by a discriminant formula for 4 miRNAs.
Figure 10B:
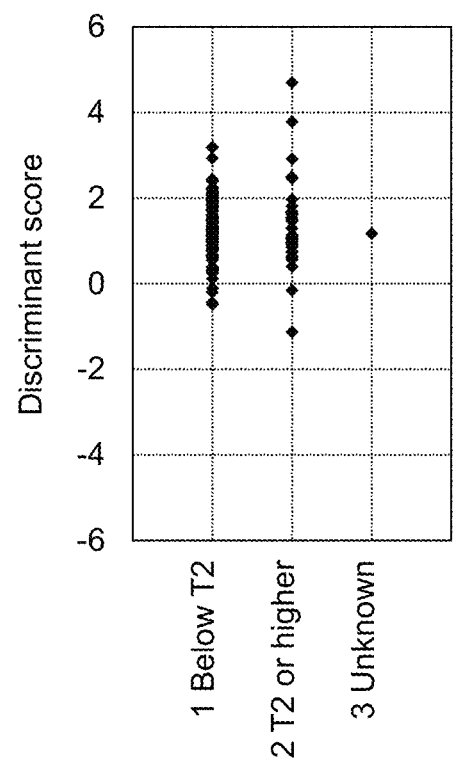
Figure 10C:
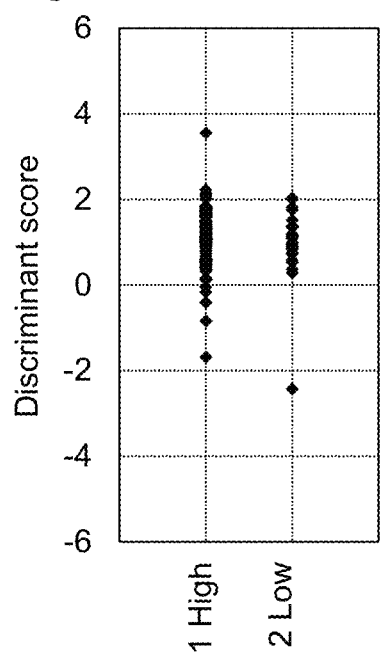
FIG. 10C and FIG. 10D show plots of discriminant scores in validation cohorts according to the histologic tumor grade (C) and primary/recurrence (D) obtained by a discriminant formula for 4 miRNAs.
Figure 10D:
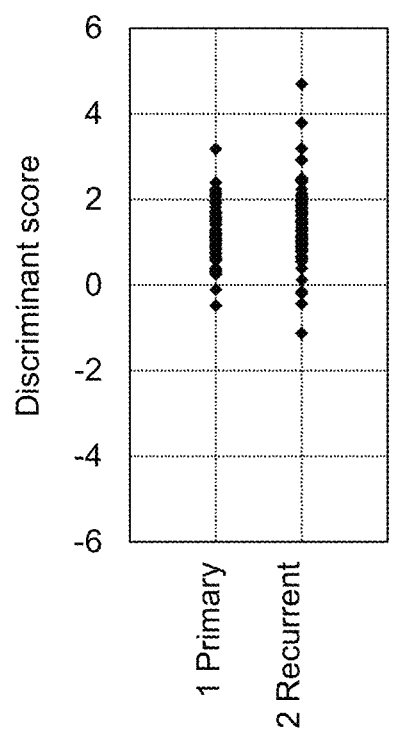

Measured values were plugged into the discriminant formula shown in No. 1 of Table 10-3 to obtain discriminant scores. Then, the discriminant scores of 261 bladder cancer patients (positive sample group) and 608 subjects without bladder cancer (negative sample group) in the training cohort were plotted, thereby showing that both groups were significantly separated, in FIG. 8A. The vertical axis of the figure represents the discriminant scores. As compared to the threshold −0.18, higher scores were determined as having bladder cancer, and lower scores were determined as not having bladder cancer. These results could be reproduced also in the validation cohort (FIG. 8B). Further, the discriminant scores in the validation cohort were plotted for each disease type, thereby showing that bladder cancer was significantly separated regardless of the disease type, in FIG. 9. The vertical axis of the figure represents the discriminant scores. As compared to the threshold 0, higher scores were determined as having bladder cancer, and lower scores were determined as not having bladder cancer.

The discriminant scores of the bladder cancer patients were illustrated separately for each stage, depth of in-wall invasion, histological grade, and primary/recurrence. As a result, it could be confirmed that bladder cancer could be detected with high accuracy in all categories (FIGS. 10A to D). The vertical axis of the figure represents the discriminant scores. As compared to the threshold 0, higher scores were determined as having bladder cancer, and lower scores were determined as not having bladder cancer.

Example 1-5

As a result of the above, the top 50 formulas ranked by the discriminant performance were obtained with number of gene combination 5. These discriminant formulas and their thresholds (determining positive or negative, where values equal to or higher than the thresholds are positive), the sensitivity, specificity, accuracy, and AUC in the training cohort and the validation cohort, and the genes used for the discriminant formulas are shown in Tables 11-1 and 11-2. The genes included in these discriminant formulas were selected as diagnostic markers capable of discriminating between bladder cancer patients and subjects without bladder cancer.

Figure 11A:
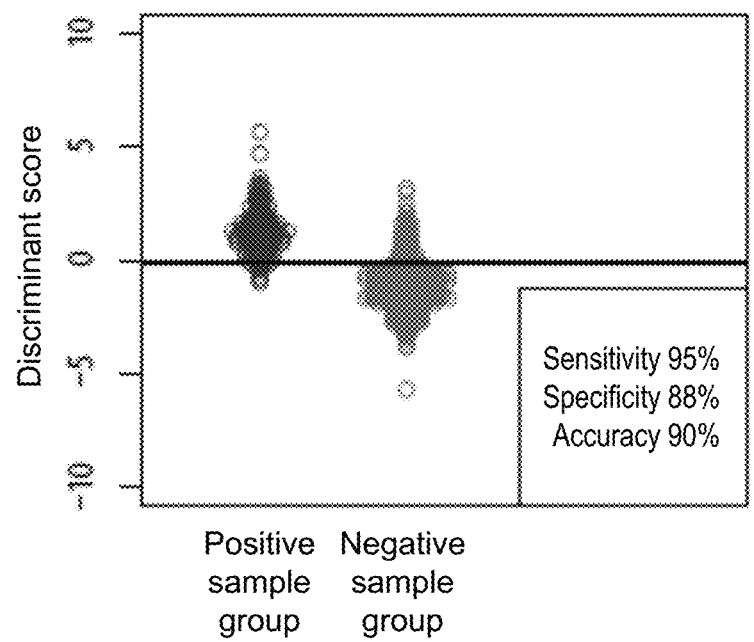
FIG. 11 shows plots of discriminant scores in a training cohort (A) and a validation cohort (B) obtained by a discriminant formula for 5 miRNAs.
Figure 11B:
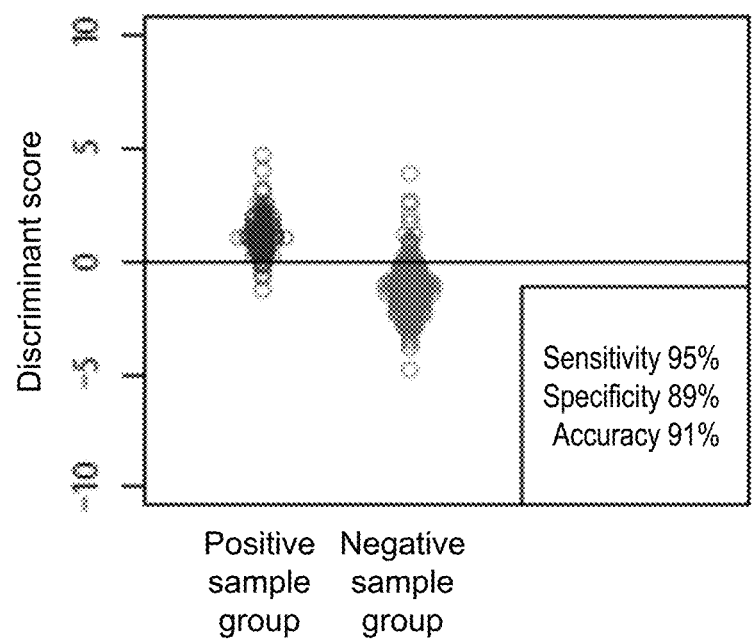
Figure 12:
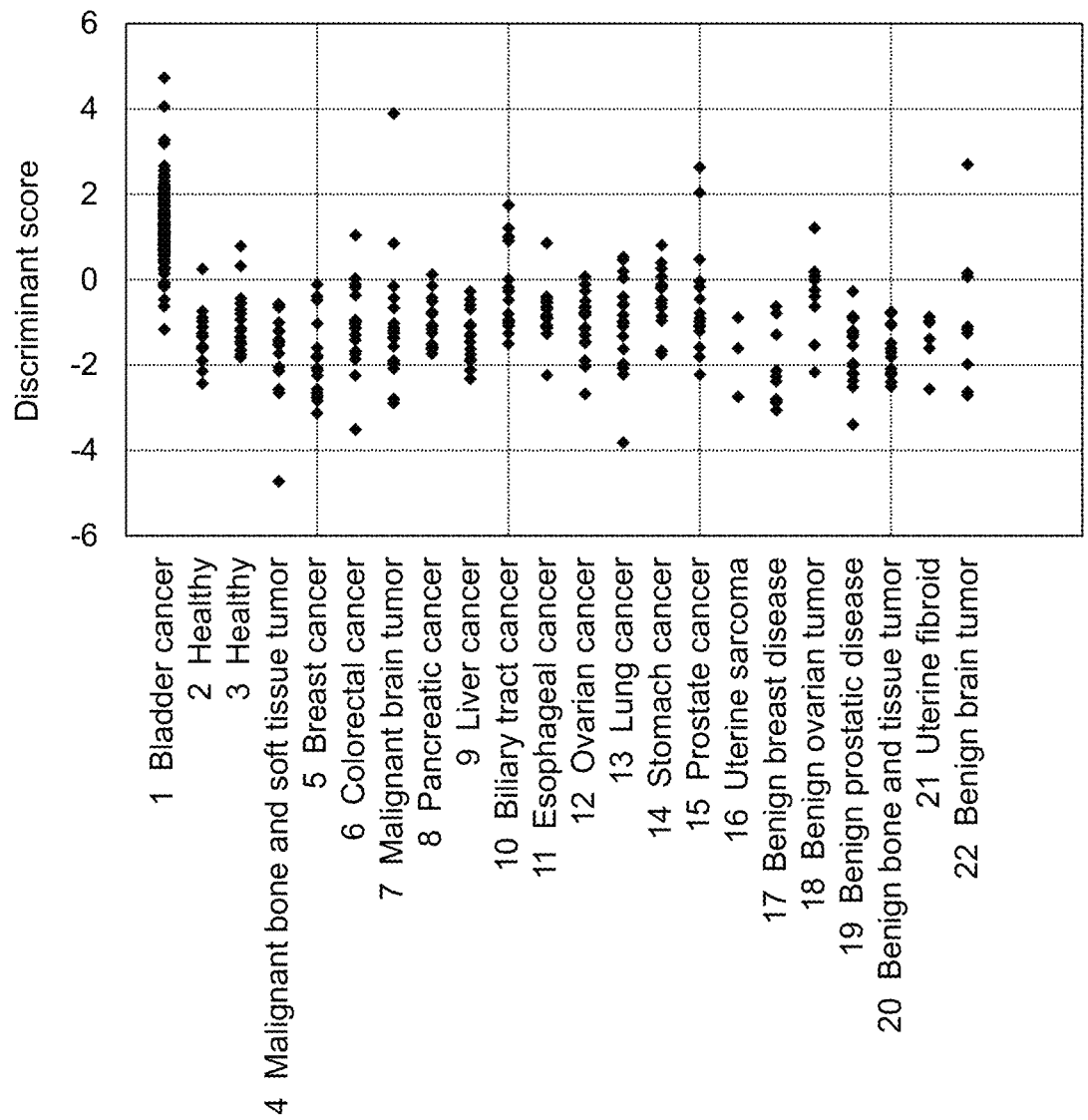
FIG. 12 shows plots of discriminant scores in validation cohorts according to the disease type obtained by a discriminant formula for 5 miRNAs.
Figure 13A:
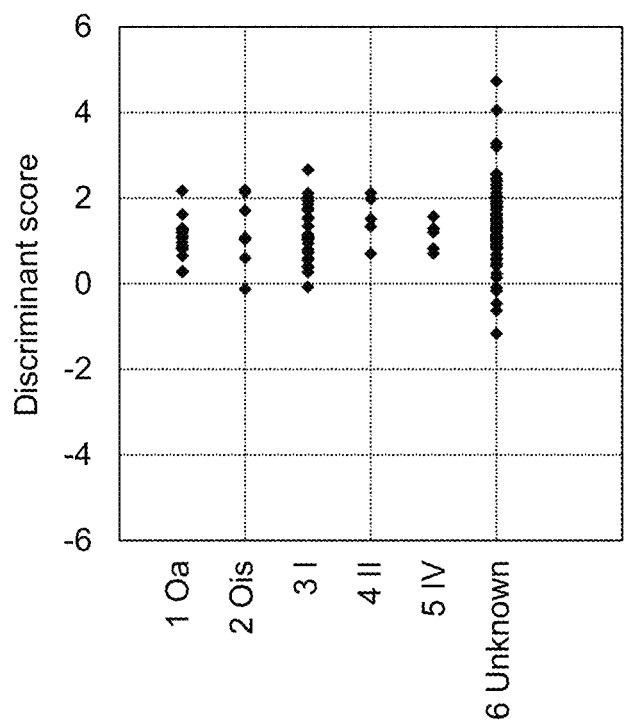
FIG. 13A and FIG. 13B show plots of discriminant scores in validation cohorts according to the stage (A) and according to the depth of intramural invasion (B) obtained by a discriminant formula for 5 miRNAs.
Figure 13B:
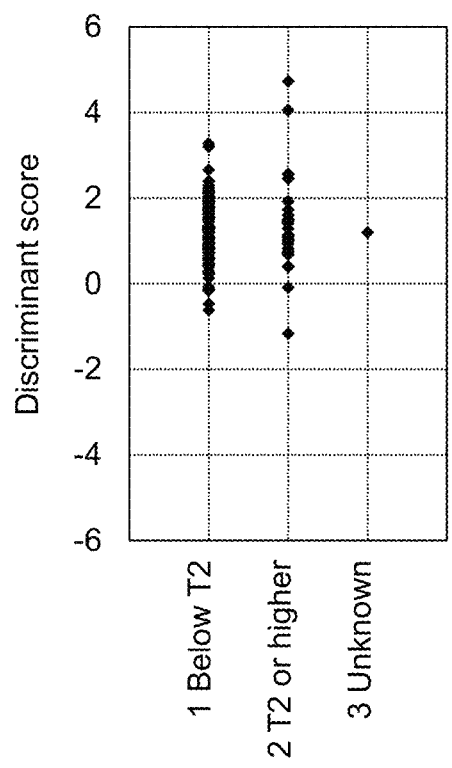
Figure 13C:
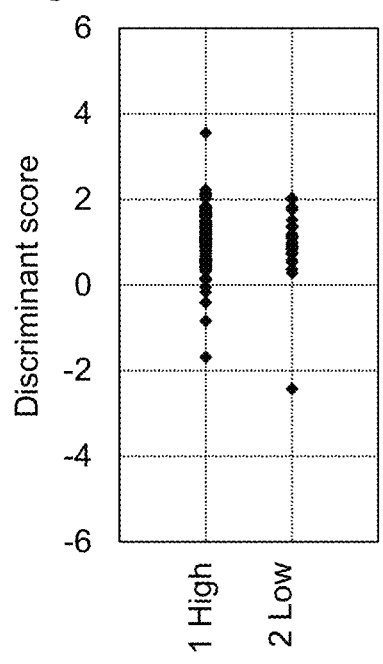
FIG. 13C and FIG. 13D show plots of discriminant scores in validation cohorts according to the histologic tumor grade (C) and primary/recurrence (D) obtained by a discriminant formula for 5 miRNAs.
Figure 13D:
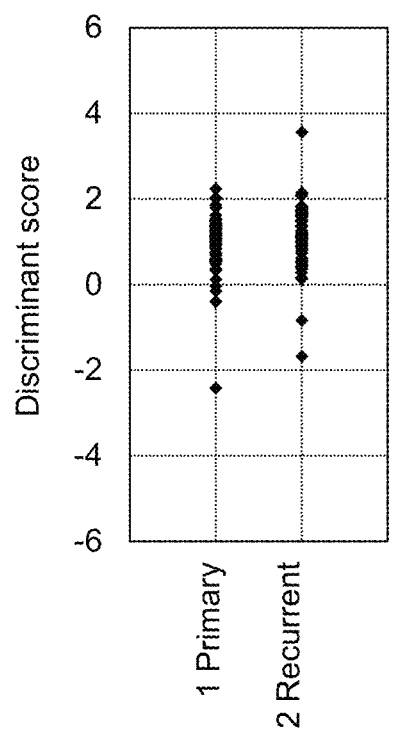

Measured values were plugged into the discriminant formula shown in No. 1 of Table 11-3 to obtain discriminant scores. Then, the discriminant scores of 261 bladder cancer patients (positive sample group) and 608 subjects without bladder cancer (negative sample group) in the training cohort were plotted, thereby showing that both groups were significantly separated, in FIG. 11A. The vertical axis of the figure represents the discriminant scores. As compared to the threshold −0.12, higher scores were determined as having bladder cancer, and lower scores were determined as not having bladder cancer. These results could be reproduced also in the validation cohort (FIG. 11B). Further, the discriminant scores in the validation cohort were plotted for each disease type, thereby showing that bladder cancer was significantly separated regardless of the disease type, in FIG. 12. The vertical axis of the figure represents the discriminant scores. As compared to the threshold 0, higher scores were determined as having bladder cancer, and lower scores were determined as not having bladder cancer.

The discriminant scores of the bladder cancer patients were illustrated separately for each stage, depth of in-wall invasion, histological grade, and primary/recurrence. As a result, it could be confirmed that bladder cancer could be detected with high accuracy in all categories (FIGS. 13A to D). The vertical axis of the figure represents the discriminant scores. As compared to the threshold 0, higher scores were determined as having bladder cancer, and lower scores were determined as not having bladder cancer.

From the above, it can be said that the polynucleotides, shown in Tables 6 to 11, which are obtained in Examples 1-1 to 1-5 are a gene group capable of specifically discriminating bladder cancer patients from any of patients of cancers other than bladder cancer, benign disease patients, and healthy subjects. Further, it was demonstrated that higher discriminant performance for bladder cancer can be obtained in the case of combining a plurality of polynucleotides than in the case of using a polynucleotide alone or a smaller number of polynucleotides. Here, the combinations of the plurality of polynucleotides that can be used for detection of bladder cancer are not limited to the above combinations, and the plurality of polynucleotides may be used in any combination.

That is, as shown in the above Example 1, one or a combination of two, three, four, or five polynucleotides can exhibit discriminant performance equal to or higher than the existing bladder cancer markers among all the polynucleotides consisting of the nucleotide sequences represented by Nos. 1 to 149 of Table 6, and they are excellent bladder cancer diagnostic markers that can detect any bladder cancer described in the aforementioned Reference Example, regardless of stage, depth of in-wall invasion, histological grade, and the primary or recurrence.

TABLE 6

| No. | Name of miRNA | SEQ ID NO |
| --- | --- | --- |
| 1 | hsa-miR-1185-1-3p | 2 |
| 2 | hsa-miR-1185-2-3p | 3 |
| 3 | hsa-miR-1228-3p | 8 |
| 4 | hsa-miR-1228-5p | 9 |
| 5 | hsa-miR-1238-5p | 11 |
| 6 | hsa-miR-1247-3p | 12 |
| 7 | hsa-miR-1268a | 13 |
| 8 | hsa-miR-1268b | 14 |
| 9 | hsa-miR-1273g-3p | 15 |
| 10 | hsa-miR-1343-3p | 17 |
| 11 | hsa-miR-1343-5p | 18 |
| 12 | hsa-miR-135a-3p | 233 |
| 13 | hsa-miR-1469 | 234 |
| 14 | hsa-miR-17-3p | 20 |
| 15 | hsa-miR-187-5p | 21 |
| 16 | hsa-miR-1909-3p | 24 |
| 17 | hsa-miR-191-5p | 238 |
| 18 | hsa-miR-210-5p | 26 |
| 19 | hsa-miR-2467-3p | 28 |
| 20 | hsa-miR-3131 | 32 |
| 21 | hsa-miR-3160-5p | 35 |
| 22 | hsa-miR-3178 | 37 |
| 23 | hsa-miR-3180-3p | 38 |
| 24 | hsa-miR-3185 | 40 |
| 25 | hsa-miR-3194-3p | 41 |
| 26 | hsa-miR-3195 | 42 |
| 27 | hsa-miR-320a | 44 |
| 28 | hsa-miR-320b | 45 |
| 29 | hsa-miR-328-5p | 46 |
| 30 | hsa-miR-345-3p | 48 |
| 31 | hsa-miR-3616-3p | 49 |
| 32 | hsa-miR-3619-3p | 50 |
| 33 | hsa-miR-3620-5p | 51 |
| 34 | hsa-miR-3621 | 52 |
| 35 | hsa-miR-3622a-5p | 53 |
| 36 | hsa-miR-3648 | 54 |
| 37 | hsa-miR-3656 | 56 |
| 38 | hsa-miR-3679-5p | 58 |
| 39 | hsa-miR-371b-5p | 59 |
| 40 | hsa-miR-3940-5p | 62 |
| 41 | hsa-miR-4258 | 64 |
| 42 | hsa-miR-4327 | 70 |
| 43 | hsa-miR-4417 | 71 |
| 44 | hsa-miR-4419b | 72 |
| 45 | hsa-miR-4430 | 74 |
| 46 | hsa-miR-4436b-5p | 76 |
| 47 | hsa-miR-4443 | 77 |
| 48 | hsa-miR-4446-3p | 78 |
| 49 | hsa-miR-4449 | 81 |
| 50 | hsa-miR-4455 | 83 |
| 51 | hsa-miR-4459 | 84 |
| 52 | hsa-miR-4462 | 85 |

TABLE 6-continued

| No. | Name of miRNA | SEQ ID NO |
| --- | --- | --- |
| 53 | hsa-miR-4466 | 86 |
| 54 | hsa-miR-4467 | 87 |
| 55 | hsa-miR-4480 | 88 |
| 56 | hsa-miR-4483 | 89 |
| 57 | hsa-miR-4485-5p | 91 |
| 58 | hsa-miR-4488 | 92 |
| 59 | hsa-miR-4492 | 93 |
| 60 | hsa-miR-4505 | 94 |
| 61 | hsa-miR-4525 | 96 |
| 62 | hsa-miR-4535 | 98 |
| 63 | hsa-miR-4651 | 103 |
| 64 | hsa-miR-4652-5p | 104 |
| 65 | hsa-miR-4658 | 107 |
| 66 | hsa-miR-4663 | 108 |
| 67 | hsa-miR-4673 | 109 |
| 68 | hsa-miR-4675 | 110 |
| 69 | hsa-miR-4687-3p | 111 |
| 70 | hsa-miR-4687-5p | 112 |
| 71 | hsa-miR-4690-5p | 113 |
| 72 | hsa-miR-4697-5p | 115 |
| 73 | hsa-miR-4706 | 116 |
| 74 | hsa-miR-4707-3p | 117 |
| 75 | hsa-miR-4707-5p | 118 |
| 76 | hsa-miR-4708-3p | 119 |
| 77 | hsa-miR-4718 | 121 |
| 78 | hsa-miR-4722-5p | 122 |
| 79 | hsa-miR-4725-3p | 123 |
| 80 | hsa-miR-4726-5p | 124 |
| 81 | hsa-miR-4727-3p | 125 |
| 82 | hsa-miR-4728-5p | 126 |
| 83 | hsa-miR-4731-5p | 127 |
| 84 | hsa-miR-4736 | 128 |
| 85 | hsa-miR-4739 | 129 |
| 86 | hsa-miR-4740-5p | 130 |
| 87 | hsa-miR-4741 | 131 |
| 88 | hsa-miR-4750-5p | 132 |
| 89 | hsa-miR-4755-3p | 133 |
| 90 | hsa-miR-4763-3p | 134 |
| 91 | hsa-miR-4771 | 135 |
| 92 | hsa-miR-4787-3p | 138 |
| 93 | hsa-miR-4792 | 139 |
| 94 | hsa-miR-5008-5p | 141 |
| 95 | hsa-miR-5010-5p | 142 |
| 96 | hsa-miR-504-3p | 143 |
| 97 | hsa-miR-550a-5p | 145 |
| 98 | hsa-miR-5572 | 146 |
| 99 | hsa-miR-6075 | 148 |
| 100 | hsa-miR-6076 | 149 |
| 101 | hsa-miR-6087 | 1 |
| 102 | hsa-miR-6088 | 150 |
| 103 | hsa-miR-6132 | 153 |
| 104 | hsa-miR-615-5p | 155 |
| 105 | hsa-miR-619-5p | 156 |
| 106 | hsa-miR-6511a-5p | 159 |
| 107 | hsa-miR-6515-3p | 160 |
| 108 | hsa-miR-663a | 240 |
| 109 | hsa-miR-6716-5p | 163 |
| 110 | hsa-miR-6717-5p | 164 |
| 111 | hsa-miR-6724-5p | 166 |
| 112 | hsa-miR-6737-5p | 168 |
| 113 | hsa-miR-6741-5p | 169 |
| 114 | hsa-miR-6742-5p | 170 |
| 115 | hsa-miR-6743-5p | 171 |
| 116 | hsa-miR-6760-5p | 174 |
| 117 | hsa-miR-6765-5p | 177 |
| 118 | hsa-miR-6766-5p | 179 |
| 119 | hsa-miR-6777-5p | 182 |
| 120 | hsa-miR-6780b-5p | 184 |
| 121 | hsa-miR-6781-5p | 185 |
| 122 | hsa-miR-6784-5p | 187 |
| 123 | hsa-miR-6787-5p | 189 |
| 124 | hsa-miR-6789-5p | 190 |
| 125 | hsa-miR-6791-5p | 191 |
| 126 | hsa-miR-6794-5p | 192 |
| 127 | hsa-miR-6800-5p | 193 |
| 128 | hsa-miR-6802-5p | 194 |
| 129 | hsa-miR-6803-5p | 195 |
| 130 | hsa-miR-6819-5p | 198 |

TABLE 6-continued

| No. | Name of miRNA | SEQ ID NO |
|---|---|---|
| 131 | hsa-miR-6821-5p | 199 |
| 132 | hsa-miR-6842-5p | 204 |
| 133 | hsa-miR-6850-5p | 205 |
| 134 | hsa-miR-6861-5p | 206 |
| 135 | hsa-miR-6870-5p | 208 |
| 136 | hsa-miR-6877-5p | 209 |
| 137 | hsa-miR-6880-5p | 212 |
| 138 | hsa-miR-6885-5p | 213 |
| 139 | hsa-miR-7107-5p | 215 |
| 140 | hsa-miR-7108-3p | 216 |
| 141 | hsa-miR-7113-3p | 219 |
| 142 | hsa-miR-7150 | 220 |
| 143 | hsa-miR-744-5p | 221 |
| 144 | hsa-miR-7975 | 222 |
| 145 | hsa-miR-8052 | 224 |
| 146 | hsa-miR-8069 | 225 |
| 147 | hsa-miR-8073 | 226 |
| 148 | hsa-miR-887-3p | 227 |
| 149 | hsa-miR-937-5p | 228 |

TABLE 7-1

| No. | Number of miRNA | miRNA marker 1 | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| 1 | 1 | hsa-miR-6087 | 1 | 0.92 | 0.83 | 0.86 | 0.90 | 0.90 | 0.84 | 0.86 | 0.91 |
| 2 | 1 | hsa-miR-6088 | 150 | 0.93 | 0.67 | 0.75 | 0.80 | 0.91 | 0.62 | 0.71 | 0.78 |
| 3 | 1 | hsa-miR-4652-5p | 104 | 0.81 | 0.82 | 0.82 | 0.87 | 0.77 | 0.84 | 0.82 | 0.88 |
| 4 | 1 | hsa-miR-615-5p | 155 | 0.77 | 0.73 | 0.74 | 0.81 | 0.76 | 0.78 | 0.78 | 0.83 |
| 5 | 1 | hsa-miR-6819-5p | 198 | 0.74 | 0.72 | 0.73 | 0.78 | 0.73 | 0.70 | 0.71 | 0.78 |
| 6 | 1 | hsa-miR-6877-5p | 209 | 0.85 | 0.59 | 0.67 | 0.77 | 0.85 | 0.58 | 0.66 | 0.77 |
| 7 | 1 | hsa-miR-8073 | 226 | 0.82 | 0.62 | 0.68 | 0.76 | 0.83 | 0.62 | 0.68 | 0.78 |
| 8 | 1 | hsa-miR-4687-3p | 111 | 0.68 | 0.75 | 0.73 | 0.76 | 0.69 | 0.78 | 0.75 | 0.76 |
| 9 | 1 | hsa-miR-4658 | 107 | 0.79 | 0.70 | 0.73 | 0.80 | 0.79 | 0.69 | 0.72 | 0.80 |
| 10 | 1 | hsa-miR-6076 | 149 | 0.83 | 0.59 | 0.66 | 0.74 | 0.76 | 0.53 | 0.60 | 0.70 |
| 11 | 1 | hsa-miR-6777-5p | 182 | 0.86 | 0.57 | 0.65 | 0.74 | 0.82 | 0.53 | 0.62 | 0.73 |
| 12 | 1 | hsa-miR-6724-5p | 166 | 0.82 | 0.58 | 0.65 | 0.75 | 0.81 | 0.58 | 0.65 | 0.75 |
| 13 | 1 | hsa-miR-3194-3p | 41 | 0.80 | 0.63 | 0.68 | 0.78 | 0.76 | 0.61 | 0.66 | 0.76 |
| 14 | 1 | hsa-miR-4436b-5p | 76 | 0.67 | 0.74 | 0.72 | 0.78 | 0.65 | 0.74 | 0.71 | 0.75 |
| 15 | 1 | hsa-miR-187-5p | 21 | 0.88 | 0.53 | 0.63 | 0.72 | 0.88 | 0.56 | 0.65 | 0.73 |
| 16 | 1 | hsa-miR-17-3p | 20 | 0.75 | 0.70 | 0.71 | 0.78 | 0.71 | 0.71 | 0.71 | 0.77 |
| 17 | 1 | hsa-miR-4750-5p | 132 | 0.80 | 0.62 | 0.67 | 0.75 | 0.85 | 0.66 | 0.72 | 0.79 |
| 18 | 1 | hsa-miR-4727-3p | 125 | 0.80 | 0.64 | 0.69 | 0.78 | 0.72 | 0.64 | 0.67 | 0.76 |
| 19 | 1 | hsa-miR-4728-5p | 126 | 0.59 | 0.81 | 0.74 | 0.74 | 0.50 | 0.81 | 0.71 | 0.75 |
| 20 | 1 | hsa-miR-6741-5p | 169 | 0.79 | 0.60 | 0.65 | 0.72 | 0.79 | 0.58 | 0.65 | 0.74 |
| 21 | 1 | hsa-miR-6717-5p | 164 | 0.88 | 0.52 | 0.63 | 0.74 | 0.84 | 0.50 | 0.60 | 0.74 |
| 22 | 1 | hsa-miR-4480 | 88 | 0.70 | 0.69 | 0.70 | 0.75 | 0.67 | 0.69 | 0.69 | 0.75 |
| 23 | 1 | hsa-miR-3160-5p | 35 | 0.77 | 0.61 | 0.66 | 0.77 | 0.76 | 0.59 | 0.64 | 0.77 |
| 24 | 1 | hsa-miR-4663 | 108 | 0.66 | 0.79 | 0.75 | 0.78 | 0.63 | 0.78 | 0.73 | 0.76 |
| 25 | 1 | hsa-miR-4417 | 71 | 0.78 | 0.60 | 0.65 | 0.73 | 0.73 | 0.64 | 0.67 | 0.75 |
| 26 | 1 | hsa-miR-1228-5p | 9 | 0.83 | 0.55 | 0.64 | 0.73 | 0.75 | 0.56 | 0.62 | 0.71 |
| 27 | 1 | hsa-miR-4483 | 89 | 0.67 | 0.72 | 0.70 | 0.74 | 0.65 | 0.74 | 0.71 | 0.74 |
| 28 | 1 | hsa-miR-3619-3p | 50 | 0.74 | 0.62 | 0.65 | 0.74 | 0.73 | 0.62 | 0.65 | 0.74 |
| 29 | 1 | hsa-miR-1343-3p | 17 | 0.91 | 0.49 | 0.61 | 0.67 | 0.90 | 0.51 | 0.63 | 0.68 |
| 30 | 1 | hsa-miR-6075 | 148 | 0.90 | 0.48 | 0.61 | 0.74 | 0.88 | 0.44 | 0.57 | 0.72 |
| 31 | 1 | hsa-miR-320b | 45 | 0.76 | 0.61 | 0.65 | 0.73 | 0.73 | 0.59 | 0.63 | 0.73 |
| 32 | 1 | hsa-miR-4718 | 121 | 0.83 | 0.54 | 0.62 | 0.70 | 0.82 | 0.52 | 0.61 | 0.70 |
| 33 | 1 | hsa-miR-4740-5p | 130 | 0.80 | 0.57 | 0.64 | 0.71 | 0.79 | 0.55 | 0.62 | 0.71 |
| 34 | 1 | hsa-miR-2467-3p | 28 | 0.69 | 0.67 | 0.68 | 0.74 | 0.68 | 0.64 | 0.65 | 0.72 |
| 35 | 1 | hsa-miR-4455 | 83 | 0.76 | 0.60 | 0.65 | 0.72 | 0.76 | 0.59 | 0.64 | 0.68 |
| 36 | 1 | hsa-miR-5572 | 146 | 0.75 | 0.61 | 0.65 | 0.74 | 0.64 | 0.61 | 0.62 | 0.68 |
| 37 | 1 | hsa-miR-4755-3p | 133 | 0.72 | 0.63 | 0.66 | 0.73 | 0.68 | 0.63 | 0.64 | 0.71 |
| 38 | 1 | hsa-miR-6760-5p | 174 | 0.93 | 0.43 | 0.58 | 0.69 | 0.90 | 0.41 | 0.56 | 0.68 |
| 39 | 1 | hsa-miR-3648 | 54 | 0.71 | 0.64 | 0.66 | 0.71 | 0.65 | 0.68 | 0.67 | 0.71 |
| 40 | 1 | hsa-miR-4525 | 96 | 0.89 | 0.47 | 0.59 | 0.73 | 0.86 | 0.50 | 0.61 | 0.74 |
| 41 | 1 | hsa-miR-371b-5p | 59 | 0.79 | 0.60 | 0.65 | 0.73 | 0.66 | 0.61 | 0.63 | 0.67 |
| 42 | 1 | hsa-miR-3622a-5p | 53 | 0.79 | 0.54 | 0.62 | 0.68 | 0.77 | 0.55 | 0.62 | 0.69 |
| 43 | 1 | hsa-miR-744-5p | 221 | 0.71 | 0.60 | 0.64 | 0.69 | 0.61 | 0.56 | 0.58 | 0.65 |
| 44 | 1 | hsa-miR-320a | 44 | 0.72 | 0.62 | 0.65 | 0.69 | 0.67 | 0.60 | 0.62 | 0.68 |
| 45 | 1 | hsa-miR-1247-3p | 12 | 0.81 | 0.51 | 0.60 | 0.68 | 0.79 | 0.51 | 0.59 | 0.70 |
| 46 | 1 | hsa-miR-4708-3p | 119 | 0.82 | 0.51 | 0.61 | 0.68 | 0.84 | 0.47 | 0.58 | 0.69 |
| 47 | 1 | hsa-miR-1238-5p | 11 | 0.86 | 0.46 | 0.58 | 0.66 | 0.88 | 0.45 | 0.58 | 0.68 |
| 48 | 1 | hsa-miR-3620-5p | 51 | 0.77 | 0.56 | 0.62 | 0.68 | 0.75 | 0.53 | 0.59 | 0.70 |
| 49 | 1 | hsa-miR-6803-5p | 195 | 0.72 | 0.63 | 0.65 | 0.70 | 0.68 | 0.60 | 0.62 | 0.70 |
| 50 | 1 | hsa-miR-6766-5p | 179 | 0.64 | 0.67 | 0.66 | 0.71 | 0.68 | 0.71 | 0.70 | 0.75 |

TABLE 7-2

| No. | Number of miRNA | Discriminant formula | Threshold |
|---|---|---|---|
| 1 | 1 | (−2.38622)*hsa-miR-6087 + 28.2057 | 0.19 |
| 2 | 1 | (−1.84282)*hsa-miR-6088 + 20.7857 | −0.29 |
| 3 | 1 | (0.428954)*hsa-miR-4652-5p − 1.99672 | 0.28 |
| 4 | 1 | (0.94437)*hsa-miR-615-5p − 6.18452 | 0.12 |
| 5 | 1 | (1.59298)*hsa-miR-6819-5p − 13.1034 | 0.04 |
| 6 | 1 | (1.26097)*hsa-miR-6877-5p − 10.0907 | −0.21 |
| 7 | 1 | (0.973077)*hsa-miR-8073 − 7.95996 | −0.02 |
| 8 | 1 | (−2.02839)*hsa-miR-4687-3p + 18.5307 | 0.10 |
| 9 | 1 | (0.459695)*hsa-miR-4658 − 2.221 | 0.14 |
| 10 | 1 | (1.31297)*hsa-miR-6076 − 10.3287 | −0.16 |
| 11 | 1 | (0.650895)*hsa-miR-6777-5p − 4.31556 | −0.04 |
| 12 | 1 | (2.5334)*hsa-miR-6724-5p − 26.8774 | −0.17 |
| 13 | 1 | (0.473015)*hsa-miR-3194-3p − 3.91032 | −0.06 |
| 14 | 1 | (0.862895)*hsa-miR-4436b-5p − 5.38183 | 0.18 |
| 15 | 1 | (0.958701)*hsa-miR-187-5p − 8.01195 | −0.20 |
| 16 | 1 | (0.464258)*hsa-miR-17-3p − 2.73158 | 0.23 |
| 17 | 1 | (0.863932)*hsa-miR-4750-5p − 5.86918 | 0.00 |
| 18 | 1 | (0.558605)*hsa-miR-4727-3p − 3.40207 | 0.09 |
| 19 | 1 | (−1.13719)*hsa-miR-4728-5p + 8.17743 | 0.18 |
| 20 | 1 | (1.22441)*hsa-miR-6741-5p − 9.85847 | −0.12 |
| 21 | 1 | (0.598595)*hsa-miR-6717-5p − 4.6341 | −0.06 |
| 22 | 1 | (0.432884)*hsa-miR-4480 − 2.72926 | 0.22 |
| 23 | 1 | (0.454592)*hsa-miR-3160-5p − 3.59088 | −0.20 |
| 24 | 1 | (0.437205)*hsa-miR-4663 − 2.3675 | 0.33 |
| 25 | 1 | (2.29198)*hsa-miR-4417 − 19.4685 | −0.07 |
| 26 | 1 | (−2.46304)*hsa-miR-1228-5p + 27.0668 | −0.12 |
| 27 | 1 | (0.529784)*hsa-miR-4483 − 3.04293 | 0.16 |
| 28 | 1 | (1.08677)*hsa-miR-3619-3p − 9.38089 | −0.21 |
| 29 | 1 | (0.901987)*hsa-miR-1343-3p − 7.36719 | −0.37 |
| 30 | 1 | (1.70213)*hsa-miR-6075 − 15.1524 | −0.50 |
| 31 | 1 | (0.619655)*hsa-miR-320b − 3.83811 | 0.08 |
| 32 | 1 | (0.491734)*hsa-miR-4718 − 4.11397 | −0.10 |
| 33 | 1 | (0.543442)*hsa-miR-4740-5p − 3.44558 | −0.06 |
| 34 | 1 | (0.566603)*hsa-miR-2467-3p − 5.23727 | 0.11 |
| 35 | 1 | (0.496896)*hsa-miR-4455 − 2.69782 | 0.04 |
| 36 | 1 | (0.78147)*hsa-miR-5572 − 4.96372 | 0.05 |
| 37 | 1 | (0.384157)*hsa-miR-4755-3p − 2.12762 | 0.14 |
| 38 | 1 | (0.482362)*hsa-miR-6760-5p − 2.59313 | −0.31 |
| 39 | 1 | (1.71731)*hsa-miR-3648 − 22.6417 | 0.07 |
| 40 | 1 | (0.618585)*hsa-miR-4525 − 6.85074 | −0.48 |
| 41 | 1 | (0.621671)*hsa-miR-371b-5p − 3.40467 | 0.11 |
| 42 | 1 | (0.69848)*hsa-miR-3622a-5p − 4.36254 | −0.02 |
| 43 | 1 | (1.34494)*hsa-miR-744-5p − 12.1875 | 0.00 |
| 44 | 1 | (0.86288)*hsa-miR-320a − 5.99984 | 0.04 |
| 45 | 1 | (1.11344)*hsa-miR-1247-3p − 7.96563 | −0.15 |
| 46 | 1 | (0.590382)*hsa-miR-4708-3p − 4.90478 | −0.21 |
| 47 | 1 | (0.892678)*hsa-miR-1238-5p − 6.81907 | −0.20 |
| 48 | 1 | (−1.68137)*hsa-miR-3620-5p + 12.8603 | −0.25 |
| 49 | 1 | (−4.57263)*hsa-miR-6803-5p + 49.8649 | −0.05 |
| 50 | 1 | (0.95846)*hsa-miR-6766-5p − 6.48535 | 0.19 |

TABLE 8-1

| No. | Number of miRNA | miRNA marker 1 | SEQ ID NO | miRNA marker 2 | SEQ ID NO |
|---|---|---|---|---|---|
| 1 | 2 | hsa-miR-6087 | 1 | hsa-miR-744-5p | 221 |
| 2 | 2 | hsa-miR-6087 | 1 | hsa-miR-4652-5p | 104 |
| 3 | 2 | hsa-miR-6087 | 1 | hsa-miR-6132 | 153 |
| 4 | 2 | hsa-miR-6087 | 1 | hsa-miR-4787-3p | 138 |
| 5 | 2 | hsa-miR-6087 | 1 | hsa-miR-1185-1-3p | 2 |
| 6 | 2 | hsa-miR-6087 | 1 | hsa-miR-4436b-5p | 76 |
| 7 | 2 | hsa-miR-6087 | 1 | hsa-miR-6789-5p | 190 |
| 8 | 2 | hsa-miR-6087 | 1 | hsa-miR-6784-5p | 187 |
| 9 | 2 | hsa-miR-6087 | 1 | hsa-miR-3160-5p | 35 |
| 10 | 2 | hsa-miR-6087 | 1 | hsa-miR-6800-5p | 193 |
| 11 | 2 | hsa-miR-6087 | 1 | hsa-miR-615-5p | 155 |
| 12 | 2 | hsa-miR-6087 | 1 | hsa-miR-1343-5p | 18 |
| 13 | 2 | hsa-miR-6087 | 1 | hsa-miR-1228-5p | 9 |
| 14 | 2 | hsa-miR-6087 | 1 | hsa-miR-6724-5p | 166 |
| 15 | 2 | hsa-miR-6087 | 1 | hsa-miR-4417 | 71 |
| 16 | 2 | hsa-miR-6087 | 1 | hsa-miR-6781-5p | 185 |
| 17 | 2 | hsa-miR-6087 | 1 | hsa-miR-3648 | 54 |
| 18 | 2 | hsa-miR-6087 | 1 | hsa-miR-937-5p | 228 |
| 19 | 2 | hsa-miR-6087 | 1 | hsa-miR-4258 | 64 |
| 20 | 2 | hsa-miR-6087 | 1 | hsa-miR-4466 | 86 |
| 21 | 2 | hsa-miR-6087 | 1 | hsa-miR-187-5p | 21 |
| 22 | 2 | hsa-miR-6087 | 1 | hsa-miR-4740-5p | 130 |
| 23 | 2 | hsa-miR-6087 | 1 | hsa-miR-4697-5p | 115 |
| 24 | 2 | hsa-miR-6087 | 1 | hsa-miR-320b | 45 |
| 25 | 2 | hsa-miR-6087 | 1 | hsa-miR-3656 | 56 |
| 26 | 2 | hsa-miR-6087 | 1 | hsa-miR-4706 | 116 |
| 27 | 2 | hsa-miR-6087 | 1 | hsa-miR-4727-3p | 125 |
| 28 | 2 | hsa-miR-6087 | 1 | hsa-miR-619-5p | 156 |
| 29 | 2 | hsa-miR-6087 | 1 | hsa-miR-663a | 240 |
| 30 | 2 | hsa-miR-6087 | 1 | hsa-miR-320a | 44 |
| 31 | 2 | hsa-miR-6087 | 1 | hsa-miR-6861-5p | 206 |
| 32 | 2 | hsa-miR-6087 | 1 | hsa-miR-6075 | 148 |
| 33 | 2 | hsa-miR-6087 | 1 | hsa-miR-4690-5p | 113 |
| 34 | 2 | hsa-miR-6087 | 1 | hsa-miR-4673 | 109 |
| 35 | 2 | hsa-miR-6087 | 1 | hsa-miR-17-3p | 20 |
| 36 | 2 | hsa-miR-6087 | 1 | hsa-miR-135a-3p | 233 |
| 37 | 2 | hsa-miR-6087 | 1 | hsa-miR-4327 | 70 |
| 38 | 2 | hsa-miR-6087 | 1 | hsa-miR-3195 | 42 |
| 39 | 2 | hsa-miR-6087 | 1 | hsa-miR-4771 | 135 |
| 40 | 2 | hsa-miR-6087 | 1 | hsa-miR-6885-5p | 213 |
| 41 | 2 | hsa-miR-6087 | 1 | hsa-miR-3194-3p | 41 |
| 42 | 2 | hsa-miR-6087 | 1 | hsa-miR-4535 | 98 |
| 43 | 2 | hsa-miR-6087 | 1 | hsa-miR-4736 | 128 |
| 44 | 2 | hsa-miR-6087 | 1 | hsa-miR-4718 | 121 |
| 45 | 2 | hsa-miR-6087 | 1 | hsa-miR-6511a-5p | 159 |
| 46 | 2 | hsa-miR-6087 | 1 | hsa-miR-4663 | 108 |
| 47 | 2 | hsa-miR-6087 | 1 | hsa-miR-550a-5p | 145 |
| 48 | 2 | hsa-miR-6087 | 1 | hsa-miR-4467 | 87 |
| 49 | 2 | hsa-miR-6087 | 1 | hsa-miR-3621 | 52 |
| 50 | 2 | hsa-miR-6087 | 1 | hsa-miR-1185-2-3p | 3 |

TABLE 8-2

| | Training cohort | | | | Validation cohort | | | |
|---|---|---|---|---|---|---|---|---|
| No. | Sensitivity | Specificity | Accuracy | AUC | Sensitivity | Specificity | Accuracy | AUC |
| 1 | 0.95 | 0.82 | 0.86 | 0.93 | 0.93 | 0.84 | 0.86 | 0.93 |
| 2 | 0.93 | 0.88 | 0.89 | 0.94 | 0.92 | 0.88 | 0.89 | 0.94 |
| 3 | 0.95 | 0.80 | 0.84 | 0.93 | 0.92 | 0.83 | 0.85 | 0.92 |
| 4 | 0.96 | 0.81 | 0.86 | 0.92 | 0.95 | 0.83 | 0.87 | 0.93 |
| 5 | 0.93 | 0.82 | 0.86 | 0.92 | 0.92 | 0.85 | 0.87 | 0.94 |
| 6 | 0.95 | 0.82 | 0.86 | 0.93 | 0.93 | 0.82 | 0.85 | 0.93 |
| 7 | 0.94 | 0.80 | 0.84 | 0.91 | 0.95 | 0.82 | 0.86 | 0.92 |
| 8 | 0.92 | 0.84 | 0.86 | 0.92 | 0.89 | 0.83 | 0.85 | 0.93 |
| 9 | 0.95 | 0.82 | 0.86 | 0.92 | 0.94 | 0.83 | 0.86 | 0.93 |
| 10 | 0.94 | 0.80 | 0.84 | 0.91 | 0.95 | 0.81 | 0.85 | 0.91 |
| 11 | 0.92 | 0.84 | 0.86 | 0.92 | 0.90 | 0.83 | 0.85 | 0.92 |
| 12 | 0.94 | 0.80 | 0.84 | 0.90 | 0.95 | 0.80 | 0.85 | 0.92 |
| 13 | 0.95 | 0.81 | 0.85 | 0.92 | 0.94 | 0.83 | 0.86 | 0.92 |
| 14 | 0.91 | 0.87 | 0.88 | 0.93 | 0.92 | 0.88 | 0.89 | 0.94 |
| 15 | 0.92 | 0.84 | 0.86 | 0.91 | 0.92 | 0.85 | 0.87 | 0.93 |
| 16 | 0.95 | 0.82 | 0.86 | 0.92 | 0.94 | 0.83 | 0.86 | 0.93 |
| 17 | 0.94 | 0.83 | 0.86 | 0.91 | 0.95 | 0.85 | 0.88 | 0.92 |
| 18 | 0.93 | 0.83 | 0.86 | 0.91 | 0.92 | 0.83 | 0.86 | 0.92 |
| 19 | 0.93 | 0.84 | 0.86 | 0.91 | 0.93 | 0.84 | 0.87 | 0.92 |
| 20 | 0.95 | 0.80 | 0.84 | 0.90 | 0.95 | 0.81 | 0.85 | 0.91 |
| 21 | 0.92 | 0.83 | 0.86 | 0.91 | 0.92 | 0.85 | 0.87 | 0.92 |
| 22 | 0.96 | 0.80 | 0.85 | 0.92 | 0.92 | 0.83 | 0.86 | 0.92 |
| 23 | 0.95 | 0.81 | 0.85 | 0.91 | 0.94 | 0.83 | 0.86 | 0.91 |
| 24 | 0.93 | 0.83 | 0.86 | 0.92 | 0.93 | 0.85 | 0.87 | 0.94 |
| 25 | 0.95 | 0.80 | 0.84 | 0.90 | 0.95 | 0.81 | 0.85 | 0.91 |
| 26 | 0.94 | 0.80 | 0.85 | 0.91 | 0.93 | 0.82 | 0.85 | 0.92 |
| 27 | 0.91 | 0.86 | 0.87 | 0.92 | 0.86 | 0.87 | 0.87 | 0.93 |
| 28 | 0.93 | 0.82 | 0.85 | 0.90 | 0.94 | 0.82 | 0.85 | 0.91 |
| 29 | 0.93 | 0.83 | 0.86 | 0.91 | 0.93 | 0.83 | 0.86 | 0.92 |
| 30 | 0.96 | 0.80 | 0.85 | 0.92 | 0.93 | 0.83 | 0.86 | 0.92 |
| 31 | 0.93 | 0.81 | 0.85 | 0.90 | 0.91 | 0.83 | 0.85 | 0.91 |
| 32 | 0.97 | 0.81 | 0.86 | 0.92 | 0.93 | 0.80 | 0.84 | 0.93 |
| 33 | 0.95 | 0.81 | 0.85 | 0.90 | 0.93 | 0.82 | 0.85 | 0.91 |

TABLE 8-2-continued

| | Training cohort | | | | Validation cohort | | | | | Training cohort | | | | Validation cohort | | | |
|---|---|---|---|---|---|---|---|---|---|---|---|---|---|---|---|---|---|
| No. | Sensitivity | Specificity | Accuracy | AUC | Sensitivity | Specificity | Accuracy | AUC | No. | Sensitivity | Specificity | Accuracy | AUC | Sensitivity | Specificity | Accuracy | AUC |
| 34 | 0.92 | 0.83 | 0.85 | 0.90 | 0.91 | 0.84 | 0.86 | 0.91 | 43 | 0.96 | 0.78 | 0.83 | 0.91 | 0.95 | 0.80 | 0.84 | 0.92 |
| 35 | 0.94 | 0.85 | 0.87 | 0.93 | 0.93 | 0.85 | 0.88 | 0.93 | 44 | 0.97 | 0.80 | 0.85 | 0.92 | 0.96 | 0.81 | 0.85 | 0.92 |
| 36 | 0.93 | 0.82 | 0.85 | 0.90 | 0.92 | 0.82 | 0.85 | 0.91 | 45 | 0.93 | 0.82 | 0.85 | 0.91 | 0.90 | 0.82 | 0.85 | 0.91 |
| 37 | 0.93 | 0.81 | 0.85 | 0.92 | 0.90 | 0.83 | 0.85 | 0.92 | 46 | 0.92 | 0.84 | 0.86 | 0.92 | 0.89 | 0.85 | 0.86 | 0.92 |
| 38 | 0.93 | 0.82 | 0.85 | 0.90 | 0.94 | 0.84 | 0.87 | 0.91 | 47 | 0.93 | 0.82 | 0.85 | 0.90 | 0.92 | 0.82 | 0.85 | 0.91 |
| 39 | 0.94 | 0.82 | 0.85 | 0.92 | 0.91 | 0.84 | 0.86 | 0.93 | 48 | 0.96 | 0.80 | 0.85 | 0.91 | 0.93 | 0.80 | 0.84 | 0.92 |
| 40 | 0.92 | 0.83 | 0.85 | 0.90 | 0.92 | 0.83 | 0.86 | 0.91 | 49 | 0.91 | 0.85 | 0.87 | 0.92 | 0.88 | 0.87 | 0.88 | 0.93 |
| 41 | 0.95 | 0.83 | 0.86 | 0.92 | 0.93 | 0.82 | 0.85 | 0.93 | 50 | 0.92 | 0.84 | 0.87 | 0.92 | 0.92 | 0.86 | 0.88 | 0.94 |
| 42 | 0.94 | 0.82 | 0.85 | 0.90 | 0.90 | 0.82 | 0.85 | 0.91 | | | | | | | | | |

TABLE 8-3

| No. | Number of miRNA | Discriminant Formula | Threshold |
|---|---|---|---|
| 1 | 2 | (−2.3378)*hsa-miR-6087 + (0.775187)*hsa-miR-744-5p + 20.6087 | −0.06 |
| 2 | 2 | (−1.82014)*hsa-miR-6087 + (0.263623)*hsa-miR-4652-5p + 20.2873 | 0.13 |
| 3 | 2 | (−2.342)*hsa-miR-6087 + (0.747161)*hsa-miR-6132 + 20.6239 | −0.10 |
| 4 | 2 | (−2.26977)*hsa-miR-6087 + (0.328067)*hsa-miR-4787-3p + 24.4629 | 0.02 |
| 5 | 2 | (−2.4398)*hsa-miR-6087 + (0.350141)*hsa-miR-1185-1-3p + 25.8489 | −0.02 |
| 6 | 2 | (−2.14971)*hsa-miR-6087 + (0.396847)*hsa-miR-4436b-5p + 22.935 | 0.02 |
| 7 | 2 | (−2.31319)*hsa-miR-6087 + (0.485485)*hsa-miR-6789-5p + 22.458 | −0.04 |
| 8 | 2 | (−2.31658)*hsa-miR-6087 + (−0.820454)*hsa-miR-6784-5p + 36.7072 | 0.17 |
| 9 | 2 | (−2.02565)*hsa-miR-6087 + (0.200577)*hsa-miR-3160-5p + 22.3592 | 0.04 |
| 10 | 2 | (−2.43999)*hsa-miR-6087 + (−0.400246)*hsa-miR-6800-5p + 31.9611 | 0.04 |
| 11 | 2 | (−2.11937)*hsa-miR-6087 + (0.336707)*hsa-miR-615-5p + 22.8464 | 0.19 |
| 12 | 2 | (−2.42752)*hsa-miR-6087 + (−0.796893)*hsa-miR-1343-5p + 36.5499 | 0.03 |
| 13 | 2 | (−2.154)*hsa-miR-6087 + (−1.03009)*hsa-miR-1228-5p + 36.7806 | 0.01 |
| 14 | 2 | (−2.14819)*hsa-miR-6087 + (1.1839)*hsa-miR-6724-5p + 12.8318 | 0.23 |
| 15 | 2 | (−2.26)*hsa-miR-6087 + (0.704186)*hsa-miR-4417 + 20.7322 | 0.18 |
| 16 | 2 | (−2.41441)*hsa-miR-6087 + (−1.20586)*hsa-miR-6781-5p + 40.3148 | −0.04 |
| 17 | 2 | (−2.20958)*hsa-miR-6087 + (0.618185)*hsa-miR-3648 + 17.9673 | 0.11 |
| 18 | 2 | (−2.46326)*hsa-miR-6087 + (−0.426017)*hsa-miR-937-5p + 32.6143 | 0.14 |
| 19 | 2 | (−2.37713)*hsa-miR-6087 + (0.352818)*hsa-miR-4258 + 24.5397 | 0.03 |
| 20 | 2 | (−2.32734)*hsa-miR-6087 + (0.611001)*hsa-miR-4466 + 19.6562 | 0.02 |
| 21 | 2 | (−2.25165)*hsa-miR-6087 + (0.222992)*hsa-miR-187-5p + 24.7515 | 0.18 |
| 22 | 2 | (−2.20735)*hsa-miR-6087 + (0.206616)*hsa-miR-4740-5p + 24.7814 | −0.03 |
| 23 | 2 | (−2.32967)*hsa-miR-6087 + (0.548334)*hsa-miR-4697-5p + 22.7714 | −0.01 |
| 24 | 2 | (−2.24507)*hsa-miR-6087 + (0.283037)*hsa-miR-320b + 24.784 | 0.13 |
| 25 | 2 | (−2.46034)*hsa-miR-6087 + (0.960217)*hsa-miR-3656 + 17.8857 | −0.01 |
| 26 | 2 | (−2.24352)*hsa-miR-6087 + (0.361123)*hsa-miR-4706 + 23.4592 | 0.04 |
| 27 | 2 | (−2.13576)*hsa-miR-6087 + (0.236818)*hsa-miR-4727-3p + 23.8029 | 0.26 |
| 28 | 2 | (−2.33994)*hsa-miR-6087 + (0.101029)*hsa-miR-619-5p + 26.8946 | 0.12 |
| 29 | 2 | (−2.33399)*hsa-miR-6087 + (0.585351)*hsa-miR-663a + 20.4173 | 0.05 |
| 30 | 2 | (−2.27949)*hsa-miR-6087 + (0.349853)*hsa-miR-320a + 24.5114 | 0.00 |
| 31 | 2 | (−2.32151)*hsa-miR-6087 + (0.225774)*hsa-miR-6861-5p + 25.6592 | 0.14 |
| 32 | 2 | (−2.12657)*hsa-miR-6087 + (0.759356)*hsa-miR-6075 + 18.3767 | −0.04 |
| 33 | 2 | (−2.34965)*hsa-miR-6087 + (0.20625)*hsa-miR-4690-5p + 26.3628 | 0.10 |
| 34 | 2 | (−2.34461)*hsa-miR-6087 + (0.108729)*hsa-miR-4673 + 27.0938 | 0.17 |
| 35 | 2 | (−2.14934)*hsa-miR-6087 + (0.229327)*hsa-miR-17-3p + 24.0564 | 0.16 |
| 36 | 2 | (−2.36577)*hsa-miR-6087 + (0.0426866)*hsa-miR-135a-3p + 27.7126 | 0.11 |
| 37 | 2 | (−2.43661)*hsa-miR-6087 + (0.746709)*hsa-miR-4327 + 21.855 | 0.00 |
| 38 | 2 | (−2.38999)*hsa-miR-6087 + (0.161276)*hsa-miR-3195 + 26.9159 | 0.14 |
| 39 | 2 | (−2.26696)*hsa-miR-6087 + (0.174565)*hsa-miR-4771 + 25.809 | 0.04 |
| 40 | 2 | (−2.44165)*hsa-miR-6087 + (0.216791)*hsa-miR-6885-5p + 26.3871 | 0.19 |
| 41 | 2 | (−2.06725)*hsa-miR-6087 + (0.200306)*hsa-miR-3194-3p + 22.7794 | 0.03 |
| 42 | 2 | (−2.33398)*hsa-miR-6087 + (0.0943401)*hsa-miR-4535 + 27.0762 | 0.08 |
| 43 | 2 | (−2.30908)*hsa-miR-6087 + (0.228957)*hsa-miR-4736 + 25.7017 | −0.11 |
| 44 | 2 | (−2.22306)*hsa-miR-6087 + (0.174636)*hsa-miR-4718 + 24.816 | −0.04 |
| 45 | 2 | (−2.31893)*hsa-miR-6087 + (0.320313)*hsa-miR-6511a-5p + 24.9405 | 0.11 |
| 46 | 2 | (−2.12785)*hsa-miR-6087 + (0.203709)*hsa-miR-4663 + 24.0486 | 0.10 |
| 47 | 2 | (−2.38066)*hsa-miR-6087 + (0.0856268)*hsa-miR-550a-5p + 27.607 | 0.12 |
| 48 | 2 | (−2.27785)*hsa-miR-6087 + (0.666284)*hsa-miR-4467 + 19.8945 | −0.06 |
| 49 | 2 | (−2.33358)*hsa-miR-6087 + (−0.824656)*hsa-miR-3621 + 36.9712 | 0.25 |
| 50 | 2 | (−2.43195)*hsa-miR-6087 + (0.283136)*hsa-miR-1185-2-3p + 26.4884 | 0.10 |

TABLE 9-1

| No. | Number of miRNA | miRNA marker 1 | SEQ ID NO | miRNA marker 2 | SEQ ID NO | miRNA marker 3 | SEQ ID NO |
|---|---|---|---|---|---|---|---|
| 1 | 3 | hsa-miR-6087 | 1 | hsa-miR-744-5p | 221 | hsa-miR-4725-3p | 123 |
| 2 | 3 | hsa-miR-6087 | 1 | hsa-miR-6132 | 153 | hsa-miR-4725-3p | 123 |
| 3 | 3 | hsa-miR-6087 | 1 | hsa-miR-744-5p | 221 | hsa-miR-1268b | 14 |
| 4 | 3 | hsa-miR-6087 | 1 | hsa-miR-6724-5p | 166 | hsa-miR-3940-5p | 62 |
| 5 | 3 | hsa-miR-6087 | 1 | hsa-miR-4652-5p | 104 | hsa-miR-4728-5p | 126 |
| 6 | 3 | hsa-miR-6087 | 1 | hsa-miR-1185-1-3p | 2 | hsa-miR-4728-5p | 126 |
| 7 | 3 | hsa-miR-6087 | 1 | hsa-miR-1185-2-3p | 3 | hsa-miR-4728-5p | 126 |
| 8 | 3 | hsa-miR-6087 | 1 | hsa-miR-4652-5p | 104 | hsa-miR-6724-5p | 166 |
| 9 | 3 | hsa-miR-6087 | 1 | hsa-miR-6724-5p | 166 | hsa-miR-8069 | 225 |
| 10 | 3 | hsa-miR-6087 | 1 | hsa-miR-6724-5p | 166 | hsa-miR-6781-5p | 185 |
| 11 | 3 | hsa-miR-6087 | 1 | hsa-miR-4652-5p | 104 | hsa-miR-6781-5p | 185 |
| 12 | 3 | hsa-miR-6087 | 1 | hsa-miR-6784-5p | 187 | hsa-miR-4728-5p | 126 |
| 13 | 3 | hsa-miR-6087 | 1 | hsa-miR-744-5p | 221 | hsa-miR-6781-5p | 185 |
| 14 | 3 | hsa-miR-6087 | 1 | hsa-miR-4652-5p | 104 | hsa-miR-6794-5p | 192 |
| 15 | 3 | hsa-miR-6087 | 1 | hsa-miR-1185-1-3p | 2 | hsa-miR-6781-5p | 185 |
| 16 | 3 | hsa-miR-6087 | 1 | hsa-miR-6724-5p | 166 | hsa-miR-3621 | 52 |
| 17 | 3 | hsa-miR-6087 | 1 | hsa-miR-6781-5p | 185 | hsa-miR-6075 | 148 |
| 18 | 3 | hsa-miR-6087 | 1 | hsa-miR-1185-1-3p | 2 | hsa-miR-6724-5p | 166 |
| 19 | 3 | hsa-miR-6087 | 1 | hsa-miR-6789-5p | 190 | hsa-miR-3940-5p | 62 |
| 20 | 3 | hsa-miR-6087 | 1 | hsa-miR-3160-5p | 35 | hsa-miR-4728-5p | 126 |
| 21 | 3 | hsa-miR-6087 | 1 | hsa-miR-6781-5p | 185 | hsa-miR-4492 | 93 |
| 22 | 3 | hsa-miR-6087 | 1 | hsa-miR-6781-5p | 185 | hsa-miR-4327 | 70 |
| 23 | 3 | hsa-miR-6087 | 1 | hsa-miR-4327 | 70 | hsa-miR-1268b | 14 |
| 24 | 3 | hsa-miR-6087 | 1 | hsa-miR-744-5p | 221 | hsa-miR-3679-5p | 58 |
| 25 | 3 | hsa-miR-6087 | 1 | hsa-miR-6132 | 153 | hsa-miR-4739 | 129 |
| 26 | 3 | hsa-miR-6087 | 1 | hsa-miR-744-5p | 221 | hsa-miR-6765-5p | 177 |
| 27 | 3 | hsa-miR-6087 | 1 | hsa-miR-6784-5p | 187 | hsa-miR-6724-5p | 166 |
| 28 | 3 | hsa-miR-6087 | 1 | hsa-miR-744-5p | 221 | hsa-miR-4505 | 94 |
| 29 | 3 | hsa-miR-6087 | 1 | hsa-miR-6781-5p | 185 | hsa-miR-6780b-5p | 184 |
| 30 | 3 | hsa-miR-6087 | 1 | hsa-miR-744-5p | 221 | hsa-miR-4728-5p | 126 |
| 31 | 3 | hsa-miR-6087 | 1 | hsa-miR-744-5p | 221 | hsa-miR-4739 | 129 |
| 32 | 3 | hsa-miR-6087 | 1 | hsa-miR-6724-5p | 166 | hsa-miR-4446-3p | 78 |
| 33 | 3 | hsa-miR-6087 | 1 | hsa-miR-6075 | 148 | hsa-miR-4741 | 131 |
| 34 | 3 | hsa-miR-6087 | 1 | hsa-miR-744-5p | 221 | hsa-miR-4459 | 84 |
| 35 | 3 | hsa-miR-6087 | 1 | hsa-miR-6132 | 153 | hsa-miR-6781-5p | 185 |
| 36 | 3 | hsa-miR-6087 | 1 | hsa-miR-6132 | 153 | hsa-miR-1268b | 14 |
| 37 | 3 | hsa-miR-6087 | 1 | hsa-miR-6781-5p | 185 | hsa-miR-4707-5p | 118 |
| 38 | 3 | hsa-miR-6087 | 1 | hsa-miR-320a | 44 | hsa-miR-4728-5p | 126 |
| 39 | 3 | hsa-miR-6087 | 1 | hsa-miR-4652-5p | 104 | hsa-miR-6800-5p | 193 |
| 40 | 3 | hsa-miR-6087 | 1 | hsa-miR-4652-5p | 104 | hsa-miR-937-5p | 228 |
| 41 | 3 | hsa-miR-6087 | 1 | hsa-miR-663a | 240 | hsa-miR-4728-5p | 126 |
| 42 | 3 | hsa-miR-6087 | 1 | hsa-miR-744-5p | 221 | hsa-miR-5572 | 146 |
| 43 | 3 | hsa-miR-6087 | 1 | hsa-miR-744-5p | 221 | hsa-miR-7113-3p | 219 |
| 44 | 3 | hsa-miR-6087 | 1 | hsa-miR-4436b-5p | 76 | hsa-miR-6724-5p | 166 |
| 45 | 3 | hsa-miR-6087 | 1 | hsa-miR-6724-5p | 166 | hsa-miR-4658 | 107 |
| 46 | 3 | hsa-miR-6087 | 1 | hsa-miR-6724-5p | 166 | hsa-miR-6850-5p | 205 |
| 47 | 3 | hsa-miR-6087 | 1 | hsa-miR-4467 | 87 | hsa-miR-4741 | 131 |
| 48 | 3 | hsa-miR-6087 | 1 | hsa-miR-744-5p | 221 | hsa-miR-345-3p | 48 |
| 49 | 3 | hsa-miR-6087 | 1 | hsa-miR-744-5p | 221 | hsa-miR-4652-5p | 104 |
| 50 | 3 | hsa-miR-6087 | 1 | hsa-miR-744-5p | 221 | hsa-miR-615-5p | 155 |

TABLE 9-2

| No. | Training cohort | | | | Validation cohort | | | |
|---|---|---|---|---|---|---|---|---|
| | Sensitivity | Specificity | Accuracy | AUC | Sensitivity | Specificity | Accuracy | AUC |
| 1 | 0.96 | 0.87 | 0.90 | 0.95 | 0.95 | 0.87 | 0.89 | 0.94 |
| 2 | 0.97 | 0.84 | 0.88 | 0.95 | 0.95 | 0.85 | 0.88 | 0.93 |
| 3 | 0.93 | 0.88 | 0.90 | 0.94 | 0.92 | 0.89 | 0.90 | 0.95 |
| 4 | 0.95 | 0.88 | 0.90 | 0.95 | 0.94 | 0.86 | 0.89 | 0.95 |
| 5 | 0.93 | 0.88 | 0.90 | 0.94 | 0.92 | 0.90 | 0.91 | 0.95 |
| 6 | 0.94 | 0.86 | 0.88 | 0.94 | 0.94 | 0.88 | 0.90 | 0.96 |
| 7 | 0.93 | 0.86 | 0.88 | 0.94 | 0.94 | 0.88 | 0.90 | 0.95 |
| 8 | 0.94 | 0.88 | 0.90 | 0.95 | 0.92 | 0.87 | 0.89 | 0.95 |
| 9 | 0.96 | 0.87 | 0.90 | 0.95 | 0.95 | 0.85 | 0.88 | 0.96 |
| 10 | 0.94 | 0.88 | 0.90 | 0.95 | 0.93 | 0.85 | 0.88 | 0.95 |
| 11 | 0.96 | 0.86 | 0.89 | 0.94 | 0.92 | 0.86 | 0.88 | 0.95 |
| 12 | 0.93 | 0.86 | 0.88 | 0.93 | 0.92 | 0.86 | 0.88 | 0.94 |
| 13 | 0.95 | 0.89 | 0.91 | 0.95 | 0.90 | 0.89 | 0.89 | 0.95 |
| 14 | 0.95 | 0.88 | 0.90 | 0.94 | 0.93 | 0.88 | 0.90 | 0.95 |
| 15 | 0.95 | 0.83 | 0.87 | 0.94 | 0.94 | 0.85 | 0.88 | 0.95 |
| 16 | 0.97 | 0.85 | 0.89 | 0.95 | 0.95 | 0.84 | 0.88 | 0.96 |
| 17 | 0.95 | 0.89 | 0.91 | 0.95 | 0.91 | 0.89 | 0.90 | 0.95 |
| 18 | 0.96 | 0.85 | 0.88 | 0.95 | 0.94 | 0.86 | 0.88 | 0.96 |
| 19 | 0.93 | 0.86 | 0.88 | 0.93 | 0.95 | 0.85 | 0.88 | 0.94 |
| 20 | 0.97 | 0.82 | 0.86 | 0.93 | 0.95 | 0.82 | 0.86 | 0.94 |
| 21 | 0.94 | 0.86 | 0.88 | 0.94 | 0.94 | 0.85 | 0.88 | 0.94 |
| 22 | 0.97 | 0.84 | 0.88 | 0.94 | 0.92 | 0.84 | 0.87 | 0.94 |
| 23 | 0.97 | 0.82 | 0.87 | 0.93 | 0.97 | 0.84 | 0.88 | 0.95 |
| 24 | 0.95 | 0.82 | 0.86 | 0.94 | 0.94 | 0.83 | 0.86 | 0.93 |
| 25 | 0.93 | 0.83 | 0.86 | 0.93 | 0.91 | 0.85 | 0.87 | 0.93 |
| 26 | 0.95 | 0.85 | 0.88 | 0.94 | 0.92 | 0.88 | 0.89 | 0.93 |
| 27 | 0.98 | 0.83 | 0.87 | 0.94 | 0.97 | 0.81 | 0.86 | 0.95 |
| 28 | 0.96 | 0.84 | 0.88 | 0.94 | 0.95 | 0.84 | 0.87 | 0.94 |

TABLE 9-2-continued

| No. | Training cohort | | | | Validation cohort | | | |
|---|---|---|---|---|---|---|---|---|
| | Sensitivity | Specificity | Accuracy | AUC | Sensitivity | Specificity | Accuracy | AUC |
| 29 | 0.96 | 0.86 | 0.89 | 0.94 | 0.92 | 0.86 | 0.88 | 0.95 |
| 30 | 0.95 | 0.85 | 0.88 | 0.94 | 0.95 | 0.87 | 0.90 | 0.94 |
| 31 | 0.97 | 0.81 | 0.86 | 0.94 | 0.95 | 0.81 | 0.85 | 0.94 |
| 32 | 0.95 | 0.84 | 0.87 | 0.93 | 0.93 | 0.84 | 0.87 | 0.93 |
| 33 | 0.97 | 0.86 | 0.89 | 0.95 | 0.96 | 0.84 | 0.88 | 0.95 |
| 34 | 0.94 | 0.86 | 0.88 | 0.94 | 0.94 | 0.86 | 0.88 | 0.94 |
| 35 | 0.95 | 0.89 | 0.90 | 0.95 | 0.90 | 0.90 | 0.90 | 0.94 |
| 36 | 0.96 | 0.85 | 0.88 | 0.94 | 0.94 | 0.87 | 0.89 | 0.95 |
| 37 | 0.92 | 0.86 | 0.88 | 0.94 | 0.92 | 0.87 | 0.88 | 0.95 |
| 38 | 0.95 | 0.84 | 0.87 | 0.93 | 0.95 | 0.86 | 0.89 | 0.95 |
| 39 | 0.96 | 0.86 | 0.89 | 0.94 | 0.92 | 0.88 | 0.89 | 0.94 |
| 40 | 0.95 | 0.88 | 0.90 | 0.94 | 0.92 | 0.91 | 0.91 | 0.95 |
| 41 | 0.95 | 0.82 | 0.86 | 0.93 | 0.97 | 0.84 | 0.88 | 0.93 |
| 42 | 0.95 | 0.83 | 0.87 | 0.94 | 0.92 | 0.85 | 0.87 | 0.93 |
| 43 | 0.95 | 0.83 | 0.87 | 0.94 | 0.92 | 0.85 | 0.87 | 0.94 |
| 44 | 0.95 | 0.86 | 0.88 | 0.94 | 0.94 | 0.86 | 0.88 | 0.95 |
| 45 | 0.96 | 0.86 | 0.89 | 0.95 | 0.92 | 0.86 | 0.88 | 0.95 |
| 46 | 0.95 | 0.86 | 0.88 | 0.94 | 0.92 | 0.87 | 0.88 | 0.95 |
| 47 | 0.92 | 0.88 | 0.89 | 0.95 | 0.91 | 0.88 | 0.89 | 0.94 |
| 48 | 0.93 | 0.84 | 0.87 | 0.94 | 0.91 | 0.85 | 0.87 | 0.93 |
| 49 | 0.94 | 0.88 | 0.90 | 0.95 | 0.90 | 0.90 | 0.90 | 0.95 |
| 50 | 0.90 | 0.87 | 0.88 | 0.94 | 0.89 | 0.88 | 0.88 | 0.94 |

TABLE 9-3

| No. | Number of miRNA | Discriminant formula | Threshold |
|---|---|---|---|
| 1 | 3 | (−1.99429)*hsa-miR-6087 + (1.10184)*hsa-miR-744-5p + (−1.10459)*hsa-miR-4725-3p + 23.8798 | −0.03 |
| 2 | 3 | (−1.95975)*hsa-miR-6087 + (1.16604)*hsa-miR-6132 + (−1.212)*hsa-miR-4725-3p + 23.4404 | −0.10 |
| 3 | 3 | (−2.20223)*hsa-miR-6087 + (0.876146)*hsa-miR-744-5p + (−1.10579)*hsa-miR-1268b + 28.7048 | 0.16 |
| 4 | 3 | (−2.05498)*hsa-miR-6087 + (1.23027)*hsa-miR-6724-5p + (−1.08782)*hsa-miR-3940-5p + 23.2838 | 0.13 |
| 5 | 3 | (−1.71841)*hsa-miR-6087 + (0.254835)*hsa-miR-4652-5p + (−0.351324)*hsa-miR-4728-5p + 21.6521 | 0.03 |
| 6 | 3 | (−2.26328)*hsa-miR-6087 + (0.405936)*hsa-miR-1185-1-3p + (−0.511144)*hsa-miR-4728-5p + 26.9615 | −0.05 |
| 7 | 3 | (−2.25177)*hsa-miR-6087 + (0.333345)*hsa-miR-1185-2-3p + (−0.514305)*hsa-miR-4728-5p + 27.6565 | 0.02 |
| 8 | 3 | (−1.7257)*hsa-miR-6087 + (0.239087)*hsa-miR-4652-5p + (0.927038)*hsa-miR-6724-5p + 9.45011 | 0.00 |
| 9 | 3 | (−2.06705)*hsa-miR-6087 + (1.74117)*hsa-miR-6724-5p + (−1.23589)*hsa-miR-8069 + 20.967 | −0.03 |
| 10 | 3 | (−2.20222)*hsa-miR-6087 + (1.33728)*hsa-miR-6724-5p + (−1.35299)*hsa-miR-6781-5p + 25.0559 | 0.03 |
| 11 | 3 | (−1.94646)*hsa-miR-6087 + (0.229418)*hsa-miR-4652-5p + (−0.851585)*hsa-miR-6781-5p + 30.2559 | −0.08 |
| 12 | 3 | (−2.10541)*hsa-miR-6087 + (−1.00455)*hsa-miR-6784-5p + (−0.533517)*hsa-miR-4728-5p + 40.1399 | 0.04 |
| 13 | 3 | (−2.41529)*hsa-miR-6087 + (0.747096)*hsa-miR-744-5p + (−1.13803)*hsa-miR-6781-5p + 32.8928 | 0.24 |
| 14 | 3 | (−1.90118)*hsa-miR-6087 + (0.273655)*hsa-miR-4652-5p + (−0.493469)*hsa-miR-6794-5p + 25.3093 | 0.09 |
| 15 | 3 | (−2.46815)*hsa-miR-6087 + (0.272974)*hsa-miR-1185-1-3p + (−0.980892)*hsa-miR-6781-5p + 36.422 | −0.07 |
| 16 | 3 | (−2.08205)*hsa-miR-6087 + (1.39686)*hsa-miR-6724-5p + (−1.02557)*hsa-miR-3621 + 21.4656 | −0.04 |
| 17 | 3 | (−2.16206)*hsa-miR-6087 + (−1.4256)*hsa-miR-6781-5p + (0.918977)*hsa-miR-6075 + 31.2971 | 0.14 |
| 18 | 3 | (−2.24404)*hsa-miR-6087 + (0.312892)*hsa-miR-1185-1-3p + (1.06503)*hsa-miR-6724-5p + 12.5539 | −0.06 |
| 19 | 3 | (−2.18147)*hsa-miR-6087 + (0.606087)*hsa-miR-6789-5p + (−1.12732)*hsa-miR-3940-5p + 32.1707 | 0.13 |
| 20 | 3 | (−1.83371)*hsa-miR-6087 + (0.213355)*hsa-miR-3160-5p + (−0.448532)*hsa-miR-4728-5p + 23.2149 | −0.22 |
| 21 | 3 | (−2.31805)*hsa-miR-6087 + (−1.46265)*hsa-miR-6781-5p + (0.800432)*hsa-miR-4492 + 33.0483 | 0.04 |
| 22 | 3 | (−2.50024)*hsa-miR-6087 + (−1.25889)*hsa-miR-6781-5p + (0.793953)*hsa-miR-4327 + 34.4615 | −0.08 |
| 23 | 3 | (−2.29625)*hsa-miR-6087 + (0.983807)*hsa-miR-4327 + (−1.19416)*hsa-miR-1268b + 29.4518 | −0.11 |
| 24 | 3 | (−2.30569)*hsa-miR-6087 + (0.839797)*hsa-miR-744-5p + (−0.188923)*hsa-miR-3679-5p + 21.0264 | −0.04 |
| 25 | 3 | (−2.19577)*hsa-miR-6087 + (0.808307)*hsa-miR-6132 + (−0.748748)*hsa-miR-4739 + 26.7689 | 0.01 |
| 26 | 3 | (−2.26014)*hsa-miR-6087 + (0.766578)*hsa-miR-744-5p + (−0.758695)*hsa-miR-6765-5p + 27.5472 | 0.11 |
| 27 | 3 | (−2.10725)*hsa-miR-6087 + (−0.819804)*hsa-miR-6784-5p + (1.1845)*hsa-miR-6724-5p + 21.6589 | −0.16 |

TABLE 9-3-continued

| No. | Number of miRNA | Discriminant formula | Threshold |
|---|---|---|---|
| 28 | 3 | (−2.25504)*hsa-miR-6087 + (1.18918)*hsa-miR-744-5p + (−0.677675)*hsa-miR-4505 + 22.5733 | −0.09 |
| 29 | 3 | (−2.39575)*hsa-miR-6087 + (−1.29)*hsa-miR-6781-5p + (0.857779)*hsa-miR-6780b-5p + 31.9168 | −0.01 |
| 30 | 3 | (−2.21584)*hsa-miR-6087 + (0.73478)*hsa-miR-744-5p + (−0.342334)*hsa-miR-4728-5p + 21.995 | −0.02 |
| 31 | 3 | (−2.21866)*hsa-miR-6087 + (0.799549)*hsa-miR-744-5p + (−0.618661)*hsa-miR-4739 + 25.9626 | −0.19 |
| 32 | 3 | (−2.12377)*hsa-miR-6087 + (1.19662)*hsa-miR-6724-5p + (−0.281989)*hsa-miR-4446-3p + 14.4302 | 0.05 |
| 33 | 3 | (−2.06861)*hsa-miR-6087 + (1.22127)*hsa-miR-6075 + (−1.5794)*hsa-miR-4741 + 28.0564 | −0.06 |
| 34 | 3 | (−2.32205)*hsa-miR-6087 + (0.932446)*hsa-miR-744-5p + (−0.658096)*hsa-miR-4459 + 25.0285 | 0.02 |
| 35 | 3 | (−2.42163)*hsa-miR-6087 + (0.767833)*hsa-miR-6132 + (−1.24265)*hsa-miR-6781-5p + 33.5051 | 0.26 |
| 36 | 3 | (−2.18388)*hsa-miR-6087 + (0.920148)*hsa-miR-6132 + (−1.25728)*hsa-miR-1268b + 29.1879 | 0.01 |
| 37 | 3 | (−2.37789)*hsa-miR-6087 + (−1.34381)*hsa-miR-6781-5p + (0.71287)*hsa-miR-4707-5p + 35.2893 | 0.09 |
| 38 | 3 | (−2.06926)*hsa-miR-6087 + (0.416135)*hsa-miR-320a + (−0.505606)*hsa-miR-4728-5p + 25.2014 | −0.05 |
| 39 | 3 | (−1.89615)*hsa-miR-6087 + (0.25591)*hsa-miR-4652-5p + (−0.317328)*hsa-miR-6800-5p + 23.6953 | 0.07 |
| 40 | 3 | (−1.91797)*hsa-miR-6087 + (0.261947)*hsa-miR-4652-5p + (−0.401191)*hsa-miR-937-5p + 24.7457 | 0.18 |
| 41 | 3 | (−2.17785)*hsa-miR-6087 + (0.582019)*hsa-miR-663a + (−0.406427)*hsa-miR-4728-5p + 21.5351 | −0.16 |
| 42 | 3 | (−2.23659)*hsa-miR-6087 + (0.742371)*hsa-miR-744-5p + (0.122665)*hsa-miR-5572 + 18.9306 | −0.06 |
| 43 | 3 | (−2.30309)*hsa-miR-6087 + (0.760621)*hsa-miR-744-5p + (0.206772)*hsa-miR-7113-3p + 19.0906 | −0.09 |
| 44 | 3 | (−2.00392)*hsa-miR-6087 + (0.335315)*hsa-miR-4436b-5p + (1.0084)*hsa-miR-6724-5p + 10.8971 | 0.10 |
| 45 | 3 | (−1.90126)*hsa-miR-6087 + (1.00918)*hsa-miR-6724-5p + (0.198648)*hsa-miR-4658 + 10.807 | 0.04 |
| 46 | 3 | (−2.1512)*hsa-miR-6087 + (1.72053)*hsa-miR-6724-5p + (−1.06042)*hsa-miR-6850-5p + 18.9069 | 0.06 |
| 47 | 3 | (−2.26287)*hsa-miR-6087 + (1.4033)*hsa-miR-4467 + (−1.81767)*hsa-miR-4741 + 28.6016 | 0.21 |
| 48 | 3 | (−2.27347)*hsa-miR-6087 + (0.769294)*hsa-miR-744-5p + (0.11717)*hsa-miR-345-3p + 19.2282 | −0.02 |
| 49 | 3 | (−1.94211)*hsa-miR-6087 + (0.532517)*hsa-miR-744-5p + (0.207835)*hsa-miR-4652-5p + 17.1632 | 0.07 |
| 50 | 3 | (−2.17617)*hsa-miR-6087 + (0.709611)*hsa-miR-744-5p + (0.226255)*hsa-miR-615-5p + 17.8108 | 0.15 |

TABLE 10-1

| No. | Number of miRNA | miRNA marker 1 | SEQ ID NO | miRNA marker 2 | SEQ ID NO | miRNA marker 3 | SEQ ID NO | miRNA marker 4 | SEQ ID NO |
|---|---|---|---|---|---|---|---|---|---|
| 1 | 4 | hsa-miR-6087 | 1 | hsa-miR-1185-1-3p | 2 | hsa-miR-4728-5p | 126 | hsa-miR-6802-5p | 194 |
| 2 | 4 | hsa-miR-6087 | 1 | hsa-miR-4652-5p | 104 | hsa-miR-4728-5p | 126 | hsa-miR-6819-5p | 198 |
| 3 | 4 | hsa-miR-6087 | 1 | hsa-miR-1185-1-3p | 2 | hsa-miR-4728-5p | 126 | hsa-miR-3648 | 54 |
| 4 | 4 | hsa-miR-6087 | 1 | hsa-miR-1185-1-3p | 2 | hsa-miR-4728-5p | 126 | hsa-miR-6075 | 148 |
| 5 | 4 | hsa-miR-6087 | 1 | hsa-miR-1185-2-3p | 3 | hsa-miR-4728-5p | 126 | hsa-miR-6802-5p | 194 |
| 6 | 4 | hsa-miR-6087 | 1 | hsa-miR-1185-1-3p | 2 | hsa-miR-4728-5p | 126 | hsa-miR-3160-5p | 35 |
| 7 | 4 | hsa-miR-6087 | 1 | hsa-miR-744-5p | 221 | hsa-miR-4725-3p | 123 | hsa-miR-4726-5p | 124 |
| 8 | 4 | hsa-miR-6087 | 1 | hsa-miR-1185-1-3p | 2 | hsa-miR-4728-5p | 126 | hsa-miR-4706 | 116 |
| 9 | 4 | hsa-miR-6087 | 1 | hsa-miR-1185-2-3p | 3 | hsa-miR-4728-5p | 126 | hsa-miR-3160-5p | 35 |
| 10 | 4 | hsa-miR-6087 | 1 | hsa-miR-744-5p | 221 | hsa-miR-4725-3p | 123 | hsa-miR-7113-3p | 219 |

TABLE 10-1-continued

| No. | Number of miRNA | miRNA marker 1 | SEQ ID NO | miRNA marker 2 | SEQ ID NO | miRNA marker 3 | SEQ ID NO | miRNA marker 4 | SEQ ID NO |
|---|---|---|---|---|---|---|---|---|---|
| 11 | 4 | hsa-miR-6087 | 1 | hsa-miR-1185-1-3p | 2 | hsa-miR-4728-5p | 126 | hsa-miR-6787-5p | 189 |
| 12 | 4 | hsa-miR-6087 | 1 | hsa-miR-744-5p | 221 | hsa-miR-4725-3p | 123 | hsa-miR-6717-5p | 164 |
| 13 | 4 | hsa-miR-6087 | 1 | hsa-miR-744-5p | 221 | hsa-miR-4725-3p | 123 | hsa-miR-4485-5p | 91 |
| 14 | 4 | hsa-miR-6087 | 1 | hsa-miR-744-5p | 221 | hsa-miR-4725-3p | 123 | hsa-miR-1343-5p | 18 |
| 15 | 4 | hsa-miR-6087 | 1 | hsa-miR-6724-5p | 166 | hsa-miR-6781-5p | 185 | hsa-miR-4727-3p | 125 |
| 16 | 4 | hsa-miR-6087 | 1 | hsa-miR-744-5p | 221 | hsa-miR-4725-3p | 123 | hsa-miR-4652-5p | 104 |
| 17 | 4 | hsa-miR-6087 | 1 | hsa-miR-744-5p | 221 | hsa-miR-4725-3p | 123 | hsa-miR-4449 | 81 |
| 18 | 4 | hsa-miR-6087 | 1 | hsa-miR-744-5p | 221 | hsa-miR-4725-3p | 123 | hsa-miR-1185-2-3p | 3 |
| 19 | 4 | hsa-miR-6087 | 1 | hsa-miR-1185-1-3p | 2 | hsa-miR-4728-5p | 126 | hsa-miR-1273g-3p | 15 |
| 20 | 4 | hsa-miR-6087 | 1 | hsa-miR-6784-5p | 187 | hsa-miR-4728-5p | 126 | hsa-miR-6802-5p | 194 |
| 21 | 4 | hsa-miR-6087 | 1 | hsa-miR-4652-5p | 104 | hsa-miR-6794-5p | 192 | hsa-miR-6802-5p | 194 |
| 22 | 4 | hsa-miR-6087 | 1 | hsa-miR-744-5p | 221 | hsa-miR-4725-3p | 123 | hsa-miR-345-3p | 48 |
| 23 | 4 | hsa-miR-6087 | 1 | hsa-miR-744-5p | 221 | hsa-miR-4725-3p | 123 | hsa-miR-5010-5p | 142 |
| 24 | 4 | hsa-miR-6087 | 1 | hsa-miR-744-5p | 221 | hsa-miR-4725-3p | 123 | hsa-miR-5572 | 146 |
| 25 | 4 | hsa-miR-6087 | 1 | hsa-miR-744-5p | 221 | hsa-miR-4725-3p | 123 | hsa-miR-371b-5p | 59 |
| 26 | 4 | hsa-miR-6087 | 1 | hsa-miR-744-5p | 221 | hsa-miR-4725-3p | 123 | hsa-miR-4419b | 72 |
| 27 | 4 | hsa-miR-6087 | 1 | hsa-miR-744-5p | 221 | hsa-miR-4725-3p | 123 | hsa-miR-191-5p | 238 |
| 28 | 4 | hsa-miR-6087 | 1 | hsa-miR-6132 | 153 | hsa-miR-4725-3p | 123 | hsa-miR-4652-5p | 104 |
| 29 | 4 | hsa-miR-6087 | 1 | hsa-miR-744-5p | 221 | hsa-miR-4725-3p | 123 | hsa-miR-7108-3p | 216 |
| 30 | 4 | hsa-miR-6087 | 1 | hsa-miR-1185-1-3p | 2 | hsa-miR-4728-5p | 126 | hsa-miR-1228-3p | 8 |
| 31 | 4 | hsa-miR-6087 | 1 | hsa-miR-744-5p | 221 | hsa-miR-4725-3p | 123 | hsa-miR-3616-3p | 49 |
| 32 | 4 | hsa-miR-6087 | 1 | hsa-miR-744-5p | 221 | hsa-miR-4725-3p | 123 | hsa-miR-4462 | 85 |
| 33 | 4 | hsa-miR-6087 | 1 | hsa-miR-744-5p | 221 | hsa-miR-4725-3p | 123 | hsa-miR-8052 | 224 |
| 34 | 4 | hsa-miR-6087 | 1 | hsa-miR-744-5p | 221 | hsa-miR-4725-3p | 123 | hsa-miR-7975 | 222 |
| 35 | 4 | hsa-miR-6087 | 1 | hsa-miR-744-5p | 221 | hsa-miR-4725-3p | 123 | hsa-miR-3622a-5p | 53 |
| 36 | 4 | hsa-miR-6087 | 1 | hsa-miR-744-5p | 221 | hsa-miR-4725-3p | 123 | hsa-miR-6870-5p | 208 |
| 37 | 4 | hsa-miR-6087 | 1 | hsa-miR-744-5p | 221 | hsa-miR-4725-3p | 123 | hsa-miR-4731-5p | 127 |
| 38 | 4 | hsa-miR-6087 | 1 | hsa-miR-744-5p | 221 | hsa-miR-4725-3p | 123 | hsa-miR-4690-5p | 113 |
| 39 | 4 | hsa-miR-6087 | 1 | hsa-miR-744-5p | 221 | hsa-miR-4725-3p | 123 | hsa-miR-3178 | 37 |
| 40 | 4 | hsa-miR-6087 | 1 | hsa-miR-744-5p | 221 | hsa-miR-4725-3p | 123 | hsa-miR-6716-5p | 163 |
| 41 | 4 | hsa-miR-6087 | 1 | hsa-miR-744-5p | 221 | hsa-miR-4725-3p | 123 | hsa-miR-6842-5p | 204 |
| 42 | 4 | hsa-miR-6087 | 1 | hsa-miR-744-5p | 221 | hsa-miR-4725-3p | 123 | hsa-miR-4430 | 74 |
| 43 | 4 | hsa-miR-6087 | 1 | hsa-miR-744-5p | 221 | hsa-miR-4725-3p | 123 | hsa-miR-6742-5p | 170 |
| 44 | 4 | hsa-miR-6087 | 1 | hsa-miR-1185-1-3p | 2 | hsa-miR-4728-5p | 126 | hsa-miR-8073 | 226 |
| 45 | 4 | hsa-miR-6087 | 1 | hsa-miR-1185-1-3p | 2 | hsa-miR-4728-5p | 126 | hsa-miR-3194-3p | 41 |
| 46 | 4 | hsa-miR-6087 | 1 | hsa-miR-1185-2-3p | 3 | hsa-miR-4728-5p | 126 | hsa-miR-4436b-5p | 76 |
| 47 | 4 | hsa-miR-6087 | 1 | hsa-miR-6724-5p | 166 | hsa-miR-8069 | 225 | hsa-miR-4488 | 92 |
| 48 | 4 | hsa-miR-6087 | 1 | hsa-miR-744-5p | 221 | hsa-miR-4725-3p | 123 | hsa-miR-5008-5p | 141 |

TABLE 10-1-continued

| No. | Number of miRNA | miRNA marker 1 | SEQ ID NO | miRNA marker 2 | SEQ ID NO | miRNA marker 3 | SEQ ID NO | miRNA marker 4 | SEQ ID NO |
|---|---|---|---|---|---|---|---|---|---|
| 49 | 4 | hsa-miR-6087 | 1 | hsa-miR-744-5p | 221 | hsa-miR-4725-3p | 123 | hsa-miR-1268a | 13 |
| 50 | 4 | hsa-miR-6087 | 1 | hsa-miR-6784-5p | 187 | hsa-miR-4728-5p | 126 | hsa-miR-6819-5p | 198 |

TABLE 10-2

| | Training cohort | | | | Validation cohort | | | |
|---|---|---|---|---|---|---|---|---|
| No. | Sensitivity | Specificity | Accuracy | AUC | Sensitivity | Specificity | Accuracy | AUC |
| 1 | 0.96 | 0.87 | 0.90 | 0.95 | 0.95 | 0.88 | 0.91 | 0.96 |
| 2 | 0.92 | 0.92 | 0.92 | 0.95 | 0.89 | 0.94 | 0.92 | 0.96 |
| 3 | 0.95 | 0.86 | 0.89 | 0.95 | 0.93 | 0.90 | 0.91 | 0.96 |
| 4 | 0.98 | 0.84 | 0.88 | 0.95 | 0.94 | 0.85 | 0.88 | 0.96 |
| 5 | 0.97 | 0.86 | 0.89 | 0.95 | 0.96 | 0.88 | 0.91 | 0.96 |
| 6 | 0.94 | 0.89 | 0.91 | 0.95 | 0.94 | 0.91 | 0.92 | 0.96 |
| 7 | 0.92 | 0.90 | 0.91 | 0.95 | 0.91 | 0.92 | 0.91 | 0.94 |
| 8 | 0.94 | 0.88 | 0.90 | 0.95 | 0.92 | 0.91 | 0.92 | 0.96 |
| 9 | 0.94 | 0.89 | 0.90 | 0.95 | 0.93 | 0.91 | 0.92 | 0.96 |
| 10 | 0.95 | 0.89 | 0.91 | 0.95 | 0.95 | 0.89 | 0.91 | 0.94 |
| 11 | 0.98 | 0.84 | 0.88 | 0.95 | 0.96 | 0.86 | 0.89 | 0.96 |
| 12 | 0.97 | 0.88 | 0.91 | 0.95 | 0.95 | 0.88 | 0.90 | 0.95 |
| 13 | 0.93 | 0.90 | 0.91 | 0.95 | 0.92 | 0.91 | 0.91 | 0.94 |
| 14 | 0.95 | 0.90 | 0.91 | 0.95 | 0.93 | 0.89 | 0.90 | 0.94 |
| 15 | 0.97 | 0.88 | 0.91 | 0.95 | 0.93 | 0.87 | 0.89 | 0.96 |
| 16 | 0.94 | 0.92 | 0.93 | 0.95 | 0.94 | 0.92 | 0.93 | 0.95 |
| 17 | 0.95 | 0.88 | 0.90 | 0.95 | 0.94 | 0.87 | 0.89 | 0.94 |
| 18 | 0.93 | 0.90 | 0.91 | 0.96 | 0.92 | 0.91 | 0.92 | 0.95 |
| 19 | 0.96 | 0.87 | 0.90 | 0.95 | 0.92 | 0.88 | 0.89 | 0.96 |
| 20 | 0.97 | 0.84 | 0.88 | 0.94 | 0.97 | 0.84 | 0.88 | 0.95 |
| 21 | 0.96 | 0.89 | 0.91 | 0.95 | 0.94 | 0.88 | 0.90 | 0.96 |
| 22 | 0.95 | 0.88 | 0.90 | 0.95 | 0.94 | 0.89 | 0.91 | 0.94 |
| 23 | 0.96 | 0.87 | 0.90 | 0.95 | 0.95 | 0.87 | 0.89 | 0.94 |
| 24 | 0.95 | 0.88 | 0.90 | 0.95 | 0.94 | 0.89 | 0.90 | 0.94 |
| 25 | 0.93 | 0.90 | 0.91 | 0.95 | 0.91 | 0.91 | 0.91 | 0.94 |
| 26 | 0.94 | 0.89 | 0.91 | 0.95 | 0.92 | 0.89 | 0.90 | 0.94 |
| 27 | 0.95 | 0.88 | 0.90 | 0.95 | 0.94 | 0.89 | 0.90 | 0.94 |
| 28 | 0.95 | 0.91 | 0.92 | 0.96 | 0.92 | 0.90 | 0.91 | 0.95 |
| 29 | 0.96 | 0.87 | 0.90 | 0.95 | 0.95 | 0.87 | 0.89 | 0.94 |
| 30 | 0.93 | 0.88 | 0.89 | 0.94 | 0.92 | 0.90 | 0.91 | 0.96 |
| 31 | 0.94 | 0.89 | 0.91 | 0.95 | 0.93 | 0.90 | 0.91 | 0.94 |
| 32 | 0.94 | 0.89 | 0.91 | 0.95 | 0.93 | 0.90 | 0.91 | 0.94 |
| 33 | 0.96 | 0.87 | 0.90 | 0.95 | 0.95 | 0.86 | 0.89 | 0.94 |
| 34 | 0.94 | 0.89 | 0.91 | 0.95 | 0.92 | 0.89 | 0.90 | 0.94 |
| 35 | 0.93 | 0.90 | 0.91 | 0.95 | 0.92 | 0.90 | 0.91 | 0.94 |
| 36 | 0.93 | 0.89 | 0.90 | 0.95 | 0.92 | 0.90 | 0.91 | 0.94 |
| 37 | 0.95 | 0.88 | 0.90 | 0.95 | 0.95 | 0.88 | 0.90 | 0.94 |
| 38 | 0.96 | 0.87 | 0.90 | 0.95 | 0.95 | 0.87 | 0.89 | 0.94 |
| 39 | 0.93 | 0.90 | 0.91 | 0.95 | 0.92 | 0.90 | 0.90 | 0.94 |
| 40 | 0.94 | 0.89 | 0.91 | 0.95 | 0.92 | 0.90 | 0.91 | 0.94 |
| 41 | 0.94 | 0.89 | 0.91 | 0.95 | 0.92 | 0.90 | 0.91 | 0.94 |
| 42 | 0.93 | 0.89 | 0.91 | 0.95 | 0.92 | 0.90 | 0.91 | 0.94 |
| 43 | 0.93 | 0.90 | 0.91 | 0.95 | 0.92 | 0.91 | 0.91 | 0.95 |
| 44 | 0.98 | 0.85 | 0.89 | 0.95 | 0.95 | 0.87 | 0.89 | 0.97 |
| 45 | 0.95 | 0.86 | 0.89 | 0.95 | 0.95 | 0.88 | 0.91 | 0.96 |
| 46 | 0.94 | 0.90 | 0.91 | 0.96 | 0.95 | 0.89 | 0.91 | 0.96 |
| 47 | 0.92 | 0.91 | 0.91 | 0.95 | 0.90 | 0.93 | 0.92 | 0.96 |
| 48 | 0.93 | 0.90 | 0.91 | 0.95 | 0.92 | 0.90 | 0.91 | 0.94 |
| 49 | 0.97 | 0.89 | 0.91 | 0.95 | 0.95 | 0.89 | 0.91 | 0.95 |
| 50 | 0.93 | 0.89 | 0.90 | 0.95 | 0.92 | 0.91 | 0.91 | 0.95 |

TABLE 10-3

| No. | Number of miRNA | Discriminant formula | Threshold |
|---|---|---|---|
| 1 | 4 | (−2.0149)*hsa-miR-6087 + (0.323769)*hsa-miR-1185-1-3p + (−0.67387)*hsa-miR-4728-5p + (0.794577)*hsa-miR-6802-5p + 18.5481 | −0.18 |
| 2 | 4 | (−1.40552)*hsa-miR-6087 + (0.197504)*hsa-miR-4652-5p + (−0.649251)*hsa-miR-4728-5p + (0.783379)*hsa-miR-6819-5p + 13.919 | 0.17 |
| 3 | 4 | (−2.1643)*hsa-miR-6087 + (0.390224)*hsa-miR-1185-1-3p + (−0.466874)*hsa-miR-4728-5p + (0.472791)*hsa-miR-3648 + 19.374 | −0.06 |
| 4 | 4 | (−2.11818)*hsa-miR-6087 + (0.349681)*hsa-miR-1185-1-3p + (−0.463979)*hsa-miR-4728-5p + (0.520867)*hsa-miR-6075 + 20.7509 | −0.25 |
| 5 | 4 | (−2.00356)*hsa-miR-6087 + (0.258483)*hsa-miR-1185-2-3p + (−0.672779)*hsa-miR-4728-5p + (0.790807)*hsa-miR-6802-5p + 19.1448 | −0.15 |
| 6 | 4 | (−1.96362)*hsa-miR-6087 + (0.358349)*hsa-miR-1185-1-3p + (−0.535871)*hsa-miR-4728-5p + (0.179607)*hsa-miR-3160-5p + 22.5849 | 0.04 |
| 7 | 4 | (−1.95533)*hsa-miR-6087 + (1.10331)*hsa-miR-744-5p + (−1.0978)*hsa-miR-4725-3p + (0.128777)*hsa-miR-4726-5p + 22.4395 | 0.29 |
| 8 | 4 | (−2.10911)*hsa-miR-6087 + (0.376593)*hsa-miR-1185-1-3p + (−0.566764)*hsa-miR-4728-5p + (0.372519)*hsa-miR-4706 + 22.6335 | 0.06 |
| 9 | 4 | (−1.93996)*hsa-miR-6087 + (0.302274)*hsa-miR-1185-2-3p + (−0.543072)*hsa-miR-4728-5p + (0.188689)*hsa-miR-3160-5p + 22.935 | 0.08 |
| 10 | 4 | (−1.98851)*hsa-miR-6087 + (1.07518)*hsa-miR-744-5p + (−1.04895)*hsa-miR-4725-3p + (0.172295)*hsa-miR-7113-3p + 22.5015 | 0.09 |
| 11 | 4 | (−2.11179)*hsa-miR-6087 + (0.457627)*hsa-miR-1185-1-3p + (−0.655672)*hsa-miR-4728-5p + (0.463185)*hsa-miR-6787-5p + 21.4526 | −0.27 |
| 12 | 4 | (−1.84615)*hsa-miR-6087 + (1.03905)*hsa-miR-744-5p + (−1.15205)*hsa-miR-4725-3p + (0.158937)*hsa-miR-6717-5p + 21.9096 | −0.04 |

TABLE 10-3-continued

| No. | Number of miRNA | Discriminant formula | Threshold |
|---|---|---|---|
| 13 | 4 | (−1.96137)*hsa-miR-6087 + (1.08997)*hsa-miR-744-5p + (−1.13739)*hsa-miR-4725-3p + (0.152475)*hsa-miR-4485-5p + 22.9711 | 0.18 |
| 14 | 4 | (−2.06413)*hsa-miR-6087 + (1.08096)*hsa-miR-744-5p + (−1.02828)*hsa-miR-4725-3p + (−0.583887)*hsa-miR-1343-5p + 29.9398 | 0.19 |
| 15 | 4 | (−2.05106)*hsa-miR-6087 + (1.29598)*hsa-miR-6724-5p + (−1.23117)*hsa-miR-6781-5p + (0.18212)*hsa-miR-4727-3p + 21.4087 | −0.03 |
| 16 | 4 | (−1.72137)*hsa-miR-6087 + (0.842266)*hsa-miR-744-5p + (−0.925472)*hsa-miR-4725-3p + (0.182057)*hsa-miR-4652-5p + 20.4898 | 0.19 |
| 17 | 4 | (−1.96551)*hsa-miR-6087 + (1.09951)*hsa-miR-744-5p + (−1.1063)*hsa-miR-4725-3p + (0.111752)*hsa-miR-4449 + 22.8233 | 0.03 |
| 18 | 4 | (−2.0773)*hsa-miR-6087 + (0.992603)*hsa-miR-744-5p + (−1.0199)*hsa-miR-4725-3p + (0.164433)*hsa-miR-1185-2-3p + 23.7506 | 0.18 |
| 19 | 4 | (−2.15523)*hsa-miR-6087 + (0.385474)*hsa-miR-1185-1-3p + (−0.580318)*hsa-miR-4728-5p + (0.252073)*hsa-miR-1273g-3p + 24.2168 | −0.04 |
| 20 | 4 | (−1.93441)*hsa-miR-6087 + (−0.645629)*hsa-miR-6784-5p + (−0.641236)*hsa-miR-4728-5p + (0.665862)*hsa-miR-6802-5p + 28.6551 | −0.20 |
| 21 | 4 | (−1.90895)*hsa-miR-6087 + (0.224641)*hsa-miR-4652-5p + (−0.861494)*hsa-miR-6794-5p + (0.776175)*hsa-miR-6802-5p + 21.5158 | 0.02 |
| 22 | 4 | (−1.92887)*hsa-miR-6087 + (1.0991)*hsa-miR-744-5p + (−1.11187)*hsa-miR-4725-3p + (0.121799)*hsa-miR-345-3p + 22.4989 | 0.05 |
| 23 | 4 | (−1.97061)*hsa-miR-6087 + (1.08863)*hsa-miR-744-5p + (−1.10606)*hsa-miR-4725-3p + (0.0346128)*hsa-miR-5010-5p + 23.5291 | −0.05 |
| 24 | 4 | (−1.90062)*hsa-miR-6087 + (1.06991)*hsa-miR-744-5p + (−1.1006)*hsa-miR-4725-3p + (0.118253)*hsa-miR-5572 + 22.2737 | 0.01 |
| 25 | 4 | (−1.905)*hsa-miR-6087 + (1.05114)*hsa-miR-744-5p + (−1.07868)*hsa-miR-4725-3p + (0.129274)*hsa-miR-371b-5p + 22.3343 | 0.19 |
| 26 | 4 | (−1.9188)*hsa-miR-6087 + (1.09374)*hsa-miR-744-5p + (−1.1391)*hsa-miR-4725-3p + (0.115326)*hsa-miR-4419b + 22.5689 | 0.15 |
| 27 | 4 | (−1.94067)*hsa-miR-6087 + (1.06815)*hsa-miR-744-5p + (−1.13252)*hsa-miR-4725-3p + (0.061833)*hsa-miR-191-5p + 23.4299 | 0.11 |
| 28 | 4 | (−1.66398)*hsa-miR-6087 + (0.90838)*hsa-miR-6132 + (−1.02495)*hsa-miR-4725-3p + (0.196746)*hsa-miR-4652-5p + 19.7201 | 0.07 |
| 29 | 4 | (−1.98976)*hsa-miR-6087 + (1.12912)*hsa-miR-744-5p + (−1.07893)*hsa-miR-4725-3p + (−0.120496)*hsa-miR-7108-3p + 24.0674 | −0.01 |
| 30 | 4 | (−2.23129)*hsa-miR-6087 + (0.375189)*hsa-miR-1185-1-3p + (−0.539722)*hsa-miR-4728-5p + (0.205572)*hsa-miR-1228-3p + 25.6132 | 0.05 |
| 31 | 4 | (−1.96604)*hsa-miR-6087 + (1.0816)*hsa-miR-744-5p + (−1.09015)*hsa-miR-4725-3p + (0.0752526)*hsa-miR-3616-3p + 23.1811 | 0.16 |
| 32 | 4 | (−1.87322)*hsa-miR-6087 + (1.10377)*hsa-miR-744-5p + (−1.12827)*hsa-miR-4725-3p + (0.106985)*hsa-miR-4462 + 22.063 | 0.12 |
| 33 | 4 | (−1.95782)*hsa-miR-6087 + (1.09779)*hsa-miR-744-5p + (−1.11868)*hsa-miR-4725-3p + (0.0622539)*hsa-miR-8052 + 23.2555 | −0.03 |
| 34 | 4 | (−1.95102)*hsa-miR-6087 + (1.07133)*hsa-miR-744-5p + (−1.13485)*hsa-miR-4725-3p + (0.0958191)*hsa-miR-7975 + 23.0654 | 0.16 |
| 35 | 4 | (−1.9509)*hsa-miR-6087 + (1.09922)*hsa-miR-744-5p + (−1.10474)*hsa-miR-4725-3p + (0.0526832)*hsa-miR-3622a-5p + 23.063 | 0.22 |
| 36 | 4 | (−1.96398)*hsa-miR-6087 + (1.13043)*hsa-miR-744-5p + (−1.15968)*hsa-miR-4725-3p + (0.112344)*hsa-miR-6870-5p + 22.9913 | 0.18 |
| 37 | 4 | (−1.99762)*hsa-miR-6087 + (1.08842)*hsa-miR-744-5p + (−1.0774)*hsa-miR-4725-3p + (0.0998503)*hsa-miR-4731-5p + 23.1902 | 0.00 |
| 38 | 4 | (−1.98872)*hsa-miR-6087 + (1.07852)*hsa-miR-744-5p + (−1.09525)*hsa-miR-4725-3p + (0.07478)*hsa-miR-4690-5p + 23.4267 | −0.04 |
| 39 | 4 | (−2.01272)*hsa-miR-6087 + (1.10487)*hsa-miR-744-5p + (−1.06224)*hsa-miR-4725-3p + (−0.147672)*hsa-miR-3178 + 25.4006 | 0.23 |
| 40 | 4 | (−1.99883)*hsa-miR-6087 + (1.11898)*hsa-miR-744-5p + (−1.09769)*hsa-miR-4725-3p + (0.053479)*hsa-miR-6716-5p + 23.3919 | 0.17 |
| 41 | 4 | (−1.95042)*hsa-miR-6087 + (1.11027)*hsa-miR-744-5p + (−1.10857)*hsa-miR-4725-3p + (0.0671621)*hsa-miR-6842-5p + 22.9281 | 0.15 |
| 42 | 4 | (−1.95428)*hsa-miR-6087 + (1.07352)*hsa-miR-744-5p + (−1.10378)*hsa-miR-4725-3p + (0.0861418)*hsa-miR-4430 + 23.0763 | 0.16 |
| 43 | 4 | (−1.98382)*hsa-miR-6087 + (1.11616)*hsa-miR-744-5p + (−1.03253)*hsa-miR-4725-3p + (0.100572)*hsa-miR-6742-5p + 22.4181 | 0.20 |
| 44 | 4 | (−2.00783)*hsa-miR-6087 + (0.364586)*hsa-miR-1185-1-3p + (−0.551076)*hsa-miR-4728-5p + (0.363576)*hsa-miR-8073 + 21.6081 | −0.20 |
| 45 | 4 | (−2.03251)*hsa-miR-6087 + (0.362574)*hsa-miR-1185-1-3p + (−0.50181)*hsa-miR-4728-5p + (0.162155)*hsa-miR-3194-3p + 23.1964 | −0.13 |
| 46 | 4 | (−2.03272)*hsa-miR-6087 + (0.263552)*hsa-miR-1185-2-3p + (−0.583117)*hsa-miR-4728-5p + (0.376584)*hsa-miR-4436b-5p + 23.77 | 0.01 |
| 47 | 4 | (−2.31168)*hsa-miR-6087 + (1.65372)*hsa-miR-6724-5p + (−1.45426)*hsa-miR-8069 + (0.6299)*hsa-miR-4488 + 19.1417 | 0.42 |
| 48 | 4 | (−1.96801)*hsa-miR-6087 + (1.09607)*hsa-miR-744-5p + (−1.10798)*hsa-miR-4725-3p + (0.102001)*hsa-miR-5008-5p + 23 | 0.19 |
| 49 | 4 | (−1.98495)*hsa-miR-6087 + (1.15587)*hsa-miR-744-5p + (−0.964683)*hsa-miR-4725-3p + (−0.701227)*hsa-miR-1268a + 29.4282 | 0.08 |
| 50 | 4 | (−1.61855)*hsa-miR-6087 + (−0.771761)*hsa-miR-6784-5p + (−0.84099)*hsa-miR-4728-5p + (0.929218)*hsa-miR-6819-5p + 26.3069 | 0.02 |

TABLE 11-1

| No. | Number of miRNA | miRNA marker 1 | SEQ ID NO | miRNA marker 2 | SEQ ID NO | miRNA marker 3 | SEQ ID NO | miRNA marker 4 | SEQ ID NO | miRNA marker 5 | SEQ ID NO |
|---|---|---|---|---|---|---|---|---|---|---|---|
| 1 | 5 | hsa-miR-6087 | 1 | hsa-miR-1185-1-3p | 2 | hsa-miR-4728-5p | 126 | hsa-miR-6802-5p | 194 | hsa-miR-6716-5p | 163 |
| 2 | 5 | hsa-miR-6087 | 1 | hsa-miR-1185-1-3p | 2 | hsa-miR-4728-5p | 126 | hsa-miR-6802-5p | 194 | hsa-miR-210-5p | 26 |
| 3 | 5 | hsa-miR-6087 | 1 | hsa-miR-1185-1-3p | 2 | hsa-miR-4728-5p | 126 | hsa-miR-6802-5p | 194 | hsa-miR-4535 | 98 |
| 4 | 5 | hsa-miR-6087 | 1 | hsa-miR-1185-1-3p | 2 | hsa-miR-4728-5p | 126 | hsa-miR-6802-5p | 194 | hsa-miR-6794-5p | 192 |
| 5 | 5 | hsa-miR-6087 | 1 | hsa-miR-1185-1-3p | 2 | hsa-miR-4728-5p | 126 | hsa-miR-6802-5p | 194 | hsa-miR-3185 | 40 |
| 6 | 5 | hsa-miR-6087 | 1 | hsa-miR-744-5p | 221 | hsa-miR-4725-3p | 123 | hsa-miR-4652-5p | 104 | hsa-miR-6780b-5p | 184 |
| 7 | 5 | hsa-miR-6087 | 1 | hsa-miR-1185-1-3p | 2 | hsa-miR-4728-5p | 126 | hsa-miR-6802-5p | 194 | hsa-miR-3648 | 54 |
| 8 | 5 | hsa-miR-6087 | 1 | hsa-miR-1185-1-3p | 2 | hsa-miR-4728-5p | 126 | hsa-miR-6802-5p | 194 | hsa-miR-6737-5p | 168 |
| 9 | 5 | hsa-miR-6087 | 1 | hsa-miR-1185-1-3p | 2 | hsa-miR-4728-5p | 126 | hsa-miR-6802-5p | 194 | hsa-miR-4725-3p | 123 |
| 10 | 5 | hsa-miR-6087 | 1 | hsa-miR-1185-1-3p | 2 | hsa-miR-4728-5p | 126 | hsa-miR-6802-5p | 194 | hsa-miR-7150 | 220 |
| 11 | 5 | hsa-miR-6087 | 1 | hsa-miR-1185-1-3p | 2 | hsa-miR-4728-5p | 126 | hsa-miR-6802-5p | 194 | hsa-miR-7107-5p | 215 |
| 12 | 5 | hsa-miR-6087 | 1 | hsa-miR-1185-2-3p | 3 | hsa-miR-4728-5p | 126 | hsa-miR-6802-5p | 194 | hsa-miR-5008-5p | 141 |
| 13 | 5 | hsa-miR-6087 | 1 | hsa-miR-744-5p | 221 | hsa-miR-4725-3p | 123 | hsa-miR-6717-5p | 164 | hsa-miR-4728-5p | 126 |
| 14 | 5 | hsa-miR-6087 | 1 | hsa-miR-1185-1-3p | 2 | hsa-miR-4728-5p | 126 | hsa-miR-6802-5p | 194 | hsa-miR-4436b-5p | 76 |
| 15 | 5 | hsa-miR-6087 | 1 | hsa-miR-1185-1-3p | 2 | hsa-miR-4728-5p | 126 | hsa-miR-6802-5p | 194 | hsa-miR-4707-3p | 117 |
| 16 | 5 | hsa-miR-6087 | 1 | hsa-miR-1185-1-3p | 2 | hsa-miR-4728-5p | 126 | hsa-miR-6802-5p | 194 | hsa-miR-4651 | 103 |
| 17 | 5 | hsa-miR-6087 | 1 | hsa-miR-1185-1-3p | 2 | hsa-miR-4728-5p | 126 | hsa-miR-6802-5p | 194 | hsa-miR-887-3p | 227 |
| 18 | 5 | hsa-miR-6087 | 1 | hsa-miR-1185-1-3p | 2 | hsa-miR-4728-5p | 126 | hsa-miR-6802-5p | 194 | hsa-miR-328-5p | 46 |
| 19 | 5 | hsa-miR-6087 | 1 | hsa-miR-1185-1-3p | 2 | hsa-miR-4728-5p | 126 | hsa-miR-6802-5p | 194 | hsa-miR-6821-5p | 199 |
| 20 | 5 | hsa-miR-6087 | 1 | hsa-miR-1185-1-3p | 2 | hsa-miR-4728-5p | 126 | hsa-miR-6802-5p | 194 | hsa-miR-4726-5p | 124 |
| 21 | 5 | hsa-miR-6087 | 1 | hsa-miR-1185-1-3p | 2 | hsa-miR-4728-5p | 126 | hsa-miR-6802-5p | 194 | hsa-miR-4792 | 139 |
| 22 | 5 | hsa-miR-6087 | 1 | hsa-miR-1185-1-3p | 2 | hsa-miR-4728-5p | 126 | hsa-miR-6802-5p | 194 | hsa-miR-3619-3p | 50 |
| 23 | 5 | hsa-miR-6087 | 1 | hsa-miR-4652-5p | 104 | hsa-miR-4728-5p | 126 | hsa-miR-6819-5p | 198 | hsa-miR-4687-5p | 112 |
| 24 | 5 | hsa-miR-6087 | 1 | hsa-miR-1185-1-3p | 2 | hsa-miR-4728-5p | 126 | hsa-miR-6802-5p | 194 | hsa-miR-3131 | 32 |
| 25 | 5 | hsa-miR-6087 | 1 | hsa-miR-1185-1-3p | 2 | hsa-miR-4728-5p | 126 | hsa-miR-6802-5p | 194 | hsa-miR-4675 | 110 |
| 26 | 5 | hsa-miR-6087 | 1 | hsa-miR-1185-1-3p | 2 | hsa-miR-4728-5p | 126 | hsa-miR-6802-5p | 194 | hsa-miR-6777-5p | 182 |
| 27 | 5 | hsa-miR-6087 | 1 | hsa-miR-4652-5p | 104 | hsa-miR-4728-5p | 126 | hsa-miR-6819-5p | 198 | hsa-miR-3940-5p | 62 |
| 28 | 5 | hsa-miR-6087 | 1 | hsa-miR-1185-2-3p | 3 | hsa-miR-4728-5p | 126 | hsa-miR-6802-5p | 194 | hsa-miR-1228-3p | 8 |
| 29 | 5 | hsa-miR-6087 | 1 | hsa-miR-1185-2-3p | 3 | hsa-miR-4728-5p | 126 | hsa-miR-6802-5p | 194 | hsa-miR-4258 | 64 |
| 30 | 5 | hsa-miR-6087 | 1 | hsa-miR-1185-1-3p | 2 | hsa-miR-4728-5p | 126 | hsa-miR-6802-5p | 194 | hsa-miR-504-3p | 143 |
| 31 | 5 | hsa-miR-6087 | 1 | hsa-miR-1185-1-3p | 2 | hsa-miR-4728-5p | 126 | hsa-miR-6802-5p | 194 | hsa-miR-3180-3p | 38 |
| 32 | 5 | hsa-miR-6087 | 1 | hsa-miR-1185-1-3p | 2 | hsa-miR-4728-5p | 126 | hsa-miR-6802-5p | 194 | hsa-miR-4722-5p | 122 |
| 33 | 5 | hsa-miR-6087 | 1 | hsa-miR-1185-1-3p | 2 | hsa-miR-4728-5p | 126 | hsa-miR-6802-5p | 194 | hsa-miR-7113-3p | 219 |
| 34 | 5 | hsa-miR-6087 | 1 | hsa-miR-1185-1-3p | 2 | hsa-miR-4728-5p | 126 | hsa-miR-6802-5p | 194 | hsa-miR-6880-5p | 212 |
| 35 | 5 | hsa-miR-6087 | 1 | hsa-miR-1185-1-3p | 2 | hsa-miR-4728-5p | 126 | hsa-miR-6802-5p | 194 | hsa-miR-4763-3p | 134 |
| 36 | 5 | hsa-miR-6087 | 1 | hsa-miR-1185-1-3p | 2 | hsa-miR-4728-5p | 126 | hsa-miR-6802-5p | 194 | hsa-miR-6515-3p | 160 |
| 37 | 5 | hsa-miR-6087 | 1 | hsa-miR-1185-1-3p | 2 | hsa-miR-4728-5p | 126 | hsa-miR-6802-5p | 194 | hsa-miR-6803-5p | 195 |
| 38 | 5 | hsa-miR-6087 | 1 | hsa-miR-1185-1-3p | 2 | hsa-miR-4728-5p | 126 | hsa-miR-6802-5p | 194 | hsa-miR-1909-3p | 24 |

TABLE 11-1-continued

| No. | Number of miRNA | miRNA marker 1 | SEQ ID NO | miRNA marker 2 | SEQ ID NO | miRNA marker 3 | SEQ ID NO | miRNA marker 4 | SEQ ID NO | miRNA marker 5 | SEQ ID NO |
|---|---|---|---|---|---|---|---|---|---|---|---|
| 39 | 5 | hsa-miR-6087 | 1 | hsa-miR-1185-1-3p | 2 | hsa-miR-4728-5p | 126 | hsa-miR-6075 | 148 | hsa-miR-4466 | 86 |
| 40 | 5 | hsa-miR-6087 | 1 | hsa-miR-1185-2-3p | 3 | hsa-miR-4728-5p | 126 | hsa-miR-6802-5p | 194 | hsa-miR-6794-5p | 192 |
| 41 | 5 | hsa-miR-6087 | 1 | hsa-miR-1185-1-3p | 2 | hsa-miR-4728-5p | 126 | hsa-miR-3160-5p | 35 | hsa-miR-4443 | 77 |
| 42 | 5 | hsa-miR-6087 | 1 | hsa-miR-1185-1-3p | 2 | hsa-miR-4728-5p | 126 | hsa-miR-3160-5p | 35 | hsa-miR-4726-5p | 124 |
| 43 | 5 | hsa-miR-6087 | 1 | hsa-miR-744-5p | 221 | hsa-miR-4725-3p | 123 | hsa-miR-1268a | 13 | hsa-miR-6780b-5p | 184 |
| 44 | 5 | hsa-miR-6087 | 1 | hsa-miR-1185-1-3p | 2 | hsa-miR-4728-5p | 126 | hsa-miR-6802-5p | 194 | hsa-miR-1228-3p | 8 |
| 45 | 5 | hsa-miR-6087 | 1 | hsa-miR-1185-1-3p | 2 | hsa-miR-4728-5p | 126 | hsa-miR-6802-5p | 194 | hsa-miR-6743-5p | 171 |
| 46 | 5 | hsa-miR-6087 | 1 | hsa-miR-1185-1-3p | 2 | hsa-miR-4728-5p | 126 | hsa-miR-6802-5p | 194 | hsa-miR-6791-5p | 191 |
| 47 | 5 | hsa-miR-6087 | 1 | hsa-miR-4652-5p | 104 | hsa-miR-4728-5p | 126 | hsa-miR-6819-5p | 198 | hsa-miR-1469 | 234 |
| 48 | 5 | hsa-miR-6087 | 1 | hsa-miR-1185-2-3p | 3 | hsa-miR-4728-5p | 126 | hsa-miR-6802-5p | 194 | hsa-miR-4535 | 98 |
| 49 | 5 | hsa-miR-6087 | 1 | hsa-miR-6784-5p | 187 | hsa-miR-4728-5p | 126 | hsa-miR-6819-5p | 198 | hsa-miR-3160-5p | 35 |
| 50 | 5 | hsa-miR-6087 | 1 | hsa-miR-1185-1-3p | 2 | hsa-miR-4728-5p | 126 | hsa-miR-6802-5p | 194 | hsa-miR-4525 | 96 |

TABLE 11-2

| | Training cohort | | | | Validation cohort | | | |
|---|---|---|---|---|---|---|---|---|
| No. | Sensitivity | Specificity | Accuracy | AUC | Sensitivity | Specificity | Accuracy | AUC |
| 1 | 0.95 | 0.88 | 0.90 | 0.95 | 0.95 | 0.89 | 0.91 | 0.96 |
| 2 | 0.93 | 0.89 | 0.90 | 0.96 | 0.94 | 0.90 | 0.91 | 0.96 |
| 3 | 0.97 | 0.87 | 0.90 | 0.95 | 0.95 | 0.89 | 0.91 | 0.96 |
| 4 | 0.97 | 0.86 | 0.90 | 0.96 | 0.97 | 0.88 | 0.91 | 0.96 |
| 5 | 0.97 | 0.86 | 0.90 | 0.96 | 0.95 | 0.88 | 0.91 | 0.96 |
| 6 | 0.95 | 0.90 | 0.92 | 0.96 | 0.94 | 0.91 | 0.92 | 0.95 |
| 7 | 0.96 | 0.88 | 0.90 | 0.96 | 0.95 | 0.91 | 0.92 | 0.96 |
| 8 | 0.97 | 0.87 | 0.90 | 0.95 | 0.95 | 0.88 | 0.90 | 0.96 |
| 9 | 0.96 | 0.88 | 0.90 | 0.95 | 0.94 | 0.90 | 0.91 | 0.96 |
| 10 | 0.97 | 0.85 | 0.89 | 0.96 | 0.97 | 0.88 | 0.91 | 0.96 |
| 11 | 0.97 | 0.87 | 0.90 | 0.96 | 0.95 | 0.87 | 0.90 | 0.96 |
| 12 | 0.97 | 0.85 | 0.89 | 0.95 | 0.95 | 0.86 | 0.89 | 0.96 |
| 13 | 0.97 | 0.88 | 0.90 | 0.96 | 0.97 | 0.88 | 0.91 | 0.95 |
| 14 | 0.92 | 0.92 | 0.92 | 0.96 | 0.92 | 0.94 | 0.93 | 0.97 |
| 15 | 0.95 | 0.88 | 0.90 | 0.95 | 0.95 | 0.89 | 0.91 | 0.96 |
| 16 | 0.97 | 0.87 | 0.90 | 0.96 | 0.95 | 0.88 | 0.91 | 0.96 |
| 17 | 0.96 | 0.87 | 0.90 | 0.96 | 0.95 | 0.89 | 0.91 | 0.96 |
| 18 | 0.96 | 0.87 | 0.90 | 0.95 | 0.95 | 0.89 | 0.91 | 0.96 |
| 19 | 0.97 | 0.87 | 0.90 | 0.95 | 0.95 | 0.88 | 0.91 | 0.96 |
| 20 | 0.96 | 0.87 | 0.90 | 0.96 | 0.95 | 0.89 | 0.91 | 0.96 |
| 21 | 0.96 | 0.87 | 0.90 | 0.95 | 0.95 | 0.88 | 0.90 | 0.96 |
| 22 | 0.97 | 0.86 | 0.90 | 0.96 | 0.96 | 0.88 | 0.91 | 0.96 |
| 23 | 0.93 | 0.91 | 0.92 | 0.95 | 0.89 | 0.93 | 0.92 | 0.96 |
| 24 | 0.95 | 0.89 | 0.91 | 0.96 | 0.95 | 0.90 | 0.92 | 0.96 |
| 25 | 0.95 | 0.88 | 0.90 | 0.96 | 0.95 | 0.89 | 0.91 | 0.97 |
| 26 | 0.95 | 0.89 | 0.91 | 0.96 | 0.95 | 0.91 | 0.92 | 0.96 |
| 27 | 0.94 | 0.91 | 0.92 | 0.96 | 0.92 | 0.91 | 0.91 | 0.96 |
| 28 | 0.94 | 0.89 | 0.90 | 0.95 | 0.94 | 0.90 | 0.91 | 0.96 |
| 29 | 0.97 | 0.86 | 0.89 | 0.95 | 0.98 | 0.87 | 0.91 | 0.96 |
| 30 | 0.96 | 0.87 | 0.90 | 0.95 | 0.95 | 0.89 | 0.91 | 0.96 |
| 31 | 0.96 | 0.87 | 0.90 | 0.95 | 0.95 | 0.89 | 0.91 | 0.96 |
| 32 | 0.96 | 0.87 | 0.90 | 0.95 | 0.95 | 0.89 | 0.91 | 0.96 |
| 33 | 0.96 | 0.89 | 0.91 | 0.96 | 0.95 | 0.90 | 0.91 | 0.96 |
| 34 | 0.96 | 0.87 | 0.90 | 0.95 | 0.95 | 0.89 | 0.91 | 0.96 |
| 35 | 0.96 | 0.87 | 0.90 | 0.95 | 0.95 | 0.89 | 0.91 | 0.96 |
| 36 | 0.96 | 0.88 | 0.90 | 0.95 | 0.94 | 0.89 | 0.91 | 0.96 |
| 37 | 0.95 | 0.88 | 0.90 | 0.96 | 0.95 | 0.90 | 0.92 | 0.96 |
| 38 | 0.95 | 0.88 | 0.90 | 0.95 | 0.96 | 0.89 | 0.91 | 0.96 |
| 39 | 0.97 | 0.85 | 0.88 | 0.95 | 0.94 | 0.86 | 0.88 | 0.96 |
| 40 | 0.97 | 0.87 | 0.90 | 0.96 | 0.96 | 0.88 | 0.91 | 0.96 |
| 41 | 0.94 | 0.89 | 0.90 | 0.95 | 0.94 | 0.91 | 0.92 | 0.96 |
| 42 | 0.94 | 0.90 | 0.91 | 0.95 | 0.92 | 0.91 | 0.92 | 0.96 |
| 43 | 0.97 | 0.89 | 0.91 | 0.96 | 0.95 | 0.89 | 0.91 | 0.95 |
| 44 | 0.95 | 0.89 | 0.91 | 0.95 | 0.95 | 0.89 | 0.91 | 0.96 |
| 45 | 0.95 | 0.88 | 0.90 | 0.95 | 0.95 | 0.90 | 0.92 | 0.96 |
| 46 | 0.95 | 0.88 | 0.90 | 0.95 | 0.95 | 0.90 | 0.91 | 0.96 |
| 47 | 0.95 | 0.88 | 0.91 | 0.95 | 0.92 | 0.89 | 0.90 | 0.96 |
| 48 | 0.96 | 0.87 | 0.90 | 0.95 | 0.96 | 0.88 | 0.91 | 0.96 |
| 49 | 0.97 | 0.87 | 0.90 | 0.95 | 0.95 | 0.88 | 0.90 | 0.96 |
| 50 | 0.95 | 0.88 | 0.90 | 0.95 | 0.95 | 0.90 | 0.92 | 0.96 |

TABLE 11-3

| No. | Number of miRNA | Discriminant formula | Threshold |
|---|---|---|---|
| 1 | 5 | (−1.97574)*hsa-miR-6087 + (0.306682)*hsa-miR-1185-1-3p + (−0.751539)*hsa-miR-4728-5p + (0.85344)*hsa-miR-6802-5p + (0.113938)*hsa-miR-6716-5p + 17.5594 | −0.12 |
| 2 | 5 | (−1.95531)*hsa-miR-6087 + (0.305415)*hsa-miR-1185-1-3p + (−0.699384)*hsa-miR-4728-5p + (0.795001)*hsa-miR-6802-5p + (0.137688)*hsa-miR-210-5p + 17.4154 | −0.03 |

TABLE 11-3-continued

| No. | Number of miRNA | Discriminant formula | Threshold |
|---|---|---|---|
| 3 | 5 | (−1.9726)*hsa-miR-6087 + (0.310345)*hsa-miR-1185-1-3p + (−0.697798)*hsa-miR-4728-5p + (0.77435)*hsa-miR-6802-5p + (0.0755933)*hsa-miR-4535 + 18.1116 | −0.16 |
| 4 | 5 | (−2.06728)*hsa-miR-6087 + (0.266954)*hsa-miR-1185-1-3p + (−0.578422)*hsa-miR-4728-5p + (1.00387)*hsa-miR-6802-5p + (−0.398203)*hsa-miR-6794-5p + 20.3473 | −0.15 |
| 5 | 5 | (−1.99673)*hsa-miR-6087 + (0.325411)*hsa-miR-1185-1-3p + (−0.697755)*hsa-miR-4728-5p + (0.761716)*hsa-miR-6802-5p + (0.188115)*hsa-miR-3185 + 17.264 | −0.21 |
| 6 | 5 | (−1.59922)*hsa-miR-6087 + (0.534051)*hsa-miR-744-5p + (−1.3171)*hsa-miR-4725-3p + (0.177022)*hsa-miR-4652-5p + (0.778345)*hsa-miR-6780b-5p + 17.3455 | 0.01 |
| 7 | 5 | (−1.97309)*hsa-miR-6087 + (0.321776)*hsa-miR-1185-1-3p + (−0.625091)*hsa-miR-4728-5p + (0.709608)*hsa-miR-6802-5p + (0.343782)*hsa-miR-3648 + 13.9735 | −0.05 |
| 8 | 5 | (−1.97998)*hsa-miR-6087 + (0.323851)*hsa-miR-1185-1-3p + (−0.702005)*hsa-miR-4728-5p + (0.784423)*hsa-miR-6802-5p + (0.059042)*hsa-miR-6737-5p + 18.0372 | −0.20 |
| 9 | 5 | (−1.94003)*hsa-miR-6087 + (0.325896)*hsa-miR-1185-1-3p + (−0.664139)*hsa-miR-4728-5p + (0.812215)*hsa-miR-6802-5p + (−0.240379)*hsa-miR-4725-3p + 19.6515 | −0.10 |
| 10 | 5 | (−2.00009)*hsa-miR-6087 + (0.305759)*hsa-miR-1185-1-3p + (−0.747234)*hsa-miR-4728-5p + (0.837692)*hsa-miR-6802-5p + (0.176885)*hsa-miR-7150 + 17.2507 | −0.28 |
| 11 | 5 | (−2.00482)*hsa-miR-6087 + (0.308847)*hsa-miR-1185-1-3p + (−0.720592)*hsa-miR-4728-5p + (0.737035)*hsa-miR-6802-5p + (0.217932)*hsa-miR-7107-5p + 17.7126 | −0.21 |
| 12 | 5 | (−1.96891)*hsa-miR-6087 + (0.236715)*hsa-miR-1185-2-3p + (−0.705818)*hsa-miR-4728-5p + (0.768652)*hsa-miR-6802-5p + (0.0835383)*hsa-miR-5008-5p + 18.8164 | −0.27 |
| 13 | 5 | (−1.69769)*hsa-miR-6087 + (0.916917)*hsa-miR-744-5p + (−1.00804)*hsa-miR-4725-3p + (0.234518)*hsa-miR-6717-5p + (−0.410221)*hsa-miR-4728-5p + 22.2844 | −0.17 |
| 14 | 5 | (−1.87799)*hsa-miR-6087 + (0.265005)*hsa-miR-1185-1-3p + (−0.708512)*hsa-miR-4728-5p + (0.668649)*hsa-miR-6802-5p + (0.317351)*hsa-miR-4436b-5p + 16.8662 | 0.20 |
| 15 | 5 | (−1.99172)*hsa-miR-6087 + (0.321678)*hsa-miR-1185-1-3p + (−0.669179)*hsa-miR-4728-5p + (0.779088)*hsa-miR-6802-5p + (0.074244)*hsa-miR-4707-3p + 17.9105 | −0.12 |
| 16 | 5 | (−2.00388)*hsa-miR-6087 + (0.323378)*hsa-miR-1185-1-3p + (−0.673168)*hsa-miR-4728-5p + (0.78929)*hsa-miR-6802-5p + (−0.109544)*hsa-miR-4651 + 19.6303 | −0.19 |
| 17 | 5 | (−2.02979)*hsa-miR-6087 + (0.330996)*hsa-miR-1185-1-3p + (−0.662212)*hsa-miR-4728-5p + (0.775558)*hsa-miR-6802-5p + (−0.0412224)*hsa-miR-887-3p + 19.0101 | −0.17 |
| 18 | 5 | (−2.04222)*hsa-miR-6087 + (0.317481)*hsa-miR-1185-1-3p + (−0.677187)*hsa-miR-4728-5p + (0.774711)*hsa-miR-6802-5p + (0.202952)*hsa-miR-328-5p + 16.8114 | −0.16 |
| 19 | 5 | (−2.02548)*hsa-miR-6087 + (0.325294)*hsa-miR-1185-1-3p + (−0.674895)*hsa-miR-4728-5p + (0.742323)*hsa-miR-6802-5p + (0.156362)*hsa-miR-6821-5p + 17.6787 | −0.19 |
| 20 | 5 | (−1.92431)*hsa-miR-6087 + (0.291659)*hsa-miR-1185-1-3p + (−0.756296)*hsa-miR-4728-5p + (0.765434)*hsa-miR-6802-5p + (0.186329)*hsa-miR-4726-5p + 17.3067 | −0.17 |
| 21 | 5 | (−1.98946)*hsa-miR-6087 + (0.325845)*hsa-miR-1185-1-3p + (−0.684016)*hsa-miR-4728-5p + (0.826354)*hsa-miR-6802-5p + (0.05751)*hsa-miR-4792 + 17.6798 | −0.18 |
| 22 | 5 | (−1.89148)*hsa-miR-6087 + (0.336172)*hsa-miR-1185-1-3p + (−0.687883)*hsa-miR-4728-5p + (0.645637)*hsa-miR-6802-5p + (0.186098)*hsa-miR-3619-3p + 16.8553 | −0.27 |
| 23 | 5 | (−1.41316)*hsa-miR-6087 + (0.182772)*hsa-miR-4652-5p + (−0.663791)*hsa-miR-4728-5p + (0.770082)*hsa-miR-6819-5p + (0.194503)*hsa-miR-4687-5p + 12.9808 | 0.10 |
| 24 | 5 | (−2.10385)*hsa-miR-6087 + (0.370769)*hsa-miR-1185-1-3p + (−0.607674)*hsa-miR-4728-5p + (0.946825)*hsa-miR-6802-5p + (−0.194202)*hsa-miR-3131 + 18.8205 | −0.03 |
| 25 | 5 | (−2.0706)*hsa-miR-6087 + (0.309769)*hsa-miR-1185-1-3p + (−0.678072)*hsa-miR-4728-5p + (0.659069)*hsa-miR-6802-5p + (0.249079)*hsa-miR-4675 + 18.541 | −0.04 |
| 26 | 5 | (−1.81895)*hsa-miR-6087 + (0.313368)*hsa-miR-1185-1-3p + (−0.763737)*hsa-miR-4728-5p + (0.697988)*hsa-miR-6802-5p + (0.169695)*hsa-miR-6777-5p + 16.7353 | −0.07 |
| 27 | 5 | (−1.45369)*hsa-miR-6087 + (0.159876)*hsa-miR-4652-5p + (−0.705944)*hsa-miR-4728-5p + (0.721583)*hsa-miR-6819-5p + (−0.761116)*hsa-miR-3940-5p + 24.0074 | 0.06 |

TABLE 11-3-continued

| No. | Number of miRNA | Discriminant formula | Threshold |
|---|---|---|---|
| 28 | 5 | (−1.97697)*hsa-miR-6087 + (0.239286)*hsa-miR-1185-2-3p + (−0.70536)*hsa-miR-4728-5p + (0.772623)*hsa-miR-6802-5p + (0.2396)*hsa-miR-1228-3p + 17.7097 | 0.01 |
| 29 | 5 | (−2.0355)*hsa-miR-6087 + (0.243538)*hsa-miR-1185-2-3p + (−0.648754)*hsa-miR-4728-5p + (0.708539)*hsa-miR-6802-5p + (0.132378)*hsa-miR-4258 + 18.8945 | −0.24 |
| 30 | 5 | (−1.98344)*hsa-miR-6087 + (0.284183)*hsa-miR-1185-1-3p + (−0.694576)*hsa-miR-4728-5p + (0.797829)*hsa-miR-6802-5p + (0.0759208)*hsa-miR-504-3p + 18.1452 | −0.14 |
| 31 | 5 | (−2.02868)*hsa-miR-6087 + (0.330511)*hsa-miR-1185-1-3p + (−0.682904)*hsa-miR-4728-5p + (0.822105)*hsa-miR-6802-5p + (−0.162048)*hsa-miR-3180-3p + 19.9246 | −0.14 |
| 32 | 5 | (−2.0024)*hsa-miR-6087 + (0.322011)*hsa-miR-1185-1-3p + (−0.701753)*hsa-miR-4728-5p + (0.720378)*hsa-miR-6802-5p + (0.13329)*hsa-miR-4722-5p + 18.4141 | −0.18 |
| 33 | 5 | (−1.96098)*hsa-miR-6087 + (0.284886)*hsa-miR-1185-1-3p + (−0.702706)*hsa-miR-4728-5p + (0.828885)*hsa-miR-6802-5p + (0.205399)*hsa-miR-7113-3p + 16.9012 | −0.11 |
| 34 | 5 | (−2.04675)*hsa-miR-6087 + (0.323234)*hsa-miR-1185-1-3p + (−0.647756)*hsa-miR-4728-5p + (0.803638)*hsa-miR-6802-5p + (−0.0639364)*hsa-miR-6880-5p + 19.1036 | −0.16 |
| 35 | 5 | (−2.01715)*hsa-miR-6087 + (0.324)*hsa-miR-1185-1-3p + (−0.675007)*hsa-miR-4728-5p + (0.784036)*hsa-miR-6802-5p + (0.0823888)*hsa-miR-4763-3p + 17.9 | −0.18 |
| 36 | 5 | (−1.98234)*hsa-miR-6087 + (0.293383)*hsa-miR-1185-1-3p + (−0.717769)*hsa-miR-4728-5p + (0.774551)*hsa-miR-6802-5p + (0.143503)*hsa-miR-6515-3p + 17.8861 | −0.16 |
| 37 | 5 | (−1.92198)*hsa-miR-6087 + (0.323857)*hsa-miR-1185-1-3p + (−0.671473)*hsa-miR-4728-5p + (0.77788)*hsa-miR-6802-5p + (−0.706715)*hsa-miR-6803-5p + 25.293 | −0.04 |
| 38 | 5 | (−2.01752)*hsa-miR-6087 + (0.305205)*hsa-miR-1185-1-3p + (−0.687511)*hsa-miR-4728-5p + (0.751667)*hsa-miR-6802-5p + (−0.441716)*hsa-miR-1909-3p + 23.0425 | −0.15 |
| 39 | 5 | (−2.1145)*hsa-miR-6087 + (0.346492)*hsa-miR-1185-1-3p + (−0.477369)*hsa-miR-4728-5p + (0.541762)*hsa-miR-6075 + (−0.100607)*hsa-miR-4466 + 21.938 | −0.23 |
| 40 | 5 | (−2.0679)*hsa-miR-6087 + (0.210868)*hsa-miR-1185-2-3p + (−0.564075)*hsa-miR-4728-5p + (1.0277)*hsa-miR-6802-5p + (−0.456643)*hsa-miR-6794-5p + 21.1161 | −0.21 |
| 41 | 5 | (−1.90504)*hsa-miR-6087 + (0.317204)*hsa-miR-1185-1-3p + (−0.60802)*hsa-miR-4728-5p + (0.183053)*hsa-miR-3160-5p + (0.161124)*hsa-miR-4443 + 21.6641 | 0.07 |
| 42 | 5 | (−1.88621)*hsa-miR-6087 + (0.328477)*hsa-miR-1185-1-3p + (−0.615267)*hsa-miR-4728-5p + (0.171483)*hsa-miR-3160-5p + (0.169775)*hsa-miR-4726-5p + 21.3692 | 0.08 |
| 43 | 5 | (−1.83671)*hsa-miR-6087 + (0.801734)*hsa-miR-744-5p + (−1.39458)*hsa-miR-4725-3p + (−0.705307)*hsa-miR-1268a + (0.87047)*hsa-miR-6780b-5p + 25.8016 | 0.03 |
| 44 | 5 | (−1.99054)*hsa-miR-6087 + (0.297474)*hsa-miR-1185-1-3p + (−0.697922)*hsa-miR-4728-5p + (0.785747)*hsa-miR-6802-5p + (0.183654)*hsa-miR-1228-3p + 17.4544 | −0.08 |
| 45 | 5 | (−2.05119)*hsa-miR-6087 + (0.333116)*hsa-miR-1185-1-3p + (−0.674012)*hsa-miR-4728-5p + (0.87884)*hsa-miR-6802-5p + (−0.280392)*hsa-miR-6743-5p + 20.9727 | −0.02 |
| 46 | 5 | (−2.04448)*hsa-miR-6087 + (0.312895)*hsa-miR-1185-1-3p + (−0.683115)*hsa-miR-4728-5p + (0.845636)*hsa-miR-6802-5p + (−0.304078)*hsa-miR-6791-5p + 21.4743 | −0.06 |
| 47 | 5 | (−1.47528)*hsa-miR-6087 + (0.177635)*hsa-miR-4652-5p + (−0.649714)*hsa-miR-4728-5p + (0.778168)*hsa-miR-6819-5p + (0.280624)*hsa-miR-1469 + 11.5525 | −0.14 |
| 48 | 5 | (−1.96453)*hsa-miR-6087 + (0.244369)*hsa-miR-1185-2-3p + (−0.692974)*hsa-miR-4728-5p + (0.777289)*hsa-miR-6802-5p + (0.0659214)*hsa-miR-4535 + 18.7085 | −0.15 |
| 49 | 5 | (−1.51864)*hsa-miR-6087 + (−0.628049)*hsa-miR-6784-5p + (−0.813322)*hsa-miR-4728-5p + (0.846001)*hsa-miR-6819-5p + (0.0984264)*hsa-miR-3160-5p + 23.2007 | −0.18 |
| 50 | 5 | (−1.97887)*hsa-miR-6087 + (0.321602)*hsa-miR-1185-1-3p + (−0.655373)*hsa-miR-4728-5p + (0.697661)*hsa-miR-6802-5p + (0.0656159)*hsa-miR-4525 + 18.1775 | −0.07 |

Example 2

<Discriminant Analysis of Bladder Cancer with 1 or Combination of 2 to 104 miRNAs>

In this Example, discriminant formulas with 1 to 104 gene markers were created using a training cohort (Table 4) including bladder cancer patients, patients of cancers other than bladder cancer, benign disease patient, and healthy subjects, to evaluate the discriminant performance in a validation cohort (Table 4). Genes used for discriminant formulas combining up to 104 genes and exhibiting high discriminant accuracy were extracted to obtain gene markers capable of detecting bladder cancer (Table 12).

Specifically, first, miRNA expression levels in the training cohort and the validation cohort obtained in the above Reference Example were together normalized in accordance with global normalization. Further, in order to acquire more reliable diagnostic markers, only 384 genes with a gene expression level of $2^6$ or larger in 50% or more of the samples were analyzed in either the positive sample group (bladder cancer patients) or the negative sample group (patients of cancers other than bladder cancer, benign disease patients, and healthy subjects).

Next, logistic regression analysis was performed from the measured values of the expression levels of the above 384 genes by the LASSO method, and discriminant formulas with one to a combination of a plurality of miRNAs were created, to construct discriminant formulas with a combination of 104 genes for discriminating the presence or absence of bladder cancer with high accuracy. Further, the discriminant formulas were used to calculate the accuracy, the sensitivity, and the specificity in the validation cohort. Then, the discriminant performance was validated in independent samples. Details are shown below for each number of genes used for discrimination.

Example 2-1

As a result of the above, a discriminant formula with a combination of three genes and its threshold (determining positive or negative, where values equal to or higher than the threshold are positive), the sensitivity, specificity, accuracy, and AUC in the training cohort and the validation cohort, and the genes used for the discriminant formula are shown in Tables 13-1 and 13-2. The genes included in these discriminant formulas were selected as diagnostic markers capable of discriminating between bladder cancer patients and subjects without bladder cancer.

Figure 14:
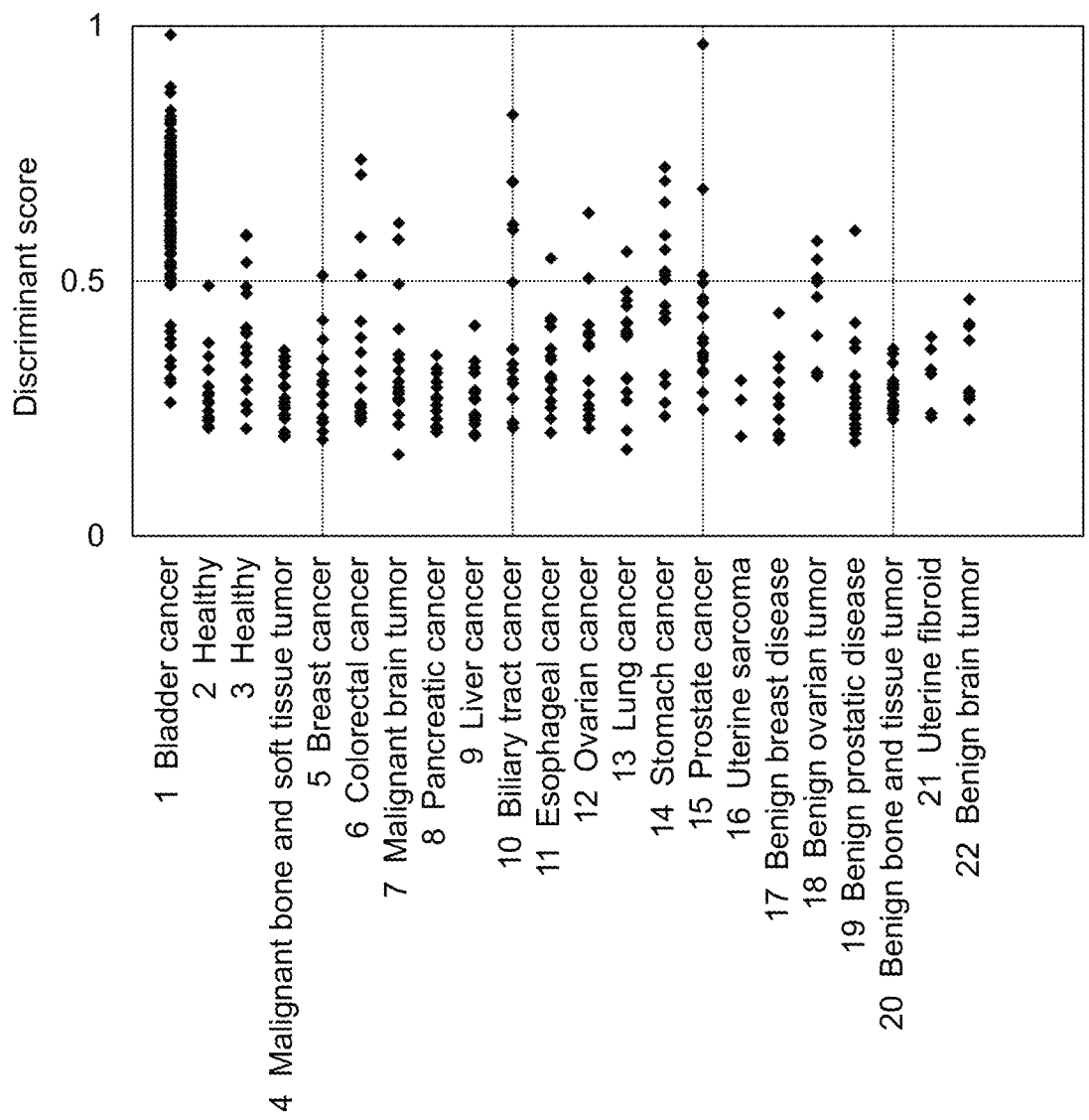
FIG. 14 shows plots of discriminant scores in validation cohorts according to the disease type obtained by a discriminant formula for 3 miRNAs.
Figure 15A:
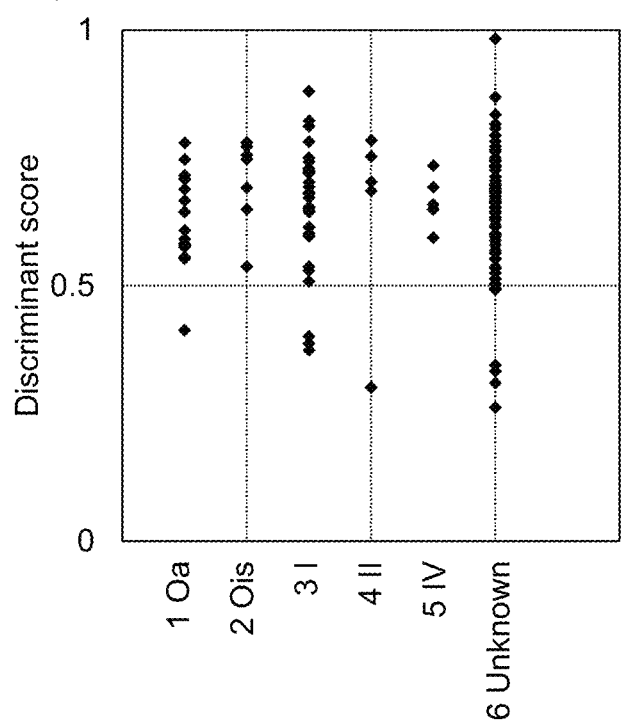
FIG. 15A and FIG. 15B show plots of discriminant scores in validation cohorts according to the stage (A) and according to the depth of intramural invasion (B) obtained by a discriminant formula for 3 miRNAs.
Figure 15B:
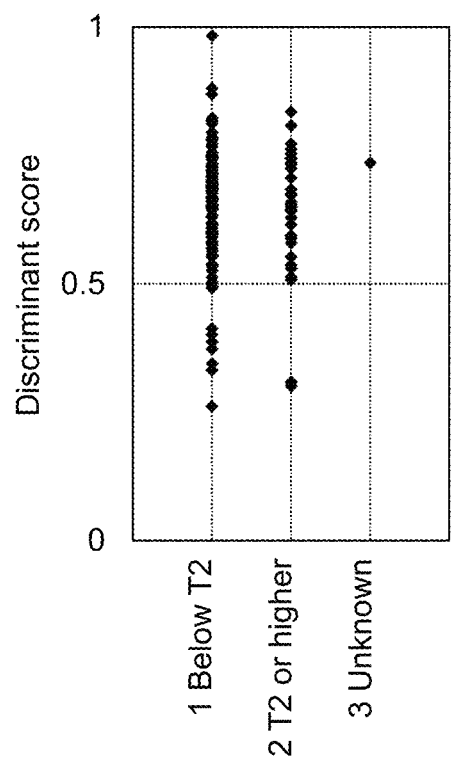
Figure 15C:
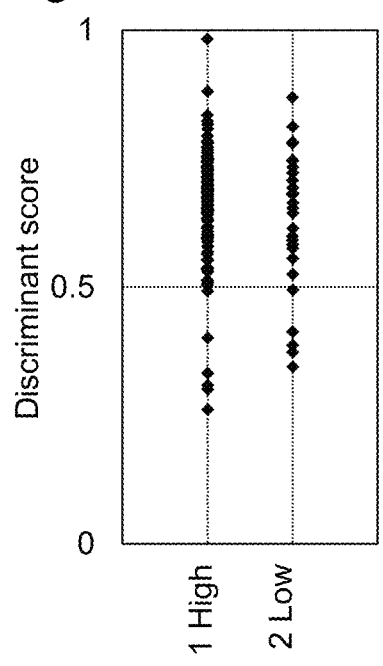
FIG. 15C and FIG. 15D show plots of discriminant scores in validation cohorts according to the histologic tumor grade (C) and primary/recurrence (D) obtained by a discriminant formula for 3 miRNAs.
Figure 15D:
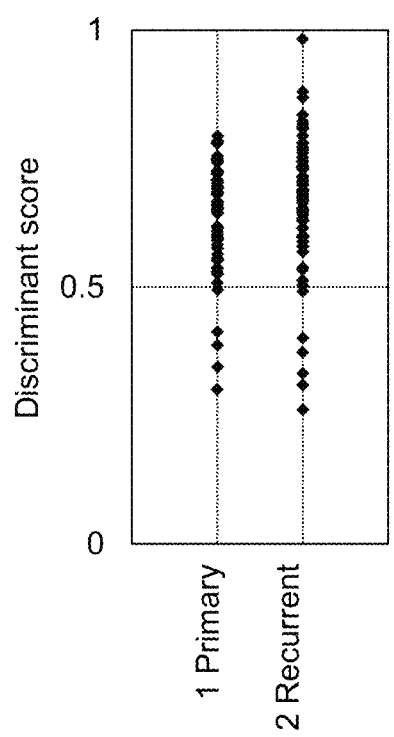

Measured values were plugged into the discriminant formula in Table 13-3 to obtain y, the values obtained by substituting y in Formula 9 were plotted as discriminant scores for each disease type in the validation cohort, thereby showing that bladder cancer was significantly separated regardless of the disease type, in FIG. 14. The vertical axis of the figure represents the discriminant scores. As compared to the threshold 0.5, higher scores were determined as having bladder cancer, and lower scores were determined as not having bladder cancer.

The discriminant scores of the bladder cancer patients were illustrated separately for each stage, depth of in-wall invasion, histological grade, and primary/recurrence. As a result, it could be confirmed that bladder cancer could be detected with high accuracy in all categories (FIGS. 15A to D). The vertical axis of the figure represents the discriminant scores. As compared to the threshold 0.5, higher scores were determined as having bladder cancer, and lower scores were determined as not having bladder cancer.

Example 2-2

Figure 16:
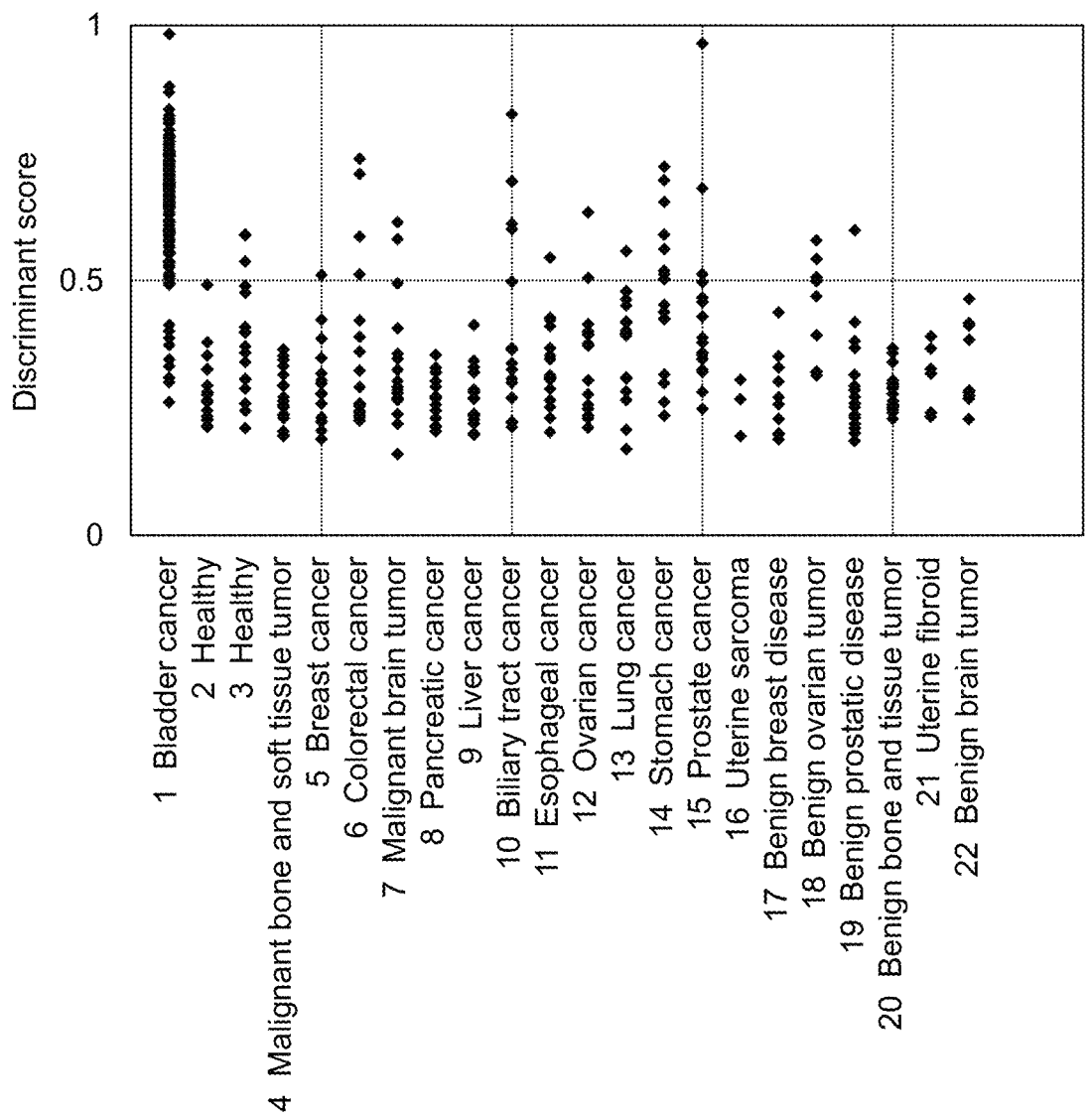
FIG. 16 shows plots of discriminant scores in validation cohorts according to the disease type obtained by a discriminant formula for 10 miRNAs.
Figure 17A:
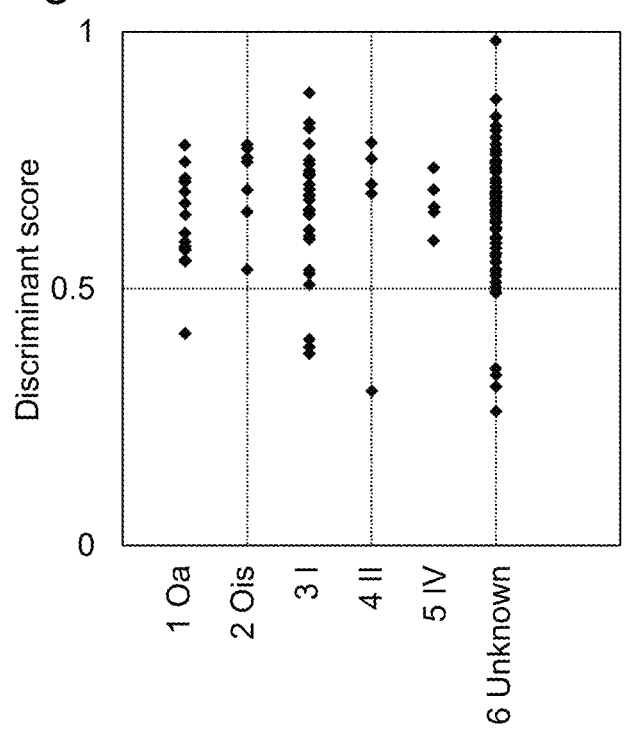
FIG. 17A and FIG. 17B show plots of discriminant scores in validation cohorts according to the stage (A) and according to the depth of intramural invasion (B) obtained by a discriminant formula for 10 miRNAs.
Figure 17B:
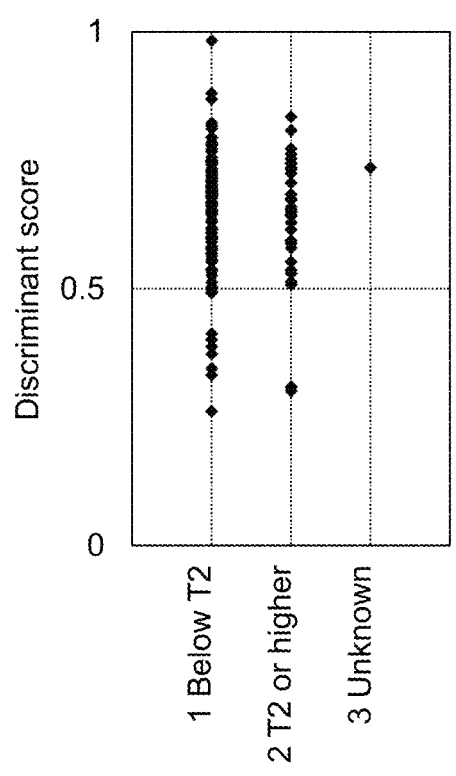
Figure 17C:
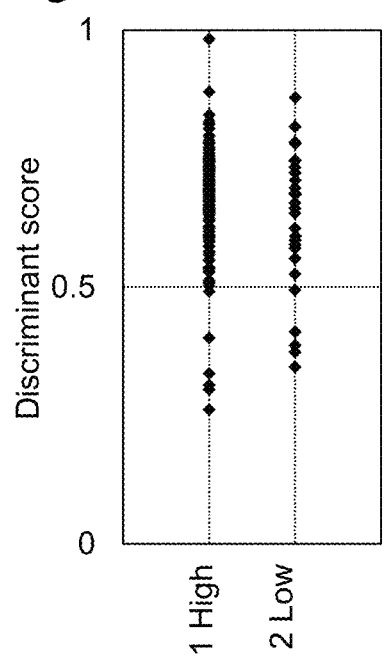
FIG. 17C and FIG. 17D show plots of discriminant scores in validation cohorts according to the histologic tumor grade (C) and primary/recurrence (D) obtained by a discriminant formula for 10 miRNAs.
Figure 17D:
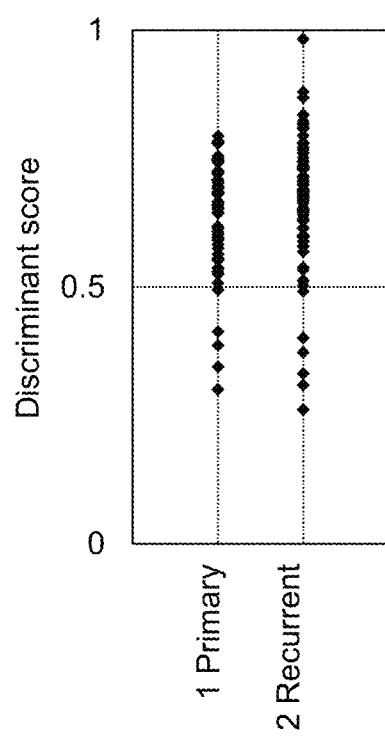

As a result of the above, a discriminant formula with a combination of ten genes and its threshold (determining positive or negative, where values equal to or higher than the threshold are positive), the sensitivity, specificity, accuracy, and AUC in the training cohort and the validation cohort, and the genes used for the discriminant formula are shown in Table 14-1. The genes included in these discriminant formulas were selected as diagnostic markers capable of discriminating between bladder cancer patients and subjects without bladder cancer. Measured values were plugged into the discriminant formula in Table 14-2 to obtain y, the values obtained by substituting y in Formula 9 were plotted as discriminant scores for each disease type in the validation cohort, thereby showing that bladder cancer was significantly separated regardless of the disease type, in FIG. 16. The vertical axis of the figure represents the discriminant scores. As compared to the threshold 0.5, higher scores were determined as having bladder cancer, and lower scores were determined as not having bladder cancer.

The discriminant scores of the bladder cancer patients were illustrated separately for each stage, depth of in-wall invasion, histological grade, and primary/recurrence. As a result, it could be confirmed that bladder cancer could be detected with high accuracy in all categories (FIGS. 17A to D). The vertical axis of the figure represents the discriminant scores. As compared to the threshold 0.5, higher scores were determined as having bladder cancer, and lower scores were determined as not having bladder cancer.

Example 2-3

As a result of the above, a discriminant formula with a combination of 104 genes and its threshold (determining positive or negative, where values equal to or higher than the threshold are positive), the sensitivity, specificity, accuracy, and AUC in the training cohort and the validation cohort, and the genes used for the discriminant formula are shown in Table 15-1. The genes included in these discriminant formula were selected as diagnostic markers capable of discriminating between bladder cancer patients and subjects without bladder cancer.

Figure 18:
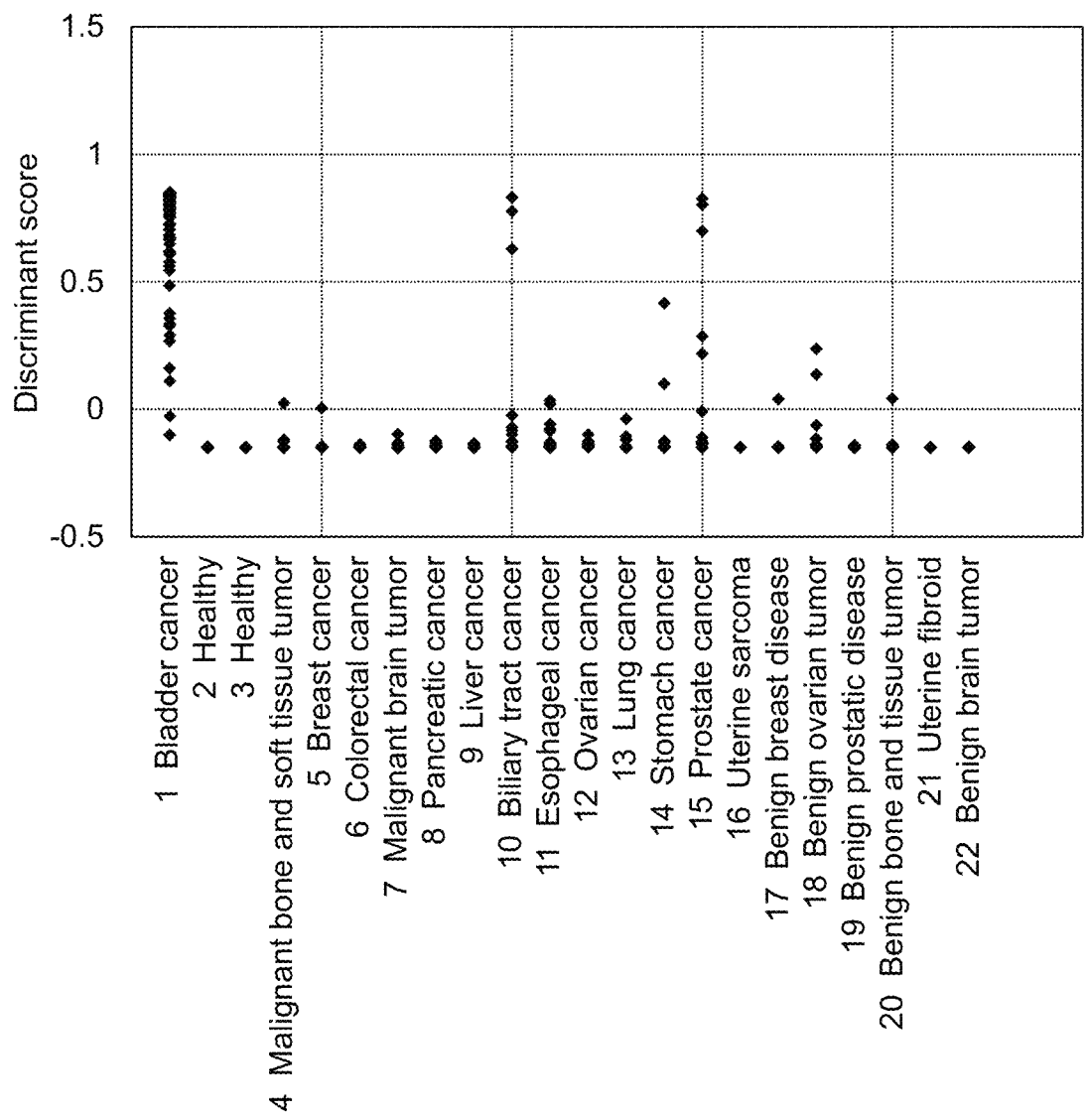
FIG. 18 shows plots of discriminant scores in validation cohorts according to the disease type obtained by a discriminant formula for 104 miRNAs.
Figure 19A:
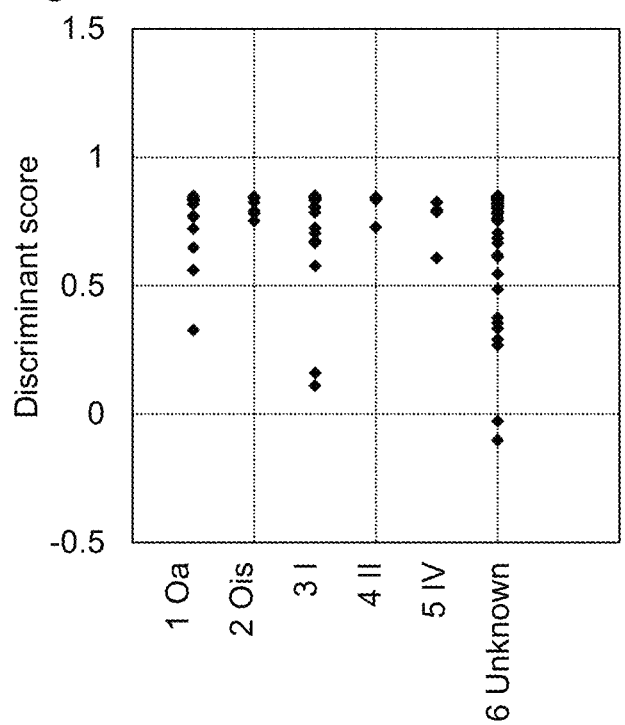
FIG. 19A and FIG. 19B show plots of discriminant scores in validation cohorts according to the stage (A) and according to the depth of intramural invasion (B) obtained by a discriminant formula for 104 miRNAs.
Figure 19B:
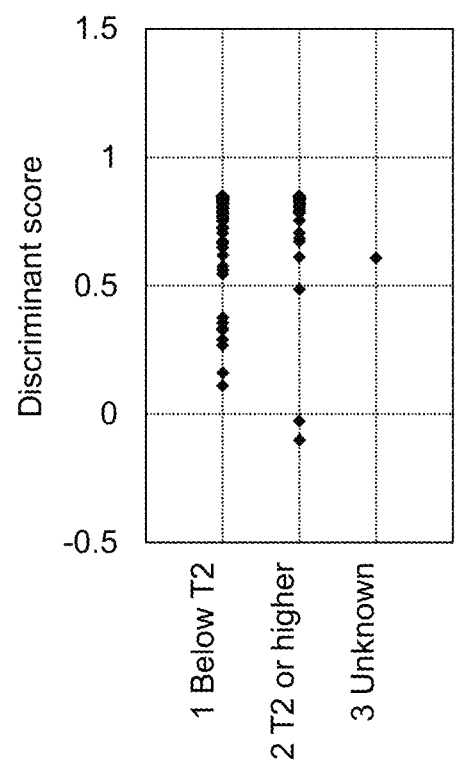
Figure 19C:
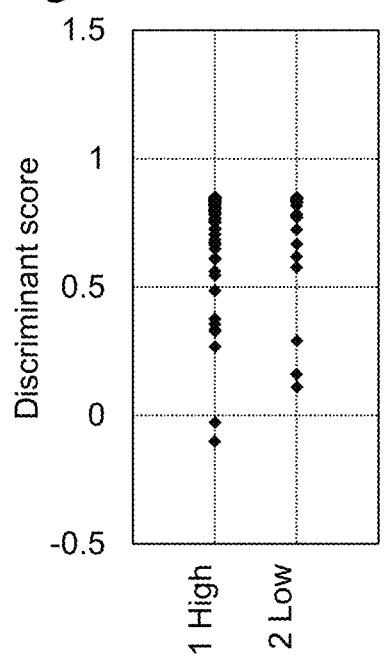
FIG. 19C and FIG. 19D show plots of discriminant scores in validation cohorts according to the histologic tumor grade (C) and primary/recurrence (D) obtained by a discriminant formula for 104 miRNAs.
Figure 19D:
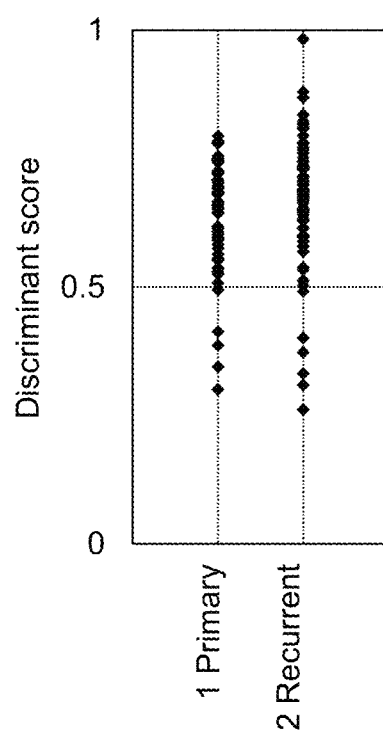
Figure 20A:
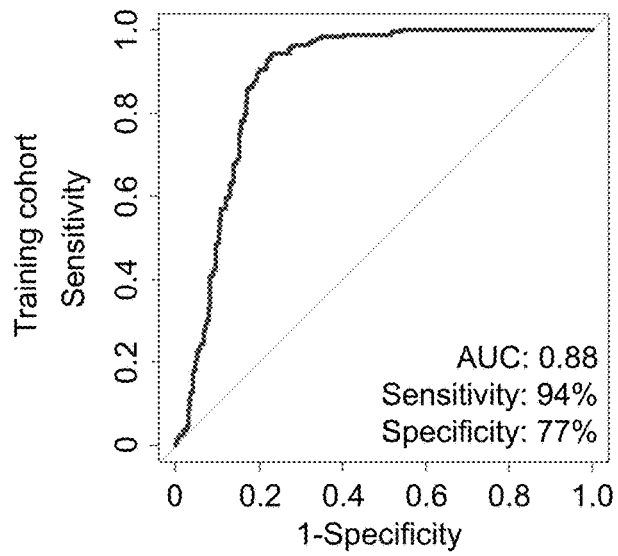
FIG. 20 shows ROC curves for the training cohort (A) and the validation cohort (C) determined with the use of 1 miRNA and ROC curves for the training cohort (B) and the validation cohort (D) determined with the use of 7 miRNAs in combination.
Figure 20B:
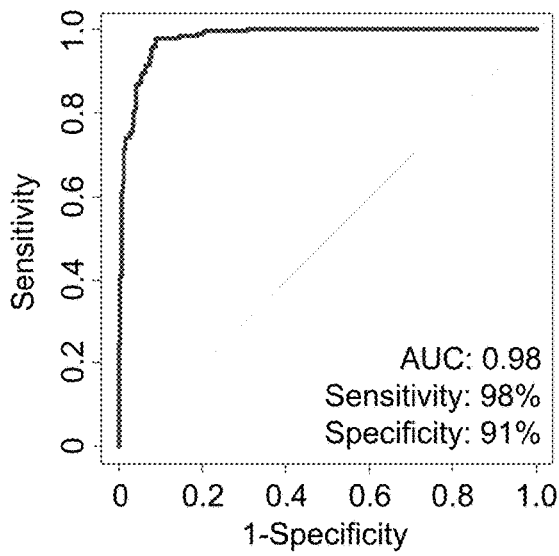
Figure 20C:
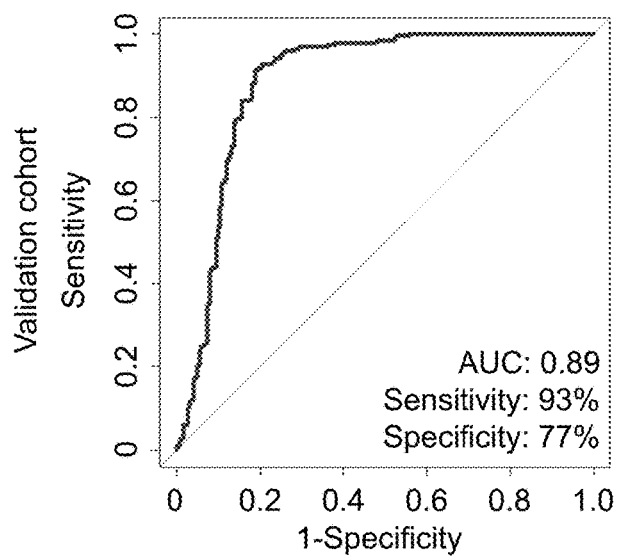
Figure 20D:
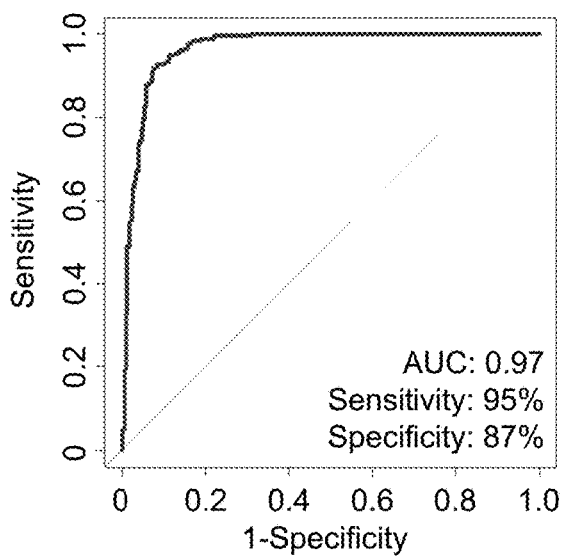

Measured values were plugged into the discriminant formula in Table 15-2 to obtain y, the values obtained by substituting y in Formula 9 were plotted as discriminant scores for each disease type in the validation cohort, thereby showing that bladder cancer was significantly separated regardless of the disease type, in FIG. 18. The vertical axis of the figure represents the discriminant scores. As compared to the threshold 0.5, higher scores were determined as having bladder cancer, and lower scores were determined as not having bladder cancer.

The discriminant scores of the bladder cancer patients were illustrated separately for each stage, depth of in-wall invasion, histological grade, and primary/recurrence. As a result, it could be confirmed that bladder cancer could be detected with high accuracy in all categories (FIGS. 19A to D). The vertical axis of the figure represents the discriminant scores. As compared to the threshold 0.5, higher scores were determined as having bladder cancer, and lower scores were determined as not having bladder cancer.

Example 2-4

As a result of the above, discriminant formulas with 1 or a combination of 2 to 103 genes and their thresholds (determining positive or negative, where values equal to or higher than the thresholds are positive), the sensitivity, specificity, accuracy, and AUC in the training cohort and the validation cohort, and the genes used for the discriminant formulas are shown in Table 16-1. The genes included in these discriminant formulas were selected as diagnostic markers capable of discriminating between bladder cancer patients and subjects without bladder cancer. The discriminant formulas and their thresholds for performing discrimination with 1 or a combination of 2 to 104 genes are shown in Table 16-2 (the 104 genes in combination are shown in Table 15-1, as described above).

From the above, it was demonstrated that higher discriminant performance for bladder cancer can be obtained in the case of combining a plurality of genes than in the case of using each gene represented by Nos. 1 to 119 in Table 12 alone. The genes included in these discriminant formulas were selected as diagnostic markers capable of discriminating between bladder cancer patients and subjects without bladder cancer.

TABLE 12

| No. | Name of miRNA | SEQ ID NO |
|---|---|---|
| 1 | hsa-miR-1185-1-3p | 2 |
| 2 | hsa-miR-1185-2-3p | 3 |
| 3 | hsa-miR-1193 | 4 |
| 4 | hsa-miR-1207-5p | 230 |
| 5 | hsa-miR-1225-5p | 6 |
| 6 | hsa-miR-1227-5p | 7 |
| 7 | hsa-miR-1228-5p | 9 |
| 8 | hsa-miR-1237-5p | 10 |
| 9 | hsa-miR-1246 | 231 |
| 10 | hsa-miR-128-2-5p | 16 |
| 11 | hsa-miR-1343-3p | 17 |
| 12 | hsa-miR-1343-5p | 18 |
| 13 | hsa-miR-149-3p | 235 |
| 14 | hsa-miR-150-3p | 236 |
| 15 | hsa-miR-1908-3p | 22 |
| 16 | hsa-miR-1908-5p | 23 |
| 17 | hsa-miR-1914-3p | 237 |
| 18 | hsa-miR-296-3p | 30 |
| 19 | hsa-miR-29b-3p | 31 |
| 20 | hsa-miR-3154 | 33 |
| 21 | hsa-miR-3158-5p | 34 |
| 22 | hsa-miR-3160-5p | 35 |
| 23 | hsa-miR-3195 | 42 |
| 24 | hsa-miR-3197 | 43 |
| 25 | hsa-miR-328-5p | 46 |
| 26 | hsa-miR-342-5p | 47 |
| 27 | hsa-miR-3619-3p | 50 |
| 28 | hsa-miR-3621 | 52 |
| 29 | hsa-miR-3648 | 54 |
| 30 | hsa-miR-3652 | 55 |
| 31 | hsa-miR-3663-3p | 57 |
| 32 | hsa-miR-371b-5p | 59 |
| 33 | hsa-miR-373-5p | 60 |
| 34 | hsa-miR-3917 | 61 |
| 35 | hsa-miR-3940-5p | 62 |
| 36 | hsa-miR-423-5p | 239 |
| 37 | hsa-miR-4270 | 66 |
| 38 | hsa-miR-4298 | 68 |
| 39 | hsa-miR-4322 | 69 |
| 40 | hsa-miR-4433a-3p | 75 |
| 41 | hsa-miR-4436b-5p | 76 |
| 42 | hsa-miR-4447 | 79 |
| 43 | hsa-miR-4448 | 80 |
| 44 | hsa-miR-4455 | 83 |
| 45 | hsa-miR-4467 | 87 |
| 46 | hsa-miR-4484 | 90 |
| 47 | hsa-miR-4534 | 97 |
| 48 | hsa-miR-4640-5p | 101 |
| 49 | hsa-miR-4649-5p | 102 |
| 50 | hsa-miR-4652-5p | 104 |
| 51 | hsa-miR-4655-5p | 105 |
| 52 | hsa-miR-4658 | 107 |

TABLE 12-continued

| No. | Name of miRNA | SEQ ID NO |
|---|---|---|
| 53 | hsa-miR-4663 | 108 |
| 54 | hsa-miR-4675 | 110 |
| 55 | hsa-miR-4687-3p | 111 |
| 56 | hsa-miR-4695-5p | 114 |
| 57 | hsa-miR-4710 | 120 |
| 58 | hsa-miR-4725-3p | 123 |
| 59 | hsa-miR-4728-5p | 126 |
| 60 | hsa-miR-4739 | 129 |
| 61 | hsa-miR-4741 | 131 |
| 62 | hsa-miR-4750-5p | 132 |
| 63 | hsa-miR-4763-3p | 134 |
| 64 | hsa-miR-4771 | 135 |
| 65 | hsa-miR-4783-3p | 136 |
| 66 | hsa-miR-498 | 140 |
| 67 | hsa-miR-5195-3p | 144 |
| 68 | hsa-miR-5739 | 147 |
| 69 | hsa-miR-6075 | 148 |
| 70 | hsa-miR-6087 | 1 |
| 71 | hsa-miR-6088 | 150 |
| 72 | hsa-miR-6124 | 151 |
| 73 | hsa-miR-6132 | 153 |
| 74 | hsa-miR-615-5p | 155 |
| 75 | hsa-miR-642b-3p | 157 |
| 76 | hsa-miR-6510-5p | 158 |
| 77 | hsa-miR-663a | 240 |
| 78 | hsa-miR-6716-5p | 163 |
| 79 | hsa-miR-6717-5p | 164 |
| 80 | hsa-miR-6722-3p | 165 |
| 81 | hsa-miR-6724-5p | 166 |
| 82 | hsa-miR-6726-5p | 167 |
| 83 | hsa-miR-6741-5p | 169 |
| 84 | hsa-miR-6749-5p | 173 |
| 85 | hsa-miR-6760-5p | 174 |
| 86 | hsa-miR-6762-5p | 175 |
| 87 | hsa-miR-6765-3p | 176 |
| 88 | hsa-miR-6766-3p | 178 |
| 89 | hsa-miR-6771-5p | 180 |
| 90 | hsa-miR-6774-5p | 181 |
| 91 | hsa-miR-6777-5p | 182 |
| 92 | hsa-miR-6778-5p | 183 |
| 93 | hsa-miR-6780b-5p | 184 |
| 94 | hsa-miR-6781-5p | 185 |
| 95 | hsa-miR-6782-5p | 186 |
| 96 | hsa-miR-6785-5p | 188 |
| 97 | hsa-miR-6791-5p | 191 |
| 98 | hsa-miR-6794-5p | 192 |
| 99 | hsa-miR-6800-5p | 193 |
| 100 | hsa-miR-6803-5p | 195 |
| 101 | hsa-miR-6812-5p | 196 |
| 102 | hsa-miR-6816-5p | 197 |
| 103 | hsa-miR-6819-5p | 198 |
| 104 | hsa-miR-6826-5p | 200 |
| 105 | hsa-miR-6836-3p | 202 |
| 106 | hsa-miR-6840-3p | 203 |
| 107 | hsa-miR-6869-5p | 207 |
| 108 | hsa-miR-6879-5p | 210 |
| 109 | hsa-miR-6880-5p | 211 |
| 110 | hsa-miR-7107-5p | 215 |
| 111 | hsa-miR-7108-3p | 216 |
| 112 | hsa-miR-711 | 218 |
| 113 | hsa-miR-744-5p | 221 |
| 114 | hsa-miR-8073 | 226 |
| 115 | hsa-miR-887-3p | 227 |
| 116 | hsa-miR-92a-2-5p | 241 |
| 117 | hsa-miR-92a-3p | 242 |
| 118 | hsa-miR-937-5p | 228 |
| 119 | hsa-miR-940 | 243 |

TABLE 13-1

| Number of miRNA | miRNA marker 1 | SEQ ID NO | miRNA marker 2 | SEQ ID NO | miRNA marker 3 | SEQ ID NO |
|---|---|---|---|---|---|---|
| 3 | hsa-miR-4652-5p | 104 | hsa-miR-6087 | 1 | hsa-miR-6724-5p | 166 |

TABLE 13-2

| | Training cohort | | | | Validation cohort | | | |
|---|---|---|---|---|---|---|---|---|
| Number of miRNA | Sensitivity | Specificity | Accuracy | AUC | Sensitivity | Specificity | Accuracy | AUC |
| 3 | 0.93 | 0.88 | 0.89 | 0.94 | 0.92 | 0.89 | 0.90 | 0.94 |

TABLE 13-3

| Number of miRNA | Discriminant formula | Threshold |
|---|---|---|
| 3 | (0.16644)*hsa-miR-4652-5p + (−1.41622)*hsa-miR-6087 + (0.02095)*hsa-miR-6724-5p + 15.02714 | 0.36 |

TABLE 14-1

| Number of miRNA | miRNA marker | SEQ ID NO | Training cohort | | | | Validation cohort | | | |
|---|---|---|---|---|---|---|---|---|---|---|
| | | | Sensitivity | Specificity | Accuracy | AUC | Sensitivity | Specificity | Accuracy | AUC |
| 10 | hsa-miR-4658 | 107 | 0.94 | 0.90 | 0.91 | 0.95 | 0.92 | 0.92 | 0.92 | 0.96 |
| | hsa-miR-4436b-5p | 76 | | | | | | | | |
| | hsa-miR-4652-5p | 104 | | | | | | | | |
| | hsa-miR-4728-5p | 126 | | | | | | | | |
| | hsa-miR-6087 | 1 | | | | | | | | |
| | hsa-miR-3160-5p | 35 | | | | | | | | |
| | hsa-miR-6724-5p | 166 | | | | | | | | |
| | hsa-miR-3940-5p | 62 | | | | | | | | |
| | hsa-miR-744-5p | 221 | | | | | | | | |
| | hsa-miR-6781-5p | 185 | | | | | | | | |

TABLE 14-2

| Number of miRNA | Discriminant formula | Threshold |
|---|---|---|
| 10 | (0.01504)*hsa-miR-4658 + (0.01562)*hsa-miR-4436b-5p + (0.20522)*hsa-miR-4652-5p + (−0.01556)*hsa-miR-4728-5p + (−1.8352)*hsa-miR-6087 + (0.02667)*hsa-miR-3160-5p + (0.43956)*hsa-miR-6724-5p + (−0.07772)*hsa-miR-3940-5p + (0.03616)*hsa-miR-744-5p + (−0.07753)*hsa-miR-6781-5p + 16.37274 | 0.38 |

TABLE 15-1

| Number of miRNA | miRNA marker | SEQ ID NO | Training cohort | | | | Validation cohort | | | |
|---|---|---|---|---|---|---|---|---|---|---|
| | | | Sensitivity | Specificity | Accuracy | AUC | Sensitivity | Specificity | Accuracy | AUC |
| 104 | hsa-miR-498 | 140 | 1.00 | 1.00 | 1.00 | 1.00 | 0.92 | 0.98 | 0.96 | 0.99 |
| | hsa-miR-4658 | 107 | | | | | | | | |
| | hsa-miR-6717-5p | 164 | | | | | | | | |
| | hsa-miR-8073 | 226 | | | | | | | | |
| | hsa-miR-92a-3p | 242 | | | | | | | | |
| | hsa-miR-3652 | 55 | | | | | | | | |
| | hsa-miR-6836-3p | 202 | | | | | | | | |
| | hsa-miR-1193 | 4 | | | | | | | | |
| | hsa-miR-4436b-5p | 76 | | | | | | | | |
| | hsa-miR-6812-5p | 196 | | | | | | | | |
| | hsa-miR-4663 | 108 | | | | | | | | |
| | hsa-miR-4652-5p | 104 | | | | | | | | |
| | hsa-miR-1343-5p | 18 | | | | | | | | |
| | hsa-miR-1246 | 231 | | | | | | | | |
| | hsa-miR-4448 | 80 | | | | | | | | |
| | hsa-miR-6722-3p | 165 | | | | | | | | |
| | hsa-miR-6826-5p | 200 | | | | | | | | |
| | hsa-miR-29b-3p | 31 | | | | | | | | |
| | hsa-miR-1908-5p | 23 | | | | | | | | |
| | hsa-miR-6840-3p | 203 | | | | | | | | |
| | hsa-miR-3197 | 43 | | | | | | | | |
| | hsa-miR-371b-5p | 59 | | | | | | | | |
| | hsa-miR-4433a-3p | 75 | | | | | | | | |
| | hsa-miR-4534 | 97 | | | | | | | | |
| | hsa-miR-6816-5p | 197 | | | | | | | | |
| | hsa-miR-6800-5p | 193 | | | | | | | | |
| | hsa-miR-150-3p | 236 | | | | | | | | |
| | hsa-miR-296-3p | 30 | | | | | | | | |
| | hsa-miR-4771 | 135 | | | | | | | | |
| | hsa-miR-1908-3p | 22 | | | | | | | | |
| | hsa-miR-4298 | 68 | | | | | | | | |
| | hsa-miR-6774-5p | 181 | | | | | | | | |
| | hsa-miR-615-5p | 155 | | | | | | | | |
| | hsa-miR-4741 | 131 | | | | | | | | |
| | hsa-miR-1227-5p | 7 | | | | | | | | |
| | hsa-miR-1185-1-3p | 2 | | | | | | | | |
| | hsa-miR-6765-3p | 176 | | | | | | | | |
| | hsa-miR-6741-5p | 169 | | | | | | | | |
| | hsa-miR-5739 | 147 | | | | | | | | |
| | hsa-miR-373-5p | 60 | | | | | | | | |
| | hsa-miR-663a | 240 | | | | | | | | |
| | hsa-miR-1228-5p | 9 | | | | | | | | |
| | hsa-miR-642b-3p | 157 | | | | | | | | |
| | hsa-miR-4728-5p | 126 | | | | | | | | |
| | hsa-miR-937-5p | 228 | | | | | | | | |
| | hsa-miR-887-3p | 227 | | | | | | | | |
| | hsa-miR-6124 | 151 | | | | | | | | |
| | hsa-miR-6075 | 148 | | | | | | | | |
| | hsa-miR-6778-5p | 183 | | | | | | | | |
| | hsa-miR-6762-5p | 175 | | | | | | | | |
| | hsa-miR-4484 | 90 | | | | | | | | |
| | hsa-miR-6087 | 1 | | | | | | | | |
| | hsa-miR-6760-5p | 174 | | | | | | | | |
| | hsa-miR-1237-5p | 10 | | | | | | | | |
| | hsa-miR-711 | 218 | | | | | | | | |
| | hsa-miR-4270 | 66 | | | | | | | | |
| | hsa-miR-4710 | 120 | | | | | | | | |
| | hsa-miR-5195-3p | 144 | | | | | | | | |
| | hsa-miR-128-2-5p | 16 | | | | | | | | |
| | hsa-miR-149-3p | 235 | | | | | | | | |
| | hsa-miR-1914-3p | 237 | | | | | | | | |
| | hsa-miR-4763-3p | 134 | | | | | | | | |
| | hsa-miR-6726-5p | 167 | | | | | | | | |
| | hsa-miR-1207-5p | 230 | | | | | | | | |
| | hsa-miR-4675 | 110 | | | | | | | | |
| | hsa-miR-328-5p | 46 | | | | | | | | |
| | hsa-miR-6716-5p | 163 | | | | | | | | |
| | hsa-miR-4455 | 83 | | | | | | | | |
| | hsa-miR-3619-3p | 50 | | | | | | | | |
| | hsa-miR-3160-5p | 35 | | | | | | | | |
| | hsa-miR-6724-5p | 166 | | | | | | | | |
| | hsa-miR-423-5p | 239 | | | | | | | | |
| | hsa-miR-92a-2-5p | 241 | | | | | | | | |
| | hsa-miR-4447 | 79 | | | | | | | | |
| | hsa-miR-3621 | 52 | | | | | | | | |

TABLE 15-1-continued

| Number of miRNA miRNA marker | SEQ ID NO | Training cohort | | | | Validation cohort | | | |
|---|---|---|---|---|---|---|---|---|---|
| | | Sensitivity | Specificity | Accuracy | AUC | Sensitivity | Specificity | Accuracy | AUC |
| hsa-miR-4739 | 129 | | | | | | | | |
| hsa-miR-6132 | 153 | | | | | | | | |
| hsa-miR-6791-5p | 191 | | | | | | | | |
| hsa-miR-4725-3p | 123 | | | | | | | | |
| hsa-miR-3158-5p | 34 | | | | | | | | |
| hsa-miR-6766-3p | 178 | | | | | | | | |
| hsa-miR-6879-5p | 210 | | | | | | | | |
| hsa-miR-940 | 243 | | | | | | | | |
| hsa-miR-4750-5p | 132 | | | | | | | | |
| hsa-miR-3154 | 33 | | | | | | | | |
| hsa-miR-3663-3p | 57 | | | | | | | | |
| hsa-miR-4655-5p | 105 | | | | | | | | |
| hsa-miR-4649-5p | 102 | | | | | | | | |
| hsa-miR-4640-5p | 101 | | | | | | | | |
| hsa-miR-4783-3p | 136 | | | | | | | | |
| hsa-miR-6869-5p | 207 | | | | | | | | |
| hsa-miR-1343-3p | 17 | | | | | | | | |
| hsa-miR-6771-5p | 180 | | | | | | | | |
| hsa-miR-7108-3p | 216 | | | | | | | | |
| hsa-miR-3195 | 42 | | | | | | | | |
| hsa-miR-4687-3p | 111 | | | | | | | | |
| hsa-miR-1185-2-3p | 3 | | | | | | | | |
| hsa-miR-1225-5p | 6 | | | | | | | | |
| hsa-miR-4322 | 69 | | | | | | | | |
| hsa-miR-6088 | 150 | | | | | | | | |
| hsa-miR-6785-5p | 188 | | | | | | | | |
| hsa-miR-6777-5p | 182 | | | | | | | | |
| hsa-miR-4695-5p | 114 | | | | | | | | |
| hsa-miR-6880-3p | 211 | | | | | | | | |

TABLE 15-2

| Number of miRNA | Discriminant formula | Threshold |
|---|---|---|
| 104 | (−0.142443)*hsa-miR-498 + (0.343385)*hsa-miR-4658 + (0.431962)*hsa-miR-6717-5p + (0.002511)*hsa-miR-8073 + (−0.337601)*hsa-miR-92a-3p + (−0.029308)*hsa-miR-3652 + (−0.106071)*hsa-miR-6836-3p + (0.006541)*hsa-miR-1193 + (0.875478)*hsa-miR-4436b-5p + (−0.168653)*hsa-miR-6812-5p + (0.053152)*hsa-miR-4663 + (0.1271)*hsa-miR-4652-5p + (−0.591585)*hsa-miR-1343-5p + (0.083892)*hsa-miR-1246 + (−0.216299)*hsa-miR-4448 + (0.733901)*hsa-miR-6722-3p + (−0.137186)*hsa-miR-6826-5p + (0.036726)*hsa-miR-29b-3p + (2.472847)*hsa-miR-1908-5p + (−0.089103)*hsa-miR-6840-3p + (−1.496956)*hsa-miR-3197 + (0.336997)*hsa-miR-371b-5p + (0.239512)*hsa-miR-4433a-3p + (−0.478043)*hsa-miR-4534 + (0.099419)*hsa-miR-6816-5p + (−0.531065)*hsa-miR-6800-5p + (−0.259498)*hsa-miR-150-3p + (−0.449811)*hsa-miR-296-3p + (0.096368)*hsa-miR-4771 + (−0.038915)*hsa-miR-1908-3p + (−0.083576)*hsa-miR-4298 + (0.128277)*hsa-miR-6774-5p + (0.014162)*hsa-miR-615-5p + (−0.162203)*hsa-miR-4741 + (1.37632)*hsa-miR-1227-5p + (0.203311)*hsa-miR-1185-1-3p + (0.2478)*hsa-miR-6765-3p + (0.659776)*hsa-miR-6741-5p + (−0.422742)*hsa-miR-5739 + (−0.062029)*hsa-miR-373-5p + (0.417561)*hsa-miR-663a + (−3.034528)*hsa-miR-1228-5p + (0.156515)*hsa-miR-642b-3p + (−0.296177)*hsa-miR-4728-5p + (−0.798202)*hsa-miR-937-5p + (−0.004472)*hsa-miR-887-3p + (0.524208)*hsa-miR-6124 + (0.169608)*hsa-miR-6075 + (−0.183942)*hsa-miR-6778-5p + (−0.117397)*hsa-miR-6762-5p + (−0.458025)*hsa-miR-4484 + (−3.409511)*hsa-miR-6087 + (0.076078)*hsa-miR-6760-5p + (0.488415)*hsa-miR-1237-5p + (−0.034753)*hsa-miR-711 + (−0.380955)*hsa-miR-4270 + (−0.292588)*hsa-miR-4710 + (0.830594)*hsa-miR-5195-3p + (0.674073)*hsa-miR-128-2-5p + (−0.603804)*hsa-miR-149-3p + (−0.440067)*hsa-miR-1914-3p + (0.573642)*hsa-miR-4763-3p + (0.088688)*hsa-miR-6726-5p + (−0.007254)*hsa-miR-1207-5p + (0.614477)*hsa-miR-4675 + (0.216859)*hsa-miR-328-5p + (−0.069761)*hsa-miR-6716-5p + (0.381322)*hsa-miR-4455 + (0.748721)*hsa-miR-3619-3p + (0.045501)*hsa-miR-3160-5p + (2.573042)*hsa-miR-6724-5p + (−0.17771)*hsa-miR-423-5p + (0.011489)*hsa-miR-92a-2-5p + (−0.344767)*hsa-miR-4447 + (−1.078043)*hsa-miR-3621 + (0.794977)*hsa-miR-4739 + (0.368263)*hsa-miR-6132 + (−2.288217)*hsa-miR-6791-5p + (−1.158644)*hsa-miR-4725-3p + (−0.156604)*hsa-miR-3158-5p + (−0.254161)*hsa-miR-6766-3p + (−0.305986)*hsa-miR-6879-5p + (−0.236762)*hsa-miR-940 + (0.414075)*hsa-miR-4750-5p + (−0.071799)*hsa-miR-3154 + (0.996824)*hsa-miR-3663-3p + (−0.282559)*hsa-miR-4655-5p + (−1.520084)*hsa-miR-4649-5p + (−0.48277)*hsa-miR-4640-5p + (0.064498)*hsa-miR-4783-3p + (0.472275)*hsa-miR-6869-5p + (−0.955611)*hsa-miR-1343-3p + (−0.204386)*hsa-miR-6771-5p + (−0.12549)*hsa-miR-7108-3p + (−0A87461)*hsa-miR-3195 + (0.872821)*hsa-miR-4687-3p + (0.203465)*hsa-miR-1185-2-3p + (−0.087519)*hsa-miR-1225-5p + (−0.01442)*hsa-miR-4322 + (−0.583521)*hsa-miR-6088 + (1.301175)*hsa- | 0.65 |

TABLE 15-2-continued

| Number of miRNA | Discriminant formula | Threshold |
|---|---|---|
| | miR-6785-5p + (0.27416)*hsa-miR-6777-5p + (−0.307199)*hsa-miR-4695-5p + (−0.11423)*hsa-miR-6880-3p + 39.943135 | |

TABLE 16-1

| No. | Number of miRNA | miRNA marker | SEQ ID NO | Training cohort ||||  Validation cohort ||||
|---|---|---|---|---|---|---|---|---|---|---|---|
| | | | | Sensitivity | Specificity | Accuracy | AUC | Sensitivity | Specificity | Accuracy | AUC |
| 1 | 1 | hsa-miR-6087 | 1 | 0.92 | 0.83 | 0.86 | 0.90 | 0.90 | 0.84 | 0.86 | 0.91 |
| 2 | 2 | hsa-miR-4652-5p | 104 | 0.94 | 0.83 | 0.86 | 0.92 | 0.94 | 0.84 | 0.87 | 0.93 |
| | | hsa-miR-6087 | 1 | | | | | | | | |
| 3 | 3 | hsa-miR-4652-5p | 104 | 0.93 | 0.88 | 0.89 | 0.94 | 0.92 | 0.89 | 0.90 | 0.94 |
| | | hsa-miR-6087 | 1 | | | | | | | | |
| | | hsa-miR-6724-5p | 166 | | | | | | | | |
| 4 | 4 | hsa-miR-4652-5p | 104 | 0.95 | 0.87 | 0.90 | 0.94 | 0.93 | 0.88 | 0.89 | 0.94 |
| | | hsa-miR-6087 | 1 | | | | | | | | |
| | | hsa-miR-3160-5p | 35 | | | | | | | | |
| | | hsa-miR-6724-5p | 166 | | | | | | | | |
| 5 | 5 | hsa-miR-4658 | 107 | 0.94 | 0.89 | 0.91 | 0.94 | 0.92 | 0.90 | 0.91 | 0.95 |
| | | hsa-miR-4652-5p | 104 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| 6 | 7 | hsa-miR-4658 | 107 | 0.95 | 0.89 | 0.91 | 0.95 | 0.92 | 0.89 | 0.90 | 0.95 |
| | | hsa-miR-4652-5p | 104 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-3940-5p | 62 | | | | | | | | |
| | | hsa-miR-744-5p | 221 | | | | | | | | |
| 7 | 10 | hsa-miR-4658 | 107 | 0.94 | 0.90 | 0.91 | 0.95 | 0.92 | 0.92 | 0.92 | 0.96 |
| | | hsa-miR-4436b-5p | 76 | | | | | | | | |
| | | hsa-miR-4652-5p | 104 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-3940-5p | 62 | | | | | | | | |
| | | hsa-miR-744-5p | 221 | | | | | | | | |
| | | hsa-miR-6781-5p | 185 | | | | | | | | |
| 8 | 11 | hsa-miR-4658 | 107 | 0.95 | 0.91 | 0.92 | 0.96 | 0.92 | 0.91 | 0.91 | 0.96 |
| | | hsa-miR-4436b-5p | 76 | | | | | | | | |
| | | hsa-miR-4652-5p | 104 | | | | | | | | |
| | | hsa-miR-1185-1-3p | 2 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-3940-5p | 62 | | | | | | | | |
| | | hsa-miR-744-5p | 221 | | | | | | | | |
| | | hsa-miR-6781-5p | 185 | | | | | | | | |
| 9 | 12 | hsa-miR-4658 | 107 | 0.95 | 0.91 | 0.92 | 0.96 | 0.93 | 0.92 | 0.92 | 0.97 |
| | | hsa-miR-4436b-5p | 76 | | | | | | | | |
| | | hsa-miR-4652-5p | 104 | | | | | | | | |
| | | hsa-miR-371b-5p | 59 | | | | | | | | |
| | | hsa-miR-1185-1-3p | 2 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-3940-5p | 62 | | | | | | | | |
| | | hsa-miR-744-5p | 221 | | | | | | | | |
| | | hsa-miR-6781-5p | 185 | | | | | | | | |
| 10 | 13 | hsa-miR-4658 | 107 | 0.95 | 0.92 | 0.93 | 0.97 | 0.92 | 0.93 | 0.93 | 0.97 |
| | | hsa-miR-4436b-5p | 76 | | | | | | | | |
| | | hsa-miR-4652-5p | 104 | | | | | | | | |
| | | hsa-miR-371b-5p | 59 | | | | | | | | |
| | | hsa-miR-615-5p | 155 | | | | | | | | |
| | | hsa-miR-1185-1-3p | 2 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-6724-5p | 166 | | | | | | | | |
| | | hsa-miR-3940-5p | 62 | | | | | | | | |
| | | hsa-miR-744-5p | 221 | | | | | | | | |
| | | hsa-miR-6781-5p | 185 | | | | | | | | |
| 11 | 15 | hsa-miR-4658 | 107 | 0.95 | 0.93 | 0.93 | 0.97 | 0.92 | 0.93 | 0.93 | 0.97 |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-371b-5p | 59 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-3940-5p | 62 | | | | | | | | |
| | | hsa-miR-744-5p | 221 | | | | | | | | |
| | | hsa-miR-6781-5p | 185 | | | | | | | | |
| 12 | 19 | hsa-miR-4658 | 107 | 0.96 | 0.91 | 0.93 | 0.97 | 0.93 | 0.91 | 0.92 | 0.97 |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-3197 | 43 | | | | | | | | |
| | | hsa-miR-371b-5p | 59 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-6132 | 153 | | | | | | | | |
| | | hsa-miR-744-5p | 221 | | | | | | | | |
| | | hsa-miR-4725-3p | 123 | | | | | | | | |
| | | hsa-miR-6781-5p | 185 | | | | | | | | |
| 13 | 20 | hsa-miR-4658 | 107 | 0.97 | 0.91 | 0.93 | 0.97 | 0.94 | 0.91 | 0.92 | 0.97 |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-3197 | 43 | | | | | | | | |
| | | hsa-miR-371b-5p | 59 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-6132 | 153 | | | | | | | | |
| | | hsa-miR-744-5p | 221 | | | | | | | | |
| | | hsa-miR-4725-3p | 123 | | | | | | | | |
| | | hsa-miR-6781-5p | 185 | | | | | | | | |
| 14 | 21 | hsa-miR-4658 | 107 | 0.94 | 0.94 | 0.94 | 0.98 | 0.91 | 0.94 | 0.93 | 0.97 |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-3197 | 43 | | | | | | | | |
| | | hsa-miR-371b-5p | 59 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-6087 | 1 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-6132 | 153 | | | | | | | | |
| | | hsa-miR-744-5p | 221 | | | | | | | | |
| | | hsa-miR-4725-3p | 123 | | | | | | | | |
| | | hsa-miR-6781-5p | 185 | | | | | | | | |
| 15 | 24 | hsa-miR-4658 | 107 | 0.95 | 0.94 | 0.94 | 0.98 | 0.92 | 0.94 | 0.94 | 0.97 |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-3197 | 43 | | | | | | | | |
| | | hsa-miR-371b-5p | 59 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-4455 | 83 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-6132 | 153 | | | | | | | | |
| | | hsa-miR-744-5p | 221 | | | | | | | | |
| | | hsa-miR-4725-3p | 123 | | | | | | | | |
| | | hsa-miR-6781-5p | 185 | | | | | | | | |
| 16 | 25 | hsa-miR-4658 | 107 | 0.96 | 0.94 | 0.94 | 0.98 | 0.92 | 0.94 | 0.93 | 0.98 |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-3197 | 43 | | | | | | | | |
| | | hsa-miR-371b-5p | 59 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-4455 | 83 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |
| | | hsa-miR-744-5p | 221 | | | | | | | | |
| | | hsa-miR-4725-3p | 123 | | | | | | | | |
| | | hsa-miR-6781-5p | 185 | | | | | | | | |
| 17 | 26 | hsa-miR-4658 | 107 | 0.96 | 0.94 | 0.94 | 0.98 | 0.92 | 0.94 | 0.94 | 0.98 |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-3197 | 43 | | | | | | | | |
| | | hsa-miR-371b-5p | 59 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-4455 | 83 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |

TABLE 16-1-continued

| No. | Number of miRNA | miRNA marker | SEQ ID NO | Training cohort ||||  Validation cohort ||||
|---|---|---|---|---|---|---|---|---|---|---|---|
| | | | | Sensitivity | Specificity | Accuracy | AUC | Sensitivity | Specificity | Accuracy | AUC |
| | | hsa-miR-744-5p | 221 | | | | | | | | |
| | | hsa-miR-4725-3p | 123 | | | | | | | | |
| | | hsa-miR-6879-5p | 210 | | | | | | | | |
| | | hsa-miR-6781-5p | 185 | | | | | | | | |
| 18 | 29 | hsa-miR-4658 | 107 | 0.96 | 0.94 | 0.95 | 0.98 | 0.94 | 0.94 | 0.94 | 0.98 |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-3197 | 43 | | | | | | | | |
| | | hsa-miR-371b-5p | 59 | | | | | | | | |
| | | hsa-miR-150-3p | 236 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-4455 | 83 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |
| | | hsa-miR-4725-3p | 123 | | | | | | | | |
| | | hsa-miR-6879-5p | 210 | | | | | | | | |
| | | hsa-miR-6781-5p | 185 | | | | | | | | |
| | | hsa-miR-7107-5p | 215 | | | | | | | | |
| 19 | 31 | hsa-miR-4658 | 107 | 0.96 | 0.94 | 0.95 | 0.98 | 0.95 | 0.94 | 0.95 | 0.98 |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-3197 | 43 | | | | | | | | |
| | | hsa-miR-371b-5p | 59 | | | | | | | | |
| | | hsa-miR-150-3p | 236 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-4455 | 83 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-6781-5p | 185 | | | | | | | | |
| | | hsa-miR-7107-5p | 215 | | | | | | | | |
| 20 | 32 | hsa-miR-4658 | 107 | 0.97 | 0.94 | 0.95 | 0.99 | 0.95 | 0.94 | 0.95 | 0.98 |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-150-3p | 236 | | | | | | | | |
| | | hsa-miR-4298 | 68 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-4455 | 83 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-6781-5p | 185 | | | | | | | | |
| | | hsa-miR-7107-5p | 215 | | | | | | | | |
| 21 | 34 | hsa-miR-4658 | 107 | 0.97 | 0.95 | 0.95 | 0.99 | 0.95 | 0.95 | 0.95 | 0.98 |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-150-3p | 236 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-328-5p | 46 | | | | | | | | |
| | | hsa-miR-4455 | 83 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-6781-5p | 185 | | | | | | | | |
| | | hsa-miR-7108-3p | 216 | | | | | | | | |
| | | hsa-miR-7107-5p | 215 | | | | | | | | |
| 22 | 35 | hsa-miR-4658 | 107 | 0.95 | 0.96 | 0.96 | 0.99 | 0.93 | 0.96 | 0.95 | 0.98 |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-150-3p | 236 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-6781-5p | 185 | | | | | | | | |
| | | hsa-miR-7108-3p | 216 | | | | | | | | |
| | | hsa-miR-7107-5p | 215 | | | | | | | | |
| 23 | 40 | hsa-miR-4658 | 107 | 0.98 | 0.95 | 0.96 | 0.99 | 0.95 | 0.94 | 0.95 | 0.98 |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-150-3p | 236 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6741-5p | 169 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-6087 | 1 | | | | | | | | |
| | | hsa-miR-1914-3p | 237 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-3940-5p | 62 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-3917 | 61 | | | | | | | | |
| | | hsa-miR-7108-3p | 216 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| 24 | 43 | hsa-miR-4658 | 107 | 0.98 | 0.95 | 0.96 | 0.99 | 0.95 | 0.95 | 0.95 | 0.98 |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-150-3p | 236 | | | | | | | | |
| | | hsa-miR-4298 | 68 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6741-5p | 169 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-6794-5p | 192 | | | | | | | | |
| | | hsa-miR-6087 | 1 | | | | | | | | |
| | | hsa-miR-4710 | 120 | | | | | | | | |
| | | hsa-miR-1914-3p | 237 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-4750-5p | 132 | | | | | | | | |
| | | hsa-miR-3917 | 61 | | | | | | | | |
| | | hsa-miR-7108-3p | 216 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| 25 | 46 | hsa-miR-498 | 140 | 0.98 | 0.96 | 0.96 | 0.99 | 0.95 | 0.95 | 0.95 | 0.99 |
| | | hsa-miR-4658 | 107 | | | | | | | | |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-150-3p | 236 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6741-5p | 169 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-6087 | 1 | | | | | | | | |
| | | hsa-miR-6760-5p | 174 | | | | | | | | |
| | | hsa-miR-4710 | 120 | | | | | | | | |
| | | hsa-miR-1914-3p | 237 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-4750-5p | 132 | | | | | | | | |
| | | hsa-miR-3917 | 61 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| 26 | 50 | hsa-miR-498 | 140 | 0.98 | 0.96 | 0.97 | 0.99 | 0.95 | 0.95 | 0.95 | 0.99 |
| | | hsa-miR-4658 | 107 | | | | | | | | |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4652-5p | 104 | | | | | | | | |

TABLE 16-1-continued

| No. | Number of miRNA | miRNA marker | SEQ ID NO | Training cohort ||||  Validation cohort ||||
|---|---|---|---|---|---|---|---|---|---|---|---|
| | | | | Sensitivity | Specificity | Accuracy | AUC | Sensitivity | Specificity | Accuracy | AUC |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-150-3p | 236 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6741-5p | 169 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-6087 | 1 | | | | | | | | |
| | | hsa-miR-6760-5p | 174 | | | | | | | | |
| | | hsa-miR-4710 | 120 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-4750-5p | 132 | | | | | | | | |
| | | hsa-miR-3917 | 61 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| 27 | 56 | hsa-miR-498 | 140 | 0.98 | 0.96 | 0.97 | 0.99 | 0.95 | 0.96 | 0.95 | 0.99 |
| | | hsa-miR-4658 | 107 | | | | | | | | |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6794-5p | 192 | | | | | | | | |
| | | hsa-miR-4467 | 87 | | | | | | | | |
| | | hsa-miR-6087 | 1 | | | | | | | | |
| | | hsa-miR-6760-5p | 174 | | | | | | | | |
| | | hsa-miR-4710 | 120 | | | | | | | | |
| | | hsa-miR-1914-3p | 237 | | | | | | | | |
| | | hsa-miR-4675 | 110 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-6879-5p | 210 | | | | | | | | |
| | | hsa-miR-4750-5p | 132 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 28 | 60 | hsa-miR-498 | 140 | 0.98 | 0.98 | 0.98 | 0.99 | 0.94 | 0.96 | 0.95 | 0.99 |
| | | hsa-miR-4658 | 107 | | | | | | | | |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6124 | 151 | | | | | | | | |
| | | hsa-miR-6794-5p | 192 | | | | | | | | |
| | | hsa-miR-4467 | 87 | | | | | | | | |
| | | hsa-miR-6087 | 1 | | | | | | | | |
| | | hsa-miR-6760-5p | 174 | | | | | | | | |
| | | hsa-miR-4710 | 120 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-3663-3p | 57 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 29 | 61 | hsa-miR-498 | 140 | 0.99 | 0.97 | 0.98 | 0.99 | 0.94 | 0.96 | 0.95 | 0.99 |
| | | hsa-miR-4658 | 107 | | | | | | | | |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6124 | 151 | | | | | | | | |
| | | hsa-miR-6794-5p | 192 | | | | | | | | |
| | | hsa-miR-4467 | 87 | | | | | | | | |
| | | hsa-miR-6087 | 1 | | | | | | | | |
| | | hsa-miR-6760-5p | 174 | | | | | | | | |
| | | hsa-miR-4710 | 120 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 30 | 62 | hsa-miR-498 | 140 | 0.99 | 0.98 | 0.98 | 1.00 | 0.94 | 0.96 | 0.95 | 0.99 |
| | | hsa-miR-4658 | 107 | | | | | | | | |
| | | hsa-miR-6717-5p | 164 | | | | | | | | |
| | | hsa-miR-4436b-5p | 76 | | | | | | | | |

TABLE 16-1-continued

| No. | Number of miRNA marker | miRNA | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-6124 | 151 | | | | | | | | |
| | | hsa-miR-6794-5p | 192 | | | | | | | | |
| | | hsa-miR-4467 | 87 | | | | | | | | |
| | | hsa-miR-6087 | 1 | | | | | | | | |
| | | hsa-miR-6760-5p | 174 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 31 | 65 | hsa-miR-498 | 140 | 0.98 | 0.99 | 0.99 | 1.00 | 0.92 | 0.97 | 0.96 | 0.99 |
| | | hsa-miR-4658 | 107 | | | | | | | | |
| | | hsa-miR-6717-5p | 164 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-3197 | 43 | | | | | | | | |
| | | hsa-miR-371b-5p | 59 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-4771 | 135 | | | | | | | | |
| | | hsa-miR-6510-5p | 158 | | | | | | | | |
| | | hsa-miR-615-5p | 155 | | | | | | | | |

TABLE 16-1-continued

| No. | Number of miRNA marker | miRNA | SEQ ID NO | Training cohort ||||Validation cohort ||||
|---|---|---|---|---|---|---|---|---|---|---|---|
| | | | | Sensitivity | Specificity | Accuracy | AUC | Sensitivity | Specificity | Accuracy | AUC |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6794-5p | 192 | | | | | | | | |
| | | hsa-miR-4467 | 87 | | | | | | | | |
| | | hsa-miR-6087 | 1 | | | | | | | | |
| | | hsa-miR-6760-5p | 174 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 32 | 71 | hsa-miR-498 | 140 | 0.98 | 0.99 | 0.99 | 1.00 | 0.92 | 0.98 | 0.96 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-4448 | 80 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-4771 | 135 | | | | | | | | |
| | | hsa-miR-6782-5p | 186 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-373-5p | 60 | | | | | | | | |
| | | hsa-miR-663a | 240 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-4467 | 87 | | | | | | | | |
| | | hsa-miR-6087 | 1 | | | | | | | | |
| | | hsa-miR-6760-5p | 174 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6749-5p | 173 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 33 | 75 | hsa-miR-498 | 140 | 0.99 | 0.99 | 0.99 | 1.00 | 0.94 | 0.97 | 0.96 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-4448 | 80 | | | | | | | | |
| | | hsa-miR-29b-3p | 31 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-4771 | 135 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4467 | 87 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-711 | 218 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6749-5p | 173 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 34 | 77 | hsa-miR-498 | 140 | 0.99 | 0.99 | 0.99 | 1.00 | 0.94 | 0.98 | 0.97 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-4448 | 80 | | | | | | | | |
| | | hsa-miR-29b-3p | 31 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |

TABLE 16-1-continued

| No. | Number of miRNA marker | miRNA | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4467 | 87 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-711 | 218 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6819-5p | 198 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6749-5p | 173 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 35 | 78 | hsa-miR-498 | 140 | 1.00 | 0.99 | 0.99 | 1.00 | 0.94 | 0.97 | 0.96 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-6780b-5p | 184 | | | | | | | | |
| | | hsa-miR-6722-3p | 165 | | | | | | | | |
| | | hsa-miR-29b-3p | 31 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |
| | | hsa-miR-1227-5p | 7 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-373-5p | 60 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4467 | 87 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-711 | 218 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4640-5p | 101 | | | | | | | | |
| | | hsa-miR-6749-5p | 173 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 36 | 85 | hsa-miR-498 | 140 | 1.00 | 0.99 | 0.99 | 1.00 | 0.95 | 0.97 | 0.97 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-4448 | 80 | | | | | | | | |
| | | hsa-miR-6722-3p | 165 | | | | | | | | |
| | | hsa-miR-29b-3p | 31 | | | | | | | | |
| | | hsa-miR-1908-5p | 23 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |
| | | hsa-miR-1227-5p | 7 | | | | | | | | |

TABLE 16-1-continued

| No. | Number of miRNA | miRNA marker | SEQ ID NO | Training cohort ||||  Validation cohort ||||
|---|---|---|---|---|---|---|---|---|---|---|---|
| | | | | Sensitivity | Specificity | Accuracy | AUC | Sensitivity | Specificity | Accuracy | AUC |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-5739 | 147 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4467 | 87 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-1237-5p | 10 | | | | | | | | |
| | | hsa-miR-711 | 218 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-940 | 243 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4649-5p | 102 | | | | | | | | |
| | | hsa-miR-4640-5p | 101 | | | | | | | | |
| | | hsa-miR-6749-5p | 173 | | | | | | | | |
| | | hsa-miR-6869-5p | 207 | | | | | | | | |
| | | hsa-miR-1343-3p | 17 | | | | | | | | |
| | | hsa-miR-7108-3p | 216 | | | | | | | | |
| | | hsa-miR-4687-3p | 111 | | | | | | | | |
| | | hsa-miR-1185-2-3p | 3 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 37 | 87 | hsa-miR-498 | 140 | 1.00 | 1.00 | 1.00 | 1.00 | 0.93 | 0.98 | 0.96 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-6836-3p | 202 | | | | | | | | |
| | | hsa-miR-4436b-5p | 76 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-4448 | 80 | | | | | | | | |
| | | hsa-miR-6722-3p | 165 | | | | | | | | |
| | | hsa-miR-29b-3p | 31 | | | | | | | | |
| | | hsa-miR-1908-5p | 23 | | | | | | | | |
| | | hsa-miR-3197 | 43 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |
| | | hsa-miR-1227-5p | 7 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-5739 | 147 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4467 | 87 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-1237-5p | 10 | | | | | | | | |
| | | hsa-miR-711 | 218 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-6803-5p | 195 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-940 | 243 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4649-5p | 102 | | | | | | | | |
| | | hsa-miR-4640-5p | 101 | | | | | | | | |
| | | hsa-miR-6749-5p | 173 | | | | | | | | |
| | | hsa-miR-6869-5p | 207 | | | | | | | | |
| | | hsa-miR-1343-3p | 17 | | | | | | | | |
| | | hsa-miR-6771-5p | 180 | | | | | | | | |
| | | hsa-miR-7108-3p | 216 | | | | | | | | |
| | | hsa-miR-4687-3p | 111 | | | | | | | | |
| | | hsa-miR-1185-2-3p | 3 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-7107-5p | 215 | | | | | | | | |
| | | hsa-miR-4695-5p | 114 | | | | | | | | |
| | | hsa-miR-6880-3p | 211 | | | | | | | | |
| 38 | 89 | hsa-miR-498 | 140 | 1.00 | 1.00 | 1.00 | 1.00 | 0.94 | 0.98 | 0.97 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |

TABLE 16-1-continued

| No. | Number of miRNA marker | SEQ ID NO | Training cohort | | | | Validation cohort | | | |
|---|---|---|---|---|---|---|---|---|---|---|
| | | | Sensitivity | Specificity | Accuracy | AUC | Sensitivity | Specificity | Accuracy | AUC |
| | hsa-miR-342-5p | 47 | | | | | | | | |
| | hsa-miR-6836-3p | 202 | | | | | | | | |
| | hsa-miR-4436b-5p | 76 | | | | | | | | |
| | hsa-miR-3648 | 54 | | | | | | | | |
| | hsa-miR-4663 | 108 | | | | | | | | |
| | hsa-miR-4652-5p | 104 | | | | | | | | |
| | hsa-miR-1343-5p | 18 | | | | | | | | |
| | hsa-miR-6780b-5p | 184 | | | | | | | | |
| | hsa-miR-4448 | 80 | | | | | | | | |
| | hsa-miR-6722-3p | 165 | | | | | | | | |
| | hsa-miR-29b-3p | 31 | | | | | | | | |
| | hsa-miR-1908-5p | 23 | | | | | | | | |
| | hsa-miR-6840-3p | 203 | | | | | | | | |
| | hsa-miR-3197 | 43 | | | | | | | | |
| | hsa-miR-371b-5p | 59 | | | | | | | | |
| | hsa-miR-4433a-3p | 75 | | | | | | | | |
| | hsa-miR-4534 | 97 | | | | | | | | |
| | hsa-miR-6800-5p | 193 | | | | | | | | |
| | hsa-miR-150-3p | 236 | | | | | | | | |
| | hsa-miR-296-3p | 30 | | | | | | | | |
| | hsa-miR-4771 | 135 | | | | | | | | |
| | hsa-miR-4298 | 68 | | | | | | | | |
| | hsa-miR-6782-5p | 186 | | | | | | | | |
| | hsa-miR-6510-5p | 158 | | | | | | | | |
| | hsa-miR-4741 | 131 | | | | | | | | |
| | hsa-miR-1227-5p | 7 | | | | | | | | |
| | hsa-miR-1185-1-3p | 2 | | | | | | | | |
| | hsa-miR-6765-3p | 176 | | | | | | | | |
| | hsa-miR-6741-5p | 169 | | | | | | | | |
| | hsa-miR-5739 | 147 | | | | | | | | |
| | hsa-miR-373-5p | 60 | | | | | | | | |
| | hsa-miR-663a | 240 | | | | | | | | |
| | hsa-miR-1228-5p | 9 | | | | | | | | |
| | hsa-miR-4728-5p | 126 | | | | | | | | |
| | hsa-miR-937-5p | 228 | | | | | | | | |
| | hsa-miR-887-3p | 227 | | | | | | | | |
| | hsa-miR-6124 | 151 | | | | | | | | |
| | hsa-miR-6075 | 148 | | | | | | | | |
| | hsa-miR-6794-5p | 192 | | | | | | | | |
| | hsa-miR-6778-5p | 183 | | | | | | | | |
| | hsa-miR-4484 | 90 | | | | | | | | |
| | hsa-miR-6087 | 1 | | | | | | | | |
| | hsa-miR-6760-5p | 174 | | | | | | | | |
| | hsa-miR-1237-5p | 10 | | | | | | | | |
| | hsa-miR-711 | 218 | | | | | | | | |
| | hsa-miR-4270 | 66 | | | | | | | | |
| | hsa-miR-4710 | 120 | | | | | | | | |
| | hsa-miR-5195-3p | 144 | | | | | | | | |
| | hsa-miR-149-3p | 235 | | | | | | | | |
| | hsa-miR-1914-3p | 237 | | | | | | | | |
| | hsa-miR-4675 | 110 | | | | | | | | |
| | hsa-miR-328-5p | 46 | | | | | | | | |
| | hsa-miR-4455 | 83 | | | | | | | | |
| | hsa-miR-3619-3p | 50 | | | | | | | | |
| | hsa-miR-3160-5p | 35 | | | | | | | | |
| | hsa-miR-6724-5p | 166 | | | | | | | | |
| | hsa-miR-6803-5p | 195 | | | | | | | | |
| | hsa-miR-423-5p | 239 | | | | | | | | |
| | hsa-miR-4447 | 79 | | | | | | | | |
| | hsa-miR-3621 | 52 | | | | | | | | |
| | hsa-miR-6132 | 153 | | | | | | | | |
| | hsa-miR-6791-5p | 191 | | | | | | | | |
| | hsa-miR-4725-3p | 123 | | | | | | | | |
| | hsa-miR-3158-5p | 34 | | | | | | | | |
| | hsa-miR-6766-3p | 178 | | | | | | | | |
| | hsa-miR-6879-5p | 210 | | | | | | | | |
| | hsa-miR-940 | 243 | | | | | | | | |
| | hsa-miR-4750-5p | 132 | | | | | | | | |
| | hsa-miR-3154 | 33 | | | | | | | | |
| | hsa-miR-3917 | 61 | | | | | | | | |
| | hsa-miR-3663-3p | 57 | | | | | | | | |
| | hsa-miR-4649-5p | 102 | | | | | | | | |
| | hsa-miR-4640-5p | 101 | | | | | | | | |
| | hsa-miR-6749-5p | 173 | | | | | | | | |
| | hsa-miR-6869-5p | 207 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-1343-3p | 17 | | | | | | | | |
| | | hsa-miR-6771-5p | 180 | | | | | | | | |
| | | hsa-miR-7108-3p | 216 | | | | | | | | |
| | | hsa-miR-4687-3p | 111 | | | | | | | | |
| | | hsa-miR-1185-2-3p | 3 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-4695-5p | 114 | | | | | | | | |
| | | hsa-miR-6880-3p | 211 | | | | | | | | |
| 39 | 91 | hsa-miR-498 | 140 | 1.00 | 1.00 | 1.00 | 1.00 | 0.94 | 0.98 | 0.97 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-342-5p | 47 | | | | | | | | |
| | | hsa-miR-6836-3p | 202 | | | | | | | | |
| | | hsa-miR-4436b-5p | 76 | | | | | | | | |
| | | hsa-miR-6812-5p | 196 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-6780b-5p | 184 | | | | | | | | |
| | | hsa-miR-4448 | 80 | | | | | | | | |
| | | hsa-miR-6722-3p | 165 | | | | | | | | |
| | | hsa-miR-29b-3p | 31 | | | | | | | | |
| | | hsa-miR-1908-5p | 23 | | | | | | | | |
| | | hsa-miR-6840-3p | 203 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-4298 | 68 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |
| | | hsa-miR-1227-5p | 7 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-5739 | 147 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-1237-5p | 10 | | | | | | | | |
| | | hsa-miR-711 | 218 | | | | | | | | |
| | | hsa-miR-4270 | 66 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4763-3p | 134 | | | | | | | | |
| | | hsa-miR-6726-5p | 167 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-423-5p | 239 | | | | | | | | |
| | | hsa-miR-4447 | 79 | | | | | | | | |

TABLE 16-1-continued

| No. | Number of miRNA | miRNA marker | SEQ ID NO | Training cohort ||||  Validation cohort ||||
|---|---|---|---|---|---|---|---|---|---|---|---|
| | | | | Sensitivity | Specificity | Accuracy | AUC | Sensitivity | Specificity | Accuracy | AUC |
| | | hsa-miR-3621 | 52 | | | | | | | | |
| | | hsa-miR-4739 | 129 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-940 | 243 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4649-5p | 102 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-6771-5p | 180 | | | | | | | | |
| | | hsa-miR-7108-3p | 216 | | | | | | | | |
| | | hsa-miR-4687-3p | 111 | | | | | | | | |
| | | hsa-miR-1185-2-3p | 3 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-4695-5p | 114 | | | | | | | | |
| | | hsa-miR-6880-3p | 211 | | | | | | | | |
| 40 | 92 | hsa-miR-498 | 140 | 1.00 | 1.00 | 1.00 | 1.00 | 0.93 | 0.98 | 0.97 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-342-5p | 47 | | | | | | | | |
| | | hsa-miR-6836-3p | 202 | | | | | | | | |
| | | hsa-miR-4436b-5p | 76 | | | | | | | | |
| | | hsa-miR-6812-5p | 196 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-4448 | 80 | | | | | | | | |
| | | hsa-miR-6722-3p | 165 | | | | | | | | |
| | | hsa-miR-29b-3p | 31 | | | | | | | | |
| | | hsa-miR-1908-5p | 23 | | | | | | | | |
| | | hsa-miR-6840-3p | 203 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-4298 | 68 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |
| | | hsa-miR-1227-5p | 7 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-5739 | 147 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-642b-3p | 157 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-1237-5p | 10 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-711 | 218 | | | | | | | | |
| | | hsa-miR-4270 | 66 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4763-3p | 134 | | | | | | | | |
| | | hsa-miR-6726-5p | 167 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-4739 | 129 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-940 | 243 | | | | | | | | |
| | | hsa-miR-4750-5p | 132 | | | | | | | | |
| | | hsa-miR-3154 | 33 | | | | | | | | |
| | | hsa-miR-3917 | 61 | | | | | | | | |
| | | hsa-miR-3663-3p | 57 | | | | | | | | |
| | | hsa-miR-4655-5p | 105 | | | | | | | | |
| | | hsa-miR-4649-5p | 102 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-6771-5p | 180 | | | | | | | | |
| | | hsa-miR-7108-3p | 216 | | | | | | | | |
| | | hsa-miR-4687-3p | 111 | | | | | | | | |
| | | hsa-miR-1185-2-3p | 3 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-4695-5p | 114 | | | | | | | | |
| | | hsa-miR-6880-3p | 211 | | | | | | | | |
| 41 | 96 | hsa-miR-498 | 140 | 1.00 | 1.00 | 1.00 | 1.00 | 0.93 | 0.98 | 0.96 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-342-5p | 47 | | | | | | | | |
| | | hsa-miR-3652 | 55 | | | | | | | | |
| | | hsa-miR-6836-3p | 202 | | | | | | | | |
| | | hsa-miR-4436b-5p | 76 | | | | | | | | |
| | | hsa-miR-6812-5p | 196 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-1246 | 231 | | | | | | | | |
| | | hsa-miR-4448 | 80 | | | | | | | | |
| | | hsa-miR-6722-3p | 165 | | | | | | | | |
| | | hsa-miR-6826-5p | 200 | | | | | | | | |
| | | hsa-miR-29b-3p | 31 | | | | | | | | |
| | | hsa-miR-1908-5p | 23 | | | | | | | | |
| | | hsa-miR-6840-3p | 203 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-4298 | 68 | | | | | | | | |
| | | hsa-miR-6782-5p | 186 | | | | | | | | |
| | | hsa-miR-6510-5p | 158 | | | | | | | | |
| | | hsa-miR-4741 | 131 | | | | | | | | |

TABLE 16-1-continued

| No. | Number of miRNA marker | miRNA | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-1227-5p | 7 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-5739 | 147 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-642b-3p | 157 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-1237-5p | 10 | | | | | | | | |
| | | hsa-miR-711 | 218 | | | | | | | | |
| | | hsa-miR-4270 | 66 | | | | | | | | |
| | | hsa-miR-4710 | 120 | | | | | | | | |
| | | hsa-miR-5195-3p | 144 | | | | | | | | |
| | | hsa-miR-149-3p | 235 | | | | | | | | |
| | | hsa-miR-1914-3p | 237 | | | | | | | | |
| | | hsa-miR-4763-3p | 134 | | | | | | | | |
| | | hsa-miR-6726-5p | 167 | | | | | | | | |
| | | hsa-miR-4675 | 110 | | | | | | | | |
| | | hsa-miR-328-5p | 46 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-4739 | 129 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-940 | 243 | | | | | | | | |
| | | hsa-miR-4750-5p | 132 | | | | | | | | |
| | | hsa-miR-3154 | 33 | | | | | | | | |
| | | hsa-miR-3663-3p | 57 | | | | | | | | |
| | | hsa-miR-4655-5p | 105 | | | | | | | | |
| | | hsa-miR-4649-5p | 102 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-6771-5p | 180 | | | | | | | | |
| | | hsa-miR-7108-3p | 216 | | | | | | | | |
| | | hsa-miR-4687-3p | 111 | | | | | | | | |
| | | hsa-miR-1185-2-3p | 3 | | | | | | | | |
| | | hsa-miR-1225-5p | 6 | | | | | | | | |
| | | hsa-miR-4322 | 69 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-4695-5p | 114 | | | | | | | | |
| | | hsa-miR-6880-3p | 211 | | | | | | | | |
| 42 | 101 | hsa-miR-498 | 140 | 1.00 | 1.00 | 1.00 | 1.00 | 0.92 | 0.98 | 0.96 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-342-5p | 47 | | | | | | | | |
| | | hsa-miR-3652 | 55 | | | | | | | | |
| | | hsa-miR-6836-3p | 202 | | | | | | | | |
| | | hsa-miR-4436b-5p | 76 | | | | | | | | |
| | | hsa-miR-6812-5p | 196 | | | | | | | | |
| | | hsa-miR-3648 | 54 | | | | | | | | |
| | | hsa-miR-3648 | 54 | | | | | | | | |

TABLE 16-1-continued

| No. | Number of miRNA miRNA marker | SEQ ID NO | Training cohort | | | | Validation cohort | | | |
|---|---|---|---|---|---|---|---|---|---|---|
| | | | Sensitivity | Specificity | Accuracy | AUC | Sensitivity | Specificity | Accuracy | AUC |
| | hsa-miR-4652-5p | 104 | | | | | | | | |
| | hsa-miR-1343-5p | 18 | | | | | | | | |
| | hsa-miR-1246 | 231 | | | | | | | | |
| | hsa-miR-4448 | 80 | | | | | | | | |
| | hsa-miR-6722-3p | 165 | | | | | | | | |
| | hsa-miR-6826-5p | 200 | | | | | | | | |
| | hsa-miR-29b-3p | 31 | | | | | | | | |
| | hsa-miR-1908-5p | 23 | | | | | | | | |
| | hsa-miR-6840-3p | 203 | | | | | | | | |
| | hsa-miR-3197 | 43 | | | | | | | | |
| | hsa-miR-371b-5p | 59 | | | | | | | | |
| | hsa-miR-4433a-3p | 75 | | | | | | | | |
| | hsa-miR-4534 | 97 | | | | | | | | |
| | hsa-miR-6800-5p | 193 | | | | | | | | |
| | hsa-miR-150-3p | 236 | | | | | | | | |
| | hsa-miR-296-3p | 30 | | | | | | | | |
| | hsa-miR-4771 | 135 | | | | | | | | |
| | hsa-miR-4298 | 68 | | | | | | | | |
| | hsa-miR-6782-5p | 186 | | | | | | | | |
| | hsa-miR-6774-5p | 181 | | | | | | | | |
| | hsa-miR-6510-5p | 158 | | | | | | | | |
| | hsa-miR-4741 | 131 | | | | | | | | |
| | hsa-miR-1227-5p | 7 | | | | | | | | |
| | hsa-miR-1185-1-3p | 2 | | | | | | | | |
| | hsa-miR-6765-3p | 176 | | | | | | | | |
| | hsa-miR-6741-5p | 169 | | | | | | | | |
| | hsa-miR-5739 | 147 | | | | | | | | |
| | hsa-miR-373-5p | 60 | | | | | | | | |
| | hsa-miR-663a | 240 | | | | | | | | |
| | hsa-miR-1228-5p | 9 | | | | | | | | |
| | hsa-miR-642b-3p | 157 | | | | | | | | |
| | hsa-miR-4728-5p | 126 | | | | | | | | |
| | hsa-miR-937-5p | 228 | | | | | | | | |
| | hsa-miR-887-3p | 227 | | | | | | | | |
| | hsa-miR-6124 | 151 | | | | | | | | |
| | hsa-miR-6075 | 148 | | | | | | | | |
| | hsa-miR-6794-5p | 192 | | | | | | | | |
| | hsa-miR-6778-5p | 183 | | | | | | | | |
| | hsa-miR-6762-5p | 175 | | | | | | | | |
| | hsa-miR-4484 | 90 | | | | | | | | |
| | hsa-miR-6087 | 1 | | | | | | | | |
| | hsa-miR-6760-5p | 174 | | | | | | | | |
| | hsa-miR-1237-5p | 10 | | | | | | | | |
| | hsa-miR-711 | 218 | | | | | | | | |
| | hsa-miR-4270 | 66 | | | | | | | | |
| | hsa-miR-4710 | 120 | | | | | | | | |
| | hsa-miR-5195-3p | 144 | | | | | | | | |
| | hsa-miR-128-2-5p | 16 | | | | | | | | |
| | hsa-miR-149-3p | 235 | | | | | | | | |
| | hsa-miR-1914-3p | 237 | | | | | | | | |
| | hsa-miR-4763-3p | 134 | | | | | | | | |
| | hsa-miR-6726-5p | 167 | | | | | | | | |
| | hsa-miR-1207-5p | 230 | | | | | | | | |
| | hsa-miR-4675 | 110 | | | | | | | | |
| | hsa-miR-328-5p | 46 | | | | | | | | |
| | hsa-miR-4455 | 83 | | | | | | | | |
| | hsa-miR-3619-3p | 50 | | | | | | | | |
| | hsa-miR-3160-5p | 35 | | | | | | | | |
| | hsa-miR-6724-5p | 166 | | | | | | | | |
| | hsa-miR-423-5p | 239 | | | | | | | | |
| | hsa-miR-4447 | 79 | | | | | | | | |
| | hsa-miR-3621 | 52 | | | | | | | | |
| | hsa-miR-4739 | 129 | | | | | | | | |
| | hsa-miR-6132 | 153 | | | | | | | | |
| | hsa-miR-6791-5p | 191 | | | | | | | | |
| | hsa-miR-4725-3p | 123 | | | | | | | | |
| | hsa-miR-3158-5p | 34 | | | | | | | | |
| | hsa-miR-6766-3p | 178 | | | | | | | | |
| | hsa-miR-6879-5p | 210 | | | | | | | | |
| | hsa-miR-940 | 243 | | | | | | | | |
| | hsa-miR-4750-5p | 132 | | | | | | | | |
| | hsa-miR-3154 | 33 | | | | | | | | |
| | hsa-miR-3663-3p | 57 | | | | | | | | |
| | hsa-miR-4655-5p | 105 | | | | | | | | |
| | hsa-miR-4649-5p | 102 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-6771-5p | 180 | | | | | | | | |
| | | hsa-miR-7108-3p | 216 | | | | | | | | |
| | | hsa-miR-3195 | 42 | | | | | | | | |
| | | hsa-miR-4687-3p | 111 | | | | | | | | |
| | | hsa-miR-1185-2-3p | 3 | | | | | | | | |
| | | hsa-miR-1225-5p | 6 | | | | | | | | |
| | | hsa-miR-4322 | 69 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-4695-5p | 114 | | | | | | | | |
| | | hsa-miR-6880-3p | 211 | | | | | | | | |
| 43 | 103 | hsa-miR-498 | 140 | 1.00 | 1.00 | 1.00 | 1.00 | 0.92 | 0.98 | 0.96 | 0.99 |
| | | hsa-miR-4658 | 107 | | | | | | | | |
| | | hsa-miR-6717-5p | 164 | | | | | | | | |
| | | hsa-miR-92a-3p | 242 | | | | | | | | |
| | | hsa-miR-3652 | 55 | | | | | | | | |
| | | hsa-miR-6836-3p | 202 | | | | | | | | |
| | | hsa-miR-4436b-5p | 76 | | | | | | | | |
| | | hsa-miR-6812-5p | 196 | | | | | | | | |
| | | hsa-miR-3648 | 54 | | | | | | | | |
| | | hsa-miR-4663 | 108 | | | | | | | | |
| | | hsa-miR-4652-5p | 104 | | | | | | | | |
| | | hsa-miR-1343-5p | 18 | | | | | | | | |
| | | hsa-miR-1246 | 231 | | | | | | | | |
| | | hsa-miR-4448 | 80 | | | | | | | | |
| | | hsa-miR-6722-3p | 165 | | | | | | | | |
| | | hsa-miR-6826-5p | 200 | | | | | | | | |
| | | hsa-miR-29b-3p | 31 | | | | | | | | |
| | | hsa-miR-1908-5p | 23 | | | | | | | | |
| | | hsa-miR-6840-3p | 203 | | | | | | | | |
| | | hsa-miR-3197 | 43 | | | | | | | | |
| | | hsa-miR-371b-5p | 59 | | | | | | | | |
| | | hsa-miR-4433a-3p | 75 | | | | | | | | |
| | | hsa-miR-4534 | 97 | | | | | | | | |
| | | hsa-miR-6800-5p | 193 | | | | | | | | |
| | | hsa-miR-150-3p | 236 | | | | | | | | |
| | | hsa-miR-296-3p | 30 | | | | | | | | |
| | | hsa-miR-4771 | 135 | | | | | | | | |
| | | hsa-miR-1908-3p | 22 | | | | | | | | |
| | | hsa-miR-4298 | 68 | | | | | | | | |
| | | hsa-miR-6782-5p | 186 | | | | | | | | |
| | | hsa-miR-6774-5p | 181 | | | | | | | | |
| | | hsa-miR-6510-5p | 158 | | | | | | | | |
| | | hsa-miR-615-5p | 155 | | | | | | | | |
| | | hsa-miR-4741 | 131 | | | | | | | | |
| | | hsa-miR-1227-5p | 7 | | | | | | | | |
| | | hsa-miR-1185-1-3p | 2 | | | | | | | | |
| | | hsa-miR-6765-3p | 176 | | | | | | | | |
| | | hsa-miR-6741-5p | 169 | | | | | | | | |
| | | hsa-miR-5739 | 147 | | | | | | | | |
| | | hsa-miR-373-5p | 60 | | | | | | | | |
| | | hsa-miR-663a | 240 | | | | | | | | |
| | | hsa-miR-1228-5p | 9 | | | | | | | | |
| | | hsa-miR-642b-3p | 157 | | | | | | | | |
| | | hsa-miR-4728-5p | 126 | | | | | | | | |
| | | hsa-miR-937-5p | 228 | | | | | | | | |
| | | hsa-miR-887-3p | 227 | | | | | | | | |
| | | hsa-miR-6124 | 151 | | | | | | | | |
| | | hsa-miR-6075 | 148 | | | | | | | | |
| | | hsa-miR-6794-5p | 192 | | | | | | | | |
| | | hsa-miR-6778-5p | 183 | | | | | | | | |
| | | hsa-miR-6762-5p | 175 | | | | | | | | |
| | | hsa-miR-4484 | 90 | | | | | | | | |
| | | hsa-miR-6087 | 1 | | | | | | | | |
| | | hsa-miR-6760-5p | 174 | | | | | | | | |
| | | hsa-miR-1237-5p | 10 | | | | | | | | |
| | | hsa-miR-711 | 218 | | | | | | | | |
| | | hsa-miR-4270 | 66 | | | | | | | | |
| | | hsa-miR-4710 | 120 | | | | | | | | |
| | | hsa-miR-5195-3p | 144 | | | | | | | | |
| | | hsa-miR-128-2-5p | 16 | | | | | | | | |

TABLE 16-1-continued

| No. | Number of miRNA | miRNA marker | SEQ ID NO | Training cohort | | | | Validation cohort | | | |
|---|---|---|---|---|---|---|---|---|---|---|---|
| | | | | Sensitivity | Specificity | Accuracy | AUC | Sensitivity | Specificity | Accuracy | AUC |
| | | hsa-miR-149-3p | 235 | | | | | | | | |
| | | hsa-miR-1914-3p | 237 | | | | | | | | |
| | | hsa-miR-4763-3p | 134 | | | | | | | | |
| | | hsa-miR-6726-5p | 167 | | | | | | | | |
| | | hsa-miR-1207-5p | 230 | | | | | | | | |
| | | hsa-miR-4675 | 110 | | | | | | | | |
| | | hsa-miR-328-5p | 46 | | | | | | | | |
| | | hsa-miR-6716-5p | 163 | | | | | | | | |
| | | hsa-miR-4455 | 83 | | | | | | | | |
| | | hsa-miR-3619-3p | 50 | | | | | | | | |
| | | hsa-miR-3160-5p | 35 | | | | | | | | |
| | | hsa-miR-6724-5p | 166 | | | | | | | | |
| | | hsa-miR-423-5p | 239 | | | | | | | | |
| | | hsa-miR-4447 | 79 | | | | | | | | |
| | | hsa-miR-3621 | 52 | | | | | | | | |
| | | hsa-miR-4739 | 129 | | | | | | | | |
| | | hsa-miR-6132 | 153 | | | | | | | | |
| | | hsa-miR-6791-5p | 191 | | | | | | | | |
| | | hsa-miR-4725-3p | 123 | | | | | | | | |
| | | hsa-miR-3158-5p | 34 | | | | | | | | |
| | | hsa-miR-6766-3p | 178 | | | | | | | | |
| | | hsa-miR-6879-5p | 210 | | | | | | | | |
| | | hsa-miR-940 | 243 | | | | | | | | |
| | | hsa-miR-4750-5p | 132 | | | | | | | | |
| | | hsa-miR-3154 | 33 | | | | | | | | |
| | | hsa-miR-3663-3p | 57 | | | | | | | | |
| | | hsa-miR-4655-5p | 105 | | | | | | | | |
| | | hsa-miR-4649-5p | 102 | | | | | | | | |
| | | hsa-miR-4640-5p | 101 | | | | | | | | |
| | | hsa-miR-6869-5p | 207 | | | | | | | | |
| | | hsa-miR-1343-3p | 17 | | | | | | | | |
| | | hsa-miR-6771-5p | 180 | | | | | | | | |
| | | hsa-miR-7108-3p | 216 | | | | | | | | |
| | | hsa-miR-3195 | 42 | | | | | | | | |
| | | hsa-miR-4687-3p | 111 | | | | | | | | |
| | | hsa-miR-1185-2-3p | 3 | | | | | | | | |
| | | hsa-miR-1225-5p | 6 | | | | | | | | |
| | | hsa-miR-4322 | 69 | | | | | | | | |
| | | hsa-miR-6088 | 150 | | | | | | | | |
| | | hsa-miR-6785-5p | 188 | | | | | | | | |
| | | hsa-miR-6777-5p | 182 | | | | | | | | |
| | | hsa-miR-4695-5p | 114 | | | | | | | | |
| | | hsa-miR-6880-3p | 211 | | | | | | | | |

TABLE 16-2

| No. | Number of miRNA | Discriminant formula | Threshold |
|---|---|---|---|
| 1 | 1 | (−0.2257)*hsa-miR-6087 + 1.8523 | 0.31 |
| 2 | 2 | (0.0164)*hsa-miR-4652-5p + (−0.5961)*hsa-miR-6087 + 6.1988 | 0.32 |
| 3 | 3 | (0.16644)*hsa-miR-4652-5p + (−1.41622)*hsa-miR-6087 + (0.02095)*hsa-miR-6724-5p + 15.02714 | 0.36 |
| 4 | 4 | (0.1808861)*hsa-miR-4652-5p + (−1.5070947)*hsa-miR-6087 + (0.0007174)*hsa-miR-3160-5p + (0.1207611)*hsa-miR-6724-5p + 14.9701037 | 0.35 |
| 5 | 5 | (0.002311)*hsa-miR-4658 + (0.202102)*hsa-miR-4652-5p + (−1.666837)*hsa-miR-6087 + (0.019725)*hsa-miR-3160-5p + (0.296171)*hsa-miR-6724-5p + 14.733283 | 0.37 |
| 6 | 7 | (0.009276)*hsa-miR-4658 + (0.20617)*hsa-miR-4652-5p + (−1.751108)*hsa-miR-6087 + (0.024037)*hsa-miR-3160-5p + (0.378666)*hsa-miR-6724-5p + (−0.051277)*hsa-miR-3940-5p + (0.011812)*hsa-miR-744-5p + 15.225552 | 0.36 |
| 7 | 10 | (0.01504)*hsa-miR-4658 + (0.01562)*hsa-miR-4436b-5p + (0.20522)*hsa-miR-4652-5p + (−0.01556)*hsa-miR-4728-5p + (−1.8352)*hsa-miR-6087 + (0.02667)*hsa-miR-3160-5p + (0.43956)*hsa-miR-6724-5p + (−0.07772)*hsa-miR-3940-5p + (0.03616)*hsa-miR-744-5p + (−0.07753)*hsa-miR-6781-5p + 16.37274 | 0.38 |
| 8 | 11 | (0.03167)*hsa-miR-4658 + (0.09435)*hsa-miR-4436b-5p + (0.19419)*hsa-miR-4652-5p + (0.01619)*hsa-miR-1185-1-3p + (−0.11191)*hsa-miR-4728-5p + (−2.06954)*hsa-miR-6087 + (0.03364)*hsa-miR-3160-5p + (0.56712)*hsa-miR-6724-5p + (−0.14439)*hsa-miR-3940-5p + (0.10593)*hsa-miR-744-5p + (−0.32248)*hsa-miR-6781-5p + 20.26016 | 0.36 |
| 9 | 12 | (0.03713)*hsa-miR-4658 + (0.11667)*hsa-miR-4436b-5p + (0.189004)*hsa-miR-4652-5p + (0.005898)*hsa-miR-371b-5p + (0.039419)*hsa-miR-1185-1-3p + (−0.146518)*hsa-miR-4728-5p + (−2.150252)*hsa-miR-6087 + (0.035932)*hsa-miR- | 0.37 |

TABLE 16-2-continued

| No. | Number of miRNA | Discriminant formula | Threshold |
|---|---|---|---|
| 10 | 13 | 3160-5p + (0.608954)*hsa-miR-6724-5p + (−0.168797)*hsa-miR-3940-5p + (0.121841)*hsa-miR-744-5p + (−0.385564)*hsa-miR-6781-5p + 21.366641 (0.0429991)*hsa-miR-4658 + (0.1381963)*hsa-miR-4436b-5p + (0.1833864)*hsa-miR-4652-5p + (0.0179274)*hsa-miR-371b-5p + (0.0001277)*hsa-miR-615-5p + (0.0616732)*hsa-miR-1185-1-3p + (−0.1811192)*hsa-miR-4728-5p + (−2.2275877)*hsa-miR-6087 + (0.0377038)*hsa-miR-3160-5p + (0.6494946)*hsa-miR-6724-5p + (−0.1937249)*hsa-miR-3940-5p + (0.1366046)*hsa-miR-744-5p + (−0.4462679)*hsa-miR-6781-5p + 22.4212387 | 0.39 |
| 11 | 15 | (0.04868)*hsa-miR-4658 + (0.1596)*hsa-miR-4436b-5p + (0.01008)*hsa-miR-3648 + (0.17694)*hsa-miR-4652-5p + (0.02936)*hsa-miR-371b-5p + (0.01377)*hsa-miR-615-5p + (−0.03414)*hsa-miR-4741 + (0.08073)*hsa-miR-1185-1-3p + (−0.2158)*hsa-miR-4728-5p + (−2.29949)*hsa-miR-6087 + (0.0386)*hsa-miR-3160-5p + (0.67766)*hsa-miR-6724-5p + (−0.20413)*hsa-miR-3940-5p + (0.15988)*hsa-miR-744-5p + (−0.49283)*hsa-miR-6781-5p + 23.30088 | 0.40 |
| 12 | 19 | (0.0545478)*hsa-miR-4658 + (0.1795112)*hsa-miR-4436b-5p + (0.048759)*hsa-miR-3648 + (0.1692288)*hsa-miR-4652-5p + (−0.0684148)*hsa-miR-3197 + (0.0431115)*hsa-miR-371b-5p + (0.0302838)*hsa-miR-615-5p + (−0.1288749)*hsa-miR-4741 + (0.1008699)*hsa-miR-1185-1-3p + (−0.2404256)*hsa-miR-4728-5p + (−2.360469)*hsa-miR-6087 + (0.0404386)*hsa-miR-3160-5p + (0.6919792)*hsa-miR-6724-5p + (0.0004152)*hsa-miR-6819-5p + (−0.1806119)*hsa-miR-3940-5p + (0.0194496)*hsa-miR-6132 + (0.1868626)*hsa-miR-744-5p + (−0.0039427)*hsa-miR-4725-3p + (−0.4901648)*hsa-miR-6781-5p + 23.9287144 | 0.33 |
| 13 | 20 | (0.06046)*hsa-miR-4658 + (0.19475)*hsa-miR-4436b-5p + (0.09219)*hsa-miR-3648 + (0.16051)*hsa-miR-4652-5p + (−0.14362)*hsa-miR-3197 + (0.05679)*hsa-miR-371b-5p + (0.04647)*hsa-miR-615-5p + (−0.20246)*hsa-miR-4741 + (0.11951)*hsa-miR-1185-1-3p + (−0.01352)*hsa-miR-1228-5p + (−0.26292)*hsa-miR-4728-5p + (−2.39084)*hsa-miR-6087 + (0.04249)*hsa-miR-3160-5p + (0.70554)*hsa-miR-6724-5p + (0.0217)*hsa-miR-6819-5p + (−0.15258)*hsa-miR-3940-5p + (0.09549)*hsa-miR-6132 + (0.17448)*hsa-miR-744-5p + (−0.06463)*hsa-miR-4725-3p + (−0.47787)*hsa-miR-6781-5p + 24.23126 | 0.31 |
| 14 | 21 | (0.066135)*hsa-miR-4658 + (0.210367)*hsa-miR-4436b-5p + (0.136069)*hsa-miR-3648 + (0.151755)*hsa-miR-4652-5p + (−0.217055)*hsa-miR-3197 + (0.070549)*hsa-miR-371b-5p + (−0.001876)*hsa-miR-4298 + (0.061013)*hsa-miR-615-5p + (−0.263946)*hsa-miR-4741 + (0.139502)*hsa-miR-1185-1-3p + (−0.046762)*hsa-miR-1228-5p + (−0.285675)*hsa-miR-4728-5p + (−2.418102)*hsa-miR-6087 + (0.044076)*hsa-miR-3160-5p + (0.719969)*hsa-miR-6724-5p + (0.043873)*hsa-miR-6819-5p + (−0.124564)*hsa-miR-3940-5p + (0.182436)*hsa-miR-6132 + (0.148256)*hsa-miR-744-5p + (−0.128576)*hsa-miR-4725-3p + (−0.465727)*hsa-miR-6781-5p + 24.630655 | 0.42 |
| 15 | 24 | (0.07227)*hsa-miR-4658 + (0.225563)*hsa-miR-4436b-5p + (0.17854)*hsa-miR-3648 + (0.143323)*hsa-miR-4652-5p + (−0.283779)*hsa-miR-3197 + (0.084485)*hsa-miR-371b-5p + (−0.008989)*hsa-miR-4298 + (0.073689)*hsa-miR-615-5p + (−0.314832)*hsa-miR-4741 + (0.158462)*hsa-miR-1185-1-3p + (−0.083694)*hsa-miR-1228-5p + (−0.30272)*hsa-miR-4728-5p + (−0.012772)*hsa-miR-6794-5p + (−2.449261)*hsa-miR-6087 + (−0.003903)*hsa-miR-1914-3p + (0.001884)*hsa-miR-4455 + (0.045298)*hsa-miR-3160-5p + (0.733649)*hsa-miR-6724-5p + (0.068992)*hsa-miR-6819-5p + (−0.106286)*hsa-miR-3940-5p + (0.270347)*hsa-miR-6132 + (0.115944)*hsa-miR-744-5p + (−0.189204)*hsa-miR-4725-3p + (−0.45218)*hsa-miR-6781-5p + 25.200838 | 0.40 |
| 16 | 25 | (0.078288)*hsa-miR-4658 + (0.234354)*hsa-miR-4436b-5p + (0.223491)*hsa-miR-3648 + (0.13527)*hsa-miR-4652-5p + (−0.325939)*hsa-miR-3197 + (0.09817)*hsa-miR-371b-5p + (−0.009864)*hsa-miR-4298 + (0.087172)*hsa-miR-615-5p + (−0.33558)*hsa-miR-4741 + (0.173811)*hsa-miR-1185-1-3p + (−0.128776)*hsa-miR-1228-5p + (−0.311676)*hsa-miR-4728-5p + (−0.053572)*hsa-miR-6794-5p + (−2.490183)*hsa-miR-6087 + (−0.054436)*hsa-miR-1914-3p + (0.010721)*hsa-miR-4455 + (0.046006)*hsa-miR-3160-5p + (0.750534)*hsa-miR-6724-5p + (0.103104)*hsa-miR-6819-5p + (−0.106925)*hsa-miR-3940-5p + (−0.019416)*hsa-miR-3621 + (0.355495)*hsa-miR-6132 + (0.073636)*hsa-miR-744-5p + (−0.237701)*hsa-miR-4725-3p + (−0.429229)*hsa-miR-6781-5p + 26.170495 | 0.39 |
| 17 | 26 | (0.083783)*hsa-miR-4658 + (0.243613)*hsa-miR-4436b-5p + (0.269101)*hsa-miR-3648 + (0.127433)*hsa-miR-4652-5p + (−0.368851)*hsa-miR-3197 + (0.112057)*hsa-miR-371b-5p + (−0.010206)*hsa-miR-4298 + (0.100065)*hsa-miR-615-5p + (−0.350807)*hsa-miR-4741 + (0.188858)*hsa-miR-1185-1-3p + (−0.176919)*hsa-miR-1228-5p + (−0.32006)*hsa-miR-4728-5p + (−0.093763)*hsa-miR-6794-5p + (−2.53136)*hsa-miR-6087 + (−0.103708)*hsa-miR-1914-3p + (0.019746)*hsa-miR-4455 + (0.046344)*hsa-miR-3160-5p + (0.769953)*hsa-miR-6724-5p + (0.138504)*hsa-miR-6819-5p + (−0.102495)*hsa-miR-3940-5p + (−0.048051)*hsa-miR-3621 + (0.437372)*hsa-miR-6132 + (0.032543)*hsa-miR-744-5p + (−0.284094)*hsa-miR-4725-3p + (−0.006406409)*hsa-miR-6879-5p + (−0.404277)*hsa-miR-6781-5p + 27.158162 | 0.37 |
| 18 | 29 | (0.087755)*hsa-miR-4658 + (0.005605)*hsa-miR-6717-5p + (0.249795)*hsa-miR-4436b-5p + (0.310768)*hsa-miR-3648 + (0.118877)*hsa-miR-4652-5p + (−0.047254)*hsa-miR-1343-5p + (−0.403849)*hsa-miR-3197 + (0.127993)*hsa-miR-371b-5p + (−0.010857)*hsa-miR-150-3p + (−0.010423)*hsa-miR-4298 + (0.11002)*hsa-miR-615-5p + (−0.35805)*hsa-miR-4741 + (0.205029)*hsa- | 0.37 |

TABLE 16-2-continued

| No. | Number of miRNA | Discriminant formula | Threshold |
|---|---|---|---|
|  |  | miR-1185-1-3p + (−0.209555)*hsa-miR-1228-5p + (−0.326719)*hsa-miR-4728-5p + (−0.130857)*hsa-miR-6794-5p + (−2.574218)*hsa-miR-6087 + (−0.142216)*hsa-miR-1914-3p + (0.030074)*hsa-miR-4455 + (0.045325)*hsa-miR-3160-5p + (0.795003)*hsa-miR-6724-5p + (0.180288)*hsa-miR-6819-5p + (−0.093405)*hsa-miR-3940-5p + (−0.084781)*hsa-miR-3621 + (0.516536)*hsa-miR-6132 + (−0.321449)*hsa-miR-4725-3p + (−0.061921)*hsa-miR-6879-5p + (−0.350956)*hsa-miR-6781-5p + (0.010576)*hsa-miR-7107-5p + 28.17408 |  |
| 19 | 31 | (0.09131)*hsa-miR-4658 + (0.02516)*hsa-miR-6717-5p + (0.25587)*hsa-miR-4436b-5p + (0.34611)*hsa-miR-3648 + (0.11032)*hsa-miR-4652-5p + (−0.12588)*hsa-miR-1343-5p + (−0.45686)*hsa-miR-3197 + (0.14448)*hsa-miR-371b-5p + (−0.03123)*hsa-miR-150-3p + (−0.01034)*hsa-miR-4298 + (0.11806)*hsa-miR-615-5p + (−0.3519)*hsa-miR-4741 + (0.21967)*hsa-miR-1185-1-3p + (−0.21585)*hsa-miR-1228-5p + (−0.32729)*hsa-miR-4728-5p + (−0.04138)*hsa-miR-937-5p + (−0.14605)*hsa-miR-6794-5p + (−2.61942)*hsa-miR-6087 + (−0.17232)*hsa-miR-1914-3p + (0.04136)*hsa-miR-4455 + (0.04466)*hsa-miR-3160-5p + (0.82488)*hsa-miR-6724-5p + (0.20759)*hsa-miR-6819-5p + (−0.08453)*hsa-miR-3940-5p + (−0.11768)*hsa-miR-3621 + (0.55873)*hsa-miR-6132 + (−0.02947)*hsa-miR-6791-5p + (−0.36678)*hsa-miR-4725-3p + (−0.11332)*hsa-miR-6879-5p + (−0.28255)*hsa-miR-6781-5p + (0.04109)*hsa-miR-7107-5p + 29.49037 | 0.38 |
| 20 | 32 | (0.094791)*hsa-miR-4658 + (0.048625)*hsa-miR-6717-5p + (0.264267)*hsa-miR-4436b-5p + (0.380769)*hsa-miR-3648 + (0.10237)*hsa-miR-4652-5p + (−0.189993)*hsa-miR-1343-5p + (−0.514811)*hsa-miR-3197 + (0.161137)*hsa-miR-371b-5p + (−0.001127)*hsa-miR-4534 + (−0.051676)*hsa-miR-150-3p + (−0.009346)*hsa-miR-4298 + (0.124758)*hsa-miR-615-5p + (−0.338756)*hsa-miR-4741 + (0.232869)*hsa-miR-1185-1-3p + (−0.227344)*hsa-miR-1228-5p + (−0.323966)*hsa-miR-4728-5p + (−0.101405)*hsa-miR-937-5p + (−0.152489)*hsa-miR-6794-5p + (−2.667492)*hsa-miR-6087 + (−0.198581)*hsa-miR-1914-3p + (0.052818)*hsa-miR-4455 + (0.044682)*hsa-miR-3160-5p + (0.854099)*hsa-miR-6724-5p + (0.234472)*hsa-miR-6819-5p + (−0.073706)*hsa-miR-3940-5p + (−0.148964)*hsa-miR-3621 + (0.603871)*hsa-miR-6132 + (−0.100126)*hsa-miR-6791-5p + (−0.413578)*hsa-miR-4725-3p + (−0.155446)*hsa-miR-6879-5p + (−0.207971)*hsa-miR-6781-5p + (0.065701)*hsa-miR-7107-5p + 30.991858 | 0.36 |
| 21 | 34 | (0.10002)*hsa-miR-4658 + (0.07199)*hsa-miR-6717-5p + (0.27417)*hsa-miR-4436b-5p + (0.41365)*hsa-miR-3648 + (0.09473)*hsa-miR-4652-5p + (−0.24021)*hsa-miR-1343-5p + (−0.55453)*hsa-miR-3197 + (0.17548)*hsa-miR-371b-5p + (−0.01999)*hsa-miR-4534 + (−0.07048)*hsa-miR-150-3p + (−0.00682)*hsa-miR-4298 + (0.12988)*hsa-miR-615-5p + (−0.33497)*hsa-miR-4741 + (0.2437)*hsa-miR-1185-1-3p + (−0.24377)*hsa-miR-1228-5p + (−0.32132)*hsa-miR-4728-5p + (−0.16401)*hsa-miR-937-5p + (−0.15936)*hsa-miR-6794-5p + (−2.71298)*hsa-miR-6087 + (−0.2154)*hsa-miR-1914-3p + (0.01945)*hsa-miR-328-5p + (0.0661)*hsa-miR-4455 + (0.04892)*hsa-miR-3160-5p + (0.88757)*hsa-miR-6724-5p + (0.261)*hsa-miR-6819-5p + (−0.0618)*hsa-miR-3940-5p + (−0.17201)*hsa-miR-3621 + (0.65157)*hsa-miR-6132 + (−0.16978)*hsa-miR-6791-5p + (−0.46802)*hsa-miR-4725-3p + (−0.18535)*hsa-miR-6879-5p + (−0.1364)*hsa-miR-6781-5p + (−0.02025)*hsa-miR-7108-3p + (0.08954)*hsa-miR-7107-5p + 32.08743 | 0.38 |
| 22 | 35 | (0.106228)*hsa-miR-4658 + (0.092222)*hsa-miR-6717-5p + (0.284732)*hsa-miR-4436b-5p + (0.439982)*hsa-miR-3648 + (0.087768)*hsa-miR-4652-5p + (−0.288995)*hsa-miR-1343-5p + (−0.591559)*hsa-miR-3197 + (0.191085)*hsa-miR-371b-5p + (−0.043247)*hsa-miR-4534 + (−0.088277)*hsa-miR-150-3p + (−0.004687)*hsa-miR-4298 + (0.133882)*hsa-miR-615-5p + (−0.318195)*hsa-miR-4741 + (0.250237)*hsa-miR-1185-1-3p + (−0.291289)*hsa-miR-1228-5p + (−0.320973)*hsa-miR-4728-5p + (−0.219894)*hsa-miR-937-5p + (−0.171833)*hsa-miR-6794-5p + (−2.756634)*hsa-miR-6087 + (−0.234623)*hsa-miR-1914-3p + (0.132945)*hsa-miR-328-5p + (0.080522)*hsa-miR-4455 + (0.022315)*hsa-miR-3619-3p + (0.04827)*hsa-miR-3160-5p + (0.929673)*hsa-miR-6724-5p + (0.278857)*hsa-miR-6819-5p + (−0.038975)*hsa-miR-3940-5p + (−0.202026)*hsa-miR-3621 + (0.694335)*hsa-miR-6132 + (−0.237541)*hsa-miR-6791-5p + (−0.521173)*hsa-miR-4725-3p + (−0.216801)*hsa-miR-6879-5p + (−0.064791)*hsa-miR-6781-5p + (−0.044588)*hsa-miR-7108-3p + (0.115002)*hsa-miR-7107-5p + 32.284424 | 0.44 |
| 23 | 40 | (0.111973)*hsa-miR-4658 + (0.108513)*hsa-miR-6717-5p + (0.294888)*hsa-miR-4436b-5p + (0.460115)*hsa-miR-3648 + (0.082018)*hsa-miR-4652-5p + (−0.334555)*hsa-miR-1343-5p + (0.026567)*hsa-miR-6780b-5p + (−0.631472)*hsa-miR-3197 + (0.20582)*hsa-miR-371b-5p + (−0.06753)*hsa-miR-4534 + (−0.107515)*hsa-miR-150-3p + (−0.001806)*hsa-miR-4298 + (0.133652)*hsa-miR-615-5p + (−0.294458)*hsa-miR-4741 + (0.257498)*hsa-miR-1185-1-3p + (0.01499)*hsa-miR-6741-5p + (−0.343534)*hsa-miR-1228-5p + (−0.326044)*hsa-miR-4728-5p + (−0.268281)*hsa-miR-937-5p + (−0.188276)*hsa-miR-6794-5p + (−2.77578)*hsa-miR-6087 + (−0.25326)*hsa-miR-1914-3p + (0.253644)*hsa-miR-328-5p + (0.093434)*hsa-miR-4455 + (0.050867)*hsa-miR-3619-3p + (0.046344)*hsa-miR-3160-5p + (0.96627)*hsa-miR-6724-5p + (0.290969)*hsa-miR-6819-5p + (−0.050563)*hsa-miR-6803-5p + | 0.34 |

TABLE 16-2-continued

| No. | Number of miRNA | Discriminant formula | Threshold |
|---|---|---|---|
| | | (−0.004193)*hsa-miR-3940-5p + (−0.233693)*hsa-miR-3621 + (0.723891)*hsa-miR-6132 + (−0.2858)*hsa-miR-6791-5p + (−0.573832)*hsa-miR-4725-3p + (−0.249571)*hsa-miR-6879-5p + (−0.015465)*hsa-miR-3917 + (−0.068567)*hsa-miR-7108-3p + (0.014349)*hsa-miR-6777-5p + (0.140758)*hsa-miR-7107-5p + (−0.014775)*hsa-miR-4695-5p + 32.49695 | |
| 24 | 43 | (0.1182475)*hsa-miR-4658 + (0.1197803)*hsa-miR-6717-5p + (0.3060598)*hsa-miR-4436b-5p + (0.4666125)*hsa-miR-3648 + (0.0768109)*hsa-miR-4652-5p + (−0.3660127)*hsa-miR-1343-5p + (0.0779078)*hsa-miR-6780b-5p + (−0.6794313)*hsa-miR-3197 + (0.2182454)*hsa-miR-371b-5p + (−0.0872664)*hsa-miR-4534 + (−0.1263997)*hsa-miR-150-3p + (−0.0009949)*hsa-miR-4298 + (0.129891)*hsa-miR-615-5p + (−0.2532054)*hsa-miR-4741 + (0.265776)*hsa-miR-1185-1-3p + (0.0488473)*hsa-miR-6741-5p + (0.013876)*hsa-miR-663a + (−0.3824752)*hsa-miR-1228-5p + (−0.3356264)*hsa-miR-4728-5p + (−0.3169805)*hsa-miR-937-5p + (−0.2061267)*hsa-miR-6794-5p + (−2.7881773)*hsa-miR-6087 + (−0.0105542)*hsa-miR-4710 + (−0.277651)*hsa-miR-1914-3p + (0.3577039)*hsa-miR-328-5p + (0.1079767)*hsa-miR-4455 + (0.0793174)*hsa-miR-3619-3p + (0.0456678)*hsa-miR-3160-5p + (0.9874969)*hsa-miR-6724-5p + (0.2962764)*hsa-miR-6819-5p + (−0.1051374)*hsa-miR-6803-5p + (−0.002844)*hsa-miR-423-5p + (−0.2295274)*hsa-miR-3621 + (0.7297914)*hsa-miR-6132 + (−0.2860436)*hsa-miR-6791-5p + (−0.6332234)*hsa-miR-4725-3p + (−0.2612573)*hsa-miR-6879-5p + (0.001209)*hsa-miR-4750-5p + (−0.037947)*hsa-miR-3917 + (−0.0908195)*hsa-miR-7108-3p + (0.0324727)*hsa-miR-6777-5p + (0.1729576)*hsa-miR-7107-5p + (−0.0517144)*hsa-miR-4695-5p + 32.856908 | 0.34 |
| 25 | 46 | (−0.005352)*hsa-miR-498 + (0.132232)*hsa-miR-4658 + (0.130356)*hsa-miR-6717-5p + (0.325461)*hsa-miR-4436b-5p + (0.478366)*hsa-miR-3648 + (0.06741)*hsa-miR-4652-5p + (−0.41825)*hsa-miR-1343-5p + (0.190918)*hsa-miR-6780b-5p + (−0.785808)*hsa-miR-3197 + (0.239585)*hsa-miR-371b-5p + (−0.11711)*hsa-miR-4534 + (−0.160321)*hsa-miR-150-3p + (0.006674)*hsa-miR-6510-5p + (0.118254)*hsa-miR-615-5p + (−0.188815)*hsa-miR-4741 + (0.286654)*hsa-miR-1185-1-3p + (0.118796)*hsa-miR-6741-5p + (0.064285)*hsa-miR-663a + (−0.493968)*hsa-miR-1228-5p + (−0.370209)*hsa-miR-4728-5p + (−0.398178)*hsa-miR-937-5p + (−0.256312)*hsa-miR-6794-5p + (−2.807161)*hsa-miR-6087 + (0.005674)*hsa-miR-6760-5p + (−0.054083)*hsa-miR-4710 + (−0.315825)*hsa-miR-1914-3p + (0.571768)*hsa-miR-328-5p + (0.141972)*hsa-miR-4455 + (0.122801)*hsa-miR-3619-3p + (0.049254)*hsa-miR-3160-5p + (1.036085)*hsa-miR-6724-5p + (0.274732)*hsa-miR-6819-5p + (−0.179594)*hsa-miR-6803-5p + (−0.040321)*hsa-miR-423-5p + (−0.228042)*hsa-miR-3621 + (0.719533)*hsa-miR-6132 + (−0.282126)*hsa-miR-6791-5p + (−0.746826)*hsa-miR-4725-3p + (−0.279081)*hsa-miR-6879-5p + (0.030356)*hsa-miR-4750-5p + (−0.077094)*hsa-miR-3917 + (−0.134091)*hsa-miR-7108-3p + (0.041245)*hsa-miR-6785-5p + (0.061812)*hsa-miR-6777-5p + (0.213941)*hsa-miR-7107-5p + (−0.096421)*hsa-miR-4695-5p + 33.494632 | 0.37 |
| 26 | 50 | (−0.016183)*hsa-miR-498 + (0.140525)*hsa-miR-4658 + (0.138752)*hsa-miR-6717-5p + (0.335968)*hsa-miR-4436b-5p + (0.487273)*hsa-miR-3648 + (0.064953)*hsa-miR-4652-5p + (−0.432112)*hsa-miR-1343-5p + (0.235363)*hsa-miR-6780b-5p + (−0.850973)*hsa-miR-3197 + (0.248658)*hsa-miR-371b-5p + (−0.126924)*hsa-miR-4534 + (−0.174476)*hsa-miR-150-3p + (0.010062)*hsa-miR-6510-5p + (0.107952)*hsa-miR-615-5p + (−0.185519)*hsa-miR-4741 + (0.29531)*hsa-miR-1185-1-3p + (0.142125)*hsa-miR-6741-5p + (0.109416)*hsa-miR-663a + (−0.582482)*hsa-miR-1228-5p + (−0.387859)*hsa-miR-4728-5p + (−0.428943)*hsa-miR-937-5p + (−0.284587)*hsa-miR-6794-5p + (−2.807321)*hsa-miR-6087 + (0.012353)*hsa-miR-6760-5p + (−0.076258)*hsa-miR-4710 + (−0.313368)*hsa-miR-1914-3p + (0.003603)*hsa-miR-4675 + (0.661524)*hsa-miR-328-5p + (0.159843)*hsa-miR-4455 + (0.141437)*hsa-miR-3619-3p + (0.051031)*hsa-miR-3160-5p + (1.074899)*hsa-miR-6724-5p + (0.263537)*hsa-miR-6819-5p + (−0.214544)*hsa-miR-6803-5p + (−0.062736)*hsa-miR-423-5p + (−0.24758)*hsa-miR-3621 + (0.705093)*hsa-miR-6132 + (−0.258836)*hsa-miR-6791-5p + (−0.803341)*hsa-miR-4725-3p + (−0.266875)*hsa-miR-6879-5p + (0.03866)*hsa-miR-4750-5p + (−0.091571)*hsa-miR-3917 + (−0.005156)*hsa-miR-4640-5p + (0.013879)*hsa-miR-6869-5p + (−0.043434)*hsa-miR-1343-3p + (−0.150872)*hsa-miR-7108-3p + (0.092865)*hsa-miR-6785-5p + (0.076104)*hsa-miR-6777-5p + (0.210867)*hsa-miR-7107-5p + (−0.113818)*hsa-miR-4695-5p + 34.071261 | 0.37 |
| 27 | 56 | (−0.025128)*hsa-miR-498 + (0.150279)*hsa-miR-4658 + (0.146413)*hsa-miR-6717-5p + (0.346091)*hsa-miR-4436b-5p + (0.488747)*hsa-miR-3648 + (0.001855)*hsa-miR-4663 + (0.063758)*hsa-miR-4652-5p + (−0.432884)*hsa-miR-1343-5p + (0.261209)*hsa-miR-6780b-5p + (−0.909694)*hsa-miR-3197 + (0.257419)*hsa-miR-371b-5p + (−0.13728)*hsa-miR-4534 + (−0.029983)*hsa-miR-6800-5p + (−0.185616)*hsa-miR-150-3p + (0.010955)*hsa-miR-6510-5p + (0.090225)*hsa-miR-615-5p + (−0.173508)*hsa-miR-4741 + (0.297756)*hsa-miR-1185-1-3p + (0.019795)*hsa-miR-6765-3p + (0.160016)*hsa-miR-6741-5p + (0.151585)*hsa-miR-663a + (−0.678957)*hsa-miR-1228-5p + (−0.403793)*hsa-miR-4728-5p + (−0.453454)*hsa-miR-937-5p + (−0.30722)*hsa-miR-6794-5p + (0.006827)*hsa-miR-4467 + (−2.812003)*hsa-miR- | 0.40 |

TABLE 16-2-continued

| No. | Number of miRNA | Discriminant formula | Threshold |
|---|---|---|---|
| | | 6087 + (0.02017)*hsa-miR-6760-5p + (−0.099839)*hsa-miR-4710 + (−0.317017)*hsa-miR-1914-3p + (0.017153)*hsa-miR-4675 + (0.718407)*hsa-miR-328-5p + (0.17689)*hsa-miR-4455 + (0.161061)*hsa-miR-3619-3p + (0.051338)*hsa-miR-3160-5p + (1.118925)*hsa-miR-6724-5p + (0.253304)*hsa-miR-6819-5p + (−0.246149)*hsa-miR-6803-5p + (−0.08142)*hsa-miR-423-5p + (−0.280917)*hsa-miR-3621 + (0.683385)*hsa-miR-6132 + (−0.236794)*hsa-miR-6791-5p + (−0.851365)*hsa-miR-4725-3p + (−0.251738)*hsa-miR-6879-5p + (0.047986)*hsa-miR-4750-5p + (−0.102195)*hsa-miR-3917 + (0.013753)*hsa-miR-3663-3p + (−0.018254)*hsa-miR-4640-5p + (0.031663)*hsa-miR-6869-5p + (−0.109953)*hsa-miR-1343-3p + (−0.163764)*hsa-miR-7108-3p + (0.15356)*hsa-miR-6785-5p + (0.094727)*hsa-miR-6777-5p + (0.216418)*hsa-miR-7107-5p + (−0.128751)*hsa-miR-4695-5p + (−0.01156)*hsa-miR-6880-3p + 35.063631 | |
| 28 | 60 | (−0.033476)*hsa-miR-498 + (0.160482)*hsa-miR-4658 + (0.153174)*hsa-miR-6717-5p + (0.357836)*hsa-miR-4436b-5p + (0.491196)*hsa-miR-3648 + (0.006556)*hsa-miR-4663 + (0.06228)*hsa-miR-4652-5p + (−0.429191)*hsa-miR-1343-5p + (0.262843)*hsa-miR-6780b-5p + (−0.965673)*hsa-miR-3197 + (0.264128)*hsa-miR-371b-5p + (−0.149303)*hsa-miR-4534 + (−0.065688)*hsa-miR-6800-5p + (−0.195996)*hsa-miR-150-3p + (0.0131)*hsa-miR-6510-5p + (0.072706)*hsa-miR-615-5p + (−0.167745)*hsa-miR-4741 + (0.299395)*hsa-miR-1185-1-3p + (0.043399)*hsa-miR-6765-3p + (0.172159)*hsa-miR-6741-5p + (0.190925)*hsa-miR-663a + (−0.779519)*hsa-miR-1228-5p + (−0.416551)*hsa-miR-4728-5p + (−0.477394)*hsa-miR-937-5p + (0.002656)*hsa-miR-6124 + (−0.330452)*hsa-miR-6794-5p + (0.04873)*hsa-miR-4467 + (−2.827049)*hsa-miR-6087 + (0.028353)*hsa-miR-6760-5p + (−0.123965)*hsa-miR-4710 + (−0.004636)*hsa-miR-149-3p + (−0.322782)*hsa-miR-1914-3p + (0.033272)*hsa-miR-4675 + (0.769227)*hsa-miR-328-5p + (0.191889)*hsa-miR-4455 + (0.178119)*hsa-miR-3619-3p + (0.052353)*hsa-miR-3160-5p + (1.159867)*hsa-miR-6724-5p + (0.245814)*hsa-miR-6819-5p + (−0.283498)*hsa-miR-6803-5p + (−0.0966)*hsa-miR-423-5p + (−0.31385)*hsa-miR-3621 + (0.658198)*hsa-miR-6132 + (−0.228957)*hsa-miR-6791-5p + (−0.891201)*hsa-miR-4725-3p + (−0.001459)*hsa-miR-3158-5p + (−0.229001)*hsa-miR-6879-5p + (0.058559)*hsa-miR-4750-5p + (−0.002053)*hsa-miR-3154 + (−0.110177)*hsa-miR-3917 + (0.029693)*hsa-miR-3663-3p + (−0.028108)*hsa-miR-4640-5p + (0.046381)*hsa-miR-6869-5p + (−0.174581)*hsa-miR-1343-3p + (−0.176201)*hsa-miR-7108-3p + (0.218288)*hsa-miR-6785-5p + (0.112388)*hsa-miR-6777-5p + (0.219305)*hsa-miR-7107-5p + (−0.149239)*hsa-miR-4695-5p + (−0.024099)*hsa-miR-6880-3p + 36.341327 | 0.45 |
| 29 | 61 | (−0.041249)*hsa-miR-498 + (0.170449)*hsa-miR-4658 + (0.166117)*hsa-miR-6717-5p + (0.370018)*hsa-miR-4436b-5p + (0.493019)*hsa-miR-3648 + (0.011021)*hsa-miR-4663 + (0.060933)*hsa-miR-4652-5p + (−0.410439)*hsa-miR-1343-5p + (0.263795)*hsa-miR-6780b-5p + (−1.026295)*hsa-miR-3197 + (0.269733)*hsa-miR-371b-5p + (−0.162985)*hsa-miR-4534 + (−0.107377)*hsa-miR-6800-5p + (−0.205333)*hsa-miR-150-3p + (0.017645)*hsa-miR-6510-5p + (0.056041)*hsa-miR-615-5p + (−0.151309)*hsa-miR-4741 + (0.303372)*hsa-miR-1185-1-3p + (0.067986)*hsa-miR-6765-3p + (0.182823)*hsa-miR-6741-5p + (0.226446)*hsa-miR-663a + (−0.871093)*hsa-miR-1228-5p + (−0.430688)*hsa-miR-4728-5p + (−0.502611)*hsa-miR-937-5p + (0.014189)*hsa-miR-6124 + (−0.350623)*hsa-miR-6794-5p + (0.080354)*hsa-miR-4467 + (−2.849998)*hsa-miR-6087 + (0.035229)*hsa-miR-6760-5p + (−0.145723)*hsa-miR-4710 + (−0.116882)*hsa-miR-149-3p + (−0.324402)*hsa-miR-1914-3p + (0.053016)*hsa-miR-4675 + (0.82584)*hsa-miR-328-5p + (0.207109)*hsa-miR-4455 + (0.201113)*hsa-miR-3619-3p + (0.051902)*hsa-miR-3160-5p + (1.199124)*hsa-miR-6724-5p + (0.236232)*hsa-miR-6819-5p + (−0.340769)*hsa-miR-6803-5p + (−0.106507)*hsa-miR-423-5p + (−0.004904)*hsa-miR-4447 + (−0.353785)*hsa-miR-3621 + (0.640129)*hsa-miR-6132 + (−0.214828)*hsa-miR-6791-5p + (−0.928244)*hsa-miR-4725-3p + (−0.00906)*hsa-miR-3158-5p + (−0.201734)*hsa-miR-6879-5p + (0.070328)*hsa-miR-4750-5p + (−0.005114)*hsa-miR-3154 + (−0.115259)*hsa-miR-3917 + (0.041601)*hsa-miR-3663-3p + (−0.035124)*hsa-miR-4640-5p + (0.050827)*hsa-miR-6869-5p + (−0.235473)*hsa-miR-1343-3p + (−0.188808)*hsa-miR-7108-3p + (0.277703)*hsa-miR-6785-5p + (0.128857)*hsa-miR-6777-5p + (0.217732)*hsa-miR-7107-5p + (−0.170371)*hsa-miR-4695-5p + (−0.034768)*hsa-miR-6880-3p + 38.711879 | 0.42 |
| 30 | 62 | (−0.054116)*hsa-miR-498 + (0.180716)*hsa-miR-4658 + (0.177206)*hsa-miR-6717-5p + (0.386132)*hsa-miR-4436b-5p + (0.493623)*hsa-miR-3648 + (0.014476)*hsa-miR-4663 + (0.060374)*hsa-miR-4652-5p + (−0.402066)*hsa-miR-1343-5p + (0.27385)*hsa-miR-6780b-5p + (−1.081641)*hsa-miR-3197 + (0.276823)*hsa-miR-371b-5p + (−0.174718)*hsa-miR-4534 + (−0.148936)*hsa-miR-6800-5p + (−0.21214)*hsa-miR-150-3p + (0.019785)*hsa-miR-6510-5p + (0.038992)*hsa-miR-615-5p + (−0.13442)*hsa-miR-4741 + (0.307253)*hsa-miR-1185-1-3p + (0.090045)*hsa-miR-6765-3p + (0.194432)*hsa-miR-6741-5p + (0.253275)*hsa-miR-663a + (−0.960451)*hsa-miR-1228-5p + (−0.450253)*hsa-miR-4728-5p + (−0.520849)*hsa-miR-937-5p + (0.030634)*hsa-miR-6124 + (−0.362679)*hsa-miR-6794-5p + (0.114534)*hsa-miR-4467 + (−2.879717)*hsa-miR-6087 + (0.042176)*hsa-miR-6760-5p + (−0.166598)*hsa-miR-4710 + (0.029749)*hsa-miR-5195-3p + (−0.21547)*hsa-miR-149-3p + (−0.330451)*hsa-miR-1914-3p + (0.066854)*hsa-miR- | 0.41 |

TABLE 16-2-continued

| No. | Number of miRNA | Discriminant formula | Threshold |
|---|---|---|---|
|  |  | 4675 + (0.873268)*hsa-miR-328-5p + (0.221817)*hsa-miR-4455 + (0.224266)*hsa-miR-3619-3p + (0.050875)*hsa-miR-3160-5p + (1.242654)*hsa-miR-6724-5p + (0.216904)*hsa-miR-6819-5p + (−0.386273)*hsa-miR-6803-5p + (−0.115325)*hsa-miR-423-5p + (−0.026966)*hsa-miR-4447 + (−0.388486)*hsa-miR-3621 + (0.627783)*hsa-miR-6132 + (−0.213112)*hsa-miR-6791-5p + (−0.973223)*hsa-miR-4725-3p + (−0.017547)*hsa-miR-3158-5p + (−0.178927)*hsa-miR-6879-5p + (0.085963)*hsa-miR-4750-5p + (−0.009668)*hsa-miR-3154 + (−0.121832)*hsa-miR-3917 + (0.05462)*hsa-miR-3663-3p + (−0.036924)*hsa-miR-4640-5p + (0.048531)*hsa-miR-6869-5p + (−0.292652)*hsa-miR-1343-3p + (−0.198013)*hsa-miR-7108-3p + (0.339604)*hsa-miR-6785-5p + (0.145972)*hsa-miR-6777-5p + (0.213095)*hsa-miR-7107-5p + (−0.183618)*hsa-miR-4695-5p + (−0.044321)*hsa-miR-6880-3p + 40.9535 |  |
| 31 | 65 | (−0.0706564)*hsa-miR-498 + (0.1901728)*hsa-miR-4658 + (0.1869807)*hsa-miR-6717-5p + (0.4053566)*hsa-miR-4436b-5p + (0.4935334)*hsa-miR-3648 + (0.0168284)*hsa-miR-4663 + (0.0602181)*hsa-miR-4652-5p + (−0.3935623)*hsa-miR-1343-5p + (0.2874051)*hsa-miR-6780b-5p + (−1.1322383)*hsa-miR-3197 + (0.2843696)*hsa-miR-371b-5p + (−0.1882854)*hsa-miR-4534 + (−0.1937783)*hsa-miR-6800-5p + (−0.2187614)*hsa-miR-150-3p + (0.0073898)*hsa-miR-4771 + (0.0219823)*hsa-miR-6510-5p + (0.0249733)*hsa-miR-615-5p + (−0.1161974)*hsa-miR-4741 + (0.3109583)*hsa-miR-1185-1-3p + (0.1092951)*hsa-miR-6765-3p + (0.2048061)*hsa-miR-6741-5p + (−0.0058854)*hsa-miR-373-5p + (0.2752621)*hsa-miR-663a + (−1.0452884)*hsa-miR-1228-5p + (−0.4710701)*hsa-miR-4728-5p + (−0.5343161)*hsa-miR-937-5p + (−0.0008246)*hsa-miR-887-3p + (0.0487656)*hsa-miR-6124 + (−0.3731047)*hsa-miR-6794-5p + (0.1482058)*hsa-miR-4467 + (−2.9164623)*hsa-miR-6087 + (0.0480848)*hsa-miR-6760-5p + (−0.1878837)*hsa-miR-4710 + (0.074284)*hsa-miR-5195-3p + (−0.3036474)*hsa-miR-149-3p + (−0.3348046)*hsa-miR-1914-3p + (0.0772677)*hsa-miR-4675 + (0.9181764)*hsa-miR-328-5p + (0.2342347)*hsa-miR-4455 + (0.2465187)*hsa-miR-3619-3p + (0.0487489)*hsa-miR-3160-5p + (1.2896106)*hsa-miR-6724-5p + (0.1918112)*hsa-miR-6819-5p + (−0.4281541)*hsa-miR-6803-5p + (−0.1229311)*hsa-miR-423-5p + (−0.050782)*hsa-miR-4447 + (−0.4205827)*hsa-miR-3621 + (0.6191909)*hsa-miR-6132 + (−0.2207379)*hsa-miR-6791-5p + (−1.0221646)*hsa-miR-4725-3p + (−0.0260544)*hsa-miR-3158-5p + (−0.1572461)*hsa-miR-6879-5p + (0.1033496)*hsa-miR-4750-5p + (−0.0157931)*hsa-miR-3154 + (−0.1265015)*hsa-miR-3917 + (0.0684396)*hsa-miR-3663-3p + (−0.0388714)*hsa-miR-4640-5p + (0.0424731)*hsa-miR-6869-5p + (−0.3483934)*hsa-miR-1343-3p + (−0.2046679)*hsa-miR-7108-3p + (0.403265)*hsa-miR-6785-5p + (0.1652951)*hsa-miR-6777-5p + (0.2032236)*hsa-miR-7107-5p + (−0.1940787)*hsa-miR-4695-5p + (−0.0544247)*hsa-miR-6880-3p + 43.1328323 | 0.51 |
| 32 | 71 | (−0.087897)*hsa-miR-498 + (0.198892)*hsa-miR-4658 + (0.202208)*hsa-miR-6717-5p + (−0.01578)*hsa-miR-92a-3p + (0.429092)*hsa-miR-4436b-5p + (0.490161)*hsa-miR-3648 + (0.020375)*hsa-miR-4663 + (0.060216)*hsa-miR-4652-5p + (−0.403015)*hsa-miR-1343-5p + (0.305822)*hsa-miR-6780b-5p + (−0.003598)*hsa-miR-4448 + (−1.179904)*hsa-miR-3197 + (0.290834)*hsa-miR-371b-5p + (0.012247)*hsa-miR-4433a-3p + (−0.202324)*hsa-miR-4534 + (−0.233942)*hsa-miR-6800-5p + (−0.226403)*hsa-miR-150-3p + (0.01761)*hsa-miR-4771 + (0.003451)*hsa-miR-6782-5p + (0.026282)*hsa-miR-6510-5p + (0.009447)*hsa-miR-615-5p + (−0.085224)*hsa-miR-4741 + (0.312998)*hsa-miR-1185-1-3p + (0.126507)*hsa-miR-6765-3p + (0.208904)*hsa-miR-6741-5p + (−0.015006)*hsa-miR-373-5p + (0.314371)*hsa-miR-663a + (−1.124148)*hsa-miR-1228-5p + (−0.488472)*hsa-miR-4728-5p + (−0.546588)*hsa-miR-937-5p + (−0.005277)*hsa-miR-887-3p + (0.071211)*hsa-miR-6124 + (0.047877)*hsa-miR-6075 + (−0.387583)*hsa-miR-6794-5p + (0.140566)*hsa-miR-4467 + (−2.964722)*hsa-miR-6087 + (0.054865)*hsa-miR-6760-5p + (−0.2064)*hsa-miR-4710 + (0.11468)*hsa-miR-5195-3p + (−0.39274)*hsa-miR-149-3p + (−0.335697)*hsa-miR-1914-3p + (0.089891)*hsa-miR-4675 + (0.958668)*hsa-miR-328-5p + (0.246056)*hsa-miR-4455 + (0.270054)*hsa-miR-3619-3p + (0.04527)*hsa-miR-3160-5p + (1.336406)*hsa-miR-6724-5p + (0.143639)*hsa-miR-6819-5p + (−0.427856)*hsa-miR-6803-5p + (−0.125715)*hsa-miR-423-5p + (−0.075233)*hsa-miR-4447 + (−0.44821)*hsa-miR-3621 + (0.6037)*hsa-miR-6132 + (−0.23944)*hsa-miR-6791-5p + (−1.067383)*hsa-miR-4725-3p + (−0.032637)*hsa-miR-3158-5p + (−0.143252)*hsa-miR-6879-5p + (0.121177)*hsa-miR-4750-5p + (−0.023571)*hsa-miR-3154 + (−0.128874)*hsa-miR-3917 + (0.083554)*hsa-miR-3663-3p + (−0.040135)*hsa-miR-4640-5p + (−0.029186)*hsa-miR-6749-5p + (0.037319)*hsa-miR-6869-5p + (−0.398115)*hsa-miR-1343-3p + (−0.208272)*hsa-miR-7108-3p + (0.47369)*hsa-miR-6785-5p + (0.184781)*hsa-miR-6777-5p + (0.185309)*hsa-miR-7107-5p + (−0.205072)*hsa-miR-4695-5p + (−0.065419)*hsa-miR-6880-3p + 45.273324 | 0.52 |
| 33 | 75 | (−0.1059352)*hsa-miR-498 + (0.2063018)*hsa-miR-4658 + (0.2215912)*hsa-miR-6717-5p + (−0.0298688)*hsa-miR-92a-3p + (0.4583753)*hsa-miR-4436b-5p + (0.483301)*hsa-miR-3648 + (0.0242259)*hsa-miR-4663 + (0.0604766)*hsa-miR-4652-5p + (−0.4425081)*hsa-miR-1343-5p + (0.309457)*hsa-miR-6780b-5p + (−0.0173718)*hsa-miR-4448 + (0.0013542)*hsa-miR-29b-3p + (−1.2151182)*hsa-miR-3197 + (0.2981005)*hsa-miR-371b-5p + (0.0190017)*hsa-miR-4433a-3p + | 0.47 |

TABLE 16-2-continued

| No. | Number of miRNA | Discriminant formula | Threshold |
|---|---|---|---|
| | | (−0.2110239)*hsa-miR-4534 + (−0.2813926)*hsa-miR-6800-5p + (−0.2327499)*hsa-miR-150-3p + (0.026306)*hsa-miR-4771 + (0.0169428)*hsa-miR-6782-5p + (0.0279943)*hsa-miR-6510-5p + (−0.0577194)*hsa-miR-4741 + (0.3161462)*hsa-miR-1185-1-3p + (0.1408323)*hsa-miR-6765-3p + (0.2085074)*hsa-miR-6741-5p + (−0.0246274)*hsa-miR-373-5p + (0.3624389)*hsa-miR-663a + (−1.2041074)*hsa-miR-1228-5p + (−0.4910598)*hsa-miR-4728-5p + (−0.5566172)*hsa-miR-937-5p + (−0.0124466)*hsa-miR-887-3p + (0.0992655)*hsa-miR-6124 + (0.094522)*hsa-miR-6075 + (−0.3922484)*hsa-miR-6794-5p + (−0.014239)*hsa-miR-6778-5p + (0.1304415)*hsa-miR-4467 + (−0.0036718)*hsa-miR-4484 + (−2.9988301)*hsa-miR-6087 + (0.0599382)*hsa-miR-6760-5p + (−0.0001349)*hsa-miR-711 + (−0.2208925)*hsa-miR-4710 + (0.1507497)*hsa-miR-5195-3p + (−0A831057)*hsa-miR-149-3p + (−0.3419503)*hsa-miR-1914-3p + (0.1010775)*hsa-miR-4675 + (1.0016789)*hsa-miR-328-5p + (0.2573836)*hsa-miR-4455 + (0.2951085)*hsa-miR-3619-3p + (0.0427975)*hsa-miR-3160-5p + (1.3967438)*hsa-miR-6724-5p + (0.0905735)*hsa-miR-6819-5p + (−0.3985998)*hsa-miR-6803-5p + (−0.1262088)*hsa-miR-423-5p + (−0.0974308)*hsa-miR-4447 + (−0.4666724)*hsa-miR-3621 + (0.5846443)*hsa-miR-6132 + (−0.2716118)*hsa-miR-6791-5p + (−1.1000198)*hsa-miR-4725-3p + (−0.0399952)*hsa-miR-3158-5p + (−0.1353441)*hsa-miR-6879-5p + (0.1381561)*hsa-miR-4750-5p + (−0.0307913)*hsa-miR-3154 + (−0.128336)*hsa-miR-3917 + (0.1073239)*hsa-miR-3663-3p + (−0.0382458)*hsa-miR-4640-5p + (−0.0837819)*hsa-miR-6749-5p + (0.0397535)*hsa-miR-6869-5p + (−0.4512182)*hsa-miR-1343-3p + (−0.2102807)*hsa-miR-7108-3p + (−0.0399303)*hsa-miR-6088 + (0.5473916)*hsa-miR-6785-5p + (0.201801)*hsa-miR-6777-5p + (0.1708449)*hsa-miR-7107-5p + (−0.2136614)*hsa-miR-4695-5p + (−0.0752741)*hsa-miR-6880-3p + 47.5111149 | |
| 34 | 77 | (−0.1209)*hsa-miR-498 + (0.213408)*hsa-miR-4658 + (0.24116)*hsa-miR-6717-5p + (−0.044149)*hsa-miR-92a-3p + (0.483209)*hsa-miR-4436b-5p + (0.475983)*hsa-miR-3648 + (0.02733)*hsa-miR-4663 + (0.062769)*hsa-miR-4652-5p + (−0.450408)*hsa-miR-1343-5p + (0.323437)*hsa-miR-6780b-5p + (−0.032802)*hsa-miR-4448 + (0.006279)*hsa-miR-29b-3p + (−1.226251)*hsa-miR-3197 + (0.303712)*hsa-miR-371b-5p + (0.032248)*hsa-miR-4433a-3p + (−0.220094)*hsa-miR-4534 + (−0.318783)*hsa-miR-6800-5p + (−0.237086)*hsa-miR-150-3p + (−0.031189)*hsa-miR-296-3p + (0.034403)*hsa-miR-4771 + (0.022256)*hsa-miR-6782-5p + (0.031466)*hsa-miR-6510-5p + (−0.021855)*hsa-miR-4741 + (0.324482)*hsa-miR-1185-1-3p + (0.158538)*hsa-miR-6765-3p + (0.210632)*hsa-miR-6741-5p + (−0.033007)*hsa-miR-373-5p + (0.400391)*hsa-miR-663a + (−1.298882)*hsa-miR-1228-5p + (−0.485454)*hsa-miR-4728-5p + (−0.57533)*hsa-miR-937-5p + (−0.023379)*hsa-miR-887-3p + (0.134703)*hsa-miR-6124 + (0.132219)*hsa-miR-6075 + (−0.388436)*hsa-miR-6794-5p + (−0.032443)*hsa-miR-6778-5p + (0.11668)*hsa-miR-4467 + (−0.068978)*hsa-miR-4484 + (−3.031394)*hsa-miR-6087 + (0.062717)*hsa-miR-6760-5p + (−0.002455)*hsa-miR-711 + (−0.232653)*hsa-miR-4710 + (0.179487)*hsa-miR-5195-3p + (−0.563043)*hsa-miR-149-3p + (−0.354414)*hsa-miR-1914-3p + (0.114788)*hsa-miR-4675 + (1.015657)*hsa-miR-328-5p + (0.265782)*hsa-miR-4455 + (0.323327)*hsa-miR-3619-3p + (0.041269)*hsa-miR-3160-5p + (1.451381)*hsa-miR-6724-5p + (0.046169)*hsa-miR-6819-5p + (−0.364269)*hsa-miR-6803-5p + (−0.128832)*hsa-miR-423-5p + (−0.115745)*hsa-miR-4447 + (−0.481969)*hsa-miR-3621 + (0.583038)*hsa-miR-6132 + (−0.313497)*hsa-miR-6791-5p + (−1.115343)*hsa-miR-4725-3p + (−0.044796)*hsa-miR-3158-5p + (−0.002015)*hsa-miR-6766-3p + (−0.126645)*hsa-miR-6879-5p + (0.157733)*hsa-miR-4750-5p + (−0.038586)*hsa-miR-3154 + (−0.128243)*hsa-miR-3917 + (0.14884)*hsa-miR-3663-3p + (−0.049227)*hsa-miR-4640-5p + (−0.133682)*hsa-miR-6749-5p + (0.040222)*hsa-miR-6869-5p + (−0.507848)*hsa-miR-1343-3p + (−0.208462)*hsa-miR-7108-3p + (−0.08765)*hsa-miR-6088 + (0.621228)*hsa-miR-6785-5p + (0.221408)*hsa-miR-6777-5p + (0.15388)*hsa-miR-7107-5p + (−0.216837)*hsa-miR-4695-5p + (−0.083832)*hsa-miR-6880-3p + 49.825891 | 0.48 |
| 35 | 78 | (−0.134198)*hsa-miR-498 + (0.219152)*hsa-miR-4658 + (0.25441)*hsa-miR-6717-5p + (−0.05957)*hsa-miR-92a-3p + (0.513433)*hsa-miR-4436b-5p + (0.448752)*hsa-miR-3648 + (0.030009)*hsa-miR-4663 + (0.066355)*hsa-miR-4652-5p + (−0.466497)*hsa-miR-1343-5p + (0.329188)*hsa-miR-6780b-5p + (−0.045734)*hsa-miR-4448 + (0.035283)*hsa-miR-6722-3p + (0.01013)*hsa-miR-29b-3p + (−1.236716)*hsa-miR-3197 + (0.309181)*hsa-miR-371b-5p + (0.046528)*hsa-miR-4433a-3p + (−0.233746)*hsa-miR-4534 + (−0.352501)*hsa-miR-6800-5p + (−0.238099)*hsa-miR-150-3p + (−0.070535)*hsa-miR-296-3p + (0.043098)*hsa-miR-4771 + (0.024703)*hsa-miR-6782-5p + (0.032974)*hsa-miR-6510-5p + (−0.022481)*hsa-miR-4741 + (0.080601)*hsa-miR-1227-5p + (0.335657)*hsa-miR-1185-1-3p + (0.173929)*hsa-miR-6765-3p + (0.218937)*hsa-miR-6741-5p + (−0.040529)*hsa-miR-373-5p + (0.444955)*hsa-miR-663a + (−1.384992)*hsa-miR-1228-5p + (−0.470094)*hsa-miR-4728-5p + (−0.614166)*hsa-miR-937-5p + (−0.032715)*hsa-miR-887-3p + (0.176516)*hsa-miR-6124 + (0.172498)*hsa-miR-6075 + (−0.369372)*hsa-miR-6794-5p + (−0.053036)*hsa-miR-6778-5p + (0.110957)*hsa-miR-4467 + | 0.45 |

TABLE 16-2-continued

| No. | Number of miRNA | Discriminant formula | Threshold |
|---|---|---|---|
|  |  | (−0.120431)*hsa-miR-4484 + (−3.051244)*hsa-miR-6087 + (0.067061)*hsa-miR-6760-5p + (−0.008193)*hsa-miR-711 + (−0.241365)*hsa-miR-4710 + (0.215809)*hsa-miR-5195-3p + (−0.641022)*hsa-miR-149-3p + (−0.362125)*hsa-miR-1914-3p + (0.119243)*hsa-miR-4675 + (1.01775)*hsa-miR-328-5p + (0.273058)*hsa-miR-4455 + (0.354655)*hsa-miR-3619-3p + (0.040135)*hsa-miR-3160-5p + (1.499939)*hsa-miR-6724-5p + (−0.341082)*hsa-miR-6803-5p + (−0.131566)*hsa-miR-423-5p + (−0.136544)*hsa-miR-4447 + (−0.522359)*hsa-miR-3621 + (0.582169)*hsa-miR-6132 + (−0.363936)*hsa-miR-6791-5p + (−1.121977)*hsa-miR-4725-3p + (−0.050657)*hsa-miR-3158-5p + (−0.020979)*hsa-miR-6766-3p + (−0.115331)*hsa-miR-6879-5p + (0.176442)*hsa-miR-4750-5p + (−0.044578)*hsa-miR-3154 + (−0.124778)*hsa-miR-3917 + (0.20127)*hsa-miR-3663-3p + (−0.075031)*hsa-miR-4640-5p + (−0.176008)*hsa-miR-6749-5p + (0.046517)*hsa-miR-6869-5p + (−0.558776)*hsa-miR-1343-3p + (−0.203898)*hsa-miR-7108-3p + (−0.149234)*hsa-miR-6088 + (0.697578)*hsa-miR-6785-5p + (0.240261)*hsa-miR-6777-5p + (0.132853)*hsa-miR-7107-5p + (−0.219847)*hsa-miR-4695-5p + (−0.086883)*hsa-miR-6880-3p + 51.681384 |  |
| 36 | 85 | (−0.14581)*hsa-miR-498 + (0.22531)*hsa-miR-4658 + (0.26419)*hsa-miR-6717-5p + (−0.07407)*hsa-miR-92a-3p + (0.54527)*hsa-miR-4436b-5p + (0.41413)*hsa-miR-3648 + (0.03236)*hsa-miR-4663 + (0.06965)*hsa-miR-4652-5p + (−0.4972)*hsa-miR-1343-5p + (0.30052)*hsa-miR-6780b-5p + (−0.05883)*hsa-miR-4448 + (0.09166)*hsa-miR-6722-3p + (0.01424)*hsa-miR-29b-3p + (0.10705)*hsa-miR-1908-5p + (−1.25898)*hsa-miR-3197 + (0.31433)*hsa-miR-371b-5p + (0.05736)*hsa-miR-4433a-3p + (−0.24959)*hsa-miR-4534 + (−0.38816)*hsa-miR-6800-5p + (−0.23476)*hsa-miR-150-3p + (−0.11246)*hsa-miR-296-3p + (0.04962)*hsa-miR-4771 + (0.02654)*hsa-miR-6782-5p + (0.03949)*hsa-miR-6510-5p + (−0.02485)*hsa-miR-4741 + (0.19194)*hsa-miR-1227-5p + (0.33412)*hsa-miR-1185-1-3p + (0.18485)*hsa-miR-6765-3p + (0.23938)*hsa-miR-6741-5p + (−0.03201)*hsa-miR-5739 + (−0.05082)*hsa-miR-373-5p + (0.4906)*hsa-miR-663a + (−1.48305)*hsa-miR-1228-5p + (−0.45347)*hsa-miR-4728-5p + (−0.64025)*hsa-miR-937-5p + (−0.04413)*hsa-miR-887-3p + (0.21688)*hsa-miR-6124 + (0.19479)*hsa-miR-6075 + (−0.33283)*hsa-miR-6794-5p + (−0.07324)*hsa-miR-6778-5p + (0.08666)*hsa-miR-4467 + (−0.1629)*hsa-miR-4484 + (−3.06046)*hsa-miR-6087 + (0.07204)*hsa-miR-6760-5p + (0.03884)*hsa-miR-1237-5p + (−0.01918)*hsa-miR-711 + (−0.24672)*hsa-miR-4710 + (0.26189)*hsa-miR-5195-3p + (−0.69246)*hsa-miR-149-3p + (−0.35773)*hsa-miR-1914-3p + (0.14506)*hsa-miR-4675 + (1.01069)*hsa-miR-328-5p + (0.27932)*hsa-miR-4455 + (0.38713)*hsa-miR-3619-3p + (0.03944)*hsa-miR-3160-5p + (1.53864)*hsa-miR-6724-5p + (−0.29601)*hsa-miR-6803-5p + (−0.1311)*hsa-miR-423-5p + (−0.15862)*hsa-miR-4447 + (−0.57986)*hsa-miR-3621 + (0.57873)*hsa-miR-6132 + (−0.44709)*hsa-miR-6791-5p + (−1.1283)*hsa-miR-4725-3p + (−0.05643)*hsa-miR-3158-5p + (−0.04547)*hsa-miR-6766-3p + (−0.09137)*hsa-miR-6879-5p + (−0.01029)*hsa-miR-940 + (0.18806)*hsa-miR-4750-5p + (−0.04859)*hsa-miR-3154 + (−0.11845)*hsa-miR-3917 + (0.25958)*hsa-miR-3663-3p + (−0.04819)*hsa-miR-4649-5p + (−0.12029)*hsa-miR-4640-5p + (−0.18232)*hsa-miR-6749-5p + (0.07005)*hsa-miR-6869-5p + (−0.61778)*hsa-miR-1343-3p + (−0.19783)*hsa-miR-7108-3p + (0.00869)*hsa-miR-4687-3p + (0.01173)*hsa-miR-1185-2-3p + (−0.19174)*hsa-miR-6088 + (0.76322)*hsa-miR-6785-5p + (0.25584)*hsa-miR-6777-5p + (0.09129)*hsa-miR-7107-5p + (−0.22627)*hsa-miR-4695-5p + (−0.08794)*hsa-miR-6880-3p + 51.88496 | 0.43 |
| 37 | 87 | (−0.157453)*hsa-miR-498 + (0.230367)*hsa-miR-4658 + (0.274585)*hsa-miR-6717-5p + (−0.09043)*hsa-miR-92a-3p + (−0.005947)*hsa-miR-6836-3p + (0.576699)*hsa-miR-4436b-5p + (0.375451)*hsa-miR-3648 + (0.033773)*hsa-miR-4663 + (0.074679)*hsa-miR-4652-5p + (−0.531107)*hsa-miR-1343-5p + (0.236115)*hsa-miR-6780b-5p + (−0.072783)*hsa-miR-4448 + (0.15246)*hsa-miR-6722-3p + (0.021538)*hsa-miR-29b-3p + (0.364676)*hsa-miR-1908-5p + (−1.294776)*hsa-miR-3197 + (0.319799)*hsa-miR-371b-5p + (0.053034)*hsa-miR-4433a-3p + (−0.26573)*hsa-miR-4534 + (−0.414734)*hsa-miR-6800-5p + (−0.227724)*hsa-miR-150-3p + (−0.158597)*hsa-miR-296-3p + (0.054483)*hsa-miR-4771 + (0.025565)*hsa-miR-6782-5p + (0.05238)*hsa-miR-6510-5p + (−0.02941)*hsa-miR-4741 + (0.345658)*hsa-miR-1227-5p + (0.312279)*hsa-miR-1185-1-3p + (0.182437)*hsa-miR-6765-3p + (0.287615)*hsa-miR-6741-5p + (−0.060375)*hsa-miR-5739 + (−0.06654)*hsa-miR-373-5p + (0.543806)*hsa-miR-663a + (−1.608171)*hsa-miR-1228-5p + (−0.440689)*hsa-miR-4728-5p + (−0.664403)*hsa-miR-937-5p + (−0.056281)*hsa-miR-887-3p + (0.25376)*hsa-miR-6124 + (0.187633)*hsa-miR-6075 + (−0.288564)*hsa-miR-6794-5p + (−0.091126)*hsa-miR-6778-5p + (0.032068)*hsa-miR-4467 + (−0.187941)*hsa-miR-4484 + (−3.0713)*hsa-miR-6087 + (0.074614)*hsa-miR-6760-5p + (0.097126)*hsa-miR-1237-5p + (−0.041877)*hsa-miR-711 + (−0.248759)*hsa-miR-4710 + (0.329991)*hsa-miR-5195-3p + (−0.737533)*hsa-miR-149-3p + (−0.344625)*hsa-miR-1914-3p + (0.213601)*hsa-miR-4675 + (0.934153)*hsa-miR-328-5p + (0.286295)*hsa-miR-4455 + (0.424054)*hsa-miR-3619-3p + (0.037511)*hsa-miR-3160-5p + (1.575866)*hsa-miR-6724-5p + (−0.190876)*hsa-miR-6803-5p + (−0.131426)*hsa-miR-423-5p + (−0.182603)*hsa-miR-4447 + (−0.652914)*hsa-miR-3621 + (0.574844)*hsa-miR-6132 + (−0.575516)*hsa-miR-6791-5p + (−1.130357)*hsa-miR-4725-3p + (−0.06239)*hsa-miR-3158-5p + (−0.074748)*hsa-miR-6766-3p + (−0.062363)*hsa-miR-6879-5p + | 0.52 |

TABLE 16-2-continued

| No. | Number of miRNA | Discriminant formula | Threshold |
|---|---|---|---|
| | | (−0.040747)*hsa-miR-940 + (0.201293)*hsa-miR-4750-5p + (−0.055379)*hsa-miR-3154 + (−0.100101)*hsa-miR-3917 + (0.329357)*hsa-miR-3663-3p + (−0.187888)*hsa-miR-4649-5p + (−0.186714)*hsa-miR-4640-5p + (−0.125967)*hsa-miR-6749-5p + (0.118941)*hsa-miR-6869-5p + (−0.669133)*hsa-miR-1343-3p + (−0.028094)*hsa-miR-6771-5p + (−0.188447)*hsa-miR-7108-3p + (0.088046)*hsa-miR-4687-3p + (0.038875)*hsa-miR-1185-2-3p + (−0.202863)*hsa-miR-6088 + (0.821338)*hsa-miR-6785-5p + (0.267602)*hsa-miR-6777-5p + (0.035056)*hsa-miR-7107-5p + (−0.238509)*hsa-miR-4695-5p + (−0.091764)*hsa-miR-6880-3p + 50.550809 | |
| 38 | 89 | (−0.168014)*hsa-miR-498 + (0.236947)*hsa-miR-4658 + (0.287021)*hsa-miR-6717-5p + (−0.107595)*hsa-miR-92a-3p + (−0.00643)*hsa-miR-342-5p + (−0.03917)*hsa-miR-6836-3p + (0.611779)*hsa-miR-4436b-5p + (0.349007)*hsa-miR-3648 + (0.034525)*hsa-miR-4663 + (0.081912)*hsa-miR-4652-5p + (−0.532693)*hsa-miR-1343-5p + (0.152994)*hsa-miR-6780b-5p + (−0.086875)*hsa-miR-4448 + (0.209604)*hsa-miR-6722-3p + (0.028549)*hsa-miR-29b-3p + (0.610171)*hsa-miR-1908-5p + (−0.034301)*hsa-miR-6840-3p + (−1.309847)*hsa-miR-3197 + (0.327547)*hsa-miR-371b-5p + (0.046607)*hsa-miR-4433a-3p + (−0.280802)*hsa-miR-4534 + (−0.427755)*hsa-miR-6800-5p + (−0.222417)*hsa-miR-150-3p + (−0.201041)*hsa-miR-296-3p + (0.058103)*hsa-miR-4771 + (−0.003334)*hsa-miR-4298 + (0.023981)*hsa-miR-6782-5p + (0.057966)*hsa-miR-6510-5p + (−0.044703)*hsa-miR-4741 + (0.529786)*hsa-miR-1227-5p + (0.292578)*hsa-miR-1185-1-3p + (0.178845)*hsa-miR-6765-3p + (0.326475)*hsa-miR-6741-5p + (−0.085267)*hsa-miR-5739 + (−0.075257)*hsa-miR-373-5p + (0.591609)*hsa-miR-663a + (−1.7456)*hsa-miR-1228-5p + (−0.425981)*hsa-miR-4728-5p + (−0.695132)*hsa-miR-937-5p + (−0.066892)*hsa-miR-887-3p + (0.293603)*hsa-miR-6124 + (0.170181)*hsa-miR-6075 + (−0.235506)*hsa-miR-6794-5p + (−0.106995)*hsa-miR-6778-5p + (−0.212924)*hsa-miR-4484 + (−3.076951)*hsa-miR-6087 + (0.073772)*hsa-miR-6760-5p + (0.163007)*hsa-miR-1237-5p + (−0.05604)*hsa-miR-711 + (−0.012622)*hsa-miR-4270 + (−0.252449)*hsa-miR-4710 + (0.401782)*hsa-miR-5195-3p + (−0.759878)*hsa-miR-149-3p + (−0.332393)*hsa-miR-1914-3p + (0.286273)*hsa-miR-4675 + (0.81901)*hsa-miR-328-5p + (0.293622)*hsa-miR-4455 + (0.456444)*hsa-miR-3619-3p + (0.038412)*hsa-miR-3160-5p + (1.623949)*hsa-miR-6724-5p + (−0.08646)*hsa-miR-6803-5p + (−0.129925)*hsa-miR-423-5p + (−0.20693)*hsa-miR-4447 + (−0.720175)*hsa-miR-3621 + (0.568054)*hsa-miR-6132 + (−0.69889)*hsa-miR-6791-5p + (−1.129294)*hsa-miR-4725-3p + (−0.068503)*hsa-miR-3158-5p + (−0.103414)*hsa-miR-6766-3p + (−0.029883)*hsa-miR-6879-5p + (−0.070227)*hsa-miR-940 + (0.218064)*hsa-miR-4750-5p + (−0.067662)*hsa-miR-3154 + (−0.079451)*hsa-miR-3917 + (0.403579)*hsa-miR-3663-3p + (−0.332048)*hsa-miR-4649-5p + (−0.261792)*hsa-miR-4640-5p + (−0.012988)*hsa-miR-6749-5p + (0.173429)*hsa-miR-6869-5p + (−0.717521)*hsa-miR-1343-3p + (−0.094348)*hsa-miR-6771-5p + (−0.177661)*hsa-miR-7108-3p + (0.175484)*hsa-miR-4687-3p + (0.063672)*hsa-miR-1185-2-3p + (−0.225836)*hsa-miR-6088 + (0.889055)*hsa-miR-6785-5p + (0.273289)*hsa-miR-6777-5p + (−0.251561)*hsa-miR-4695-5p + (−0.095305)*hsa-miR-6880-3p + 48.552977 | 0.49 |
| 39 | 91 | (−0.1714341)*hsa-miR-498 + (0.2463315)*hsa-miR-4658 + (0.3041014)*hsa-miR-6717-5p + (−0.123549)*hsa-miR-92a-3p + (−0.0154482)*hsa-miR-342-5p + (−0.0483869)*hsa-miR-6836-3p + (0.6473762)*hsa-miR-4436b-5p + (−0.0229318)*hsa-miR-6812-5p + (0.2948587)*hsa-miR-3648 + (0.0369404)*hsa-miR-4663 + (0.0890896)*hsa-miR-4652-5p + (−0.5085905)*hsa-miR-1343-5p + (0.0309708)*hsa-miR-6780b-5p + (−0.102887)*hsa-miR-4448 + (0.2640522)*hsa-miR-6722-3p + (0.0305644)*hsa-miR-29b-3p + (0.8642005)*hsa-miR-1908-5p + (−0.0148678)*hsa-miR-6840-3p + (−1.3529752)*hsa-miR-3197 + (0.3278804)*hsa-miR-371b-5p + (0.0556899)*hsa-miR-4433a-3p + (−0.2977769)*hsa-miR-4534 + (−0.4677857)*hsa-miR-6800-5p + (−0.2184172)*hsa-miR-150-3p + (−0.2380794)*hsa-miR-296-3p + (0.0634247)*hsa-miR-4771 + (−0.0141326)*hsa-miR-4298 + (0.0254648)*hsa-miR-6782-5p + (0.0577028)*hsa-miR-6510-5p + (−0.025078)*hsa-miR-4741 + (0.6880234)*hsa-miR-1227-5p + (0.2784081)*hsa-miR-1185-1-3p + (0.1796644)*hsa-miR-6765-3p + (0.3870641)*hsa-miR-6741-5p + (−0.1127696)*hsa-miR-5739 + (−0.0761122)*hsa-miR-373-5p + (0.645536)*hsa-miR-663a + (−1.886436)*hsa-miR-1228-5p + (−0.3981721)*hsa-miR-4728-5p + (−0.7314395)*hsa-miR-937-5p + (−0.0764468)*hsa-miR-887-3p + (0.32948)*hsa-miR-6124 + (0.1340597)*hsa-miR-6075 + (−0.1834973)*hsa-miR-6794-5p + (−0.116519)*hsa-miR-6778-5p + (−0.237926)*hsa-miR-4484 + (−3.0932453)*hsa-miR-6087 + (0.074448)*hsa-miR-6760-5p + (0.1941518)*hsa-miR-1237-5p + (−0.0666095)*hsa-miR-711 + (−0.0702674)*hsa-miR-4270 + (−0.2559669)*hsa-miR-4710 + (0.4648048)*hsa-miR-5195-3p + (−0.7575425)*hsa-miR-149-3p + (−0.3350432)*hsa-miR-1914-3p + (0.0006176)*hsa-miR-4763-3p + (0.03025)*hsa-miR-6726-5p + (0.3538286)*hsa-miR-4675 + (0.7209416)*hsa-miR-328-5p + (0.2998346)*hsa-miR-4455 + (0.4944758)*hsa-miR-3619-3p + (0.0378202)*hsa-miR-3160-5p + (1.7012313)*hsa-miR-6724-5p + (−0.1298117)*hsa-miR-423-5p + (−0.2194125)*hsa-miR-4447 + (−0.7956141)*hsa-miR-3621 + (0.1045181)*hsa-miR-4739 + (0.560624)*hsa-miR-6132 + (−0.8742633)*hsa-miR-6791-5p + (−1.1202944)*hsa-miR-4725-3p + (−0.0803233)*hsa-miR-3158-5p + (−0.1336422)*hsa-miR-6766-3p + | 0.50 |

TABLE 16-2-continued

| No. | Number of miRNA | Discriminant formula | Threshold |
|---|---|---|---|
|  |  | (−0.0121954)*hsa-miR-6879-5p + (−0.1097786)*hsa-miR-940 + (0.2300339)*hsa-miR-4750-5p + (−0.0722714)*hsa-miR-3154 + (−0.0497431)*hsa-miR-3917 + (0.4532214)*hsa-miR-3663-3p + (−0.4743401)*hsa-miR-4649-5p + (−0.3228496)*hsa-miR-4640-5p + (0.2205531)*hsa-miR-6869-5p + (−0.7541939)*hsa-miR-1343-3p + (−0.1376129)*hsa-miR-6771-5p + (−0.1690947)*hsa-miR-7108-3p + (0.2477765)*hsa-miR-4687-3p + (0.0806414)*hsa-miR-1185-2-3p + (−0.261447)*hsa-miR-6088 + (0.9380335)*hsa-miR-6785-5p + (0.2769353)*hsa-miR-6777-5p + (−0.2671711)*hsa-miR-4695-5p + (−0.1020476)*hsa-miR-6880-3p + 47.1759401 |  |
| 40 | 92 | (−0.17162)*hsa-miR-498 + (0.25392)*hsa-miR-4658 + (0.31749)*hsa-miR-6717-5p + (−O.14299)*hsamiR-92a-3p + (−0.02031)*hsa-miR-342-5p + (−0.06732)*hsa-miR-6836-3p + (0.68248)*hsa-miR-4436b-5p + (−0.04608)*hsa-miR-6812-5p + (0.23512)*hsa-miR-3648 + (0.03833)*hsa-miR-4663 + (0.09481)*hsa-miR-4652-5p + (−0.5289)*hsa-miR-1343-5p + (−0.1133)*hsa-miR-4448 + (0.32071)*hsa-miR-6722-3p + (0.03138)*hsa-miR-29b-3p + (1.06906)*hsa-miR-1908-5p + (−0.01004)*hsa-miR-6840-3p + (−1.39664)*hsa-miR-3197 + (0.32948)*hsa-miR-371b-5p + (0.06811)*hsa-miR-4433a-3p + (−0.31743)*hsa-miR-4534 + (−0.49913)*hsa-miR-6800-5p + (−0.21824)*hsa-miR-150-3p + (−0.27121)*hsa-miR-296-3p + (0.07165)*hsa-miR-4771 + (−0.01974)*hsa-miR-4298 + (0.02632)*hsa-miR-6782-5p + (0.04795)*hsa-miR-6510-5p + (−0.0424)*hsa-miR-4741 + (0.81323)*hsa-miR-1227-5p + (0.27353)*hsa-miR-1185-1-3p + (0.18259)*hsa-miR-6765-3p + (0.44128)*hsa-miR-6741-5p + (−0.13711)*hsa-miR-5739 + (−0.0791)*hsa-miR-373-5p + (0.66386)*hsa-miR-663a + (−2.0331)*hsa-miR-1228-5p + (0.05132)*hsa-miR-642b-3p + (−0.36336)*hsa-miR-4728-5p + (−0.7776)*hsa-miR-937-5p + (−0.07906)*hsa-miR-887-3p + (0.35931)*hsa-miR-6124 + (0.10676)*hsa-miR-6075 + (−0.12638)*hsa-miR-6794-5p + (−0.12716)*hsa-miR-6778-5p + (−0.25232)*hsa-miR-4484 + (−3.10712)*hsa-miR-6087 + (0.07362)*hsa-miR-6760-5p + (0.22424)*hsa-miR-1237-5p + (−0.06079)*hsa-miR-711 + (−0.10901)*hsa-miR-4270 + (−0.26279)*hsa-miR-4710 + (0.51342)*hsa-miR-5195-3p + (−0.76783)*hsa-miR-149-3p + (−0.34897)*hsa-miR-1914-3p + (0.06333)*hsa-miR-4763-3p + (0.087)*hsa-miR-6726-5p + (0.41177)*hsa-miR-4675 + (0.6519)*hsa-miR-328-5p + (0.30781)*hsa-miR-4455 + (0.52968)*hsa-miR-3619-3p + (0.03472)*hsa-miR-3160-5p + (1.79729)*hsa-miR-6724-5p + (−0.13457)*hsa-miR-423-5p + (−0.23011)*hsa-miR-4447 + (−0.85987)*hsa-miR-3621 + (0.18197)*hsa-miR-4739 + (0.52647)*hsa-miR-6132 + (−1.0189)*hsa-miR-6791-5p + (−1.12745)*hsa-miR-4725-3p + (−0.09467)*hsa-miR-3158-5p + (−0.15787)*hsa-miR-6766-3p + (−0.03789)*hsa-miR-6879-5p + (−0.13591)*hsa-miR-940 + (0.24161)*hsa-miR-4750-5p + (−0.07684)*hsa-miR-3154 + (−0.01999)*hsa-miR-3917 + (0.49788)*hsa-miR-3663-3p + (−0.0175)*hsa-miR-4655-5p + (−0.61636)*hsa-miR-4649-5p + (−0.36528)*hsa-miR-4640-5p + (0.27398)*hsa-miR-6869-5p + (−0.7861)*hsa-miR-1343-3p + (−0.15303)*hsa-miR-6771-5p + (−0.16323)*hsa-miR-7108-3p + (0.31315)*hsa-miR-4687-3p + (0.0902)*hsa-miR-1185-2-3p + (−0.31405)*hsa-miR-6088 + (0.98964)*hsa-miR-6785-5p + (0.27636)*hsa-miR-6777-5p + (−0.28112)*hsa-miR-4695-5p + (−0.10755)*hsa-miR-6880-3p + 46.9107 | 0.50 |
| 41 | 96 | (−0.168327)*hsa-miR-498 + (0.26188)*hsa-miR-4658 + (0.33408)*hsa-miR-6717-5p + (−0.169046)*hsa-miR-92a-3p + (−0.017541)*hsa-miR-342-5p + (−0.005558)*hsa-miR-3652 + (−0.090229)*hsa-miR-6836-3p + (0.720749)*hsa-miR-4436b-5p + (−0.067056)*hsa-miR-6812-5p + (0.176077)*hsa-miR-3648 + (0.040991)*hsa-miR-4663 + (0.100265)*hsa-miR-4652-5p + (−0.551882)*hsa-miR-1343-5p + (0.01134)*hsa-miR-1246 + (−0.124139)*hsa-miR-4448 + (0.372669)*hsa-miR-6722-3p + (−0.024981)*hsa-miR-6826-5p + (0.030499)*hsa-miR-29b-3p + (1.276243)*hsa-miR-1908-5p + (−0.009367)*hsa-miR-6840-3p + (−1.418431)*hsa-miR-3197 + (0.332244)*hsa-miR-371b-5p + (0.076143)*hsa-miR-4433a-3p + (−0.33333)*hsa-miR-4534 + (−0.519439)*hsa-miR-6800-5p + (−0.217395)*hsa-miR-150-3p + (−0.30554)*hsa-miR-296-3p + (0.076408)*hsa-miR-4771 + (−0.029634)*hsa-miR-4298 + (0.026415)*hsa-miR-6782-5p + (0.03805)*hsa-miR-6510-5p + (−0.049401)*hsa-miR-4741 + (0.928068)*hsa-miR-1227-5p + (0.268277)*hsa-miR-1185-1-3p + (0.183168)*hsa-miR-6765-3p + (0.492267)*hsa-miR-6741-5p + (−0.161027)*hsa-miR-5739 + (−0.084522)*hsa-miR-373-5p + (0.660405)*hsa-miR-663a + (−2.186924)*hsa-miR-1228-5p + (0.102916)*hsa-miR-642b-3p + (−0.337328)*hsa-miR-4728-5p + (−0.825603)*hsa-miR-937-5p + (−0.080196)*hsa-miR-887-3p + (0.394368)*hsa-miR-6124 + (0.067784)*hsa-miR-6075 + (−0.074642)*hsa-miR-6794-5p + (−0.139875)*hsa-miR-6778-5p + (−0.271245)*hsa-miR-4484 + (−3.128285)*hsa-miR-6087 + (0.072986)*hsa-miR-6760-5p + (0.24932)*hsa-miR-1237-5p + (−0.053059)*hsa-miR-711 + (−0.142799)*hsa-miR-4270 + (−0.269275)*hsa-miR-4710 + (0.569167)*hsa-miR-5195-3p + (−0.781094)*hsa-miR-149-3p + (−0.365003)*hsa-miR-1914-3p + (0.130811)*hsa-miR-4763-3p + (0.122118)*hsa-miR-6726-5p + (0.467105)*hsa-miR-4675 + (0.585686)*hsa-miR-328-5p + (0.314904)*hsa-miR-4455 + (0.567628)*hsa-miR-3619-3p + (0.031226)*hsa-miR-3160-5p + (1.891636)*hsa-miR-6724-5p + (−0.138551)*hsa-miR-423-5p + (−0.244677)*hsa-miR-4447 + (−0.915858)*hsa-miR-3621 + (0.24268)*hsa-miR-4739 + (0.49819)*hsa-miR-6132 + (−1.160239)*hsa-miR-6791-5p + (−1.14036)*hsa-miR-4725-3p + (−0.105191)*hsa-miR-3158-5p + (−0.177439)*hsa-miR-6766-3p + (−0.073091)*hsa-miR-6879-5p + (−0.164485)*hsa- | 0.51 |

TABLE 16-2-continued

| No. | Number of miRNA | Discriminant formula | Threshold |
|---|---|---|---|
| | | miR-940 + (0.252274)*hsa-miR-4750-5p + (−0.08018)*hsa-miR-3154 + (0.549568)*hsa-miR-3663-3p + (−0.038808)*hsa-miR-4655-5p + (−0.744936)*hsa-miR-4649-5p + (−0.392245)*hsa-miR-4640-5p + (0.324248)*hsa-miR-6869-5p + (−0.818355)*hsa-miR-1343-3p + (−0.165573)*hsa-miR-6771-5p + (−0.154436)*hsa-miR-7108-3p + (0.38698)*hsa-miR-4687-3p + (0.104229)*hsa-miR-1185-2-3p + (−0.022416)*hsa-miR-1225-5p + (−0.006255)*hsa-miR-4322 + (−0.361259)*hsa-miR-6088 + (1.039438)*hsa-miR-6785-5p + (0.276739)*hsa-miR-6777-5p + (−0.290883)*hsa-miR-4695-5p + (−0.10815)*hsa-miR-6880-3p + 46.950799 | |
| 42 | 101 | (−0.164886)*hsa-miR-498 + (0.271746)*hsa-miR-4658 + (0.342635)*hsa-miR-6717-5p + (−0.195075)*hsa-miR-92a-3p + (−0.005004)*hsa-miR-342-5p + (−0.01172)*hsa-miR-3652 + (−0.095324)*hsa-miR-6836-3p + (0.751026)*hsa-miR-4436b-5p + (−0.089433)*hsa-miR-6812-5p + (0.128132)*hsa-miR-3648 + (0.043433)*hsa-miR-4663 + (0.104041)*hsa-miR-4652-5p + (−0.549339)*hsa-miR-1343-5p + (0.023385)*hsa-miR-1246 + (−0.138751)*hsa-miR-4448 + (0.431639)*hsa-miR-6722-3p + (−0.051407)*hsa-miR-6826-5p + (0.030158)*hsa-miR-29b-3p + (1.522322)*hsa-miR-1908-5p + (−0.020371)*hsa-miR-6840-3p + (−1.446668)*hsa-miR-3197 + (0.331537)*hsa-miR-371b-5p + (0.105015)*hsa-miR-4433a-3p + (−0.356045)*hsa-miR-4534 + (−0.530676)*hsa-miR-6800-5p + (−0.22 miR-296-3p + (0.079662)*hsa-miR-4771 + (−0.04181)*hsa-miR-4298 + (0.023304)*hsa-miR-6782-5p + (0.00421)*hsa-miR-6774-5p + (0.028565)*hsa-miR-6510-5p + (−0.040035)*hsa-miR-4741 + (1.002338)*hsa-miR-1227-5p + (0.258342)*hsa-miR-1185-1-3p + (0.190108)*hsa-miR-6765-3p + (0.547435)*hsa-miR-6741-5p + (−0.192605)*hsa-miR-5739 + (−0.086166)*hsa-miR-373-5p + (0.611532)*hsa-miR-663a + (−2.321989)*hsa-miR-1228-5p + (0.124905)*hsa-miR-642b-3p + (−0.322833)*hsa-miR-4728-5p + (−0.831493)*hsa-miR-937-5p + (−0.07426)*hsa-miR-887-3p + (0.425246)*hsa-miR-6124 + (0.051568)*hsa-miR-6075 + (−0.048001)*hsa-miR-6794-5p + (−0.148839)*hsa-miR-6778-5p + (−0.002104)*hsa-miR-6762-5p + (−0.299278)*hsa-miR-4484 + (−3.147393)*hsa-miR-6087 + (0.075137)*hsa-miR-6760-5p + (0.280394)*hsa-miR-1237-5p + (−0.05035)*hsa-miR-711 + (−0.194744)*hsa-miR-4270 + (−0.271665)*hsa-miR-4710 + (0.618923)*hsa-miR-5195-3p + (0.142587)*hsa-miR-128-2-5p + (−0.749714)*hsa-miR-149-3p + (−0.382437)*hsa-miR-1914-3p + (0.203352)*hsa-miR-4763-3p + (0.129049)*hsa-miR-6726-5p + (−0.007147)*hsa-miR-1207-5p + (0.509897)*hsa-miR-4675 + (0.48708)*hsa-miR-328-5p + (0.324524)*hsa-miR-4455 + (0.606476)*hsa-miR-3619-3p + (0.029777)*hsa-miR-3160-5p + (2.012171)*hsa-miR-6724-5p + (−0.145669)*hsa-miR-423-5p + (−0.263466)*hsa-miR-4447 + (−0.960745)*hsa-miR-3621 + (0.332861)*hsa-miR-4739 + (0.485793)*hsa-miR-6132 + (−1.356838)*hsa-miR-6791-5p + (−1.14425)*hsa-miR-4725-3p + (−0.112144)*hsa-miR-3158-5p + (−0.194603)*hsa-miR-6766-3p + (−0.122519)*hsa-miR-6879-5p + (−0.191731)*hsa-miR-940 + (0.273396)*hsa-miR-4750-5p + (−0.07369)*hsa-miR-3154 + (0.617814)*hsa-miR-3663-3p + (−0.073282)*hsa-miR-4655-5p + (−0.918353)*hsa-miR-4649-5p + (−0.403564)*hsa-miR-4640-5p + (0.345987)*hsa-miR-6869-5p + (−0.831031)*hsa-miR-1343-3p + (−0.173685)*hsa-miR-6771-5p + (−0.142973)*hsa-miR-7108-3p + (−0.07332)*hsa-miR-3195 + (0.474989)*hsa-miR-4687-3p + (0.12152)*hsa-miR-1185-2-3p + (−0.037743)*hsa-miR-1225-5p + (−0.007735)*hsa-miR-4322 + (−0.400051)*hsa-miR-6088 + (1.086969)*hsa-miR-6785-5p + (0.272056)*hsa-miR-6777-5p + (−0.295919)*hsa-miR-4695-5p + (−0.110911)*hsa-miR-6880-3p + 45.893174 | 0.51 |
| 43 | 103 | (−0.1601394)*hsa-miR-498 + (0.2850617)*hsa-miR-4658 + (0.3576893)*hsa-miR-6717-5p + (−0.2212451)*hsa-miR-92a-3p + (−0.0169346)*hsa-miR-3652 + (−0.1033467)*hsa-miR-6836-3p + (0.7803107)*hsa-miR-4436b-5p + (−0.1053903)*hsa-miR-6812-5p + (0.0989707)*hsa-miR-3648 + (0.0452842)*hsa-miR-4663 + (0.1070454)*hsa-miR-4652-5p + (−0.5645943)*hsa-miR-1343-5p + (0.0372825)*hsa-miR-1246 + (−0.1524387)*hsa-miR-4448 + (0.493455)*hsa-miR-6722-3p + (−0.063272)*hsa-miR-6826-5p + (0.0300947)*hsa-miR-29b-3p + (1.7253231)*hsa-miR-1908-5p + (−0.0304343)*hsa-miR-6840-3p + (−1.4718543)*hsa-miR-3197 + (0.3327945)*hsa-miR-371b-5p + (0.1389311)*hsa-miR-4433a-3p + (−0.3786207)*hsa-miR-4534 + (−0.5330388)*hsa-miR-6800-5p + (−0.2281238)*hsa-miR-150-3p + (−0.3571327)*hsa-miR-296-3p + (0.0821236)*hsa-miR-4771 + (−0.000483)*hsa-miR-1908-3p + (−0.0484521)*hsa-miR-4298 + (0.0188425)*hsa-miR-6782-5p + (0.0291535)*hsa-miR-6774-5p + (0.0167763)*hsa-miR-6510-5p + (0.0008741)*hsa-miR-615-5p + (−0.0710587)*hsa-miR-4741 + (1.0816373)*hsa-miR-1227-5p + (0.2452467)*hsa-miR-1185-1-3p + (0.2018208)*hsa-miR-6765-3p + (0.5697991)*hsa-miR-6741-5p + (−0.2300502)*hsa-miR-5739 + (−0.0846453)*hsa-miR-373-5p + (0.5710604)*hsa-miR-663a + (−2.4571022)*hsa-miR-1228-5p + (0.1295403)*hsa-miR-642b-3p + (−0.3104713)*hsa-miR-4728-5p + (−0.8254877)*hsa-miR-937-5p + (−0.0633134)*hsa-miR-887-3p + (0.4501435)*hsa-miR-6124 + (0.0532032)*hsa-miR-6075 + (−0.0167539)*hsa-miR-6794-5p + (−0.159077)*hsa-miR-6778-5p + (−0.0313716)*hsa-miR-6762-5p + (−0.3303255)*hsa-miR-4484 + (−3.1773215)*hsa-miR-6087 + (0.0739993)*hsa-miR-6760-5p + (0.3358439)*hsa-miR-1237-5p + (−0.0440618)*hsa-miR-711 + (−0.2404605)*hsa-miR-4270 + (−0.2751142)*hsa-miR-4710 + (0.6544662)*hsa-miR- | 0.51 |

TABLE 16-2-continued

| No. | Number of miRNA | Discriminant formula | Threshold |
|---|---|---|---|
|  |  | 5195-3p + (0.295192)*hsa-miR-128-2-5p + (−0.7253273)*hsa-miR-149-3p + (−0.3974438)*hsa-miR-1914-3p + (0.2908112)*hsa-miR-4763-3p + (0.1248389)*hsa-miR-6726-5p + (−0.0067125)*hsa-miR-1207-5p + (0.5368467)*hsa-miR-4675 + (0.4202241)*hsa-miR-328-5p + (−0.007049)*hsa-miR-6716-5p + (0.3352917)*hsa-miR-4455 + (0.6409634)*hsa-miR-3619-3p + (0.0309696)*hsa-miR-3160-5p + (2.146443)*hsa-miR-6724-5p + (−0.152149)*hsa-miR-423-5p + (−0.2819543)*hsa-miR-4447 + (−0.9913437)*hsa-miR-3621 + (0.4200105)*hsa-miR-4739 + (0.4525662)*hsa-miR-6132 + (−1.5422233)*hsa-miR-6791-5p + (−1.1506838)*hsa-miR-4725-3p + (−0.1197616)*hsa-miR-3158-5p + (−0.2090465)*hsa-miR-6766-3p + (−0.1497135)*hsa-miR-6879-5p + (−0.2037203)*hsa-miR-940 + (0.2991638)*hsa-miR-4750-5p + (−0.0716387)*hsa-miR-3154 + (0.6954744)*hsa-miR-3663-3p + (−0.1041385)*hsa-miR-4655-5p + (−1.0860398)*hsa-miR-4649-5p + (−0.4193025)*hsa-miR-4640-5p + (0.3758715)*hsa-miR-6869-5p + (−0.8624156)*hsa-miR-1343-3p + (−0.1870276)*hsa-miR-6771-5p + (−0.1372597)*hsa-miR-7108-3p + (−0.1506052)*hsa-miR-3195 + (0.5473537)*hsa-miR-4687-3p + (0.1403362)*hsa-miR-1185-2-3p + (−0.0498392)*hsa-miR-1225-5p + (−0.0090745)*hsa-miR-4322 + (−0.4368464)*hsa-miR-6088 + (1.1299979)*hsa-miR-6785-5p + (0.2718584)*hsa-miR-6777-5p + (−0.3008688)*hsa-miR-4695-5p + (−0.1117853)*hsa-miR-6880-3p + 44.5219553 |  |
| 44 | 104 | (−0.142443)*hsa-miR-498 + (0.343385)*hsa-miR-4658 + (0.431962)*hsa-miR-6717-5p + (0.002511)*hsa-miR-8073 + (−0.337601)*hsa-miR-92a-3p + (−0.029308)*hsa-miR-3652 + (−0.106071)*hsa-miR-6836-3p + (0.006541)*hsa-miR-1193 + (0.875478)*hsa-miR-4436b-5p + (−0.168653)*hsa-miR-6812-5p + (0.053152)*hsa-miR-4663 + (0.1271)*hsa-miR-4652-5p + (−0.591585)*hsa-miR-1343-5p + (0.083892)*hsa-miR-1246 + (−0.216299)*hsa-miR-4448 + (0.733901)*hsa-miR-6722-3p + (−0.137186)*hsa-miR-6826-5p + (0.036726)*hsa-miR-29b-3p + (2.472847)*hsa-miR-1908-5p + (−0.089103)*hsa-miR-6840-3p + (−1.496956)*hsa-miR-3197 + (0.336997)*hsa-miR-371b-5p + (0.239512)*hsa-miR-4433a-3p + (−0.478043)*hsa-miR-4534 + (0.099419)*hsa-miR-6816-5p + (−0.531065)*hsa-miR-6800-5p + (−0.259498)*hsa-miR-150-3p + (−0.449811)*hsa-miR-296-3p + (0.096368)*hsa-miR-4771 + (−0.038915)*hsa-miR-1908-3p + (−0.083576)*hsa-miR-4298 + (0.128277)*hsa-miR-6774-5p + (0.014162)*hsa-miR-615-5p + (−0.162203)*hsa-miR-4741 + (1.37632)*hsa-miR-1227-5p + (0.203311)*hsa-miR-1185-1-3p + (0.2478)*hsa-miR-6765-3p + (0.659776)*hsa-miR-6741-5p + (−0.422742)*hsa-miR-5739 + (−0.062029)*hsa-miR-373-5p + (0.417561)*hsa-miR-663a + (−3.034528)*hsa-miR-1228-5p + (0.156515)*hsa-miR-642b-3p + (−0.296177)*hsa-miR-4728-5p + (−0.798202)*hsa-miR-937-5p + (−0.004472)*hsa-miR-887-3p + (0.524208)*hsa-miR-6124 + (0.169608)*hsa-miR-6075 + (−0.183942)*hsa-miR-6778-5p + (−0.117397)*hsa-miR-6762-5p + (−0.458025)*hsa-miR-4484 + (−3.409511)*hsa-miR-6087 + (0.076078)*hsa-miR-6760-5p + (0.488415)*hsa-miR-1237-5p + (−0.034753)*hsa-miR-711 + (−0.380955)*hsa-miR-4270 + (−0.292588)*hsa-miR-4710 + (0.830594)*hsa-miR-5195-3p + (0.674073)*hsa-miR-128-2-5p + (−0.603804)*hsa-miR-149-3p + (−0.440067)*hsa-miR-1914-3p + (0.573642)*hsa-miR-4763-3p + (0.088688)*hsa-miR-6726-5p + (−0.007254)*hsa-miR-1207-5p + (0.614477)*hsa-miR-4675 + (0.216859)*hsa-miR-328-5p + (−0.069761)*hsa-miR-6716-5p + (0.381322)*hsa-miR-4455 + (0.748721)*hsa-miR-3619-3p + (0.045501)*hsa-miR-3160-5p + (2.573042)*hsa-miR-6724-5p + (−0.17771)*hsa-miR-423-5p + (0.011489)*hsa-miR-92a-2-5p + (−0.344767)*hsa-miR-4447 + (−1.078043)*hsa-miR-3621 + (0.794977)*hsa-miR-4739 + (0.368263)*hsa-miR-6132 + (−2.288217)*hsa-miR-6791-5p + (−1.158644)*hsa-miR-4725-3p + (−0.156604)*hsa-miR-3158-5p + (−0.254161)*hsa-miR-6766-3p + (−0.305986)*hsa-miR-6879-5p + (−0.236762)*hsa-miR-940 + (0.414075)*hsa-miR-4750-5p + (−0.071799)*hsa-miR-3154 + (0.996824)*hsa-miR-3663-3p + (−0.282559)*hsa-miR-4655-5p + (−1.520084)*hsa-miR-4649-5p + (−0.48277)*hsa-miR-4640-5p + (0.064498)*hsa-miR-4783-3p + (0.472275)*hsa-miR-6869-5p + (−0.955611)*hsa-miR-1343-3p + (−0.204386)*hsa-miR-6771-5p + (−0.12549)*hsa-miR-7108-3p + (−0.487461)*hsa-miR-3195 + (0.872821)*hsa-miR-4687-3p + (0.203465)*hsa-miR-1185-2-3p + (−0.087519)*hsa-miR-1225-5p + (−0.01442)*hsa-miR-4322 + (−0.583521)*hsa-miR-6088 + (1.301175)*hsa-miR-6785-5p + (0.27416)*hsa-miR-6777-5p + (−0.307199)*hsa-miR-4695-5p + (−0.11423)*hsa-miR-6880-3p + 39.943135 | 0.65 |

Example 3

<Comparison of miRNA Expression Levels in Serum Between Bladder Cancer Patients and Patients of Cancers Other than Bladder Cancer, Benign Disease Patients, and Healthy Subjects>

In this Example, the miRNA expression levels in serum of bladder cancer patients were compared with those of patients of cancers other than bladder cancer, benign disease patients, and healthy subjects using the training cohort (Table 4) the gene expression levels of which were measured in the above Reference Example. Specifically, first, miRNA expression levels in the training cohort including 261 bladder cancer patients as a positive sample group and including 408 patients of cancers other than bladder cancer, 133 benign disease patients, and 67 healthy subjects as a negative sample group were together normalized in accordance with global normalization, as shown in the above Reference Example. Next, in order to evaluate more reliable diagnostic markers, only genes having a gene expression level of $2^6$ or more in 50% or more samples in either the positive sample group or the negative sample group were selected. Further, to evaluate genes having a statistically significant difference in the gene expression level between the positive sample group and the negative sample group, an equal-variance-assumed two-sided t test was conducted to calculate the P values, which were corrected by Bonferroni correction. Further, in order to evaluate the susceptibility to noise during measurement, the absolute value of the difference (Fold change) in the gene expression levels in the positive sample group or the negative sample group that were logarithmically converted was calculated. Genes with a P value after the correction of 0.01 or less and an absolute value of Fold change of 0.5 or more were extracted as genes with expression varied, to obtain 89 diagnostic markers capable of detecting bladder cancer (Table 17). The mean and SD of the expression levels of the selected genes in the positive sample group and the negative sample group, the P value after Bonferroni correction, and the absolute value of Fold change are shown in Table 17. Among these, genes newly found as markers to examine the presence or absence of bladder cancer are polynucleotides consisting of nucleotide sequences represented by SEQ ID NOs: 1, 2, 3, 4, 5, 11, 12, 15, 17, 19, 20, 21, 26, 27, 28, 31, 35, 36, 41, 44, 45, 47, 48, 49, 50, 53, 59, 65, 67, 72, 73, 74, 76, 80, 82, 83, 85, 88, 89, 95, 96, 98, 99, 104, 107, 108, 119, 120, 121, 125, 126, 128, 130, 132, 133, 135, 136, 137, 138, 142, 146, 148, 149, 150, 152, 154, 155, 156, 161, 164, 169, 172, 174, 176, 179, 182, 198, 201, 204, 209, 219, 222, 223, 224, and 226.

TABLE 17

| No. | Name of miRNA | SEQ ID NO | Bladder cancer mean | SD | Negative group mean | SD | P value | Fold change |
|---|---|---|---|---|---|---|---|---|
| 1 | hsa-miR-4652-5p | 104 | 6.30 | 1.78 | 3.01 | 2.53 | 8.49E−65 | 3.30 |
| 2 | hsa-miR-3160-5p | 35 | 9.03 | 2.13 | 6.77 | 2.23 | 1.65E−36 | 2.27 |
| 3 | hsa-miR-4658 | 107 | 5.96 | 1.40 | 3.70 | 2.43 | 5.46E−37 | 2.26 |
| 4 | hsa-miR-4755-3p | 133 | 6.58 | 1.79 | 4.50 | 2.88 | 3.17E−22 | 2.08 |
| 5 | hsa-miR-3194-3p | 41 | 9.28 | 1.43 | 7.25 | 2.35 | 4.76E−32 | 2.03 |
| 6 | hsa-miR-4663 | 108 | 6.42 | 1.76 | 4.41 | 2.48 | 4.95E−27 | 2.02 |
| 7 | hsa-miR-17-3p | 20 | 6.82 | 1.10 | 4.95 | 2.47 | 3.58E−26 | 1.87 |
| 8 | hsa-miR-29b-3p | 31 | 6.00 | 1.48 | 4.14 | 2.86 | 8.95E−19 | 1.86 |
| 9 | hsa-miR-4480 | 88 | 7.18 | 1.61 | 5.43 | 2.55 | 7.73E−20 | 1.75 |
| 10 | hsa-miR-6831-5p | 201 | 6.02 | 1.15 | 4.35 | 2.04 | 4.28E−29 | 1.67 |
| 11 | hsa-miR-4633-3p | 99 | 5.90 | 2.18 | 4.36 | 3.07 | 1.44E−09 | 1.53 |
| 12 | hsa-miR-4727-3p | 125 | 6.85 | 1.17 | 5.33 | 2.00 | 4.13E−25 | 1.52 |
| 13 | hsa-miR-4455 | 83 | 6.19 | 1.48 | 4.67 | 2.20 | 1.43E−19 | 1.51 |
| 14 | hsa-miR-6760-5p | 174 | 6.11 | 1.16 | 4.64 | 2.36 | 2.53E−17 | 1.47 |
| 15 | hsa-miR-4483 | 89 | 6.47 | 1.75 | 5.02 | 1.94 | 1.69E−20 | 1.45 |
| 16 | hsa-miR-2467-3p | 28 | 9.97 | 1.29 | 8.52 | 1.93 | 2.23E−23 | 1.45 |
| 17 | hsa-miR-4771 | 135 | 6.36 | 1.66 | 4.95 | 2.55 | 1.88E−12 | 1.41 |
| 18 | hsa-miR-4718 | 121 | 9.05 | 1.20 | 7.68 | 2.30 | 2.21E−15 | 1.36 |
| 19 | hsa-miR-4525 | 96 | 11.73 | 1.23 | 10.42 | 1.76 | 1.05E−22 | 1.31 |
| 20 | hsa-miR-4740-5p | 130 | 6.99 | 1.32 | 5.69 | 2.02 | 2.83E−17 | 1.30 |
| 21 | hsa-miR-6717-5p | 164 | 8.39 | 0.82 | 7.09 | 1.92 | 4.91E−21 | 1.30 |
| 22 | hsa-miR-1246 | 231 | 8.73 | 1.83 | 7.44 | 3.47 | 4.78E−05 | 1.29 |
| 23 | hsa-miR-4783-5p | 137 | 6.65 | 1.78 | 5.43 | 2.10 | 2.58E−12 | 1.21 |
| 24 | hsa-miR-191-5p | 238 | 6.77 | 1.59 | 5.57 | 2.78 | 2.8E−07 | 1.20 |
| 25 | hsa-miR-4448 | 80 | 9.33 | 1.31 | 8.14 | 1.99 | 1.08E−14 | 1.19 |
| 26 | hsa-miR-371b-5p | 59 | 6.05 | 1.06 | 4.91 | 1.79 | 2.28E−17 | 1.14 |
| 27 | hsa-miR-6777-5p | 182 | 7.19 | 0.84 | 6.07 | 1.75 | 3.14E−18 | 1.12 |
| 28 | hsa-miR-4462 | 85 | 6.06 | 1.29 | 4.95 | 1.91 | 8.34E−14 | 1.12 |
| 29 | hsa-miR-320b | 45 | 6.75 | 0.92 | 5.64 | 1.83 | 4.13E−16 | 1.11 |
| 30 | hsa-miR-4708-3p | 119 | 8.86 | 1.21 | 7.76 | 1.86 | 2.61E−14 | 1.10 |
| 31 | hsa-miR-6131 | 152 | 11.70 | 1.75 | 10.63 | 2.83 | 5.61E−05 | 1.07 |
| 32 | hsa-miR-4515 | 95 | 7.41 | 1.27 | 6.40 | 1.90 | 2.41E−11 | 1.01 |
| 33 | hsa-miR-4436b-5p | 76 | 6.73 | 0.71 | 5.75 | 1.30 | 9.23E−25 | 0.98 |
| 34 | hsa-miR-342-5p | 47 | 7.09 | 0.96 | 6.12 | 1.81 | 2.91E−12 | 0.97 |
| 35 | hsa-miR-8073 | 226 | 8.65 | 0.62 | 7.71 | 1.16 | 9.48E−29 | 0.94 |
| 36 | hsa-miR-5572 | 146 | 6.82 | 0.74 | 5.89 | 1.45 | 2.22E−18 | 0.93 |
| 37 | hsa-miR-4710 | 120 | 8.76 | 1.31 | 7.83 | 1.92 | 4.47E−09 | 0.93 |
| 38 | hsa-miR-615-5p | 155 | 7.01 | 0.60 | 6.09 | 1.20 | 1.48E−26 | 0.93 |
| 39 | hsa-miR-3619-3p | 50 | 9.05 | 0.96 | 8.22 | 0.90 | 2.98E−28 | 0.83 |
| 40 | hsa-miR-4750-5p | 132 | 7.21 | 0.68 | 6.38 | 1.31 | 1.89E−17 | 0.82 |
| 41 | hsa-miR-5010-5p | 142 | 6.30 | 1.94 | 5.50 | 1.79 | 1.25E−05 | 0.80 |
| 42 | hsa-miR-6515-5p | 161 | 5.87 | 1.38 | 5.08 | 2.18 | 0.000249 | 0.79 |
| 43 | hsa-miR-6877-5p | 209 | 8.37 | 0.54 | 7.63 | 0.88 | 4.61E−30 | 0.74 |
| 44 | hsa-miR-3622a-5p | 53 | 6.61 | 1.11 | 5.88 | 1.55 | 1.65E−08 | 0.74 |
| 45 | hsa-miR-4259 | 65 | 5.98 | 1.38 | 5.26 | 2.05 | 0.000472 | 0.73 |
| 46 | hsa-miR-614 | 154 | 10.69 | 0.88 | 9.96 | 1.38 | 2.54E−11 | 0.73 |
| 47 | hsa-miR-6087 | 1 | 11.46 | 0.26 | 12.18 | 0.47 | 3.48E−90 | 0.72 |
| 48 | hsa-miR-4454 | 82 | 11.66 | 0.73 | 10.94 | 1.22 | 1.39E−14 | 0.72 |
| 49 | hsa-miR-4787-3p | 138 | 7.57 | 0.65 | 6.86 | 1.37 | 7.14E−12 | 0.71 |
| 50 | hsa-miR-24-3p | 27 | 6.76 | 1.35 | 6.05 | 1.93 | 0.000223 | 0.71 |
| 51 | hsa-miR-1199-5p | 5 | 5.88 | 1.54 | 5.19 | 1.83 | 0.000313 | 0.69 |
| 52 | hsa-miR-345-3p | 48 | 6.09 | 1.12 | 5.41 | 1.58 | 9.41E−07 | 0.68 |
| 53 | hsa-miR-320a | 44 | 7.29 | 0.80 | 6.61 | 1.28 | 2.05E−11 | 0.68 |
| 54 | hsa-miR-4430 | 74 | 7.07 | 1.01 | 6.39 | 1.44 | 3.51E−08 | 0.67 |
| 55 | hsa-miR-3616-3p | 49 | 5.83 | 1.26 | 5.16 | 1.67 | 2.28E−05 | 0.67 |
| 56 | hsa-miR-4535 | 98 | 5.76 | 1.48 | 5.10 | 1.87 | 0.001443 | 0.66 |
| 57 | hsa-miR-1193 | 4 | 6.63 | 0.83 | 5.97 | 1.31 | 5.18E−10 | 0.66 |

TABLE 17-continued

| No. | Name of miRNA | SEQ ID NO | Bladder cancer mean | Bladder cancer SD | Negative group mean | Negative group SD | P value | Fold change |
|---|---|---|---|---|---|---|---|---|
| 58 | hsa-miR-187-5p | 21 | 8.68 | 0.53 | 8.03 | 1.20 | 3.81E−13 | 0.65 |
| 59 | hsa-miR-1343-3p | 17 | 8.49 | 0.60 | 7.84 | 1.27 | 1.91E−11 | 0.65 |
| 60 | hsa-miR-6766-5p | 179 | 7.09 | 0.87 | 6.45 | 1.11 | 8.81E−13 | 0.64 |
| 61 | hsa-miR-4419b | 72 | 7.37 | 0.73 | 6.73 | 1.46 | 8.02E−08 | 0.64 |
| 62 | hsa-miR-1470 | 19 | 5.34 | 1.54 | 5.97 | 1.27 | 1.01E−06 | 0.64 |
| 63 | hsa-miR-1238-5p | 11 | 7.95 | 0.59 | 7.33 | 1.28 | 3.53E−10 | 0.62 |
| 64 | hsa-miR-4728-5p | 126 | 6.89 | 0.85 | 7.50 | 0.89 | 1.33E−16 | 0.61 |
| 65 | hsa-miR-1254 | 232 | 6.58 | 0.87 | 5.98 | 1.33 | 7.11E−08 | 0.60 |
| 66 | hsa-miR-3162-5p | 36 | 7.80 | 0.65 | 7.21 | 1.29 | 9.37E−09 | 0.59 |
| 67 | hsa-miR-210-5p | 26 | 5.84 | 1.15 | 5.26 | 1.51 | 8.79E−05 | 0.58 |
| 68 | hsa-miR-4429 | 73 | 7.50 | 0.59 | 6.92 | 1.35 | 1.42E−07 | 0.58 |
| 69 | hsa-miR-6076 | 149 | 8.15 | 0.53 | 7.58 | 0.84 | 8.13E−20 | 0.58 |
| 70 | hsa-miR-7977 | 223 | 9.77 | 0.81 | 9.19 | 1.07 | 4.45E−11 | 0.58 |
| 71 | hsa-miR-4286 | 67 | 7.66 | 0.73 | 7.08 | 1.22 | 8.57E−09 | 0.57 |
| 72 | hsa-miR-619-5p | 156 | 7.85 | 1.28 | 7.28 | 1.78 | 0.008063 | 0.57 |
| 73 | hsa-miR-1185-2-3p | 3 | 8.26 | 1.38 | 7.69 | 1.70 | 0.00471 | 0.57 |
| 74 | hsa-miR-6741-5p | 169 | 8.34 | 0.50 | 7.77 | 0.92 | 8.86E−17 | 0.57 |
| 75 | hsa-miR-6842-5p | 204 | 6.15 | 1.09 | 5.58 | 1.68 | 0.001537 | 0.57 |
| 76 | hsa-miR-6765-3p | 176 | 8.50 | 0.67 | 7.93 | 1.04 | 2.66E−12 | 0.57 |
| 77 | hsa-miR-4783-3p | 136 | 8.37 | 1.20 | 7.80 | 1.51 | 0.00024 | 0.57 |
| 78 | hsa-miR-1273g-3p | 15 | 8.76 | 0.80 | 8.22 | 1.29 | 1.09E−06 | 0.54 |
| 79 | hsa-miR-7975 | 222 | 9.26 | 0.79 | 8.72 | 1.30 | 2.15E−06 | 0.54 |
| 80 | hsa-miR-6819-5p | 198 | 8.49 | 0.43 | 7.96 | 0.69 | 2.07E−25 | 0.54 |
| 81 | hsa-miR-6088 | 150 | 11.01 | 0.32 | 11.55 | 0.61 | 3.53E−33 | 0.53 |
| 82 | hsa-miR-6746-5p | 172 | 7.85 | 0.55 | 7.32 | 1.11 | 1.04E−09 | 0.53 |
| 83 | hsa-miR-8052 | 224 | 6.06 | 1.10 | 5.54 | 1.47 | 0.000729 | 0.52 |
| 84 | hsa-miR-4736 | 128 | 7.21 | 1.03 | 6.69 | 1.20 | 4.11E−06 | 0.52 |
| 85 | hsa-miR-7113-3p | 219 | 6.26 | 0.96 | 5.74 | 1.38 | 0.000112 | 0.52 |
| 86 | hsa-miR-6075 | 148 | 9.16 | 0.46 | 8.65 | 0.63 | 1.54E−26 | 0.51 |
| 87 | hsa-miR-1247-3p | 12 | 7.41 | 0.54 | 6.90 | 1.01 | 1.72E−10 | 0.51 |
| 88 | hsa-miR-1202 | 229 | 7.43 | 0.59 | 6.93 | 1.03 | 8.32E−10 | 0.51 |
| 89 | hsa-miR-1185-1-3p | 2 | 8.79 | 1.19 | 8.29 | 1.43 | 0.001914 | 0.50 |

Example 4

<Discriminant Analysis Between Bladder Cancer Patients of T2 or Higher and Bladder Cancer Patients of Below T2 in TNM Classification>

In this Example, a discriminant formula with one gene marker was created using a training cohort (Table 5) including patients of T2 or higher to be treated by total removal of the bladder and patients of below T2 to be treated by endoscopy or BCG injection in terms of T classification showing the depth of in-wall invasion of the primary tumor in the TNM classification, the discriminant performance was evaluated in the validation cohort (Table 5), and the top 14 genes ranked by the accuracy were extracted from the following group of 398 genes, to obtain gene markers capable of detecting bladder cancer of T2 or higher (Table 18).

Specifically, first, miRNA expression levels in the T2 or higher group and the below T2 group obtained in the above Reference Example were together normalized in accordance with global normalization. Further, in order to acquire more reliable diagnostic markers, only 398 genes with a gene expression level of $2^6$ or larger in 50% or more of the samples were analyzed in either the T2 or higher group or the below T2 group.

Next, Fisher's discriminant analysis was performed on the measured values of the expression levels of the aforementioned 398 genes, to construct discriminant formulas for discriminating the presence or absence of bladder cancer. At this time, discriminant formulas with high discriminant performance were searched for by a modified greedy algorithm. Further, the above-prepared discriminant formulas were used to calculate the accuracy, the sensitivity, and the specificity in the validation cohort. Then, the discriminant performance was validated in independent samples. As a result, the top 14 formulas ranked by the discriminant performance were obtained. These discriminant formulas and their thresholds (determining positive or negative, where values equal to or higher than the thresholds are positive), the sensitivity, specificity, accuracy, and AUC in the training cohort and the validation cohort, and the genes used for the discriminant formulas are shown in Table 19-1 and 19-2. The genes included in these discriminant formulas were selected as diagnostic markers capable of distinguishing between bladder cancer patients of T2 or higher and bladder cancer patients of below T2. In the validation cohort, the accuracy was 43% to 78%, the sensitivity was 13% to 81%, and the specificity was 36% to 91%, thereby showing a possibility of discrimination with a miRNA marker alone or a combination of miRNA markers according to the priority order of sensitivity and specificity.

TABLE 18

| No. | Name of miRNA | SEQ ID NO |
|---|---|---|
| 1 | hsa-miR-1273g-3p | 15 |
| 2 | hsa-miR-2861 | 29 |
| 3 | hsa-miR-663b | 162 |
| 4 | hsa-miR-128-2-5p | 16 |
| 5 | hsa-miR-4673 | 109 |
| 6 | hsa-miR-4649-5p | 102 |
| 7 | hsa-miR-4436b-5p | 76 |
| 8 | hsa-miR-1915-3p | 25 |
| 9 | hsa-miR-4656 | 106 |
| 10 | hsa-miR-6887-5p | 214 |
| 11 | hsa-miR-6789-5p | 190 |
| 12 | hsa-miR-4634 | 100 |
| 13 | hsa-miR-6885-5p | 213 |
| 14 | hsa-miR-6869-5p | 207 |

TABLE 19-1

| No. | miRNA marker | SEQ ID NO | Training cohort | | | | Validation cohort | | | |
|---|---|---|---|---|---|---|---|---|---|---|
| | | | Sensitivity | Specificity | Accuracy | AUC | Sensitivity | Specificity | Accuracy | AUC |
| 1 | hsa-miR-1273g-3p | 15 | 0.3103 | 0.8978 | 0.7231 | 0.6232 | 0.2812 | 0.8834 | 0.7846 | 0.5652 |
| 2 | hsa-miR-2861 | 29 | 0.8448 | 0.438 | 0.559 | 0.6369 | 0.8125 | 0.3558 | 0.4308 | 0.5671 |
| 3 | hsa-miR-663b | 162 | 0.2759 | 0.927 | 0.7333 | 0.6204 | 0.125 | 0.908 | 0.7795 | 0.5395 |
| 4 | hsa-miR-128-2-5p | 16 | 0.7931 | 0.438 | 0.5436 | 0.6175 | 0.5 | 0.5399 | 0.5333 | 0.4958 |
| 5 | hsa-miR-4673 | 109 | 0.3103 | 0.8467 | 0.6872 | 0.5882 | 0.1875 | 0.7485 | 0.6564 | 0.5242 |
| 6 | hsa-miR-4649-5p | 102 | 0.6379 | 0.6204 | 0.6256 | 0.6188 | 0.4375 | 0.5951 | 0.5692 | 0.5405 |
| 7 | hsa-miR-4436b-5p | 76 | 0.5517 | 0.5912 | 0.5795 | 0.578 | 0.4375 | 0.5399 | 0.5231 | 0.5067 |
| 8 | hsa-miR-1915-3p | 25 | 0.569 | 0.5985 | 0.5897 | 0.5797 | 0.5625 | 0.5828 | 0.5795 | 0.573 |
| 9 | hsa-miR-4656 | 106 | 0.5172 | 0.6131 | 0.5846 | 0.5563 | 0.4375 | 0.6196 | 0.5897 | 0.5742 |
| 10 | hsa-miR-6887-5p | 214 | 0.3276 | 0.8175 | 0.6718 | 0.5472 | 0.1875 | 0.7975 | 0.6974 | 0.5192 |
| 11 | hsa-miR-6789-5p | 190 | 0.5862 | 0.6496 | 0.6308 | 0.6318 | 0.5 | 0.546 | 0.5385 | 0.5289 |
| 12 | hsa-miR-4634 | 100 | 0.6379 | 0.5766 | 0.5949 | 0.6102 | 0.5938 | 0.5644 | 0.5692 | 0.5828 |
| 13 | hsa-miR-6885-5p | 213 | 0.8448 | 0.3796 | 0.5179 | 0.6114 | 0.7188 | 0.3804 | 0.4359 | 0.5615 |
| 14 | hsa-miR-6869-5p | 207 | 0.6207 | 0.5401 | 0.5641 | 0.5732 | 0.5 | 0.6258 | 0.6051 | 0.5811 |

TABLE 19-2

| No | Discriminant formula | Threshold |
|---|---|---|
| 1 | (1.34571)*hsa-miR-1273g-3p − 11.9051 | 0.9104 |
| 2 | (5.43533)*hsa-miR-2861 − 66.1197 | −0.4464 |
| 3 | (1.2903)*hsa-miR-663b − 11.7566 | 1.07 |
| 4 | (1.5771)*hsa-miR-1282-5p − 17.8517 | −0.3764 |
| 5 | (−0.930503)*hsa-miR-4673 + 5.53046 | 0.3233 |
| 6 | (1.4893)*hsa-miR-4649-5p − 15.8607 | 0.08691 |
| 7 | (−1.32879)*hsa-miR-4436b-5p + 8.9169 | −0.00369 |
| 8 | (2.49604)*hsa-miR-1915-3p − 26.8687 | 0.07825 |
| 9 | (1.90635)*hsa-miR-4656 − 14.7212 | 0.0203 |
| 10 | (−0.926102)*hsa-miR-6887-5p + 6.37662 | 0.4298 |
| 11 | (2.4365)*hsa-miR-6789-5p − 24.9263 | −0.06067 |
| 12 | (2.11662)*hsa-miR-4634 − 19.3942 | −0.1283 |
| 13 | (1.42045)*hsa-miR-6885-5p − 16.331 | −0.5798 |
| 14 | (1.75884)*hsa-miR-6869-5p − 23.1502 | −0.1197 |

Example 5

(Common miRNAs in Examples 1 to 3)

In this Example, genes common in Examples 1 and 2 were extracted from the genes shown in each of Examples 1 to 3 capable of discriminating between bladder cancer patients and subjects without bladder cancer, to obtain 43 gene markers capable of detecting bladder cancer with higher versatility (Table 20). Further, genes common in Examples 1 and 3 were extracted to obtain 62 gene markers capable of detecting bladder cancer with higher versatility (Table 21). Further, genes common in Examples 2 and 3 were extracted to obtain 30 gene markers capable of detecting bladder cancer with higher versatility (Table 22). Further, genes common in all Examples 1 to 3 were extracted to obtain 23 gene markers capable of detecting bladder cancer with higher versatility (Table 23). It can be said that the genes shown in Tables 20 to 23 are markers that can detect bladder cancer with high versatility and can be commonly used in various analytical techniques.

TABLE 20

| No. | Name of miRNA | SEQ ID NO |
|---|---|---|
| 1 | hsa-miR-4658 | 107 |
| 2 | hsa-miR-6717-5p | 164 |
| 3 | hsa-miR-8073 | 226 |
| 4 | hsa-miR-4436b-5p | 76 |
| 5 | hsa-miR-4663 | 108 |
| 6 | hsa-miR-4652-5p | 104 |
| 7 | hsa-miR-1343-5p | 18 |
| 8 | hsa-miR-371b-5p | 59 |
| 9 | hsa-miR-6800-5p | 193 |
| 10 | hsa-miR-4771 | 135 |
| 11 | hsa-miR-615-5p | 155 |
| 12 | hsa-miR-4741 | 131 |
| 13 | hsa-miR-1185-1-3p | 2 |
| 14 | hsa-miR-6741-5p | 169 |
| 15 | hsa-miR-663a | 240 |
| 16 | hsa-miR-1228-5p | 9 |
| 17 | hsa-miR-4728-5p | 126 |
| 18 | hsa-miR-937-5p | 228 |
| 19 | hsa-miR-887-3p | 227 |
| 20 | hsa-miR-6075 | 148 |
| 21 | hsa-miR-6087 | 1 |
| 22 | hsa-miR-6760-5p | 174 |
| 23 | hsa-miR-4763-3p | 134 |
| 24 | hsa-miR-4675 | 110 |
| 25 | hsa-miR-328-5p | 46 |
| 26 | hsa-miR-6716-5p | 163 |
| 27 | hsa-miR-4455 | 83 |
| 28 | hsa-miR-3619-3p | 50 |
| 29 | hsa-miR-3160-5p | 35 |
| 30 | hsa-miR-6724-5p | 166 |
| 31 | hsa-miR-3621 | 52 |
| 32 | hsa-miR-4739 | 129 |
| 33 | hsa-miR-6132 | 153 |
| 34 | hsa-miR-6791-5p | 191 |
| 35 | hsa-miR-4725-3p | 123 |
| 36 | hsa-miR-4750-5p | 132 |
| 37 | hsa-miR-1343-3p | 17 |
| 38 | hsa-miR-7108-3p | 216 |
| 39 | hsa-miR-3195 | 42 |
| 40 | hsa-miR-4687-3p | 111 |
| 41 | hsa-miR-1185-2-3p | 3 |
| 42 | hsa-miR-6088 | 150 |
| 43 | hsa-miR-6777-5p | 182 |

TABLE 21

| No. | Name of miRNA | SEQ ID NO |
|---|---|---|
| 1 | hsa-miR-4652-5p | 104 |
| 2 | hsa-miR-3160-5p | 35 |
| 3 | hsa-miR-4658 | 107 |
| 4 | hsa-miR-4755-3p | 133 |
| 5 | hsa-miR-3194-3p | 41 |
| 6 | hsa-miR-4663 | 108 |
| 7 | hsa-miR-17-3p | 20 |
| 8 | hsa-miR-4480 | 88 |
| 9 | hsa-miR-4727-3p | 125 |
| 10 | hsa-miR-4455 | 83 |
| 11 | hsa-miR-6760-5p | 174 |

TABLE 21-continued

| No. | Name of miRNA | SEQ ID NO |
|---|---|---|
| 12 | hsa-miR-4483 | 89 |
| 13 | hsa-miR-2467-3p | 28 |
| 14 | hsa-miR-4771 | 135 |
| 15 | hsa-miR-4718 | 121 |
| 16 | hsa-miR-4525 | 96 |
| 17 | hsa-miR-4740-5p | 130 |
| 18 | hsa-miR-6717-5p | 164 |
| 19 | hsa-miR-191-5p | 238 |
| 20 | hsa-miR-371b-5p | 59 |
| 21 | hsa-miR-6777-5p | 182 |
| 22 | hsa-miR-4462 | 85 |
| 23 | hsa-miR-320b | 45 |
| 24 | hsa-miR-4708-3p | 119 |
| 25 | hsa-miR-4436b-5p | 76 |
| 26 | hsa-miR-8073 | 226 |
| 27 | hsa-miR-5572 | 146 |
| 28 | hsa-miR-615-5p | 155 |
| 29 | hsa-miR-3619-3p | 50 |
| 30 | hsa-miR-4750-5p | 132 |
| 31 | hsa-miR-5010-5p | 142 |
| 32 | hsa-miR-6877-5p | 209 |
| 33 | hsa-miR-3622a-5p | 53 |
| 34 | hsa-miR-6087 | 1 |
| 35 | hsa-miR-4787-3p | 138 |
| 36 | hsa-miR-345-3p | 48 |
| 37 | hsa-miR-320a | 44 |
| 38 | hsa-miR-4430 | 74 |
| 39 | hsa-miR-3616-3p | 49 |
| 40 | hsa-miR-4535 | 98 |
| 41 | hsa-miR-187-5p | 21 |
| 42 | hsa-miR-1343-3p | 17 |
| 43 | hsa-miR-6766-5p | 179 |
| 44 | hsa-miR-4419b | 72 |
| 45 | hsa-miR-1238-5p | 11 |
| 46 | hsa-miR-4728-5p | 126 |
| 47 | hsa-miR-210-5p | 26 |
| 48 | hsa-miR-6076 | 149 |
| 49 | hsa-miR-619-5p | 156 |
| 50 | hsa-miR-1185-2-3p | 3 |
| 51 | hsa-miR-6741-5p | 169 |
| 52 | hsa-miR-6842-5p | 204 |
| 53 | hsa-miR-1273g-3p | 15 |
| 54 | hsa-miR-7975 | 222 |
| 55 | hsa-miR-6819-5p | 198 |
| 56 | hsa-miR-6088 | 150 |
| 57 | hsa-miR-8052 | 224 |
| 58 | hsa-miR-4736 | 128 |
| 59 | hsa-miR-7113-3p | 219 |
| 60 | hsa-miR-6075 | 148 |
| 61 | hsa-miR-1247-3p | 12 |
| 62 | hsa-miR-1185-1-3p | 2 |

TABLE 22

| No. | Name of miRNA | SEQ ID NO |
|---|---|---|
| 1 | hsa-miR-4652-5p | 104 |
| 2 | hsa-miR-3160-5p | 35 |
| 3 | hsa-miR-4658 | 107 |
| 4 | hsa-miR-4663 | 108 |
| 5 | hsa-miR-29b-3p | 31 |
| 6 | hsa-miR-4455 | 83 |
| 7 | hsa-miR-6760-5p | 174 |
| 8 | hsa-miR-4771 | 135 |
| 9 | hsa-miR-6717-5p | 164 |
| 10 | hsa-miR-1246 | 231 |
| 11 | hsa-miR-4448 | 80 |
| 12 | hsa-miR-371b-5p | 59 |
| 13 | hsa-miR-6777-5p | 182 |
| 14 | hsa-miR-4436b-5p | 76 |
| 15 | hsa-miR-8073 | 226 |
| 16 | hsa-miR-4710 | 120 |
| 17 | hsa-miR-615-5p | 155 |
| 18 | hsa-miR-3619-3p | 50 |
| 19 | hsa-miR-4750-5p | 132 |
| 20 | hsa-miR-6087 | 1 |
| 21 | hsa-miR-1193 | 4 |
| 22 | hsa-miR-1343-3p | 17 |
| 23 | hsa-miR-4728-5p | 126 |
| 24 | hsa-miR-1185-2-3p | 3 |
| 25 | hsa-miR-6741-5p | 169 |
| 26 | hsa-miR-6765-3p | 176 |
| 27 | hsa-miR-4783-3p | 136 |
| 28 | hsa-miR-6088 | 150 |
| 29 | hsa-miR-6075 | 148 |
| 30 | hsa-miR-1185-1-3p | 2 |

TABLE 23

| No. | Name of miRNA | SEQ ID NO |
|---|---|---|
| 1 | hsa-miR-4652-5p | 104 |
| 2 | hsa-miR-3160-5p | 35 |
| 3 | hsa-miR-4658 | 107 |
| 4 | hsa-miR-4663 | 108 |
| 5 | hsa-miR-4455 | 83 |
| 6 | hsa-miR-6760-5p | 174 |
| 7 | hsa-miR-4771 | 135 |
| 8 | hsa-miR-6717-5p | 164 |
| 9 | hsa-miR-371b-5p | 59 |
| 10 | hsa-miR-6777-5p | 182 |
| 11 | hsa-miR-4436b-5p | 76 |
| 12 | hsa-miR-8073 | 226 |
| 13 | hsa-miR-615-5p | 155 |
| 14 | hsa-miR-3619-3p | 50 |
| 15 | hsa-miR-4750-5p | 132 |
| 16 | hsa-miR-6087 | 1 |
| 17 | hsa-miR-1343-3p | 17 |
| 18 | hsa-miR-4728-5p | 126 |
| 19 | hsa-miR-1185-2-3p | 3 |
| 20 | hsa-miR-6741-5p | 169 |
| 21 | hsa-miR-6088 | 150 |
| 22 | hsa-miR-6075 | 148 |
| 23 | hsa-miR-1185-1-3p | 2 |

Example 6

<Discriminant Analysis of Bladder Cancer from Other Cancers>

In this Example, the analysis was performed on sera of 972 people including 392 bladder cancer patients, 40 patients each of the cancers other than the bladder cancer patients shown in the Reference Example, 0 uterine sarcoma patients, and 100 healthy subjects. ½ of the samples of each group were sorted into a training cohort, and rest ½ of the samples were sorted into a validation cohort (Table 24).

In this Example, discriminant formulas with 1 to 9 gene markers were created using a training cohort including bladder cancer patients and subjects without bladder cancer including healthy subjects and patients of cancers other than bladder cancer, the discriminant performance in the validation cohort was evaluated, and genes used for a total of 9 discriminant formulas exhibiting the best discriminant performance in each case of combining 1 to 9 genes were extracted, to obtain 18 gene markers capable of detecting bladder cancer (Table 25).

Figure 21:
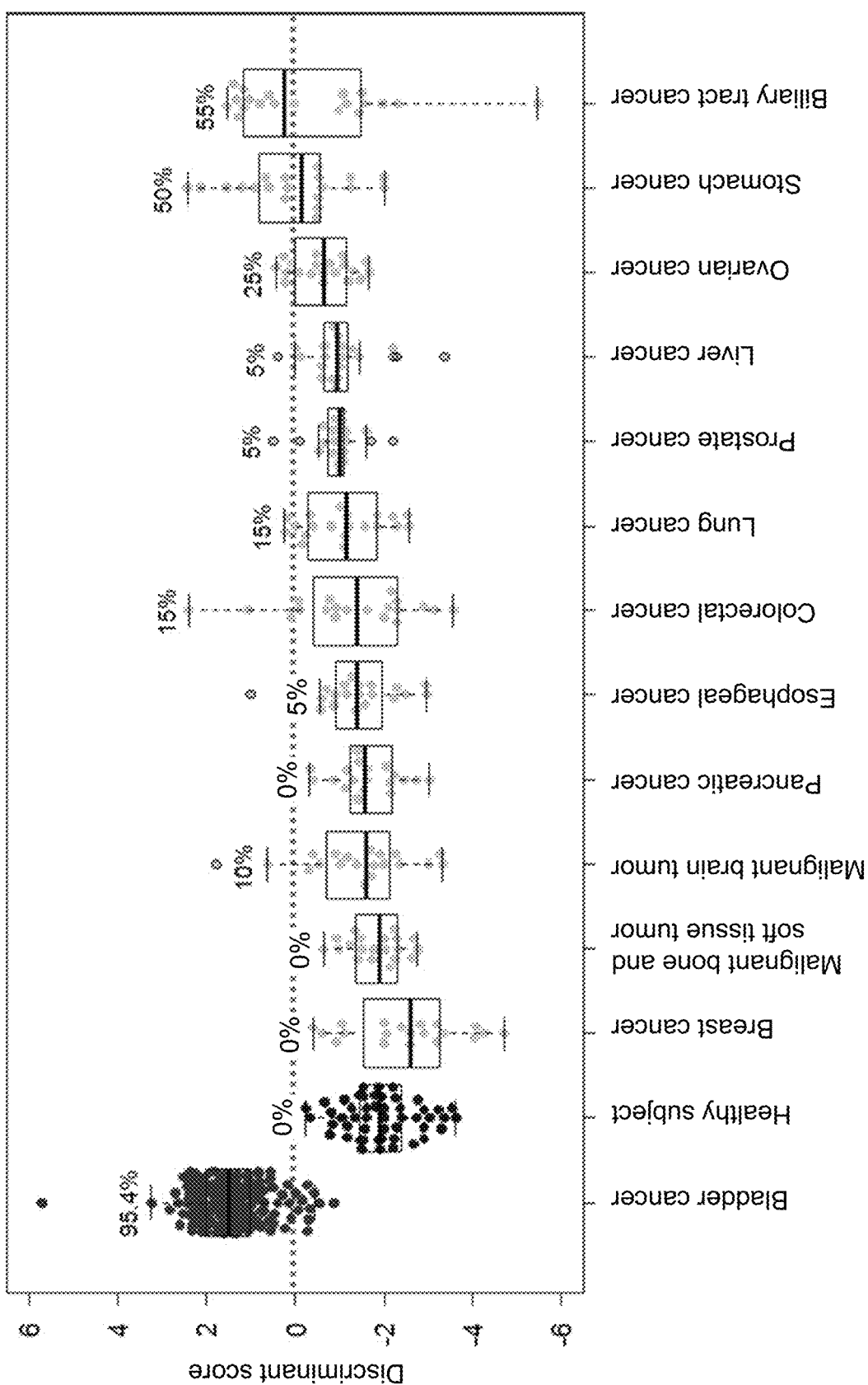
FIG. 21 shows plots of discriminant scores according to the disease type determined with the use of 7 miRNAs in combination.

Specifically, first, miRNA expression levels in the training cohort and the validation cohort obtained as in the above Reference Example were together normalized in accordance with global normalization. Further, in order to acquire more reliable diagnostic markers, only 386 genes with a gene expression level of $2^6$ or larger in 50% or more of the samples were analyzed in either the positive sample group (bladder cancer patients) or the negative sample group (patients of cancers other than bladder cancer, benign disease patients, and healthy subjects). Next, Fisher's discriminant analysis was performed on the measured values of the expression levels of a combination of 1 to 9 genes out of the aforementioned 386 genes, to construct discriminant formulas for discriminating the presence or absence of bladder cancer. At this time, discriminant formulas with high discriminant performance were searched for by a modified greedy algorithm. Further, the above-prepared discriminant formulas were used to calculate the accuracy, the sensitivity, and the specificity in the validation cohort. Then, the discriminant performance was validated in independent samples. The marker, discriminant formula, and the like exhibiting the highest performance is shown for each number of genes used for discrimination (Tables 26-1 and 26-2). Further, the ROC curves of the training cohort and the validation cohort with a combination of 1 or 7 miRNAs are shown in FIG. 20, and the discriminant scores with 7 miRNAs are plotted for each disease type in FIG. 21.

TABLE 24

| Characteristics | Training cohort (n = 546) | Validation cohort (n = 546) |
|---|---|---|
| Bladder cancer | 196 | 196 |
| Median age, yr(range) | 69(60-76) | 68(62-74) |
| Sex, n(%) | | |
| Male | 137(69.9) | 146(74.5) |
| Female | 59(30.1) | 50(25.5) |
| Pathological Tstage, n(%) | | |
| T2 or lower | 150(76.5) | 150(76.5) |
| T2 or higher | 46(23.5) | 44(22.4) |
| Unknown | 0 | 2(1.0) |
| Pathological grade, n(%) | | |
| Low grade | 36(18.4) | 41(20.9) |
| high grade | 160(81.6) | 155(79.1) |

TABLE 24-continued

| Characteristics | Training cohort (n = 546) | Validation cohort (n = 546) |
|---|---|---|
| Healthy | 50 | 50 |
| Median age, yr(range) | 61(51-59) | 68(52-68) |
| Sex, n(%) | | |
| Male | 23(46.0) | 25(50.0) |
| Female | 27(54.0) | 25(50.0) |
| Other cancers | 240 | 240 |
| Median age, yr(range) | 63(56-71) | 63(54-70) |
| Sex, n(%) | | |
| Male | 150(62.5) | 136(56.7) |
| Female | 90(37.5) | 104(43.3) |

TABLE 25

| No. | Name of miRNA | SEQ ID NO |
|---|---|---|
| 1 | hsa-miR-1185-1-3p | 2 |
| 2 | hsa-miR-1185-2-3p | 3 |
| 3 | hsa-miR-1343-5p | 18 |
| 4 | hsa-miR-3184-5p | 39 |
| 5 | hsa-miR-3940-5p | 62 |
| 6 | hsa-miR-3960 | 63 |
| 7 | hsa-miR-4658 | 107 |
| 8 | hsa-miR-4695-5p | 114 |
| 9 | hsa-miR-4728-5p | 126 |
| 10 | hsa-miR-6087 | 1 |
| 11 | hsa-miR-663a | 240 |
| 12 | hsa-miR-6724-5p | 166 |
| 13 | hsa-miR-6781-5p | 185 |
| 14 | hsa-miR-6819-5p | 198 |
| 15 | hsa-miR-6831-5p | 201 |
| 16 | hsa-miR-7108-3p | 216 |
| 17 | hsa-miR-7109-5p | 217 |
| 18 | hsa-miR-744-5p | 221 |

TABLE 26-1

| No. | Number of miRNA | miRNA marker | SEQ ID NO | Validation cohort Sensitivity | Specificity | Accuracy | AUC |
|---|---|---|---|---|---|---|---|
| 1 | 1 | hsa-miR-6087 | 1 | 0.94 | 0.77 | 0.84 | 0.88 |
| 2 | 2 | hsa-miR-6087 | 1 | 0.95 | 0.81 | 0.86 | 0.91 |
| | | hsa-miR-663a | 240 | | | | |
| 3 | 3 | hsa-miR-6087 | 1 | 0.95 | 0.87 | 0.90 | 0.94 |
| | | hsa-miR-6781-5p | 185 | | | | |
| | | hsa-miR-744-5p | 221 | | | | |
| 4 | 4 | hsa-miR-6087 | 1 | 0.97 | 0.86 | 0.91 | 0.95 |
| | | hsa-miR-3940-5p | 62 | | | | |
| | | hsa-miR-4728-5p | 126 | | | | |
| | | hsa-miR-6819-5p | 198 | | | | |
| 5 | 5 | hsa-miR-6087 | 1 | 0.98 | 0.87 | 0.91 | 0.97 |
| | | hsa-miR-6724-5p | 166 | | | | |
| | | hsa-miR-3960 | 63 | | | | |
| | | hsa-miR-1343-5p | 18 | | | | |
| | | hsa-miR-1185-2-3p | 3 | | | | |
| 6 | 6 | hsa-miR-6087 | 1 | 0.97 | 0.90 | 0.93 | 0.97 |
| | | hsa-miR-6724-5p | 166 | | | | |
| | | hsa-miR-3960 | 63 | | | | |
| | | hsa-miR-1343-5p | 18 | | | | |
| | | hsa-miR-1185-2-3p | 3 | | | | |
| | | hsa-miR-4658 | 107 | | | | |
| 7 | 7 | hsa-miR-6087 | 1 | 0.98 | 0.91 | 0.94 | 0.98 |
| | | hsa-miR-6724-5p | 166 | | | | |
| | | hsa-miR-3960 | 63 | | | | |
| | | hsa-miR-1343-5p | 18 | | | | |
| | | hsa-miR-1185-1-3p | 2 | | | | |
| | | hsa-miR-6831-5p | 201 | | | | |
| | | hsa-miR-4695-5p | 114 | | | | |

TABLE 26-1-continued

| No. | Number of miRNA | miRNA marker | SEQ ID NO | Validation cohort Sensitivity | Specificity | Accuracy | AUC |
|---|---|---|---|---|---|---|---|
| 8 | 8 | hsa-miR-6087 | 1 | 0.98 | 0.91 | 0.94 | 0.98 |
|   |   | hsa-miR-6724-5p | 166 | | | | |
|   |   | hsa-miR-3960 | 63 | | | | |
|   |   | hsa-miR-1343-5p | 18 | | | | |
|   |   | hsa-miR-1185-1-3p | 2 | | | | |
|   |   | hsa-miR-6831-5p | 201 | | | | |
|   |   | hsa-miR-4695-5p | 114 | | | | |
|   |   | hsa-miR-7109-5p | 217 | | | | |
| 9 | 9 | hsa-miR-6087 | 1 | 1.00 | 0.90 | 0.94 | 0.98 |
|   |   | hsa-miR-6724-5p | 166 | | | | |
|   |   | hsa-miR-3960 | 63 | | | | |
|   |   | hsa-miR-1343-5p | 18 | | | | |
|   |   | hsa-miR-1185-1-3p | 2 | | | | |
|   |   | hsa-miR-6831-5p | 201 | | | | |
|   |   | hsa-miR-3184-5p | 39 | | | | |
|   |   | hsa-miR-7108-3p | 216 | | | | |
|   |   | hsa-miR-4695-5p | 114 | | | | |

TABLE 26-2

| No. | Number of miRNA | Discriminant formula |
|---|---|---|
| 1 | 1 | (−2.47083)*hsa-miR-6087 + 29.1765 |
| 2 | 2 | (−2.45684)*hsa-miR-6087 + (0.674768)*hsa-miR-663a + 20.7712 |
| 3 | 3 | (−2.47956)*hsa-miR-6087 + (−1.18834)*hsa-miR-6781-5p + (0.662579)*hsa-miR-744-5p + 34.9109 |
| 4 | 4 | (−1.67453)*hsa-miR-6087 + (−1.07965)*hsa-miR-3940-5p + (−0.865343)*hsa-miR-4728-5p + (0.936314)*hsa-miR-6819-5p + 30.2466 |
| 5 | 5 | (−2.33489)*hsa-miR-6087 + (2.1135)*hsa-miR-6724-5p + (−1.28296)*hsa-miR-3960 + (−1.33813)*hsa-miR-1343-5p + (0.211841)*hsa-miR-1185-2-3p + 35.6487 |
| 6 | 6 | (−2.22483)*hsa-miR-6087 + (1.96229)*hsa-miR-6724-5p + (−1.1623)*hsa-miR-3960 + (−1.24909)*hsa-miR-1343-5p + (0.191799)*hsa-miR-1185-2-3p + (0.0988384)*hsa-miR-4658 + 32.9756 |
| 7 | 7 | (−2.21832)*hsa-miR-6087 + (2.17809)*hsa-miR-6724-5p + (−1.04605)*hsa-miR-3960 + (−1.57609)*hsa-miR-1343-5p + (0.202966)*hsa-miR-1185-1-3p + (0.203839)*hsa-miR-6831-5p + (−0.411172)*hsa-miR-4695-5p + 34.7121 |
| 8 | 8 | (−2.23426)*hsa-miR-6087 + (2.10616)*hsa-miR-6724-5p + (−1.09832)*hsa-miR-3960 + (−1.49652)*hsa-miR-1343-5p + (0.233803)*hsa-miR-1185-1-3p + (0.209904)*hsa-miR-6831-5p + (−0.365926)*hsa-miR-4695-5p + (−0.195056)*hsa-miR-7109-5p + 36.4566 |
| 9 | 9 | (−2.18021)*hsa-miR-6087 + (2.14473)*hsa-miR-6724-5p + (−0.990552)*hsa-miR-3960 + (−1.3526)*hsa-miR-1343-5p + (0.201392)*hsa-miR-1185-1-3p + (0.215897)*hsa-miR-6831-5p + (−0.117666)*hsa-miR-3184-5p + (−0.0946823)*hsa-miR-7108-3p + (−0.373914)*hsa-miR-4695-5p + 32.4599 |

INDUSTRIAL APPLICABILITY

The present invention enables bladder cancer of various histological types and stages to be effectively detected by an easy and inexpensive method, thereby enabling detection, diagnosis, and treatment of bladder cancer at an early stage. Further, the method of the present invention enables bladder cancer to be detected minimally invasively using patient blood, thereby enabling bladder cancer to be detected simply and quickly.

All the publications, patents, and patent applications cited herein are incorporated herein by reference.

The invention claimed is:

1. A method for detecting bladder cancer, comprising:
measuring an expression level of miR-4652-5p in a sample from a human subject;
determining that the level of miR-4652-5p in the sample from the human subject is increased in comparison to a level of miR-4652-5p in a control sample from a human subject without bladder cancer;
determining that the human subject has bladder cancer based on the increased expression level of miR-4652-5p; and
treating the human subject for the bladder cancer;
wherein the sample is blood, serum, or plasma; and
wherein the treating comprises surgery, radiotherapy, chemotherapy, or a combination thereof.

2. The method according to claim 1, comprising: plugging the expression level of miR-4652-5p in the sample from the subject into a discriminant formula capable of discriminating the presence or absence of a bladder cancer distinctively, wherein the discriminant formula is created by using expression levels in samples from subjects known to have bladder cancer and expression levels in samples from subjects having no bladder cancer as training samples.

3. The method according to claim 1, comprising: measuring an expression level of miR-4652-5p by using a nucleic acid(s) capable of specifically binding to miR-4652-5p or the complement thereof, wherein the nucleic acid(s) is a polynucleotide(s) selected from the group consisting of:
(a) a polynucleotide consisting of SEQ ID NO: 104 or the complement thereof;
(b) a polynucleotide comprising SEQ ID NO: 104 or the complement thereof; and
(c) a polynucleotide derived from SEQ ID NO: 104, wherein the uracils have been replaced with thymines, or a complement thereof.

4. The method according to claim 1, further comprising: measuring an expression level(s) of at least one polynucleotide selected from miR-1202, miR-1207-5p, miR-1246, miR-1254, miR-135a-3p, miR-1469, miR-149-3p, miR-150-3p, miR-1914-3p, miR-191-5p, miR-423-5p, miR-663a, miR-92a-2-5p, miR-92a-3p, and miR-940.

5. The method according to claim 4, comprising: measuring an expression level of the at least one polynucleotide by using a nucleic acid(s) capable of specifically binding to the at least one polynucleotide or the complement thereof, wherein the nucleic acid(s) is a polynucleotide(s) selected from the group consisting of:
(a) a polynucleotide consisting of any of SEQ ID NOs: 229-243 or the complements thereof;
(b) a polynucleotide comprising any of SEQ ID NOs: 229-243 or the complements thereof; and
(c) a polynucleotide derived from any of SEQ ID NOs: 229-243, wherein the uracils have been replaced with thymines, or the complements thereof.

6. The method according to claim 1, wherein the sample is serum or plasma.

7. The method according to claim 1, wherein the method further comprises measuring an expression level(s) of at least one polynucleotide selected from miR-6087, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR- 320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p and miR-937-5p in the sample.

8. A method for detecting bladder cancer, comprising:
measuring an expression level of miR-4652-5p in a sample from a human subject;
determining that the level of miR-4652-5p in the sample from the human subject is increased in comparison to a level of miR-4652-5p in a control sample from a human subject without bladder cancer;
determining that the human subject has bladder cancer based on the increased expression level of miR-4652-5p; and
treating the human subject for the bladder cancer;
wherein the treating comprises surgery, radiotherapy, chemotherapy, or a combination thereof;
wherein the sample is blood, serum, or plasma; and
wherein the measuring is performed using a kit comprising a nucleic acid(s) capable of specifically binding to miR-4652-5p or a complement thereof.

9. The method according to claim 8, wherein the method further comprises measuring an expression level(s) of at least one polynucleotide selected from miR-6087, miR-1185-2-3p, miR-1193, miR-1199-5p, miR-1225-5p, miR-1227-5p, miR-1228-3p, miR-1228-5p, miR-1237-5p, miR-1238-5p, miR-1247-3p, miR-1268a, miR-1268b, miR-1273g-3p, miR-128-2-5p, miR-1343-3p, miR-1343-5p, miR-1470, miR-17-3p, miR-187-5p, miR-1908-3p, miR-1908-5p, miR-1909-3p, miR-1915-3p, miR-210-5p, miR-24-3p, miR-2467-3p, miR-2861, miR-296-3p, miR-29b-3p, miR-3131, miR-3154, miR-3158-5p, miR-3160-5p, miR-3162-5p, miR-3178, miR-3180-3p, miR-3184-5p, miR-3185, miR-3194-3p, miR-3195, miR-3197, miR-320a, miR-320b, miR-328-5p, miR-342-5p, miR-345-3p, miR-3616-3p, miR-3619-3p, miR-3620-5p, miR-3621, miR-3622a-5p, miR-3648, miR-3652, miR-3656, miR-3663-3p, miR-3679-5p, miR-371b-5p, miR-373-5p, miR-3917, miR-3940-5p, miR-3960, miR-4258, miR-4259, miR-4270, miR-4286, miR-4298, miR-4322, miR-4327, miR-4417, miR-4419b, miR-4429, miR-4430, miR-4433a-3p, miR-4436b-5p, miR-4443, miR-4446-3p, miR-4447, miR-4448, miR-4449, miR-4454, miR-4455, miR-4459, miR-4462, miR-4466, miR-4467, miR-4480, miR-4483, miR-4484, miR-4485-5p, miR-4488, miR-4492, miR-4505, miR-4515, miR-4525, miR-4534, miR-4535, miR-4633-3p, miR-4634, miR-4640-5p, miR-4649-5p, miR-4651, miR-4655-5p, miR-4656, miR-4658, miR-4663, miR-4673, miR-4675, miR-4687-3p, miR-4687-5p, miR-4690-5p, miR-4695-5p, miR-4697-5p, miR-4706, miR-4707-3p, miR-4707-5p, miR-4708-3p, miR-4710, miR-4718, miR-4722-5p, miR-4725-3p, miR-4726-5p, miR-4727-3p, miR-4728-5p, miR-4731-5p, miR-4736, miR-4739, miR-4740-5p, miR-4741, miR-4750-5p, miR-4755-3p, miR-4763-3p, miR-4771, miR-4783-3p, miR-4783-5p, miR-4787-3p, miR-4792, miR-498, miR-5008-5p, miR-5010-5p, miR-504-3p, miR-5195-3p, miR-550a-5p, miR-5572, miR-5739, miR-6075, miR-6076, miR-6088, miR-6124, miR-6131, miR-6132, miR-614, miR-615-5p, miR-619-5p, miR-642b-3p, miR-6510-5p, miR-6511a-5p, miR-6515-3p, miR-6515-5p, miR-663b, miR-6716-5p, miR-6717-5p, miR-6722-3p, miR-6724-5p, miR-6726-5p, miR-6737-5p, miR-6741-5p, miR-6742-5p, miR-6743-5p, miR-6746-5p, miR-6749-5p, miR-6760-5p, miR-6762-5p, miR-6765-3p, miR-6765-5p, miR-6766-3p, miR-6766-5p, miR-6771-5p, miR-6774-5p, miR-6777-5p, miR-6778-5p, miR-6780b-5p, miR-6781-5p, miR-6782-5p, miR-6784-5p, miR-6785-5p, miR-6787-5p, miR-6789-5p, miR-6791-5p, miR-6794-5p, miR-6800-5p, miR-6802-5p, miR-6803-5p, miR-6812-5p, miR-6816-5p, miR-6819-5p, miR-6821-5p, miR-6826-5p, miR-6831-5p, miR-6836-3p, miR-6840-3p, miR-6842-5p, miR-6850-5p, miR-6861-5p, miR-6869-5p, miR-6870-5p, miR-6877-5p, miR-6879-5p, miR-6880-3p, miR-6880-5p, miR-6885-5p, miR-6887-5p, miR-7107-5p, miR-7108-3p, miR-7109-5p, miR-711, miR-7113-3p, miR-7150, miR-744-5p, miR-7975, miR-7977, miR-8052, miR-8069, miR-8073, miR-887-3p and miR-937-5p in the sample.

\* \* \* \* \*

SEQUENCE LISTING

```
Sequence total quantity: 766
SEQ ID NO: 1                 moltype = RNA   length = 18
FEATURE                      Location/Qualifiers
source                       1..18
                             mol_type = transcribed RNA
                             organism = Homo sapiens
SEQUENCE: 1
tgaggcgggg gggcgagc                                                   18

SEQ ID NO: 2                 moltype = RNA   length = 22
FEATURE                      Location/Qualifiers
source                       1..22
```

```
                         mol_type = transcribed RNA
                         organism = Homo sapiens
SEQUENCE: 2
atatacaggg ggagactctt at                                          22

SEQ ID NO: 3             moltype = RNA   length = 22
FEATURE                  Location/Qualifiers
source                   1..22
                         mol_type = transcribed RNA
                         organism = Homo sapiens
SEQUENCE: 3
atatacaggg ggagactctc at                                          22

SEQ ID NO: 4             moltype = RNA   length = 23
FEATURE                  Location/Qualifiers
source                   1..23
                         mol_type = transcribed RNA
                         organism = Homo sapiens
SEQUENCE: 4
gggatggtag accggtgacg tgc                                         23

SEQ ID NO: 5             moltype = RNA   length = 20
FEATURE                  Location/Qualifiers
source                   1..20
                         mol_type = transcribed RNA
                         organism = Homo sapiens
SEQUENCE: 5
cctgagcccg ggccgcgcag                                             20

SEQ ID NO: 6             moltype = RNA   length = 22
FEATURE                  Location/Qualifiers
source                   1..22
                         mol_type = transcribed RNA
                         organism = Homo sapiens
SEQUENCE: 6
gtgggtacgg cccagtgggg gg                                          22

SEQ ID NO: 7             moltype = RNA   length = 17
FEATURE                  Location/Qualifiers
source                   1..17
                         mol_type = transcribed RNA
                         organism = Homo sapiens
SEQUENCE: 7
gtggggccag gcggtgg                                                17

SEQ ID NO: 8             moltype = RNA   length = 20
FEATURE                  Location/Qualifiers
source                   1..20
                         mol_type = transcribed RNA
                         organism = Homo sapiens
SEQUENCE: 8
tcacacctgc ctcgcccccc                                             20

SEQ ID NO: 9             moltype = RNA   length = 21
FEATURE                  Location/Qualifiers
source                   1..21
                         mol_type = transcribed RNA
                         organism = Homo sapiens
SEQUENCE: 9
gtgggcgggg gcaggtgtgt g                                           21

SEQ ID NO: 10            moltype = RNA   length = 21
FEATURE                  Location/Qualifiers
source                   1..21
                         mol_type = transcribed RNA
                         organism = Homo sapiens
SEQUENCE: 10
cgggggcggg gccgaagcgc g                                           21

SEQ ID NO: 11            moltype = RNA   length = 23
FEATURE                  Location/Qualifiers
source                   1..23
                         mol_type = transcribed RNA
                         organism = Homo sapiens
SEQUENCE: 11
gtgagtggga gccccagtgt gtg                                         23

SEQ ID NO: 12            moltype = RNA   length = 24
FEATURE                  Location/Qualifiers
```

```
source                  1..24
                        mol_type = transcribed RNA
                        organism = Homo sapiens
SEQUENCE: 12
ccccgggaac gtcgagactg gagc                                              24

SEQ ID NO: 13           moltype = RNA   length = 18
FEATURE                 Location/Qualifiers
source                  1..18
                        mol_type = transcribed RNA
                        organism = Homo sapiens
SEQUENCE: 13
cgggcgtggt ggtgggg                                                      18

SEQ ID NO: 14           moltype = RNA   length = 20
FEATURE                 Location/Qualifiers
source                  1..20
                        mol_type = transcribed RNA
                        organism = Homo sapiens
SEQUENCE: 14
cgggcgtggt ggtggggtg                                                    20

SEQ ID NO: 15           moltype = RNA   length = 21
FEATURE                 Location/Qualifiers
source                  1..21
                        mol_type = transcribed RNA
                        organism = Homo sapiens
SEQUENCE: 15
accactgcac tccagcctga g                                                 21

SEQ ID NO: 16           moltype = RNA   length = 23
FEATURE                 Location/Qualifiers
source                  1..23
                        mol_type = transcribed RNA
                        organism = Homo sapiens
SEQUENCE: 16
gggggccgat acactgtacg aga                                               23

SEQ ID NO: 17           moltype = RNA   length = 22
FEATURE                 Location/Qualifiers
source                  1..22
                        mol_type = transcribed RNA
                        organism = Homo sapiens
SEQUENCE: 17
ctcctggggc ccgcactctc gc                                                22

SEQ ID NO: 18           moltype = RNA   length = 22
FEATURE                 Location/Qualifiers
source                  1..22
                        mol_type = transcribed RNA
                        organism = Homo sapiens
SEQUENCE: 18
tggggagcgg cccccgggtg gg                                                22

SEQ ID NO: 19           moltype = RNA   length = 21
FEATURE                 Location/Qualifiers
source                  1..21
                        mol_type = transcribed RNA
                        organism = Homo sapiens
SEQUENCE: 19
gccctccgcc cgtgcacccc g                                                 21

SEQ ID NO: 20           moltype = RNA   length = 22
FEATURE                 Location/Qualifiers
source                  1..22
                        mol_type = transcribed RNA
                        organism = Homo sapiens
SEQUENCE: 20
actgcagtga aggcacttgt ag                                                22

SEQ ID NO: 21           moltype = RNA   length = 22
FEATURE                 Location/Qualifiers
source                  1..22
                        mol_type = transcribed RNA
                        organism = Homo sapiens
SEQUENCE: 21
ggctacaaca caggacccgg gc                                                22

SEQ ID NO: 22           moltype = RNA   length = 21
```

```
                        -continued

FEATURE                 Location/Qualifiers
source                  1..21
                        mol_type = transcribed RNA
                        organism = Homo sapiens
SEQUENCE: 22
ccggccgccg gctccgcccc g                                              21

SEQ ID NO: 23           moltype = RNA   length = 21
FEATURE                 Location/Qualifiers
source                  1..21
                        mol_type = transcribed RNA
                        organism = Homo sapiens
SEQUENCE: 23
cggcggggac ggcgattggt c                                              21

SEQ ID NO: 24           moltype = RNA   length = 22
FEATURE                 Location/Qualifiers
source                  1..22
                        mol_type = transcribed RNA
                        organism = Homo sapiens
SEQUENCE: 24
cgcagggcc gggtgctcac cg                                              22

SEQ ID NO: 25           moltype = RNA   length = 20
FEATURE                 Location/Qualifiers
source                  1..20
                        mol_type = transcribed RNA
                        organism = Homo sapiens
SEQUENCE: 25
ccccagggcg acgcggcggg                                                20

SEQ ID NO: 26           moltype = RNA   length = 22
FEATURE                 Location/Qualifiers
source                  1..22
                        mol_type = transcribed RNA
                        organism = Homo sapiens
SEQUENCE: 26
agcccctgcc caccgcacac tg                                             22

SEQ ID NO: 27           moltype = RNA   length = 22
FEATURE                 Location/Qualifiers
source                  1..22
                        mol_type = transcribed RNA
                        organism = Homo sapiens
SEQUENCE: 27
tggctcagtt cagcaggaac ag                                             22

SEQ ID NO: 28           moltype = RNA   length = 22
FEATURE                 Location/Qualifiers
source                  1..22
                        mol_type = transcribed RNA
                        organism = Homo sapiens
SEQUENCE: 28
agcagaggca gagaggctca gg                                             22

SEQ ID NO: 29           moltype = RNA   length = 19
FEATURE                 Location/Qualifiers
source                  1..19
                        mol_type = transcribed RNA
                        organism = Homo sapiens
SEQUENCE: 29
ggggcctggc ggtgggcgg                                                 19

SEQ ID NO: 30           moltype = RNA   length = 22
FEATURE                 Location/Qualifiers
source                  1..22
                        mol_type = transcribed RNA
                        organism = Homo sapiens
SEQUENCE: 30
gagggttggg tggaggctct cc                                             22

SEQ ID NO: 31           moltype = RNA   length = 23
FEATURE                 Location/Qualifiers
source                  1..23
                        mol_type = transcribed RNA
                        organism = Homo sapiens
SEQUENCE: 31
tagcaccatt tgaaatcagt gtt                                            23
```

-continued

```
SEQ ID NO: 32          moltype = RNA   length = 23
FEATURE                Location/Qualifiers
source                 1..23
                       mol_type = transcribed RNA
                       organism = Homo sapiens
SEQUENCE: 32
tcgaggactg gtggaagggc ctt                                              23

SEQ ID NO: 33          moltype = RNA   length = 22
FEATURE                Location/Qualifiers
source                 1..22
                       mol_type = transcribed RNA
                       organism = Homo sapiens
SEQUENCE: 33
cagaagggga gttgggagca ga                                               22

SEQ ID NO: 34          moltype = RNA   length = 21
FEATURE                Location/Qualifiers
source                 1..21
                       mol_type = transcribed RNA
                       organism = Homo sapiens
SEQUENCE: 34
cctgcagaga ggaagccctt c                                                21

SEQ ID NO: 35          moltype = RNA   length = 22
FEATURE                Location/Qualifiers
source                 1..22
                       mol_type = transcribed RNA
                       organism = Homo sapiens
SEQUENCE: 35
ggctttctag tctcagctct cc                                               22

SEQ ID NO: 36          moltype = RNA   length = 23
FEATURE                Location/Qualifiers
source                 1..23
                       mol_type = transcribed RNA
                       organism = Homo sapiens
SEQUENCE: 36
ttagggagta gaagggtggg gag                                              23

SEQ ID NO: 37          moltype = RNA   length = 17
FEATURE                Location/Qualifiers
source                 1..17
                       mol_type = transcribed RNA
                       organism = Homo sapiens
SEQUENCE: 37
ggggcgcggc cggatcg                                                     17

SEQ ID NO: 38          moltype = RNA   length = 22
FEATURE                Location/Qualifiers
source                 1..22
                       mol_type = transcribed RNA
                       organism = Homo sapiens
SEQUENCE: 38
tggggcggag cttccggagg cc                                               22

SEQ ID NO: 39          moltype = RNA   length = 24
FEATURE                Location/Qualifiers
source                 1..24
                       mol_type = transcribed RNA
                       organism = Homo sapiens
SEQUENCE: 39
tgagggcct cagaccgagc tttt                                              24

SEQ ID NO: 40          moltype = RNA   length = 23
FEATURE                Location/Qualifiers
source                 1..23
                       mol_type = transcribed RNA
                       organism = Homo sapiens
SEQUENCE: 40
agaagaaggc ggtcggtctg cgg                                              23

SEQ ID NO: 41          moltype = RNA   length = 22
FEATURE                Location/Qualifiers
source                 1..22
                       mol_type = transcribed RNA
                       organism = Homo sapiens
SEQUENCE: 41
agctctgctg ctcactggca gt                                               22
```

```
SEQ ID NO: 42           moltype = RNA   length = 17
FEATURE                 Location/Qualifiers
source                  1..17
                        mol_type = transcribed RNA
                        organism = Homo sapiens
SEQUENCE: 42
cgcgccgggc ccgggtt                                                      17

SEQ ID NO: 43           moltype = RNA   length = 23
FEATURE                 Location/Qualifiers
source                  1..23
                        mol_type = transcribed RNA
                        organism = Homo sapiens
SEQUENCE: 43
ggaggcgcag gctcggaaag gcg                                               23

SEQ ID NO: 44           moltype = RNA   length = 22
FEATURE                 Location/Qualifiers
source                  1..22
                        mol_type = transcribed RNA
                        organism = Homo sapiens
SEQUENCE: 44
aaaagctggg ttgagagggc ga                                                22

SEQ ID NO: 45           moltype = RNA   length = 22
FEATURE                 Location/Qualifiers
source                  1..22
                        mol_type = transcribed RNA
                        organism = Homo sapiens
SEQUENCE: 45
aaaagctggg ttgagagggc aa                                                22

SEQ ID NO: 46           moltype = RNA   length = 23
FEATURE                 Location/Qualifiers
source                  1..23
                        mol_type = transcribed RNA
                        organism = Homo sapiens
SEQUENCE: 46
ggggggggcag gagggctca ggg                                               23

SEQ ID NO: 47           moltype = RNA   length = 21
FEATURE                 Location/Qualifiers
source                  1..21
                        mol_type = transcribed RNA
                        organism = Homo sapiens
SEQUENCE: 47
aggggtgcta tctgtgattg a                                                 21

SEQ ID NO: 48           moltype = RNA   length = 22
FEATURE                 Location/Qualifiers
source                  1..22
                        mol_type = transcribed RNA
                        organism = Homo sapiens
SEQUENCE: 48
gccctgaacg aggggtctgg ag                                                22

SEQ ID NO: 49           moltype = RNA   length = 23
FEATURE                 Location/Qualifiers
source                  1..23
                        mol_type = transcribed RNA
                        organism = Homo sapiens
SEQUENCE: 49
cgagggcatt tcatgatgca ggc                                               23

SEQ ID NO: 50           moltype = RNA   length = 22
FEATURE                 Location/Qualifiers
source                  1..22
                        mol_type = transcribed RNA
                        organism = Homo sapiens
SEQUENCE: 50
gggaccatcc tgcctgctgt gg                                                22

SEQ ID NO: 51           moltype = RNA   length = 22
FEATURE                 Location/Qualifiers
source                  1..22
                        mol_type = transcribed RNA
                        organism = Homo sapiens
SEQUENCE: 51
```

```
gtgggctggg ctgggctggg cc                                                    22

SEQ ID NO: 52           moltype = RNA   length = 20
FEATURE                 Location/Qualifiers
source                  1..20
                        mol_type = transcribed RNA
                        organism = Homo sapiens
SEQUENCE: 52
cgcgggtcgg ggtctgcagg                                                       20

SEQ ID NO: 53           moltype = RNA   length = 22
FEATURE                 Location/Qualifiers
source                  1..22
                        mol_type = transcribed RNA
                        organism = Homo sapiens
SEQUENCE: 53
caggcacggg agctcaggtg ag                                                    22

SEQ ID NO: 54           moltype = RNA   length = 21
FEATURE                 Location/Qualifiers
source                  1..21
                        mol_type = transcribed RNA
                        organism = Homo sapiens
SEQUENCE: 54
agccgcgggg atcgccgagg g                                                     21

SEQ ID NO: 55           moltype = RNA   length = 18
FEATURE                 Location/Qualifiers
source                  1..18
                        mol_type = transcribed RNA
                        organism = Homo sapiens
SEQUENCE: 55
cggctggagg tgtgagga                                                         18

SEQ ID NO: 56           moltype = RNA   length = 17
FEATURE                 Location/Qualifiers
source                  1..17
                        mol_type = transcribed RNA
                        organism = Homo sapiens
SEQUENCE: 56
ggcgggtgcg ggggtgg                                                          17

SEQ ID NO: 57           moltype = RNA   length = 23
FEATURE                 Location/Qualifiers
source                  1..23
                        mol_type = transcribed RNA
                        organism = Homo sapiens
SEQUENCE: 57
tgagcaccac acaggccggg cgc                                                   23

SEQ ID NO: 58           moltype = RNA   length = 23
FEATURE                 Location/Qualifiers
source                  1..23
                        mol_type = transcribed RNA
                        organism = Homo sapiens
SEQUENCE: 58
tgaggatatg gcagggaagg gga                                                   23

SEQ ID NO: 59           moltype = RNA   length = 22
FEATURE                 Location/Qualifiers
source                  1..22
                        mol_type = transcribed RNA
                        organism = Homo sapiens
SEQUENCE: 59
actcaaaaga tggcggcact tt                                                    22

SEQ ID NO: 60           moltype = RNA   length = 22
FEATURE                 Location/Qualifiers
source                  1..22
                        mol_type = transcribed RNA
                        organism = Homo sapiens
SEQUENCE: 60
actcaaaatg ggggcgcttt cc                                                    22

SEQ ID NO: 61           moltype = RNA   length = 20
FEATURE                 Location/Qualifiers
source                  1..20
                        mol_type = transcribed RNA
                        organism = Homo sapiens
```

```
SEQUENCE: 61
gctcggactg agcaggtggg                                                          20

SEQ ID NO: 62           moltype = RNA   length = 20
FEATURE                 Location/Qualifiers
source                  1..20
                        mol_type = transcribed RNA
                        organism = Homo sapiens
SEQUENCE: 62
gtgggttggg gcgggctctg                                                          20

SEQ ID NO: 63           moltype = RNA   length = 20
FEATURE                 Location/Qualifiers
source                  1..20
                        mol_type = transcribed RNA
                        organism = Homo sapiens
SEQUENCE: 63
ggcggcggcg gaggcggggg                                                          20

SEQ ID NO: 64           moltype = RNA   length = 17
FEATURE                 Location/Qualifiers
source                  1..17
                        mol_type = transcribed RNA
                        organism = Homo sapiens
SEQUENCE: 64
ccccgccacc gccttgg                                                             17

SEQ ID NO: 65           moltype = RNA   length = 22
FEATURE                 Location/Qualifiers
source                  1..22
                        mol_type = transcribed RNA
                        organism = Homo sapiens
SEQUENCE: 65
cagttgggtc tagggtcag ga                                                        22

SEQ ID NO: 66           moltype = RNA   length = 20
FEATURE                 Location/Qualifiers
source                  1..20
                        mol_type = transcribed RNA
                        organism = Homo sapiens
SEQUENCE: 66
tcagggagtc agggaggc                                                            20

SEQ ID NO: 67           moltype = RNA   length = 17
FEATURE                 Location/Qualifiers
source                  1..17
                        mol_type = transcribed RNA
                        organism = Homo sapiens
SEQUENCE: 67
accccactcc tggtacc                                                             17

SEQ ID NO: 68           moltype = RNA   length = 22
FEATURE                 Location/Qualifiers
source                  1..22
                        mol_type = transcribed RNA
                        organism = Homo sapiens
SEQUENCE: 68
ctgggacagg aggaggaggc ag                                                       22

SEQ ID NO: 69           moltype = RNA   length = 21
FEATURE                 Location/Qualifiers
source                  1..21
                        mol_type = transcribed RNA
                        organism = Homo sapiens
SEQUENCE: 69
ctgtgggctc agcgcgtggg g                                                        21

SEQ ID NO: 70           moltype = RNA   length = 19
FEATURE                 Location/Qualifiers
source                  1..19
                        mol_type = transcribed RNA
                        organism = Homo sapiens
SEQUENCE: 70
ggcttgcatg ggggactgg                                                           19

SEQ ID NO: 71           moltype = RNA   length = 18
FEATURE                 Location/Qualifiers
source                  1..18
                        mol_type = transcribed RNA
```

```
                                organism = Homo sapiens
SEQUENCE: 71
ggtgggcttc ccggaggg                                                          18

SEQ ID NO: 72           moltype = RNA   length = 18
FEATURE                 Location/Qualifiers
source                  1..18
                        mol_type = transcribed RNA
                        organism = Homo sapiens
SEQUENCE: 72
gaggctgaag gaagatgg                                                          18

SEQ ID NO: 73           moltype = RNA   length = 20
FEATURE                 Location/Qualifiers
source                  1..20
                        mol_type = transcribed RNA
                        organism = Homo sapiens
SEQUENCE: 73
aaaagctggg ctgagaggcg                                                        20

SEQ ID NO: 74           moltype = RNA   length = 18
FEATURE                 Location/Qualifiers
source                  1..18
                        mol_type = transcribed RNA
                        organism = Homo sapiens
SEQUENCE: 74
aggctggagt gagcggag                                                          18

SEQ ID NO: 75           moltype = RNA   length = 21
FEATURE                 Location/Qualifiers
source                  1..21
                        mol_type = transcribed RNA
                        organism = Homo sapiens
SEQUENCE: 75
acaggagtgg gggtgggaca t                                                      21

SEQ ID NO: 76           moltype = RNA   length = 22
FEATURE                 Location/Qualifiers
source                  1..22
                        mol_type = transcribed RNA
                        organism = Homo sapiens
SEQUENCE: 76
gtccacttct gcctgccctg cc                                                     22

SEQ ID NO: 77           moltype = RNA   length = 17
FEATURE                 Location/Qualifiers
source                  1..17
                        mol_type = transcribed RNA
                        organism = Homo sapiens
SEQUENCE: 77
ttggaggcgt gggtttt                                                           17

SEQ ID NO: 78           moltype = RNA   length = 22
FEATURE                 Location/Qualifiers
source                  1..22
                        mol_type = transcribed RNA
                        organism = Homo sapiens
SEQUENCE: 78
cagggctggc agtgacatgg gt                                                     22

SEQ ID NO: 79           moltype = RNA   length = 17
FEATURE                 Location/Qualifiers
source                  1..17
                        mol_type = transcribed RNA
                        organism = Homo sapiens
SEQUENCE: 79
ggtgggggct gttgttt                                                           17

SEQ ID NO: 80           moltype = RNA   length = 20
FEATURE                 Location/Qualifiers
source                  1..20
                        mol_type = transcribed RNA
                        organism = Homo sapiens
SEQUENCE: 80
ggctccttgg tctagggta                                                         20

SEQ ID NO: 81           moltype = RNA   length = 22
FEATURE                 Location/Qualifiers
source                  1..22
```

```
                            -continued mol_type = transcribed RNA
                            organism = Homo sapiens
SEQUENCE: 81
cgtcccgggg ctgcgcgagg ca                                              22

SEQ ID NO: 82               moltype = RNA   length = 20
FEATURE                     Location/Qualifiers
source                      1..20
                            mol_type = transcribed RNA
                            organism = Homo sapiens
SEQUENCE: 82
ggatccgagt cacggcacca                                                 20

SEQ ID NO: 83               moltype = RNA   length = 17
FEATURE                     Location/Qualifiers
source                      1..17
                            mol_type = transcribed RNA
                            organism = Homo sapiens
SEQUENCE: 83
agggtgtgtg tgttttt                                                    17

SEQ ID NO: 84               moltype = RNA   length = 22
FEATURE                     Location/Qualifiers
source                      1..22
                            mol_type = transcribed RNA
                            organism = Homo sapiens
SEQUENCE: 84
ccaggaggcg gaggaggtgg ag                                              22

SEQ ID NO: 85               moltype = RNA   length = 23
FEATURE                     Location/Qualifiers
source                      1..23
                            mol_type = transcribed RNA
                            organism = Homo sapiens
SEQUENCE: 85
tgacacggag ggtggcttgg gaa                                             23

SEQ ID NO: 86               moltype = RNA   length = 18
FEATURE                     Location/Qualifiers
source                      1..18
                            mol_type = transcribed RNA
                            organism = Homo sapiens
SEQUENCE: 86
gggtgcgggc cggcgggg                                                   18

SEQ ID NO: 87               moltype = RNA   length = 22
FEATURE                     Location/Qualifiers
source                      1..22
                            mol_type = transcribed RNA
                            organism = Homo sapiens
SEQUENCE: 87
tggcggcggt agttatgggc tt                                              22

SEQ ID NO: 88               moltype = RNA   length = 21
FEATURE                     Location/Qualifiers
source                      1..21
                            mol_type = transcribed RNA
                            organism = Homo sapiens
SEQUENCE: 88
agccaagtgg aagttacttt a                                               21

SEQ ID NO: 89               moltype = RNA   length = 17
FEATURE                     Location/Qualifiers
source                      1..17
                            mol_type = transcribed RNA
                            organism = Homo sapiens
SEQUENCE: 89
ggggtggtct gttgttg                                                    17

SEQ ID NO: 90               moltype = RNA   length = 20
FEATURE                     Location/Qualifiers
source                      1..20
                            mol_type = transcribed RNA
                            organism = Homo sapiens
SEQUENCE: 90
aaaaggcggg agaagcccca                                                 20

SEQ ID NO: 91               moltype = RNA   length = 16
FEATURE                     Location/Qualifiers
```

```
source                          1..16
                                mol_type = transcribed RNA
                                organism = Homo sapiens
SEQUENCE: 91
accgcctgcc cagtga                                                         16

SEQ ID NO: 92                   moltype = RNA   length = 18
FEATURE                         Location/Qualifiers
source                          1..18
                                mol_type = transcribed RNA
                                organism = Homo sapiens
SEQUENCE: 92
aggggggcggg ctccggcg                                                      18

SEQ ID NO: 93                   moltype = RNA   length = 17
FEATURE                         Location/Qualifiers
source                          1..17
                                mol_type = transcribed RNA
                                organism = Homo sapiens
SEQUENCE: 93
ggggctgggc gcgcgcc                                                        17

SEQ ID NO: 94                   moltype = RNA   length = 18
FEATURE                         Location/Qualifiers
source                          1..18
                                mol_type = transcribed RNA
                                organism = Homo sapiens
SEQUENCE: 94
aggctgggct gggacgga                                                       18

SEQ ID NO: 95                   moltype = RNA   length = 22
FEATURE                         Location/Qualifiers
source                          1..22
                                mol_type = transcribed RNA
                                organism = Homo sapiens
SEQUENCE: 95
aggactggac tcccggcagc cc                                                  22

SEQ ID NO: 96                   moltype = RNA   length = 21
FEATURE                         Location/Qualifiers
source                          1..21
                                mol_type = transcribed RNA
                                organism = Homo sapiens
SEQUENCE: 96
gggggggatgt gcatgctggt t                                                  21

SEQ ID NO: 97                   moltype = RNA   length = 17
FEATURE                         Location/Qualifiers
source                          1..17
                                mol_type = transcribed RNA
                                organism = Homo sapiens
SEQUENCE: 97
ggatggagga ggggtct                                                        17

SEQ ID NO: 98                   moltype = RNA   length = 17
FEATURE                         Location/Qualifiers
source                          1..17
                                mol_type = transcribed RNA
                                organism = Homo sapiens
SEQUENCE: 98
gtggacctgg ctgggac                                                        17

SEQ ID NO: 99                   moltype = RNA   length = 22
FEATURE                         Location/Qualifiers
source                          1..22
                                mol_type = transcribed RNA
                                organism = Homo sapiens
SEQUENCE: 99
aggagctagc caggcatatg ca                                                  22

SEQ ID NO: 100                  moltype = RNA   length = 19
FEATURE                         Location/Qualifiers
source                          1..19
                                mol_type = transcribed RNA
                                organism = Homo sapiens
SEQUENCE: 100
cggcgcgacc ggcccgggg                                                      19

SEQ ID NO: 101                  moltype = RNA   length = 23
```

```
FEATURE                 Location/Qualifiers
source                  1..23
                        mol_type = transcribed RNA
                        organism = Homo sapiens
SEQUENCE: 101
tgggccaggg agcagctggt ggg                                               23

SEQ ID NO: 102          moltype = RNA   length = 24
FEATURE                 Location/Qualifiers
source                  1..24
                        mol_type = transcribed RNA
                        organism = Homo sapiens
SEQUENCE: 102
tgggcgaggg gtgggctctc agag                                              24

SEQ ID NO: 103          moltype = RNA   length = 20
FEATURE                 Location/Qualifiers
source                  1..20
                        mol_type = transcribed RNA
                        organism = Homo sapiens
SEQUENCE: 103
cggggtgggt gaggtcgggc                                                   20

SEQ ID NO: 104          moltype = RNA   length = 22
FEATURE                 Location/Qualifiers
source                  1..22
                        mol_type = transcribed RNA
                        organism = Homo sapiens
SEQUENCE: 104
agggactgg ttaatagaac ta                                                 22

SEQ ID NO: 105          moltype = RNA   length = 22
FEATURE                 Location/Qualifiers
source                  1..22
                        mol_type = transcribed RNA
                        organism = Homo sapiens
SEQUENCE: 105
caccggggat ggcagagggt cg                                                22

SEQ ID NO: 106          moltype = RNA   length = 23
FEATURE                 Location/Qualifiers
source                  1..23
                        mol_type = transcribed RNA
                        organism = Homo sapiens
SEQUENCE: 106
tgggctgagg gcaggaggcc tgt                                               23

SEQ ID NO: 107          moltype = RNA   length = 23
FEATURE                 Location/Qualifiers
source                  1..23
                        mol_type = transcribed RNA
                        organism = Homo sapiens
SEQUENCE: 107
gtgagtgtgg atcctggagg aat                                               23

SEQ ID NO: 108          moltype = RNA   length = 24
FEATURE                 Location/Qualifiers
source                  1..24
                        mol_type = transcribed RNA
                        organism = Homo sapiens
SEQUENCE: 108
agctgagctc catggacgtg cagt                                              24

SEQ ID NO: 109          moltype = RNA   length = 22
FEATURE                 Location/Qualifiers
source                  1..22
                        mol_type = transcribed RNA
                        organism = Homo sapiens
SEQUENCE: 109
tccaggcagg agccggactg ga                                                22

SEQ ID NO: 110          moltype = RNA   length = 22
FEATURE                 Location/Qualifiers
source                  1..22
                        mol_type = transcribed RNA
                        organism = Homo sapiens
SEQUENCE: 110
ggggctgtga ttgaccagca gg                                                22
```

```
SEQ ID NO: 111         moltype = RNA   length = 21
FEATURE                Location/Qualifiers
source                 1..21
                       mol_type = transcribed RNA
                       organism = Homo sapiens
SEQUENCE: 111
tggctgttgg aggggggcagg c                                                21

SEQ ID NO: 112         moltype = RNA   length = 22
FEATURE                Location/Qualifiers
source                 1..22
                       mol_type = transcribed RNA
                       organism = Homo sapiens
SEQUENCE: 112
cagccctcct cccgcaccca aa                                                22

SEQ ID NO: 113         moltype = RNA   length = 22
FEATURE                Location/Qualifiers
source                 1..22
                       mol_type = transcribed RNA
                       organism = Homo sapiens
SEQUENCE: 113
gagcaggcga ggctgggctg aa                                                22

SEQ ID NO: 114         moltype = RNA   length = 22
FEATURE                Location/Qualifiers
source                 1..22
                       mol_type = transcribed RNA
                       organism = Homo sapiens
SEQUENCE: 114
caggaggcag tgggcgagca gg                                                22

SEQ ID NO: 115         moltype = RNA   length = 22
FEATURE                Location/Qualifiers
source                 1..22
                       mol_type = transcribed RNA
                       organism = Homo sapiens
SEQUENCE: 115
aggggggcgca gtcactgacg tg                                               22

SEQ ID NO: 116         moltype = RNA   length = 25
FEATURE                Location/Qualifiers
source                 1..25
                       mol_type = transcribed RNA
                       organism = Homo sapiens
SEQUENCE: 116
agcggggagg aagtgggcgc tgctt                                             25

SEQ ID NO: 117         moltype = RNA   length = 22
FEATURE                Location/Qualifiers
source                 1..22
                       mol_type = transcribed RNA
                       organism = Homo sapiens
SEQUENCE: 117
agcccgcccc agccgaggtt ct                                                22

SEQ ID NO: 118         moltype = RNA   length = 23
FEATURE                Location/Qualifiers
source                 1..23
                       mol_type = transcribed RNA
                       organism = Homo sapiens
SEQUENCE: 118
gccccggcgc gggcgggttc tgg                                               23

SEQ ID NO: 119         moltype = RNA   length = 22
FEATURE                Location/Qualifiers
source                 1..22
                       mol_type = transcribed RNA
                       organism = Homo sapiens
SEQUENCE: 119
agcaaggcgg catctctctg at                                                22

SEQ ID NO: 120         moltype = RNA   length = 18
FEATURE                Location/Qualifiers
source                 1..18
                       mol_type = transcribed RNA
                       organism = Homo sapiens
SEQUENCE: 120
gggtgagggc aggtggtt                                                     18
```

```
SEQ ID NO: 121           moltype = RNA   length = 21
FEATURE                  Location/Qualifiers
source                   1..21
                         mol_type = transcribed RNA
                         organism = Homo sapiens
SEQUENCE: 121
agctgtacct gaaaccaagc a                                                    21

SEQ ID NO: 122           moltype = RNA   length = 23
FEATURE                  Location/Qualifiers
source                   1..23
                         mol_type = transcribed RNA
                         organism = Homo sapiens
SEQUENCE: 122
ggcaggaggg ctgtgccagg ttg                                                  23

SEQ ID NO: 123           moltype = RNA   length = 22
FEATURE                  Location/Qualifiers
source                   1..22
                         mol_type = transcribed RNA
                         organism = Homo sapiens
SEQUENCE: 123
tggggaaggc gtcagtgtcg gg                                                   22

SEQ ID NO: 124           moltype = RNA   length = 23
FEATURE                  Location/Qualifiers
source                   1..23
                         mol_type = transcribed RNA
                         organism = Homo sapiens
SEQUENCE: 124
agggccagag gagcctggag tgg                                                  23

SEQ ID NO: 125           moltype = RNA   length = 22
FEATURE                  Location/Qualifiers
source                   1..22
                         mol_type = transcribed RNA
                         organism = Homo sapiens
SEQUENCE: 125
atagtgggaa gctggcagat tc                                                   22

SEQ ID NO: 126           moltype = RNA   length = 23
FEATURE                  Location/Qualifiers
source                   1..23
                         mol_type = transcribed RNA
                         organism = Homo sapiens
SEQUENCE: 126
tgggagggga gaggcagcaa gca                                                  23

SEQ ID NO: 127           moltype = RNA   length = 22
FEATURE                  Location/Qualifiers
source                   1..22
                         mol_type = transcribed RNA
                         organism = Homo sapiens
SEQUENCE: 127
tgctgggggc cacatgagtg tg                                                   22

SEQ ID NO: 128           moltype = RNA   length = 19
FEATURE                  Location/Qualifiers
source                   1..19
                         mol_type = transcribed RNA
                         organism = Homo sapiens
SEQUENCE: 128
aggcaggtta tctgggctg                                                       19

SEQ ID NO: 129           moltype = RNA   length = 25
FEATURE                  Location/Qualifiers
source                   1..25
                         mol_type = transcribed RNA
                         organism = Homo sapiens
SEQUENCE: 129
aagggaggag gagcggaggg gccct                                                25

SEQ ID NO: 130           moltype = RNA   length = 22
FEATURE                  Location/Qualifiers
source                   1..22
                         mol_type = transcribed RNA
                         organism = Homo sapiens
SEQUENCE: 130
```

-continued

```
aggactgatc ctctcgggca gg                                              22

SEQ ID NO: 131         moltype = RNA   length = 23
FEATURE                Location/Qualifiers
source                 1..23
                       mol_type = transcribed RNA
                       organism = Homo sapiens
SEQUENCE: 131
cgggctgtcc ggaggggtcg gct                                             23

SEQ ID NO: 132         moltype = RNA   length = 22
FEATURE                Location/Qualifiers
source                 1..22
                       mol_type = transcribed RNA
                       organism = Homo sapiens
SEQUENCE: 132
ctcgggcgga ggtggttgag tg                                              22

SEQ ID NO: 133         moltype = RNA   length = 22
FEATURE                Location/Qualifiers
source                 1..22
                       mol_type = transcribed RNA
                       organism = Homo sapiens
SEQUENCE: 133
agccaggctc tgaagggaaa gt                                              22

SEQ ID NO: 134         moltype = RNA   length = 24
FEATURE                Location/Qualifiers
source                 1..24
                       mol_type = transcribed RNA
                       organism = Homo sapiens
SEQUENCE: 134
aggcaggggc tggtgctggg cggg                                            24

SEQ ID NO: 135         moltype = RNA   length = 21
FEATURE                Location/Qualifiers
source                 1..21
                       mol_type = transcribed RNA
                       organism = Homo sapiens
SEQUENCE: 135
agcagacttg acctacaatt a                                               21

SEQ ID NO: 136         moltype = RNA   length = 23
FEATURE                Location/Qualifiers
source                 1..23
                       mol_type = transcribed RNA
                       organism = Homo sapiens
SEQUENCE: 136
ccccggtgtt ggggcgcgtc tgc                                             23

SEQ ID NO: 137         moltype = RNA   length = 21
FEATURE                Location/Qualifiers
source                 1..21
                       mol_type = transcribed RNA
                       organism = Homo sapiens
SEQUENCE: 137
ggcgcgccca gctcccgggc t                                               21

SEQ ID NO: 138         moltype = RNA   length = 24
FEATURE                Location/Qualifiers
source                 1..24
                       mol_type = transcribed RNA
                       organism = Homo sapiens
SEQUENCE: 138
gatgcgccgc ccactgcccc gcgc                                            24

SEQ ID NO: 139         moltype = RNA   length = 18
FEATURE                Location/Qualifiers
source                 1..18
                       mol_type = transcribed RNA
                       organism = Homo sapiens
SEQUENCE: 139
cggtgagcgc tcgctggc                                                   18

SEQ ID NO: 140         moltype = RNA   length = 23
FEATURE                Location/Qualifiers
source                 1..23
                       mol_type = transcribed RNA
                       organism = Homo sapiens
```

-continued

```
SEQUENCE: 140
tttcaagcca gggggcgttt ttc                                                  23

SEQ ID NO: 141          moltype = RNA    length = 22
FEATURE                 Location/Qualifiers
source                  1..22
                        mol_type = transcribed RNA
                        organism = Homo sapiens
SEQUENCE: 141
tgaggccctt ggggcacagt gg                                                   22

SEQ ID NO: 142          moltype = RNA    length = 22
FEATURE                 Location/Qualifiers
source                  1..22
                        mol_type = transcribed RNA
                        organism = Homo sapiens
SEQUENCE: 142
aggggatgg cagagcaaaa tt                                                    22

SEQ ID NO: 143          moltype = RNA    length = 21
FEATURE                 Location/Qualifiers
source                  1..21
                        mol_type = transcribed RNA
                        organism = Homo sapiens
SEQUENCE: 143
gggagtgcag ggcagggttt c                                                    21

SEQ ID NO: 144          moltype = RNA    length = 21
FEATURE                 Location/Qualifiers
source                  1..21
                        mol_type = transcribed RNA
                        organism = Homo sapiens
SEQUENCE: 144
atccagttct ctgaggggc t                                                     21

SEQ ID NO: 145          moltype = RNA    length = 23
FEATURE                 Location/Qualifiers
source                  1..23
                        mol_type = transcribed RNA
                        organism = Homo sapiens
SEQUENCE: 145
agtgcctgag ggagtaagag ccc                                                  23

SEQ ID NO: 146          moltype = RNA    length = 21
FEATURE                 Location/Qualifiers
source                  1..21
                        mol_type = transcribed RNA
                        organism = Homo sapiens
SEQUENCE: 146
gttggggtgc aggggtctgc t                                                    21

SEQ ID NO: 147          moltype = RNA    length = 20
FEATURE                 Location/Qualifiers
source                  1..20
                        mol_type = transcribed RNA
                        organism = Homo sapiens
SEQUENCE: 147
gcggagagag aatggggagc                                                      20

SEQ ID NO: 148          moltype = RNA    length = 21
FEATURE                 Location/Qualifiers
source                  1..21
                        mol_type = transcribed RNA
                        organism = Homo sapiens
SEQUENCE: 148
acggcccagg cggcattggt g                                                    21

SEQ ID NO: 149          moltype = RNA    length = 21
FEATURE                 Location/Qualifiers
source                  1..21
                        mol_type = transcribed RNA
                        organism = Homo sapiens
SEQUENCE: 149
agcatgacag aggagaggtg g                                                    21

SEQ ID NO: 150          moltype = RNA    length = 20
FEATURE                 Location/Qualifiers
source                  1..20
                        mol_type = transcribed RNA
```

```
                                  organism = Homo sapiens
SEQUENCE: 150
agagatgaag cgggggggcg                                                    20

SEQ ID NO: 151            moltype = RNA  length = 20
FEATURE                   Location/Qualifiers
source                    1..20
                          mol_type = transcribed RNA
                          organism = Homo sapiens
SEQUENCE: 151
gggaaaagga aggggagga                                                     20

SEQ ID NO: 152            moltype = RNA  length = 19
FEATURE                   Location/Qualifiers
source                    1..19
                          mol_type = transcribed RNA
                          organism = Homo sapiens
SEQUENCE: 152
ggctggtcag atgggagtg                                                     19

SEQ ID NO: 153            moltype = RNA  length = 19
FEATURE                   Location/Qualifiers
source                    1..19
                          mol_type = transcribed RNA
                          organism = Homo sapiens
SEQUENCE: 153
agcagggctg gggattgca                                                     19

SEQ ID NO: 154            moltype = RNA  length = 23
FEATURE                   Location/Qualifiers
source                    1..23
                          mol_type = transcribed RNA
                          organism = Homo sapiens
SEQUENCE: 154
gaacgcctgt tcttgccagg tgg                                                23

SEQ ID NO: 155            moltype = RNA  length = 22
FEATURE                   Location/Qualifiers
source                    1..22
                          mol_type = transcribed RNA
                          organism = Homo sapiens
SEQUENCE: 155
gggggtcccc ggtgctcgga tc                                                 22

SEQ ID NO: 156            moltype = RNA  length = 22
FEATURE                   Location/Qualifiers
source                    1..22
                          mol_type = transcribed RNA
                          organism = Homo sapiens
SEQUENCE: 156
gctgggatta caggcatgag cc                                                 22

SEQ ID NO: 157            moltype = RNA  length = 22
FEATURE                   Location/Qualifiers
source                    1..22
                          mol_type = transcribed RNA
                          organism = Homo sapiens
SEQUENCE: 157
agacacattt ggagagggac cc                                                 22

SEQ ID NO: 158            moltype = RNA  length = 22
FEATURE                   Location/Qualifiers
source                    1..22
                          mol_type = transcribed RNA
                          organism = Homo sapiens
SEQUENCE: 158
cagcagggga gagagaggag tc                                                 22

SEQ ID NO: 159            moltype = RNA  length = 23
FEATURE                   Location/Qualifiers
source                    1..23
                          mol_type = transcribed RNA
                          organism = Homo sapiens
SEQUENCE: 159
caggcagaag tggggctgac agg                                                23

SEQ ID NO: 160            moltype = RNA  length = 20
FEATURE                   Location/Qualifiers
source                    1..20
```

```
                        mol_type = transcribed RNA
                        organism = Homo sapiens
SEQUENCE: 160
tctcttcatc tacccccag                                                    20

SEQ ID NO: 161          moltype = RNA  length = 21
FEATURE                 Location/Qualifiers
source                  1..21
                        mol_type = transcribed RNA
                        organism = Homo sapiens
SEQUENCE: 161
ttggagggtg tggaagacat c                                                 21

SEQ ID NO: 162          moltype = RNA  length = 22
FEATURE                 Location/Qualifiers
source                  1..22
                        mol_type = transcribed RNA
                        organism = Homo sapiens
SEQUENCE: 162
ggtggcccgg ccgtgcctga gg                                                22

SEQ ID NO: 163          moltype = RNA  length = 20
FEATURE                 Location/Qualifiers
source                  1..20
                        mol_type = transcribed RNA
                        organism = Homo sapiens
SEQUENCE: 163
tgggaatggg ggtaagggcc                                                   20

SEQ ID NO: 164          moltype = RNA  length = 22
FEATURE                 Location/Qualifiers
source                  1..22
                        mol_type = transcribed RNA
                        organism = Homo sapiens
SEQUENCE: 164
aggcgatgtg gggatgtaga ga                                                22

SEQ ID NO: 165          moltype = RNA  length = 22
FEATURE                 Location/Qualifiers
source                  1..22
                        mol_type = transcribed RNA
                        organism = Homo sapiens
SEQUENCE: 165
tgcaggggtc gggtgggcca gg                                                22

SEQ ID NO: 166          moltype = RNA  length = 23
FEATURE                 Location/Qualifiers
source                  1..23
                        mol_type = transcribed RNA
                        organism = Homo sapiens
SEQUENCE: 166
ctgggcccgc ggcgggcgtg ggg                                               23

SEQ ID NO: 167          moltype = RNA  length = 21
FEATURE                 Location/Qualifiers
source                  1..21
                        mol_type = transcribed RNA
                        organism = Homo sapiens
SEQUENCE: 167
cgggagctgg ggtctgcagg t                                                 21

SEQ ID NO: 168          moltype = RNA  length = 21
FEATURE                 Location/Qualifiers
source                  1..21
                        mol_type = transcribed RNA
                        organism = Homo sapiens
SEQUENCE: 168
ttggggtggt cggccctgga g                                                 21

SEQ ID NO: 169          moltype = RNA  length = 22
FEATURE                 Location/Qualifiers
source                  1..22
                        mol_type = transcribed RNA
                        organism = Homo sapiens
SEQUENCE: 169
gtgggtgctg gtgggagccg tg                                                22

SEQ ID NO: 170          moltype = RNA  length = 22
FEATURE                 Location/Qualifiers
```

```
source                  1..22
                        mol_type = transcribed RNA
                        organism = Homo sapiens
SEQUENCE: 170
agtggggtgg gacccagctg tt                                                  22

SEQ ID NO: 171          moltype = RNA   length = 22
FEATURE                 Location/Qualifiers
source                  1..22
                        mol_type = transcribed RNA
                        organism = Homo sapiens
SEQUENCE: 171
aaggggcagg gacgggtggc cc                                                  22

SEQ ID NO: 172          moltype = RNA   length = 22
FEATURE                 Location/Qualifiers
source                  1..22
                        mol_type = transcribed RNA
                        organism = Homo sapiens
SEQUENCE: 172
ccgggagaag gaggtggcct gg                                                  22

SEQ ID NO: 173          moltype = RNA   length = 22
FEATURE                 Location/Qualifiers
source                  1..22
                        mol_type = transcribed RNA
                        organism = Homo sapiens
SEQUENCE: 173
tcgggcctgg ggttggggga gc                                                  22

SEQ ID NO: 174          moltype = RNA   length = 23
FEATURE                 Location/Qualifiers
source                  1..23
                        mol_type = transcribed RNA
                        organism = Homo sapiens
SEQUENCE: 174
cagggagaag gtggaagtgc aga                                                 23

SEQ ID NO: 175          moltype = RNA   length = 23
FEATURE                 Location/Qualifiers
source                  1..23
                        mol_type = transcribed RNA
                        organism = Homo sapiens
SEQUENCE: 175
cggggccatg gagcagcctg tgt                                                 23

SEQ ID NO: 176          moltype = RNA   length = 21
FEATURE                 Location/Qualifiers
source                  1..21
                        mol_type = transcribed RNA
                        organism = Homo sapiens
SEQUENCE: 176
tcacctggct ggcccgccca g                                                   21

SEQ ID NO: 177          moltype = RNA   length = 25
FEATURE                 Location/Qualifiers
source                  1..25
                        mol_type = transcribed RNA
                        organism = Homo sapiens
SEQUENCE: 177
gtgaggcggg gccaggaggg tgtgt                                               25

SEQ ID NO: 178          moltype = RNA   length = 22
FEATURE                 Location/Qualifiers
source                  1..22
                        mol_type = transcribed RNA
                        organism = Homo sapiens
SEQUENCE: 178
tgattgtctt cccccaccct ca                                                  22

SEQ ID NO: 179          moltype = RNA   length = 24
FEATURE                 Location/Qualifiers
source                  1..24
                        mol_type = transcribed RNA
                        organism = Homo sapiens
SEQUENCE: 179
cgggtgggag cagatcttat tgag                                                24

SEQ ID NO: 180          moltype = RNA   length = 22
```

```
FEATURE                 Location/Qualifiers
source                  1..22
                        mol_type = transcribed RNA
                        organism = Homo sapiens
SEQUENCE: 180
ctcgggaggg catgggccag gc                                             22

SEQ ID NO: 181          moltype = RNA   length = 25
FEATURE                 Location/Qualifiers
source                  1..25
                        mol_type = transcribed RNA
                        organism = Homo sapiens
SEQUENCE: 181
acttgggcag gagggaccct gtatg                                          25

SEQ ID NO: 182          moltype = RNA   length = 23
FEATURE                 Location/Qualifiers
source                  1..23
                        mol_type = transcribed RNA
                        organism = Homo sapiens
SEQUENCE: 182
acggggagtc aggcagtggt gga                                            23

SEQ ID NO: 183          moltype = RNA   length = 22
FEATURE                 Location/Qualifiers
source                  1..22
                        mol_type = transcribed RNA
                        organism = Homo sapiens
SEQUENCE: 183
agtgggagga caggaggcag gt                                             22

SEQ ID NO: 184          moltype = RNA   length = 23
FEATURE                 Location/Qualifiers
source                  1..23
                        mol_type = transcribed RNA
                        organism = Homo sapiens
SEQUENCE: 184
tggggaaggc ttggcaggga aga                                            23

SEQ ID NO: 185          moltype = RNA   length = 21
FEATURE                 Location/Qualifiers
source                  1..21
                        mol_type = transcribed RNA
                        organism = Homo sapiens
SEQUENCE: 185
cgggccggag gtcaagggcg t                                              21

SEQ ID NO: 186          moltype = RNA   length = 25
FEATURE                 Location/Qualifiers
source                  1..25
                        mol_type = transcribed RNA
                        organism = Homo sapiens
SEQUENCE: 186
tagggggtggg ggaattcagg ggtgt                                         25

SEQ ID NO: 187          moltype = RNA   length = 20
FEATURE                 Location/Qualifiers
source                  1..20
                        mol_type = transcribed RNA
                        organism = Homo sapiens
SEQUENCE: 187
gccggggctt tgggtgaggg                                                20

SEQ ID NO: 188          moltype = RNA   length = 22
FEATURE                 Location/Qualifiers
source                  1..22
                        mol_type = transcribed RNA
                        organism = Homo sapiens
SEQUENCE: 188
tgggagggcg tggatgatgg tg                                             22

SEQ ID NO: 189          moltype = RNA   length = 22
FEATURE                 Location/Qualifiers
source                  1..22
                        mol_type = transcribed RNA
                        organism = Homo sapiens
SEQUENCE: 189
tggcgggggt agagctggct gc                                             22
```

| | | |
|---|---|---|
| SEQ ID NO: 190 | moltype = RNA length = 24 | |
| FEATURE | Location/Qualifiers | |
| source | 1..24 | |
| | mol_type = transcribed RNA | |
| | organism = Homo sapiens | |
| SEQUENCE: 190 | | |
| gtaggggcgt cccggcgcg cggg | | 24 |
| | | |
| SEQ ID NO: 191 | moltype = RNA length = 22 | |
| FEATURE | Location/Qualifiers | |
| source | 1..22 | |
| | mol_type = transcribed RNA | |
| | organism = Homo sapiens | |
| SEQUENCE: 191 | | |
| cccctggggc tgggcaggcg ga | | 22 |
| | | |
| SEQ ID NO: 192 | moltype = RNA length = 20 | |
| FEATURE | Location/Qualifiers | |
| source | 1..20 | |
| | mol_type = transcribed RNA | |
| | organism = Homo sapiens | |
| SEQUENCE: 192 | | |
| caggggact gggggtgagc | | 20 |
| | | |
| SEQ ID NO: 193 | moltype = RNA length = 21 | |
| FEATURE | Location/Qualifiers | |
| source | 1..21 | |
| | mol_type = transcribed RNA | |
| | organism = Homo sapiens | |
| SEQUENCE: 193 | | |
| gtaggtgaca gtcaggggcg g | | 21 |
| | | |
| SEQ ID NO: 194 | moltype = RNA length = 20 | |
| FEATURE | Location/Qualifiers | |
| source | 1..20 | |
| | mol_type = transcribed RNA | |
| | organism = Homo sapiens | |
| SEQUENCE: 194 | | |
| ctaggtgggg ggcttgaagc | | 20 |
| | | |
| SEQ ID NO: 195 | moltype = RNA length = 22 | |
| FEATURE | Location/Qualifiers | |
| source | 1..22 | |
| | mol_type = transcribed RNA | |
| | organism = Homo sapiens | |
| SEQUENCE: 195 | | |
| ctgggggtgg ggggctgggc gt | | 22 |
| | | |
| SEQ ID NO: 196 | moltype = RNA length = 25 | |
| FEATURE | Location/Qualifiers | |
| source | 1..25 | |
| | mol_type = transcribed RNA | |
| | organism = Homo sapiens | |
| SEQUENCE: 196 | | |
| atggggtgag atgggagga gcagc | | 25 |
| | | |
| SEQ ID NO: 197 | moltype = RNA length = 21 | |
| FEATURE | Location/Qualifiers | |
| source | 1..21 | |
| | mol_type = transcribed RNA | |
| | organism = Homo sapiens | |
| SEQUENCE: 197 | | |
| tgggcgggg caggtccctg c | | 21 |
| | | |
| SEQ ID NO: 198 | moltype = RNA length = 22 | |
| FEATURE | Location/Qualifiers | |
| source | 1..22 | |
| | mol_type = transcribed RNA | |
| | organism = Homo sapiens | |
| SEQUENCE: 198 | | |
| ttggggtgga gggccaagga gc | | 22 |
| | | |
| SEQ ID NO: 199 | moltype = RNA length = 23 | |
| FEATURE | Location/Qualifiers | |
| source | 1..23 | |
| | mol_type = transcribed RNA | |
| | organism = Homo sapiens | |
| SEQUENCE: 199 | | |
| gtgcgtggtg gctcgaggcg ggg | | 23 |

-continued

```
SEQ ID NO: 200          moltype = RNA   length = 23
FEATURE                 Location/Qualifiers
source                  1..23
                        mol_type = transcribed RNA
                        organism = Homo sapiens
SEQUENCE: 200
tcaataggaa agaggtggga cct                                              23

SEQ ID NO: 201          moltype = RNA   length = 24
FEATURE                 Location/Qualifiers
source                  1..24
                        mol_type = transcribed RNA
                        organism = Homo sapiens
SEQUENCE: 201
taggtagagt gtgaggagga ggtc                                             24

SEQ ID NO: 202          moltype = RNA   length = 21
FEATURE                 Location/Qualifiers
source                  1..21
                        mol_type = transcribed RNA
                        organism = Homo sapiens
SEQUENCE: 202
atgcctcccc cggccccgca g                                                21

SEQ ID NO: 203          moltype = RNA   length = 22
FEATURE                 Location/Qualifiers
source                  1..22
                        mol_type = transcribed RNA
                        organism = Homo sapiens
SEQUENCE: 203
gcccaggact ttgtgcgggg tg                                               22

SEQ ID NO: 204          moltype = RNA   length = 22
FEATURE                 Location/Qualifiers
source                  1..22
                        mol_type = transcribed RNA
                        organism = Homo sapiens
SEQUENCE: 204
tgggggtggt ctctagccaa gg                                               22

SEQ ID NO: 205          moltype = RNA   length = 22
FEATURE                 Location/Qualifiers
source                  1..22
                        mol_type = transcribed RNA
                        organism = Homo sapiens
SEQUENCE: 205
gtgcggaacg ctggccgggg cg                                               22

SEQ ID NO: 206          moltype = RNA   length = 22
FEATURE                 Location/Qualifiers
source                  1..22
                        mol_type = transcribed RNA
                        organism = Homo sapiens
SEQUENCE: 206
actgggtagg tggggctcca gg                                               22

SEQ ID NO: 207          moltype = RNA   length = 22
FEATURE                 Location/Qualifiers
source                  1..22
                        mol_type = transcribed RNA
                        organism = Homo sapiens
SEQUENCE: 207
gtgagtagtg gcgcgcggcg gc                                               22

SEQ ID NO: 208          moltype = RNA   length = 19
FEATURE                 Location/Qualifiers
source                  1..19
                        mol_type = transcribed RNA
                        organism = Homo sapiens
SEQUENCE: 208
tgggggagat gggggttga                                                   19

SEQ ID NO: 209          moltype = RNA   length = 22
FEATURE                 Location/Qualifiers
source                  1..22
                        mol_type = transcribed RNA
                        organism = Homo sapiens
SEQUENCE: 209
```

```
agggccgaag ggtggaagct gc                                              22

SEQ ID NO: 210          moltype = RNA   length = 22
FEATURE                 Location/Qualifiers
source                  1..22
                        mol_type = transcribed RNA
                        organism = Homo sapiens
SEQUENCE: 210
cagggcaggg aaggtgggag ag                                              22

SEQ ID NO: 211          moltype = RNA   length = 21
FEATURE                 Location/Qualifiers
source                  1..21
                        mol_type = transcribed RNA
                        organism = Homo sapiens
SEQUENCE: 211
ccgccttctc tcctccccca g                                               21

SEQ ID NO: 212          moltype = RNA   length = 22
FEATURE                 Location/Qualifiers
source                  1..22
                        mol_type = transcribed RNA
                        organism = Homo sapiens
SEQUENCE: 212
tggtggagga agagggcagc tc                                              22

SEQ ID NO: 213          moltype = RNA   length = 25
FEATURE                 Location/Qualifiers
source                  1..25
                        mol_type = transcribed RNA
                        organism = Homo sapiens
SEQUENCE: 213
agggggggcac tgcgcaagca aagcc                                          25

SEQ ID NO: 214          moltype = RNA   length = 23
FEATURE                 Location/Qualifiers
source                  1..23
                        mol_type = transcribed RNA
                        organism = Homo sapiens
SEQUENCE: 214
tgggggggaca gatggagagg aca                                            23

SEQ ID NO: 215          moltype = RNA   length = 22
FEATURE                 Location/Qualifiers
source                  1..22
                        mol_type = transcribed RNA
                        organism = Homo sapiens
SEQUENCE: 215
tcggcctggg gaggaggaag gg                                              22

SEQ ID NO: 216          moltype = RNA   length = 20
FEATURE                 Location/Qualifiers
source                  1..20
                        mol_type = transcribed RNA
                        organism = Homo sapiens
SEQUENCE: 216
acccgcccgt ctccccacag                                                 20

SEQ ID NO: 217          moltype = RNA   length = 21
FEATURE                 Location/Qualifiers
source                  1..21
                        mol_type = transcribed RNA
                        organism = Homo sapiens
SEQUENCE: 217
ctgggggag gagaccctgc t                                                21

SEQ ID NO: 218          moltype = RNA   length = 22
FEATURE                 Location/Qualifiers
source                  1..22
                        mol_type = transcribed RNA
                        organism = Homo sapiens
SEQUENCE: 218
gggacccagg gagagacgta ag                                              22

SEQ ID NO: 219          moltype = RNA   length = 23
FEATURE                 Location/Qualifiers
source                  1..23
                        mol_type = transcribed RNA
                        organism = Homo sapiens
```

```
SEQUENCE: 219
cctccctgcc cgcctctctg cag                                               23

SEQ ID NO: 220         moltype = RNA   length = 18
FEATURE                Location/Qualifiers
source                 1..18
                       mol_type = transcribed RNA
                       organism = Homo sapiens
SEQUENCE: 220
ctggcagggg gagaggta                                                     18

SEQ ID NO: 221         moltype = RNA   length = 22
FEATURE                Location/Qualifiers
source                 1..22
                       mol_type = transcribed RNA
                       organism = Homo sapiens
SEQUENCE: 221
tgcggggcta gggctaacag ca                                                22

SEQ ID NO: 222         moltype = RNA   length = 18
FEATURE                Location/Qualifiers
source                 1..18
                       mol_type = transcribed RNA
                       organism = Homo sapiens
SEQUENCE: 222
atcctagtca cggcacca                                                     18

SEQ ID NO: 223         moltype = RNA   length = 18
FEATURE                Location/Qualifiers
source                 1..18
                       mol_type = transcribed RNA
                       organism = Homo sapiens
SEQUENCE: 223
ttcccagcca acgcacca                                                     18

SEQ ID NO: 224         moltype = RNA   length = 22
FEATURE                Location/Qualifiers
source                 1..22
                       mol_type = transcribed RNA
                       organism = Homo sapiens
SEQUENCE: 224
cgggactgta gagggcatga gc                                                22

SEQ ID NO: 225         moltype = RNA   length = 23
FEATURE                Location/Qualifiers
source                 1..23
                       mol_type = transcribed RNA
                       organism = Homo sapiens
SEQUENCE: 225
ggatggttgg gggcggtcgg cgt                                               23

SEQ ID NO: 226         moltype = RNA   length = 22
FEATURE                Location/Qualifiers
source                 1..22
                       mol_type = transcribed RNA
                       organism = Homo sapiens
SEQUENCE: 226
acctggcagc agggagcgtc gt                                                22

SEQ ID NO: 227         moltype = RNA   length = 22
FEATURE                Location/Qualifiers
source                 1..22
                       mol_type = transcribed RNA
                       organism = Homo sapiens
SEQUENCE: 227
gtgaacgggc gccatcccga gg                                                22

SEQ ID NO: 228         moltype = RNA   length = 20
FEATURE                Location/Qualifiers
source                 1..20
                       mol_type = transcribed RNA
                       organism = Homo sapiens
SEQUENCE: 228
gtgagtcagg gtggggctgg                                                   20

SEQ ID NO: 229         moltype = RNA   length = 21
FEATURE                Location/Qualifiers
source                 1..21
                       mol_type = transcribed RNA
```

```
                        organism = Homo sapiens
SEQUENCE: 229
gtgccagctg cagtggggga g                                              21

SEQ ID NO: 230          moltype = RNA   length = 21
FEATURE                 Location/Qualifiers
source                  1..21
                        mol_type = transcribed RNA
                        organism = Homo sapiens
SEQUENCE: 230
tggcagggag gctgggaggg g                                              21

SEQ ID NO: 231          moltype = RNA   length = 19
FEATURE                 Location/Qualifiers
source                  1..19
                        mol_type = transcribed RNA
                        organism = Homo sapiens
SEQUENCE: 231
aatggatttt tggagcagg                                                 19

SEQ ID NO: 232          moltype = RNA   length = 24
FEATURE                 Location/Qualifiers
source                  1..24
                        mol_type = transcribed RNA
                        organism = Homo sapiens
SEQUENCE: 232
agcctggaag ctggagcctg cagt                                           24

SEQ ID NO: 233          moltype = RNA   length = 22
FEATURE                 Location/Qualifiers
source                  1..22
                        mol_type = transcribed RNA
                        organism = Homo sapiens
SEQUENCE: 233
tatagggatt ggagccgtgg cg                                             22

SEQ ID NO: 234          moltype = RNA   length = 22
FEATURE                 Location/Qualifiers
source                  1..22
                        mol_type = transcribed RNA
                        organism = Homo sapiens
SEQUENCE: 234
ctcggcgcgg ggcgcgggct cc                                             22

SEQ ID NO: 235          moltype = RNA   length = 21
FEATURE                 Location/Qualifiers
source                  1..21
                        mol_type = transcribed RNA
                        organism = Homo sapiens
SEQUENCE: 235
agggagggac gggggctgtg c                                              21

SEQ ID NO: 236          moltype = RNA   length = 22
FEATURE                 Location/Qualifiers
source                  1..22
                        mol_type = transcribed RNA
                        organism = Homo sapiens
SEQUENCE: 236
ctggtacagg cctgggggac ag                                             22

SEQ ID NO: 237          moltype = RNA   length = 22
FEATURE                 Location/Qualifiers
source                  1..22
                        mol_type = transcribed RNA
                        organism = Homo sapiens
SEQUENCE: 237
ggagggtcc cgcactggga gg                                              22

SEQ ID NO: 238          moltype = RNA   length = 23
FEATURE                 Location/Qualifiers
source                  1..23
                        mol_type = transcribed RNA
                        organism = Homo sapiens
SEQUENCE: 238
caacggaatc ccaaaagcag ctg                                            23

SEQ ID NO: 239          moltype = RNA   length = 23
FEATURE                 Location/Qualifiers
source                  1..23
```

```
                              mol_type = transcribed RNA
                              organism = Homo sapiens
SEQUENCE: 239
tgagggcag agagcgagac ttt                                          23

SEQ ID NO: 240          moltype = RNA   length = 22
FEATURE                 Location/Qualifiers
source                  1..22
                        mol_type = transcribed RNA
                        organism = Homo sapiens
SEQUENCE: 240
aggcggggcg ccgcgggacc gc                                          22

SEQ ID NO: 241          moltype = RNA   length = 22
FEATURE                 Location/Qualifiers
source                  1..22
                        mol_type = transcribed RNA
                        organism = Homo sapiens
SEQUENCE: 241
gggtggggat ttgttgcatt ac                                          22

SEQ ID NO: 242          moltype = RNA   length = 22
FEATURE                 Location/Qualifiers
source                  1..22
                        mol_type = transcribed RNA
                        organism = Homo sapiens
SEQUENCE: 242
tattgcactt gtcccggcct gt                                          22

SEQ ID NO: 243          moltype = RNA   length = 21
FEATURE                 Location/Qualifiers
source                  1..21
                        mol_type = transcribed RNA
                        organism = Homo sapiens
SEQUENCE: 243
aaggcagggc ccccgctccc c                                           21

SEQ ID NO: 244          moltype = RNA   length = 49
FEATURE                 Location/Qualifiers
source                  1..49
                        mol_type = transcribed RNA
                        organism = Homo sapiens
SEQUENCE: 244
ggtgaggcgg gggggcgagc cctgaggggc tctcgcttct ggcgccaag             49

SEQ ID NO: 245          moltype = RNA   length = 86
FEATURE                 Location/Qualifiers
source                  1..86
                        mol_type = transcribed RNA
                        organism = Homo sapiens
SEQUENCE: 245
tttggtactt gaagagagga tacccttgt atgttcactt gattaatggc gaatatacag  60
ggggagactc ttatttgcgt atcaaa                                      86

SEQ ID NO: 246          moltype = RNA   length = 86
FEATURE                 Location/Qualifiers
source                  1..86
                        mol_type = transcribed RNA
                        organism = Homo sapiens
SEQUENCE: 246
tttggtactt aaagagagga tacccttgt atgttcactt gattaatggc gaatatacag  60
ggggagactc tcatttgcgt atcaaa                                      86

SEQ ID NO: 247          moltype = RNA   length = 78
FEATURE                 Location/Qualifiers
source                  1..78
                        mol_type = transcribed RNA
                        organism = Homo sapiens
SEQUENCE: 247
gtagctgagg ggatggtaga ccggtgacgt gcacttcatt tacgatgtag gtcacccgtt 60
tgactatcca ccagcgcc                                               78

SEQ ID NO: 248          moltype = RNA   length = 119
FEATURE                 Location/Qualifiers
source                  1..119
                        mol_type = transcribed RNA
                        organism = Homo sapiens
SEQUENCE: 248
agcctgcgcc ggagccgggg cctgagcccg ggccgcgcag gccgtgaact cgtcgagctg 60
```

```
                                            cgcgtgcggc cggtgctcaa cctgccgggt cctggcccgc cgctcccgcg cgccctgga    119

SEQ ID NO: 249          moltype = RNA  length = 90
FEATURE                 Location/Qualifiers
source                  1..90
                        mol_type = transcribed RNA
                        organism = Homo sapiens
SEQUENCE: 249
gtgggtacgg cccagtgggg gggagaggga cacgccctgg gctctgccca gggtgcagcc    60
ggactgactg agccctgtg ccgcccccag                                      90

SEQ ID NO: 250          moltype = RNA  length = 88
FEATURE                 Location/Qualifiers
source                  1..88
                        mol_type = transcribed RNA
                        organism = Homo sapiens
SEQUENCE: 250
gtggggccag gcggtggtgg gcactgctgg ggtgggcaca gcagccatgc agagcgggca    60
tttgaccccg tgccaccctt ttccccag                                       88

SEQ ID NO: 251          moltype = RNA  length = 73
FEATURE                 Location/Qualifiers
source                  1..73
                        mol_type = transcribed RNA
                        organism = Homo sapiens
SEQUENCE: 251
gtgggcgggg gcaggtgtgt ggtgggtggt ggcctgcggt gagcagggcc ctcacacctg    60
cctcgccccc cag                                                       73

SEQ ID NO: 252          moltype = RNA  length = 73
FEATURE                 Location/Qualifiers
source                  1..73
                        mol_type = transcribed RNA
                        organism = Homo sapiens
SEQUENCE: 252
gtgggcgggg gcaggtgtgt ggtgggtggt ggcctgcggt gagcagggcc ctcacacctg    60
cctcgccccc cag                                                       73

SEQ ID NO: 253          moltype = RNA  length = 102
FEATURE                 Location/Qualifiers
source                  1..102
                        mol_type = transcribed RNA
                        organism = Homo sapiens
SEQUENCE: 253
gtgggagggc ccaggcgcgg gcaggggtgg gggtggcaga gcgctgtccc ggggcgggg     60
ccgaagcgcg gcgaccgtaa ctccttctgc tccgtccccc ag                       102

SEQ ID NO: 254          moltype = RNA  length = 83
FEATURE                 Location/Qualifiers
source                  1..83
                        mol_type = transcribed RNA
                        organism = Homo sapiens
SEQUENCE: 254
gtgagtggga gccccagtgt gtggttgggg ccatggcggg tgggcagccc agcctctgag    60
ccttcctcgt ctgtctgccc cag                                            83

SEQ ID NO: 255          moltype = RNA  length = 136
FEATURE                 Location/Qualifiers
source                  1..136
                        mol_type = transcribed RNA
                        organism = Homo sapiens
SEQUENCE: 255
ccgcttgcct cgcccagcgc agccccggcc gctgggcgca cccgtcccgt tcgtccccgg    60
acgttgctct ctaccccggg aacgtcgaga ctggagcgcc cgaactgagc caccttcgcg    120
gaccccgaga gcggcg                                                    136

SEQ ID NO: 256          moltype = RNA  length = 52
FEATURE                 Location/Qualifiers
source                  1..52
                        mol_type = transcribed RNA
                        organism = Homo sapiens
SEQUENCE: 256
tagccggcg tggtggtggg ggcctgtggt cccagctact ttggaggctg ag              52

SEQ ID NO: 257          moltype = RNA  length = 50
FEATURE                 Location/Qualifiers
source                  1..50
                        mol_type = transcribed RNA
                        organism = Homo sapiens
```

```
SEQUENCE: 257
acccgggcgt ggtggtgggg gtgggtgcct gtaattccag ctagttggga              50

SEQ ID NO: 258             moltype = RNA   length = 100
FEATURE                    Location/Qualifiers
source                     1..100
                           mol_type = transcribed RNA
                           organism = Homo sapiens
SEQUENCE: 258
gaggtgggag gattgcttga gtcagggtgg ttgaggctgc agtaagttgt gatcatacca    60
ctgcactcca gcctgagtga cagagcaaga ccttgtctca                        100

SEQ ID NO: 259             moltype = RNA   length = 84
FEATURE                    Location/Qualifiers
source                     1..84
                           mol_type = transcribed RNA
                           organism = Homo sapiens
SEQUENCE: 259
tgtgcagtgg aagggggggc cgatacactg tacgagagtg agtagcaggt ctcacagtga    60
accggtctct ttccctactg tgtc                                          84

SEQ ID NO: 260             moltype = RNA   length = 84
FEATURE                    Location/Qualifiers
source                     1..84
                           mol_type = transcribed RNA
                           organism = Homo sapiens
SEQUENCE: 260
gctggcgtcg gtgctgggga gcggcccccg ggtgggcctc tgctctggcc cctcctgggg    60
cccgcactct cgctctgggc ccgc                                          84

SEQ ID NO: 261             moltype = RNA   length = 84
FEATURE                    Location/Qualifiers
source                     1..84
                           mol_type = transcribed RNA
                           organism = Homo sapiens
SEQUENCE: 261
gctggcgtcg gtgctgggga gcggcccccg ggtgggcctc tgctctggcc cctcctgggg    60
cccgcactct cgctctgggc ccgc                                          84

SEQ ID NO: 262             moltype = RNA   length = 61
FEATURE                    Location/Qualifiers
source                     1..61
                           mol_type = transcribed RNA
                           organism = Homo sapiens
SEQUENCE: 262
gccctccgcc cgtgcacccc ggggcaggag accccgcggg acgcgccgag gtaggggga     60
c                                                                   61

SEQ ID NO: 263             moltype = RNA   length = 84
FEATURE                    Location/Qualifiers
source                     1..84
                           mol_type = transcribed RNA
                           organism = Homo sapiens
SEQUENCE: 263
gtcagaataa tgtcaaagtg cttacagtgc aggtagtgat atgtgcatct actgcagtga    60
aggcacttgt agcattatgg tgac                                          84

SEQ ID NO: 264             moltype = RNA   length = 109
FEATURE                    Location/Qualifiers
source                     1..109
                           mol_type = transcribed RNA
                           organism = Homo sapiens
SEQUENCE: 264
ggtcgggctc accatgacac agtgtgagac ctcgggctac aacacaggac ccgggcgctg    60
ctctgacccc tcgtgtcttg tgttgcagcc ggagggacgc aggtccgca              109

SEQ ID NO: 265             moltype = RNA   length = 80
FEATURE                    Location/Qualifiers
source                     1..80
                           mol_type = transcribed RNA
                           organism = Homo sapiens
SEQUENCE: 265
cgggaatgcc gcggcgggga cggcgattgg tccgtatgtg tggtgccacc ggccgccggc    60
tccgccccgg ccccgccccc                                               80

SEQ ID NO: 266             moltype = RNA   length = 80
FEATURE                    Location/Qualifiers
source                     1..80
                           mol_type = transcribed RNA
```

```
                    organism = Homo sapiens
SEQUENCE: 266
cgggaatgcc gcggcgggga cggcgattgg tccgtatgtg tggtgccacc ggccgccggc    60
tccgccccgg cccccgcccc                                                80

SEQ ID NO: 267          moltype = RNA   length = 80
FEATURE                 Location/Qualifiers
source                  1..80
                        mol_type = transcribed RNA
                        organism = Homo sapiens
SEQUENCE: 267
catccaggac aatggtgagt gccggtgcct gccctggggc cgtccctgcg caggggccgg    60
gtgctcaccg catctgcccc                                                80

SEQ ID NO: 268          moltype = RNA   length = 80
FEATURE                 Location/Qualifiers
source                  1..80
                        mol_type = transcribed RNA
                        organism = Homo sapiens
SEQUENCE: 268
tgagaggccg caccttgcct tgctgcccgg gccgtgcacc cgtgggcccc agggcgacgc    60
ggcggggcg gccctagcga                                                 80

SEQ ID NO: 269          moltype = RNA   length = 110
FEATURE                 Location/Qualifiers
source                  1..110
                        mol_type = transcribed RNA
                        organism = Homo sapiens
SEQUENCE: 269
acccggcagt gcctccaggc gcagggcagc ccctgcccac cgcacactgc gctgccccag    60
acccactgtg cgtgtgacag cggctgatct gtgcctgggc agcgcgaccc               110

SEQ ID NO: 270          moltype = RNA   length = 81
FEATURE                 Location/Qualifiers
source                  1..81
                        mol_type = transcribed RNA
                        organism = Homo sapiens
SEQUENCE: 270
ggacaggcac ctgaggctct gttagccttg gctctgggtc ctgctcctta gagcagaggc    60
agagaggctc agggtctgtc t                                              81

SEQ ID NO: 271          moltype = RNA   length = 90
FEATURE                 Location/Qualifiers
source                  1..90
                        mol_type = transcribed RNA
                        organism = Homo sapiens
SEQUENCE: 271
ggcgcctctg cagctccggc tcccctggc ctctcgggaa ctacaagtcc cagggggcct     60
ggcggtgggc ggcgggcgga agaggcgggg                                     90

SEQ ID NO: 272          moltype = RNA   length = 80
FEATURE                 Location/Qualifiers
source                  1..80
                        mol_type = transcribed RNA
                        organism = Homo sapiens
SEQUENCE: 272
aggacccttc cagagggccc cccctcaatc ctgttgtgcc taattcagag ggttgggtgg    60
aggctctcct gaagggctct                                                80

SEQ ID NO: 273          moltype = RNA   length = 63
FEATURE                 Location/Qualifiers
source                  1..63
                        mol_type = transcribed RNA
                        organism = Homo sapiens
SEQUENCE: 273
gagtcgagga ctggtggaag ggcctttccc ctcagaccaa ggccctggcc ccagcttctt    60
ctc                                                                  63

SEQ ID NO: 274          moltype = RNA   length = 84
FEATURE                 Location/Qualifiers
source                  1..84
                        mol_type = transcribed RNA
                        organism = Homo sapiens
SEQUENCE: 274
ggcccctcct tctcagcccc agctcccgct cacccctgcc acgtcaaagg aggcagaagg    60
ggagttggga gcagagaggg gacc                                           84

SEQ ID NO: 275          moltype = RNA   length = 82
FEATURE                 Location/Qualifiers
```

```
                          source            1..82
                                            mol_type = transcribed RNA
                                            organism = Homo sapiens
SEQUENCE: 275
ctgactttt  tagggagtag  aagggtgggg  agcatgaaca  atgtttctca  ctccctaccc    60
ctccactccc  caaaaaagtc  ag                                                82

SEQ ID NO: 276            moltype = RNA   length = 84
FEATURE                   Location/Qualifiers
source                    1..84
                          mol_type = transcribed RNA
                          organism = Homo sapiens
SEQUENCE: 276
gaggctgggc  ggggcgcggc  cggatcggtc  gagagcgtcc  tggctgatga  cggtctcccg    60
tgcccacgcc  ccaaacgcag  tctc                                              84

SEQ ID NO: 277            moltype = RNA   length = 75
FEATURE                   Location/Qualifiers
source                    1..75
                          mol_type = transcribed RNA
                          organism = Homo sapiens
SEQUENCE: 277
aagcaagact  gaggggcctc  agaccgagct  tttggaaaat  agaaaagtct  cgctctctgc    60
ccctcagcct  aactt                                                         75

SEQ ID NO: 278            moltype = RNA   length = 68
FEATURE                   Location/Qualifiers
source                    1..68
                          mol_type = transcribed RNA
                          organism = Homo sapiens
SEQUENCE: 278
gaatggaaga  agaaggcggt  cggtctgcgg  gagccaggcc  gcagagccat  ccgccttctg    60
tccatgtc                                                                  68

SEQ ID NO: 279            moltype = RNA   length = 73
FEATURE                   Location/Qualifiers
source                    1..73
                          mol_type = transcribed RNA
                          organism = Homo sapiens
SEQUENCE: 279
aggtggcagg  gccagccacc  aggagggctg  cgtgccaccc  gggcagctct  gctgctcact    60
ggcagtgtca  cct                                                           73

SEQ ID NO: 280            moltype = RNA   length = 84
FEATURE                   Location/Qualifiers
source                    1..84
                          mol_type = transcribed RNA
                          organism = Homo sapiens
SEQUENCE: 280
ccgcagccgc  cgcgccgggc  ccggttggc  cgctgacccc  cgcggggccc  ccggcggccg    60
gggcggggc  gggggctgcc  ccgg                                               84

SEQ ID NO: 281            moltype = RNA   length = 73
FEATURE                   Location/Qualifiers
source                    1..73
                          mol_type = transcribed RNA
                          organism = Homo sapiens
SEQUENCE: 281
ggcgagggga  ggcgcaggct  cggaaaggcg  cgcgaggctc  caggctcctt  cccgatccac    60
cgctctcctc  gct                                                           73

SEQ ID NO: 282            moltype = RNA   length = 82
FEATURE                   Location/Qualifiers
source                    1..82
                          mol_type = transcribed RNA
                          organism = Homo sapiens
SEQUENCE: 282
gcttcgctcc  cctccgcctt  ctcttcccgg  ttcttcccgg  agtcgggaaa  agctgggttg    60
agagggcgaa  aaaggatgag  gt                                                82

SEQ ID NO: 283            moltype = RNA   length = 75
FEATURE                   Location/Qualifiers
source                    1..75
                          mol_type = transcribed RNA
                          organism = Homo sapiens
SEQUENCE: 283
tggagtgggg  gggcaggagg  ggctcaggga  gaaagtgcat  acagccctg  gccctctctg    60
cccttccgtc  ccctg                                                         75
```

```
SEQ ID NO: 284              moltype = RNA   length = 99
FEATURE                     Location/Qualifiers
source                      1..99
                            mol_type = transcribed RNA
                            organism = Homo sapiens
SEQUENCE: 284
gaaactgggc tcaaggtgag gggtgctatc tgtgattgag ggacatggtt aatggaattg    60
tctcacacag aaatcgcacc cgtcaccttg gcctactta                           99

SEQ ID NO: 285              moltype = RNA   length = 98
FEATURE                     Location/Qualifiers
source                      1..98
                            mol_type = transcribed RNA
                            organism = Homo sapiens
SEQUENCE: 285
acccaaaccc taggtctgct gactcctagt ccagggctcg tgatggctgg tgggccctga    60
acgaggggtc tggaggcctg ggtttgaata tcgacagc                            98

SEQ ID NO: 286              moltype = RNA   length = 92
FEATURE                     Location/Qualifiers
source                      1..92
                            mol_type = transcribed RNA
                            organism = Homo sapiens
SEQUENCE: 286
tgtcactccg ccagcatcat gaagtgcact catgatatgt ttgccccatc agcgtgtcac    60
gagggcattt catgatgcag gcggggttgg ca                                  92

SEQ ID NO: 287              moltype = RNA   length = 83
FEATURE                     Location/Qualifiers
source                      1..83
                            mol_type = transcribed RNA
                            organism = Homo sapiens
SEQUENCE: 287
acggcatctt tgcactcagc aggcaggctg gtgcagcccg tggtggggga ccatcctgcc    60
tgctgtgggg taaggacggc tgt                                            83

SEQ ID NO: 288              moltype = RNA   length = 79
FEATURE                     Location/Qualifiers
source                      1..79
                            mol_type = transcribed RNA
                            organism = Homo sapiens
SEQUENCE: 288
gtgaggtggg ggccagcagg gagtgggctg ggctgggctg gccaaggta caaggcctca    60
ccctgcatcc cgcacccag                                                 79

SEQ ID NO: 289              moltype = RNA   length = 85
FEATURE                     Location/Qualifiers
source                      1..85
                            mol_type = transcribed RNA
                            organism = Homo sapiens
SEQUENCE: 289
gtgagctgct ggggacgcgg gtcggggtct gcagggcggt gcggcagccg ccacctgacg    60
ccgcgccttt gtctgtgtcc cacag                                          85

SEQ ID NO: 290              moltype = RNA   length = 83
FEATURE                     Location/Qualifiers
source                      1..83
                            mol_type = transcribed RNA
                            organism = Homo sapiens
SEQUENCE: 290
aatagagggt gcacaggcac gggagctcag gtgaggcagg gagctgagct cacctgacct    60
cccatgcctg tgcaccctct att                                            83

SEQ ID NO: 291              moltype = RNA   length = 131
FEATURE                     Location/Qualifiers
source                      1..131
                            mol_type = transcribed RNA
                            organism = Homo sapiens
SEQUENCE: 291
cggctggagg tgtgaggatc cgaacccagg ggtgggggt ggaggcggct cctgcgatcg    60
aagggacttt gagactcacc ggccgcacgc catgagggcc ctgtgggtgc tgggcctctg   120
ctgcgtcctg c                                                        131

SEQ ID NO: 292              moltype = RNA   length = 69
FEATURE                     Location/Qualifiers
source                      1..69
                            mol_type = transcribed RNA
                            organism = Homo sapiens
SEQUENCE: 292
```

```
ctttcggcca gcgggacggc atccgaggtg ggctaggctc gggcccgtgg cgggtgcggg    60
ggtgggagg                                                            69

SEQ ID NO: 293          moltype = RNA  length = 97
FEATURE                 Location/Qualifiers
source                  1..97
                        mol_type = transcribed RNA
                        organism = Homo sapiens
SEQUENCE: 293
cccgggacct tggtccaggc gctggtctgc gtggtgctcg ggtggataag tctgatctga    60
gcaccacaca ggccgggcgc cgggaccaag ggggctc                             97

SEQ ID NO: 294          moltype = RNA  length = 68
FEATURE                 Location/Qualifiers
source                  1..68
                        mol_type = transcribed RNA
                        organism = Homo sapiens
SEQUENCE: 294
cgtggtgagg atatggcagg gaaggggagt ttccctctat tcccttcccc ccagtaatct    60
tcatcatg                                                             68

SEQ ID NO: 295          moltype = RNA  length = 66
FEATURE                 Location/Qualifiers
source                  1..66
                        mol_type = transcribed RNA
                        organism = Homo sapiens
SEQUENCE: 295
ggtaacactc aaaagatggc ggcactttca ccagagagca gaaagtgccc ccacagtttg    60
agtgcc                                                               66

SEQ ID NO: 296          moltype = RNA  length = 69
FEATURE                 Location/Qualifiers
source                  1..69
                        mol_type = transcribed RNA
                        organism = Homo sapiens
SEQUENCE: 296
gggatactca aaatgggggc gctttccttt ttgtctgtac tgggaagtgc ttcgattttg    60
gggtgtccc                                                            69

SEQ ID NO: 297          moltype = RNA  length = 93
FEATURE                 Location/Qualifiers
source                  1..93
                        mol_type = transcribed RNA
                        organism = Homo sapiens
SEQUENCE: 297
ggcgcttttg tgcgcgcccg ggtctgttgg tgctcagagt gtggtcaggc ggctcggact    60
gagcaggtgg gtgcggggct cggaggaggc ggc                                 93

SEQ ID NO: 298          moltype = RNA  length = 102
FEATURE                 Location/Qualifiers
source                  1..102
                        mol_type = transcribed RNA
                        organism = Homo sapiens
SEQUENCE: 298
gcttatcgag gaaaagatcg aggtgggttg gggcgggctc tggggatttg gtctcacagc    60
ccggatccca gcccacttac cttggttact ctccttcctt ct                       102

SEQ ID NO: 299          moltype = RNA  length = 91
FEATURE                 Location/Qualifiers
source                  1..91
                        mol_type = transcribed RNA
                        organism = Homo sapiens
SEQUENCE: 299
ggcgccccgg ctcccccgcgc ccccgatcgg ggccgccgct agtagtggcg gcggcggagg    60
cggggggcagc ggcggcggcg gcggaggcgc c                                   91

SEQ ID NO: 300          moltype = RNA  length = 91
FEATURE                 Location/Qualifiers
source                  1..91
                        mol_type = transcribed RNA
                        organism = Homo sapiens
SEQUENCE: 300
acgccccccg ccccgccacc gccttggagg ctgacctctt actttcggtc ggtcttcttc    60
cctgggcttg gtttgggggc gggggagtgt c                                   91

SEQ ID NO: 301          moltype = RNA  length = 101
FEATURE                 Location/Qualifiers
source                  1..101
                        mol_type = transcribed RNA
```

```
                        organism = Homo sapiens
SEQUENCE: 301
gatgggcccc ttgtgtcctg aattgggtgg gggctctgag tggggaaagt gggggcctag    60
gggaggtcac agttgggtct aggggtcagg agggcccagg a                        101

SEQ ID NO: 302          moltype = RNA   length = 70
FEATURE                 Location/Qualifiers
source                  1..70
                        mol_type = transcribed RNA
                        organism = Homo sapiens
SEQUENCE: 302
acaaatagct tcagggagtc aggggagggc agaaatagat ggccttcccc tgctgggaag    60
aaagtgggtc                                                           70

SEQ ID NO: 303          moltype = RNA   length = 93
FEATURE                 Location/Qualifiers
source                  1..93
                        mol_type = transcribed RNA
                        organism = Homo sapiens
SEQUENCE: 303
tacttatggc accccactcc tggtaccata gtcataagtt aggagatgtt agagctgtga    60
gtaccatgac ttaagtgtgg tggcttaaac atg                                 93

SEQ ID NO: 304          moltype = RNA   length = 73
FEATURE                 Location/Qualifiers
source                  1..73
                        mol_type = transcribed RNA
                        organism = Homo sapiens
SEQUENCE: 304
ggggaggtac ctgggacagg aggaggaggc agccttgcct cagaaaccaa actgtcaaaa    60
gtgtaggttc cac                                                       73

SEQ ID NO: 305          moltype = RNA   length = 73
FEATURE                 Location/Qualifiers
source                  1..73
                        mol_type = transcribed RNA
                        organism = Homo sapiens
SEQUENCE: 305
accgcgagtt ccgcgcctgg ccgtgtcgcc ccacgagggg gactgtgggc tcagcgcgtg    60
gggcccggag cat                                                       73

SEQ ID NO: 306          moltype = RNA   length = 85
FEATURE                 Location/Qualifiers
source                  1..85
                        mol_type = transcribed RNA
                        organism = Homo sapiens
SEQUENCE: 306
ggcctgggta ggcttgcatg ggggactggg aagagaccat gaacaggtta gtccagggag    60
ttctcatcaa gcctttactc agtag                                          85

SEQ ID NO: 307          moltype = RNA   length = 73
FEATURE                 Location/Qualifiers
source                  1..73
                        mol_type = transcribed RNA
                        organism = Homo sapiens
SEQUENCE: 307
gaaaacaacc aggtgggctt cccggagggc ggaacaccca gccccagcat ccagggctca    60
cctaccacgt ttg                                                       73

SEQ ID NO: 308          moltype = RNA   length = 68
FEATURE                 Location/Qualifiers
source                  1..68
                        mol_type = transcribed RNA
                        organism = Homo sapiens
SEQUENCE: 308
ctcaggctca gtggtgcatg cttatagtcc cagccactct ggaggctgaa ggaagatggc    60
ttgagcct                                                             68

SEQ ID NO: 309          moltype = RNA   length = 73
FEATURE                 Location/Qualifiers
source                  1..73
                        mol_type = transcribed RNA
                        organism = Homo sapiens
SEQUENCE: 309
agggagaaaa gctgggctga gaggcgactg gtgtctaatt tgtttgtctc tccaactcag    60
actgcctggc cca                                                       73

SEQ ID NO: 310          moltype = RNA   length = 49
FEATURE                 Location/Qualifiers
```

```
source                   1..49
                         mol_type = transcribed RNA
                         organism = Homo sapiens
SEQUENCE: 310
gtgaggctgg agtgagcgga gatcgtacca ctgcactcca acctggtga            49

SEQ ID NO: 311           moltype = RNA   length = 81
FEATURE                  Location/Qualifiers
source                   1..81
                         mol_type = transcribed RNA
                         organism = Homo sapiens
SEQUENCE: 311
catcctcctt acgtcccacc ccccactcct gtttctggtg aaatattcaa acaggagtgg  60
gggtgggaca taaggaggat a                                           81

SEQ ID NO: 312           moltype = RNA   length = 53
FEATURE                  Location/Qualifiers
source                   1..53
                         mol_type = transcribed RNA
                         organism = Homo sapiens
SEQUENCE: 312
ggtgggggtt ggaggcgtgg gttttagaac ctatcccttt ctagccctga gca         53

SEQ ID NO: 313           moltype = RNA   length = 67
FEATURE                  Location/Qualifiers
source                   1..67
                         mol_type = transcribed RNA
                         organism = Homo sapiens
SEQUENCE: 313
ctggtccatt tccctgccat tcccttggct tcaatttact cccagggctg gcagtgacat  60
gggtcaa                                                           67

SEQ ID NO: 314           moltype = RNA   length = 91
FEATURE                  Location/Qualifiers
source                   1..91
                         mol_type = transcribed RNA
                         organism = Homo sapiens
SEQUENCE: 314
gttctagagc atggtttctc atcatttgca ctactgatac ttggggtcag ataattgttt  60
gtggtggggg ctgttgtttg cattgtagga t                                91

SEQ ID NO: 315           moltype = RNA   length = 86
FEATURE                  Location/Qualifiers
source                   1..86
                         mol_type = transcribed RNA
                         organism = Homo sapiens
SEQUENCE: 315
aggagtgacc aaaagacaag agtgcgagcc ttctattatg cccagacagg gccaccagag  60
ggctccttgg tctaggggta atgcca                                      86

SEQ ID NO: 316           moltype = RNA   length = 66
FEATURE                  Location/Qualifiers
source                   1..66
                         mol_type = transcribed RNA
                         organism = Homo sapiens
SEQUENCE: 316
agcagccctc ggcggcccgg ggggcgggcg gcggtgcccg tcccggggct gcgcgaggca  60
caggcg                                                            66

SEQ ID NO: 317           moltype = RNA   length = 55
FEATURE                  Location/Qualifiers
source                   1..55
                         mol_type = transcribed RNA
                         organism = Homo sapiens
SEQUENCE: 317
ccggatccga gtcacggcac caaatttcat gcgtgtccgt gtgaagagac cacca        55

SEQ ID NO: 318           moltype = RNA   length = 58
FEATURE                  Location/Qualifiers
source                   1..58
                         mol_type = transcribed RNA
                         organism = Homo sapiens
SEQUENCE: 318
agaagggtgt gtgtgttttt cctgagaata agagaaggaa ggacagccaa attcttca    58

SEQ ID NO: 319           moltype = RNA   length = 66
FEATURE                  Location/Qualifiers
source                   1..66
                         mol_type = transcribed RNA
```

```
                          -continued
                         organism = Homo sapiens
SEQUENCE: 319
acccaggagg cggaggaggt ggaggttgca gtgagccaag atcgtggcac tgactccagc    60
ctgggg                                                               66

SEQ ID NO: 320           moltype = RNA  length = 58
FEATURE                  Location/Qualifiers
source                   1..58
                         mol_type = transcribed RNA
                         organism = Homo sapiens
SEQUENCE: 320
cttcccagct gccctaagtc aggagtggct ttcctgacac ggagggtggc ttgggaaa      58

SEQ ID NO: 321           moltype = RNA  length = 54
FEATURE                  Location/Qualifiers
source                   1..54
                         mol_type = transcribed RNA
                         organism = Homo sapiens
SEQUENCE: 321
acgcgggtgc gggccggcgg ggtagaagcc acccggcccg gcccggcccg gcga          54

SEQ ID NO: 322           moltype = RNA  length = 63
FEATURE                  Location/Qualifiers
source                   1..63
                         mol_type = transcribed RNA
                         organism = Homo sapiens
SEQUENCE: 322
tggtggcggc ggtagttatg ggcttctctt tctcaccagc agccctggg ccgccgcctc     60
cct                                                                  63

SEQ ID NO: 323           moltype = RNA  length = 71
FEATURE                  Location/Qualifiers
source                   1..71
                         mol_type = transcribed RNA
                         organism = Homo sapiens
SEQUENCE: 323
gcagaggtga gttgacctcc acagggccac ccagggagta agtagccaag tggaagttac    60
tttacctctg t                                                         71

SEQ ID NO: 324           moltype = RNA  length = 62
FEATURE                  Location/Qualifiers
source                   1..62
                         mol_type = transcribed RNA
                         organism = Homo sapiens
SEQUENCE: 324
aaaaaacaac atacttagtg catacccata taatattagg ggtggtctgt tgttgttttt    60
ct                                                                   62

SEQ ID NO: 325           moltype = RNA  length = 83
FEATURE                  Location/Qualifiers
source                   1..83
                         mol_type = transcribed RNA
                         organism = Homo sapiens
SEQUENCE: 325
gggtttcctc tgccttttt tccaatgaaa ataacgaaac ctgttatttc ccattgaggg     60
ggaaaaaggc gggagaagcc cca                                            83

SEQ ID NO: 326           moltype = RNA  length = 57
FEATURE                  Location/Qualifiers
source                   1..57
                         mol_type = transcribed RNA
                         organism = Homo sapiens
SEQUENCE: 326
agaggcaccg cctgcccagt gacatgcgtt taacggccgc ggtaccctaa ctgtgca       57

SEQ ID NO: 327           moltype = RNA  length = 62
FEATURE                  Location/Qualifiers
source                   1..62
                         mol_type = transcribed RNA
                         organism = Homo sapiens
SEQUENCE: 327
ggtaggggc gggctccggc gctgggaccc cactagggtg gcgccttggc cccgcccgc      60
cc                                                                   62

SEQ ID NO: 328           moltype = RNA  length = 80
FEATURE                  Location/Qualifiers
source                   1..80
                         mol_type = transcribed RNA
                         organism = Homo sapiens
```

-continued

```
SEQUENCE: 328
ctgcagcgtg cttctccagg ccccgcgcgc ggacagacac acggacaagt cccgccaggg    60
gctgggcgcg cgccagccgg                                                80

SEQ ID NO: 329          moltype = RNA   length = 73
FEATURE                 Location/Qualifiers
source                  1..73
                        mol_type = transcribed RNA
                        organism = Homo sapiens
SEQUENCE: 329
ggaggctggg ctgggacgga cacccggcct ccactttctg tggcaggtac ctcctccatg    60
tcggcccgcc ttg                                                       73

SEQ ID NO: 330          moltype = RNA   length = 81
FEATURE                 Location/Qualifiers
source                  1..81
                        mol_type = transcribed RNA
                        organism = Homo sapiens
SEQUENCE: 330
gcgggaggtg taacaggact ggactcccgg cagccccagg gcagggcgt ggggagctgg     60
tcctagctca gcgctcccgg a                                              81

SEQ ID NO: 331          moltype = RNA   length = 75
FEATURE                 Location/Qualifiers
source                  1..75
                        mol_type = transcribed RNA
                        organism = Homo sapiens
SEQUENCE: 331
gtcagagggg ggatgtgcat gctggttggg gtgggctgcc tgtggaccaa tcagcgtgca    60
cttccccacc ctgaa                                                     75

SEQ ID NO: 332          moltype = RNA   length = 60
FEATURE                 Location/Qualifiers
source                  1..60
                        mol_type = transcribed RNA
                        organism = Homo sapiens
SEQUENCE: 332
tgtgaatgac ccccttccag agccaaaatc accagggatg gaggaggggt cttgggtact    60

SEQ ID NO: 333          moltype = RNA   length = 59
FEATURE                 Location/Qualifiers
source                  1..59
                        mol_type = transcribed RNA
                        organism = Homo sapiens
SEQUENCE: 333
aactgggtcc cagtcttcac agttggtttc tgacacgtgg acctggctgg gacgatgtg     59

SEQ ID NO: 334          moltype = RNA   length = 79
FEATURE                 Location/Qualifiers
source                  1..79
                        mol_type = transcribed RNA
                        organism = Homo sapiens
SEQUENCE: 334
tggcaagtct ccgcatatgc ctggctagct cctccacaaa tgcgtgtgga ggagctagcc    60
aggcatatgc agagcgtca                                                 79

SEQ ID NO: 335          moltype = RNA   length = 54
FEATURE                 Location/Qualifiers
source                  1..54
                        mol_type = transcribed RNA
                        organism = Homo sapiens
SEQUENCE: 335
ggacaagggc ggcgcgaccg gcccggggct cttgggcggc cgcgtttccc ctcc          54

SEQ ID NO: 336          moltype = RNA   length = 90
FEATURE                 Location/Qualifiers
source                  1..90
                        mol_type = transcribed RNA
                        organism = Homo sapiens
SEQUENCE: 336
ctgtgggctg ggccagggag cagctggtgg gtgggaagta agatctgacc tggactccat    60
cccacccacc ccctgtttcc tggcccacag                                     90

SEQ ID NO: 337          moltype = RNA   length = 64
FEATURE                 Location/Qualifiers
source                  1..64
                        mol_type = transcribed RNA
                        organism = Homo sapiens
SEQUENCE: 337
```

```
tctgggcgag gggtgggctc tcagaggggc tggcagtact gctctgaggc ctgcctctcc   60
ccag                                                                64

SEQ ID NO: 338          moltype = RNA  length = 73
FEATURE                 Location/Qualifiers
source                  1..73
                        mol_type = transcribed RNA
                        organism = Homo sapiens
SEQUENCE: 338
cggcgacggc ggggtgggtg aggtcgggcc ccaagactcg gggtttgccg ggcgcctcag   60
ttcaccgcgg ccg                                                     73

SEQ ID NO: 339          moltype = RNA  length = 78
FEATURE                 Location/Qualifiers
source                  1..78
                        mol_type = transcribed RNA
                        organism = Homo sapiens
SEQUENCE: 339
tattggacga ggggactggt taatagaact aactaaccag aactattttg ttctgttaac   60
ccatcccctc atctaata                                                78

SEQ ID NO: 340          moltype = RNA  length = 74
FEATURE                 Location/Qualifiers
source                  1..74
                        mol_type = transcribed RNA
                        organism = Homo sapiens
SEQUENCE: 340
ccaagggcac accggggatg gcagagggtc gtgggaaagt gttgaccctc gtcaggtccc   60
cggggagccc ctgg                                                    74

SEQ ID NO: 341          moltype = RNA  length = 75
FEATURE                 Location/Qualifiers
source                  1..75
                        mol_type = transcribed RNA
                        organism = Homo sapiens
SEQUENCE: 341
aggctggcgt gggctgaggg caggaggcct gtggccggtc ccaggcctcc tgcttcctgg   60
gctcaggctc ggttt                                                   75

SEQ ID NO: 342          moltype = RNA  length = 65
FEATURE                 Location/Qualifiers
source                  1..65
                        mol_type = transcribed RNA
                        organism = Homo sapiens
SEQUENCE: 342
gctgccctc actcagagca tctacaccca ctaccggtga gtgtggatcc tggaggaatc   60
gtggc                                                              65

SEQ ID NO: 343          moltype = RNA  length = 76
FEATURE                 Location/Qualifiers
source                  1..76
                        mol_type = transcribed RNA
                        organism = Homo sapiens
SEQUENCE: 343
ctgtggtgga gctgagctcc atggacgtgc agtggcatct gtcattgctg ccttcctgga   60
gctcaggccc ttgcag                                                  76

SEQ ID NO: 344          moltype = RNA  length = 59
FEATURE                 Location/Qualifiers
source                  1..59
                        mol_type = transcribed RNA
                        organism = Homo sapiens
SEQUENCE: 344
gtccaggcag gagccggact ggacctcagg gaagaggctg acccggcccc tcttgcggc    59

SEQ ID NO: 345          moltype = RNA  length = 77
FEATURE                 Location/Qualifiers
source                  1..77
                        mol_type = transcribed RNA
                        organism = Homo sapiens
SEQUENCE: 345
catgagaaat cctgctggtc aaccatagcc ctggtcagac tctccggggc tgtgattgac   60
cagcaggact tctcatg                                                 77

SEQ ID NO: 346          moltype = RNA  length = 80
FEATURE                 Location/Qualifiers
source                  1..80
                        mol_type = transcribed RNA
                        organism = Homo sapiens
```

```
SEQUENCE: 346
acctgaggag ccagccctcc tcccgcaccc aaacttggag cacttgacct ttggctgttg    60
gaggggcag gctcgcgggt                                                 80

SEQ ID NO: 347          moltype = RNA   length = 80
FEATURE                 Location/Qualifiers
source                  1..80
                        mol_type = transcribed RNA
                        organism = Homo sapiens
SEQUENCE: 347
acctgaggag ccagccctcc tcccgcaccc aaacttggag cacttgacct ttggctgttg    60
gaggggcag gctcgcgggt                                                 80

SEQ ID NO: 348          moltype = RNA   length = 60
FEATURE                 Location/Qualifiers
source                  1..60
                        mol_type = transcribed RNA
                        organism = Homo sapiens
SEQUENCE: 348
gagcaggcga ggctgggctg aacccgtggg tgaggagtgc agcccagctg aggcctctgc    60

SEQ ID NO: 349          moltype = RNA   length = 74
FEATURE                 Location/Qualifiers
source                  1..74
                        mol_type = transcribed RNA
                        organism = Homo sapiens
SEQUENCE: 349
cctgcaggag gcagtgggcg agcaggcggg gcagcccaat gccatgggcc tgatctcacc    60
gctgcctcct tccc                                                      74

SEQ ID NO: 350          moltype = RNA   length = 78
FEATURE                 Location/Qualifiers
source                  1..78
                        mol_type = transcribed RNA
                        organism = Homo sapiens
SEQUENCE: 350
gggcccagaa gggggcgcag tcactgacgt gaagggacca catcccgctt catgtcagtg    60
actcctgccc cttggtct                                                  78

SEQ ID NO: 351          moltype = RNA   length = 82
FEATURE                 Location/Qualifiers
source                  1..82
                        mol_type = transcribed RNA
                        organism = Homo sapiens
SEQUENCE: 351
gctacgggga gcggggagga agtgggcgct gcttctgcgt tatctggaag gagcagccca    60
ctcctgtcct gggctctgtg gt                                             82

SEQ ID NO: 352          moltype = RNA   length = 80
FEATURE                 Location/Qualifiers
source                  1..80
                        mol_type = transcribed RNA
                        organism = Homo sapiens
SEQUENCE: 352
ggttccggag ccccggcgcg ggcgggttct ggggtgtaga cgctgctggc cagcccgccc    60
cagccgaggt tctcggcacc                                                80

SEQ ID NO: 353          moltype = RNA   length = 80
FEATURE                 Location/Qualifiers
source                  1..80
                        mol_type = transcribed RNA
                        organism = Homo sapiens
SEQUENCE: 353
ggttccggag ccccggcgcg ggcgggttct ggggtgtaga cgctgctggc cagcccgccc    60
cagccgaggt tctcggcacc                                                80

SEQ ID NO: 354          moltype = RNA   length = 67
FEATURE                 Location/Qualifiers
source                  1..67
                        mol_type = transcribed RNA
                        organism = Homo sapiens
SEQUENCE: 354
tttaggagag agatgccgcc ttgctccttg aacaggagga gcaaggcggc atctctctga    60
tactaaa                                                              67

SEQ ID NO: 355          moltype = RNA   length = 56
FEATURE                 Location/Qualifiers
source                  1..56
                        mol_type = transcribed RNA
```

```
                              organism = Homo sapiens
SEQUENCE: 355
gaccgagtgg ggtgagggca ggtggttctt cccgaagcag ctctcgcctc ttcgtc        56

SEQ ID NO: 356           moltype = RNA   length = 51
FEATURE                  Location/Qualifiers
source                   1..51
                         mol_type = transcribed RNA
                         organism = Homo sapiens
SEQUENCE: 356
agctgtacct gaaaccaagc acctgtttgt gacttggctt cagttactag c              51

SEQ ID NO: 357           moltype = RNA   length = 60
FEATURE                  Location/Qualifiers
source                   1..60
                         mol_type = transcribed RNA
                         organism = Homo sapiens
SEQUENCE: 357
ggcaggaggg ctgtgccagg ttggctgggc caggcctgac ctgccagcac ctccctgcag     60

SEQ ID NO: 358           moltype = RNA   length = 90
FEATURE                  Location/Qualifiers
source                   1..90
                         mol_type = transcribed RNA
                         organism = Homo sapiens
SEQUENCE: 358
gtgtctctct ggagaccctg cagccttccc acccaccagg gagctttcca tgggctgtgg     60
ggaaggcgtc agtgtcgggt gagggaacac                                      90

SEQ ID NO: 359           moltype = RNA   length = 58
FEATURE                  Location/Qualifiers
source                   1..58
                         mol_type = transcribed RNA
                         organism = Homo sapiens
SEQUENCE: 359
agggccagag gagcctggag tggtcgggtc gactgaaccc aggttccctc tggccgca       58

SEQ ID NO: 360           moltype = RNA   length = 55
FEATURE                  Location/Qualifiers
source                   1..55
                         mol_type = transcribed RNA
                         organism = Homo sapiens
SEQUENCE: 360
aatctgccag cttccacagt ggcagatttt cccatagtgg gaagctggca gattc          55

SEQ ID NO: 361           moltype = RNA   length = 67
FEATURE                  Location/Qualifiers
source                   1..67
                         mol_type = transcribed RNA
                         organism = Homo sapiens
SEQUENCE: 361
gtgggagggg agaggcagca agcacacagg gcctgggact agcatgctga cctccctcct     60
gccccag                                                               67

SEQ ID NO: 362           moltype = RNA   length = 70
FEATURE                  Location/Qualifiers
source                   1..70
                         mol_type = transcribed RNA
                         organism = Homo sapiens
SEQUENCE: 362
ccctgccagt gctgggggcc acatgagtgt gcagtcatcc acacacaagt ggcccccaac     60
actggcaggg                                                            70

SEQ ID NO: 363           moltype = RNA   length = 47
FEATURE                  Location/Qualifiers
source                   1..47
                         mol_type = transcribed RNA
                         organism = Homo sapiens
SEQUENCE: 363
aggcaggtta tctgggctgc catctcccac tggctgcttg cctgcct                   47

SEQ ID NO: 364           moltype = RNA   length = 74
FEATURE                  Location/Qualifiers
source                   1..74
                         mol_type = transcribed RNA
                         organism = Homo sapiens
SEQUENCE: 364
gggaggaaga agggaggagg agcggagggg cccttgtctt cccagagcct ctcccttcct     60
cccctccccc tccc                                                       74
```

```
SEQ ID NO: 365          moltype = RNA   length = 63
FEATURE                 Location/Qualifiers
source                  1..63
                        mol_type = transcribed RNA
                        organism = Homo sapiens
SEQUENCE: 365
gccaaggact gatcctctcg ggcagggagt cagaggggac cgcccgagag gatccgtccc   60
tgc                                                                63

SEQ ID NO: 366          moltype = RNA   length = 90
FEATURE                 Location/Qualifiers
source                  1..90
                        mol_type = transcribed RNA
                        organism = Homo sapiens
SEQUENCE: 366
cgggcgggge gggtccggcc gcctccgagc ccggccggca gcccccggcc ttaaagcgcg   60
ggctgtccgg aggggtcggc tttcccaccg                                   90

SEQ ID NO: 367          moltype = RNA   length = 56
FEATURE                 Location/Qualifiers
source                  1..56
                        mol_type = transcribed RNA
                        organism = Homo sapiens
SEQUENCE: 367
cgctcgggcg gaggtggttg agtgccgact ggcgcctgac ccaccccctc ccgcag       56

SEQ ID NO: 368          moltype = RNA   length = 72
FEATURE                 Location/Qualifiers
source                  1..72
                        mol_type = transcribed RNA
                        organism = Homo sapiens
SEQUENCE: 368
agattcagct ttcccttcag agcctggctt tggcatctat gaaagccagg ctctgaaggg   60
aaagttgaat ct                                                      72

SEQ ID NO: 369          moltype = RNA   length = 92
FEATURE                 Location/Qualifiers
source                  1..92
                        mol_type = transcribed RNA
                        organism = Homo sapiens
SEQUENCE: 369
cctgtccctc ctgccctgcg cctgcccagc cctcctgctc tggtgactga ggaccgccag   60
gcaggggctg gtgctgggcg gggggcggcg gg                                92

SEQ ID NO: 370          moltype = RNA   length = 82
FEATURE                 Location/Qualifiers
source                  1..82
                        mol_type = transcribed RNA
                        organism = Homo sapiens
SEQUENCE: 370
gggaaagcgg agggcgcgcc cagctcccgg gctgattgcg ctaacagtgg ccccggtgtt   60
ggggcgcgtc tgccgctgcc cc                                           82

SEQ ID NO: 371          moltype = RNA   length = 82
FEATURE                 Location/Qualifiers
source                  1..82
                        mol_type = transcribed RNA
                        organism = Homo sapiens
SEQUENCE: 371
gggaaagcgg agggcgcgcc cagctcccgg gctgattgcg ctaacagtgg ccccggtgtt   60
ggggcgcgtc tgccgctgcc cc                                           82

SEQ ID NO: 372          moltype = RNA   length = 84
FEATURE                 Location/Qualifiers
source                  1..84
                        mol_type = transcribed RNA
                        organism = Homo sapiens
SEQUENCE: 372
cggtccagac gtggcggggg tggcggcggc atcccggacg gcctgtgagg gatgcgccgc   60
ccactgcccc gcgccgcctg accg                                         84

SEQ ID NO: 373          moltype = RNA   length = 74
FEATURE                 Location/Qualifiers
source                  1..74
                        mol_type = transcribed RNA
                        organism = Homo sapiens
SEQUENCE: 373
gcagcccggt gagcgctcgc tggcctggca gtgcgtcgga agaacagggc gggtggggcc   60
```
gcgcacatct ctgc 74

SEQ ID NO: 374    moltype = RNA   length = 124
FEATURE           Location/Qualifiers
source            1..124
                  mol_type = transcribed RNA
                  organism = Homo sapiens
SEQUENCE: 374
aaccctcctt gggaagtgaa gctcaggctg tgatttcaag ccaggggcg ttttctata    60
actggatgaa aagcacctcc agagcttgaa gctcacagtt tgagagcaat cgtctaagga  120
agtt                                                                124

SEQ ID NO: 375    moltype = RNA   length = 94
FEATURE           Location/Qualifiers
source            1..94
                  mol_type = transcribed RNA
                  organism = Homo sapiens
SEQUENCE: 375
gggctgaccc ctagggtcag gtgaggccct tggggcacag tggtgccatc tccctgtgc   60
tcccagggcc tcgcctgtcc cttgaggtcg gccc                              94

SEQ ID NO: 376    moltype = RNA   length = 120
FEATURE           Location/Qualifiers
source            1..120
                  mol_type = transcribed RNA
                  organism = Homo sapiens
SEQUENCE: 376
gatccaggga accctagagc aggggatgg cagagcaaaa ttcatggcct acagctgcct    60
cttgccaaac tgcactggat tttgtgtctc ccattcccca gagctgtctg aggtgctttg  120

SEQ ID NO: 377    moltype = RNA   length = 83
FEATURE           Location/Qualifiers
source            1..83
                  mol_type = transcribed RNA
                  organism = Homo sapiens
SEQUENCE: 377
gctgctgttg ggagaccctg gtctgcactc tatctgtatt cttactgaag ggagtgcagg   60
gcagggtttc ccatacagag ggc                                          83

SEQ ID NO: 378    moltype = RNA   length = 115
FEATURE           Location/Qualifiers
source            1..115
                  mol_type = transcribed RNA
                  organism = Homo sapiens
SEQUENCE: 378
gagcaaaaac cagagaacaa catgggagcg ttcctaaccc ctaaggcaac tggatgggag   60
acctgaccca tccagttctc tgaggggct cttgtgtgtt ctacaaggtt gttca         115

SEQ ID NO: 379    moltype = RNA   length = 137
FEATURE           Location/Qualifiers
source            1..137
                  mol_type = transcribed RNA
                  organism = Homo sapiens
SEQUENCE: 379
agccagacaa gagggtcatg gggagtcact gtcaacccag agcaggcact gcccctgcga   60
ccagcctggg gcatcggttg gggtgcaggg gtctgctggt gatgctttcc atctctttgc  120
tttgtcctga ttgtagc                                                  137

SEQ ID NO: 380    moltype = RNA   length = 80
FEATURE           Location/Qualifiers
source            1..80
                  mol_type = transcribed RNA
                  organism = Homo sapiens
SEQUENCE: 380
ggttggctat aactatcatt tccaaggttg tgcttttagg aaatgttggc tgtcctgcgg   60
agagagaatg gggagccagg                                              80

SEQ ID NO: 381    moltype = RNA   length = 95
FEATURE           Location/Qualifiers
source            1..95
                  mol_type = transcribed RNA
                  organism = Homo sapiens
SEQUENCE: 381
gacaccacat gctcctccag gcctgcctgc cctccaggtc atgttccagt gtcccacaga   60
tgcagcacca cggcccaggc ggcattggtg tcacc                              95

SEQ ID NO: 382    moltype = RNA   length = 113
FEATURE           Location/Qualifiers
source            1..113

```
                            mol_type = transcribed RNA
                            organism = Homo sapiens
SEQUENCE: 382
agcatgacag aggagaggtg gaggtaggcg agagtaatat aatttctcca ggagaacatc    60
tgagagggga agttgctttc ctgccctggc cctttcaccc tcctgagttt ggg          113

SEQ ID NO: 383              moltype = RNA   length = 51
FEATURE                     Location/Qualifiers
source                      1..51
                            mol_type = transcribed RNA
                            organism = Homo sapiens
SEQUENCE: 383
agagatgaag cgggggggcg gggtcttgct ctattgccta cgctgatctc a             51

SEQ ID NO: 384              moltype = RNA   length = 85
FEATURE                     Location/Qualifiers
source                      1..85
                            mol_type = transcribed RNA
                            organism = Homo sapiens
SEQUENCE: 384
ggggaggtag ggaaaaggaa gggggaggag aaggtgagac caatgtcctg ggtgccactc    60
ctgcccagtg cctcccttcc tcgtt                                          85

SEQ ID NO: 385              moltype = RNA   length = 109
FEATURE                     Location/Qualifiers
source                      1..109
                            mol_type = transcribed RNA
                            organism = Homo sapiens
SEQUENCE: 385
tcccgcattc cctctgcttt ggtcaggtgg tgccctcctt ccatgggtag agccagagat    60
ggtgggttct ggctggtcag atgggagtgg acagagaccc gggtcctc                109

SEQ ID NO: 386              moltype = RNA   length = 109
FEATURE                     Location/Qualifiers
source                      1..109
                            mol_type = transcribed RNA
                            organism = Homo sapiens
SEQUENCE: 386
tgctattgtc ttactgctac agcagggctg gggattgcag tatccgctgt tgctgctgct    60
cccagtcctg cccctgctgc tacctagtcc agcctcaccg catcccaga              109

SEQ ID NO: 387              moltype = RNA   length = 90
FEATURE                     Location/Qualifiers
source                      1..90
                            mol_type = transcribed RNA
                            organism = Homo sapiens
SEQUENCE: 387
tctaagaaac gcagtggtct ctgaagcctg cagggggcagg ccagccctgc actgaacgcc   60
tgttcttgcc aggtggcaga aggttgctgc                                     90

SEQ ID NO: 388              moltype = RNA   length = 96
FEATURE                     Location/Qualifiers
source                      1..96
                            mol_type = transcribed RNA
                            organism = Homo sapiens
SEQUENCE: 388
ctcgggaggg gcgggagggg ggtccccggt gctcggatct cgagggtgct tattgttcgg    60
tccgagcctg ggtctcccctc ttcccccccaa cccccc                            96

SEQ ID NO: 389              moltype = RNA   length = 99
FEATURE                     Location/Qualifiers
source                      1..99
                            mol_type = transcribed RNA
                            organism = Homo sapiens
SEQUENCE: 389
cgcccacctc agcctcccaa aatgctggga ttacaggcat gagccactgc ggtcgaccat    60
gacctggaca tgtttgtgcc cagtactgtc agtttgcag                           99

SEQ ID NO: 390              moltype = RNA   length = 77
FEATURE                     Location/Qualifiers
source                      1..77
                            mol_type = transcribed RNA
                            organism = Homo sapiens
SEQUENCE: 390
gagttgggag gttccctctc caaatgtgtc ttgatccccc accccaagac acatttggag    60
agggaccctc ccaactc                                                   77

SEQ ID NO: 391              moltype = RNA   length = 54
FEATURE                     Location/Qualifiers
```

```
                           -continued source                  1..54
                        mol_type = transcribed RNA
                        organism = Homo sapiens
SEQUENCE: 391
agcagcaggg gagagagagg agtcctctag acaccgactc tgtctcctgc agat         54

SEQ ID NO: 392          moltype = RNA   length = 57
FEATURE                 Location/Qualifiers
source                  1..57
                        mol_type = transcribed RNA
                        organism = Homo sapiens
SEQUENCE: 392
cattggaggg tgtggaagac atctgggcca actctgatct cttcatctac cccccag      57

SEQ ID NO: 393          moltype = RNA   length = 57
FEATURE                 Location/Qualifiers
source                  1..57
                        mol_type = transcribed RNA
                        organism = Homo sapiens
SEQUENCE: 393
cattggaggg tgtggaagac atctgggcca actctgatct cttcatctac cccccag      57

SEQ ID NO: 394          moltype = RNA   length = 115
FEATURE                 Location/Qualifiers
source                  1..115
                        mol_type = transcribed RNA
                        organism = Homo sapiens
SEQUENCE: 394
ggtgccgagg gccgtccggc atcctaggcg ggtcgctgcg gtacctccct cctgtctgtg   60
gcggtgggat cccgtggccg tgttttcctg gtggcccggc cgtgcctgag gtttc        115

SEQ ID NO: 395          moltype = RNA   length = 80
FEATURE                 Location/Qualifiers
source                  1..80
                        mol_type = transcribed RNA
                        organism = Homo sapiens
SEQUENCE: 395
gagaggccaa gaccttggga atgggggtaa gggccttctg agcccaggtc cgaactctcc   60
attcctctgc agagcgctct                                               80

SEQ ID NO: 396          moltype = RNA   length = 73
FEATURE                 Location/Qualifiers
source                  1..73
                        mol_type = transcribed RNA
                        organism = Homo sapiens
SEQUENCE: 396
ctggtgtttg aggcgatgtg gggatgtaga gacaacttcc cagtctcatt tcctcatcct   60
gccaggccac cat                                                      73

SEQ ID NO: 397          moltype = RNA   length = 78
FEATURE                 Location/Qualifiers
source                  1..78
                        mol_type = transcribed RNA
                        organism = Homo sapiens
SEQUENCE: 397
ggcctcaggc aggcgcaccc gaccacatgc atggctggtg gcggcgtgca ggggtcgggt   60
gggccaggct gtggggcg                                                 78

SEQ ID NO: 398          moltype = RNA   length = 61
FEATURE                 Location/Qualifiers
source                  1..61
                        mol_type = transcribed RNA
                        organism = Homo sapiens
SEQUENCE: 398
gggggcggga gctgggtct gcaggttcgc actgatgcct gctcgccctg tctcccgcta    60
g                                                                   61

SEQ ID NO: 399          moltype = RNA   length = 70
FEATURE                 Location/Qualifiers
source                  1..70
                        mol_type = transcribed RNA
                        organism = Homo sapiens
SEQUENCE: 399
ttgggttggg gtggtcggcc ctggagggggg tttgtttgct tattcccctc tgtgcttcac  60
ccctacccag                                                          70

SEQ ID NO: 400          moltype = RNA   length = 63
FEATURE                 Location/Qualifiers
source                  1..63
```

```
                         mol_type = transcribed RNA
                         organism = Homo sapiens
SEQUENCE: 400
aatgggtggg tgctggtggg agccgtgccc tggccactca ttcggctctc tccctcaccc   60
tag                                                                 63

SEQ ID NO: 401           moltype = RNA    length = 62
FEATURE                  Location/Qualifiers
source                   1..62
                         mol_type = transcribed RNA
                         organism = Homo sapiens
SEQUENCE: 401
gagggagtgg ggtgggaccc agctgttggc catggcgaca cacctgggt tgtccctct     60
ag                                                                  62

SEQ ID NO: 402           moltype = RNA    length = 71
FEATURE                  Location/Qualifiers
source                   1..71
                         mol_type = transcribed RNA
                         organism = Homo sapiens
SEQUENCE: 402
gggtaaaggg gcagggacgg gtggccccag gaagaagggc ctggtggagc cgctcttctc   60
cctgcccaca g                                                        71

SEQ ID NO: 403           moltype = RNA    length = 63
FEATURE                  Location/Qualifiers
source                   1..63
                         mol_type = transcribed RNA
                         organism = Homo sapiens
SEQUENCE: 403
cttgcccggg agaaggaggt ggcctggaga gctgctgtct ccagccgccg cctgtctcca   60
cag                                                                 63

SEQ ID NO: 404           moltype = RNA    length = 69
FEATURE                  Location/Qualifiers
source                   1..69
                         mol_type = transcribed RNA
                         organism = Homo sapiens
SEQUENCE: 404
ggccctcggg cctggggttg ggggagctct gtcctgtctc actcattgct cctccctgc    60
ctggcccag                                                           69

SEQ ID NO: 405           moltype = RNA    length = 68
FEATURE                  Location/Qualifiers
source                   1..68
                         mol_type = transcribed RNA
                         organism = Homo sapiens
SEQUENCE: 405
cagtgcaggg agaaggtgga agtgcagagt gggctcacct ctcgcccaca ctgtcccctt   60
ctccccag                                                            68

SEQ ID NO: 406           moltype = RNA    length = 86
FEATURE                  Location/Qualifiers
source                   1..86
                         mol_type = transcribed RNA
                         organism = Homo sapiens
SEQUENCE: 406
agagccgggg ccatggagca gcctgtgtag acggggacct gccctgcatg ggcacccct    60
cactggctgc ttcccttggt ctccag                                        86

SEQ ID NO: 407           moltype = RNA    length = 87
FEATURE                  Location/Qualifiers
source                   1..87
                         mol_type = transcribed RNA
                         organism = Homo sapiens
SEQUENCE: 407
gtgaggcggg gccaggaggg tgtgtggcgt gggtgctgcg gggccgtcag ggtgcctgcg   60
ggacgctcac ctggctggcc cgcccag                                       87

SEQ ID NO: 408           moltype = RNA    length = 87
FEATURE                  Location/Qualifiers
source                   1..87
                         mol_type = transcribed RNA
                         organism = Homo sapiens
SEQUENCE: 408
gtgaggcggg gccaggaggg tgtgtggcgt gggtgctgcg gggccgtcag ggtgcctgcg   60
ggacgctcac ctggctggcc cgcccag                                       87

SEQ ID NO: 409           moltype = RNA    length = 72
```

```
FEATURE                 Location/Qualifiers
source                  1..72
                        mol_type = transcribed RNA
                        organism = Homo sapiens
SEQUENCE: 409
atgagcgggt gggagcagat cttattgaga gttccttctc ctgctcctga ttgtcttccc   60
ccaccctcac ag                                                       72

SEQ ID NO: 410          moltype = RNA  length = 72
FEATURE                 Location/Qualifiers
source                  1..72
                        mol_type = transcribed RNA
                        organism = Homo sapiens
SEQUENCE: 410
atgagcgggt gggagcagat cttattgaga gttccttctc ctgctcctga ttgtcttccc   60
ccaccctcac ag                                                       72

SEQ ID NO: 411          moltype = RNA  length = 60
FEATURE                 Location/Qualifiers
source                  1..60
                        mol_type = transcribed RNA
                        organism = Homo sapiens
SEQUENCE: 411
ggtgcctcgg gagggcatgg gccaggccac ataatgagcc aaaccctgt ctacccgcag    60

SEQ ID NO: 412          moltype = RNA  length = 70
FEATURE                 Location/Qualifiers
source                  1..70
                        mol_type = transcribed RNA
                        organism = Homo sapiens
SEQUENCE: 412
tgtgcacttg ggcaggaggg accctgtatg tctccccgca gcaccgtcat cgtgtccctc   60
ttgtccacag                                                          70

SEQ ID NO: 413          moltype = RNA  length = 66
FEATURE                 Location/Qualifiers
source                  1..66
                        mol_type = transcribed RNA
                        organism = Homo sapiens
SEQUENCE: 413
tcaagacggg gagtcaggca gtggtggaga tggagagccc tgagcctcca ctctcctggc   60
ccccag                                                              66

SEQ ID NO: 414          moltype = RNA  length = 73
FEATURE                 Location/Qualifiers
source                  1..73
                        mol_type = transcribed RNA
                        organism = Homo sapiens
SEQUENCE: 414
gttcaagtgg gaggacagga ggcaggtgtg gttggaggaa gcagcctgaa cctgcctccc   60
tgacattcca cag                                                      73

SEQ ID NO: 415          moltype = RNA  length = 79
FEATURE                 Location/Qualifiers
source                  1..79
                        mol_type = transcribed RNA
                        organism = Homo sapiens
SEQUENCE: 415
cagcctgggg aaggcttggc agggaagaca catgagcagt gcctccactt cacgcctctc   60
ccttgtctcc tttccctag                                                79

SEQ ID NO: 416          moltype = RNA  length = 64
FEATURE                 Location/Qualifiers
source                  1..64
                        mol_type = transcribed RNA
                        organism = Homo sapiens
SEQUENCE: 416
aaccccgggc cggaggtcaa gggcgtcgct tctccctaat gttgcctctt ttccacggcc   60
tcag                                                                64

SEQ ID NO: 417          moltype = RNA  length = 69
FEATURE                 Location/Qualifiers
source                  1..69
                        mol_type = transcribed RNA
                        organism = Homo sapiens
SEQUENCE: 417
tggggtaggg gtgggggaat tcagggtgt cgaactcatg gctgccacct ttgtgtcccc    60
atcctgcag                                                           69
```

```
SEQ ID NO: 418            moltype = RNA   length = 67
FEATURE                   Location/Qualifiers
source                    1..67
                          mol_type = transcribed RNA
                          organism = Homo sapiens
SEQUENCE: 418
tacaggccgg ggctttgggt gagggacccc cggagtctgt cacggtctca ccccaactct    60
gccccag                                                              67

SEQ ID NO: 419            moltype = RNA   length = 81
FEATURE                   Location/Qualifiers
source                    1..81
                          mol_type = transcribed RNA
                          organism = Homo sapiens
SEQUENCE: 419
ctccctggga gggcgtggat gatggtggga gaggagcccc actgtggaag tctgaccccc    60
acatcgcccc accttcccca g                                              81

SEQ ID NO: 420            moltype = RNA   length = 61
FEATURE                   Location/Qualifiers
source                    1..61
                          mol_type = transcribed RNA
                          organism = Homo sapiens
SEQUENCE: 420
tcggctggcg ggggtagagc tggctgcagg cccggcccct ctcagctgct gccctctcca    60
g                                                                    61

SEQ ID NO: 421            moltype = RNA   length = 98
FEATURE                   Location/Qualifiers
source                    1..98
                          mol_type = transcribed RNA
                          organism = Homo sapiens
SEQUENCE: 421
cgaggtaggg gcgtcccggg cgcgcgggcg ggtcccaggc tgggcccctc ggaggccggg    60
tgctcactgc cccgtcccgg cgcccgtgtc tcctccag                            98

SEQ ID NO: 422            moltype = RNA   length = 67
FEATURE                   Location/Qualifiers
source                    1..67
                          mol_type = transcribed RNA
                          organism = Homo sapiens
SEQUENCE: 422
ccagacccct ggggctgggc aggcggaaag aggtctgaac tgcctctgcc tccttggtct    60
ccggcag                                                              67

SEQ ID NO: 423            moltype = RNA   length = 68
FEATURE                   Location/Qualifiers
source                    1..68
                          mol_type = transcribed RNA
                          organism = Homo sapiens
SEQUENCE: 423
gggcgcaggg ggactgggggg tgagcaggcc cagaacccag ctcgtgctca ctctcagtcc    60
ctccctag                                                             68

SEQ ID NO: 424            moltype = RNA   length = 82
FEATURE                   Location/Qualifiers
source                    1..82
                          mol_type = transcribed RNA
                          organism = Homo sapiens
SEQUENCE: 424
acctgtaggt gacagtcagg ggcggggtgt ggtggggctg gggctggccc cctcctcaca    60
cctctcctgg catcgccccc ag                                             82

SEQ ID NO: 425            moltype = RNA   length = 65
FEATURE                   Location/Qualifiers
source                    1..65
                          mol_type = transcribed RNA
                          organism = Homo sapiens
SEQUENCE: 425
gagggctagg tggggggctt gaagcccccga gatgcctcac gtcttcaccc ctctcaccta    60
agcag                                                                65

SEQ ID NO: 426            moltype = RNA   length = 65
FEATURE                   Location/Qualifiers
source                    1..65
                          mol_type = transcribed RNA
                          organism = Homo sapiens
SEQUENCE: 426
ctcctctggg ggtgggggc tgggcgtggt ggacagcgat gcatccctcg ccttctcacc     60
```

```
ctcag                                                                    65

SEQ ID NO: 427          moltype = RNA   length = 64
FEATURE                 Location/Qualifiers
source                  1..64
                        mol_type = transcribed RNA
                        organism = Homo sapiens
SEQUENCE: 427
tgaggatggg gtgagatggg gaggagcagc cagtcctgtc tcaccgctct tcccctgacc         60
ccag                                                                     64

SEQ ID NO: 428          moltype = RNA   length = 66
FEATURE                 Location/Qualifiers
source                  1..66
                        mol_type = transcribed RNA
                        organism = Homo sapiens
SEQUENCE: 428
ccgagtgggg cggggcaggt ccctgcaggg actgtgacac tgaaggacct gcaccttcgc         60
ccacag                                                                   66

SEQ ID NO: 429          moltype = RNA   length = 61
FEATURE                 Location/Qualifiers
source                  1..61
                        mol_type = transcribed RNA
                        organism = Homo sapiens
SEQUENCE: 429
gagggttggg gtggagggcc aaggagctgg gtggggtgcc aagcctctgt ccccacccca        60
g                                                                        61

SEQ ID NO: 430          moltype = RNA   length = 74
FEATURE                 Location/Qualifiers
source                  1..74
                        mol_type = transcribed RNA
                        organism = Homo sapiens
SEQUENCE: 430
gtgcgtggtg gctcgaggcg ggggtggggg cctcgccctg cttgggccct ccctgacctc        60
tccgctccgc acag                                                          74

SEQ ID NO: 431          moltype = RNA   length = 98
FEATURE                 Location/Qualifiers
source                  1..98
                        mol_type = transcribed RNA
                        organism = Homo sapiens
SEQUENCE: 431
cttggtcaat aggaaagagg tgggacctcc tggcttttcc tctgcagcat ggctcggacc        60
tagtgcaatg tttaagctcc cctctctttc ctgttcag                                98

SEQ ID NO: 432          moltype = RNA   length = 81
FEATURE                 Location/Qualifiers
source                  1..81
                        mol_type = transcribed RNA
                        organism = Homo sapiens
SEQUENCE: 432
gtaggtagag tgtgaggagg aggtctgagc ccatgtgtgg acctaggtct gctgttaaac        60
tgactaactc ccactctaca g                                                  81

SEQ ID NO: 433          moltype = RNA   length = 63
FEATURE                 Location/Qualifiers
source                  1..63
                        mol_type = transcribed RNA
                        organism = Homo sapiens
SEQUENCE: 433
ggctccgcag ggccctggcg caggcatcca gacagcgggc gaatgcctcc cccggccccg        60
cag                                                                      63

SEQ ID NO: 434          moltype = RNA   length = 71
FEATURE                 Location/Qualifiers
source                  1..71
                        mol_type = transcribed RNA
                        organism = Homo sapiens
SEQUENCE: 434
tgaccacccc cgggcaaaga cctgcagatc ccctgttaga gacgggccca ggactttgtg        60
cggggtgccc a                                                             71

SEQ ID NO: 435          moltype = RNA   length = 65
FEATURE                 Location/Qualifiers
source                  1..65
                        mol_type = transcribed RNA
                        organism = Homo sapiens
```

```
SEQUENCE: 435
agccctgggg gtggtctcta gccaaggctc tggggtctca cccttggctg gtctctgctc    60
cgcag                                                                65

SEQ ID NO: 436          moltype = RNA   length = 61
FEATURE                 Location/Qualifiers
source                  1..61
                        mol_type = transcribed RNA
                        organism = Homo sapiens
SEQUENCE: 436
gtgcggaacg ctggccgggg cgggagggga agggacgccc ggccggaacg ccgcactcac    60
g                                                                    61

SEQ ID NO: 437          moltype = RNA   length = 64
FEATURE                 Location/Qualifiers
source                  1..64
                        mol_type = transcribed RNA
                        organism = Homo sapiens
SEQUENCE: 437
gaggcactgg gtaggtgggg ctccagggct cctgacacct ggacctctcc tccccaggcc    60
caca                                                                 64

SEQ ID NO: 438          moltype = RNA   length = 62
FEATURE                 Location/Qualifiers
source                  1..62
                        mol_type = transcribed RNA
                        organism = Homo sapiens
SEQUENCE: 438
gtgagtagtg gcgcgcggcg gctcggagta cctctgccgc cgcgcgcatc ggctcagcat    60
gc                                                                   62

SEQ ID NO: 439          moltype = RNA   length = 60
FEATURE                 Location/Qualifiers
source                  1..60
                        mol_type = transcribed RNA
                        organism = Homo sapiens
SEQUENCE: 439
caaggtgggg gagatggggg ttgaacttca tttctcatgc tcatccccat ctcctttcag    60

SEQ ID NO: 440          moltype = RNA   length = 64
FEATURE                 Location/Qualifiers
source                  1..64
                        mol_type = transcribed RNA
                        organism = Homo sapiens
SEQUENCE: 440
agttcagggc cgaagggtgg aagctgctgg tgctcatctc agcctctgcc cttggcctcc    60
ccag                                                                 64

SEQ ID NO: 441          moltype = RNA   length = 66
FEATURE                 Location/Qualifiers
source                  1..66
                        mol_type = transcribed RNA
                        organism = Homo sapiens
SEQUENCE: 441
cagagcaggg cagggaaggt gggagagggg cccagctgac cctcctgtca cccgctcctt    60
gcccag                                                               66

SEQ ID NO: 442          moltype = RNA   length = 62
FEATURE                 Location/Qualifiers
source                  1..62
                        mol_type = transcribed RNA
                        organism = Homo sapiens
SEQUENCE: 442
gagggtggtg gaggaagagg gcagctccca tgactgcctg accgccttct ctcctccccc    60
ag                                                                   62

SEQ ID NO: 443          moltype = RNA   length = 62
FEATURE                 Location/Qualifiers
source                  1..62
                        mol_type = transcribed RNA
                        organism = Homo sapiens
SEQUENCE: 443
gagggtggtg gaggaagagg gcagctccca tgactgcctg accgccttct ctcctccccc    60
ag                                                                   62

SEQ ID NO: 444          moltype = RNA   length = 66
FEATURE                 Location/Qualifiers
source                  1..66
                        mol_type = transcribed RNA
```

```
                    organism = Homo sapiens
SEQUENCE: 444
cctggagggg ggcactgcgc aagcaaagcc agggaccctg agaggctttg cttcctgctc    60
ccctag                                                               66

SEQ ID NO: 445          moltype = RNA    length = 65
FEATURE                 Location/Qualifiers
source                  1..65
                        mol_type = transcribed RNA
                        organism = Homo sapiens
SEQUENCE: 445
gagaatgggg ggacagatgg agaggacaca ggctggcact gaggtcccct ccactttcct    60
cctag                                                                65

SEQ ID NO: 446          moltype = RNA    length = 80
FEATURE                 Location/Qualifiers
source                  1..80
                        mol_type = transcribed RNA
                        organism = Homo sapiens
SEQUENCE: 446
tgccgtcggc ctggggagga ggaagggcaa gtccaaaggt atacagttgg tctgttcatt    60
ctctcttttt ggcctacaag                                                80

SEQ ID NO: 447          moltype = RNA    length = 87
FEATURE                 Location/Qualifiers
source                  1..87
                        mol_type = transcribed RNA
                        organism = Homo sapiens
SEQUENCE: 447
gtgtggccgg caggcgggtg ggcggggggcg gccggtggga accccgcccc gccccgcgcc    60
cgcactcacc cgcccgtctc cccacag                                        87

SEQ ID NO: 448          moltype = RNA    length = 65
FEATURE                 Location/Qualifiers
source                  1..65
                        mol_type = transcribed RNA
                        organism = Homo sapiens
SEQUENCE: 448
gtctcctggg gggaggagac cctgctctcc ctggcagcaa gcctctcctg cccttccaga    60
ttagc                                                                65

SEQ ID NO: 449          moltype = RNA    length = 76
FEATURE                 Location/Qualifiers
source                  1..76
                        mol_type = transcribed RNA
                        organism = Homo sapiens
SEQUENCE: 449
actgactttg agtctctcct cagggtgctg caggcaaagc tggggaccca gggagagacg    60
taagtgaggg gagatg                                                    76

SEQ ID NO: 450          moltype = RNA    length = 59
FEATURE                 Location/Qualifiers
source                  1..59
                        mol_type = transcribed RNA
                        organism = Homo sapiens
SEQUENCE: 450
ctccagggag acagtgtgtg aggcctcttg ccatggcctc cctgcccgcc tctctgcag     59

SEQ ID NO: 451          moltype = RNA    length = 94
FEATURE                 Location/Qualifiers
source                  1..94
                        mol_type = transcribed RNA
                        organism = Homo sapiens
SEQUENCE: 451
cacggtgtcc cctggtggaa cctggcaggg ggagaggtaa ggtctttcag cctctccaaa    60
gcccatggtc aggtactcag gtgggggagc cctg                                94

SEQ ID NO: 452          moltype = RNA    length = 98
FEATURE                 Location/Qualifiers
source                  1..98
                        mol_type = transcribed RNA
                        organism = Homo sapiens
SEQUENCE: 452
ttgggcaagg tgcggggcta gggctaacag cagtcttact gaaggtttcc tggaaaccac    60
gcacatgctg ttgccactaa cctcaacctt actcggtc                            98

SEQ ID NO: 453          moltype = RNA    length = 68
FEATURE                 Location/Qualifiers
source                  1..68
```

```
                        mol_type = transcribed RNA
                        organism = Homo sapiens
SEQUENCE: 453
gtgcaaagag caggaggaca ggggatttat ctcccaaggg aggtcccctg atcctagtca    60
cggcacca                                                             68

SEQ ID NO: 454          moltype = RNA   length = 49
FEATURE                 Location/Qualifiers
source                  1..49
                        mol_type = transcribed RNA
                        organism = Homo sapiens
SEQUENCE: 454
ttcccagcca acgcaccaaa aatgatatgg gtctgttgtc tggagaaac                49

SEQ ID NO: 455          moltype = RNA   length = 69
FEATURE                 Location/Qualifiers
source                  1..69
                        mol_type = transcribed RNA
                        organism = Homo sapiens
SEQUENCE: 455
tggagggctg cgggactgta gagggcatga gctcaggagc tcaggccagc tcatggtgca    60
aggcctctg                                                            69

SEQ ID NO: 456          moltype = RNA   length = 72
FEATURE                 Location/Qualifiers
source                  1..72
                        mol_type = transcribed RNA
                        organism = Homo sapiens
SEQUENCE: 456
gatttcagtg acctggcagc agggagcgtc gtcagtgttt gactgtttat ggtatgtcag    60
ggagctggtt cc                                                        72

SEQ ID NO: 457          moltype = RNA   length = 79
FEATURE                 Location/Qualifiers
source                  1..79
                        mol_type = transcribed RNA
                        organism = Homo sapiens
SEQUENCE: 457
gtgcagatcc ttgggagccc tgttagactc tggattttac acttggagtg aacgggcgcc    60
atcccgaggc tttgcacag                                                 79

SEQ ID NO: 458          moltype = RNA   length = 86
FEATURE                 Location/Qualifiers
source                  1..86
                        mol_type = transcribed RNA
                        organism = Homo sapiens
SEQUENCE: 458
agcactgccc ccggtgagtc agggtggggc tggcccctg cttcgtgccc atccgcgctc    60
tgactctctg cccacctgca ggagct                                         86

SEQ ID NO: 459          moltype = RNA   length = 83
FEATURE                 Location/Qualifiers
source                  1..83
                        mol_type = transcribed RNA
                        organism = Homo sapiens
SEQUENCE: 459
cctgctgcag aggtgccagc tgcagtgggg gaggcactgc cagggctgcc cactctgctt    60
agccagcagg tgccaagaac agg                                            83

SEQ ID NO: 460          moltype = RNA   length = 87
FEATURE                 Location/Qualifiers
source                  1..87
                        mol_type = transcribed RNA
                        organism = Homo sapiens
SEQUENCE: 460
gcagggctgg cagggaggct gggaggggct ggctgggtct ggtagtgggc atcagctggc    60
cctcatttct taagacagca cttctgt                                        87

SEQ ID NO: 461          moltype = RNA   length = 73
FEATURE                 Location/Qualifiers
source                  1..73
                        mol_type = transcribed RNA
                        organism = Homo sapiens
SEQUENCE: 461
tgtatccttg aatggatttt tggagcagga gtggacacct gacccaaagg aaatcaatcc    60
ataggctagc aat                                                       73

SEQ ID NO: 462          moltype = RNA   length = 90
FEATURE                 Location/Qualifiers
```

|  |  |  |
|---|---|---|
| source | 1..90<br>mol_type = transcribed RNA<br>organism = Homo sapiens | |
| SEQUENCE: 462 | | |
| aggcctcgct gttctctatg gcttttatt cctatgtgat tctactgctc actcatatag | | 60 |
| ggattggagc cgtggcgcac ggcggggaca | | 90 |
| SEQ ID NO: 463<br>FEATURE<br>source | moltype = RNA   length = 47<br>Location/Qualifiers<br>1..47<br>mol_type = transcribed RNA<br>organism = Homo sapiens | |
| SEQUENCE: 463 | | |
| ctcggcgcgg ggcgcgggct ccgggttggg gcgagccaac gccgggg | | 47 |
| SEQ ID NO: 464<br>FEATURE<br>source | moltype = RNA   length = 89<br>Location/Qualifiers<br>1..89<br>mol_type = transcribed RNA<br>organism = Homo sapiens | |
| SEQUENCE: 464 | | |
| gccggcgccc gagctctggc tccgtgtctt cactcccgtg cttgtccgag gagggaggga | | 60 |
| gggacgggg ctgtgctggg gcagctgga | | 89 |
| SEQ ID NO: 465<br>FEATURE<br>source | moltype = RNA   length = 84<br>Location/Qualifiers<br>1..84<br>mol_type = transcribed RNA<br>organism = Homo sapiens | |
| SEQUENCE: 465 | | |
| ctccccatgg ccctgtctcc caaccttgt accagtgctg ggctcagacc ctggtacagg | | 60 |
| cctgggggac agggacctgg ggac | | 84 |
| SEQ ID NO: 466<br>FEATURE<br>source | moltype = RNA   length = 80<br>Location/Qualifiers<br>1..80<br>mol_type = transcribed RNA<br>organism = Homo sapiens | |
| SEQUENCE: 466 | | |
| cgtgtgagcc cgccctgtgc ccggcccact tctgcttcct cttagcgcag gagggggtccc | | 60 |
| gcactgggag gggccctcac | | 80 |
| SEQ ID NO: 467<br>FEATURE<br>source | moltype = RNA   length = 92<br>Location/Qualifiers<br>1..92<br>mol_type = transcribed RNA<br>organism = Homo sapiens | |
| SEQUENCE: 467 | | |
| cggctggaca gcgggcaacg gaatcccaaa agcagctgtt gtctccagag cattccagct | | 60 |
| gcgcttggat ttcgtcccct gctctcctgc ct | | 92 |
| SEQ ID NO: 468<br>FEATURE<br>source | moltype = RNA   length = 94<br>Location/Qualifiers<br>1..94<br>mol_type = transcribed RNA<br>organism = Homo sapiens | |
| SEQUENCE: 468 | | |
| ataaaggaag ttaggctgag gggcagagag cgagactttt ctattttcca aaagctcggt | | 60 |
| ctgaggcccc tcagtcttgc ttcctaaccc gcgc | | 94 |
| SEQ ID NO: 469<br>FEATURE<br>source | moltype = RNA   length = 93<br>Location/Qualifiers<br>1..93<br>mol_type = transcribed RNA<br>organism = Homo sapiens | |
| SEQUENCE: 469 | | |
| ccttccggcg tcccaggcgg ggcgccgcgg gaccgccctc gtgtctgtgg cggtgggatc | | 60 |
| ccgcggccgt gttttcctgg tggcccggcc atg | | 93 |
| SEQ ID NO: 470<br>FEATURE<br>source | moltype = RNA   length = 75<br>Location/Qualifiers<br>1..75<br>mol_type = transcribed RNA<br>organism = Homo sapiens | |
| SEQUENCE: 470 | | |
| tcatccctgg gtggggattt gttgcattac ttgtgttcta tataaagtat tgcacttgtc | | 60 |
| ccggcctgtg gaaga | | 75 |
| SEQ ID NO: 471 | moltype = RNA   length = 94 | |

| FEATURE | Location/Qualifiers |
|---|---|
| source | 1..94 |
| | mol_type = transcribed RNA |
| | organism = Homo sapiens |

SEQUENCE: 471
```
gtgaggtgtg ggcccggccc caggagcggg gcctgggcag ccccgtgtgt tgaggaagga   60
aggcagggcc cccgctcccc gggcctgacc ccac                                94
```

| SEQ ID NO: 472 | moltype = RNA length = 68 |
|---|---|
| FEATURE | Location/Qualifiers |
| source | 1..68 |
| | mol_type = transcribed RNA |
| | organism = Homo sapiens |

SEQUENCE: 472
```
ctccggtgcc tactgagctg atatcagttc tcattttaca cactggctca gttcagcagg   60
aacaggag                                                             68
```

| SEQ ID NO: 473 | moltype = RNA length = 81 |
|---|---|
| FEATURE | Location/Qualifiers |
| source | 1..81 |
| | mol_type = transcribed RNA |
| | organism = Homo sapiens |

SEQUENCE: 473
```
cttcaggaag ctggtttcat atggtggttt agatttaaat agtgattgtc tagcaccatt   60
tgaaatcagt gttcttgggg g                                              81
```

| SEQ ID NO: 474 | moltype = RNA length = 81 |
|---|---|
| FEATURE | Location/Qualifiers |
| source | 1..81 |
| | mol_type = transcribed RNA |
| | organism = Homo sapiens |

SEQUENCE: 474
```
attcaggccg gtcctgcaga gaggaagccc ttctgcttac aggtattgga agggcttcct   60
ctctgcagga ccggcctgaa t                                              81
```

| SEQ ID NO: 475 | moltype = RNA length = 85 |
|---|---|
| FEATURE | Location/Qualifiers |
| source | 1..85 |
| | mol_type = transcribed RNA |
| | organism = Homo sapiens |

SEQUENCE: 475
```
ggacctgccc tgggctttct agtctcagct ctcctccagc tcagctggtc aggagagctg   60
agactagaaa gcccagggca ggttc                                          85
```

| SEQ ID NO: 476 | moltype = RNA length = 79 |
|---|---|
| FEATURE | Location/Qualifiers |
| source | 1..79 |
| | mol_type = transcribed RNA |
| | organism = Homo sapiens |

SEQUENCE: 476
```
aattaatccc tctctttcta gttcttccta gagtgaggaa aagctgggtt gagagggcaa   60
acaaattaac taattaatt                                                 79
```

| SEQ ID NO: 477 | moltype = RNA length = 180 |
|---|---|
| FEATURE | Location/Qualifiers |
| source | 1..180 |
| | mol_type = transcribed RNA |
| | organism = Homo sapiens |

SEQUENCE: 477
```
cgcgactgcg gcggcggtgg tgggggagc cgcggggatc gccgagggcc ggtcggccgc    60
cccgggtgcc gcgcggtgcc gcggcggcg gtgaggcccc gcgcgtgtgt cccggctgcg   120
gtcggccgcg ctcgaggggt ccccgtggcg tccccttccc cgccggccgc ctttctcgcg  180
```

| SEQ ID NO: 478 | moltype = RNA length = 91 |
|---|---|
| FEATURE | Location/Qualifiers |
| source | 1..91 |
| | mol_type = transcribed RNA |
| | organism = Homo sapiens |

SEQUENCE: 478
```
gtgtcctcac ttgtccactt ctgcctgccc tgcccaaatg gtggagcaga ttcgaggggc   60
agggcaggaa gaagtggaca agtgaggcca t                                   91
```

| SEQ ID NO: 479 | moltype = RNA length = 74 |
|---|---|
| FEATURE | Location/Qualifiers |
| source | 1..74 |
| | mol_type = transcribed RNA |
| | organism = Homo sapiens |

SEQUENCE: 479
```
gctctagcct aattttagat ctggtctgct tcagtttcac tccaagcaga cttgacctac   60
```

```
                                                -continued aattagccta gagc                                              74

SEQ ID NO: 480           moltype = RNA    length = 97
FEATURE                  Location/Qualifiers
source                   1..97
                         mol_type = transcribed RNA
                         organism = Homo sapiens
SEQUENCE: 480
tgatgctttg ctggctggtg cagtgcctga gggagtaaga gccctgttgt tgtaagatag   60
tgtcttactc cctcaggcac atctccaaca agtctct                            97

SEQ ID NO: 481           moltype = RNA    length = 86
FEATURE                  Location/Qualifiers
source                   1..86
                         mol_type = transcribed RNA
                         organism = Homo sapiens
SEQUENCE: 481
cgcctgagcg tgcagcagga catcttcctg acctggtaat aattaggtga gaaggatggt   60
tggggcggt cggcgtaact caggga                                         86

SEQ ID NO: 482           moltype = RNA    length = 97
FEATURE                  Location/Qualifiers
source                   1..97
                         mol_type = transcribed RNA
                         organism = Homo sapiens
SEQUENCE: 482
ggtgggagga ttgcttgagc ctggaagctg gagcctgcag tgaactatca ttgtgccact   60
gtactccagc ctaggcaaca aaatgaaatc ctgtcta                            97

SEQ ID NO: 483           moltype = RNA    length = 78
FEATURE                  Location/Qualifiers
source                   1..78
                         mol_type = transcribed RNA
                         organism = Homo sapiens
SEQUENCE: 483
cttttctacac aggttgggat cggttgcaat gctgtgtttc tgtatggtat tgcacttgtc  60
ccggcctgtt gagtttgg                                                 78

SEQ ID NO: 484           moltype = RNA    length = 73
FEATURE                  Location/Qualifiers
source                   1..73
                         mol_type = transcribed RNA
                         organism = Homo sapiens
SEQUENCE: 484
ctctgcctcc cgtgcctact gagctgaaac acagttggtt tgtgtacact ggctcagttc   60
agcaggaaca ggg                                                      73

SEQ ID NO: 485           moltype = RNA    length = 81
FEATURE                  Location/Qualifiers
source                   1..81
                         mol_type = transcribed RNA
                         organism = Homo sapiens
SEQUENCE: 485
cttctggaag ctggtttcac atggtggctt agattttcc atctttgtat ctagcaccat    60
ttgaaatcag tgttttagga g                                             81

SEQ ID NO: 486           moltype = RNA    length = 81
FEATURE                  Location/Qualifiers
source                   1..81
                         mol_type = transcribed RNA
                         organism = Homo sapiens
SEQUENCE: 486
attcaggccg gtcctgcaga gaggaagccc ttccaatacc tgtaagcaga agggcttcct   60
ctctgcagga ccggcctgaa t                                             81

SEQ ID NO: 487           moltype = RNA    length = 81
FEATURE                  Location/Qualifiers
source                   1..81
                         mol_type = transcribed RNA
                         organism = Homo sapiens
SEQUENCE: 487
acctgccctg ggctttctag tctcagctct cctgaccagc tgagctggag gagagctgag   60
actagaaagc ccagggcagg t                                             81

SEQ ID NO: 488           moltype = RNA    length = 138
FEATURE                  Location/Qualifiers
source                   1..138
                         mol_type = transcribed RNA
                         organism = Homo sapiens
```

```
SEQUENCE: 488
tgttattttt tgtcttctac ctaagaattc tgtctcttag gctttctctt cccagatttc    60
ccaaagttgg gaaaagctgg gttgagaggg caaaaggaaa aaaaaagaat tctgtctctg   120
acataattag atagggaa                                                 138

SEQ ID NO: 489          moltype = RNA    length = 180
FEATURE                 Location/Qualifiers
source                  1..180
                        mol_type = transcribed RNA
                        organism = Homo sapiens
SEQUENCE: 489
cgcgactgcg gcggcggtgg tgggggagc cgcggggatc gccgagggcc ggtcggccgc    60
cccgggtgcc gcgcggtgcc gccggcggcg gtgaggcccc gcgcgtgtgt cccggctgcg  120
gtcggccgc ctcgaggggt ccccgtggcg tccccttccc cgccggccgc ctttctcgcg   180

SEQ ID NO: 490          moltype = RNA    length = 91
FEATURE                 Location/Qualifiers
source                  1..91
                        mol_type = transcribed RNA
                        organism = Homo sapiens
SEQUENCE: 490
gtgtcctcac ttgtccactt ctgcctgccc tgcccaaatg gtggagcaga ttcgaggggc    60
agggcaggaa gaagtggaca agtgaggcca t                                   91

SEQ ID NO: 491          moltype = RNA    length = 74
FEATURE                 Location/Qualifiers
source                  1..74
                        mol_type = transcribed RNA
                        organism = Homo sapiens
SEQUENCE: 491
gctctagcct aattttagat ctggtctgct tcagtttcac tccaagcaga cttgacctac    60
aattagccta gagc                                                      74

SEQ ID NO: 492          moltype = RNA    length = 97
FEATURE                 Location/Qualifiers
source                  1..97
                        mol_type = transcribed RNA
                        organism = Homo sapiens
SEQUENCE: 492
tgatgctttg ctggctggtg cagtgcctga gggagtaaga gccctgttgt tgtcagatag    60
tgtcttactc cctcaggcac atctccagcg agtctct                             97

SEQ ID NO: 493          moltype = RNA    length = 86
FEATURE                 Location/Qualifiers
source                  1..86
                        mol_type = transcribed RNA
                        organism = Homo sapiens
SEQUENCE: 493
cgcctgagcg tgcagcagga catcttcctg acctggtaat aattaggtga gaaggatggt    60
tgggggcggt cggcgtaact caggga                                         86

SEQ ID NO: 494          moltype = RNA    length = 63
FEATURE                 Location/Qualifiers
source                  1..63
                        mol_type = transcribed RNA
                        organism = Homo sapiens
SEQUENCE: 494
ctgagcctgg aagctggagc ctgcagtgag ctatgatcat gtccctgtac tctagcctgg    60
gca                                                                  63

SEQ ID NO: 495          moltype = RNA    length = 75
FEATURE                 Location/Qualifiers
source                  1..75
                        mol_type = transcribed RNA
                        organism = Homo sapiens
SEQUENCE: 495
tcatccctgg gtggggattt gttgcattac ttgtgttcta tataaagtat tgcacttgtc    60
ccggcctgtg gaaga                                                     75

SEQ ID NO: 496          moltype = RNA    length = 94
FEATURE                 Location/Qualifiers
source                  1..94
                        mol_type = transcribed RNA
                        organism = Homo sapiens
SEQUENCE: 496
cagtgcgacg ggcggagctt ccagacgctc cgcccacgt cgcatgcgcc ccgggaaagc     60
gtggggcgga gcttccggag gccccgccct gctg                                94

SEQ ID NO: 497          moltype = RNA    length = 88
```

```
FEATURE                     Location/Qualifiers
source                      1..88
                            mol_type = transcribed RNA
                            organism = Homo sapiens
SEQUENCE: 497
gcgacgggcg gagcttccag acgctccgcc ccacgtcgca tgcgcccegg gaaagcgtgg    60
ggcggagctt ccggaggccc cgccctgc                                      88

SEQ ID NO: 498              moltype = RNA   length = 94
FEATURE                     Location/Qualifiers
source                      1..94
                            mol_type = transcribed RNA
                            organism = Homo sapiens
SEQUENCE: 498
cagtgcgacg ggcggagctt ccagacgctc cgcccacgt cgcatgcgcc ccgggaaagc     60
gtggggcgga gcttccggag gccccgccct gctg                               94

SEQ ID NO: 499              moltype = RNA   length = 67
FEATURE                     Location/Qualifiers
source                      1..67
                            mol_type = transcribed RNA
                            organism = Homo sapiens
SEQUENCE: 499
cctgcaggca gaagtggggc tgacagggca gagggttgcg ccccctcacc atcccttctg    60
cctgcag                                                             67

SEQ ID NO: 500              moltype = RNA   length = 92
FEATURE                     Location/Qualifiers
source                      1..92
                            mol_type = transcribed RNA
                            organism = Homo sapiens
SEQUENCE: 500
cgctgcgctt ctgggcccgc ggcgggcgtg gggctgcccg ggccggtcga ccagcgcgcc    60
gtagctcccg aggcccgagc cgcgacccgc gg                                 92

SEQ ID NO: 501              moltype = RNA   length = 67
FEATURE                     Location/Qualifiers
source                      1..67
                            mol_type = transcribed RNA
                            organism = Homo sapiens
SEQUENCE: 501
cctgcaggca gaagtggggc tgacagggca gagggttgcg ccccctcacc atcccttctg    60
cctgcag                                                             67

SEQ ID NO: 502              moltype = RNA   length = 92
FEATURE                     Location/Qualifiers
source                      1..92
                            mol_type = transcribed RNA
                            organism = Homo sapiens
SEQUENCE: 502
cgctgcgctt ctgggcccgc ggcgggcgtg gggctgcccg ggccggtcga ccagcgcgcc    60
gtagctcccg aggcccgagc cgcgacccgc gg                                 92

SEQ ID NO: 503              moltype = RNA   length = 67
FEATURE                     Location/Qualifiers
source                      1..67
                            mol_type = transcribed RNA
                            organism = Homo sapiens
SEQUENCE: 503
cctgcaggca gaagtggggc tgacagggca gagggttgcg ccccctcacc atcccttctg    60
cctgcag                                                             67

SEQ ID NO: 504              moltype = RNA   length = 92
FEATURE                     Location/Qualifiers
source                      1..92
                            mol_type = transcribed RNA
                            organism = Homo sapiens
SEQUENCE: 504
cgctgcgctt ctgggcccgc ggcgggcgtg gggctgcccg ggccggtcga ccagcgcgcc    60
gtagctcccg aggcccgagc cgcgacccgc gg                                 92

SEQ ID NO: 505              moltype = RNA   length = 67
FEATURE                     Location/Qualifiers
source                      1..67
                            mol_type = transcribed RNA
                            organism = Homo sapiens
SEQUENCE: 505
cctgcaggca gaagtggggc tgacagggca gagggttgcg ccccctcacc atcccttctg    60
cctgcag                                                             67
```

```
SEQ ID NO: 506          moltype = RNA    length = 92
FEATURE                 Location/Qualifiers
source                  1..92
                        mol_type = transcribed RNA
                        organism = Homo sapiens
SEQUENCE: 506
cgctgcgctt ctgggcccgc ggcgggcgtg gggctgcccg ggccggtcga ccagcgcgcc    60
gtagctcccg aggcccgagc cgcgacccgc gg                                  92

SEQ ID NO: 507          moltype = RNA    length = 26
FEATURE                 Location/Qualifiers
source                  1..26
                        mol_type = transcribed RNA
                        organism = Homo sapiens
SEQUENCE: 507
gaggggctct cgcttctggc gccaag                                         26

SEQ ID NO: 508          moltype = RNA    length = 23
FEATURE                 Location/Qualifiers
source                  1..23
                        mol_type = transcribed RNA
                        organism = Homo sapiens
SEQUENCE: 508
aatatacagg gggagactct tat                                            23

SEQ ID NO: 509          moltype = RNA    length = 24
FEATURE                 Location/Qualifiers
source                  1..24
                        mol_type = transcribed RNA
                        organism = Homo sapiens
SEQUENCE: 509
atatacaggg ggagactctc attt                                           24

SEQ ID NO: 510          moltype = RNA    length = 22
FEATURE                 Location/Qualifiers
source                  1..22
                        mol_type = transcribed RNA
                        organism = Homo sapiens
SEQUENCE: 510
cctcacacct gcctcgcccc cc                                             22

SEQ ID NO: 511          moltype = RNA    length = 22
FEATURE                 Location/Qualifiers
source                  1..22
                        mol_type = transcribed RNA
                        organism = Homo sapiens
SEQUENCE: 511
gtgggcgggg gcaggtgtgt gg                                             22

SEQ ID NO: 512          moltype = RNA    length = 15
FEATURE                 Location/Qualifiers
source                  1..15
                        mol_type = transcribed RNA
                        organism = Homo sapiens
SEQUENCE: 512
tggcagagcg ctgtc                                                     15

SEQ ID NO: 513          moltype = RNA    length = 22
FEATURE                 Location/Qualifiers
source                  1..22
                        mol_type = transcribed RNA
                        organism = Homo sapiens
SEQUENCE: 513
ccgggaacgt cgagactgga gc                                             22

SEQ ID NO: 514          moltype = RNA    length = 21
FEATURE                 Location/Qualifiers
source                  1..21
                        mol_type = transcribed RNA
                        organism = Homo sapiens
SEQUENCE: 514
gccgggcgtg gtggtggggg c                                              21

SEQ ID NO: 515          moltype = RNA    length = 24
FEATURE                 Location/Qualifiers
source                  1..24
                        mol_type = transcribed RNA
                        organism = Homo sapiens
```

```
SEQUENCE: 515
cgggcgtggt ggtggggtg ggtg                                                      24

SEQ ID NO: 516          moltype = RNA   length = 19
FEATURE                 Location/Qualifiers
source                  1..19
                        mol_type = transcribed RNA
                        organism = Homo sapiens
SEQUENCE: 516
ctccagcctg agtgacaga                                                           19

SEQ ID NO: 517          moltype = RNA   length = 23
FEATURE                 Location/Qualifiers
source                  1..23
                        mol_type = transcribed RNA
                        organism = Homo sapiens
SEQUENCE: 517
gggggccgat acactgtacg aga                                                      23

SEQ ID NO: 518          moltype = RNA   length = 23
FEATURE                 Location/Qualifiers
source                  1..23
                        mol_type = transcribed RNA
                        organism = Homo sapiens
SEQUENCE: 518
ctcctggggc ccgcactctc gct                                                      23

SEQ ID NO: 519          moltype = RNA   length = 25
FEATURE                 Location/Qualifiers
source                  1..25
                        mol_type = transcribed RNA
                        organism = Homo sapiens
SEQUENCE: 519
actgcagtga aggcacttgt agcat                                                    25

SEQ ID NO: 520          moltype = RNA   length = 22
FEATURE                 Location/Qualifiers
source                  1..22
                        mol_type = transcribed RNA
                        organism = Homo sapiens
SEQUENCE: 520
gggctacaac acaggacccg gg                                                       22

SEQ ID NO: 521          moltype = RNA   length = 20
FEATURE                 Location/Qualifiers
source                  1..20
                        mol_type = transcribed RNA
                        organism = Homo sapiens
SEQUENCE: 521
accggccgcc ggctccgccc                                                          20

SEQ ID NO: 522          moltype = RNA   length = 23
FEATURE                 Location/Qualifiers
source                  1..23
                        mol_type = transcribed RNA
                        organism = Homo sapiens
SEQUENCE: 522
tgcgcagggg ccgggtgctc acc                                                      23

SEQ ID NO: 523          moltype = RNA   length = 20
FEATURE                 Location/Qualifiers
source                  1..20
                        mol_type = transcribed RNA
                        organism = Homo sapiens
SEQUENCE: 523
ccccagggcg acgcggcggg                                                          20

SEQ ID NO: 524          moltype = RNA   length = 23
FEATURE                 Location/Qualifiers
source                  1..23
                        mol_type = transcribed RNA
                        organism = Homo sapiens
SEQUENCE: 524
agcccctgcc caccgcacac tgc                                                      23

SEQ ID NO: 525          moltype = RNA   length = 48
FEATURE                 Location/Qualifiers
source                  1..48
                        mol_type = transcribed RNA
```

```
                             -continued organism = Homo sapiens
SEQUENCE: 525
tggctcagtt cagcaggaac aggactggct cagttcagca ggaacagg              48

SEQ ID NO: 526          moltype = RNA   length = 23
FEATURE                 Location/Qualifiers
source                  1..23
                        mol_type = transcribed RNA
                        organism = Homo sapiens
SEQUENCE: 526
agcagaggca gagaggctca ggg                                         23

SEQ ID NO: 527          moltype = RNA   length = 16
FEATURE                 Location/Qualifiers
source                  1..16
                        mol_type = transcribed RNA
                        organism = Homo sapiens
SEQUENCE: 527
ggcggtgggc ggcggg                                                 16

SEQ ID NO: 528          moltype = RNA   length = 22
FEATURE                 Location/Qualifiers
source                  1..22
                        mol_type = transcribed RNA
                        organism = Homo sapiens
SEQUENCE: 528
gagggttggg tggaggctct cc                                          22

SEQ ID NO: 529          moltype = RNA   length = 26
FEATURE                 Location/Qualifiers
source                  1..26
                        mol_type = transcribed RNA
                        organism = Homo sapiens
SEQUENCE: 529
tagcaccatt tgaaatcagt gttctt                                      26

SEQ ID NO: 530          moltype = RNA   length = 24
FEATURE                 Location/Qualifiers
source                  1..24
                        mol_type = transcribed RNA
                        organism = Homo sapiens
SEQUENCE: 530
tcgaggactg gtggaagggc cttt                                        24

SEQ ID NO: 531          moltype = RNA   length = 22
FEATURE                 Location/Qualifiers
source                  1..22
                        mol_type = transcribed RNA
                        organism = Homo sapiens
SEQUENCE: 531
cagaagggga gttgggagca ga                                          22

SEQ ID NO: 532          moltype = RNA   length = 22
FEATURE                 Location/Qualifiers
source                  1..22
                        mol_type = transcribed RNA
                        organism = Homo sapiens
SEQUENCE: 532
tcctgcagag aggaagccct tc                                          22

SEQ ID NO: 533          moltype = RNA   length = 23
FEATURE                 Location/Qualifiers
source                  1..23
                        mol_type = transcribed RNA
                        organism = Homo sapiens
SEQUENCE: 533
agggagtaga agggtgggga gca                                         23

SEQ ID NO: 534          moltype = RNA   length = 24
FEATURE                 Location/Qualifiers
source                  1..24
                        mol_type = transcribed RNA
                        organism = Homo sapiens
SEQUENCE: 534
gatcggtcga gagcgtcctg gctg                                        24

SEQ ID NO: 535          moltype = RNA   length = 23
FEATURE                 Location/Qualifiers
source                  1..23
```

```
                              mol_type = transcribed RNA
                              organism = Homo sapiens
SEQUENCE: 535
tgggcggag cttccggagg ccc                                          23

SEQ ID NO: 536                moltype = RNA   length = 17
FEATURE                       Location/Qualifiers
source                        1..17
                              mol_type = transcribed RNA
                              organism = Homo sapiens
SEQUENCE: 536
ggggcggggg cgggggc                                                17

SEQ ID NO: 537                moltype = RNA   length = 23
FEATURE                       Location/Qualifiers
source                        1..23
                              mol_type = transcribed RNA
                              organism = Homo sapiens
SEQUENCE: 537
ggaggcgcag gctcggaaag gcg                                         23

SEQ ID NO: 538                moltype = RNA   length = 27
FEATURE                       Location/Qualifiers
source                        1..27
                              mol_type = transcribed RNA
                              organism = Homo sapiens
SEQUENCE: 538
gaaaagctgg gttgagaggg cgaaaaa                                     27

SEQ ID NO: 539                moltype = RNA   length = 24
FEATURE                       Location/Qualifiers
source                        1..24
                              mol_type = transcribed RNA
                              organism = Homo sapiens
SEQUENCE: 539
gaaaagctgg gttgagaggg caaa                                        24

SEQ ID NO: 540                moltype = RNA   length = 16
FEATURE                       Location/Qualifiers
source                        1..16
                              mol_type = transcribed RNA
                              organism = Homo sapiens
SEQUENCE: 540
gtgggggggc aggagg                                                 16

SEQ ID NO: 541                moltype = RNA   length = 28
FEATURE                       Location/Qualifiers
source                        1..28
                              mol_type = transcribed RNA
                              organism = Homo sapiens
SEQUENCE: 541
aggggtgcta tctgtgattg agggacat                                    28

SEQ ID NO: 542                moltype = RNA   length = 58
FEATURE                       Location/Qualifiers
source                        1..58
                              mol_type = transcribed RNA
                              organism = Homo sapiens
SEQUENCE: 542
gctgactcct agtccagggc tcgtgatggc tggtgggccc tgaacgaggg gtctggag   58

SEQ ID NO: 543                moltype = RNA   length = 22
FEATURE                       Location/Qualifiers
source                        1..22
                              mol_type = transcribed RNA
                              organism = Homo sapiens
SEQUENCE: 543
cgagggcatt tcatgatgca gg                                          22

SEQ ID NO: 544                moltype = RNA   length = 23
FEATURE                       Location/Qualifiers
source                        1..23
                              mol_type = transcribed RNA
                              organism = Homo sapiens
SEQUENCE: 544
gtgggctggg ctgggctggg cca                                         23

SEQ ID NO: 545                moltype = RNA   length = 29
FEATURE                       Location/Qualifiers
```

```
source                  1..29
                        mol_type = transcribed RNA
                        organism = Homo sapiens
SEQUENCE: 545
gggagccgcg gggatcgccg agggccggt                                          29

SEQ ID NO: 546          moltype = RNA  length = 22
FEATURE                 Location/Qualifiers
source                  1..22
                        mol_type = transcribed RNA
                        organism = Homo sapiens
SEQUENCE: 546
cggctggagg tgtgaggatc cg                                                 22

SEQ ID NO: 547          moltype = RNA  length = 19
FEATURE                 Location/Qualifiers
source                  1..19
                        mol_type = transcribed RNA
                        organism = Homo sapiens
SEQUENCE: 547
tggcgggtgc gggggtggg                                                     19

SEQ ID NO: 548          moltype = RNA  length = 23
FEATURE                 Location/Qualifiers
source                  1..23
                        mol_type = transcribed RNA
                        organism = Homo sapiens
SEQUENCE: 548
tgaggatatg gcagggaagg gga                                                23

SEQ ID NO: 549          moltype = RNA  length = 29
FEATURE                 Location/Qualifiers
source                  1..29
                        mol_type = transcribed RNA
                        organism = Homo sapiens
SEQUENCE: 549
ggtcaggcgg ctcggactga gcaggtggg                                          29

SEQ ID NO: 550          moltype = RNA  length = 19
FEATURE                 Location/Qualifiers
source                  1..19
                        mol_type = transcribed RNA
                        organism = Homo sapiens
SEQUENCE: 550
gtgggttggg gcgggctct                                                     19

SEQ ID NO: 551          moltype = RNA  length = 18
FEATURE                 Location/Qualifiers
source                  1..18
                        mol_type = transcribed RNA
                        organism = Homo sapiens
SEQUENCE: 551
ggcagcggcg gcggcggc                                                      18

SEQ ID NO: 552          moltype = RNA  length = 20
FEATURE                 Location/Qualifiers
source                  1..20
                        mol_type = transcribed RNA
                        organism = Homo sapiens
SEQUENCE: 552
caccccactc ctggtaccat                                                    20

SEQ ID NO: 553          moltype = RNA  length = 15
FEATURE                 Location/Qualifiers
source                  1..15
                        mol_type = transcribed RNA
                        organism = Homo sapiens
SEQUENCE: 553
aggaggagga ggcag                                                         15

SEQ ID NO: 554          moltype = RNA  length = 17
FEATURE                 Location/Qualifiers
source                  1..17
                        mol_type = transcribed RNA
                        organism = Homo sapiens
SEQUENCE: 554
gcgtggggcc cggagca                                                       17

SEQ ID NO: 555          moltype = RNA  length = 18
```

```
FEATURE              Location/Qualifiers
source               1..18
                     mol_type = transcribed RNA
                     organism = Homo sapiens
SEQUENCE: 555
ggtgggcttc ccggaggg                                                 18

SEQ ID NO: 556       moltype = RNA   length = 18
FEATURE              Location/Qualifiers
source               1..18
                     mol_type = transcribed RNA
                     organism = Homo sapiens
SEQUENCE: 556
gaggctgaag gaagatgg                                                 18

SEQ ID NO: 557       moltype = RNA   length = 22
FEATURE              Location/Qualifiers
source               1..22
                     mol_type = transcribed RNA
                     organism = Homo sapiens
SEQUENCE: 557
aaaagctggg ctgagaggcg ac                                            22

SEQ ID NO: 558       moltype = RNA   length = 19
FEATURE              Location/Qualifiers
source               1..19
                     mol_type = transcribed RNA
                     organism = Homo sapiens
SEQUENCE: 558
gaggctggag tgagcggag                                                19

SEQ ID NO: 559       moltype = RNA   length = 23
FEATURE              Location/Qualifiers
source               1..23
                     mol_type = transcribed RNA
                     organism = Homo sapiens
SEQUENCE: 559
acaggagtgg gggtgggaca taa                                           23

SEQ ID NO: 560       moltype = RNA   length = 21
FEATURE              Location/Qualifiers
source               1..21
                     mol_type = transcribed RNA
                     organism = Homo sapiens
SEQUENCE: 560
gttggaggcg tgggttttag a                                             21

SEQ ID NO: 561       moltype = RNA   length = 23
FEATURE              Location/Qualifiers
source               1..23
                     mol_type = transcribed RNA
                     organism = Homo sapiens
SEQUENCE: 561
ccagggctgg cagtgacatg ggt                                           23

SEQ ID NO: 562       moltype = RNA   length = 20
FEATURE              Location/Qualifiers
source               1..20
                     mol_type = transcribed RNA
                     organism = Homo sapiens
SEQUENCE: 562
ggctccttgg tctagggta                                                20

SEQ ID NO: 563       moltype = RNA   length = 24
FEATURE              Location/Qualifiers
source               1..24
                     mol_type = transcribed RNA
                     organism = Homo sapiens
SEQUENCE: 563
gtgcccgtcc cggggctgcg cgag                                          24

SEQ ID NO: 564       moltype = RNA   length = 21
FEATURE              Location/Qualifiers
source               1..21
                     mol_type = transcribed RNA
                     organism = Homo sapiens
SEQUENCE: 564
cggatccgag tcacggcacc a                                             21
```

```
SEQ ID NO: 565          moltype = RNA   length = 23
FEATURE                 Location/Qualifiers
source                  1..23
                        mol_type = transcribed RNA
                        organism = Homo sapiens
SEQUENCE: 565
ccaggaggcg gaggaggtgg agg                                                  23

SEQ ID NO: 566          moltype = RNA   length = 19
FEATURE                 Location/Qualifiers
source                  1..19
                        mol_type = transcribed RNA
                        organism = Homo sapiens
SEQUENCE: 566
gggtgcgggc cggcggggt                                                       19

SEQ ID NO: 567          moltype = RNA   length = 25
FEATURE                 Location/Qualifiers
source                  1..25
                        mol_type = transcribed RNA
                        organism = Homo sapiens
SEQUENCE: 567
tggcggcggt agttatgggc ttctc                                                25

SEQ ID NO: 568          moltype = RNA   length = 16
FEATURE                 Location/Qualifiers
source                  1..16
                        mol_type = transcribed RNA
                        organism = Homo sapiens
SEQUENCE: 568
ggggtggtct gttgtt                                                          16

SEQ ID NO: 569          moltype = RNA   length = 20
FEATURE                 Location/Qualifiers
source                  1..20
                        mol_type = transcribed RNA
                        organism = Homo sapiens
SEQUENCE: 569
ggaaaaaggc gggagaagcc                                                      20

SEQ ID NO: 570          moltype = RNA   length = 24
FEATURE                 Location/Qualifiers
source                  1..24
                        mol_type = transcribed RNA
                        organism = Homo sapiens
SEQUENCE: 570
agaggcaccg cctgcccagt gaca                                                 24

SEQ ID NO: 571          moltype = RNA   length = 19
FEATURE                 Location/Qualifiers
source                  1..19
                        mol_type = transcribed RNA
                        organism = Homo sapiens
SEQUENCE: 571
aggggggcggg ctccggcgc                                                      19

SEQ ID NO: 572          moltype = RNA   length = 17
FEATURE                 Location/Qualifiers
source                  1..17
                        mol_type = transcribed RNA
                        organism = Homo sapiens
SEQUENCE: 572
aggggctggg cgcgcgc                                                         17

SEQ ID NO: 573          moltype = RNA   length = 30
FEATURE                 Location/Qualifiers
source                  1..30
                        mol_type = transcribed RNA
                        organism = Homo sapiens
SEQUENCE: 573
gctgggctgg gacggacacc cggcctccac                                           30

SEQ ID NO: 574          moltype = RNA   length = 23
FEATURE                 Location/Qualifiers
source                  1..23
                        mol_type = transcribed RNA
                        organism = Homo sapiens
SEQUENCE: 574
aggactggac tcccggcagc ccc                                                  23
```

```
SEQ ID NO: 575         moltype = RNA   length = 23
FEATURE                Location/Qualifiers
source                 1..23
                       mol_type = transcribed RNA
                       organism = Homo sapiens
SEQUENCE: 575
gggggatgt gcatgctggt tgg                                                 23

SEQ ID NO: 576         moltype = RNA   length = 25
FEATURE                Location/Qualifiers
source                 1..25
                       mol_type = transcribed RNA
                       organism = Homo sapiens
SEQUENCE: 576
ctgggccagg gagcagctgg tgggt                                              25

SEQ ID NO: 577         moltype = RNA   length = 23
FEATURE                Location/Qualifiers
source                 1..23
                       mol_type = transcribed RNA
                       organism = Homo sapiens
SEQUENCE: 577
ggtgggtgag gtcgggcccc aag                                                23

SEQ ID NO: 578         moltype = RNA   length = 22
FEATURE                Location/Qualifiers
source                 1..22
                       mol_type = transcribed RNA
                       organism = Homo sapiens
SEQUENCE: 578
acaccgggga tggcagaggg tc                                                 22

SEQ ID NO: 579         moltype = RNA   length = 24
FEATURE                Location/Qualifiers
source                 1..24
                       mol_type = transcribed RNA
                       organism = Homo sapiens
SEQUENCE: 579
caggcaggag ccggactgga cctc                                               24

SEQ ID NO: 580         moltype = RNA   length = 20
FEATURE                Location/Qualifiers
source                 1..20
                       mol_type = transcribed RNA
                       organism = Homo sapiens
SEQUENCE: 580
tggctgttgg aggggcagg                                                     20

SEQ ID NO: 581         moltype = RNA   length = 19
FEATURE                Location/Qualifiers
source                 1..19
                       mol_type = transcribed RNA
                       organism = Homo sapiens
SEQUENCE: 581
gcaggcgagg ctgggctga                                                     19

SEQ ID NO: 582         moltype = RNA   length = 21
FEATURE                Location/Qualifiers
source                 1..21
                       mol_type = transcribed RNA
                       organism = Homo sapiens
SEQUENCE: 582
aggaggcagt gggcgagcag g                                                  21

SEQ ID NO: 583         moltype = RNA   length = 25
FEATURE                Location/Qualifiers
source                 1..25
                       mol_type = transcribed RNA
                       organism = Homo sapiens
SEQUENCE: 583
agcggggagg aagtgggcgc tgctt                                              25

SEQ ID NO: 584         moltype = RNA   length = 23
FEATURE                Location/Qualifiers
source                 1..23
                       mol_type = transcribed RNA
                       organism = Homo sapiens
SEQUENCE: 584
```

```
cagcccgccc cagccgaggt tct                                            23

SEQ ID NO: 585         moltype = RNA   length = 23
FEATURE                Location/Qualifiers
source                 1..23
                       mol_type = transcribed RNA
                       organism = Homo sapiens
SEQUENCE: 585
gccccggcgc gggcgggttc tgg                                            23

SEQ ID NO: 586         moltype = RNA   length = 22
FEATURE                Location/Qualifiers
source                 1..22
                       mol_type = transcribed RNA
                       organism = Homo sapiens
SEQUENCE: 586
aggagcaagg cggcatctct ct                                             22

SEQ ID NO: 587         moltype = RNA   length = 23
FEATURE                Location/Qualifiers
source                 1..23
                       mol_type = transcribed RNA
                       organism = Homo sapiens
SEQUENCE: 587
tggggaaggc gtcagtgtcg ggt                                            23

SEQ ID NO: 588         moltype = RNA   length = 27
FEATURE                Location/Qualifiers
source                 1..27
                       mol_type = transcribed RNA
                       organism = Homo sapiens
SEQUENCE: 588
agggccagag gagcctggag tggtcgg                                        27

SEQ ID NO: 589         moltype = RNA   length = 22
FEATURE                Location/Qualifiers
source                 1..22
                       mol_type = transcribed RNA
                       organism = Homo sapiens
SEQUENCE: 589
tgggagggga gaggcagcaa gc                                             22

SEQ ID NO: 590         moltype = RNA   length = 21
FEATURE                Location/Qualifiers
source                 1..21
                       mol_type = transcribed RNA
                       organism = Homo sapiens
SEQUENCE: 590
tgctgggggc cacatgagtg t                                              21

SEQ ID NO: 591         moltype = RNA   length = 23
FEATURE                Location/Qualifiers
source                 1..23
                       mol_type = transcribed RNA
                       organism = Homo sapiens
SEQUENCE: 591
aagggaggag gagcggaggg gcc                                            23

SEQ ID NO: 592         moltype = RNA   length = 26
FEATURE                Location/Qualifiers
source                 1..26
                       mol_type = transcribed RNA
                       organism = Homo sapiens
SEQUENCE: 592
gcgggctgtc cggaggggtc ggcttt                                         26

SEQ ID NO: 593         moltype = RNA   length = 24
FEATURE                Location/Qualifiers
source                 1..24
                       mol_type = transcribed RNA
                       organism = Homo sapiens
SEQUENCE: 593
cgctcgggcg gaggtggttg agtg                                           24

SEQ ID NO: 594         moltype = RNA   length = 22
FEATURE                Location/Qualifiers
source                 1..22
                       mol_type = transcribed RNA
                       organism = Homo sapiens
```

```
SEQUENCE: 594
agccaggctc tgaagggaaa gt                                              22

SEQ ID NO: 595         moltype = RNA   length = 24
FEATURE                Location/Qualifiers
source                 1..24
                       mol_type = transcribed RNA
                       organism = Homo sapiens
SEQUENCE: 595
aggcaggggc tggtgctggg cggg                                            24

SEQ ID NO: 596         moltype = RNA   length = 22
FEATURE                Location/Qualifiers
source                 1..22
                       mol_type = transcribed RNA
                       organism = Homo sapiens
SEQUENCE: 596
taattttaga tctggtctgc tt                                              22

SEQ ID NO: 597         moltype = RNA   length = 22
FEATURE                Location/Qualifiers
source                 1..22
                       mol_type = transcribed RNA
                       organism = Homo sapiens
SEQUENCE: 597
ccccggtgtt ggggcgcgtc tg                                              22

SEQ ID NO: 598         moltype = RNA   length = 15
FEATURE                Location/Qualifiers
source                 1..15
                       mol_type = transcribed RNA
                       organism = Homo sapiens
SEQUENCE: 598
gagcgctcgc tggcc                                                      15

SEQ ID NO: 599         moltype = RNA   length = 26
FEATURE                Location/Qualifiers
source                 1..26
                       mol_type = transcribed RNA
                       organism = Homo sapiens
SEQUENCE: 599
gagggctct cgcttctggc gccaag                                           26

SEQ ID NO: 600         moltype = RNA   length = 22
FEATURE                Location/Qualifiers
source                 1..22
                       mol_type = transcribed RNA
                       organism = Homo sapiens
SEQUENCE: 600
gggagtgcag ggcagggttt cc                                              22

SEQ ID NO: 601         moltype = RNA   length = 16
FEATURE                Location/Qualifiers
source                 1..16
                       mol_type = transcribed RNA
                       organism = Homo sapiens
SEQUENCE: 601
tgctggtgat gctttc                                                     16

SEQ ID NO: 602         moltype = RNA   length = 15
FEATURE                Location/Qualifiers
source                 1..15
                       mol_type = transcribed RNA
                       organism = Homo sapiens
SEQUENCE: 602
tgaagcgggg gggcg                                                      15

SEQ ID NO: 603         moltype = RNA   length = 18
FEATURE                Location/Qualifiers
source                 1..18
                       mol_type = transcribed RNA
                       organism = Homo sapiens
SEQUENCE: 603
aaaaggaagg gggaggag                                                   18

SEQ ID NO: 604         moltype = RNA   length = 20
FEATURE                Location/Qualifiers
source                 1..20
                       mol_type = transcribed RNA
```

```
                              organism = Homo sapiens
SEQUENCE: 604
ggctggtcag atgggagtgg                                                   20

SEQ ID NO: 605           moltype = RNA  length = 23
FEATURE                  Location/Qualifiers
source                   1..23
                         mol_type = transcribed RNA
                         organism = Homo sapiens
SEQUENCE: 605
acagcagggc tgggattgc agt                                                23

SEQ ID NO: 606           moltype = RNA  length = 17
FEATURE                  Location/Qualifiers
source                   1..17
                         mol_type = transcribed RNA
                         organism = Homo sapiens
SEQUENCE: 606
tgcaggggca ggccagc                                                      17

SEQ ID NO: 607           moltype = RNA  length = 23
FEATURE                  Location/Qualifiers
source                   1..23
                         mol_type = transcribed RNA
                         organism = Homo sapiens
SEQUENCE: 607
gggggtcccc ggtgctcgga tct                                               23

SEQ ID NO: 608           moltype = RNA  length = 22
FEATURE                  Location/Qualifiers
source                   1..22
                         mol_type = transcribed RNA
                         organism = Homo sapiens
SEQUENCE: 608
gctgggatta caggcatgag cc                                                22

SEQ ID NO: 609           moltype = RNA  length = 20
FEATURE                  Location/Qualifiers
source                   1..20
                         mol_type = transcribed RNA
                         organism = Homo sapiens
SEQUENCE: 609
aagacacatt tggagaggga                                                   20

SEQ ID NO: 610           moltype = RNA  length = 21
FEATURE                  Location/Qualifiers
source                   1..21
                         mol_type = transcribed RNA
                         organism = Homo sapiens
SEQUENCE: 610
cagcagggga gagagaggag t                                                 21

SEQ ID NO: 611           moltype = RNA  length = 25
FEATURE                  Location/Qualifiers
source                   1..25
                         mol_type = transcribed RNA
                         organism = Homo sapiens
SEQUENCE: 611
tgcaggcaga agtggggctg acagg                                             25

SEQ ID NO: 612           moltype = RNA  length = 22
FEATURE                  Location/Qualifiers
source                   1..22
                         mol_type = transcribed RNA
                         organism = Homo sapiens
SEQUENCE: 612
attggagggt gtggaagaca tc                                                22

SEQ ID NO: 613           moltype = RNA  length = 23
FEATURE                  Location/Qualifiers
source                   1..23
                         mol_type = transcribed RNA
                         organism = Homo sapiens
SEQUENCE: 613
ggcccggccg tgcctgaggt ttc                                               23

SEQ ID NO: 614           moltype = RNA  length = 21
FEATURE                  Location/Qualifiers
source                   1..21
```

```
                              mol_type = transcribed RNA
                              organism = Homo sapiens
SEQUENCE: 614
tgggaatggg ggtaagggcc t                                                 21

SEQ ID NO: 615            moltype = RNA  length = 21
FEATURE                   Location/Qualifiers
source                    1..21
                          mol_type = transcribed RNA
                          organism = Homo sapiens
SEQUENCE: 615
gaggcgatgt ggggatgtag a                                                 21

SEQ ID NO: 616            moltype = RNA  length = 25
FEATURE                   Location/Qualifiers
source                    1..25
                          mol_type = transcribed RNA
                          organism = Homo sapiens
SEQUENCE: 616
ttctgggccc gcggcgggcg tgggg                                             25

SEQ ID NO: 617            moltype = RNA  length = 16
FEATURE                   Location/Qualifiers
source                    1..16
                          mol_type = transcribed RNA
                          organism = Homo sapiens
SEQUENCE: 617
ggacccaggg agagac                                                       16

SEQ ID NO: 618            moltype = RNA  length = 25
FEATURE                   Location/Qualifiers
source                    1..25
                          mol_type = transcribed RNA
                          organism = Homo sapiens
SEQUENCE: 618
tgcggggcta gggctaacag cagtc                                             25

SEQ ID NO: 619            moltype = RNA  length = 27
FEATURE                   Location/Qualifiers
source                    1..27
                          mol_type = transcribed RNA
                          organism = Homo sapiens
SEQUENCE: 619
gtgaacgggc gccatcccga ggctttg                                           27

SEQ ID NO: 620            moltype = RNA  length = 21
FEATURE                   Location/Qualifiers
source                    1..21
                          mol_type = transcribed RNA
                          organism = Homo sapiens
SEQUENCE: 620
gtgagtcagg gtggggctgg c                                                 21

SEQ ID NO: 621            moltype = RNA  length = 21
FEATURE                   Location/Qualifiers
source                    1..21
                          mol_type = transcribed RNA
                          organism = Homo sapiens
SEQUENCE: 621
gaatggattt ttggagcagg a                                                 21

SEQ ID NO: 622            moltype = RNA  length = 27
FEATURE                   Location/Qualifiers
source                    1..27
                          mol_type = transcribed RNA
                          organism = Homo sapiens
SEQUENCE: 622
agcctggaag ctggagcctg cagtgaa                                           27

SEQ ID NO: 623            moltype = RNA  length = 22
FEATURE                   Location/Qualifiers
source                    1..22
                          mol_type = transcribed RNA
                          organism = Homo sapiens
SEQUENCE: 623
atatagggat tggagccgtg gc                                                22

SEQ ID NO: 624            moltype = RNA  length = 23
FEATURE                   Location/Qualifiers
```

```
source                    1..23
                          mol_type = transcribed RNA
                          organism = Homo sapiens
SEQUENCE: 624
gagggaggga cgggggctgt gct                                              23

SEQ ID NO: 625            moltype = RNA   length = 24
FEATURE                   Location/Qualifiers
source                    1..24
                          mol_type = transcribed RNA
                          organism = Homo sapiens
SEQUENCE: 625
tggtacaggc ctgggggaca ggga                                             24

SEQ ID NO: 626            moltype = RNA   length = 23
FEATURE                   Location/Qualifiers
source                    1..23
                          mol_type = transcribed RNA
                          organism = Homo sapiens
SEQUENCE: 626
aggaggggtc ccgcactggg agg                                              23

SEQ ID NO: 627            moltype = RNA   length = 29
FEATURE                   Location/Qualifiers
source                    1..29
                          mol_type = transcribed RNA
                          organism = Homo sapiens
SEQUENCE: 627
caacggaatc ccaaaagcag ctgttgtct                                        29

SEQ ID NO: 628            moltype = RNA   length = 30
FEATURE                   Location/Qualifiers
source                    1..30
                          mol_type = transcribed RNA
                          organism = Homo sapiens
SEQUENCE: 628
tgaggggcag agagcgagac ttttctattt                                       30

SEQ ID NO: 629            moltype = RNA   length = 22
FEATURE                   Location/Qualifiers
source                    1..22
                          mol_type = transcribed RNA
                          organism = Homo sapiens
SEQUENCE: 629
ggcgtcccag gcggggcgcc gc                                               22

SEQ ID NO: 630            moltype = RNA   length = 25
FEATURE                   Location/Qualifiers
source                    1..25
                          mol_type = transcribed RNA
                          organism = Homo sapiens
SEQUENCE: 630
gggtggggat tgttgcatt acttg                                             25

SEQ ID NO: 631            moltype = RNA   length = 28
FEATURE                   Location/Qualifiers
source                    1..28
                          mol_type = transcribed RNA
                          organism = Homo sapiens
SEQUENCE: 631
gtatggtatt gcacttgtcc cggcctgt                                         28

SEQ ID NO: 632            moltype = RNA   length = 23
FEATURE                   Location/Qualifiers
source                    1..23
                          mol_type = transcribed RNA
                          organism = Homo sapiens
SEQUENCE: 632
aggaaggaag gcagggcccc cgc                                              23

SEQ ID NO: 633            moltype = RNA   length = 15
FEATURE                   Location/Qualifiers
source                    1..15
                          mol_type = transcribed RNA
                          organism = Homo sapiens
SEQUENCE: 633
ggtgaggcgg ggggg                                                       15

SEQ ID NO: 634            moltype = RNA   length = 15
```

```
                        -continued

FEATURE                 Location/Qualifiers
source                  1..15
                        mol_type = transcribed RNA
                        organism = Homo sapiens
SEQUENCE: 634
atatacaggg ggaga                                                    15

SEQ ID NO: 635          moltype = RNA   length = 15
FEATURE                 Location/Qualifiers
source                  1..15
                        mol_type = transcribed RNA
                        organism = Homo sapiens
SEQUENCE: 635
atatacaggg ggaga                                                    15

SEQ ID NO: 636          moltype = RNA   length = 21
FEATURE                 Location/Qualifiers
source                  1..21
                        mol_type = transcribed RNA
                        organism = Homo sapiens
SEQUENCE: 636
taggtcaccc gtttgactat c                                             21

SEQ ID NO: 637          moltype = RNA   length = 15
FEATURE                 Location/Qualifiers
source                  1..15
                        mol_type = transcribed RNA
                        organism = Homo sapiens
SEQUENCE: 637
tcacacctgc ctcgc                                                    15

SEQ ID NO: 638          moltype = RNA   length = 15
FEATURE                 Location/Qualifiers
source                  1..15
                        mol_type = transcribed RNA
                        organism = Homo sapiens
SEQUENCE: 638
cgggggcagg tgtgt                                                    15

SEQ ID NO: 639          moltype = RNA   length = 15
FEATURE                 Location/Qualifiers
source                  1..15
                        mol_type = transcribed RNA
                        organism = Homo sapiens
SEQUENCE: 639
tggcagagcg ctgtc                                                    15

SEQ ID NO: 640          moltype = RNA   length = 15
FEATURE                 Location/Qualifiers
source                  1..15
                        mol_type = transcribed RNA
                        organism = Homo sapiens
SEQUENCE: 640
cgggaacgtc gagac                                                    15

SEQ ID NO: 641          moltype = RNA   length = 15
FEATURE                 Location/Qualifiers
source                  1..15
                        mol_type = transcribed RNA
                        organism = Homo sapiens
SEQUENCE: 641
tagccgggcg tggtg                                                    15

SEQ ID NO: 642          moltype = RNA   length = 15
FEATURE                 Location/Qualifiers
source                  1..15
                        mol_type = transcribed RNA
                        organism = Homo sapiens
SEQUENCE: 642
cgggcgtggt ggtgg                                                    15

SEQ ID NO: 643          moltype = RNA   length = 15
FEATURE                 Location/Qualifiers
source                  1..15
                        mol_type = transcribed RNA
                        organism = Homo sapiens
SEQUENCE: 643
actgcactcc agcct                                                    15
```

```
SEQ ID NO: 644          moltype = RNA   length = 20
FEATURE                 Location/Qualifiers
source                  1..20
                        mol_type = transcribed RNA
                        organism = Homo sapiens
SEQUENCE: 644
gggggccgat acactgtacg                                                   20

SEQ ID NO: 645          moltype = RNA   length = 18
FEATURE                 Location/Qualifiers
source                  1..18
                        mol_type = transcribed RNA
                        organism = Homo sapiens
SEQUENCE: 645
ctcctggggc ccgcactc                                                     18

SEQ ID NO: 646          moltype = RNA   length = 15
FEATURE                 Location/Qualifiers
source                  1..15
                        mol_type = transcribed RNA
                        organism = Homo sapiens
SEQUENCE: 646
cccgcgggac gcgcc                                                        15

SEQ ID NO: 647          moltype = RNA   length = 15
FEATURE                 Location/Qualifiers
source                  1..15
                        mol_type = transcribed RNA
                        organism = Homo sapiens
SEQUENCE: 647
actgcagtga aggca                                                        15

SEQ ID NO: 648          moltype = RNA   length = 22
FEATURE                 Location/Qualifiers
source                  1..22
                        mol_type = transcribed RNA
                        organism = Homo sapiens
SEQUENCE: 648
gctacaacac aggacccggg cg                                                22

SEQ ID NO: 649          moltype = RNA   length = 17
FEATURE                 Location/Qualifiers
source                  1..17
                        mol_type = transcribed RNA
                        organism = Homo sapiens
SEQUENCE: 649
ccggccgccg gctccgc                                                      17

SEQ ID NO: 650          moltype = RNA   length = 19
FEATURE                 Location/Qualifiers
source                  1..19
                        mol_type = transcribed RNA
                        organism = Homo sapiens
SEQUENCE: 650
cgcaggggcc gggtgctca                                                    19

SEQ ID NO: 651          moltype = RNA   length = 15
FEATURE                 Location/Qualifiers
source                  1..15
                        mol_type = transcribed RNA
                        organism = Homo sapiens
SEQUENCE: 651
cgcggcgggg gcggc                                                        15

SEQ ID NO: 652          moltype = RNA   length = 16
FEATURE                 Location/Qualifiers
source                  1..16
                        mol_type = transcribed RNA
                        organism = Homo sapiens
SEQUENCE: 652
agccctgcc caccgc                                                        16

SEQ ID NO: 653          moltype = RNA   length = 15
FEATURE                 Location/Qualifiers
source                  1..15
                        mol_type = transcribed RNA
                        organism = Homo sapiens
SEQUENCE: 653
agttcagcag gaaca                                                        15
```

```
SEQ ID NO: 654          moltype = RNA  length = 15
FEATURE                 Location/Qualifiers
source                  1..15
                        mol_type = transcribed RNA
                        organism = Homo sapiens
SEQUENCE: 654
agcagaggca gagag                                                          15

SEQ ID NO: 655          moltype = RNA  length = 15
FEATURE                 Location/Qualifiers
source                  1..15
                        mol_type = transcribed RNA
                        organism = Homo sapiens
SEQUENCE: 655
ggcctctcgg gaact                                                          15

SEQ ID NO: 656          moltype = RNA  length = 15
FEATURE                 Location/Qualifiers
source                  1..15
                        mol_type = transcribed RNA
                        organism = Homo sapiens
SEQUENCE: 656
gagggttggg tggag                                                          15

SEQ ID NO: 657          moltype = RNA  length = 15
FEATURE                 Location/Qualifiers
source                  1..15
                        mol_type = transcribed RNA
                        organism = Homo sapiens
SEQUENCE: 657
ctagcaccat ttgaa                                                          15

SEQ ID NO: 658          moltype = RNA  length = 17
FEATURE                 Location/Qualifiers
source                  1..17
                        mol_type = transcribed RNA
                        organism = Homo sapiens
SEQUENCE: 658
actggtggaa gggcctt                                                        17

SEQ ID NO: 659          moltype = RNA  length = 16
FEATURE                 Location/Qualifiers
source                  1..16
                        mol_type = transcribed RNA
                        organism = Homo sapiens
SEQUENCE: 659
gaagggagt tgggag                                                          16

SEQ ID NO: 660          moltype = RNA  length = 18
FEATURE                 Location/Qualifiers
source                  1..18
                        mol_type = transcribed RNA
                        organism = Homo sapiens
SEQUENCE: 660
cctgcagaga ggaagccc                                                       18

SEQ ID NO: 661          moltype = RNA  length = 16
FEATURE                 Location/Qualifiers
source                  1..16
                        mol_type = transcribed RNA
                        organism = Homo sapiens
SEQUENCE: 661
tagggagtag aagggt                                                         16

SEQ ID NO: 662          moltype = RNA  length = 15
FEATURE                 Location/Qualifiers
source                  1..15
                        mol_type = transcribed RNA
                        organism = Homo sapiens
SEQUENCE: 662
gctgggcggg gcgcg                                                          15

SEQ ID NO: 663          moltype = RNA  length = 15
FEATURE                 Location/Qualifiers
source                  1..15
                        mol_type = transcribed RNA
                        organism = Homo sapiens
SEQUENCE: 663
```

```
gccccgggaa agcgt                                                        15

SEQ ID NO: 664          moltype = RNA   length = 21
FEATURE                 Location/Qualifiers
source                  1..21
                        mol_type = transcribed RNA
                        organism = Homo sapiens
SEQUENCE: 664
aagaaggcgg tcggtctgcg g                                                 21

SEQ ID NO: 665          moltype = RNA   length = 20
FEATURE                 Location/Qualifiers
source                  1..20
                        mol_type = transcribed RNA
                        organism = Homo sapiens
SEQUENCE: 665
agctctgctg ctcactggca                                                   20

SEQ ID NO: 666          moltype = RNA   length = 15
FEATURE                 Location/Qualifiers
source                  1..15
                        mol_type = transcribed RNA
                        organism = Homo sapiens
SEQUENCE: 666
cgcgccgggc ccggg                                                        15

SEQ ID NO: 667          moltype = RNA   length = 15
FEATURE                 Location/Qualifiers
source                  1..15
                        mol_type = transcribed RNA
                        organism = Homo sapiens
SEQUENCE: 667
gcaggctcgg aaagg                                                        15

SEQ ID NO: 668          moltype = RNA   length = 15
FEATURE                 Location/Qualifiers
source                  1..15
                        mol_type = transcribed RNA
                        organism = Homo sapiens
SEQUENCE: 668
cttctcttcc cggtt                                                        15

SEQ ID NO: 669          moltype = RNA   length = 15
FEATURE                 Location/Qualifiers
source                  1..15
                        mol_type = transcribed RNA
                        organism = Homo sapiens
SEQUENCE: 669
gaaaagctgg gttga                                                        15

SEQ ID NO: 670          moltype = RNA   length = 19
FEATURE                 Location/Qualifiers
source                  1..19
                        mol_type = transcribed RNA
                        organism = Homo sapiens
SEQUENCE: 670
gggggcagg aggggctca                                                     19

SEQ ID NO: 671          moltype = RNA   length = 15
FEATURE                 Location/Qualifiers
source                  1..15
                        mol_type = transcribed RNA
                        organism = Homo sapiens
SEQUENCE: 671
gctatctgtg attga                                                        15

SEQ ID NO: 672          moltype = RNA   length = 17
FEATURE                 Location/Qualifiers
source                  1..17
                        mol_type = transcribed RNA
                        organism = Homo sapiens
SEQUENCE: 672
gccctgaacg aggggtc                                                      17

SEQ ID NO: 673          moltype = RNA   length = 16
FEATURE                 Location/Qualifiers
source                  1..16
                        mol_type = transcribed RNA
                        organism = Homo sapiens
```

| | | |
|---|---|---|
| SEQUENCE: 673 gggcatttca tgatgc | | 16 |
| SEQ ID NO: 674 FEATURE source | moltype = RNA length = 15 Location/Qualifiers 1..15 mol_type = transcribed RNA organism = Homo sapiens | |
| SEQUENCE: 674 gggctgggct gggct | | 15 |
| SEQ ID NO: 675 FEATURE source | moltype = RNA length = 18 Location/Qualifiers 1..18 mol_type = transcribed RNA organism = Homo sapiens | |
| SEQUENCE: 675 gcacgggagc tcaggtga | | 18 |
| SEQ ID NO: 676 FEATURE source | moltype = RNA length = 15 Location/Qualifiers 1..15 mol_type = transcribed RNA organism = Homo sapiens | |
| SEQUENCE: 676 ggcggcggtg gtggg | | 15 |
| SEQ ID NO: 677 FEATURE source | moltype = RNA length = 16 Location/Qualifiers 1..16 mol_type = transcribed RNA organism = Homo sapiens | |
| SEQUENCE: 677 gctggaggtg tgagga | | 16 |
| SEQ ID NO: 678 FEATURE source | moltype = RNA length = 15 Location/Qualifiers 1..15 mol_type = transcribed RNA organism = Homo sapiens | |
| SEQUENCE: 678 tggcgggtgc ggggg | | 15 |
| SEQ ID NO: 679 FEATURE source | moltype = RNA length = 19 Location/Qualifiers 1..19 mol_type = transcribed RNA organism = Homo sapiens | |
| SEQUENCE: 679 tgaggatatg gcagggaag | | 19 |
| SEQ ID NO: 680 FEATURE source | moltype = RNA length = 15 Location/Qualifiers 1..15 mol_type = transcribed RNA organism = Homo sapiens | |
| SEQUENCE: 680 agagtgtggt caggc | | 15 |
| SEQ ID NO: 681 FEATURE source | moltype = RNA length = 19 Location/Qualifiers 1..19 mol_type = transcribed RNA organism = Homo sapiens | |
| SEQUENCE: 681 gtgggttggg gcgggctct | | 19 |
| SEQ ID NO: 682 FEATURE source | moltype = RNA length = 15 Location/Qualifiers 1..15 mol_type = transcribed RNA organism = Homo sapiens | |
| SEQUENCE: 682 gctccccgcg ccccc | | 15 |
| SEQ ID NO: 683 FEATURE source | moltype = RNA length = 15 Location/Qualifiers 1..15 mol_type = transcribed RNA | |

```
                            organism = Homo sapiens
SEQUENCE: 683
ccccactcct ggtac                                                            15

SEQ ID NO: 684          moltype = RNA   length = 15
FEATURE                 Location/Qualifiers
source                  1..15
                        mol_type = transcribed RNA
                        organism = Homo sapiens
SEQUENCE: 684
aggaggagga ggcag                                                            15

SEQ ID NO: 685          moltype = RNA   length = 15
FEATURE                 Location/Qualifiers
source                  1..15
                        mol_type = transcribed RNA
                        organism = Homo sapiens
SEQUENCE: 685
ggtgggcttc ccgga                                                            15

SEQ ID NO: 686          moltype = RNA   length = 15
FEATURE                 Location/Qualifiers
source                  1..15
                        mol_type = transcribed RNA
                        organism = Homo sapiens
SEQUENCE: 686
gaggctgaag gaaga                                                            15

SEQ ID NO: 687          moltype = RNA   length = 15
FEATURE                 Location/Qualifiers
source                  1..15
                        mol_type = transcribed RNA
                        organism = Homo sapiens
SEQUENCE: 687
aaagctgggc tgaga                                                            15

SEQ ID NO: 688          moltype = RNA   length = 15
FEATURE                 Location/Qualifiers
source                  1..15
                        mol_type = transcribed RNA
                        organism = Homo sapiens
SEQUENCE: 688
aggctggagt gagcg                                                            15

SEQ ID NO: 689          moltype = RNA   length = 20
FEATURE                 Location/Qualifiers
source                  1..20
                        mol_type = transcribed RNA
                        organism = Homo sapiens
SEQUENCE: 689
acaggagtgg gggtgggaca                                                       20

SEQ ID NO: 690          moltype = RNA   length = 15
FEATURE                 Location/Qualifiers
source                  1..15
                        mol_type = transcribed RNA
                        organism = Homo sapiens
SEQUENCE: 690
gttggaggcg tgggt                                                            15

SEQ ID NO: 691          moltype = RNA   length = 19
FEATURE                 Location/Qualifiers
source                  1..19
                        mol_type = transcribed RNA
                        organism = Homo sapiens
SEQUENCE: 691
cagggctggc agtgacatg                                                        19

SEQ ID NO: 692          moltype = RNA   length = 15
FEATURE                 Location/Qualifiers
source                  1..15
                        mol_type = transcribed RNA
                        organism = Homo sapiens
SEQUENCE: 692
cttggtctag gggta                                                            15

SEQ ID NO: 693          moltype = RNA   length = 17
FEATURE                 Location/Qualifiers
source                  1..17
```

```
                            mol_type = transcribed RNA
                            organism = Homo sapiens
SEQUENCE: 693
ccggggctgc gcgaggc                                                      17

SEQ ID NO: 694              moltype = RNA   length = 15
FEATURE                     Location/Qualifiers
source                      1..15
                            mol_type = transcribed RNA
                            organism = Homo sapiens
SEQUENCE: 694
tccgagtcac ggcac                                                        15

SEQ ID NO: 695              moltype = RNA   length = 15
FEATURE                     Location/Qualifiers
source                      1..15
                            mol_type = transcribed RNA
                            organism = Homo sapiens
SEQUENCE: 695
acccaggagg cggag                                                        15

SEQ ID NO: 696              moltype = RNA   length = 15
FEATURE                     Location/Qualifiers
source                      1..15
                            mol_type = transcribed RNA
                            organism = Homo sapiens
SEQUENCE: 696
tgcgggccgg cgggg                                                        15

SEQ ID NO: 697              moltype = RNA   length = 15
FEATURE                     Location/Qualifiers
source                      1..15
                            mol_type = transcribed RNA
                            organism = Homo sapiens
SEQUENCE: 697
ggcgggagaa gcccc                                                        15

SEQ ID NO: 698              moltype = RNA   length = 15
FEATURE                     Location/Qualifiers
source                      1..15
                            mol_type = transcribed RNA
                            organism = Homo sapiens
SEQUENCE: 698
gaggcaccgc ctgcc                                                        15

SEQ ID NO: 699              moltype = RNA   length = 15
FEATURE                     Location/Qualifiers
source                      1..15
                            mol_type = transcribed RNA
                            organism = Homo sapiens
SEQUENCE: 699
gtaggggcg ggctc                                                         15

SEQ ID NO: 700              moltype = RNA   length = 15
FEATURE                     Location/Qualifiers
source                      1..15
                            mol_type = transcribed RNA
                            organism = Homo sapiens
SEQUENCE: 700
cagggctgg gcgcg                                                         15

SEQ ID NO: 701              moltype = RNA   length = 18
FEATURE                     Location/Qualifiers
source                      1..18
                            mol_type = transcribed RNA
                            organism = Homo sapiens
SEQUENCE: 701
gcgtggggag ctggtcct                                                     18

SEQ ID NO: 702              moltype = RNA   length = 15
FEATURE                     Location/Qualifiers
source                      1..15
                            mol_type = transcribed RNA
                            organism = Homo sapiens
SEQUENCE: 702
atcagcgtgc acttc                                                        15

SEQ ID NO: 703              moltype = RNA   length = 20
FEATURE                     Location/Qualifiers
```

```
source                  1..20
                        mol_type = transcribed RNA
                        organism = Homo sapiens
SEQUENCE: 703
tgggccaggg agcagctggt                                                    20

SEQ ID NO: 704          moltype = RNA   length = 20
FEATURE                 Location/Qualifiers
source                  1..20
                        mol_type = transcribed RNA
                        organism = Homo sapiens
SEQUENCE: 704
caccggggat ggcagagggt                                                    20

SEQ ID NO: 705          moltype = RNA   length = 17
FEATURE                 Location/Qualifiers
source                  1..17
                        mol_type = transcribed RNA
                        organism = Homo sapiens
SEQUENCE: 705
gtgagtgtgg atcctgg                                                       17

SEQ ID NO: 706          moltype = RNA   length = 21
FEATURE                 Location/Qualifiers
source                  1..21
                        mol_type = transcribed RNA
                        organism = Homo sapiens
SEQUENCE: 706
tccaggcagg agccggactg g                                                  21

SEQ ID NO: 707          moltype = RNA   length = 15
FEATURE                 Location/Qualifiers
source                  1..15
                        mol_type = transcribed RNA
                        organism = Homo sapiens
SEQUENCE: 707
ggaggggggca ggctc                                                        15

SEQ ID NO: 708          moltype = RNA   length = 21
FEATURE                 Location/Qualifiers
source                  1..21
                        mol_type = transcribed RNA
                        organism = Homo sapiens
SEQUENCE: 708
cagccctcct cccgcaccca a                                                  21

SEQ ID NO: 709          moltype = RNA   length = 16
FEATURE                 Location/Qualifiers
source                  1..16
                        mol_type = transcribed RNA
                        organism = Homo sapiens
SEQUENCE: 709
aggcgaggct gggctg                                                        16

SEQ ID NO: 710          moltype = RNA   length = 21
FEATURE                 Location/Qualifiers
source                  1..21
                        mol_type = transcribed RNA
                        organism = Homo sapiens
SEQUENCE: 710
aggaggcagt gggcgagcag g                                                  21

SEQ ID NO: 711          moltype = RNA   length = 21
FEATURE                 Location/Qualifiers
source                  1..21
                        mol_type = transcribed RNA
                        organism = Homo sapiens
SEQUENCE: 711
agcggggagg aagtgggcgc t                                                  21

SEQ ID NO: 712          moltype = RNA   length = 17
FEATURE                 Location/Qualifiers
source                  1..17
                        mol_type = transcribed RNA
                        organism = Homo sapiens
SEQUENCE: 712
agcccgcccc agccgag                                                       17

SEQ ID NO: 713          moltype = RNA   length = 16
```

```
FEATURE                 Location/Qualifiers
source                  1..16
                        mol_type = transcribed RNA
                        organism = Homo sapiens
SEQUENCE: 713
ggagccccgg cgcggg                                                          16

SEQ ID NO: 714          moltype = RNA   length = 18
FEATURE                 Location/Qualifiers
source                  1..18
                        mol_type = transcribed RNA
                        organism = Homo sapiens
SEQUENCE: 714
gagcaaggcg gcatctct                                                        18

SEQ ID NO: 715          moltype = RNA   length = 15
FEATURE                 Location/Qualifiers
source                  1..15
                        mol_type = transcribed RNA
                        organism = Homo sapiens
SEQUENCE: 715
gggtgagggc aggtg                                                           15

SEQ ID NO: 716          moltype = RNA   length = 17
FEATURE                 Location/Qualifiers
source                  1..17
                        mol_type = transcribed RNA
                        organism = Homo sapiens
SEQUENCE: 716
ggcaggaggg ctgtgcc                                                         17

SEQ ID NO: 717          moltype = RNA   length = 16
FEATURE                 Location/Qualifiers
source                  1..16
                        mol_type = transcribed RNA
                        organism = Homo sapiens
SEQUENCE: 717
tggggaaggc gtcagt                                                          16

SEQ ID NO: 718          moltype = RNA   length = 23
FEATURE                 Location/Qualifiers
source                  1..23
                        mol_type = transcribed RNA
                        organism = Homo sapiens
SEQUENCE: 718
agggccagag gagcctggag tgg                                                  23

SEQ ID NO: 719          moltype = RNA   length = 19
FEATURE                 Location/Qualifiers
source                  1..19
                        mol_type = transcribed RNA
                        organism = Homo sapiens
SEQUENCE: 719
atagtgggaa gctggcaga                                                       19

SEQ ID NO: 720          moltype = RNA   length = 22
FEATURE                 Location/Qualifiers
source                  1..22
                        mol_type = transcribed RNA
                        organism = Homo sapiens
SEQUENCE: 720
tgggagggga gaggcagcaa gc                                                   22

SEQ ID NO: 721          moltype = RNA   length = 20
FEATURE                 Location/Qualifiers
source                  1..20
                        mol_type = transcribed RNA
                        organism = Homo sapiens
SEQUENCE: 721
gctgggggcc acatgagtgt                                                      20

SEQ ID NO: 722          moltype = RNA   length = 15
FEATURE                 Location/Qualifiers
source                  1..15
                        mol_type = transcribed RNA
                        organism = Homo sapiens
SEQUENCE: 722
gggaggagga gcgga                                                           15
```

| | | |
|---|---|---|
| SEQ ID NO: 723<br>FEATURE<br>source<br><br>SEQUENCE: 723<br>gctgtccgga ggggtc | moltype = RNA   length = 16<br>Location/Qualifiers<br>1..16<br>mol_type = transcribed RNA<br>organism = Homo sapiens | <br><br><br><br><br>16 |
| SEQ ID NO: 724<br>FEATURE<br>source<br><br>SEQUENCE: 724<br>tcgggcggag gtggttg | moltype = RNA   length = 17<br>Location/Qualifiers<br>1..17<br>mol_type = transcribed RNA<br>organism = Homo sapiens | <br><br><br><br><br>17 |
| SEQ ID NO: 725<br>FEATURE<br>source<br><br>SEQUENCE: 725<br>gaagggaaag ttgaa | moltype = RNA   length = 15<br>Location/Qualifiers<br>1..15<br>mol_type = transcribed RNA<br>organism = Homo sapiens | <br><br><br><br><br>15 |
| SEQ ID NO: 726<br>FEATURE<br>source<br><br>SEQUENCE: 726<br>gggcgggggg cggcg | moltype = RNA   length = 15<br>Location/Qualifiers<br>1..15<br>mol_type = transcribed RNA<br>organism = Homo sapiens | <br><br><br><br><br>15 |
| SEQ ID NO: 727<br>FEATURE<br>source<br><br>SEQUENCE: 727<br>aattttagat ctggtctgc | moltype = RNA   length = 19<br>Location/Qualifiers<br>1..19<br>mol_type = transcribed RNA<br>organism = Homo sapiens | <br><br><br><br><br>19 |
| SEQ ID NO: 728<br>FEATURE<br>source<br><br>SEQUENCE: 728<br>cccggtgttg gggcgcgtct g | moltype = RNA   length = 21<br>Location/Qualifiers<br>1..21<br>mol_type = transcribed RNA<br>organism = Homo sapiens | <br><br><br><br><br>21 |
| SEQ ID NO: 729<br>FEATURE<br>source<br><br>SEQUENCE: 729<br>gcccactgcc ccgcg | moltype = RNA   length = 15<br>Location/Qualifiers<br>1..15<br>mol_type = transcribed RNA<br>organism = Homo sapiens | <br><br><br><br><br>15 |
| SEQ ID NO: 730<br>FEATURE<br>source<br><br>SEQUENCE: 730<br>cggtgagcgc tcgct | moltype = RNA   length = 15<br>Location/Qualifiers<br>1..15<br>mol_type = transcribed RNA<br>organism = Homo sapiens | <br><br><br><br><br>15 |
| SEQ ID NO: 731<br>FEATURE<br>source<br><br>SEQUENCE: 731<br>ggtgaggcgg ggggg | moltype = RNA   length = 15<br>Location/Qualifiers<br>1..15<br>mol_type = transcribed RNA<br>organism = Homo sapiens | <br><br><br><br><br>15 |
| SEQ ID NO: 732<br>FEATURE<br>source<br><br>SEQUENCE: 732<br>agggagtgca gggcaggg | moltype = RNA   length = 18<br>Location/Qualifiers<br>1..18<br>mol_type = transcribed RNA<br>organism = Homo sapiens | <br><br><br><br><br>18 |

| | | |
|---|---|---|
| SEQ ID NO: 733<br>FEATURE<br>source | moltype = RNA   length = 15<br>Location/Qualifiers<br>1..15<br>mol_type = transcribed RNA<br>organism = Homo sapiens | |
| SEQUENCE: 733<br>gagggagtaa gagcc | | 15 |
| SEQ ID NO: 734<br>FEATURE<br>source | moltype = RNA   length = 16<br>Location/Qualifiers<br>1..16<br>mol_type = transcribed RNA<br>organism = Homo sapiens | |
| SEQUENCE: 734<br>tgctggtgat gctttc | | 16 |
| SEQ ID NO: 735<br>FEATURE<br>source | moltype = RNA   length = 15<br>Location/Qualifiers<br>1..15<br>mol_type = transcribed RNA<br>organism = Homo sapiens | |
| SEQUENCE: 735<br>tgaagcgggg gggcg | | 15 |
| SEQ ID NO: 736<br>FEATURE<br>source | moltype = RNA   length = 16<br>Location/Qualifiers<br>1..16<br>mol_type = transcribed RNA<br>organism = Homo sapiens | |
| SEQUENCE: 736<br>aaggaagggg gaggag | | 16 |
| SEQ ID NO: 737<br>FEATURE<br>source | moltype = RNA   length = 20<br>Location/Qualifiers<br>1..20<br>mol_type = transcribed RNA<br>organism = Homo sapiens | |
| SEQUENCE: 737<br>ggctggtcag atgggagtgg | | 20 |
| SEQ ID NO: 738<br>FEATURE<br>source | moltype = RNA   length = 17<br>Location/Qualifiers<br>1..17<br>mol_type = transcribed RNA<br>organism = Homo sapiens | |
| SEQUENCE: 738<br>tgcagggca ggccagc | | 17 |
| SEQ ID NO: 739<br>FEATURE<br>source | moltype = RNA   length = 20<br>Location/Qualifiers<br>1..20<br>mol_type = transcribed RNA<br>organism = Homo sapiens | |
| SEQUENCE: 739<br>gggggtcccc ggtgctcgga | | 20 |
| SEQ ID NO: 740<br>FEATURE<br>source | moltype = RNA   length = 15<br>Location/Qualifiers<br>1..15<br>mol_type = transcribed RNA<br>organism = Homo sapiens | |
| SEQUENCE: 740<br>gattacaggc atgag | | 15 |
| SEQ ID NO: 741<br>FEATURE<br>source | moltype = RNA   length = 16<br>Location/Qualifiers<br>1..16<br>mol_type = transcribed RNA<br>organism = Homo sapiens | |
| SEQUENCE: 741<br>agacacattt ggagag | | 16 |
| SEQ ID NO: 742<br>FEATURE<br>source | moltype = RNA   length = 20<br>Location/Qualifiers<br>1..20<br>mol_type = transcribed RNA<br>organism = Homo sapiens | |
| SEQUENCE: 742 | | |

```
cagcagggga gagagaggag                                                    20

SEQ ID NO: 743          moltype = RNA   length = 20
FEATURE                 Location/Qualifiers
source                  1..20
                        mol_type = transcribed RNA
                        organism = Homo sapiens
SEQUENCE: 743
ctgcaggcag aagtggggct                                                    20

SEQ ID NO: 744          moltype = RNA   length = 16
FEATURE                 Location/Qualifiers
source                  1..16
                        mol_type = transcribed RNA
                        organism = Homo sapiens
SEQUENCE: 744
ttggagggtg tggaag                                                        16

SEQ ID NO: 745          moltype = RNA   length = 15
FEATURE                 Location/Qualifiers
source                  1..15
                        mol_type = transcribed RNA
                        organism = Homo sapiens
SEQUENCE: 745
tgttttcctg gtggc                                                         15

SEQ ID NO: 746          moltype = RNA   length = 15
FEATURE                 Location/Qualifiers
source                  1..15
                        mol_type = transcribed RNA
                        organism = Homo sapiens
SEQUENCE: 746
cttctgagcc caggt                                                         15

SEQ ID NO: 747          moltype = RNA   length = 20
FEATURE                 Location/Qualifiers
source                  1..20
                        mol_type = transcribed RNA
                        organism = Homo sapiens
SEQUENCE: 747
cccagtctca tttcctcatc                                                    20

SEQ ID NO: 748          moltype = RNA   length = 15
FEATURE                 Location/Qualifiers
source                  1..15
                        mol_type = transcribed RNA
                        organism = Homo sapiens
SEQUENCE: 748
cgcggcgggc gtggg                                                         15

SEQ ID NO: 749          moltype = RNA   length = 16
FEATURE                 Location/Qualifiers
source                  1..16
                        mol_type = transcribed RNA
                        organism = Homo sapiens
SEQUENCE: 749
ggacccaggg agagac                                                        16

SEQ ID NO: 750          moltype = RNA   length = 15
FEATURE                 Location/Qualifiers
source                  1..15
                        mol_type = transcribed RNA
                        organism = Homo sapiens
SEQUENCE: 750
tgcggggcta gggct                                                         15

SEQ ID NO: 751          moltype = RNA   length = 17
FEATURE                 Location/Qualifiers
source                  1..17
                        mol_type = transcribed RNA
                        organism = Homo sapiens
SEQUENCE: 751
tcctagtcac ggcacca                                                       17

SEQ ID NO: 752          moltype = RNA   length = 16
FEATURE                 Location/Qualifiers
source                  1..16
                        mol_type = transcribed RNA
                        organism = Homo sapiens
```

```
SEQUENCE: 752
gtgaacgggc gccatc                                                       16

SEQ ID NO: 753         moltype = RNA  length = 21
FEATURE                Location/Qualifiers
source                 1..21
                       mol_type = transcribed RNA
                       organism = Homo sapiens
SEQUENCE: 753
gtgagtcagg gtggggctgg c                                                 21

SEQ ID NO: 754         moltype = RNA  length = 15
FEATURE                Location/Qualifiers
source                 1..15
                       mol_type = transcribed RNA
                       organism = Homo sapiens
SEQUENCE: 754
gctgcagtgg gggag                                                        15

SEQ ID NO: 755         moltype = RNA  length = 15
FEATURE                Location/Qualifiers
source                 1..15
                       mol_type = transcribed RNA
                       organism = Homo sapiens
SEQUENCE: 755
ggattttttgg agcag                                                       15

SEQ ID NO: 756         moltype = RNA  length = 15
FEATURE                Location/Qualifiers
source                 1..15
                       mol_type = transcribed RNA
                       organism = Homo sapiens
SEQUENCE: 756
ggtgggagga ttgct                                                        15

SEQ ID NO: 757         moltype = RNA  length = 20
FEATURE                Location/Qualifiers
source                 1..20
                       mol_type = transcribed RNA
                       organism = Homo sapiens
SEQUENCE: 757
atatagggat tggagccgtg                                                   20

SEQ ID NO: 758         moltype = RNA  length = 15
FEATURE                Location/Qualifiers
source                 1..15
                       mol_type = transcribed RNA
                       organism = Homo sapiens
SEQUENCE: 758
gaggagggag ggagg                                                        15

SEQ ID NO: 759         moltype = RNA  length = 19
FEATURE                Location/Qualifiers
source                 1..19
                       mol_type = transcribed RNA
                       organism = Homo sapiens
SEQUENCE: 759
ggtacaggcc tgggggaca                                                    19

SEQ ID NO: 760         moltype = RNA  length = 15
FEATURE                Location/Qualifiers
source                 1..15
                       mol_type = transcribed RNA
                       organism = Homo sapiens
SEQUENCE: 760
tgggaggggc cctca                                                        15

SEQ ID NO: 761         moltype = RNA  length = 15
FEATURE                Location/Qualifiers
source                 1..15
                       mol_type = transcribed RNA
                       organism = Homo sapiens
SEQUENCE: 761
caacggaatc ccaaa                                                        15

SEQ ID NO: 762         moltype = RNA  length = 15
FEATURE                Location/Qualifiers
source                 1..15
                       mol_type = transcribed RNA
```

```
                        organism = Homo sapiens
SEQUENCE: 762
cagagagcga gactt                                                                    15

SEQ ID NO: 763          moltype = RNA  length = 15
FEATURE                 Location/Qualifiers
source                  1..15
                        mol_type = transcribed RNA
                        organism = Homo sapiens
SEQUENCE: 763
gcgccgcggg accgc                                                                    15

SEQ ID NO: 764          moltype = RNA  length = 20
FEATURE                 Location/Qualifiers
source                  1..20
                        mol_type = transcribed RNA
                        organism = Homo sapiens
SEQUENCE: 764
gggtggggat ttgttgcatt                                                               20

SEQ ID NO: 765          moltype = RNA  length = 15
FEATURE                 Location/Qualifiers
source                  1..15
                        mol_type = transcribed RNA
                        organism = Homo sapiens
SEQUENCE: 765
tattgcactt gtccc                                                                    15

SEQ ID NO: 766          moltype = RNA  length = 15
FEATURE                 Location/Qualifiers
source                  1..15
                        mol_type = transcribed RNA
                        organism = Homo sapiens
SEQUENCE: 766
gggccccgc tcccc                                                                     15
```